(12) United States Patent
Narayanan et al.

(10) Patent No.: US 11,873,282 B2
(45) Date of Patent: *Jan. 16, 2024

(54) SELECTIVE ANDROGEN RECEPTOR DEGRADER (SARD) LIGANDS AND METHODS OF USE THEREOF

(71) Applicant: University of Tennessee Research Foundation, Knoxville, TN (US)

(72) Inventors: Ramesh Narayanan, Cordova, TN (US); Duane D. Miller, Collierville, TN (US); Thamarai Ponnusamy, Memphis, TN (US); Dong-Jin Hwang, Arlington, TN (US); Yali He, Germantown, TN (US)

(73) Assignee: University of Tennessee Research Foundation, Knoxville, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/027,707

(22) Filed: Sep. 22, 2020

(65) Prior Publication Data

US 2021/0253525 A1 Aug. 19, 2021

Related U.S. Application Data

(63) Continuation of application No. 16/122,862, filed on Sep. 5, 2018, now Pat. No. 10,865,184, which is a (Continued)

(51) Int. Cl.

| C07D 209/08 | (2006.01) |
|---|---|
| A61P 5/26 | (2006.01) |
| C07D 401/12 | (2006.01) |
| C07D 235/06 | (2006.01) |
| C07D 471/04 | (2006.01) |
| C07D 231/56 | (2006.01) |
| C07D 249/18 | (2006.01) |
| C07D 215/06 | (2006.01) |
| C07D 217/04 | (2006.01) |

(Continued)

(52) U.S. Cl.
CPC .......... *C07D 209/08* (2013.01); *A61K 31/403* (2013.01); *A61K 31/404* (2013.01); *A61K 31/416* (2013.01); *A61K 31/4184* (2013.01); *A61K 31/4192* (2013.01); *A61K 31/437* (2013.01); *A61K 31/47* (2013.01); *A61K 31/472* (2013.01); *A61P 5/26* (2018.01); *A61P 17/10* (2018.01); *A61P 17/14* (2018.01); *A61P 25/00* (2018.01); *A61P 35/00* (2018.01); *C07D 209/42* (2013.01); *C07D 209/86* (2013.01); *C07D 209/88* (2013.01); *C07D 215/06* (2013.01); *C07D 217/04* (2013.01); *C07D 231/56* (2013.01); *C07D 235/06* (2013.01); *C07D 249/18* (2013.01); *C07D 401/12* (2013.01); *C07D 471/04* (2013.01)

(58) Field of Classification Search
CPC .. C07D 209/08; C07D 209/42; C07D 209/86; C07D 209/88; C07D 249/18; C07D 215/06; C07D 217/04; C07D 231/56; C07D 235/06; C07D 401/12; A61P 17/10; A61P 17/14; A61P 25/00; A61P 35/00; A61K 31/403; A61K 31/404; A61K 31/415; A61K 31/4184; A61K 31/4192; A61K 31/437; A61K 31/47; A61K 31/472
See application file for complete search history.

(56) References Cited

U.S. PATENT DOCUMENTS

| 5,480,656 A | 1/1996 | Okada et al. |
| 5,575,987 A | 11/1996 | Kamei et al. |

(Continued)

FOREIGN PATENT DOCUMENTS

| CN | 1597662 A | 3/2005 |
| CN | 102884057 A | 1/2013 |

(Continued)

OTHER PUBLICATIONS

Andersen et al. "Regression of castrate-recurrent prostate cancer by a small-molecule inhibitor of the amino-terminus domain of the androgen receptor" Cancer cell. Jun. 15, 2010;17(6):535-46.

Antonarakis et al. "AR-V7 and resistance is enzalutamide and abiraterone in prostate cancer" New England Journal of Medicine. Sep. 11, 2014;371(11):1028-38.

Attard et al. "Selective inhibition at CYP17 with abiraterone acetate is highly active in the treatment at castration-resistant prostate cancer" Journal of clinical oncology. May 26, 2009;27(23):3742-8.

Baek et al. "Ligand-specific allosteric regulation of coactivator functions of androgen receptor in prostate cancer cells" Proceedings of the National Academy of Sciences of the United States of America. Feb. 28, 2006;103(9):3100-5.

(Continued)

*Primary Examiner* — D Margaret M Seaman

(74) *Attorney, Agent, or Firm* — Knobbe, Martens, Olson & Bear, LLP

(57) ABSTRACT

This invention provides novel indole, indazole, benzimidazole, benzotriazole, indoline, quinolone, isoquinoline, and carbazole selective androgen receptor degrader (SARD) compounds, pharmaceutical compositions and uses thereof in treating hyperproliferations of the prostate including pre-malignancies and benign prostatic hyperplasia, prostate cancer, advanced prostate cancer, castration resistant prostate cancer, other AR-expressing cancers, androgenic alopecia or other hyper androgenic dermal diseases, Kennedy's disease, amyotrophic lateral sclerosis (ALS), abdominal aortic aneurysm (AAA), and uterine fibroids, and to methods for reducing the levels (through degradation) and/or activity (through inhibition) of any androgen receptor including androgen receptor-full length (AR-FL) including pathogenic and/or resistance mutations, AR-splice variants (AR-SV), and pathogenic polyglutamine (polyQ) polymorphisms of AR in a subject.

21 Claims, 83 Drawing Sheets

Related U.S. Application Data continuation-in-part of application No. 15/981,636, filed on May 16, 2018, now Pat. No. 10,441,570, which is a continuation-in-part of application No. 15/331,777, filed on Oct. 21, 2016, now Pat. No. 10,035,763, which is a continuation-in-part of application No. 15/222,734, filed on Jul. 28, 2016, now Pat. No. 10,017,471, which is a continuation-in-part of application No. 15/135,334, filed on Apr. 21, 2016, now Pat. No. 9,814,698.

(60) Provisional application No. 62/150,763, filed on Apr. 21, 2015, provisional application No. 62/220,057, filed on Sep. 17, 2015, provisional application No. 62/220,187, filed on Sep. 17, 2015, provisional application No. 62/219,859, filed on Sep. 17, 2015, provisional application No. 62/241,532, filed on Oct. 14, 2015.

(51) Int. Cl.

| | | |
|---|---|---|
| *C07D 209/88* | (2006.01) | |
| *C07D 209/86* | (2006.01) | |
| *A61P 35/00* | (2006.01) | |
| *A61P 25/00* | (2006.01) | |
| *A61P 17/10* | (2006.01) | |
| *A61P 17/14* | (2006.01) | |
| *C07D 209/42* | (2006.01) | |
| *A61K 31/403* | (2006.01) | |
| *A61K 31/404* | (2006.01) | |
| *A61K 31/416* | (2006.01) | |
| *A61K 31/4184* | (2006.01) | |
| *A61K 31/4192* | (2006.01) | |
| *A61K 31/437* | (2006.01) | |
| *A61K 31/47* | (2006.01) | |
| *A61K 31/472* | (2006.01) | |

(56) References Cited

U.S. PATENT DOCUMENTS

| | | | |
|---|---|---|---|
| 5,631,020 A | 5/1997 | Okada et al. | |
| 5,643,607 A | 7/1997 | Okada et al. | |
| 5,716,640 A | 2/1998 | Kamei et al. | |
| 5,814,342 A | 9/1998 | Okada et al. | |
| 6,036,976 A | 3/2000 | Takechi et al. | |
| 6,472,415 B1 | 10/2002 | Sovak et al. | |
| 7,022,870 B2 | 4/2006 | Dalton et al. | |
| 7,118,552 B2 | 10/2006 | Shaw et al. | |
| 7,186,854 B2 | 3/2007 | Thijs et al. | |
| 7,220,247 B2 | 5/2007 | Shaw et al. | |
| 7,500,964 B2 | 3/2009 | Shaw et al. | |
| 7,741,371 B2 | 6/2010 | Dalton et al. | |
| 8,735,440 B2 | 5/2014 | McKnight et al. | |
| 9,550,742 B2 | 1/2017 | Marugan et al. | |
| 9,814,698 B2* | 11/2017 | Narayanan | A61K 31/403 |
| 9,815,776 B2 | 11/2017 | Narayanan et al. | |
| 9,834,507 B2 | 12/2017 | Narayanan et al. | |
| 10,017,471 B2* | 7/2018 | Narayanan | C07D 215/00 |
| 10,035,763 B2* | 7/2018 | Narayanan | C07D 235/06 |
| 10,093,613 B2 | 10/2018 | Narayanan et al. | |
| 10,314,797 B2* | 6/2019 | Narayanan | A61P 17/14 |
| 10,441,570 B2* | 10/2019 | Narayanan | A61K 31/437 |
| 10,597,354 B2 | 3/2020 | Narayanan et al. | |
| 10,654,809 B2* | 5/2020 | Narayanan | C07D 207/34 |
| 10,806,719 B2* | 10/2020 | Narayanan | C07C 317/46 |
| 10,806,720 B2* | 10/2020 | Narayanan | A61K 31/415 |
| 10,865,184 B2* | 12/2020 | Narayanan | C07D 217/04 |
| 11,230,523 B2* | 1/2022 | Narayanan | C07C 255/60 |
| 11,230,531 B2* | 1/2022 | Narayanan | C07D 249/04 |
| 11,273,147 B2* | 3/2022 | Narayanan | A61K 31/47 |
| 11,591,290 B2 | 2/2023 | Narayanan et al. | |
| 11,648,234 B2 | 5/2023 | Narayanan et al. | |
| 2005/0101657 A1 | 5/2005 | Furuya et al. | |
| 2006/0142387 A1 | 6/2006 | Cadilla et al. | |
| 2006/0160845 A1 | 7/2006 | Schlienger et al. | |
| 2006/0173037 A1 | 8/2006 | Schlienger et al. | |
| 2006/0241180 A1 | 10/2006 | Dalton et al. | |
| 2007/0049629 A1 | 3/2007 | Scanlan et al. | |
| 2007/0123512 A1 | 5/2007 | Ratilainen | |
| 2007/0123563 A1 | 5/2007 | Dalton et al. | |
| 2007/0173546 A1 | 7/2007 | Dalton et al. | |
| 2007/0265290 A1 | 11/2007 | Dalton et al. | |
| 2008/0293766 A1 | 11/2008 | Diamond et al. | |
| 2009/0042844 A1 | 2/2009 | Labrie et al. | |
| 2009/0060873 A1 | 3/2009 | Sporn et al. | |
| 2009/0142323 A1 | 6/2009 | Quarles et al. | |
| 2010/0227846 A1 | 9/2010 | Ito et al. | |
| 2010/0331418 A1 | 12/2010 | Koh et al. | |
| 2011/0028719 A1 | 2/2011 | Slon-Usakiewicz | |
| 2013/0116258 A1 | 5/2013 | Smith et al. | |
| 2013/0253035 A1 | 9/2013 | McDonnell et al. | |
| 2013/0274501 A1 | 10/2013 | Shrawat et al. | |
| 2014/0018433 A1 | 1/2014 | Dalton et al. | |
| 2014/0094474 A1 | 4/2014 | Törmakängas et al. | |
| 2016/0264540 A1 | 9/2016 | Wipf et al. | |
| 2017/0029370 A1 | 2/2017 | Narayanan et al. | |
| 2017/0066712 A1 | 3/2017 | Breslow et al. | |
| 2017/0095446 A1 | 4/2017 | Narayanan et al. | |
| 2017/0166526 A1 | 6/2017 | Narayanan et al. | |
| 2017/0368003 A1 | 12/2017 | Narayanan et al. | |
| 2018/0028521 A1 | 2/2018 | Gottardis et al. | |
| 2018/0271849 A1 | 9/2018 | Ge et al. | |
| 2018/0273487 A1 | 9/2018 | Narayanan et al. | |
| 2018/0360805 A1 | 12/2018 | Narayanan et al. | |
| 2019/0202800 A1 | 7/2019 | Freeman et al. | |
| 2020/0039924 A1* | 2/2020 | Narayanan | C07C 255/60 |
| 2020/0222365 A1* | 7/2020 | Narayanan | A61K 31/47 |
| 2020/0299243 A1* | 9/2020 | Narayanan | C07D 295/15 |
| 2021/0024458 A1 | 1/2021 | Ponnusamy et al. | |
| 2021/0161864 A1 | 6/2021 | Miller et al. | |
| 2021/0196678 A1* | 7/2021 | Narayanan | C07D 213/84 |
| 2021/0340122 A1 | 11/2021 | Narayanan et al. | |
| 2022/0081401 A1 | 3/2022 | Narayanan et al. | |
| 2023/0002326 A1 | 1/2023 | Narayanan et al. | |
| 2023/0041951 A1 | 2/2023 | Narayanan et al. | |
| 2023/0115515 A1 | 4/2023 | Narayanan et al. | |
| 2023/0146829 A1 | 5/2023 | Narayanan et al. | |

FOREIGN PATENT DOCUMENTS

| | | |
|---|---|---|
| CN | 106551934 A | 9/2016 |
| EP | 0253503 | 1/1988 |
| EP | 0524781 A1 | 1/1993 |
| EP | 100172 A1 | 2/2004 |
| EP | 2159049 A1 | 3/2010 |
| JP | 2008526888 A | 7/2008 |
| JP | 2013544768 A | 12/2013 |
| WO | WO 2001/058855 A1 | 8/2001 |
| WO | WO 2002/016310 A1 | 2/2002 |
| WO | WO 2002/046164 A1 | 6/2002 |
| WO | WO 2003/074473 A2 | 9/2003 |
| WO | WO 2003/106401 A1 | 12/2003 |
| WO | WO 2004/035737 A2 | 4/2004 |
| WO | WO 2004/035738 | 4/2004 |
| WO | WO 2005/000794 A1 | 1/2005 |
| WO | WO 2005/094531 | 10/2005 |
| WO | WO 2005/120477 A2 | 12/2005 |
| WO | WO 2006/014420 | 2/2006 |
| WO | WO 2006/044359 A2 | 4/2006 |
| WO | WO 2007/005887 A2 | 1/2007 |
| WO | WO 2007/126988 A2 | 11/2007 |
| WO | WO 2008/011072 A2 | 1/2008 |
| WO | WO 2008/044033 A1 | 4/2008 |
| WO | WO 2008/076918 A2 | 6/2008 |
| WO | WO 2008/124000 A2 | 10/2008 |
| WO | WO 2008/137038 A1 | 11/2008 |
| WO | WO 2009/010480 A1 | 1/2009 |
| WO | WO 2009/069736 A1 | 6/2009 |
| WO | WO 2009/082437 A2 | 7/2009 |
| WO | WO 2012/007644 A1 | 1/2012 |

(56) References Cited

FOREIGN PATENT DOCUMENTS

| WO | WO 2013/064681 | | 5/2013 |
|---|---|---|---|
| WO | WO 2014/113260 | A1 | 7/2014 |
| WO | WO 2015/042297 | A1 | 3/2015 |
| WO | WO 2016/172358 | A1 | 10/2016 |
| WO | WO 2017/041040 | A1 | 3/2017 |
| WO | WO 2017/214634 | A1 | 12/2017 |
| WO | WO 2017/216772 | A2 | 12/2017 |
| WO | WO 2019/222556 | A1 | 11/2019 |

OTHER PUBLICATIONS

Berrevoets et al. "Effects of antiandrogens on transformation and transcription activation of wild-type and mutated (LNCaP) androgen receptors" The Journal of steroid biochemistry and molecular biology. Dec. 31, 1993;46(6):731-6.

Bohl et al. "Structural basis for antagonism and resistance of bicalutamide in prostate cancer" Proceedings of the National Academy of Sciences. Apr. 26, 2005;102(17):6201-6.

Bohl et al. "A ligand-based approach to identify quantitative structure-activity relationships for the androgen receptor" Journal of medicinal chemistry. Jul. 15, 2004;47(15):3765.

Bohl et al. "Structural basis for accommodation of nonsteroidal ligands in the androgen receptor" Journal of Biological Chemistry. Nov. 11, 2005;280(45):37747-54.

Claessens et al. "Diverse roles of androgen receptor (AR) domains in AR-mediated signaling" Nuclear receptor signaling. Jun. 27, 2008;6:e008.

Clegg et al. "ARN-509: a novel antiandrogen for prostate cancer treatment" Cancer research. Mar. 15, 2012;72(6):1494-503.

Danquah et al. "Combination therapy of antiandrogen and XIAP inhibitor for treating advanced prostate cancer" Pharmaceutical research. Aug. 1, 2012;29(8):2079-91.

Database Caplus Chemical Abstracts Serivce; Database Accession No. 2005:14358, Abstract of WO 2005000794, published Jan. 6, 2005.

De Bono et al. "Abiraterone and increased survival in metastatic prostate cancer" New England Journal of Medicine. May 26, 2011;364(21):1995-2005.

Dehm et al. "Alternatively spliced androgen receptor variants" Endocrine-related cancer. Oct. 1, 2011;18(5):R183-96.

Dehm et al. "Splicing of a novel androgen receptor exon generates a constitutively active androgen receptor that mediates prostate cancer therapy resistance" Cancer research. Jul. 1, 2008;68(13):5469-77.

Duke III, Charles B., et al. "Synthesis and biological studies of androgen receptor ligands: Towards mutation-resistant nonsteroidal antagonism." Abstracts of Papers of the American Chemical Society. vol. 240. 1155 16th St, NW, Washsngton, DC 20036 USA: Amer Chemical Soc, 2010.

Extended EP Search Report for corresponding EP Application No. 16 78 3846.5 dated Oct. 23, 2018.

Hu et al. "Distinct transcriptional programs mediated by the ligand-dependent full-length androgen receptor and its splice variants in castration-resistant prostate cancer" Cancer research. Jul. 15, 2012;72(14):3457-62.

Hwang et al. "Arylisothiocyanato selective androgen receptor modulators (SARMs) for prostate cancer" Bioorganic & medicinal chemistry. Oct. 1, 2006;14(19):6525-38.

International Search Report for PCT Application No. PCTUS1628674 dated Sep. 6, 2016.

Jin, et al; "Synthesis and biological evaluation of 1-substituted-3(5)-(6-methylpyridin-2-yl)-4-(quinoxalin-6-yl)pyrazoles as transforming growth factor-β type 1 receptor kinase inhibitors"; European Journal of Medicinal Chemistry 46(2011) 3917-3925.

Kim et al. "Ribosomal proteins as unrevealed caretakers for cellular stress and genomic instability" Oncotarget. Feb. 1, 2014;5(4):860-71.

Klotz L. "Maximal androgen blockade for advanced prostate cancer" Best Practice & Research Clinical Endocrinology & Metabolism. Apr. 30, 2008;22(2):331-40.

Li et al. "Androgen receptor splice variants mediate enzalutamide resistance in castration-resistant prostate cancer cell lines" Cancer research. Jan. 15, 2013;73(2):483-9.

MacLean et al. "Spinal and bulbar muscular atrophy: androgen receptor dysfunction caused by a trinucleotide repeat expansion" Journal of the neurological sciences. Feb. 29, 1996;135(2):149-57.

Marhefka et al. "Homology modeling using multiple molecular dynamics simulations and docking studies of the human androgen receptor ligand binding domain bound to testosterone and nonsteroidal ligands" Journal of medicinal chemistry. May 24, 2001;44(11):1729-40.

Marhefka et al. "Design, synthesis, and biological characterization of metabolically stable selective androgen receptor modulators" Journal of medicinal chemistry. Feb. 12, 2004;47(4):993.

McGinley et al. "Circumventing anti-androgen resistance by molecular design" Journal of the American Chemical Society. Apr. 4, 2007;129(13):3822-3.

Miller Irreversible Nonsteroida SARMs for Prostate Cancer at http://grantome.com/grant/NIH/R01-DK065227-20, 2003.

Mitsiades N. "A road map to comprehensive androgen receptor axis targeting for castration-resistant prostate cancer" Cancer research. Aug. 1, 2013;73(15):4599-605.

Mohler, et al.; "Androgen receptor antagonists: a patent review (2008-2011);" *Expert Opinion Ther. Patents* (2012): 22(5): 541-565.

Monge et al. "Unfaithfulness and promiscuity of a mutant androgen receptor in a hormone-refractory prostate-cancer" Cellular and molecular life sciences. Feb. 1, 2006;63(4):487-97.

Narayanan et al., "Selective Androgen Receptor Modulators (SARMs) Negatively Regulate Triple-Negative Breast Cancer Growth and Epithelial: Mesenchymal Stem Cell Signaling"; PLOS ONE, Jul. 2014, vol. 9, Issue 7, 1-12.

Nazareth et al. "Activation of the human androgen receptor through a protein kinase A signaling pathway" Journal of Biological Chemistry. Aug. 16, 1996;271(33):19900-7.

Nyquist et al. "TALEN-engineered AR gene rearrangements reveal endocrine uncoupling of androgen receptor in prostate cancer" Proceedings of the National Academy of Sciences. Oct. 22, 2013;110(43):17492-7.

Ponnusamy, et al; "Novel Selective Agents for the Degradation of Androgen Receptor Variants to Treat Castration-Resistant Prostate Cancer"; Cancer Research (2017) 77(22): 6282-6298.

Sadar MD. "Androgen-independent induction of prostate-specific antigen gene expression via cross-talk between the androgen receptor and protein kinase A signal transduction pathways" Journal of Biological Chemistry. Mar. 19, 1999;274(12):7777-83.

Sadar et al. "Ligand-independent activation of the androgen receptor by the differentiation agent butyrate in human prostate cancer cells" Cancer research. Oct. 15, 2000:60(20):5825-31.

Sartor et al. "Androgen receptor variant-7: an important predictive biomarker in castrate resistant prostate cancer" Asian journal of andrology. May 2015;17(3):439.

Scher et al. "Increased survival with enzalutamide in prostate cancer after chemotherapy" New England Journal of Medicine. Sep. 27, 2012;367(13):1187-97.

Sieber PR. "Treatment of bicalutamide-induced breast events" Expert review of anticancer therapy. Dec. 1, 2007;7(12):1773-9.

Siegel et al. "Cancer statistics" CA Cancer. J. Clin. 2014;64:9-29.

Supplementary EP Search Report for corresponding EP Application No. 16 78 3866 dated Nov. 7, 2018.

Tran et al. "Development of a second-generation antiandrogen for treatment of advanced prostate cancer" Science. May 8, 2009;324(5928):787-90.

Ueda et al. Ligand-independent activation of the androgen receptor by interleukin-6 and the role of steroid receptor coactivator-1 in prostate cancer cells: Journal of Biological Chemistry. Oct. 11, 2002;277(41):38087-94.

Weiner LP. "Possible role of androgen receptors in amyotrophic lateral sclerosis: a hypothesis" Archives of neurology. Mar. 1, 1980;37(3):129-31.

(56) References Cited

OTHER PUBLICATIONS

Wen et al. "LHRH-conjugated micelles for targeted delivery of antiandrogen to treat advancad prostate cancer" Pharmaceutical research. Oct. 1, 2014;31(10):2784-95.
Xu et al. "hSSB1 binds and protects p21 from ubiquitin-mediated degradation and positively correlates with p21 in human hepatocelluar carcinomas" Oncogene. May 12, 2011;30(19):2219-29.
Yamashita et al. "ASC-J9 suppresses castration-resistant prostate cancer growth through degradation of full-length and splice variant androgen receptors" Neoplasia. Jan. 1, 2012;14(1):74IN9-83IN12.
Yoshida et al. "Antiandrogen bicalutamide promotes tumor growth in a novel androgen-dependent prostate cancer xenograft model derived from a bicalutamide-treated patient" Cancer Research. Nov. 1, 2005;65(21):9611-6.
Zhou et al. "Study of the impact of the T877A mutation on ligand-induced helix-12 positioning of the androgen receptor resulted in design and synthesis of novel antiandrogens" Proteins: Structure, Function, and Bioinformatics. Feb. 15, 2010;78(3):623-37.
International Preliminary Report on Patentability for PCT Application No. PCT/US2019/049618 dated Mar. 18, 2021.
Aggarwal et al., "Androgens affect muscle, motor neuron, and survival in a mouse model of SOD1-related amyotrophic lateral sclerosis," Neurobiol Aging, 2014, 35: 1929-1938.
Antonarakis et al., Clinical significance of androgen receptor splice variant-y mRNA detection in circulating tumor cells of men with metastatic castration-resistant prostate cancer treated with first- and second-line abiraterone and enzalutamide. J Clin Oncol., Jul. 1, 2017;35(19): 2149-2156.
Aradi et al., "DFTB+, a sparse matrix-based implementation of the DFTB method", J Phys Chem. A. Jul. 5, 2007;111(26): 5678-5684.
Arora et al., "Glucocorticoid receptor confers resistance to antiandrogens by bypassing androgen receptor blockage", Cell. Dec. 5, 2013;155(6): 1309-1322.
Baniahmad A., "Inhibition of the androgen receptor by antiandrogens in spinobulbar muscle atrophy", J Mol Neurosci. Mar. 2016;58(3): 343-347.
Bassetto et al., "Design and synthesis of novel bicalutamide and enzalutamide derivatives as antiproliferative agents for the treatment of prostate cancer", Eur J Med Chem. Aug. 8, 2016;118: 230-243.
Bratenko et al., "Polyfunctional pyrazoles. 3. Synthesis of 3-(3-aryl-4-formyl-1-pyrazolyl) propionic acids and their amides", Chem Heter Compounds. Oct. 2004;40(10): 1279-1282.
Bryce et al., "Androgen receptor splice variant 7 in castration-resistant prostate cancer: Clinical considerations", Int J Urology. Aug. 2016;23(8): 646-653.
CAS Registry No. 55734-18-4; STN Entry Date: Nov. 16, 1984.
CAS Registry No. 945553-38-8; STN Entry Date: Aug. 24, 2007.
CAS Registry No. 1349723-51-8; STN Entry Date: Dec. 6, 2011.
CAS Registry No. 1480139-15-8; STN Entry Date: Nov. 24, 2013.
CAS Registry No. 1526624-00-9; STN Entry Date: Jan. 21, 2014.
CAS Registry No. 1839720-91-0; STN Entry Date: Jan. 1, 2016.
CAS Registry No. 1919463-97-0; STN Entry Date: May 27, 2016.
CAS Registry No. 1928217-46-2; STN Entry Date: Nov. 16, 2016.
Choi et al., "Collision tumor of hepatocellular carcinoma and neuroendocrine carcinoma involving the liver: case report and review of the literature", World J Gastroenterol. Nov. 7, 2016;22(41): 9229-9234.
ClinicalTrials.gov; "Enzalutamide in patients with androgen receptor positive (AR+) ovarian, primary peritoneal or fallopian tube cancer and one, two or three prior therapies", Study Sponsor: Memorial Sloan Kettering Cancer Center/Medivation, Inc., last update: Jun. 2017 in 6 pages.
Cochrane et al., "Role of the androgen receptor in breast cancer and preclinical analysis of enzalutamide", Breast Cancer Res. Feb. 2014;16(1): 1-9.
Colin et al., "New Access to fluorinated ketoglycolic acid derivatives from trifluoropyruvamides", Tetrahe Letts. Jul. 12, 2004;45(29): 5611-5613.

Dalvit et al., "Identification of compounds with binding affinity to proteins via magnetization transfer from bulk water", J Biomolecular NMR. Sep. 2000;18(1): 65-68.
Davis et al., "Pharmacologic blockade and genetic deletion of androgen receptor attenuates aortic aneurysm formation", J Vasc Surgery. Jun. 1, 2016;63(6): 1602-1612.
Dias et al., "NMR approaches in structure-based lead discovery: recent develpments and new frontiers for targeting multi-protein complexes", Prog Biophys Mol Biol. Nov. 1, 2014;116(2-3): 101-112.
Elstner et al., "Self-consistent-charge density-functional tight-binding method for simulations of complex materials properties", Phys Rev B. Sep. 15, 1998;58(11): 7260-7268.
Epps et al., "Determination of the affinity of drugs toward serum albumin by measurement of the quenching of the intrinsic tryptophan fluorescence of the protein", J Pharm Pharmacol. Jan. 1999;51(1): 41-48.
Gal et al., "Efficient isothermal titration calorimetry technique identifies direct interation of small molecule inhibitors with the target protein", Combin Chem High Throughput Screen. Jan. 1, 2016;19(1): 4-13.
Galbiati et al., "The anabolic/androgenic steroid nandrolone exacerbates gene expression modifications induced by mutant SOD1 in muscles of mice models of amyotrophic lateral sclerosis", Pharma Res. Feb. 1, 2012;65(2): 221-230.
Gibson et al., "Evidence of androgen action in endometrial and ovarian cancers", Endocrine-related cancer. Aug. 1, 2014;21(4): T203-T218.
Gottlieb et al., "Androgen insensitivity syndrome", University of Washington, Seattle (WA) Publication, initial Posting: Mar. 24, 1999; last Update: May 11, 2017, in 15 pages.
Hara et al., "Novel mutations of androgen receptor: a possible mechanism of bicalutamide withdrawal syndrome", Cancer Res. Jan. 1, 2003;63(1): 149-153.
He et al., "ASC-J9 suppresses renal cell carcinoma progression by targeting an androgen receptor-dependent HIF2α/VEGF Signaling Pathway", Cancer Res. Aug. 2014;74(16): 4420-4430.
Hebenbrock K-F., "Preparation and reaction of 1-aryl-3-hydroxy-3-methyl-2,5-pyrrolidinediones", Justus Liebig's Annals of Chemistry, Aug. 1, 1978;vol. 2, pp. 320-336 (Abstract).
Hsieh et al., "Androgen receptor trinucleotide polymorphism in leiomyoma", J Ass Repro Genetics. Dec. 2004;21(12): 453-457.
Isikbay et al., "Glucocorticoid receptor activity contributes to resistance to androgen-targeted therapy in prostate cancer", Horm Cancer. Apr. 2014;5(2): 72-89.
Jin et al., "Synthesis and biological evaluation of 1-substituted-3(5)-(6-methylpyridin-2-yl)-4-(quinolin-6-yl)pyrazoles as transforming growth factor-β type 1 receptor kinase inhibitors", Bioorg Med Chem. 2011;19: 2633-2640.
Joseph et al., "A clinically relevant androgen receptor mutation confers resistance to second-generation antiandrogens enzalutamide and ARM-509", Cancer Discov. Sep. 1, 2013;3(9): 1020-1029.
Kamal et al., "Androgen receptors are acquired by healthy postmenopausal endometrial epithelium and their subsequent loss in endometrial cancer is associated with poor survival", Br J Cancer. Mar. 2016;114(6): 688-696.
Kanda et al., "Androgen receptor signaling in hepatocellular carcinoma and pancreatic cancers", World J Gastroenter.: WJG. Jul. 28, 2014;20(28): 9229-9236.
Kawahara et al., "ELK1 is up-regulated by androgen in bladder cancer cells and promotes tumor progression", Oncotarget. Oct. 6, 2015;6(30): 29860=29876.
Kominea et al., "Androgen receptor (AR) expression is an independent unfavorable prognostic factor in gastric cancer", J Cancer Res Clin Oncol. May 2004;130(5): 253-258.
Lallous et al., "Functional analysis of androgen receptor mutations that confer anti-androgen resistance identified in circulating cell-free DNA from prostate cancer patients", Gen Biol. Dec. 2016;17(1): 1-5.
La Spada et al., "Androgen receptor gene mutations in X-linked spinal and bulbar muscular atrophy", Nature. Jul. 1991;352(6330): 77-79.

(56) References Cited

OTHER PUBLICATIONS

Lazar et al., "Hyperandrogenism as a cause of early polycystic ovary syndrome (PCOS) in girls with central precocious puberty (CPP)", Pediatric Research. May 1993;33(5): S14; Abstract 64.
Li et al., "On the physical origin of blue-shifted hydrogen bonds", J Am Chem Soc. Aug. 14, 2002;124(32): 9639-9647.
Lieberman et al., "Peripheral androgen receptor gene suppression rescues disease in mouse models of spinal and bulbar muscular atrophy", Cell Reports. May 8, 2014;7(3): 774-784.
Lieberman et al., [Eds.] Pharmaceutical Dosage Forms: Tablets; Marcel Dekker, 1989, TOC in 11 pages.
Locati et al., "Clinical activity of androgen deprivation therapy in patients with metastatic/relapsed androgen receptor-positive salivary gland cancers", Head Neck. May 2016;38(5): 724-731.
Mayo Clinic, "Uterine Fibroids—Overview", Mayo Clinic Staff; printed Aug. 7, 2017; 2 pages.
McBeth et al., "Involvement of the androgen and glucocorticoid receptors in bladder cancer", Int J Endocrin. Aug. 10, 2015;2015:Art. ID384860 in 10 pages.
Mikkonen et al., "Androgen receptor and androgen-dependent gene expression in lung", Mol Cell Endocrinol. Apr. 12, 2010;317(1-2): 14-24.
Miller et al., "Phase III, randomized, placebo-controlled study of once-daily oral zibotentan (ZD4054) in patients with non-metastatic castration-resistant prostate cancer", Prost Canc Prost Dis. Jun. 2013;16(2): 187-192.
Mohler et al., "Nonsteroidal selective androgen receptor modulators (SARMs): Dissociating the anabolic and androgenic activities of the androgen receptor for therapeutic benefit", J Med Chem., Jun. 2009;52(12): 3597-3617.
Morris et al., "Non-steroidal antiandrogens. Design of novel compounds based on an infrared study of the dominant conformation and hydrogen-bonding properties of a series of anilide antiandrogens", J Med Chem. Jan. 1991;34(1): 447-455.
Morvillo et al., "Androgen receptors in human melonoma cell lines IIB-MEL-LES and IIB-MEL-IAN and in human melanoma metastases", Melanomoa Res. Dec. 2002;12(6): 529-538 [Abstract].
Mostaghel et al., "Androgen receptor expression in mantle cell lymphoma: Potential novel therapeutic implications", Exp Hematol. May 2017;49: 34-38.e2.
Munoz et al., "Androgen receptors beyond prostate cancer: An old marker as a new target", Oncotarget. Jan. 2015;6(2): 592-603.
Nagata et al., "Preparation and reactions of cyclic α-monocarbonyl azo-compounds: 1-pyrazolin-3-one derivatives", J Chem Soc. C: Organic. 1970(4): 540-550.
Narayanan et al., "Biological synthesis of metal nanoparticles by microbes", Adv Colloid Interface Science. Apr. 22, 2010;156(1-2): 1-3.
Park et al., "Expression of DBC1 and androgen receptor predict poor prognosis in diffuse large B cell lymphoma", Transl Oncol. Jun. 1, 2013;6(3): 370-381.
Pubchem, CID 3145286.09, Aug. 9, 2005, pp. 1-12; retrieved from the Internet <URL: https:llpubchem.ncbl.nlm.nih.gov/compound/3145286> in 12 pages.
Pubmed, CID 20221988, "Compound Summary for CID 20221988-C12H13N30"; Dec. 5, 2007, pp. 1-11; retrieved from the Internet <URL: https://pubchem.ncbi.nlm.nih.gov/compound/20221988>.
Rawel et al., "Determining the binding affinities of phenolic compounds to proteins by quenching of the intrinsic tryptophan fluorescence", Mol Nutri Food Res. Aug. 2006;50(8): 705-713.
Gennaro A.R. [Ed.], "Remington's pharmaceutical sciences", Mack Publishing Company, 18th Edition; 1990, TOC in 6 pages.
Rowe R.C. [Ed.], "Handbook of Pharmaceutical Excipients", American Pharmaceutical Association; Fifth Edition, 2006, TOC in 6 pages.
Renier et al., "Antiandrogen flutamide protects male mice from androgen-dependent toxicity in three models of spinal bulbar muscular atrophy," Neuroendocrinol. Jul. 1, 2014; 155(7): 2624-2634.

Rosa et al., "Polymorphisms of CYP17A1, CYP19, and androgen in Brazilian women with uterine leiomyomas", Clin Chem Lab Med. Jun. 1, 2008;46(6): 814-823.
Rygula et al., "Raman spectroscopy of proteins: a review", J Raman Spectrosc. Aug. 2013;44(8): 1061-1076.
Schragl et al., "Novel pathway for the synthesis of arylpropionamide-derived selective androgen receptor modulator (SARM) metabolites of andarine and ostarine", Tetra Lettrs. May 1, 2013;54(18): 2239-2242.
Seligson et al., "Development of Fluridil, a topical suppressor of the androgen receptor in androgenetic alopecia", Drug Devel Res. Jul. 2003;59(3): 292-306.
Shortridge et al., "Estimating protein-ligand binding affinity using high-throughput screening by NMR", J Comb Chem. Nov. 10, 2008;10(6): 948-958.
Simanainen et al., "Androgen receptor actions modify skin structure and chemical carcinogen-induced skin cancer susceptibility in mice", Hormones and Cancer. Feb. 2015;6(1): 45-53.
Soper et al., "Definitive treatment of androgen receptor-positive salivary duct carcinoma with androgen deprivation therapy and external beam radiotherapy", Head Neck. Jan. 2014;36(1): E4-E7.
Sukocheva et al., "Androgens and esophageal cancer: What do we know?" World J Gastroenterol. May 28, 2015;21(20): 6146-6156.
Sun et al., Castration resistance in human prostate cancer is conferred by a frequently occurring androgen receptor splice variant, J Clin Invest. Aug. 2, 2010;120(8): 2715-2730.
Tan et al., "Dehydroepiandrosterone activates mutant androgen receptors expressed in the androgen-dependent human prostate cancer xenograft CWR22 and LNCaP cells", Mol Endocrin. Apr. 1, 1997;11(4): 450-459.
Tangen et al., "Androgen receptor as potential therapeutic target in metastatic endometrial cancer", Oncotarget. Aug. 2, 2016;7(31): 49289-49298.
Tarikogullari et al., "Synthesis and anticonvulsant activity of some alkanamide derivatives", Arzneimittelforschung. Oct. 2010;60(10): 593-598 (Abstract).
Tucker et al., "Nonsteroidal antiandrogens. Synthesis and structure-activity relationships of 3-substituted derivatives of 2-hydroxypropionanilides", J Med Chem. May 1988;31(5): 954-959.
Tutton et al., "The influence of androgens, anti-androgens, and castration on cell proliferation in the jejunal and colonic crypt epithelia, and in dimehylhydrazine-induced adenocarcinoma of rat colon", Virchows Arch B Cell Pathol Incl Mol Pathol. 1982;38(3): 351-356 [Abstract].
Wang et al., "Small molecule inhibition of the steroid receptor coactivators, SRC-3 and SRC-1", Mol Endocrin. Dec. 1, 2011;25(12): 2041-2053.
Wang et al., "Effects of hydrogen bond and solvent polarity on the C=O stretching of bis (2-thienyl)ketone in solution", J Chem Physics. Mar. 28, 2012;136(12): 03B614.
Watson et al., "Constitutively active androgen receptor splice variants expressed in castration-resistant prostate cancer require full-length androgen receptor", PNAS. Sep. 28, 2010;107(39): 16759-16765.
Wen et al., "Targeting fatty acid synthase with ASC-J9 suppresses proliferation and invasion of prostate cancer cells", Mol Carcino. Dec. 2016;55(12): 2278-2290.
West A.R., "Solid state chemistry and its applications", John Wiley & Sons; 1988; Chapter 10; pp. 358, 365.
Wikipedia, "Hyperandrogenism", downloaded Aug. 7, 2017 in 8 pages.
Wong et al., "Circulating sex hormones and risk of uterine fibroids: Study of women's health across the nation (SWAN)," J Clin Endocrinol. Jan. 1, 2016;101(1): 123-130.
Yepuru et al., "Steroidogenic enzyme AKR1C3 is a novel androgen receptor-selective coactivator that promotes prostate cancer growth", Clin Cancer Res. Oct. 15, 2013;19(20): 5613-5625.
Yu et al., "Androgen receptor signaling regulates growth of glioblastoma multiforme in men", Tumour Biol. Feb. 2015;36(2): 967-972 [Abstract].
Dellis et al. "Apalutamide: the established and emerging roles in the treatment of advanced prostate cancer". Exp Opin Invest Drugs. Jun. 3, 2018;27(6): 553-559.

(56) References Cited

OTHER PUBLICATIONS

Egan et al., "Mirfentanil and A-4334: Tritiation at High Specific Activity". Appl Rad Isotopes. Jan. 1, 2010,68(1): 120-121.

Hwang et al., "New Generation of Selective Androgen Receptor Degraders: Our Initial Design, Synthesis, and Biological Evaluation of New Compounds with Enzalutamide-resistant Prostate Cancer Activity", J Med Chem. Dec. 7, 2018;62(2): 491-511.

Ponnusamy et al., "Orally Bioavailable Androgen Receptor Degrader, Potential Next-Generation Therapeutic for Enzalutamide-Resistant Prostate CancerA Novel AR Degrader for the Treatment of Prostate Cancer". Clin Cancer Res. Nov. 15, 2019;25(22): 6764-6780. (pub. online Sep. 3, 2019 in 53 pages).

Pubmed, CID 62853043, "3-(Ethylamino)-2-methyl-N-phenylpropanamide"; Oct. 22, 2012, pp. 1-8; retrieved from the Internet <URL: https://pubchem.ncbi.nlm.nih.gov/compound/62853043>.; 10 pages.

Pubmed, CID 79195973, "2-Mehtyl-3-(methylamino)-N-phenylpropanamide"; Oct. 19, 2014, pp. 1-8; retrieved from the Internet <URL: https://pubchem.ncbi.nlm.nih.gov/compound/79195973>.; 10 pages.

Webb et al., "Photoaffinity Labeling and Mass Spectrometry Identify Ribosomal Protein S3 as a Potential Target for Hybrid Polar Cytodifferentiation Agents". J Biol Chem. May 14, 1999;274(20): 14280-14287.

\* cited by examiner

All these data were generated in LNCaP cells

All these data were generated in 22RV-1 cells

All experiments in this figure were done in LNCaP cells.

This experiment was done in 22RV-1 cells.

All experiments in this figure were done in LNCaP cells.

LNCaP

LNCaP

LNCaP

22RV1

SELECTIVE ANDROGEN RECEPTOR DEGRADER (SARD) LIGANDS AND METHODS OF USE THEREOF

CROSS REFERENCE TO RELATED APPLICATIONS

This application is a continuation application of U.S. application Ser. No. 16/122,862, filed on Sep. 5, 2018, which is a continuation-in-part application of U.S. application Ser. No. 15/981,636, filed on May 16, 2018, now U.S. Pat. No. 10,441,570, which is a continuation-in-part application of U.S. application Ser. No. 15/331,777, filed on Oct. 21, 2016, now U.S. Pat. No. 10,035,763, which is a continuation-in-part application of U.S. application Ser. No. 15/222,734, filed on Jul. 28, 2016, now U.S. Pat. No. 10,017,471, which is a continuation-in-part application of U.S. application Ser. No. 15/135,334, filed on Apr. 21, 2016, now U.S. Pat. No. 9,814,698, which claims the benefit of U.S. Provisional Application Ser. No. 62/150,763, filed on Apr. 21, 2015, U.S. Provisional Application Ser. No. 62/220,057, filed on Sep. 17, 2015, U.S. Provisional Application Ser. No. 62/241,532, filed on Oct. 14, 2015, U.S. Provisional Application Ser. No. 62/220,187, filed on Sep. 17, 2015, and U.S. Provisional Application Ser. No. 62/219,859, filed on Sep. 17, 2015, all of which are incorporated in their entirety herein by reference.

FIELD OF THE INVENTION

This invention is directed to novel indole, indazole, benzimidazole, benzotriazole, indoline, quinolone, isoquinoline, and carbazole selective androgen receptor degrader (SARD) compounds including A-ring heterocyles, pharmaceutical compositions and uses thereof in treating hyperproliferations of the prostate including pre-malignancies and benign prostatic hypertrophy, prostate cancer, advanced prostate cancer, castration resistant prostate cancer, other AR-expressing cancers, androgenic alopecia or other hyper androgenic dermal diseases, Kennedy's disease, amyotrophic lateral sclerosis (ALS), abdominal aortic aneurysm (AAA), and uterine fibroids, and to methods for reducing the levels (through degradation) and/or activity (through inhibition) of any androgen receptor including androgen receptor-full length (AR-FL) including pathogenic and/or resistance mutations, AR-splice variants (AR-SV), and pathogenic polyglutamine (polyQ) polymorphisms of AR in a subject.

BACKGROUND OF THE INVENTION

Prostate cancer (PCa) is one of the most frequently diagnosed noncutaneous cancers among men in the US and is the second most common cause of cancer deaths with more than 200,000 new cases and over 30,000 deaths each year in the United States. PCa therapeutics market is growing at an annual rate of 15-20% globally.

Androgen-deprivation therapy (ADT) is the standard of treatment for advanced PCa. Patients with advanced prostate cancer undergo ADT, either by luteinizing hormone releasing hormone (LHRH) agonists, LHRH antagonists or by bilateral orchidectomy. Despite initial response to ADT, disease progression is inevitable and the cancer emerges as castration-resistant prostate cancer (CRPC). Up to 30% of patients with prostate cancer that undergo primary treatment by radiation or surgery will develop metastatic disease within 10 years of the primary treatment. Approximately 50,000 patients a year will develop metastatic disease, which is termed metastatic CRPC (mCRPC).

Patients with CRPC have a median survival of 12-18 months. Though castration-resistant, CRPC is still dependent on the androgen receptor (AR) signaling axis for continued growth. The primary reason for CRPC re-emergence is re-activation of AR by alternate mechanisms such as 1) intracrine androgen synthesis, 2) AR splice variants (AR-SV), e.g., that lack ligand binding domain (LBD), 3) AR-LBD mutations with potential to resist AR antagonists (i.e., mutants that are not sensitive to inhibition by AR antagonists, and in some cases AR antagonists act as agonists of the AR bearing these LBD mutations); and 4) amplications of the AR gene within the tumor.

A critical barrier to progress in treating CRPC is that AR signaling inhibitors such as enzalutamide, flutamide, bicalutamide, and abiraterone, acting through the LBD, fail to inhibit growth driven by the N-terminal domain (NTD)-dependent constitutively active AR-SV. Recent high-impact clinical trials with enzalutamide and abiraterone in CRPC patients demonstrated that 0% of AR-V7 (the predominant AR-SV) expressing patients responded to either of the treatments, indicating the requirement for next generation AR antagonists that target AR-SVs. In addition, a significant number of CRPC patients are becoming refractory to abiraterone or enzalutamide, emphasizing the need for next generation AR antagonists.

Current evidences demonstrate that CRPC growth is dependent on constitutively active AR including AR-SV's that lack the LBD such as AR-V7 and therefore cannot be inhibited by conventional antagonists. AR inhibition and degradation through binding to a domain that is distinct from the AR LBD provides alternate strategies to manage CRPC.

Herein the NTD is biophysically characterized to interact with the SARDs of this invention via fluorescence polarization (FP), surface plasmon resonance (SPR), and NMR (Example 12). Biochemical evidence also supports the SARDs of this invention binding to a domain other than the LBD. E.g., SARDs of this invention degrade AR-SV in D567es cells lacking the expression of any AR containing the LBD (Example 7). Further, the R- and S-isomers of the SARDs of this invention possess equipotent SARD activity despite demonstrated differences in the binding and inhibition of androgen-dependent transactivation via the LBD (Example 7, FIG. 42D). The report of SARD activity mediated through the NTD of AR is an unprecedented observation that may help explanation the prodigious AR antagonism profiles seen with the SARDs of this invention.

Molecules that degrade the AR prevent any inadvertent AR activation through growth factors or signaling pathways, or promiscuous ligand-dependent AR activation. In addition, molecules that inhibit the constitutive activation of AR-SVs are extremely important to provide extended benefit to CRPC patients.

Currently only a few chemotypes are known to degrade AR which include the SARDs AZD-3514, ARN-509 and ASC-J9. However, these molecules degrade AR indirectly at much higher concentrations than their binding coefficient and they fail to degrade the AR-SVs that have become in recent years the primary reason for resurgence of treatment-resistant CRPC.

This invention describes novel AR antagonists with unique pharmacology that strongly (high potency and efficacy) and selectively bind AR (better than known antagonists), antagonize AR, and degrade AR full length (AR-FL) and AR-SV. Selective androgen receptor degrader (SARD) compounds possess dual degradation and AR-SV inhibitory functions and hence are distinct from any available CRPC therapeutics. These novel selective androgen receptor degrader (SARD) compounds inhibit the growth of PCa cells and tumors that are dependent on AR-FL and AR-SV for proliferation.

SARDs have the potential to evolve as new therapeutics to treat CRPCs that are untreatable with any other antagonists. This unique property of degrading AR-SV has extremely important health consequences for prostate cancer. Till date only one synthetic molecule (EPI-001) and some marine natural products such as sinkotamides and glycerol ether Napthetenone B, are reported to bind to AR-NTD and inhibit AR function and PCa cell growth, albeit at lower affinity and it has an inability to degrade the receptor. The SARDs of this invention also bind AR-NTD and inhibit NTD-driven (e.g., ligand independent) AR activity.

The positive correlation between AR and PCa and the lack of a fail-safe AR antagonist, emphasizes the need for molecules that inhibit AR function through novel or alternate mechanisms and/or binding sites, and that can elicit antagonistic activities within an altered cellular environment.

Although traditional antiandrogens such as enzalutamide, bicalutamide and flutamide and androgen deprivation therapies (ADT) were approved for use in prostate cancer, there is significant evidence that antiandrogens could also be used in a variety of other hormonal dependent and hormone independent cancers. For example, antiandrogens have been tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (World J. Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876; Int J. Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Many hormonal and non-hormonal cancers may benefit from SARD treatment such as breast cancer, testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer.

Traditional antiandrogens such as bicalutamide and flutamide were approved for use in prostate cancer. Subsequent studies have demonstrated the utility of antiandrogens (e.g., flutamide, spironolactone, cyproterone acetate, finasteride and chlormadinone acetate) in androgen-dependent dermatological conditions such as androgenic alopecia (male pattern baldness), acne vulgaris, and hirsutism. Prepubertal castration prevents sebum production and androgenic alopecia but this can be reversed by use of testosterone, suggesting its androgen-dependence.

The AR gene has a polymorphism of glutamine repeats (polyQ) within exon 1 which when shortened may augment AR transactivation (i.e., hyperandrogenism). It has been found that shortened polyQ polymorphisms are more common in people with alopecia, hirsutism, and acne. Classic antiandrogens are undesirable for these purposes because they are ineffective through dermal dosing and their long-term systemic use raises the risks of untoward sexual effects such as gynecomastia and impotence. Further, similar to CRPC discussed above, inhibition of ligand-dependent AR activity alone may not be sufficient as AR can be activated by various cellular factors other than the endogeneous androgens testosterone (T) and dihydrotestosterone (DHT), such as growth factors, kinases, co-activator overexpression and/or promiscuous activation by other hormones (e.g., estrogens or glucocorticoids). Consequently, blocking the binding of T and DHT to AR with a classical antiandrogen may not be sufficient to have the desired efficacy.

An emerging concept is the topical application of a SARD to destroy the AR local to the affected areas of the skin or other tissue(s) without exerting any systemic antiandrogenism. For this use, a SARD that does not penetrate the skin or is rapidly metabolized would be preferable.

Supporting this approach is the observation that cutaneous wound healing has been demonstrated to be suppressed by androgens. Castration of mice accelerates cutaneous wound healing while attenuating the inflammation in the wounds. The negative correlation between androgen levels and cutaneous healing and inflammation, in part, explains another mechanism by which high levels of endogenous androgens exacerbate hyperandrogenic dermatological conditions such those described herein. Further, it provides a rationale for the treatment of wounds such as diabetic ulcers or even trauma, or skin disorders with an inflammatory component such as acne or psoriasis, with a topical SARD.

Androgenic alopecia occurs in ~50% of Caucasian males by midlife and up to 90% by 80 years old. Minoxidil (a topical vasodilator) and finasteride (a systemic 5-alpha reductase type II inhibitor) are FDA approved for alopecia but require 4-12 months of treatment to produce a therapeutic effect and only arrest hair loss in most with mild to moderate hair regrowth in 30-60%. Since currently available treatments have slow and limited efficacy that vary widely between individuals, and produce unwanted sexual side effects, it is important to find a novel approach to treat androgenic alopecia and other hyperandrogenic dermatologic diseases.

Amyotrophic lateral sclerosis (ALS) is a fatal neurodegenerative disease. Patients with ALS are characterized by extended AR polyglutamine repeats. Riluzole is an available drug for ALS treatment, however, only provides short-term effects. There is an urgent need for drugs that extend the survival of ALS patients. Transgenic animals of ALS were shown to survive longer upon castration and reduction in AR levels compared to castration+nandrolone (agonist) supplementation. Castration reduces the AR level, which may be the reason for extended survival.

Uterine fibroids are common reproductive-age benign tumors that contribute to severe morbidity and infertility. Cumulative incidence is 4 times higher in African-Americans compared to Caucasians and constitutes a major health disparity challenge. Fibroids are the leading indication for hysterectomy and their management averages $21 billion annually in the US. No long term minimally invasive therapies exist. Thus, promising drug therapies, with novel chemistry and pharmacological approaches are needed to improve clinical efficacy. Androgens promote uterine proliferation. Higher testosterone levels increase the risk of uterine fibroids. Treatment of uterine fibroids with SARDs would help prevent or treat uterine fibroids.

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it's necessary. Emergency surgery for a ruptured abdominal aortic aneurysm can be risky. AR blockade (pharmacologic or genetic) reduces AAA. Davis et al. (Davis J P, Salmon M, Pope N H, Lu G, Su G, Meher A, Ailawadi G, Upchurch G R Jr. J Vasc Surg (2016) 63(6): 1602-1612) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR −/− mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

X-linked spinal-bulbar muscular atrophy (SBMA—also known as Kennedy's disease) is a muscular atrophy that arises from a defect in the androgen receptor gene on the X chromosome. Proximal limb and bulbar muscle weakness results in physical limitations including dependence on a wheelchair in some cases. The mutation results in a protracted polyglutamine tract added to the N-terminal domain of the androgen receptor (polyQ AR). Binding and activation of this lengthened polyQ AR by endogenous androgens (testosterone and DHT) results in unfolding and nuclear translocation of the mutant androgen receptor. These steps are required for pathogenesis and result in partial loss of the transactivation function (i.e., an androgen insensitivity) and a poorly understood neuromuscular degeneration. Currently there are no disease-modifying treatments but rather only symptom directed treatments. Efforts to target the polyQ AR of Kennedy's disease as the proximal mediator of toxicity by harnessing cellular machinery to promote its degradation, i.e., through the use of a SARD, hold promise for therapeutic intervention. Selective androgen receptor degraders such as those reported herein bind to and degrade a variety of androgen receptors (full length, splice variant, antiandrogen resistance mutants, and are likely to degrade polyQ AR polymorphisms as well), indicating that they are promising leads for treatment of SBMA.

Here we describe indole, indazole, benzimidazole, benzotriazole, indoline, quinolone, isoquinoline, and carbazole SARDs that bind to LBD and an alternate binding and degradation domain (BDD; located outside the LBD in the NTD), antagonize AR, and degrade AR thereby blocking ligand-dependent and ligand-independent AR activities. This novel mechanism produces improved efficacy when dosed systemically (e.g., for prostate cancer) or topically (e.g., for dermatological diseases).

SUMMARY OF THE INVENTION

One embodiment of the invention encompasses a selective androgen receptor degrader (SARD) compound, or its isomer, pharmaceutically acceptable salt, pharmaceutical product, polymorph, hydrate or any combination thereof, wherein said SARD compound is represented by the structure of formula XVII:

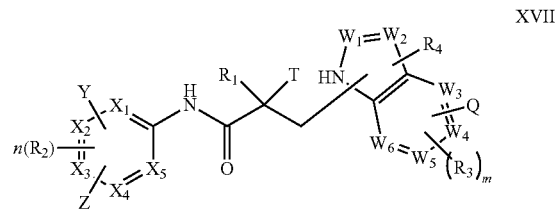

XVII wherein
$X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted; wherein at least one of $X_1$, $X_2$, $X_3$, $X_4$, or $X_5$ is nitrogen;
$W_1$ and $W_2$ are each independently selected from N or CH;
$W_3$, $W_4$, $W_5$ and $W_6$ are each independently selected from CH or N;
wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;
T is OH, OR, —NHCOCH$_3$, NHCOR or

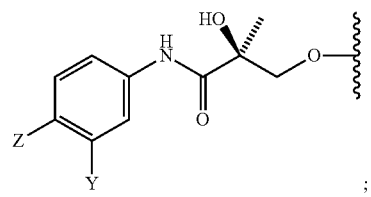

;

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
$R_1$ is CH$_3$, CH$_2$F, CHF$_2$, CF$_3$, CH$_2$CH$_3$, or CF$_2$CF$_3$;
$R_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, keto, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3; or its isomer, pharmaceutically acceptable salt, pharmaceutical product, polymorph, hydrate or any combination thereof.

In another embodiment, the compound of formula XVII is represented by the structure formula XVII(1):

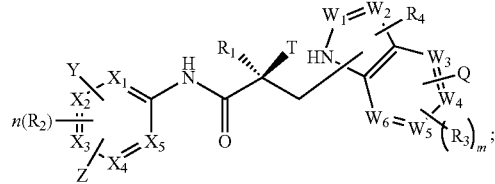

XVII(1)

wherein X$_1$, X$_2$, X$_3$, X$_4$, X$_5$, W$_1$, W$_2$, W$_3$, W$_4$, W$_5$, W$_6$, T, Q, Y, Z, R$_1$, R$_2$, R$_3$, R$_4$, n and m are as defined for structure XVII.

In another embodiment, the compound of formula XVII is represented by the structure formula XVII(2):

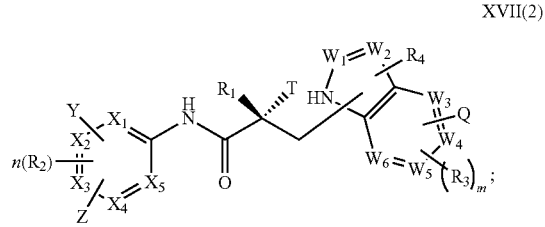

XVII(2)

wherein X$_1$, X$_2$, X$_3$, X$_4$, X$_5$, W$_1$, W$_2$, W$_3$, W$_4$, W$_5$, W$_6$, T, Q, Y, Z, R$_1$, R$_2$, R$_3$, R$_4$, n and m are as defined for structure XVII.

In another embodiment, W$_1$, W$_2$, W$_3$, W$_4$, W$_5$, and W$_6$ are CH. In another embodiment, W$_2$ is N and W$_1$, W$_3$, W$_4$, W$_5$, and W$_6$ are CH. In another embodiment W$_3$ is N and W$_1$, W$_2$, W$_4$, W$_5$, and W$_6$ are CH. In another embodiment, W$_1$ is N and W$_2$, W$_3$, W$_4$, W$_5$, W$_6$ are CH. In one embodiment, only one of X$_1$, X$_2$, X$_3$, X$_4$, and X$_5$ is N. In another embodiment X$_1$ or X$_5$ is N. In another embodiment, X$_2$ or X$_4$ is N. In another embodiment, X$_3$ is N. In another embodiment X$_4$ is N and X$_1$, X$_2$, X$_3$, and X$_5$ are CH. In another embodiment, Q is H, NO$_2$, COR, alkyl, alkoxy, aryl, CN, CF$_3$, F, Cl, Br or I. In another embodiment, Z is CN. In another embodiment, Y is Cl or CF$_3$.

In another embodiment, the compound is represented by the structure of formula XIX:

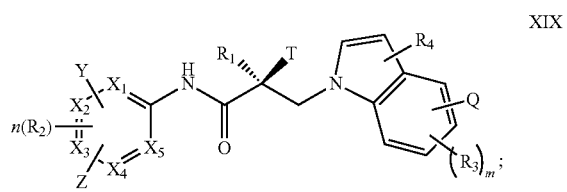

XIX wherein X$_1$, X$_2$, X$_3$, X$_4$, X$_5$, T, Q, Y, Z, R$_1$, R$_2$, R$_3$, R$_4$, n and m are as defined for structure XVII.

In another embodiment, the compound of formula XVII (1) is represented by the structure of the following compounds:

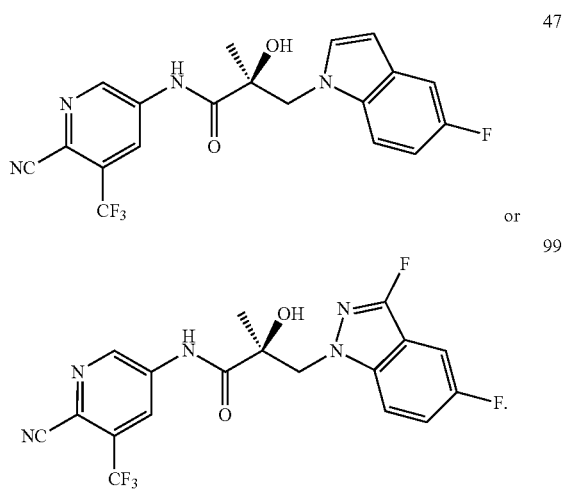

One embodiment of the invention encompasses the SARD compound having at least one of the following properties: binds to the AR through an alternate binding and degradation domain (BDD), e.g. in the NTD; binds to the AR through the AR ligand binding domain (LBD); exhibits AR-splice variant (AR-SV) degradation activity; exhibits AR-full length (AR-FL) degradation activity including pathogenic mutations thereof; exhibits AR-SV inhibitory activity (i.e., is an AR-SV antagonist); exhibits AR-FL inhibitory activity (i.e., is an AR-FL antagonist) including pathogenic mutations thereof; possesses dual AR-SV degradation and AR-SV inhibitory functions; and/or dual AR-FL degradation and AR-FL inhibitory functions.

Another embodiment of the invention encompasses pharmaceutical compositions comprising a SARD compound according to this invention, or its isomer, pharmaceutically acceptable salt, pharmaceutical product, polymorph, hydrate or any combination thereof, and a pharmaceutically acceptable carrier. The pharmaceutical composition may be formulated for topical use. The topical pharmaceutical composition may be a solution, lotion, salve, cream, ointment, liposome, spray, gel, foam, roller stick, cleansing soaps or bars, emulsion, mousse, aerosol, or shampoo.

The invention encompasses a method of treating prostate cancer (PCa) or increasing survival in a male subject in need of treatment comprising administering to the subject a therapeutically effective amount of a compound of this invention. The prostate cancer includes, but is not limited to, advanced prostate cancer, castration resistant prostate cancer (CRPC), metastatic CRPC (mCRPC), non-metastatic CRPC (nmCRPC), high-risk nmCRPC or any combination thereof. Another embodiment of the invention encompasses the method further comprising administering androgen deprivation therapy. Alternatively, the method may treat a prostate or other cancer that is resistant to treatment with known androgen receptor antagonist(s) or ADT. In another embodiment, the method may treat enzalutamide resistant prostate cancer. In another embodiment, the method may treat apalutamide resistant prostate cancer. In another embodiment, the method may treat abiraterone resistant prostate cancer. Yet another embodiment of the invention encompasses a method of treating prostate or other AR antagonist resistant cancer with a SARD compound of the invention wherein the androgen receptor antagonist(s) is at least one of enzalutamide, apalutamide, bicalutamide, abiraterone, ODM-201, EPI-001, EPI-506, AZD-3514, galeterone, ASC-J9, flutamide, hydroxyflutamide, nilutamide, cyproterone acetate, ketoconazole, or spironolactone.

In some embodiments, the prostate cancer is AR antagonist resistant prostate cancer which overexpresses the glucocorticoid receptor (GR). In some embodiments, activation of the GR provides support for growth of the prostate cancer and/or confers antiandrogen resistance to the prostate cancer. In some embodiments, SARDs of this invention can be used to treat GR-dependent or GR-overexpressing prostate cancers, whether antiandrogen resistant or not.

Yet another embodiment of the invention encompasses a method of treating prostate or other cancers using a SARD compound of the invention wherein the other cancers are selected from breast cancer such as triple negative breast cancer (TNBC), testicular cancer, cancers associated with partial androgen insensitivity syndromes (PAIS) such as gonadal tumors and seminoma, uterine cancer, ovarian cancer, cancer of the fallopian tubes or peritoneum, salivary gland cancer, bladder cancer, urogenital cancer, brain cancer, skin cancer, lymphoma, mantle cell lymphoma, liver cancer, hepatocellular carcinoma, renal cancer, renal cell carcinoma, osteosarcoma, pancreatic cancer, endometrial cancer, lung cancer, non-small cell lung cancer (NSCLC), gastric cancer, colon cancer, perianal adenoma, or central nervous system cancer. In another embodiment, the breast cancer is triple negative breast cancer (TNBC).

The invention encompasses a method of reducing the levels of AR-splice variants in a subject comprising administering to the subject a therapeutically effective amount of a compound of this invention, or its isomer, pharmaceutically acceptable salt, pharmaceutical product, polymorph, hydrate or any combination thereof. The method may comprise further reducing the levels of AR-full length in the subject.

Another embodiment of the invention encompasses a method of treating Kennedy's disease in a subject comprising administering to the subject a compound of this invention.

Yet another embodiment of the invention encompasses a method of: (a) treating acne in a subject, e.g., acne vulgaris; (b) decreasing sebum production in a subject, e.g., treats sehorrhea, seborrheic dermatitis, or acne; (c) treating hirsutism in a subject, e.g., female facial hair; (d) treating alopecia in a subject, e.g., androgenic alopecia, alopecia areata, alopecia secondary to chemotherapy, alopecia secondary to radiation therapy, alopecia induced by scarring, or alopecia induced by stress; (e) treating a hormonal condition in female, e.g., precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, or vaginal dryness; (f) treating sexual perversion, hypersexuality, or paraphilias in a subject; (g) treating androgen psychosis in a subject; (h) treating virilization in a subject; (i) treating complete or partial androgen insensitivity syndrome in a subject; (j) increasing or modulating ovulation in an animal; (k) treating of cancer in a subject; or any combination thereof, by administering a compound of this invention or a pharmaceutical composition thereof.

One embodiment of the invention encompasses methods of reducing the levels of polyglutamine (polyQ) AR polymorphs in a subject comprising administering a compound according to this invention. The method may inhibit, degrade, or both the function of the polyglutamine (polyQ) AR polymorphs (polyQ-AR). The polyQ-AR may be a short polyQ polymorph or a long polyQ polymorph. When the polyQ-AR is a short polyQ polymorph, the method further treats dermal disease. When the polyQ-AR is a long polyQ polymorph, the method further treats Kennedy's disease.

Another embodiment of the invention encompasses methods of treating amyotrophic lateral sclerosis (ALS) in a subject by administering a therapeutically effective amount of the compound of the invention, or its isomer, pharmaceutically acceptable salt, pharmaceutical product, polymorph, hydrate or any combination thereof; or a pharmaceutical composition thereof.

Another embodiment of the invention encompasses methods of treating abdominal aortic aneurysm (AAA) in a subject by administering a therapeutically effective amount of the compound of the invention, or its isomer, pharmaceutically acceptable salt, pharmaceutical product, polymorph, hydrate or any combination thereof; or a pharmaceutical composition thereof.

Yet another embodiment of the invention encompasses methods of treating uterine fibroids in a subject by administering a therapeutically effective amount of the compound of this invention, or its isomer, pharmaceutically acceptable salt, pharmaceutical product, polymorph, hydrate or any combination thereof; or a pharmaceutical composition thereof.

In yet another aspect, the invention provides a method of treating, suppressing, reducing the incidence, reducing the severity, or inhibiting the progression of a hormonal condition in a male in need thereof, comprising administering to the subject a therapeutically effective amount of a selective androgen receptor degrader (SARD) compound of the invention. In one embodiment, the condition in the method of the invention is hypergonadism, hypersexuality, sexual dysfunction, gynecomastia, precocious puberty in a male, alterations in cognition and mood, depression, hair loss, hyperandrogenic dermatological disorders, precancerous lesions of the prostate, benign prostate hyperplasia, prostate cancer and/or other androgen-dependent cancers.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

(FIG. 1A) 14, 18, and 20; (FIG. 1B) 11 and 12; and (FIG. 1C) 11, 23 and 27; of this invention. (Example 5)

(FIG. 7A) AR ABCD increases GRE-LUC reporter activity. AR ABCD construct that lacks the ligand binding domain or empty vector was transfected into HEK-293 cells along with GRE-LUC and CMV-renilla LUC. Forty eight hours after transfection cells were harvested and luciferase assay performed. (FIG. 7B) AR ABCD activity was inhibited by 11. The ABCD AR construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. (FIG. 7C) and (FIG. 7D) Non-SARD antagonists ARN-509 and enzalutamide did not inhibit the activity of this AR construct lacking the LBD, suggesting that of the compounds tested, only SARDs of this invention have the ability to inhibit ligand independent AR activity. (Example 9)

(FIG. 8A) 11, 12, and 14, galeterone, EPI-001, and enzalutamide; and (FIG. 8B) 11, galeterone, and enzaluatamide. SARDs of this invention more potently inhibited (AR-FL) transactivation. (Example 10)

(FIG. 9A) 11 significantly reduced tumor volume and (FIG. 9B) tumor weight in a 22RV-1 xenograft tumor study, whereas AR antagonist enzalutamide did not have any effect compared to vehicle. (FIG. 9C) shows tumor expressed levels of AR-FL and AR-V7 were decreased by 11 but not enzalutamide, demonstrating that in vivo activity correlated with AR degradation in the tumors; and (FIG. 9D) demonstrates an in vivo antiandrogenic tone in gene expression as the serum PSA in these animals was decreased by 11 but not enzalutamide in this 22RV-1 xenograft study. (Example 11)

(FIG. 17A) A dose-dependent shift in the fluorescence intensity, i.e., fluorescent quenching, was observed with 11 when incubated with AR AF-1. (FIG. 17B) The fluorescence shoulder observed at 307 nm, which corresponds to tyrosine residues in the AF-1, is shifted by 11. The overall fluorescence is also markedly altered by 11. (FIG. 17C) Data shown was plotted as difference in fluorescence between control and 11 treated samples (fluorescence in the absence of compound—fluorescence in the presence of compound), a dose dependent increase was observed in the presence of 11. Cumulatively, these data suggest a direct interaction between 11 and AR AF-1. (Example 12)

(FIG. 29A) presents transactivation data for 42 ($IC_{50}$=1015 nM) and binding ($K_i$=86.1 nM). (Example 5) (FIG. 29B) presents transactivation data for 41 ($IC_{50}$=>10,000 nM) and binding ($K_i$=84.3 nM). (Example 5) (FIG. 29C) presents (1) transactivation data for 132 ($IC_{50}$=978.1 nM) and binding ($K_i$=353.2 nM), (2) AR full length degradation for 132, and (3) AR splice variant degradation for 132. (Example 6) (FIG. 29D) presents transactivation data for 40 ($IC_{50}$=1032.1 nM) and binding ($K_i$=134.9 nM). (Example 5) (FIG. 29E) presents (1) transactivation data for 92 ($IC_{50}$=946.8 nM) and binding ($K_i$=nM), (2) AR full length degradation for 92, and (3) AR splice variant D567es degradation for 92. (Example 5) (FIG. 29F) presents (1) transactivation data for 39 ($IC_{50}$=233.8 nM) and binding ($K_i$=719.9 nM), (2) AR full length degradation for 39. (Example 5) (FIG. 29G) presents (1) transactivation data for 38 ($IC_{50}$=318.4 nM) and binding ($K_i$=331.8 nM), (2) AR full length degradation for 38, and (3) AR splice variant AR-V7 degradation for 38. (Example 5) (FIG. 29H) presents (1) transactivation data for 11 ($IC_{50}$=96.4 nM) and 37 ($IC_{50}$=94.0 nM) and binding ($K_i$=252.6 nM), (2) AR full length degradation for 37, and (3) AR splice variant degradation for 37. (Example 5) (FIG. 29I) presents (1) transactivation data for 36 ($IC_{50}$=1142.0 nM) and binding ($K_i$=315.3 nM), (2) AR full length degradation for 36. (Example 5) (FIG. 29J) presents (1) transactivation data for 115 ($IC_{50}$=244.4 nM) and binding ($K_i$=71.5 nM), (2) AR full length degradation for 115, and (3) AR splice variant AR-V7 degradation for 115. (Example 6) (FIG. 29K) presents (1) transactivation data for 35 ($IC_{50}$=98.47 nM) and binding ($K_i$=155.7 nM) and (2) AR full length degradation for 35. (Example 5) (FIG. 29L) presents (1) transactivation data for 205 ($IC_{50}$=1079.1 nM) and binding ($K_i$=90.7 nM), (2) AR full length degradation for 205, and (3) AR splice variant AR-V7 degradation for 205. (Example 13) (FIG. 29M) presents (1) transactivation data for 114 ($IC_{50}$=834.7 nM) and binding ($K_i$=204.4 nM), (2) AR full length degradation for 114, and (3) AR splice variant AR-V7 degradation for 114. (Example 6) (FIG. 29N) presents transactivation data for 204 ($IC_{50}$=1025.4 nM) and binding ($K_i$=809.6 nM). (Example 13) (FIG. 29O) presents (1) transactivation data for 34 ($IC_{50}$=nM) and binding ($K_i$=nM), (2) AR full length degradation for 34, and (3) AR splice variant degradation for 34. (Example 5)

(FIG. 30A) and (FIG. 30D)

Figure 30A:
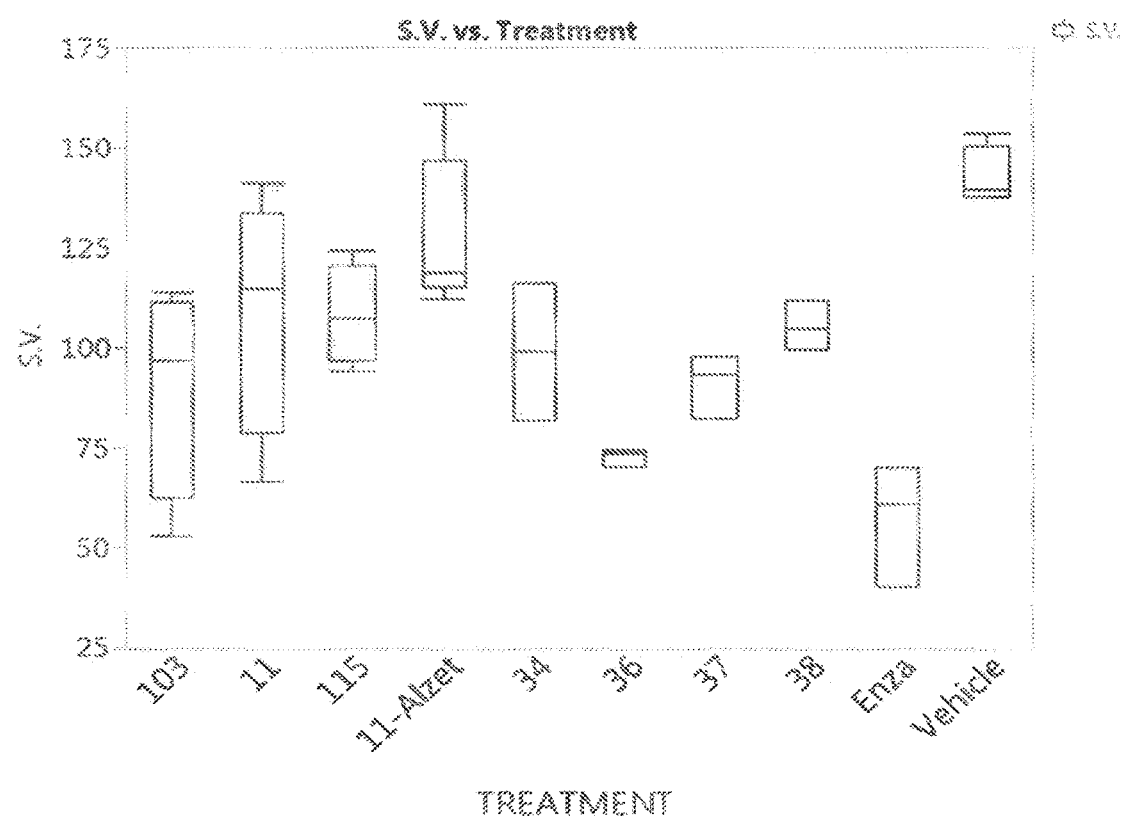
FIGS. 30A-30D present Hershberger assay: Mice (6-7 weeks old) were treated with vehicle or indicated SARDs (100 mg/kg/day twice daily) for 14 days orally. Animals were sacrificed, and seminal vesicles weights were recorded and represented. Results.

SARDs demonstrated various degrees of decreased seminal vesicles (S.V.) weight, (FIG. 30B) increased in body weight (B.Wt.), and (FIG. 30C) decreased prostate weight. This behavior is consistent with an in vivo antiandrogenic effect exerted by SARDs of this invention. (Example 16)

Figure 31:
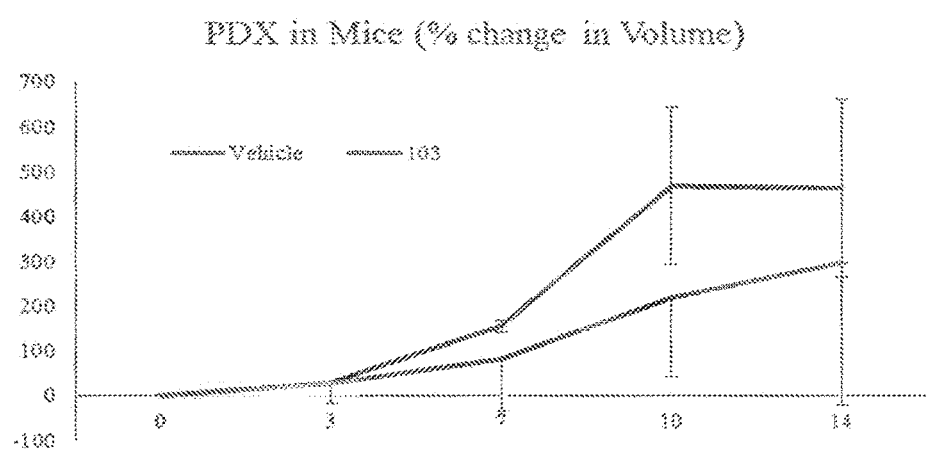

FIG. 31 demonstrates that 103 slowed prostate cancer tumor growth in patient-derived xenografts (PDX) despite low levels in the plasma. SARD 103 selectively accumulated in tumor. NSG mice were implanted with patient-derived prostate cancer xenografts (PDX). Animals were treated for 14 days and tumor volumes were measured twice weekly, as shown in the graph. Animals were sacrificed, 103 was extracted from the serum and tumor and measured using LC-MS/MS method. 103 selectively accumulated in tumor with almost 10 times more tumor accumulation than in plasma (see Example 16, Table 15), possibly providing an explanation for anti-tumor activity despite low levels of SARD in the plasma. (Example 16)

Figure 32:
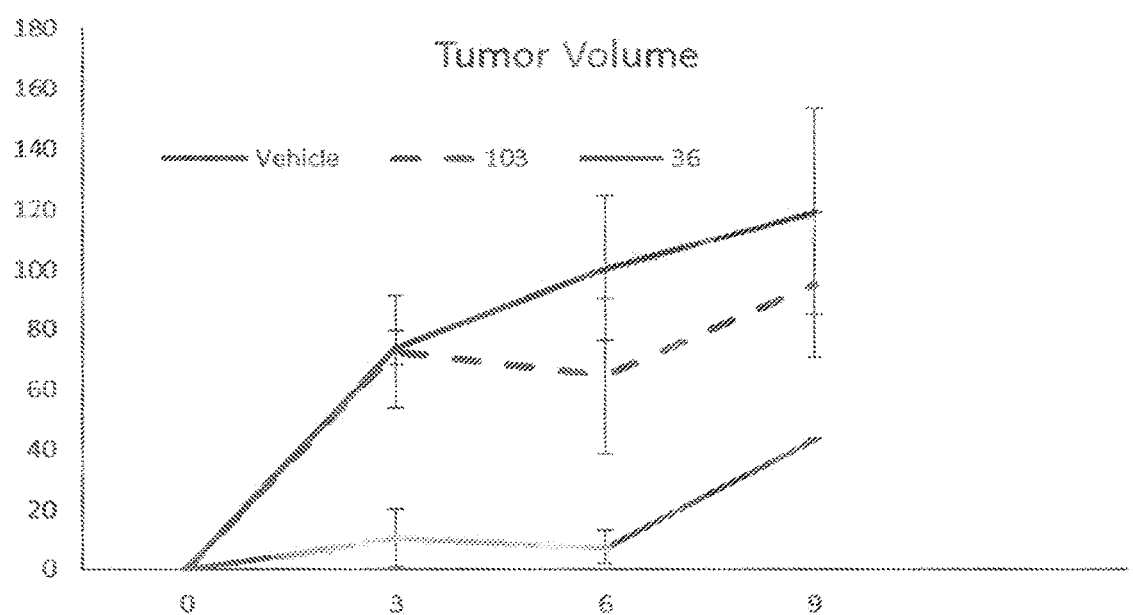
Figure 33A:
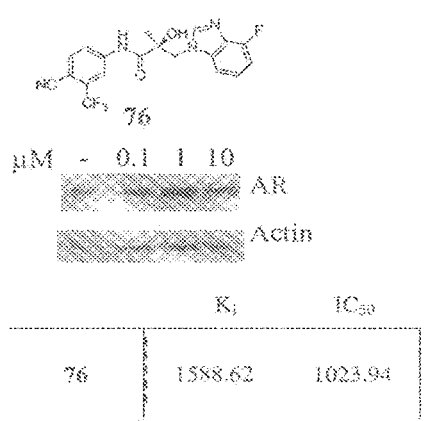
Figure 33B:
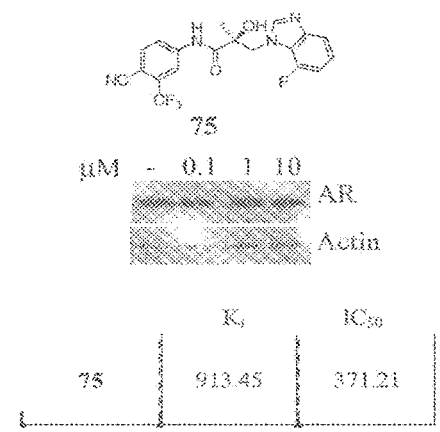
Figure 33C:
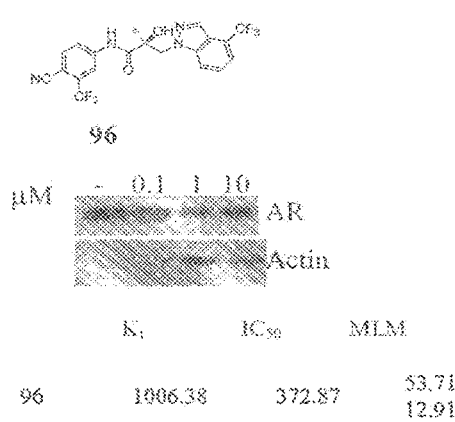
Figure 33D:
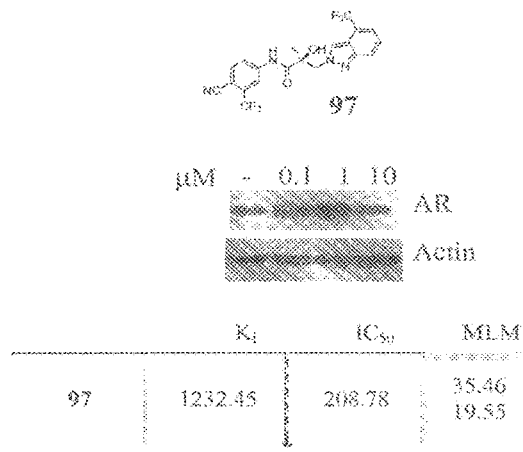

FIG. 32 presents data in a mouse xenograft model treated with 103 and 36. The % change in tumor volume is presented using 103 and 36. LNCaP cells were implanted (5 million cells/mouse) in NSG mice. Once tumors reach 70-200 mm$^3$, animals were randomized and treated with SARDs (100 mg/kg/twice daily). Tumor volume was measured at regular intervals and represented as % change from baseline. 36 significantly inhibited tumor growth. (Example 16)

FIGS. 33A-33D present binding ($K_i$), transactivation ($IC_{50}$), half-life in liver microsomes (MLM; $t_{1/2}$ (minutes)) and full-length AR degradation via Western blot of the androgen receptor with AD1 cells treated with: (FIG. 33A) 76, (FIG. 33B) 75, (FIG. 33C) 96, and (FIG. 33D) 97. (Example 7)

Figure 34:
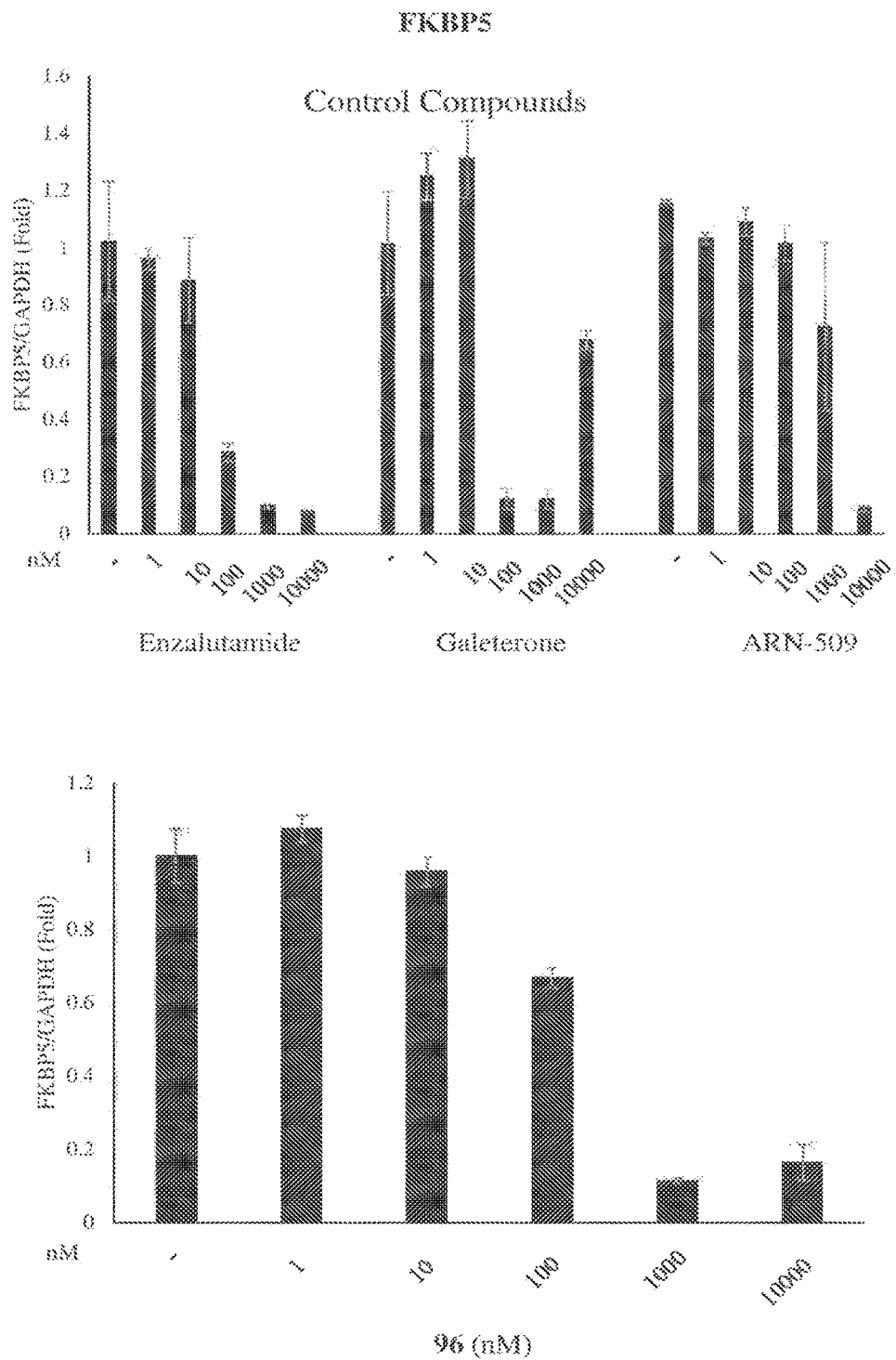

FIG. 34 presents the effect of known AR antagonists compared to SARD 96 on the AR-dependent gene FKBP5. 96 suppressed the AR-responsive gene FKBP5 to a comparable extent as did enzalutamide, galeterone, and ARN-509, demonstrating that 96 is a potent AR antagonist in vitro. (Example 10)

Figure 35:
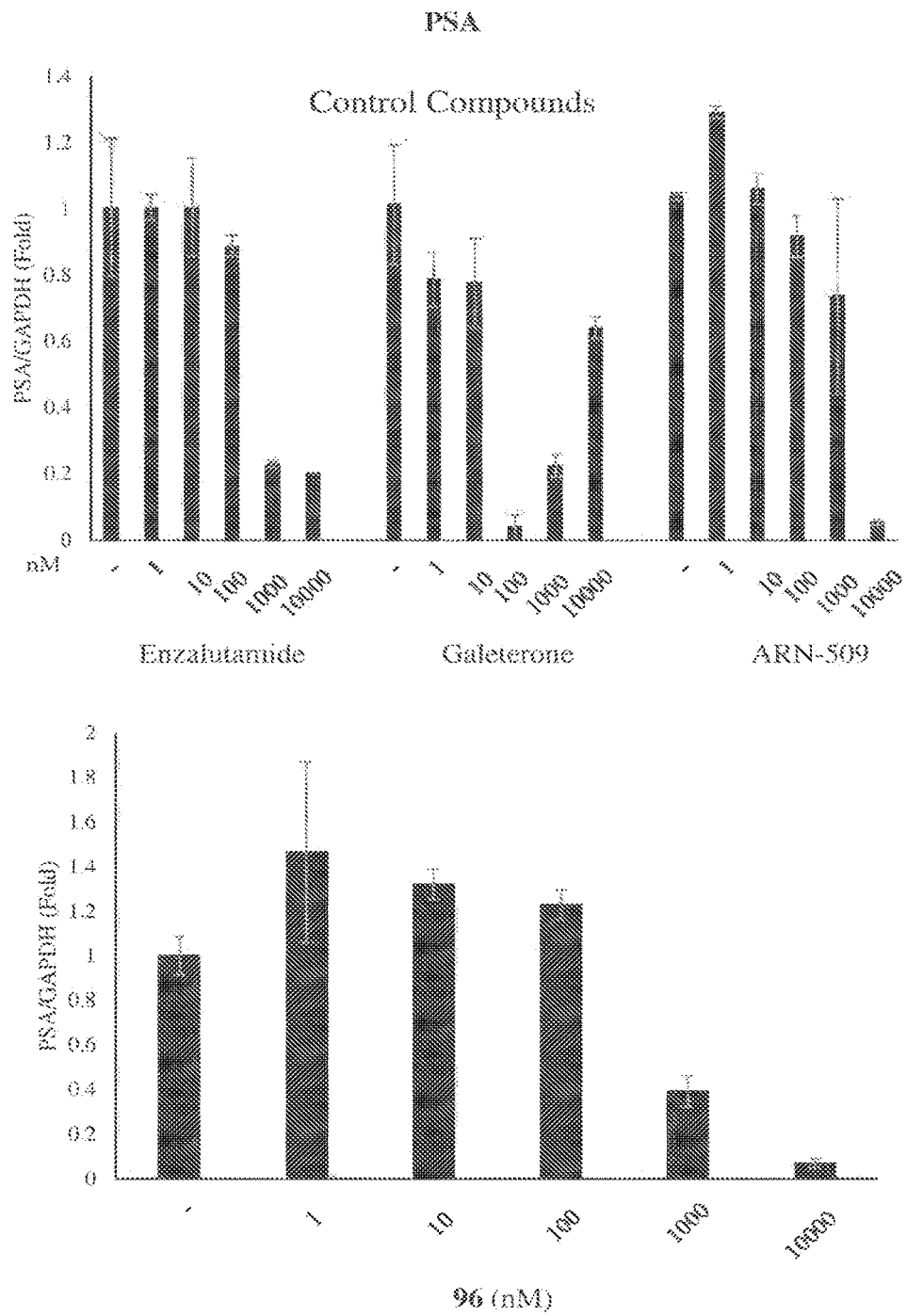

FIG. 35 presents the effect of known AR antagonists compared to SARD 96 on the AR-dependent gene PSA. 96 suppressed the AR-responsive gene PSA to a comparable extent as did enzalutamide and greater than ARN-509. In this case, galeterone potently suppressed at 100 nM but the effect was not dose responsive, reversing at higher doses. (Example 10)

Figure 36:
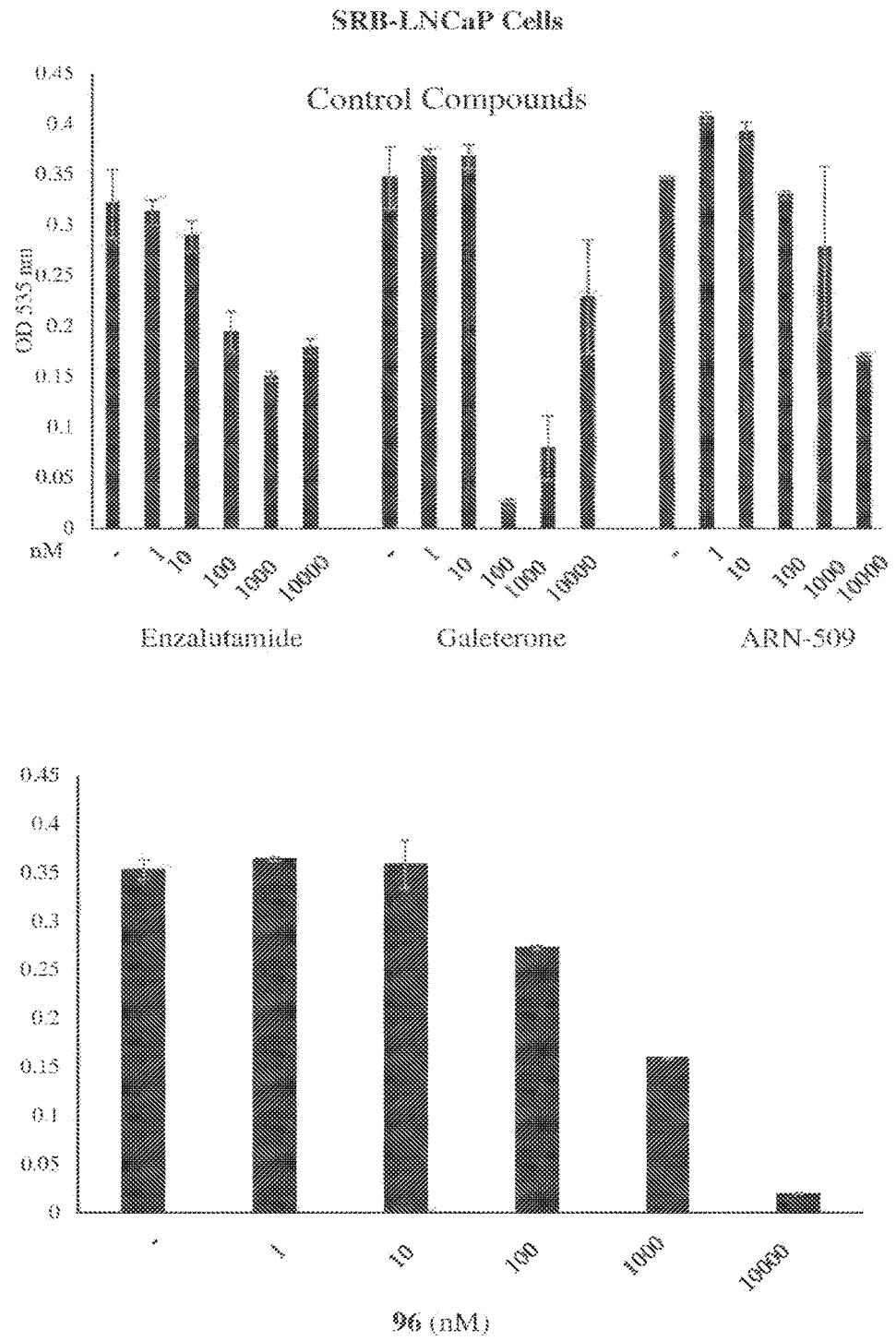

FIG. 36 presents the effect of known AR antagonists compared to SARD 96 on SRB-LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue (SRB) stain. 96 demonstrated a robust and dose-dependent anti-proliferative effect whereas enzalutamide and ARN-509 only partially suppressed growth and galeterone did not exhibit dose-dependent effects. (Example 10).

Figure 37A:
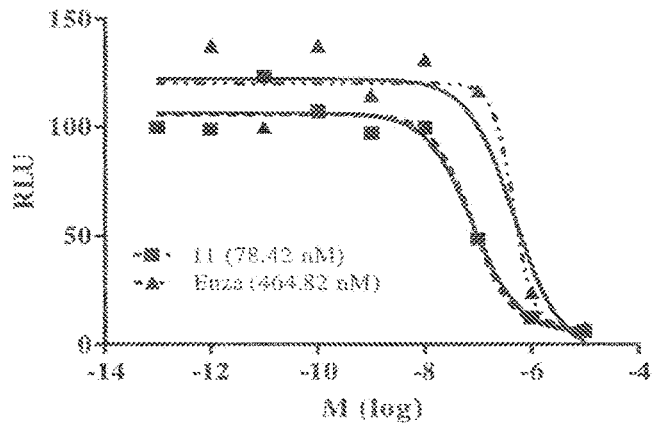
Figure 37B:
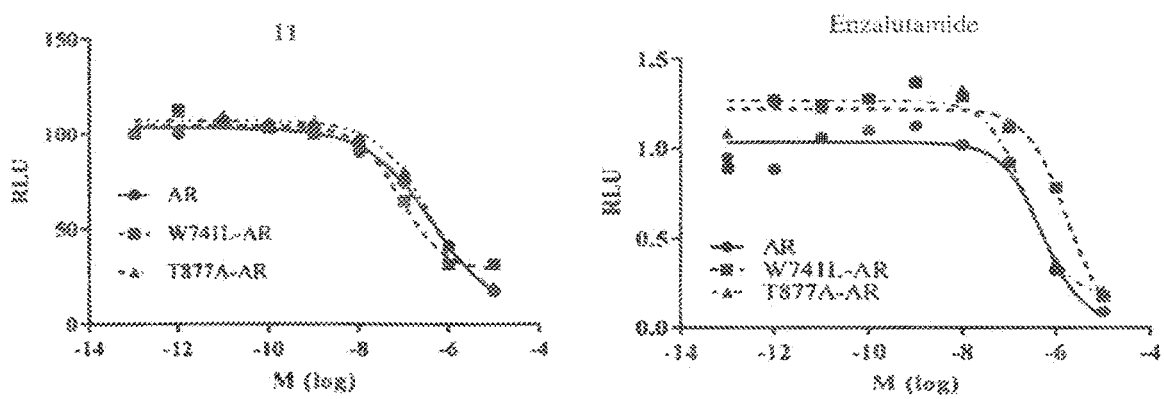
Figure 37C:
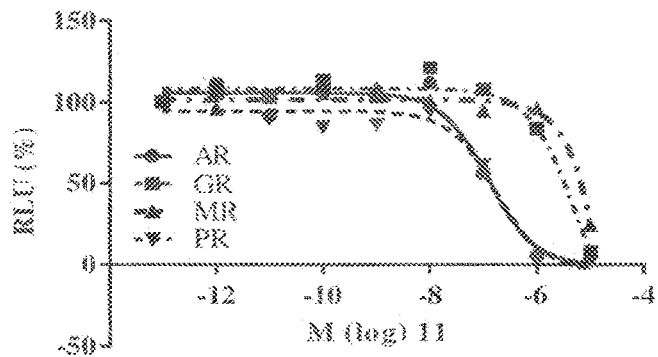
Figure 37D:
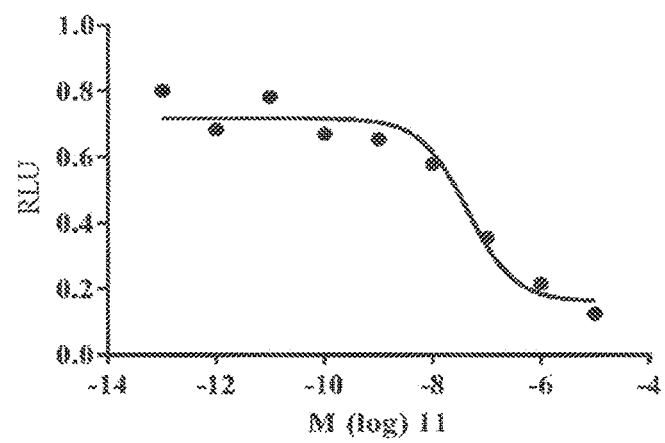
Figure 37E:
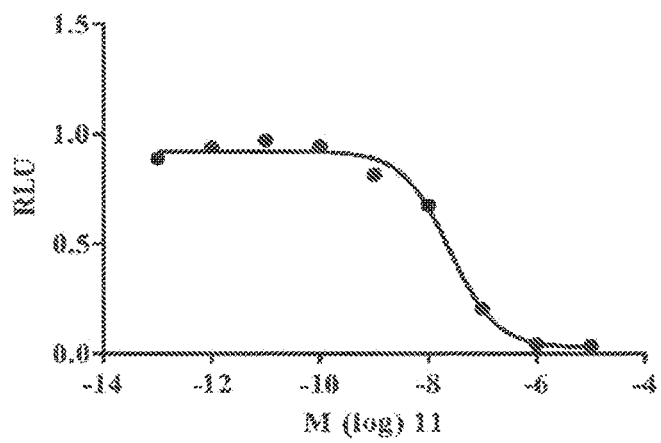

FIGS. 37A-37E depict inhibition of AR function by 11. AR ligand binding assay was performed with GST-tagged purified human AR-LBD protein producing a $K_i$ of 78.06 nM (data not shown). 11 potently inhibits AR transactivation. AR transactivation was performed by transfecting human AR cDNA, GRE-LUC, and CMV-renilla LUC into HEK-293 cells. Cells were treated 24 hrs after transfection with a dose response of antagonists in combination with 0.1 nM R1881 and luciferase assay was performed 48 hrs after transfection. Values provided are $IC_{50}$ (FIG. 37A). 11, but not enzalutamide, comparably inhibits transactivation of wildtype and LBD-mutant AR. Transactivation assay with 11 or enzalutamide was performed with wildtype AR or AR carrying commonly known LBD mutants (FIG. 37B). 11 cross-reacts with progesterone receptor (PR), but minimally with mineralocorticoid receptor (MR) or glucocorticoid receptor (GR). Transactivation was performed by transfecting human AR, PR, GR, or MR cDNA, GRE-LUC, and CMV-renilla LUC into HEK-293 cells. Cells were treated 24 hrs after transfection with indicated doses of 11 in combination with 0.1 nM progesterone (PR), dexamethasone (GR), and aldosterone (MR) and luciferase assay was performed 48 hrs after transfection (FIG. 37C). 11 inhibits AR-65Q transactivation. Transactivation assay with an AR cDNA that has extended poly-glutamide repeat (65Q) was performed (FIG. 37D). 11 inhibits AR N—C interaction. Mammalian two hybrid assay was performed by transfecting HEK-293 cells with VP16-ARNTD, Gal-4-DBD-ARLBD, Gal-4-RE-LUC, and CMV-renilla-luciferase. Cells were treated 24 hours after transfection with a dose response of 11 in combination with 0.1 nM R1881, and luciferase assay was performed 48 hours after transfection. All experiments were performed at least twice with a dose range of 1 pM to M. Enza-Enzalutamide. (FIG. 37E).

Figure 38A:
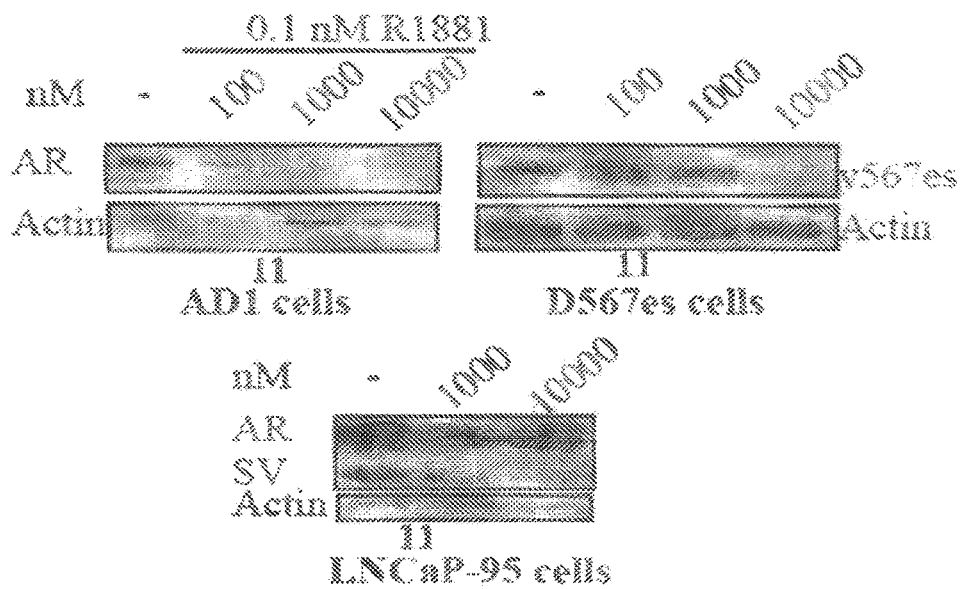
Figure 38B:
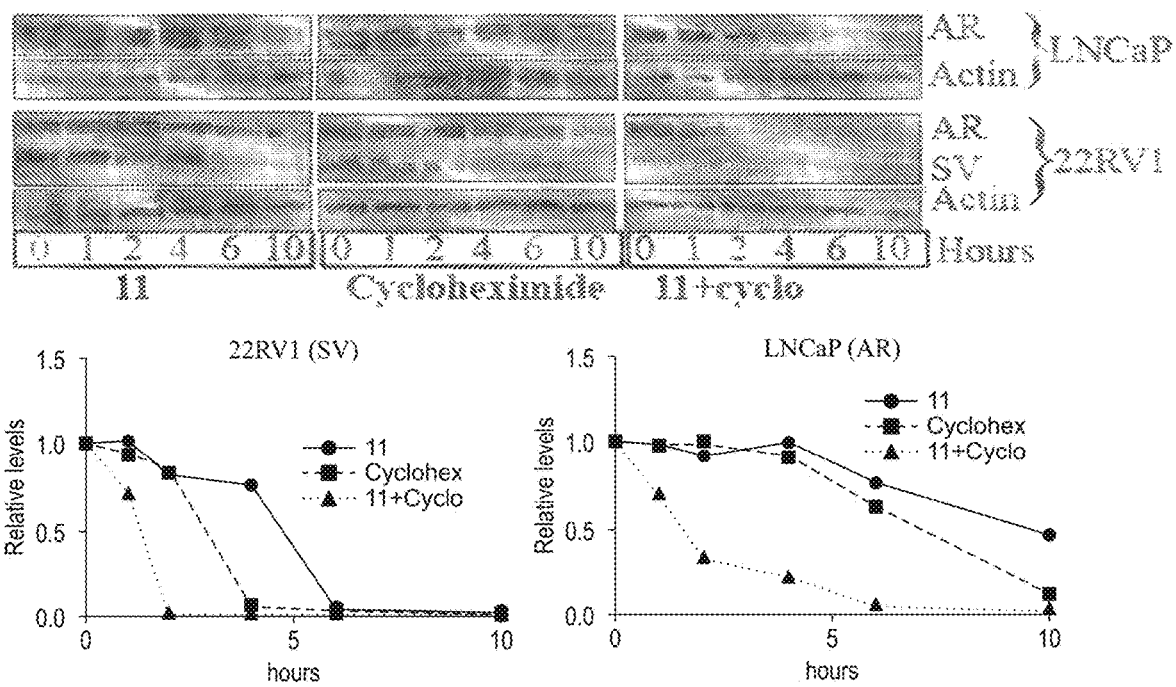
Figure 38C:
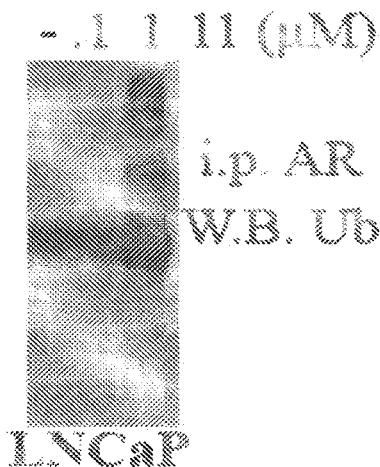

FIGS. 38A-38C: 11 degrades AR and splice variant ARs. 11 degrades AR full length in AD1 cells (left panel), AR-V567es in D567es cells (middle panel), and AR-SV in LNCaP-95 cells (lower panel). AD1 cells expressing AR were maintained in charcoal-stripped serum containing medium, while D567es cells expressing AR-v567es and LNCaP-95 cells expressing AR and AR-SV were maintained in growth medium for 2 days. Cells were treated for 24 hrs, protein extracted, and Western blot for AR and actin was performed (FIG. 38A). Inhibition of protein synthesis accelerates AR and AR-SV degradation by 11. 22RV1 cells (lower panel) and LNCaP cells (upper panel) were plated in growth medium and treated with 10 µM 11, 50 µM cycloheximide, or combination of 11 and cycloheximide for the indicated time-points. Cells were harvested, protein extracted, and Western blotted for AR and actin. Results from quantification of the blots are provided below (FIG. 38B). 11 promotes AR and ubiquitin interaction. LNCaP cells maintained in charcoal stripped serum containing medium were treated with vehicle or indicated concentrations of 11 for 4 hrs. Protein extracts were immunoprecipitated with AR antibody and Western blot for ubiquitin was performed (FIG. 38C).

Figure 39A:
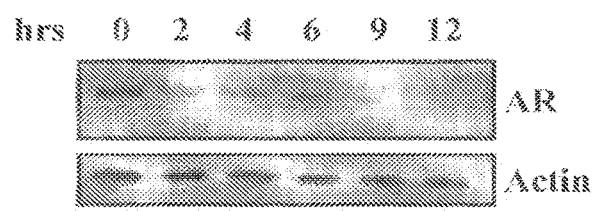
Figure 39B:
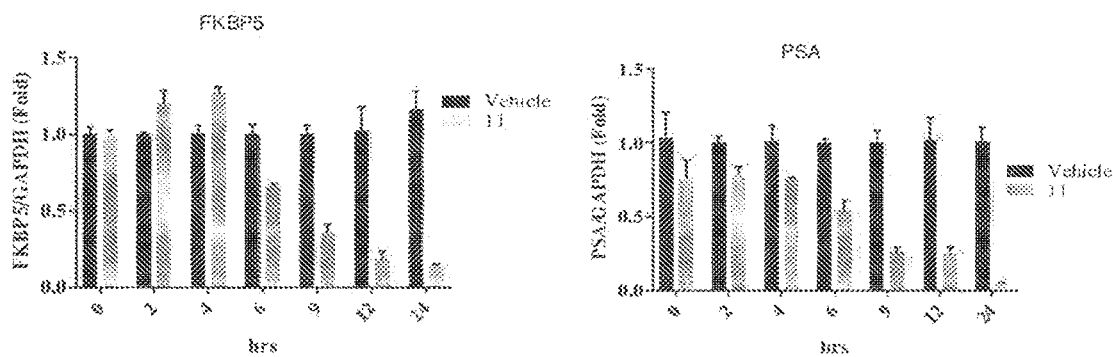
Figure 39C:
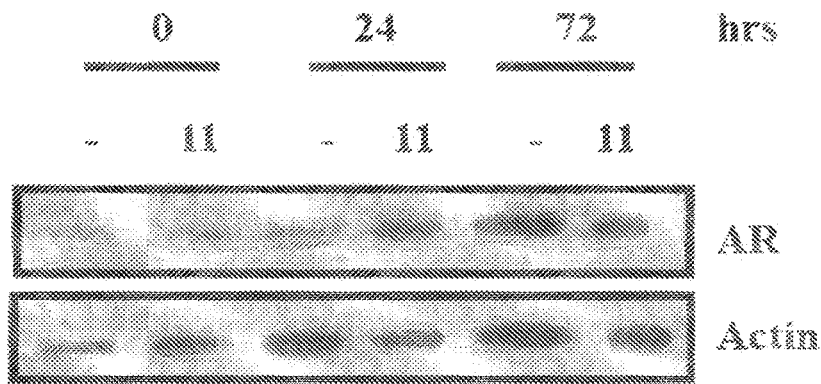

FIGS. 39A-39C: 11-dependent degradation is rapid and sustained. LNCaP cells were plated in charcoal stripped serum containing medium and treated with 10 µM 11 in combination with 0.1 nM R1881 for the indicated time-points. Western blot for the AR and actin was performed (FIG. 39A). LNCaP cells maintained in RPMI+1% csFBS w/o phenol red for 2 days were treated with 0.1 nM R1881 alone or in combination with 10 µM 11. Cells were harvested at the indicated time-points, RNA isolated, and expression of genes was measured and normalized to GAPDH (FIG. 39B). 11-induced degradation is sustained. 22RV1 cells were plated in growth medium containing 10% FBS and treated with 10 µM of 11 for 24 hrs. Twenty four hours after treatment, cells were washed with medium and fed with charcoal-stripped serum containing medium. One set of cells was immediately harvested (time point 0 hrs), while the remaining. Subsequently, cells were harvested 24 and 72 hrs after washing the SARD. Protein was extracted and Western blot for the AR and actin was performed (FIG. 39C).

Figure 40A:
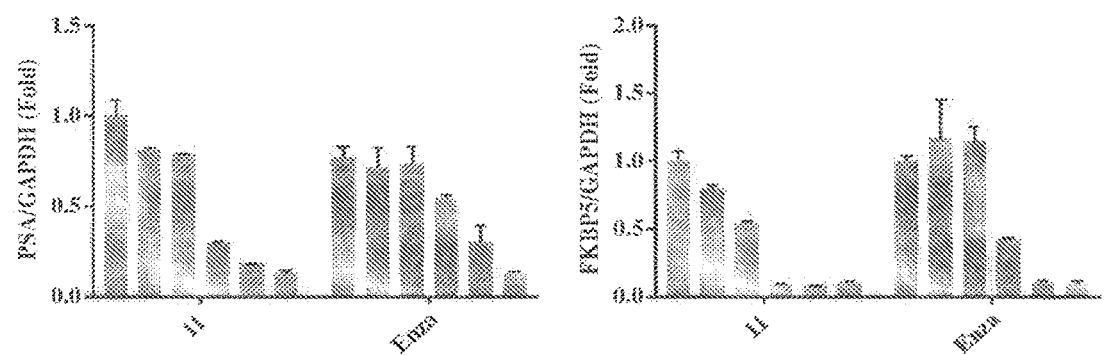
Figure 40B:
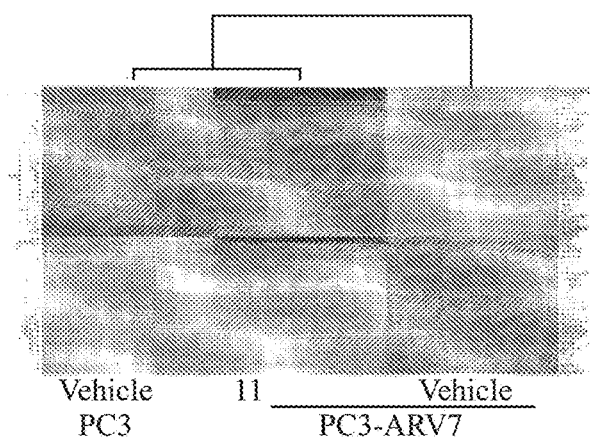
Figure 40B:
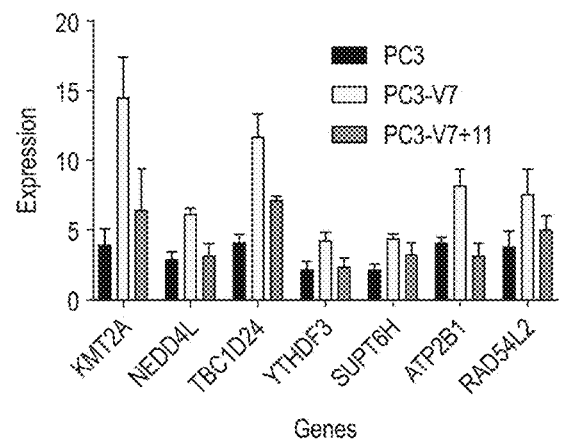
Figure 40C:
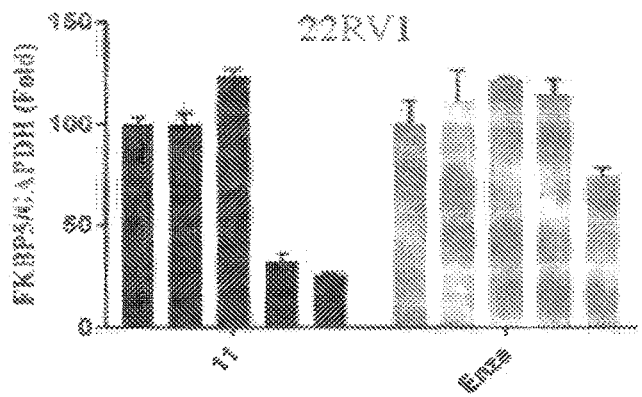
Figure 40D:
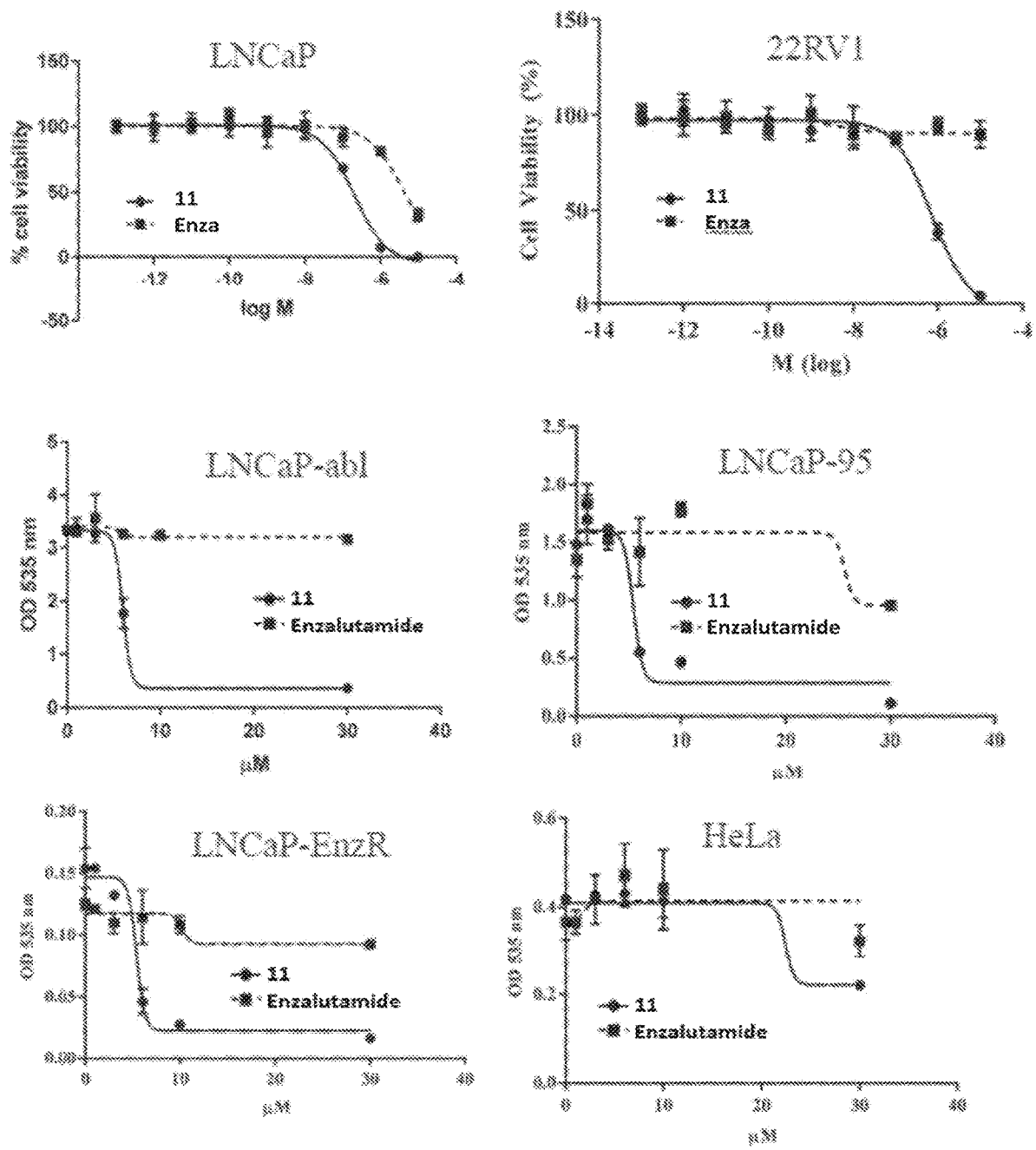
Figure 40E:
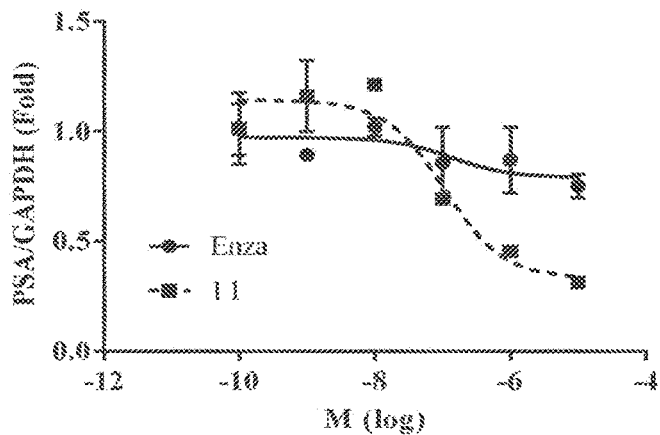

FIGS. 40A-40E: 11 inhibits the expression of AR-target genes and proliferation of prostate cancer cells. 11 potently inhibits the expression of AR-target genes in LNCaP cells. LNCaP cells were maintained in charcoal stripped serum containing medium for two days and treated with vehicle or indicated compounds (11 or enzalutamide with dose of 1, 10, 100, 1000, and 10,000 nM) in the presence of 0.1 nM R1881 for 24 hours. RNA was isolated and expression of PSA (left) or FKBP5 (right) was quantified and normalized to GAPDH by realtime PCR (FIG. 40A). 11 inhibits expression of a subset of genes induced by AR-V7 in PC3 cells. PC3 cells or PC3 cells stably transfected with AR-V7 (PC3-ARV7) were treated with vehicle or 10 μM 11 (n=3). RNA was isolated ~16 hrs after treatment and RNA-Sequencing was performed in Ion Torrent next-generation sequencer. Heatmap shows the top 50 genes differentially expressed in PC3-AR-V7 vehicle-treated but not in 11-treated cells compared to PC3 vehicle-treated cells. Bar graph on the right shows representative genes that were differentially expressed in RNA (FIG. 40B). 11 inhibits AR-target gene expression in 22RV1 cells. 22RV1 cells were plated in charcoal stripped serum, treated with vehicle (right-most bars of each chart) or indicated compounds (11 or enzalutamide with 10, 100, 1000, and 10,000 nM) for 3 days and the expression of AR-target genes was measured by realtime PCR (FIG. 40C). SARDs are potent inhibitors of prostate cancer cell proliferation. LNCaP cells maintained in charcoal stripped serum containing medium were treated with vehicle or indicated compounds (1 pM-10 μM) in the presence of 0.1 nM R1881. Cells were re-treated three days later and the cell viability was measured after 6 days of treatment using SRB assay. Castration-resistant prostate cancer (CRPC) cells 22RV1, LNCaP-abl, LNCaP-95, LNCaP-EnzR, and Hela cells were plated in charcoal-stripped serum containing medium and were treated as indicated for LNCaP cells in the absence of R1881 stimulation. SRB assay was performed 6 days after treatment (FIG. 40D). 11 inhibits enzalutamide-resistant AR-target gene expression and growth in enzalutamide-resistant (EnzR) prostate cancer cells. EnzR LNCaP cells were maintained in charcoal stripped serum containing medium for 2 days and treated with vehicle, enzalutamide, or 11 (1-10,000 nM) in the presence of 0.1 nM R1881 (FIG. 40E). Cells were harvested 24 hrs after treatment and expression of PSA was measured by realtime PCR. Cell proliferation in response to enzalutamide or SARDs and 0.1 nM R1881 was performed as described for LNCaP in panel 40D. Values in panels 40A-40C are represented as average±S.E. with n=3.

Figure 41A:
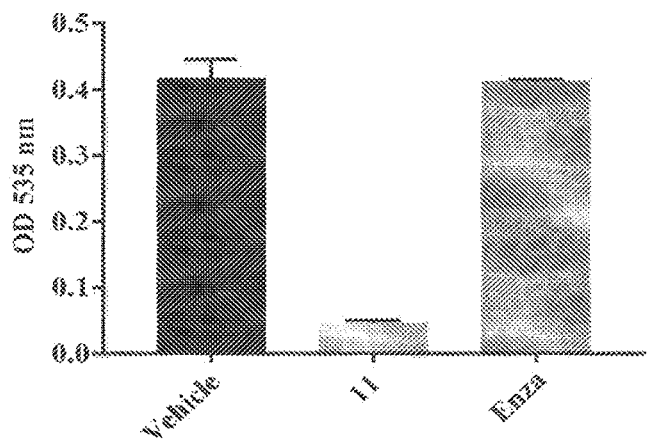
Figure 41B:
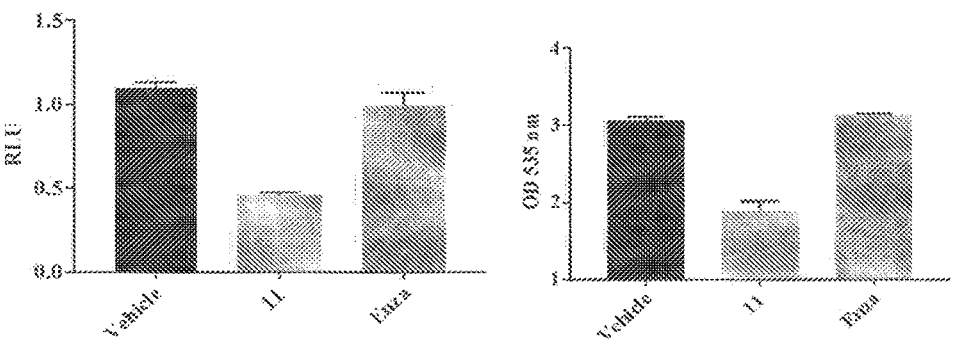

FIGS. 41A-41B: 11 inhibits transactivation of AD1 and D567es AR and cell proliferation. 11 inhibits AD1-AR-transactivation and cell growth. AR transactivation was performed by transfecting human GRE-LUC and CMV-renilla LUC into AD-1 cells. Cells were treated with vehicle, 0.1 nM R1881 alone or in combination with 10 μM 11 or enzalutamide 24 hrs after transfection and luciferase assay was performed 48 hrs after transfection (data not shown). AD1 cells maintained in charcoal stripped serum containing medium were treated with 10 μM UT-155 or enzalutamide in the presence of 0.1 nM R1881. Cells were re-treated three days later and the cell viability was measured after 6 days of treatment using SRB assay. (FIG. 41A). 11 inhibits D567es-AR-transactivation and cell growth. AR transactivation was performed by transfecting human GRE-LUC and CMV-renilla LUC into D567es cells. Cells were treated with vehicle, 10 μM 11, or enzalutamide 24 hrs after transfection and luciferase assay was performed 48 hrs after transfection (left panel). Right: D567es cells plated in growth medium were treated with vehicle, 10 M 11 or enzalutamide (FIG. 41B). Left: Cells were re-treated three days later and the cell viability was measured after 6 days of treatment using SRB assay (FIG. 41B).

Figure 42A:
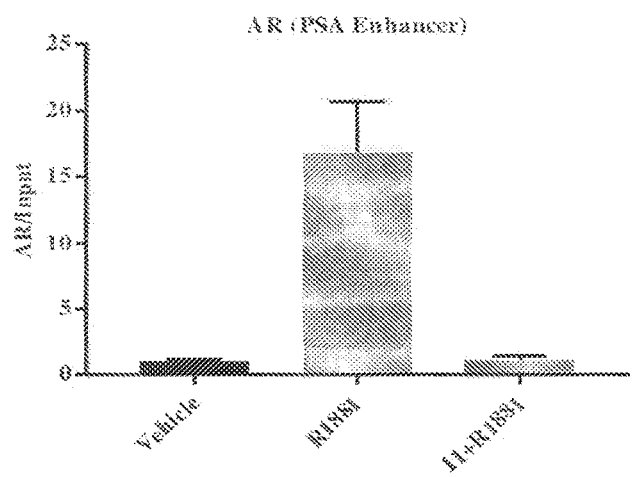
Figure 42B:
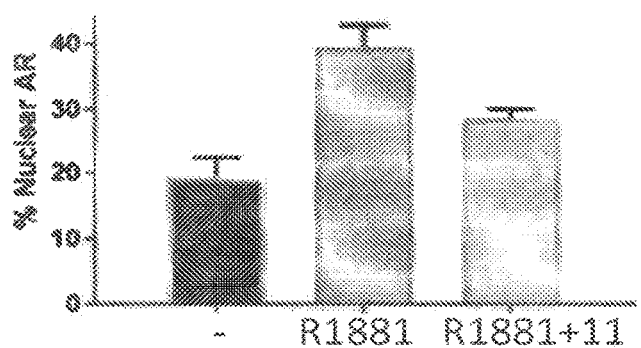
Figure 42C:
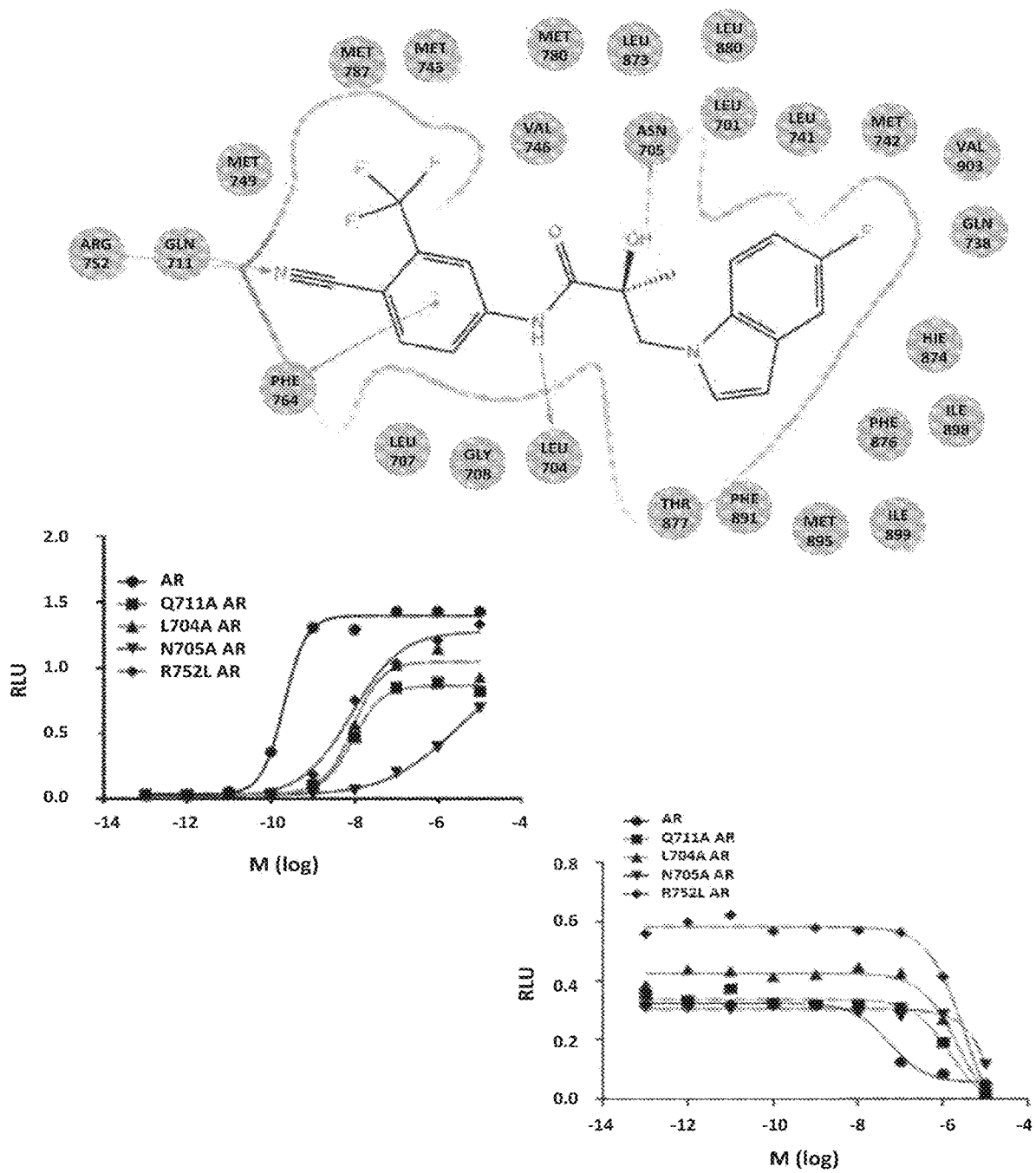
Figure 42D:
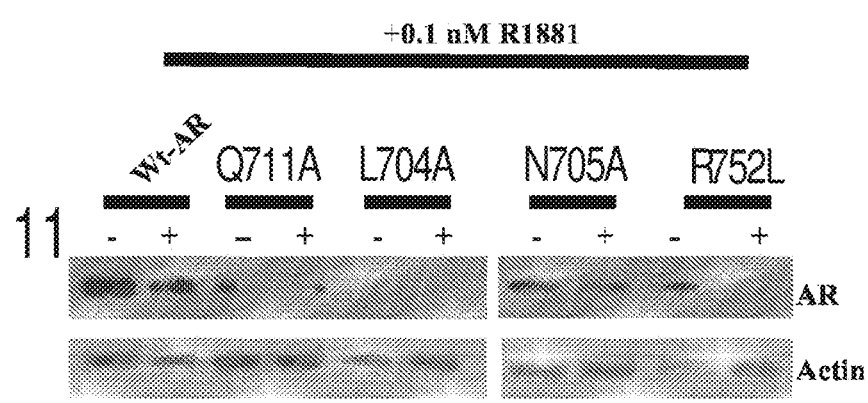

FIGS. 42A-42D: 11 inhibits nuclear translocation and DNA binding of the AR. 11 inhibits recruitment of AR to the androgen response element (ARE). LNCaP cells were serum starved for 2 days and were treated with 0.1 nM R1881 in the presence or absence of 10 μM 11 for 2 hrs. DNA-protein complex was cross-linked and AR was immunoprecipitated and its recruitment to PSA enhancer ARE was measured by realtime PCR. N=3. Values are expressed as average±S.E. (FIG. 42A). 11 inhibits nuclear translocation of enzalutamide-resistant AR (EnzR AR). EnzR LNCaP cells were maintained in charcoal-stripped serum (CSS) containing medium and treated with 10 μM 11 in the presence or absence of 0.1 nM R1881 for 4 hours. Translocation of the AR into nucleus was measured by immunofluorescence and quantified (FIG. 42B). Ligand binding of SARDs was critical for transactivation, but not for degradation. Molecular modeling shows the critical amino acids in the AR-LBD interacting with 11. The amino acids with which 11 forms hydrogen bond were mutated and transactivation assay was performed in HEK-293 cells. Left panel: shows that the mutants have weakened the R1881-induced transactivation. Right panel: was performed with a dose response of 11 in combination with 0.1 nM R1881 for wildtype AR, 10 nM R1881 for Q711A, R752L, and L704A, and 1 μM for N705A (FIG. 42C). Degradation of the wildtype and mutant AR by 11 was evaluated by transfecting the AR constructs in HeLa cells and treated as indicated in panel 42C for transactivation (FIG. 42D). Values in the graphs are $IC_{50}$. Enh-enhancer. ARE-Androgen Responsive Element. SRB-Sulforhodamine B. CSS—charcoal-stripped serum. DFCI—Dana-Farber Cancer Institute.

Figure 43:
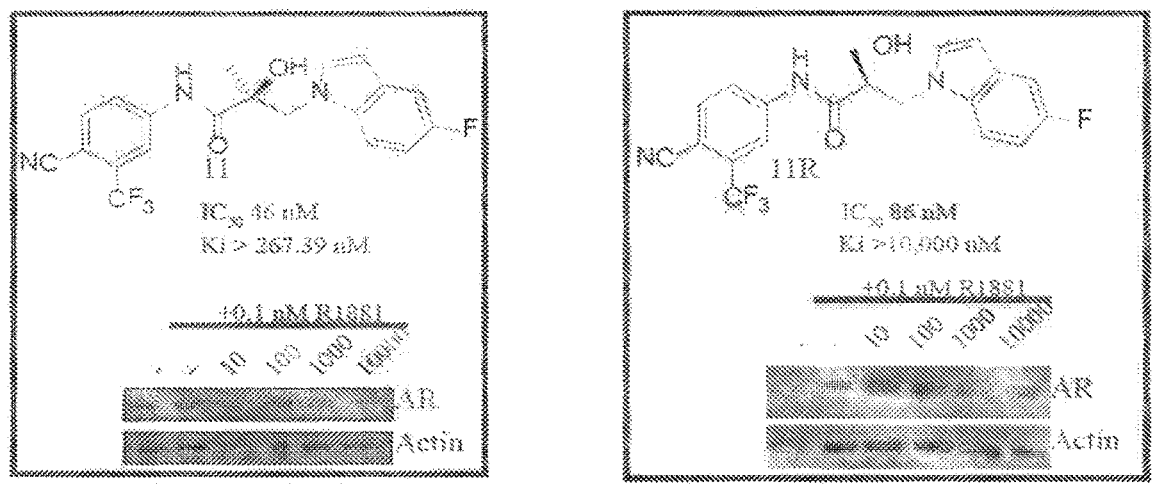

FIG. 43: The R-isomer of 11 (11R) was weaker in AR transactivation, but not in degradation. Structures of S- and R-isomers of 11 is shown. Transactivation $IC_{50}$ and Western blot for the AR are shown in the figure.

Figure 44:
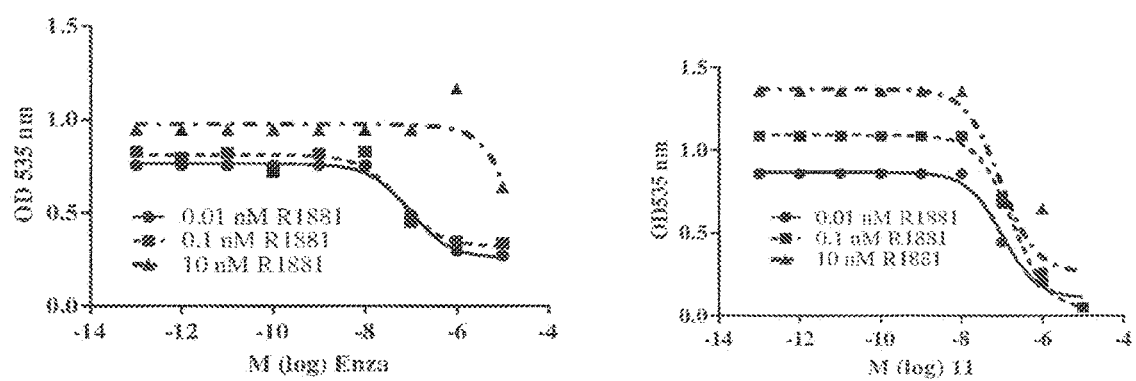

FIG. 44: Increasing concentrations of R1881 decreased enzalutamide's, but not 11's, potential to inhibit LNCaP cell proliferation. LNCaP cells were plated in charcoal stripped serum containing medium and treated with a dose response of 11 (left panel) or enzalutamide (right panel) in combination with 0.1 or 10 nM R1881. Medium was changed and the cells were re-treated after 3 days. At the end of 6 days of treatment, cells were fixed and SRB assay, a measure of cell viability, was performed.

Figure 45:
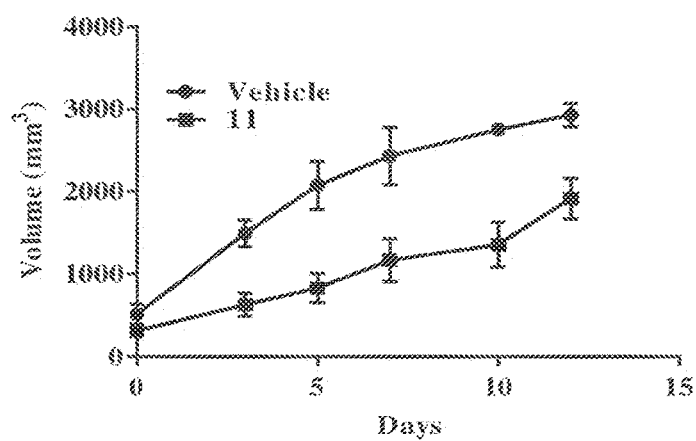

FIG. 45: 11 inhibited androgen-dependent and castration-resistant PCa growth in vivo. LNCaP cells (5 million/mouse) mixed with matrigel were implanted subcutaneously on the flanks of intact NSG mice (n=6-8 mice/group). Once tumors reached 100-200 mm$^3$, animals were randomized and treated with vehicle or 11 (50 mg/kg/day s.c.). Tumor volume was measured twice weekly. Tumor weights were recorded at sacrifice. 11 inhibited growth of patient-derived xenograft, Pr-3001. Pr-3001 was implanted as 1 mm$^3$ fragment subcutaneously in castrated NSG mice (n=8-10/group) and the study was performed as described above. Tumor volume was measured thrice weekly. At sacrifice tumor weights were recorded (not shown). * significance from vehicle-treated mice at p<0.05.

Figure 46A:
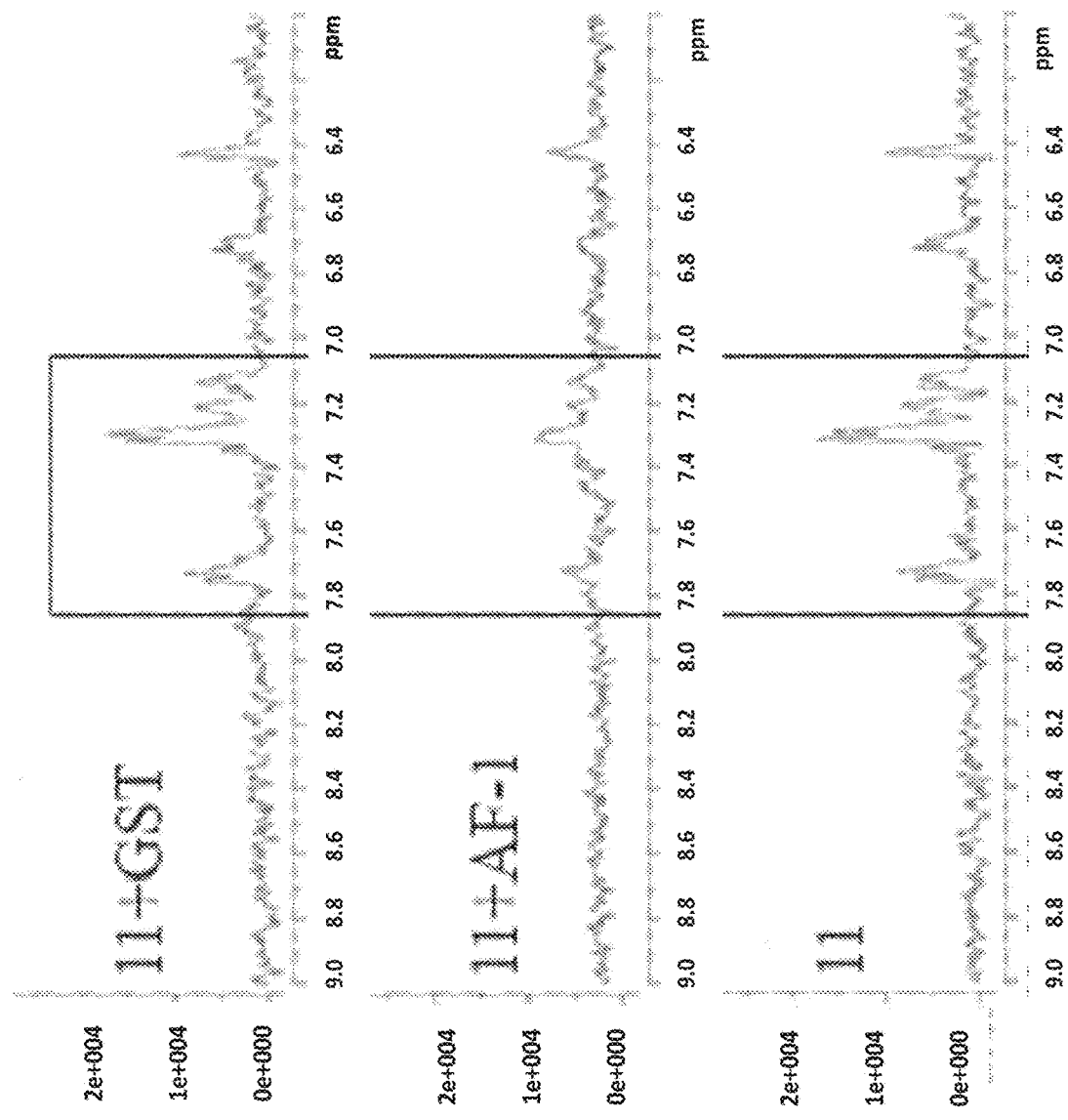
Figure 46B:
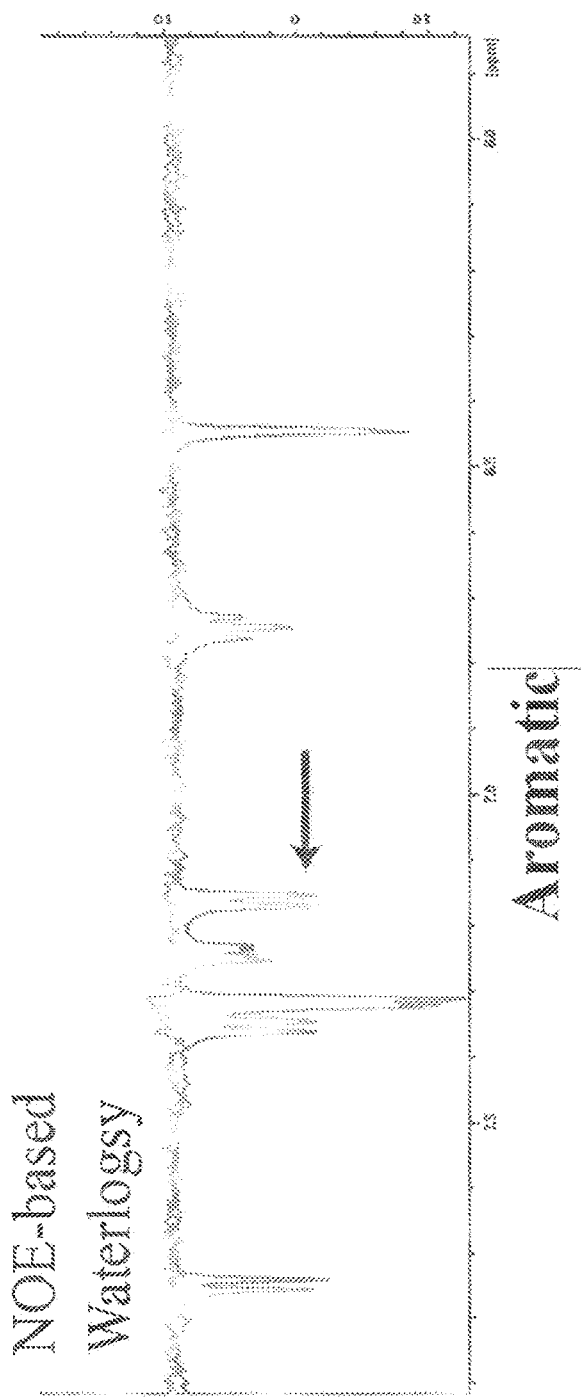
Figure 46C:
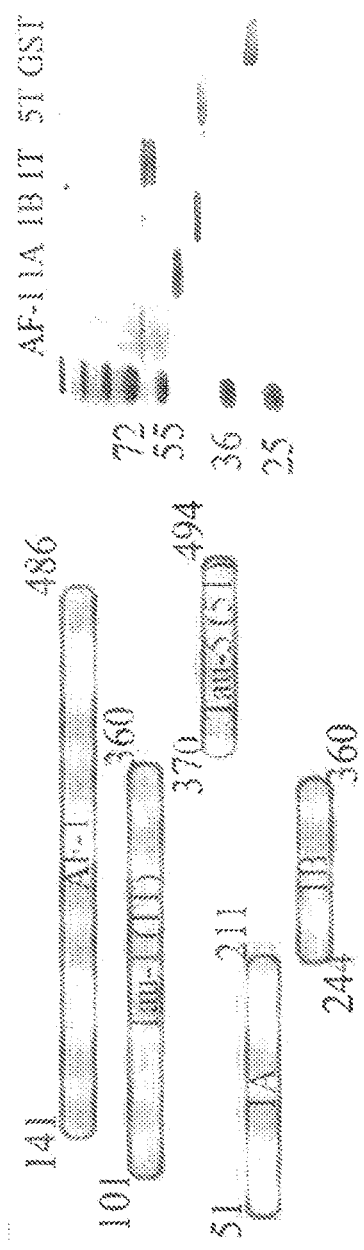
Figure 46D:
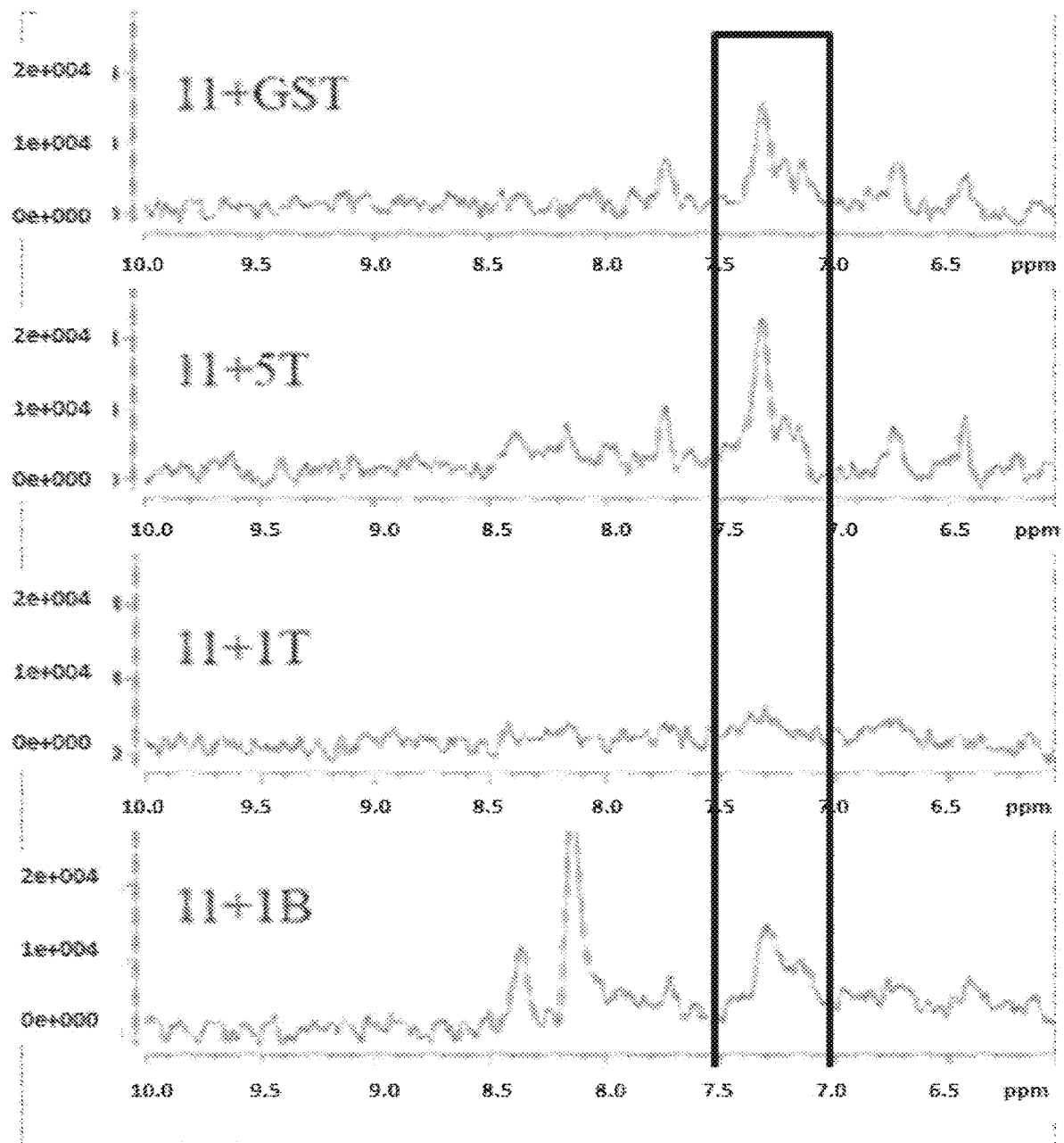
Figure 46D:
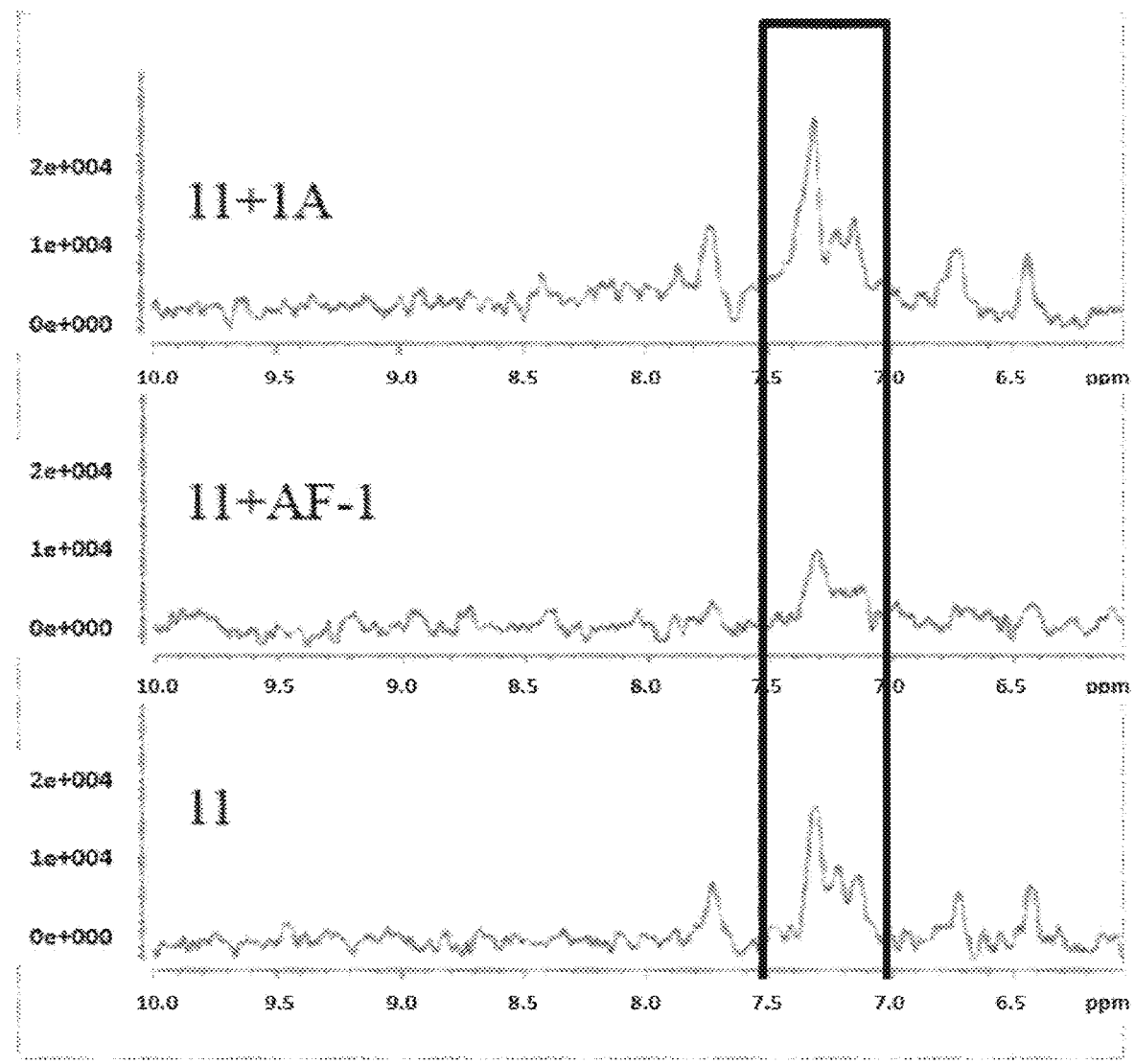

FIGS. 46A-46D: 11 binds to the AR Activation Function Domain 1 (AF-1) between amino acids 244 and 360. Nuclear magnetic resonance (NMR) studies confirm the binding to AR-AF-1. 11 or enzalutamide (500 μM) dissolved in deuterated-DMSO were either added to an NMR tube alone or in combination with 5 µM GST (negative control) or GST-AF-1 purified protein. The intensity of nuclear spin was measured at different magnetic fields (6 ppm). The peaks between 7 and 8 ppm (shown in box) correspond to the aromatic rings of 11 and enzalutamide (FIG. 46A). Waterlogsy experiment with 11 (200 µM) alone or in combination with 2 µM purified GST-AR-AF-1 was performed as a confirmation for binding (FIG. 46B). Map of various N-terminal domain fragments cloned, expressed, and corresponding proteins purified. Purified proteins and molecular weight markers are shown (M.Wt. of fragments=M.Wt.+ GST M.Wt. of 26 KDa) (FIG. 46C). NMR studies were performed with 11 (500 µM) was performed with 5 M of various N-terminal domain fragments as described in panel 46C (FIG. 46D).

Figure 47:
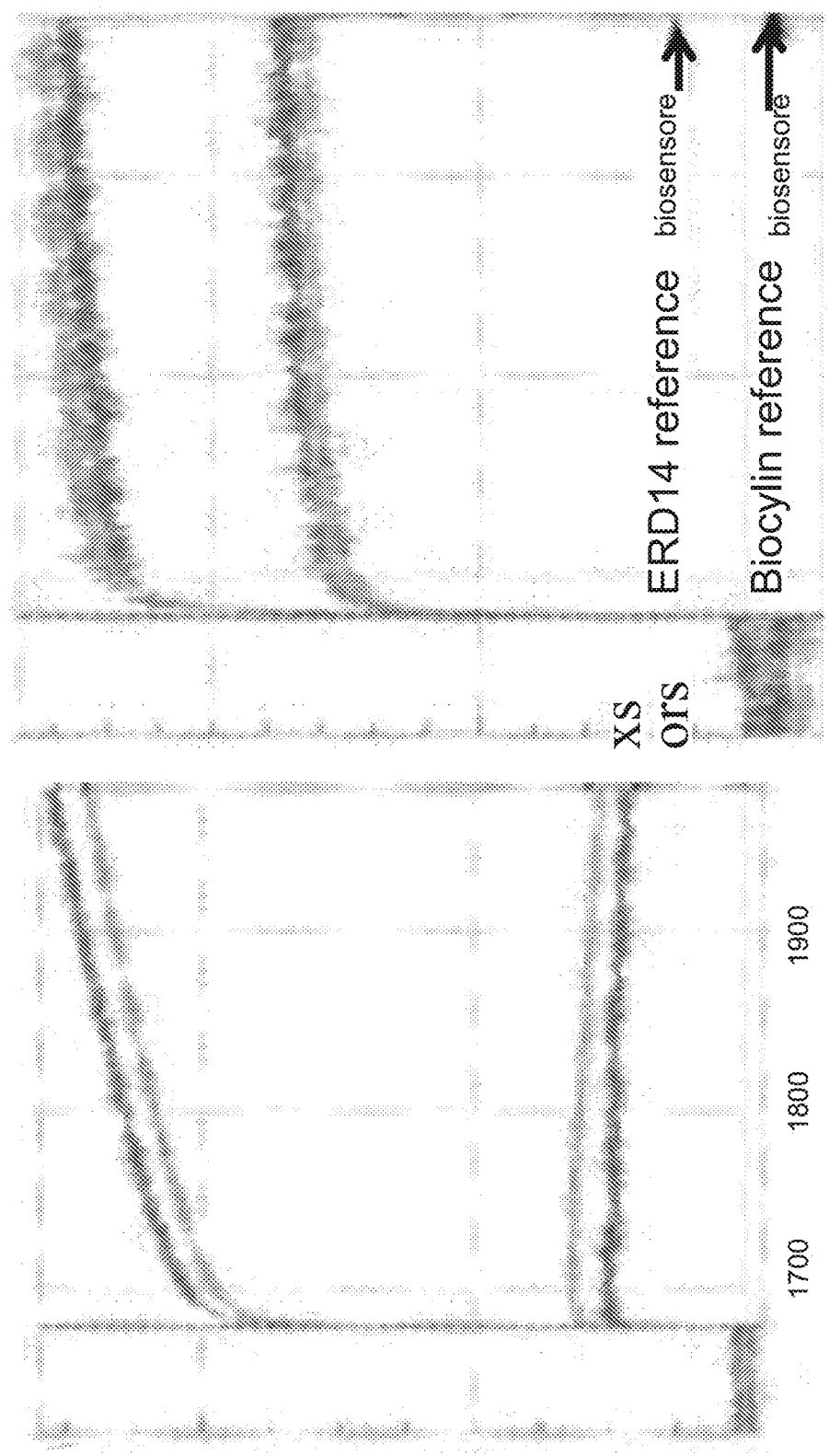

FIG. 47: 11 binds to AR AF-1 domain based on surface plasmon resonance. Biocore assay was performed with purified activation function domain 1 (AF-1) of the androgen receptor (AR) in the presence of 11.

Figure 48:
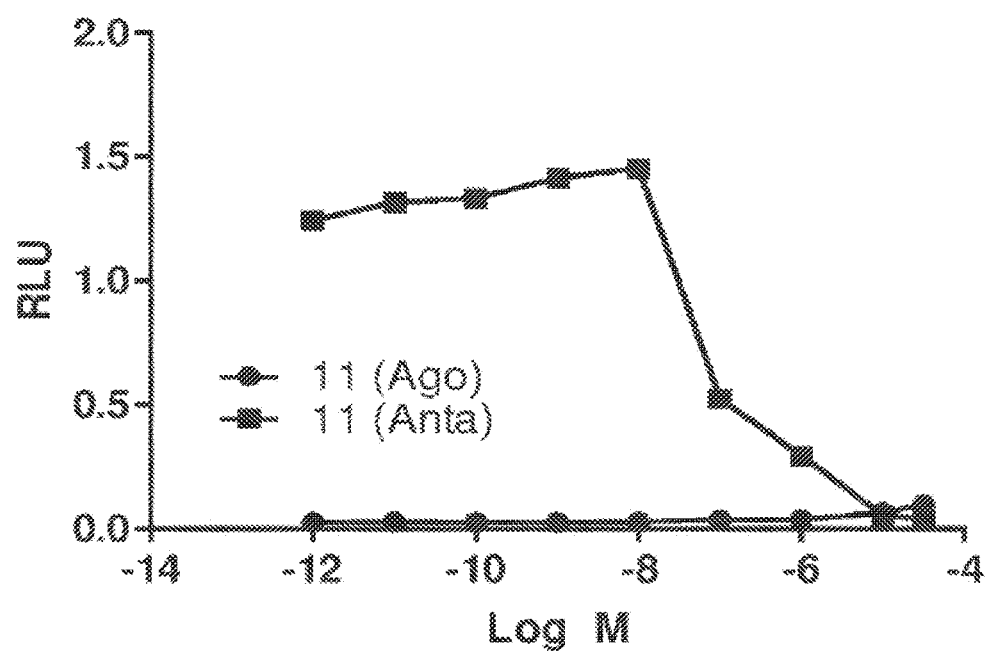

FIG. 48: 11 is a full antagonist with no agonist activity in transactivation studies.

Figure 49A:
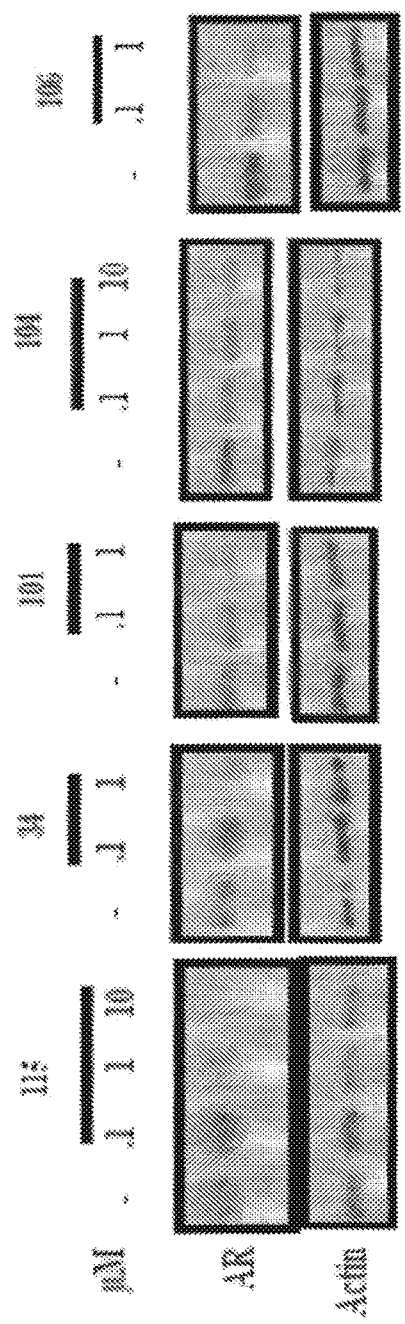
Figure 49B:
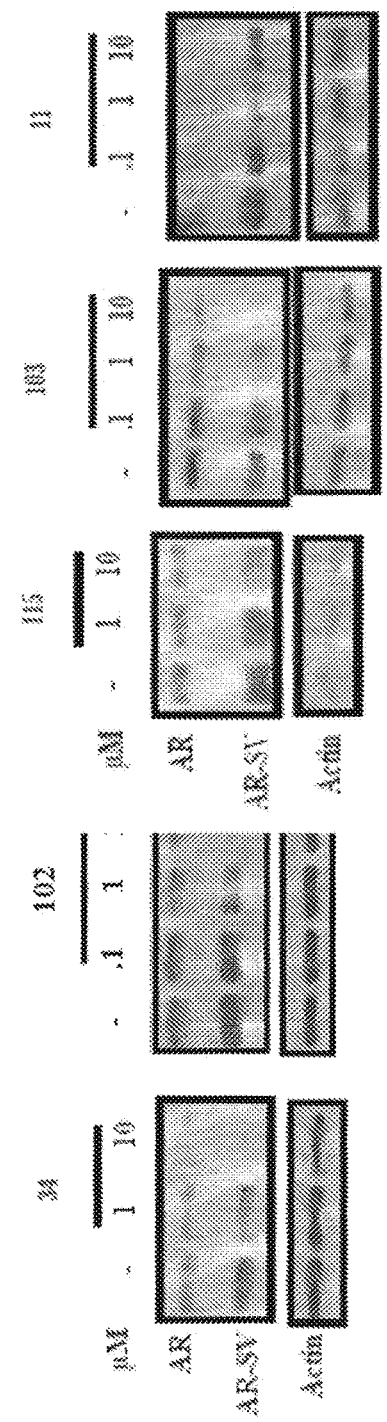

FIGS. 49A and 49B: Degradation of FL AR and AR SV by selected SARDs. LNCaP (FIG. 49A) or 22RV1 (FIG. 49B) cells were plated in full-serum containing medium. Medium was changed to 1% charcoal-stripped serum containing medium and maintained in this medium for 2 days. Medium was changed again and the cells were treated with 0.1 nM R1881 (agonist) and either vehicle or a titration of SARD as indicated in the figure. Twenty-four hours after treatment, cells were harvested, protein extracted, and the proteins were blotted with AR-N20 antibody. Blots were stripped and re-probed with an actin antibody. AR—full length androgen receptor; AR-SV-androgen receptor splice variant.

Figure 50A:
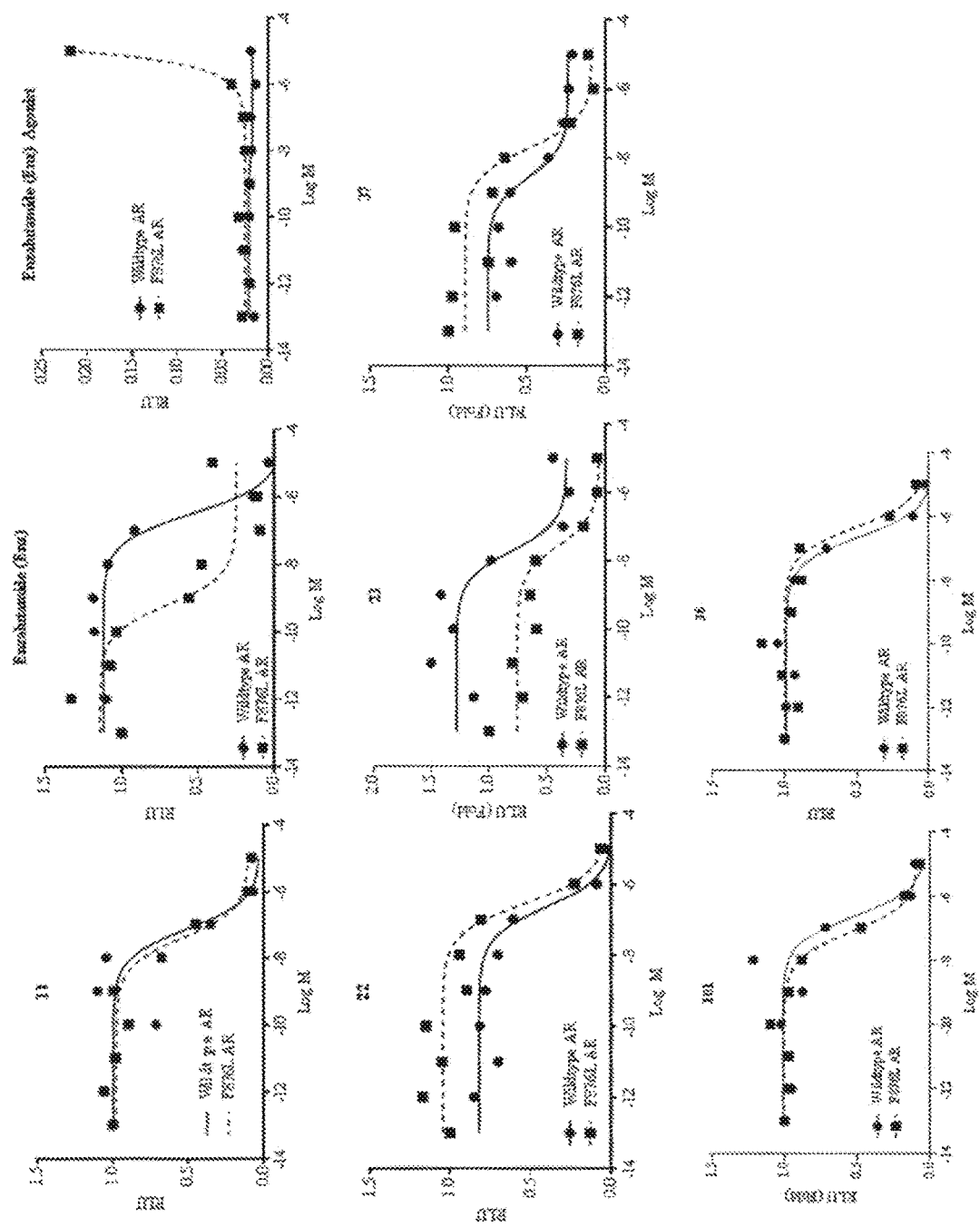
Figure 50B:
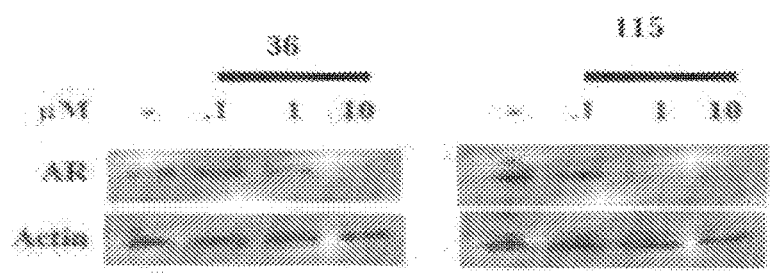

FIGS. 50A and 50B: SARDs antagonized transactivation of and degraded an enzalutamide resistance (Enz-R) conferring escape mutant AR. FIG. 50A: AR with phenylalanine 876 mutated to leucine (F876L), GRE-LUC, and CMV-renilla LUC were transfected in COS cells. Cells were treated 24 h after transfection with 0.1 nM R1881 (agonist) and a dose response of antagonists. Luciferase assay was performed 48 h after transfection. FIG. 50B: Enzalutamide-resistant LNCaP cells (MR49F) were maintained in charcoal-stripped, serum containing medium for 2 d and treated with 0.1 nM R1881 (agonist) and a titration of the SARD as indicated in the figure.

Figure 51:
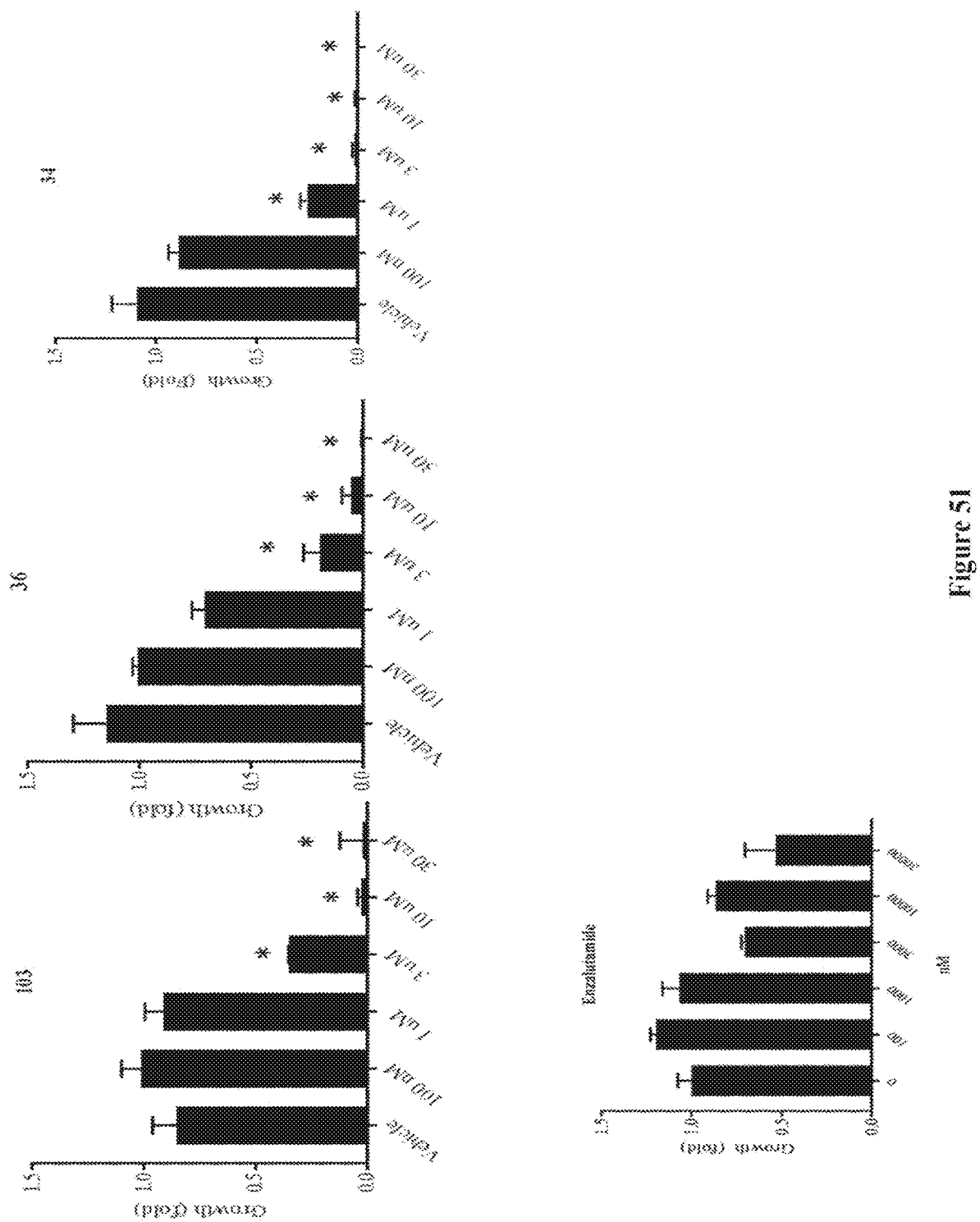

FIG. 51: Enzalutamide-resistant LNCaP (MR49F) cellular anti-proliferation: Enzalutamide-resistant LNCaP (MR49F) cells were plated in 1% charcoal-stripped, serum-containing medium and treated with 0.1 nM R1881 and titration of antagonist as indicated in the figure. Cells were re-treated 3 d after the first treatment and the number of viable cells measured by Cell-Titer Glo assay (Promega, Madison, Wis.). N=3. *=p<0.05.

Figure 52A:
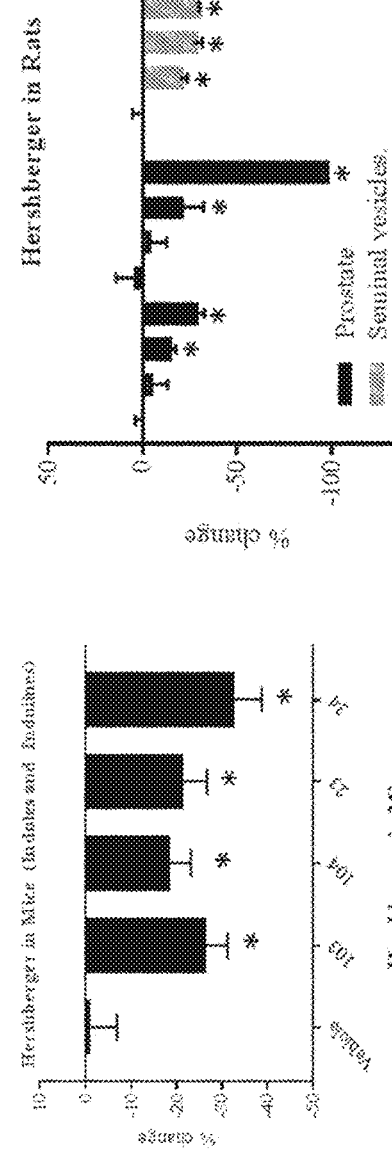
Figure 52B:

FIGS. 52A and 52B: SARDs inhibit androgen-dependent organs in mice and rats and inhibit growth of enzalutamide-resistant prostate cancer. FIG. 52A: Mice (left) or rats (right) were treated with vehicle or indicated SARDs (40 mg/kg/day left panel) orally (n=5/group). Animals were sacrificed 14 d after treatment and weights of prostate and seminal vesicles were measured and normalized to body weight. FIG. 52B: Enzalutamide resistant LNCaP cells (5 million/mouse) were implanted subcutaneously in male NOD SCID Gamma (NSG) mice (n=7-9 per group). Animals were castrated when the tumors reached 100-200 mm$^3$ and allowed to regrow as castration-resistant tumors. Animals were treated orally with vehicle (DMSO:PEG-300 15:85) or 100 mg/kg/day of SARD. Tumor volume was measured twice weekly and represented as percent change. Values are expressed as average±S.E. *=p<0.05.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Androgens act in cells by binding to the AR, a member of the steroid receptor superfamily of transcription factors. As the growth and maintenance of prostate cancer (PCa) is largely controlled by circulating androgens, treatment of PCa heavily relies on therapies that target AR. Treatment with AR antagonists such as enzalutamide, flutamide, bicalutamide or hydroxyflutamide to disrupt receptor activation has been successfully used in the past to reduce PCa growth. All currently available AR antagonists competitively bind AR and recruit corepressors such as NCoR and SMRT to repress transcription of target genes. However, altered intracellular signaling, AR mutations, and increased expression of coactivators lead to functional impairment of antagonists or even transformation of antagonists into agonists. Studies have demonstrated that mutation of W741, T877, and F876 within AR converts bicalutamide, hydroxyflutamide, and enzalutamide respectively, to agonists. Similarly, increased intracellular cytokines recruit coactivators instead of corepressors to AR-responsive promoters subsequently converting bicalutamide to an agonist.

Despite initial response to androgen deprivation therapy (ADT), PCa disease progression is inevitable and the cancer emerges as castration resistant prostate cancer (CRPC). The primary reason for castration resistant prostate cancer (CRPC) re-emergence is re-activation of androgen receptor (AR) by alternate mechanisms such as:
 (a) intracrine androgen synthesis;
 (b) expression of AR splice variants (AR-SV) that lack ligand binding domain (LBD);
 (c) AR-LBD mutations with potential to resist antagonists;
 (d) hyper-sensitization of AR to low androgen levels or promiscuous AR activation via other hormones (e.g., progestins, mineralocorticoids, estrogens, glucocorticoids, etc.), possibly due to AR gene amplification or AR mutation;
 (e) amplification of the AR gene within the tumor; and
 (f) over expression of coactivators.

In one embodiment, this invention is directed to novel selective androgen receptor degrader (SARD) compounds, which inhibit the growth of prostate cancer (PCa) cells and tumors that are dependent on AR full length (AR-FL) including pathogenic and resistance-conferring mutation and/or wildtype, and/or AR splice variants (AR-SV) for proliferation.

Alternatively, a "selective androgen receptor degrader" (SARD) compound is an androgen receptor antagonist capable of causing degradation of a variety of pathogenic mutant variant AR's and wildtype AR and hence are capable of exerting anti-androgenism is a wide variety of pathogenic altered cellular environments found in the disease states embodied in this invention. In one embodiment, the SARD is orally active. In another embodiment, the SARD is applied topically to the site of action.

According to this invention, a "selective androgen receptor degrader" (SARD) compound is an androgen receptor antagonist that is capable of inhibiting the growth of PCa cells and tumors that are dependent on AR-full length (AR-FL) and/or AR splice variants (AR-SV) for proliferation. In another embodiment, the SARD compound does not bind to the ligand binding domain (LBD). In another embodiment, the SARD compound binds to the N-terminal domain (NTD) of the AR. In another embodiment, the SARD compound binds to an alternate binding and degradation domain (BDD) of the AR. In another embodiment, the SARD compound binds both to the AR ligand binding domain (LBD) and to an alternate binding and degradation domain (BDD). In another embodiment, the SARD compound binds both to the N-terminal domain (NTD) and to the ligand binding domain (LBD) of the AR. In another embodiment, the SARD compound is capable of inhibiting growth driven by the N-terminal domain (NTD)-dependent constitutively active AR-SV. In another embodiment, the SARD compound inhibits the AR through binding to a domain that is distinct from the AR LBD. In another embodiment, the SARD compound is a strong (i.e., highly potent and highly efficacious) selective androgen receptor antagonist, which antagonizes the AR more robustly than other known AR antagonists (e.g., enzalutamide, flutamide, bicalutamide and abiraterone). In another embodiment, the SARD compound is a selective androgen receptor antagonist, which targets AR-SVs, which cannot be inhibited by conventional antagonists. In another embodiment, the SARD compound exhibits AR-splice variant (AR-SV) degradation activity. In another embodiment, the SARD compound further exhibits AR-full length (AR-FL) degradation activity. In another embodiment, the SARD compound exhibits AR-splice variant (AR-SV) inhibitory activity (i.e., is an AR-SV antagonist). In another embodiment, the SARD compound further exhibits AR-full length (AR-FL) inhibitory activity (i.e., is an AR-FL antagonist). In another embodiment, the SARD compound possesses dual AR-SV degradation and AR-SV inhibitory functions. In another embodiment, the SARD compound further possesses dual AR-FL degradation and AR-FL inhibitory functions. In another embodiment, the SARD compound is a selective androgen receptor antagonist, which targets AR-SVs. In another embodiment, the SARD compound further targets AR-FLs. In another embodiment, the SARD compound inhibits the constitutive activation of AR-SVs. In another embodiment, the SARD compound further inhibits the constitutive activation of AR-FLs. In another embodiment, the SARD compound is a selective androgen receptor antagonist, which degrades AR-full length (AR-FL) and AR splice variants (AR-SV). In another embodiment, the SARD compound degrades the AR through binding to a domain that is distinct from the AR LBD. In another embodiment, the SARD compound possesses dual degradation and AR-SV inhibitory functions, that are distinct from any available CRPC therapeutics. In another embodiment, the SARD compound inhibits the re-activation of the AR by alternate mechanisms such as: intracrine androgen synthesis, expression of AR splice variants (AR-SV) that lack ligand binding domain (LBD) and AR-LBD mutations with potential to resist antagonists. In another embodiment, the SARD compound inhibits re-activated androgen receptors present in pathogenically altered cellular environments.

Nonlimiting examples of AR-splice variants (AR-SVs) are: AR-V7 and ARv567es (a.k.a. AR-V12). Nonlimiting examples of AR mutations conferring antiandrogen resistance are: W741L, T877A, H874Y, T877S, or F876L. AR-V7 is a splice variant of AR that lacks the LBD. It is constitutively active and has been demonstrated to be responsible for aggressive PCa and resistance to endocrine therapy.

In one embodiment, this invention is directed to novel selective androgen receptor degrader (SARD) compounds, which bind to the AR through an alternate binding and degradation domain (BDD). In another embodiment, the SARD further binds the AR ligand binding domain (LBD).

In one embodiment, this invention is directed to novel selective androgen receptor degrader (SARD) compounds, which exhibit AR-splice variant (AR-SV) inhibitory activity (i.e., is an AR-SV antagonist). In another embodiment, the novel selective androgen receptor degrader (SARD) compounds, further exhibit AR-full length (AR-FL) inhibitory activity (i.e., is an AR-FL antagonist).

In one embodiment, this invention is directed to novel selective androgen receptor degrader (SARD) compounds, which exhibit AR-splice variant (AR-SV) degradation activity. In another embodiment, the novel selective androgen receptor degrader (SARD) compounds, further exhibit AR-full length (AR-FL) degradation activity.

In one embodiment, this invention is directed to novel selective androgen receptor degrader (SARD) compounds, which possess dual AR-SV degradation and AR-SV inhibitory functions. In another embodiment, the SARDs further possess dual AR-FL degradation and AR-FL inhibitory functions. In another embodiment, this invention is directed to novel selective androgen receptor degrader (SARD) compounds, which possess dual AR-SV and AR-FL degradation, and AR-SV and AR-FL inhibitory functions.

In one embodiment, this invention is directed to novel selective androgen receptor degrader (SARD) compounds, for use in treating CRPC that cannot be treated with any other antagonist.

In one embodiment, this invention is directed to selective androgen receptor degrader (SARD) compounds, for use in treating CRPC, by degrading AR-SVs.

In one embodiment, the novel SARD compounds according to this invention maintain their antagonistic activity in AR mutants that normally convert AR antagonists to agonists. In another embodiment, the SARD compounds maintain their antagonistic activity to AR mutants such as any of the following mutations: W741L, T877A, H874Y, T877S, or F876L. In another embodiment, the SARD compounds elicit antagonistic activity within an altered cellular environment in which LBD-targeted agents are not effective. In another embodiment, the SARD compounds elicit antagonistic activity within an altered cellular environment in which NTD-dependent AR activity is constitutively active.

Selective Androgen Receptor Degrader (SARD) Compounds

In one embodiment, this invention is directed to a selective androgen receptor degrader (SARD) compound represented by the structure of formula XVII, XVIIa, XVIIb, XVIIc, or XVIId:

XVII

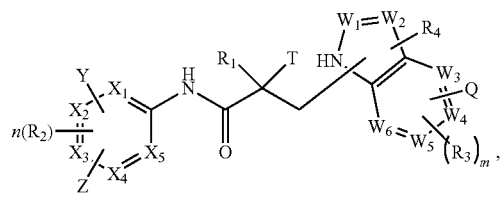

XVIIa

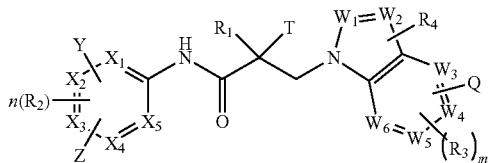

XVIIb

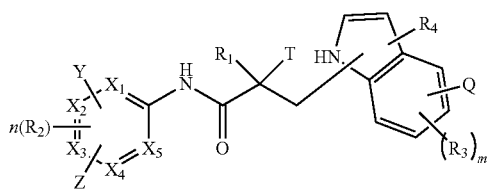

XVIIc

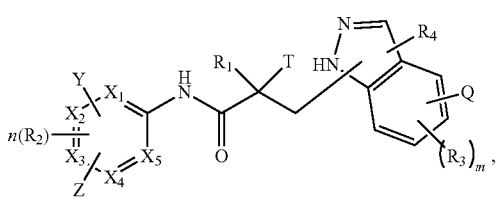

XVIId

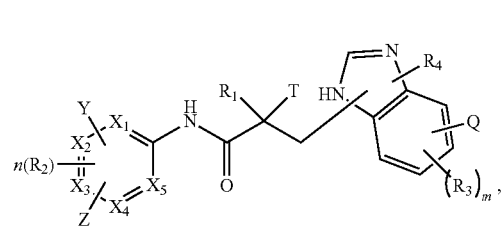

or

XVIIe

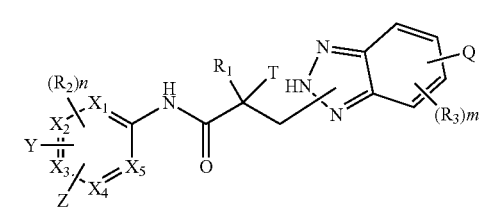

wherein
- $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
- $W_1$ and $W_2$ are each independently selected from N or CH;
- $W_3$, $W_4$, $W_5$ and $W_6$ are each independently selected from CH or N;
- wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —NHCOCH$_3$, NHCOR or

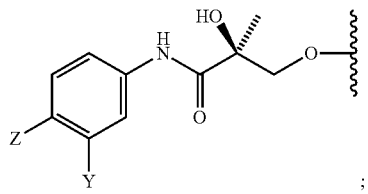

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ and $R_4$ are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, $X_1$, $X_2$, $X_3$, $X_4$, and $X_5$ are CH. In one embodiment, $X_1$ or $X_5$ is N. In one embodiment, at least one of $X_1$, $X_2$, $X_3$, $X_4$, and $X_5$ is N. In one embodiment, $X_2$ or $X_4$ is N. In one embodiment, $X_3$ is N. In one embodiment, $X_1$ is N and $X_2$, $X_3$, $X_4$, and $X_5$ are CH. In one embodiment, $X_2$ is N and $X_1$, $X_3$, $X_4$, and $X_5$ are CH. In one embodiment, $X_3$ is N and $X_1$, $X_2$, $X_4$, and $X_5$ are CH. In one embodiment, two of $X_1$, $X_2$, $X_3$, $X_4$, and $X_5$ are N. In one embodiment, $X_1$ and $X_3$ are both N. In one embodiment, $X_1$ and $X_5$ are both N. In one embodiment, $X_2$ and $X_4$ are both N. In one embodiment, $X_4$ is N and $X_1$, $X_2$, $X_3$, and $X_5$ are CH.

In another embodiment, $W_1$, $W_2$, $W_3$, $W_4$, $W_5$, and $W_6$ of formula XVII or XVIIa, are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N.

In another embodiment, $W_1$ is N and $W_1$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula XVII(1), XVIIa(1), XVIIb(1), XVIIc(1), or XVIId(1):

XVII(1)
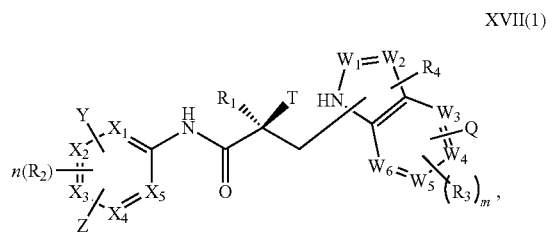

XVIIa(1)
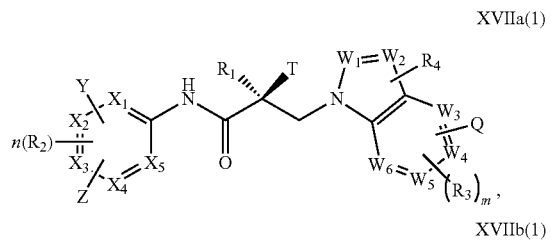

XVIIb(1)
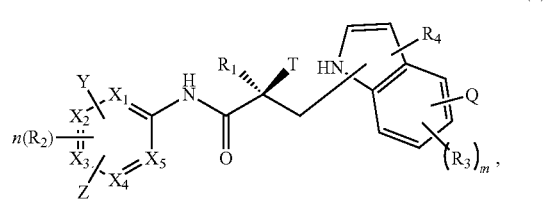

XVIIc(1)

XVIId(1)
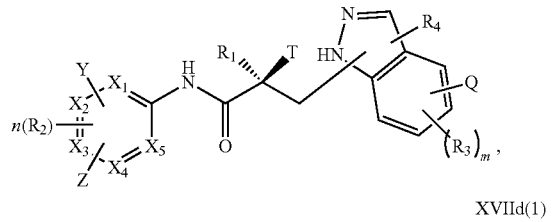
or

XVIIe(1)
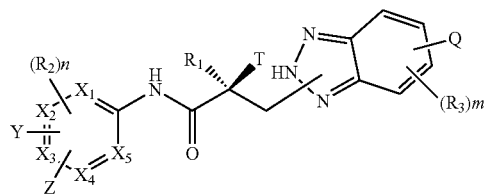

wherein
  $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
  $W_1$ and $W_2$ are each independently selected from N or CH;
  $W_3$, $W_4$, $W_5$ and $W_6$ are each independently selected from CH or N;
  wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;
  T is OH, OR, —NHCOCH$_3$, NHCOR or

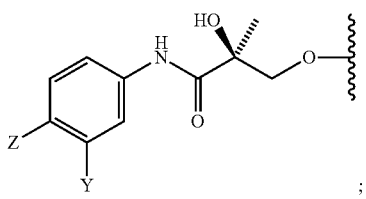;

Z is NO$_2$, CN, COOH, COR, NHCOR or CONHR;
  Y is CF$_3$, F, I, Br, Cl, CN or C(R)$_3$;
  R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
  R$_1$ is CH$_3$, CH$_2$F, CHF$_2$, CF$_3$, CH$_2$CH$_3$, or CF$_2$CF$_3$;
  R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
  Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
  R$_3$ and R$_4$ are independently selected from hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, $X_1$, $X_2$, $X_3$, $X_4$, and $X_5$ are CH. In one embodiment, at least one of $X_1$, $X_2$, $X_3$, $X_4$, and $X_5$ is N. In one embodiment, $X_1$ or $X_5$ is N. In one embodiment, $X_2$ or $X_4$ is N. In one embodiment, $X_3$ is N. In one embodiment, $X_1$ is N and $X_2$, $X_3$, $X_4$, and $X_5$ are CH. In one embodiment, $X_2$ is N and $X_1$, $X_3$, $X_4$, and $X_5$ are CH. In one embodiment, $X_3$ is N and $X_1$, $X_2$, $X_4$, and $X_5$ are CH. In one embodiment, two of $X_1$, $X_2$, $X_3$, $X_4$, and $X_5$ are N. In one embodiment, $X_1$ and $X_3$ are both N. In one embodiment, $X_1$ and $X_5$ are both N. In one embodiment, $X_2$ and $X_4$ are both N. In one embodiment, $X_4$ is N and $X_1$, $X_2$, $X_3$, and $X_5$ are CH.

In another embodiment, $W_1$, $W_2$, $W_3$, $W_4$, $W_5$, and $W_6$ of formula XVII(1) or XVIIa(1), are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N.

In another embodiment, $W_1$ is N and $W_2$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula XVII(2), XVIIa(2), XVIIb(2), XVIIc(2), or XVIId(2):

XVII(2)

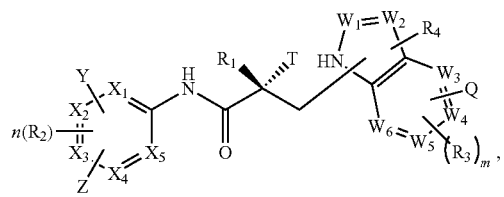

XVIIa(2)

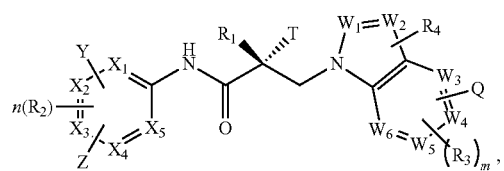

XVIIb(2)

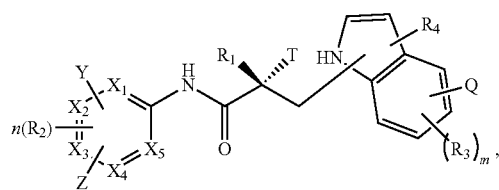

XVIIc(2)

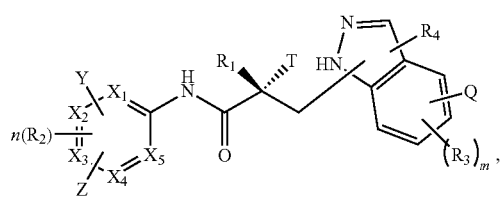

XVIId(2)

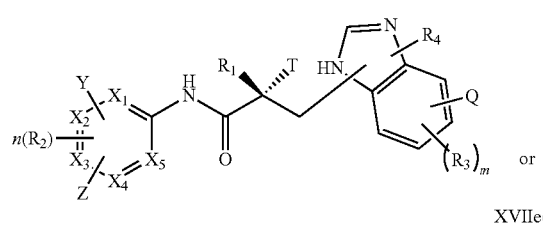

XVIIe(2)

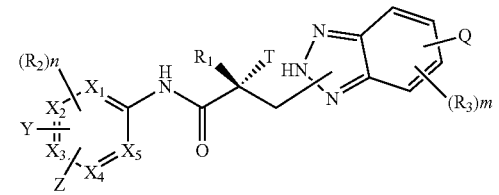

wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

$W_1$ and $W_2$ are each independently selected from N or CH;

$W_3$, $W_4$, $W_5$ and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —NHCOCH$_3$, NHCOR or

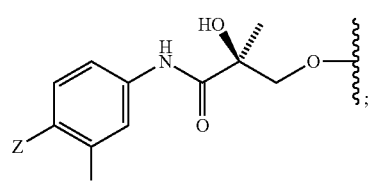

Z is NO$_2$, CN, COOH, COR, NHCOR or CONHR;

Y is CF$_3$, F, I, Br, Cl, CN or C(R)$_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ and $R_4$ are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, $X_1$, $X_2$, $X_3$, $X_4$, and $X_5$ are CH. In one embodiment, $X_1$ or $X_5$ is N. In one embodiment, at least one of $X_1$, $X_2$, $X_3$, $X_4$, and $X_5$ is N. In one embodiment, $X_2$ or $X_4$ is N. In one embodiment, $X_3$ is N. In one embodiment, $X_1$ is N and $X_2$, $X_3$, $X_4$, and $X_5$ are CH. In one embodiment, $X_2$ is N and $X_1$, $X_3$, $X_4$, and $X_5$ are CH. In one embodiment, $X_3$ is N and $X_1$, $X_2$, $X_4$, and $X_5$ are CH. In one embodiment, two of $X_1$, $X_2$, $X_3$, $X_4$, and $X_5$ are N. In one embodiment, $X_1$ and $X_3$ are both N. In one embodiment, $X_1$ and $X_5$ are both N. In one embodiment, $X_2$ and $X_4$ are both N. In one embodiment, $X_4$ is N and $X_1$, $X_2$, $X_3$, and $X_5$ are CH.

In another embodiment, $W_1$, $W_2$, $W_3$, $W_4$, $W_5$, and $W_6$ of formula XVII or XVIIa, are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N. In another embodiment, $W_1$ is N and $W_2$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula XVIII:

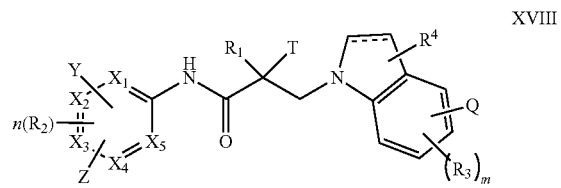

XVIII wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

====== is a single or double bond;

T is OH, OR, —$NHCOCH_3$, NHCOR or

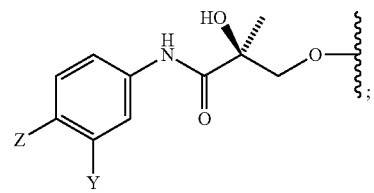

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, F, Cl, Br, I, CF$_3$, CN, NO$_2$, NH$_2$, SH, keto, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3 or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XVIII(1):

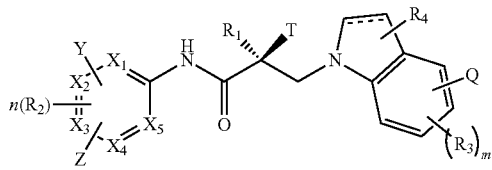

XVIII(1)

wherein

X$_1$, X$_2$, X$_3$, X$_4$, and X$_5$ are each independently N or CH, wherein if any one of X$_1$, X$_2$, X$_3$, X$_4$, and X$_5$ is CH, then the H is optionally replaced with R$_2$, Y, or Z in the respective position, and if any one of X$_1$, X$_2$, X$_3$, X$_4$, and X$_5$ is not CH, then the respective position is unsubstituted;

===== is a single or double bond;

T is OH, OR, —NHCOCH$_3$, NHCOR or

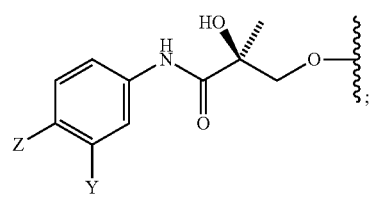

Z is NO$_2$, CN, COOH, COR, NHCOR or CONHR;

Y is CF$_3$, F, I, Br, Cl, CN or C(R)$_3$;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;

R$_1$ is CH$_3$, CH$_2$F, CHF$_2$, CF$_3$, CH$_2$CH$_3$, or CF$_2$CF$_3$;

R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, F, Cl, Br, I, CF$_3$, CN, NO$_2$, NH$_2$, SH, keto, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIX:

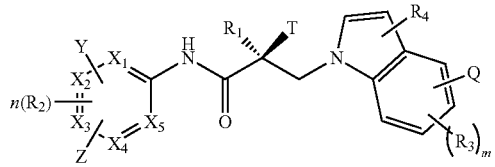

XIX wherein

X$_1$, X$_2$, X$_3$, X$_4$, and X$_5$ are each independently N or CH, wherein if any one of X$_1$, X$_2$, X$_3$, X$_4$, and X$_5$ is CH, then the H is optionally replaced with R$_2$, Y, or Z in the respective position, and if any one of X$_1$, X$_2$, X$_3$, X$_4$, and X$_5$ is not CH, then the respective position is unsubstituted;

T is OH, OR, —NHCOCH₃, NHCOR or

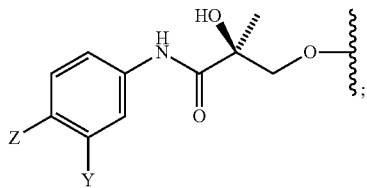

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₄ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XX:

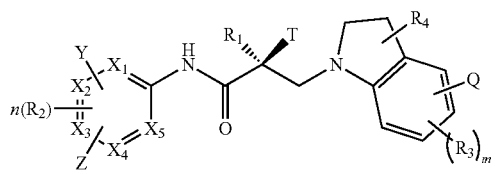

XX wherein
X₁, X₂, X₃, X₄, and X₅ are each independently N or CH, wherein if any one of X₁, X₂, X₃, X₄, and X₅ is CH, then the H is optionally replaced with R₂, Y, or Z in the respective position, and if any one of X₁, X₂, X₃, X₄, and X₅ is not CH, then the respective position is unsubstituted;
T is OH, OR, —NHCOCH₃, NHCOR or

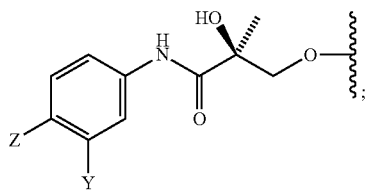

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_4$ is hydrogen, F, Cl, Br, I, CF$_3$, CN, NO$_2$, NH$_2$, SH, keto, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula I, Ia, Ib, Ic, or Id:

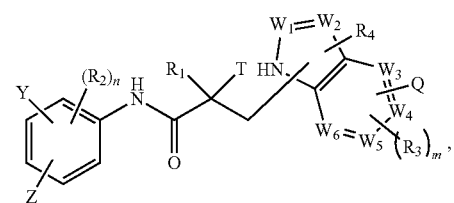

I

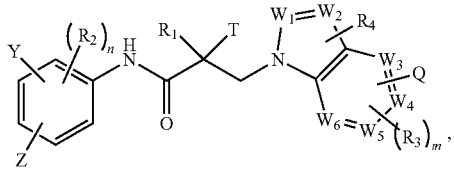

Ia

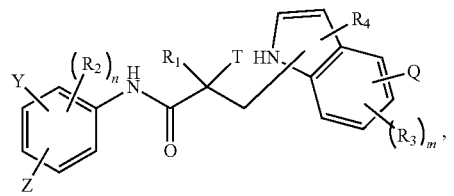

Ib

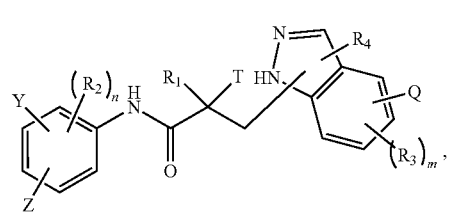

Ic

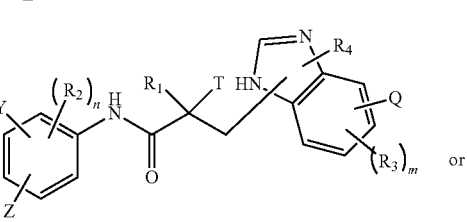

Id or

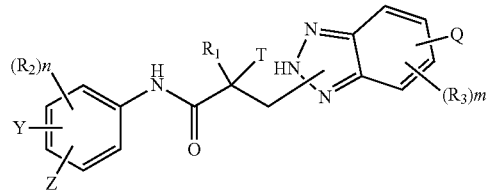

Ie wherein

W$_1$ and W$_2$ are each independently selected from N or CH;

W$_3$, W$_4$, W$_5$ and W$_6$ are each independently selected from CH or N;

wherein if any one of W$_1$, W$_2$, W$_3$, W$_4$, W$_5$, and W$_6$ is CH, then the H is optionally replaced with R$_4$, Q or R$_3$ in the respective position, and if any one of W$_1$, W$_2$, W$_3$, W$_4$, W$_5$, and W$_6$ is not CH, then the respective position is unsubstituted;

T is OH, OR, —NHCOCH$_3$, NHCOR or

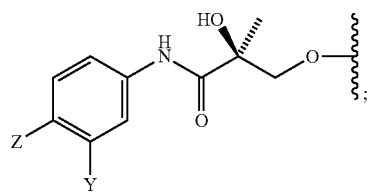

Z is NO$_2$, CN, COOH, COR, NHCOR or CONHR;

Y is CF$_3$, F, I, Br, Cl, CN or C(R)$_3$;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;

R$_1$ is CH$_3$, CH$_2$F, CHF$_2$, CF$_3$, CH$_2$CH$_3$, or CF$_2$CF$_3$;

R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ and R$_4$ are independently selected from hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, W$_1$, W$_2$, W$_3$, W$_4$, W$_5$, and W$_6$ of formula I or Ia, are each independently CH. In another embodiment, W$_1$ is N. In another embodiment, W$_2$ is N. In another embodiment, W$_1$ is CH. In another embodiment, W$_2$ is CH. In another embodiment, W$_3$ is N. In another embodiment, W$_4$ is N. In another embodiment, W$_5$ is N. In another embodiment, W$_6$ is N.

In another embodiment, W$_1$ is N and W$_1$, W$_3$, W$_4$, W$_5$, and W$_6$ are CH. In another embodiment, W$_2$ is N and W$_1$, W$_3$, W$_4$, W$_5$, and W$_6$ are CH. In another embodiment, W$_3$ is N and W$_1$, W$_2$, W$_4$, W$_5$, and W$_6$ are CH. In another embodiment, W$_4$ is N and W$_1$, W$_2$, W$_3$, W$_5$, and W$_6$ are CH. In another embodiment, W$_5$ is N and W$_1$, W$_2$, W$_3$, W$_4$, and W$_6$ are CH. In another embodiment, W$_6$ is N and W$_1$, W$_2$, W$_3$, W$_4$, and W$_5$ are CH.

In one embodiment, this invention is directed to a selective androgen receptor degrader (SARD) compound represented by the structure of formula I(1), Ia(1), Ib(1), Ic(1), or Id(1):

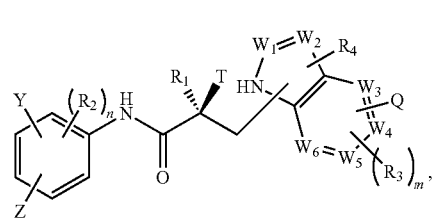

I(1)

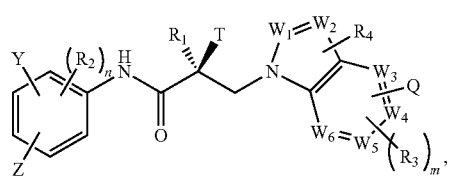

Ia(1)

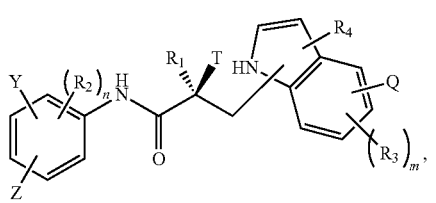

Ib(1)

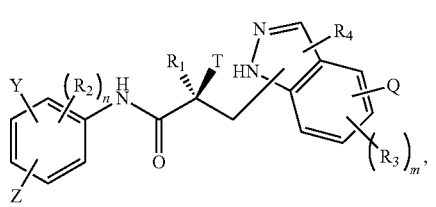

Ic(1)

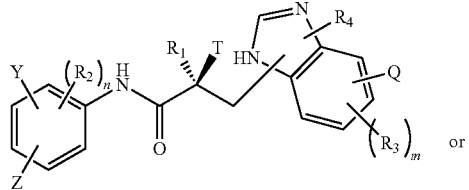

Id(1)

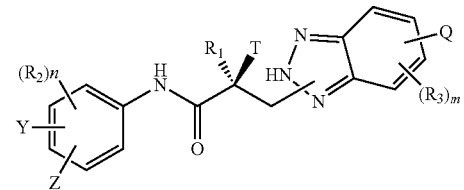

Ie(1)

wherein

W$_1$ and W$_2$ are each independently selected from N or CH;

W$_3$, W$_4$, W$_5$ and W$_6$ are each independently selected from CH or N;

wherein if any one of W$_1$, W$_2$, W$_3$, W$_4$, W$_5$, and W$_6$ is CH, then the H is optionally replaced with R$_4$, Q or R$_3$ in the respective position, and if any one of W$_1$, W$_2$, W$_3$, W$_4$, W$_5$, and W$_6$ is not CH, then the respective position is unsubstituted;

T is OH, OR, —NHCOCH$_3$, NHCOR or

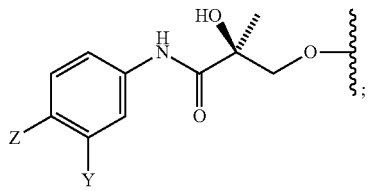

Z is NO$_2$, CN, COOH, COR, NHCOR or CONHR;

Y is CF$_3$, F, I, Br, Cl, CN or C(R)$_3$;

R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;

R$_1$ is CH$_3$, CH$_2$F, CHF$_2$, CF$_3$, CH$_2$CH$_3$, or CF$_2$CF$_3$;

R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;

Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R$_3$ and R$_4$ are independently selected from hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, $W_1$, $W_2$, $W_3$, $W_4$, $W_5$, and $W_6$ of formula I(1) or Ia(1), are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N.

In another embodiment, $W_1$ is N and $W_1$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula I(2), Ia(2), Ib(2), Ic(2), or Id(2):

I(2)

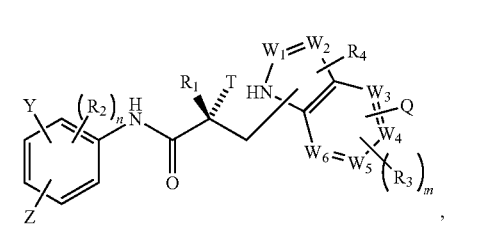

Ia(2)

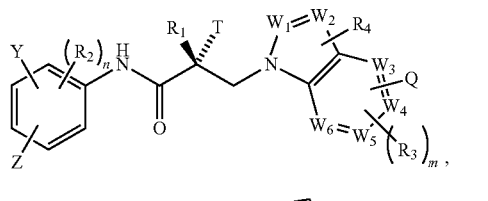

Ib(2)

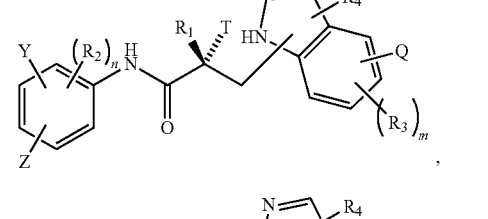

Ic(2)

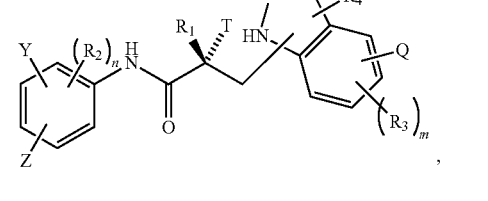

-continued

Id(2)

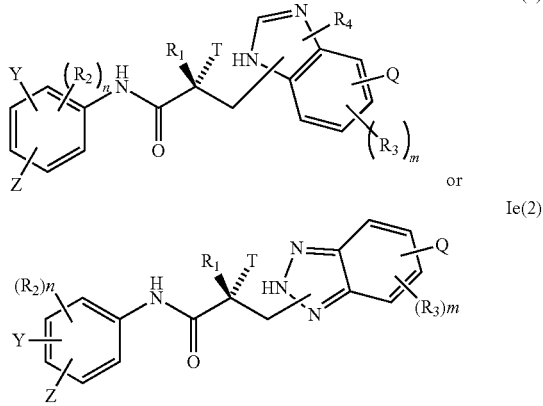

or

Ie(2)

wherein $W_1$ and $W_2$ are each independently selected from N or CH;

$W_3$, $W_4$, $W_5$ and $W_6$ are each independently selected from CH or N;

wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;

T is OH, OR, —$NHCOCH_3$, NHCOR or

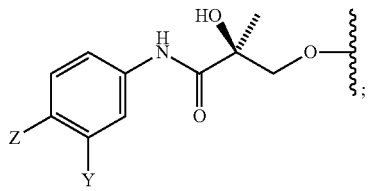

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ and $R_4$ are independently selected from hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In another embodiment, $W_1$, $W_2$, $W_3$, $W_4$, $W_5$, and $W_6$ of formula I or Ia, are each independently CH. In another embodiment, $W_1$ is N. In another embodiment, $W_2$ is N. In another embodiment, $W_1$ is CH. In another embodiment, $W_2$ is CH. In another embodiment, $W_3$ is N. In another embodiment, $W_4$ is N. In another embodiment, $W_5$ is N. In another embodiment, $W_6$ is N. In another embodiment, $W_1$ is N and $W_1$, $W_3$, $W_4$, $W_5$, and $W_6$ are CH. In another embodiment, $W_2$ is N and $W_1$, $W_3$, $W_4$, $W_5$, and $W_6$ are CH. In another embodiment, $W_3$ is N and $W_1$, $W_2$, $W_4$, $W_5$, and $W_6$ are CH. In another embodiment, $W_4$ is N and $W_1$, $W_2$, $W_3$, $W_5$, and $W_6$ are CH. In another embodiment, $W_5$ is N and $W_1$, $W_2$, $W_3$, $W_4$, and $W_6$ are CH. In another embodiment, $W_6$ is N and $W_1$, $W_2$, $W_3$, $W_4$, and $W_5$ are CH.

In one embodiment, this invention is directed to a selective androgen receptor degrader (SARD) compound represented by the structure of formula II:

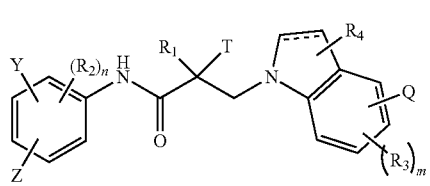

II wherein

====== is a single or double bond;

T is OH, OR, —$NHCOCH_3$, NHCOR or

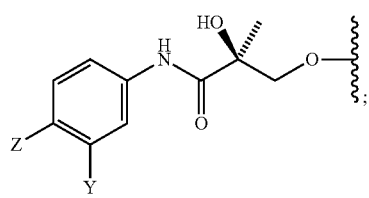

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, $C_1$, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3 or its isomer, pharmaceutically acceptable salt, pharmaceutical product, polymorph, hydrate or any combination thereof.

In one embodiment, this invention is directed to a selective androgen receptor degrader (SARD) compound represented by the structure of formula II(1):

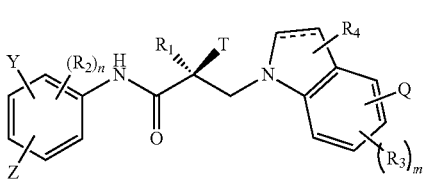

II(1)

wherein

====== is a single or double bond;

T is OH, OR, —$NHCOCH_3$, NHCOR or

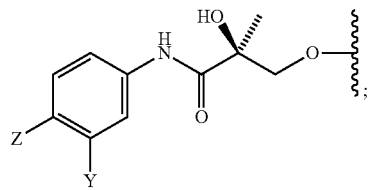

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, $C_1$, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula III:

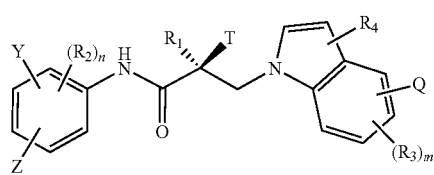

III wherein
T is OH, OR, —$NHCOCH_3$, NHCOR or

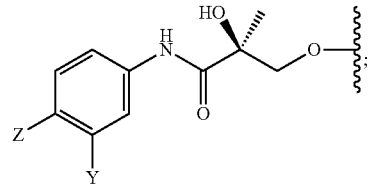

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula IV:

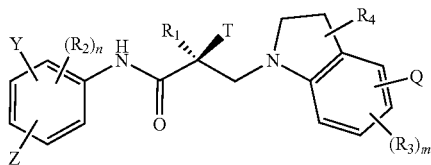

wherein
T is OH, OR, —NHCOCH₃, NHCOR or

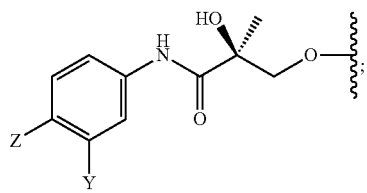

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, C₁, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₄ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXI:

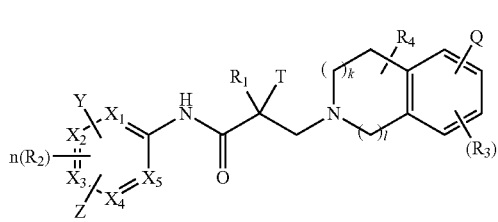

wherein
X₁, X₂, X₃, X₄, and X₅ are each independently N or CH, wherein if any one of X₁, X₂, X₃, X₄, and X₅ is CH, then the H is optionally replaced with R₂, Y, or Z in the respective position, and if any one of X₁, X₂, X₃, X₄, and X₅ is not CH, then the respective position is unsubstituted;
T is OH, OR, —NHCOCH₃, NHCOR or

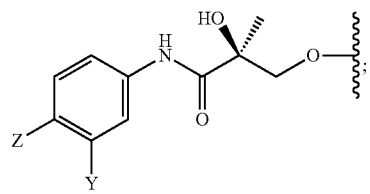

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;
m is an integer between 1-3;
l is 0 or 1; and
k is 0, 1 or 2;

or its isomer, pharmaceutically acceptable salt, pharmaceutical product, polymorph, hydrate or any combination thereof.

In one embodiment, X₁, X₂, X₃, X₄, and X₅ are CH. In one embodiment, X₁ or X₅ is N. In one embodiment, at least one of X₁, X₂, X₃, X₄, and X₅ is N. In one embodiment, X₂ or X₄ is N. In one embodiment, X₃ is N. In one embodiment, X₁ is N and X₂, X₃, X₄, and X₅ are CH. In one embodiment, X₂ is N and X₁, X₃, X₄, and X₅ are CH. In one embodiment, X₃ is N and X₁, X₂, X₄, and X₅ are CH. In one embodiment, two of X₁, X₂, X₃, X₄, and X₅ are N. In one embodiment, X₁ and X₃ are both N. In one embodiment, X₁ and X₅ are both N. In one embodiment, X₂ and X₄ are both N. In one embodiment, X₄ is N and X₁, X₂, X₃, and X₅ are CH.

In one embodiment, this invention is directed to a selective androgen receptor degrader (SARD) compound represented by the structure of formula XXI(1):

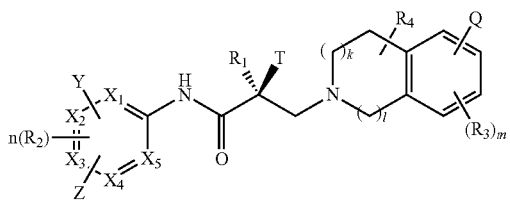

XXI(1)

wherein
X₁, X₂, X₃, X₄, and X₅ are each independently N or CH, wherein if any one of X₁, X₂, X₃, X₄, and X₅ is CH, then the H is optionally replaced with R₂, Y, or Z in the respective position, and if any one of X₁, X₂, X₃, X₄, and X₅ is not CH, then the respective position is unsubstituted;

T is OH, OR, —NHCOCH₃, NHCOR or

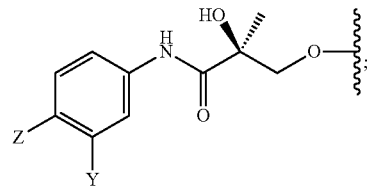

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;
m is an integer between 1-3;
l is 0 or 1; and
k is 0, 1 or 2;

or its isomer, pharmaceutically acceptable salt, pharmaceutical product, polymorph, hydrate or any combination thereof.

In one embodiment, $X_1$, $X_2$, $X_3$, $X_4$, and $X_5$ are CH. In one embodiment, $X_1$ or $X_5$ is N. In one embodiment, at least one of $X_1$, $X_2$, $X_3$, $X_4$, and $X_5$ is N. In one embodiment, $X_2$ or $X_4$ is N. In one embodiment, $X_3$ is N. In one embodiment, $X_1$ is N and $X_2$, $X_3$, $X_4$, and $X_5$ are CH. In one embodiment, $X_2$ is N and $X_1$, $X_3$, $X_4$, and $X_5$ are CH. In one embodiment, $X_3$ is N and $X_1$, $X_2$, $X_4$, and $X_5$ are CH. In one embodiment, two of $X_1$, $X_2$, $X_3$, $X_4$, and $X_5$ are N. In one embodiment, $X_1$ and $X_3$ are both N. In one embodiment, $X_1$ and $X_5$ are both N. In one embodiment, $X_2$ and $X_4$ are both N. In one embodiment, $X_4$ is N and $X_1$, $X_2$, $X_3$, and $X_5$ are CH.

In one embodiment, this invention is directed to a selective androgen receptor degrader (SARD) compound represented by the structure of formula XXI(2):

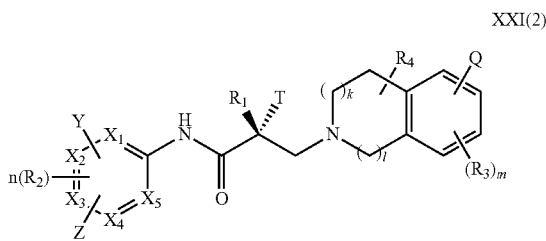

XXI(2)

wherein
- $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
- T is OH, OR, —NHCOCH$_3$, NHCOR or

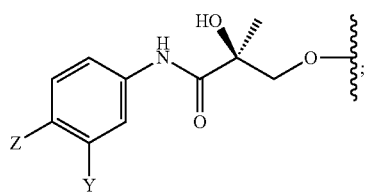

- Z is NO$_2$, CN, COOH, COR, NHCOR or CONHR;
- Y is CF$_3$, F, I, Br, Cl, CN or C(R)$_3$;
- R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
- $R_1$ is CH$_3$, CH$_2$F, CHF$_2$, CF$_3$, CH$_2$CH$_3$, or CF$_2$CF$_3$;
- $R_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
- Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- n is an integer between 1-3;
- m is an integer between 1-3;
- l is 0 or 1; and
- k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXII:

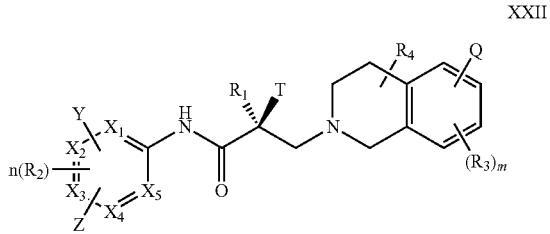

XXII wherein
- $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
- T is OH, OR, —NHCOCH$_3$, NHCOR or

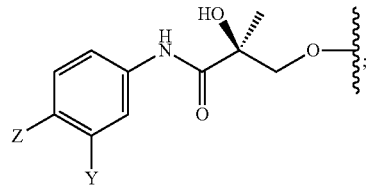

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIII:

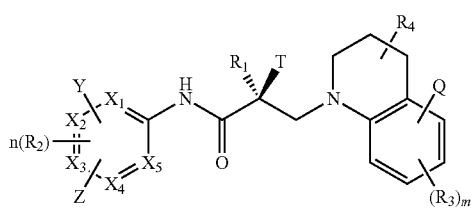

XXIII wherein
$X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
T is OH, OR, —$NHCOCH_3$, NHCOR or

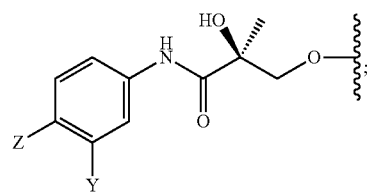

Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;
$R_1$ is $CH_3$, $CH_2F$, $CHF_2$, $CF_3$, $CH_2CH_3$, or $CF_2CF_3$;
$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;
$R_4$ is hydrogen, F, Cl, Br, I, $CF_3$, CN, $NO_2$, $NH_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIV:

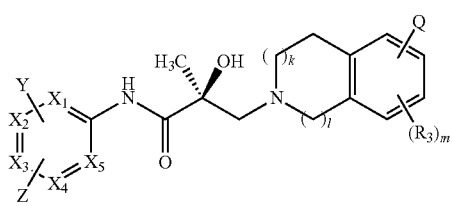

XXIV wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

m is an integer between 1-3;

l is 0 or 1; and k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXVa, XXVb, XXVc, XXVd, XXVe, XXVf, XXVg or XXVh:

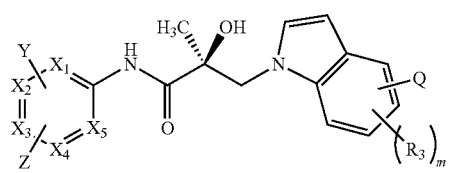

XXVa

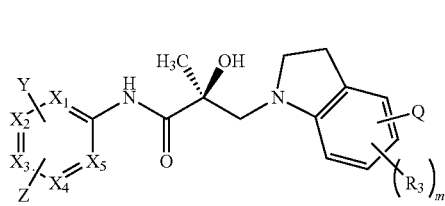

XXVb

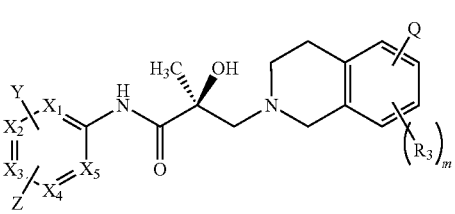

XXVc

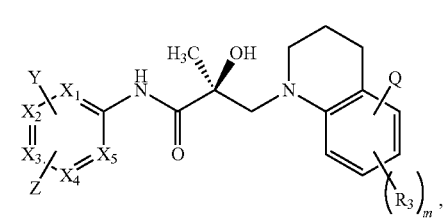

XXVd

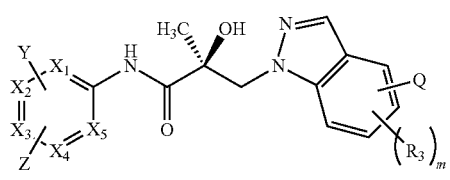

XXVe

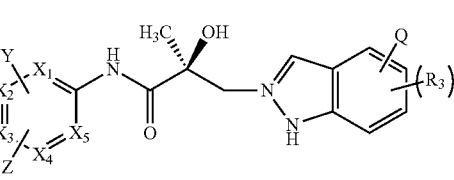

XXVf

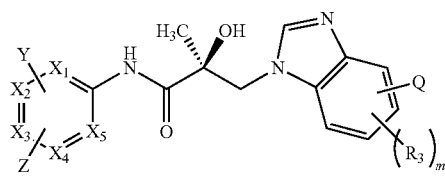

XXVg

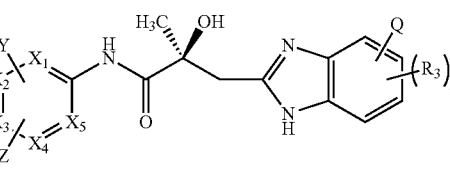

XXVh

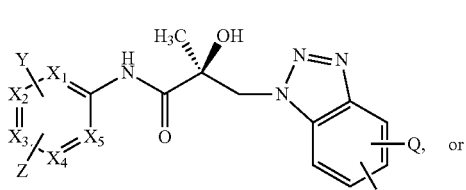

XXVi

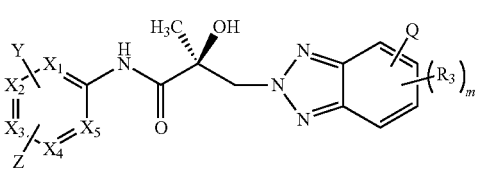

XXVj wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXVI:

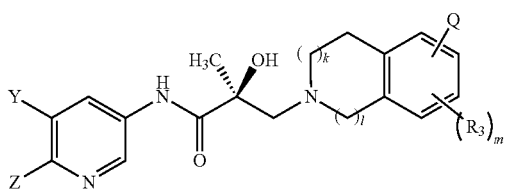

XXVI wherein

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

m is an integer between 1-3;

l is 0 or 1; and k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXVIIa, XXVIIb, XXVIIc, XXVIId, XXVIIe, XXVIIf, XXVIIg, or XXVIIh:

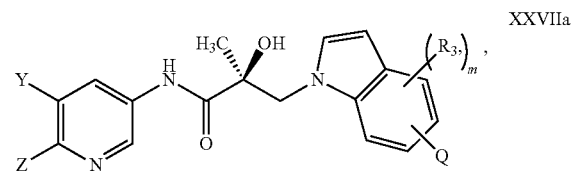

XXVIIa

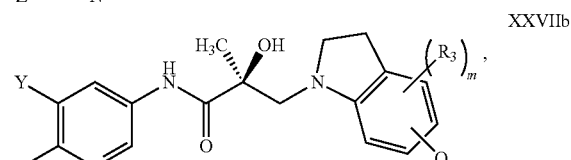

XXVIIb

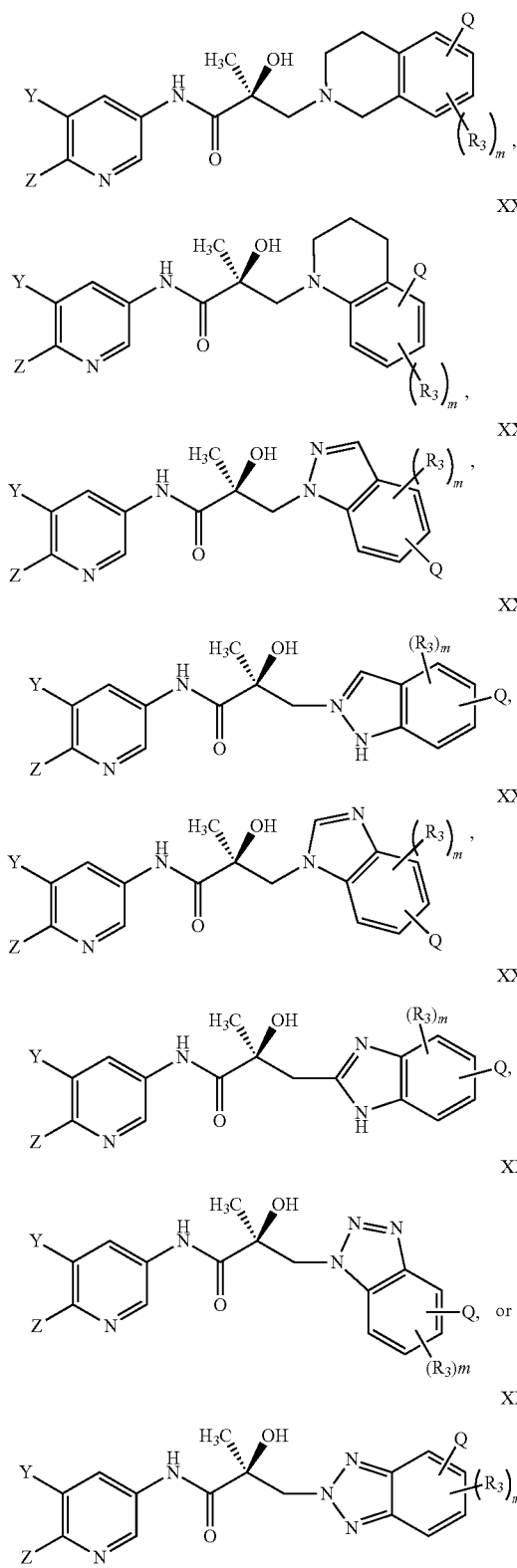

wherein
Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXVIII:

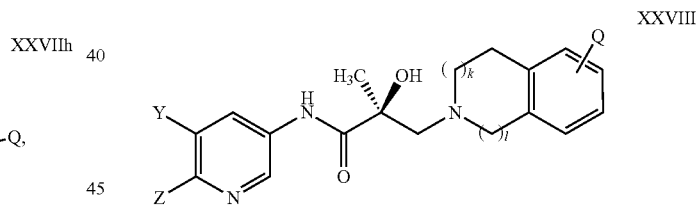

wherein
Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
l is 0 or 1; and
k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXIXa, XXIXb, XXIXc, XXIXd, XXIXe, XXIXf, XXIXg, or XXIXh:

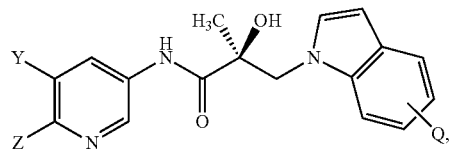
XXIXa

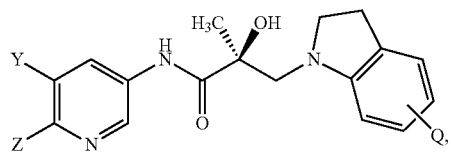
XXIXb

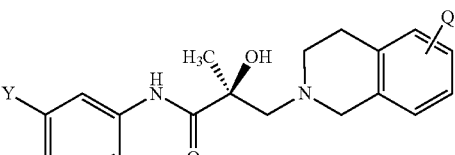
XXIXc

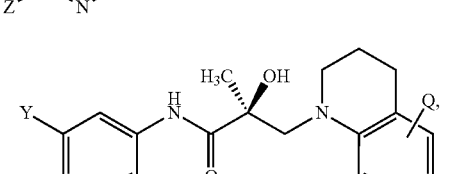
XXIXd

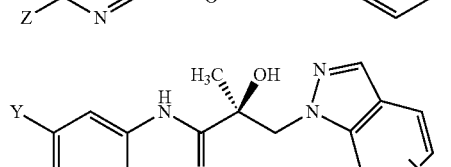
XXIXe

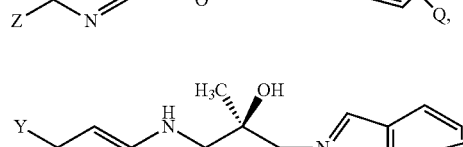
XXIXf

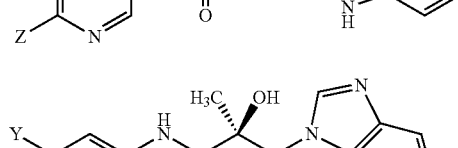
XXIXg

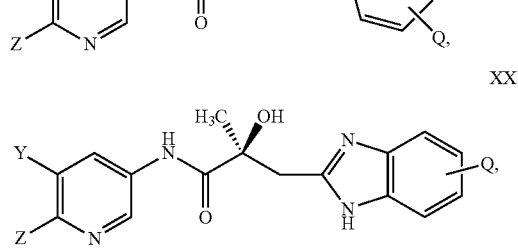
XXIXh

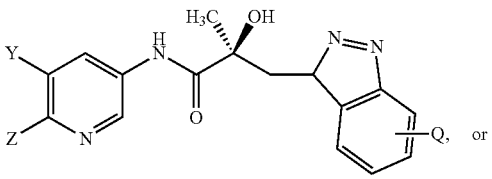
XXIXi

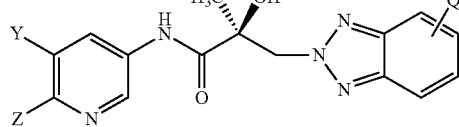
XXIXj wherein
Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH; and
Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXX:

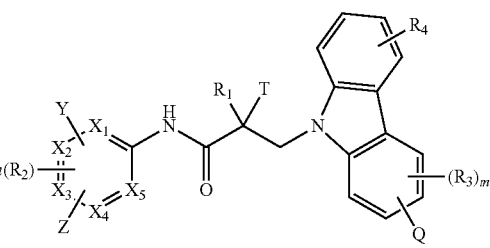
XXX wherein
$X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
T is OH, OR, —$NHCOCH_3$, or NHCOR;
Z is $NO_2$, CN, COOH, COR, NHCOR or CONHR;
Y is $CF_3$, F, I, Br, Cl, CN or $C(R)_3$;
R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXX(1):

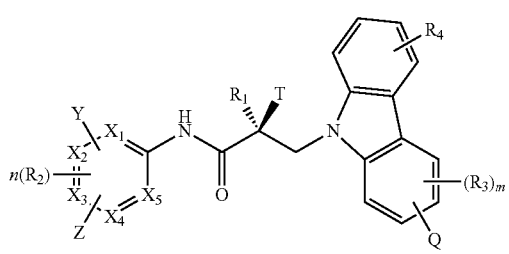

XXX(1)

wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

T is OH, OR, —$NHCOCH_3$, or NHCOR;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXX(2):

XXX(2)

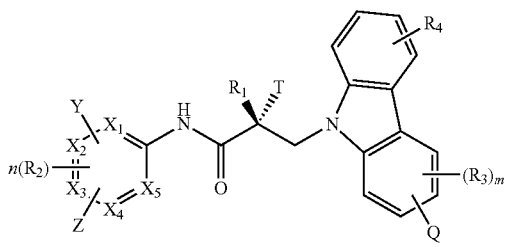

wherein
- $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;
- T is OH, OR, —NHCOCH$_3$, or NHCOR;
- Z is NO$_2$, CN, COOH, COR, NHCOR or CONHR;
- Y is CF$_3$, F, I, Br, Cl, CN or C(R)$_3$;
- R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
- $R_1$ is CH$_3$, CH$_2$F, CHF$_2$, CF$_3$, CH$_2$CH$_3$, or CF$_2$CF$_3$;
- $R_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
- Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_4$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- n is an integer between 1-3; and
- m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXXI:

XXXI

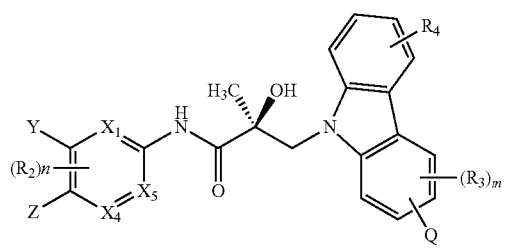

wherein
- $X_1$, $X_4$, and $X_5$ are each independently N or CH, wherein if any one of $X_1$, $X_4$, and $X_5$ is CH, then the H is optionally replaced with $R_2$, in the respective position, and if any one of $X_1$, $X_4$, and $X_5$ is not CH, then the respective position is unsubstituted;
- Z is NO$_2$, CN, COOH, COR, NHCOR or CONHR;
- Y is CF$_3$, F, I, Br, Cl, CN or C(R)$_3$;
- R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
- $R_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
- Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

R₄ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XXXIIa, XXXIIb, XXXIIa(1), XXXIIb(1), XXXIIa(2), XXXIIb(2):

XXXIIa
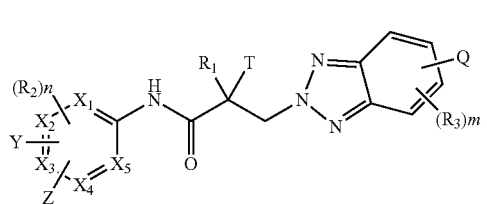

XXXIIb
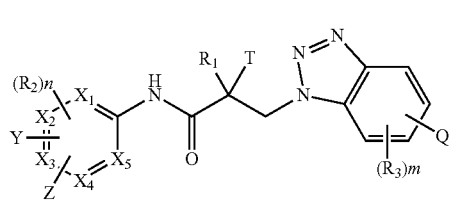

XXXIIa(1)
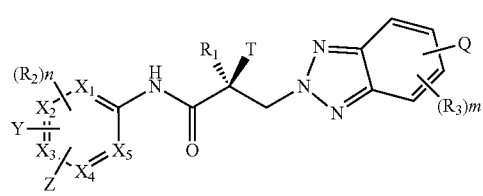

XXXIIb(1)
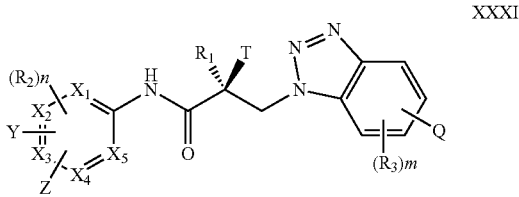

XXXIIa(2)
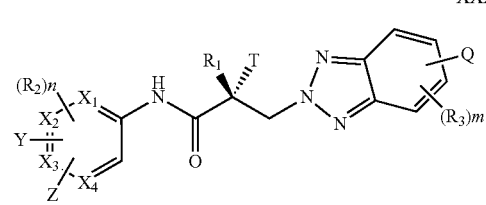

XXXIIb(2)
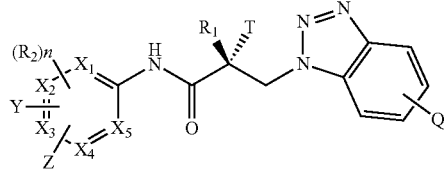

wherein $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted;

T is OH, OR, —NHCOCH₃, or NHCOR;

Z is NO₂, CN, COOH, COR, NHCOR or CONHR;

Y is CF₃, F, I, Br, Cl, CN or C(R)₃;

R is alkyl, haloalkyl, dihaloalkyl, trihaloalkyl, CH₂F, CHF₂, CF₃, CF₂CF₃, aryl, phenyl, F, Cl, Br, I, alkenyl or OH;

R₁ is CH₃, CH₂F, CHF₂, CF₃, CH₂CH₃, or CF₂CF₃;

R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;

Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula V:

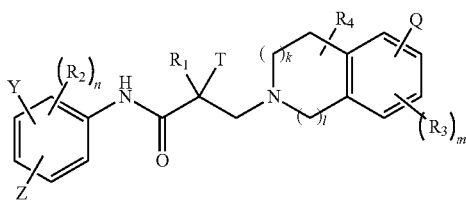

wherein
T is OH, OR, —NHCOCH$_3$, NHCOR or

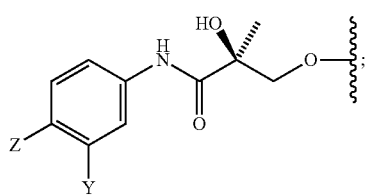

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3;
m is an integer between 1-3;
l is 0 or 1; and
k is 0, 1 or 2;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula V(1):

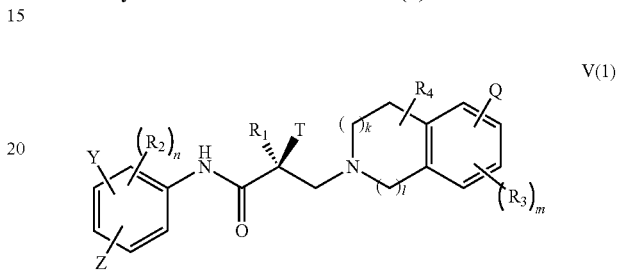

wherein
T is OH, OR, —NHCOCH$_3$, NHCOR or

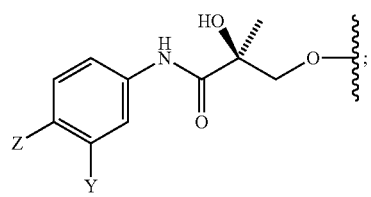

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;
m is an integer between 1-3;
l is 0 or 1; and
k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula V(2):

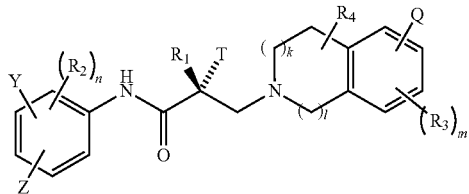

V(2)

wherein
T is OH, OR, —NHCOCH₃, NHCOR or

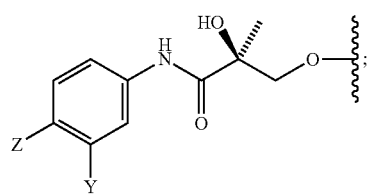

Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₁ is CH₃, CH₂F, CHF₂, CF₃, CH₂CH₃, or CF₂CF₃;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3;
m is an integer between 1-3;
l is 0 or 1; and
k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula VI:

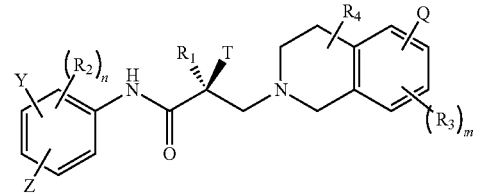

VI wherein
T is OH, OR, —NHCOCH₃, NHCOR or

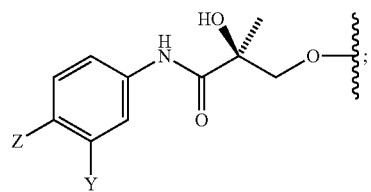

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, C$_1$, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula VII:

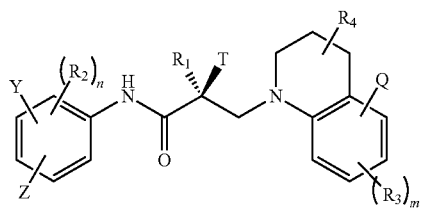

VII wherein
T is OH, OR, —NHCOCH$_3$, NHCOR or

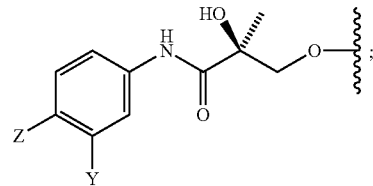

Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, C$_1$, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_4$ is hydrogen, F, Cl, Br, I, CF$_3$, CN, NO$_2$, NH$_2$, SH, COOH, COOR, keto (=O), alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula VIII:

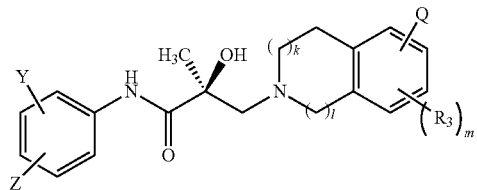

VIII wherein
- Z is NO₂, CN, COOH, COR, NHCOR or CONHR;
- Y is CF₃, F, I, Br, Cl, CN or C(R)₃;
- R is alkyl, haloalkyl, dihaloalkyl, trihaloalkyl, CH₂F, CHF₂, CF₃, CF₂CF₃, aryl, phenyl, F, C₁, Br, I, alkenyl or OH;
- Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- m is an integer between 1-3;
- l is 0 or 1; and
- k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula IXa, IXb, IXc, IXd, IXe, IXf, IXg or IXh:

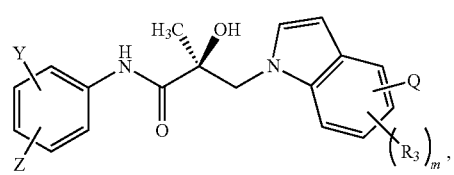

IXa

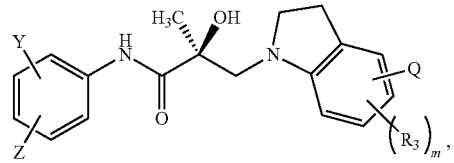

IXb

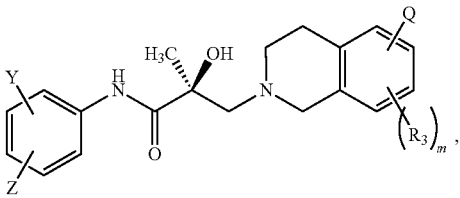

IXc

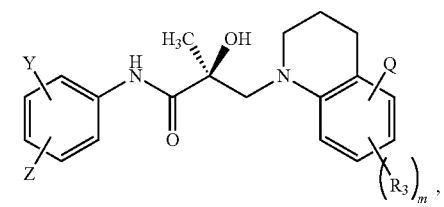

IXd

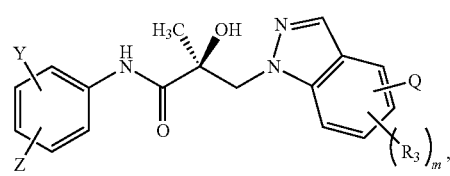

IXe

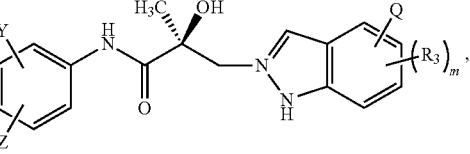

IXf

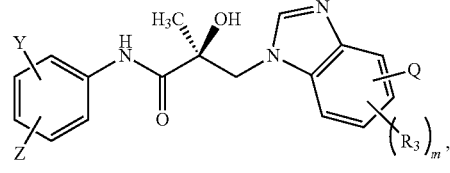

IXg

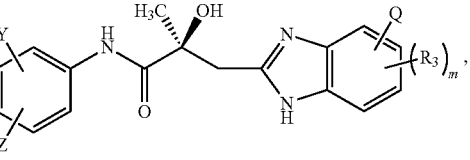

IXh

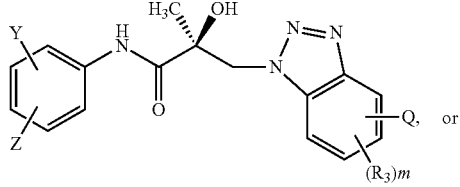

IXi

, or

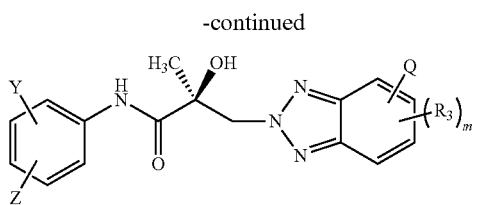

IXj wherein
- Z is NO₂, CN, COOH, COR, NHCOR or CONHR;
- Y is CF₃, F, I, Br, Cl, CN or C(R)₃;
- R is alkyl, haloalkyl, dihaloalkyl, trihaloalkyl, CH₂F, CHF₂, CF₃, CF₂CF₃, aryl, phenyl, F, C₁, Br, I, alkenyl or OH;
- Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN; and
- m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula X:

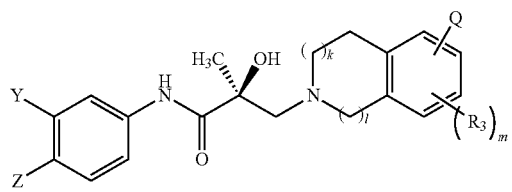

X wherein
- Z is NO₂, CN, COOH, COR, NHCOR or CONHR;
- Y is CF₃, F, I, Br, Cl, CN or C(R)₃;
- R is alkyl, haloalkyl, dihaloalkyl, trihaloalkyl, CH₂F, CHF₂, CF₃, CF₂CF₃, aryl, phenyl, F, C₁, Br, I, alkenyl or OH;
- Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
- m is an integer between 1-3;
- l is 0 or 1; and
- k is 0, 1 or 2;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIa, XIb, XIc, XId, XIe, XIf, XIg, or XIh:

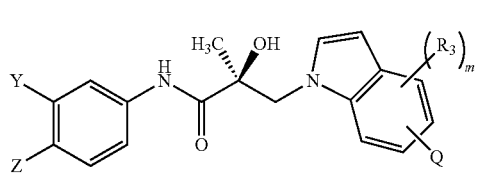

XIa

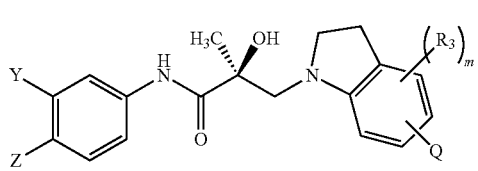

XIb

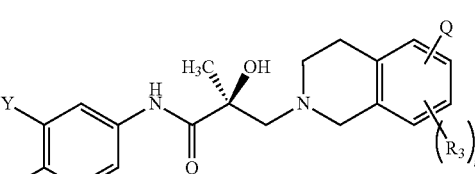

XIc

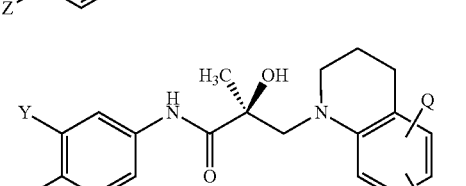

XId

-continued

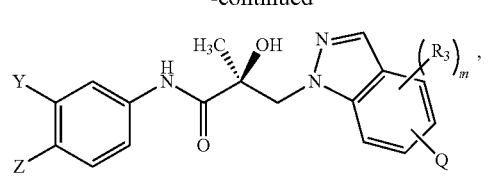
XIe

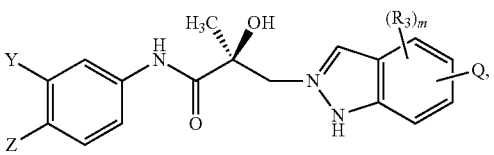
XIf

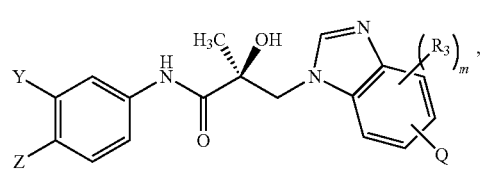
XIg

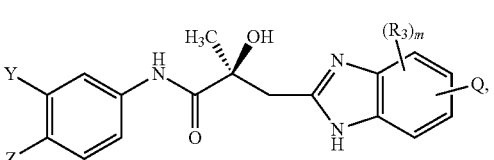
XIh

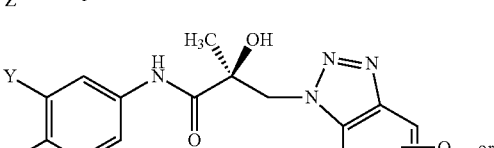
XIi

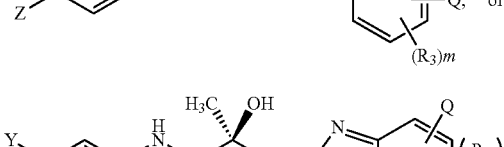

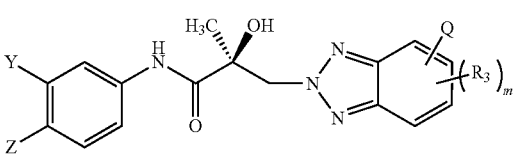
XIj wherein
Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, C₁, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN; and
m is an integer between 1-3;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XII:

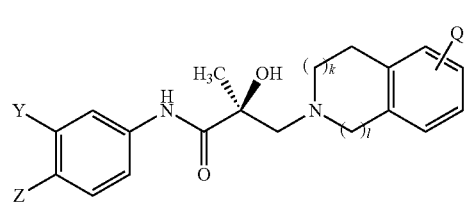
XII wherein
Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, C₁, Br, I, alkenyl or OH;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;
l is 0 or 1; and
k is 0, 1 or 2;
or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIIIa, XIIIb, XIIIc, XIIId, XIIIe, XIIIf, XIIIg, or XIIIh:

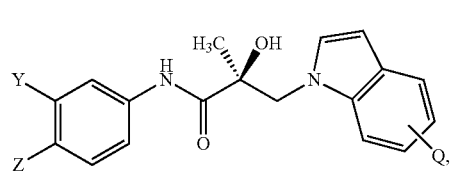
XIIIa

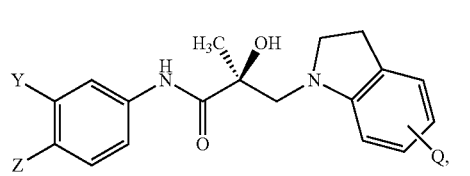
XIIIb

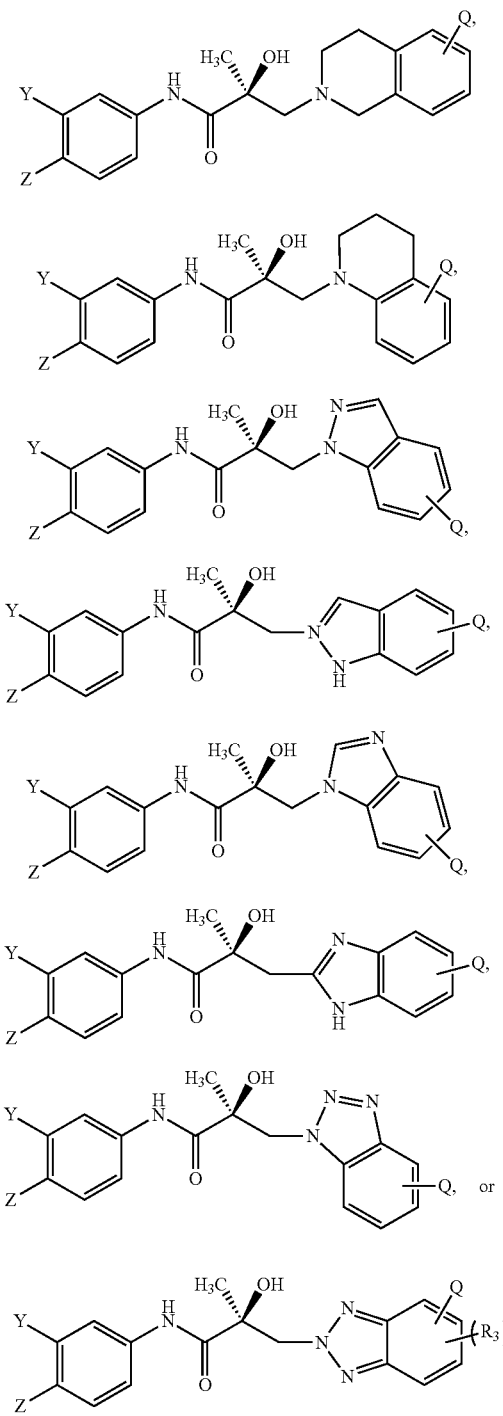

wherein
Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, C$_1$, Br, I, alkenyl or OH; and
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV:

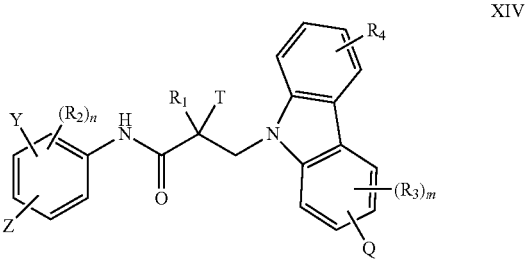

wherein
T is OH, OR, —NHCOCH$_3$, or NHCOR;
Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, C$_1$, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_4$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV(1):

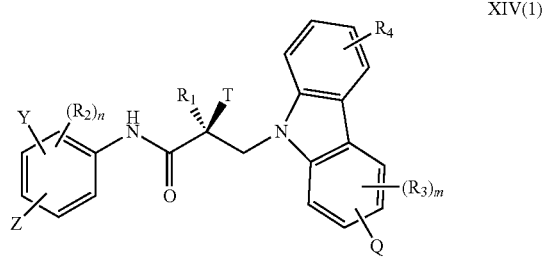

XIV(1)

wherein

T is OH, OR, —$NHCOCH_3$, or NHCOR;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_4$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XIV(2):

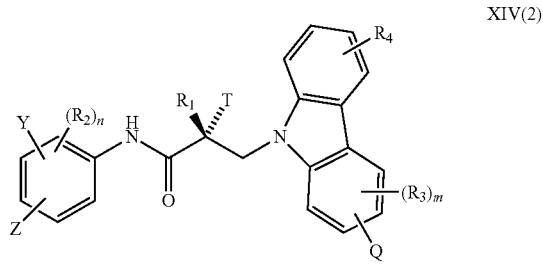

XIV(2)

wherein

T is OH, OR, —$NHCOCH_3$, or NHCOR;

Z is $NO_2$, CN, COOH, COR, NHCOR or CONHR;

Y is $CF_3$, F, I, Br, Cl, CN or $C(R)_3$;

R is alkyl, haloalkyl, dihaloalkyl, trihaloalkyl, $CH_2F$, $CHF_2$, $CF_3$, $CF_2CF_3$, aryl, phenyl, F, Cl, Br, I, alkenyl or OH;

$R_1$ is $CH_3$, $CH_2F$, $CHF_2$, $CF_3$, $CH_2CH_3$, or $CF_2CF_3$;

$R_2$ is hydrogen, halogen, CN, $NO_2$, COOH, COOR, COR, NHCOR, CONHR, OH, OR, SH, SR, $NH_2$, NHR, $NR_2$, $C_1$-$C_{12}$-alkyl, $C_1$-$C_{12}$-haloalkyl, O—$C_1$-$C_{12}$-alkyl, O—$C_1$-$C_{12}$-haloalkyl, —$SO_2$-aryl, —$SO_2$-phenyl, —CO-aryl, arylalkyl, benzyl, aryl, or $C_3$-$C_7$-cycloalkyl;

Q is hydrogen, F, Cl, Br, I, $CF_3$, CN, $NO_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, $C(R)_3$, $N(R)_2$, $NHCOCH_3$, $NHCOCF_3$, NHCOR, NHCONHR, NHCOOR, OCONHR, CONHR, $NHCSCH_3$, $NHCSCF_3$, NHCSR, $NHSO_2CH_3$, $NHSO_2R$, OR, COR, OCOR, $OSO_2R$, $SO_2R$, SR, NCS, SCN, NCO or OCN;

$R_3$ is hydrogen, F, Cl, Br, I, $CF_3$, CN, $NO_2$, $NH_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XV:

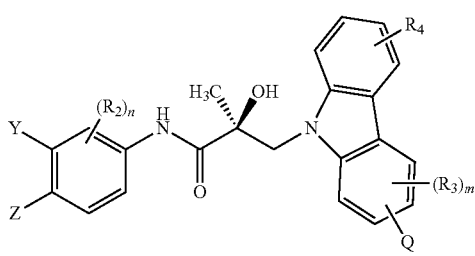

XV wherein
Z is NO₂, CN, COOH, COR, NHCOR or CONHR;
Y is CF₃, F, I, Br, Cl, CN or C(R)₃;
R is alkyl, haloalkyl, dihaloalkyl, trihaloalkyl, CH₂F, CHF₂, CF₃, CF₂CF₃, aryl, phenyl, F, Cl, Br, I, alkenyl or OH;
R₂ is hydrogen, halogen, CN, NO₂, COOH, COOR, COR, NHCOR, CONHR, OH, OR, SH, SR, NH₂, NHR, NR₂, C₁-C₁₂-alkyl, C₁-C₁₂-haloalkyl, O—C₁-C₁₂-alkyl, O—C₁-C₁₂-haloalkyl, —SO₂-aryl, —SO₂-phenyl, —CO-aryl, arylalkyl, benzyl, aryl, or C₃-C₇-cycloalkyl;
Q is hydrogen, F, Cl, Br, I, CF₃, CN, NO₂, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₃ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

R₄ is hydrogen, F, Cl, Br, I, CF₃, CN, NO₂, NH₂, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)₃, N(R)₂, NHCOCH₃, NHCOCF₃, NHCOR, NHCONHR, NHCOOR, OCONHR, CONHR, NHCSCH₃, NHCSCF₃, NHCSR, NHSO₂CH₃, NHSO₂R, OR, COR, OCOR, OSO₂R, SO₂R, SR, NCS, SCN, NCO or OCN;

n is an integer between 1-3; and m is an integer between 1-3;

or its isomer, pharmaceutically acceptable salt, pharmaceutical product, polymorph, hydrate or any combination thereof.

In one embodiment, this invention is directed to a selective androgen receptor degrader (SARD) compound represented by the structure of formula XVIa, XVIb, XVIa(1), XVIb(1), XVIa(2), XVIb(2):

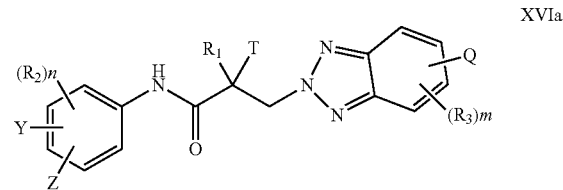

XVIa

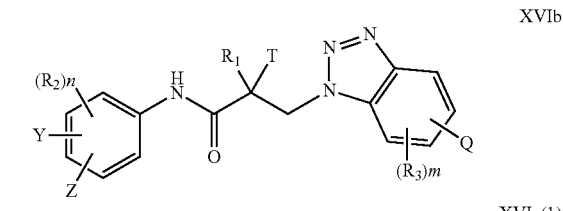

XVIb

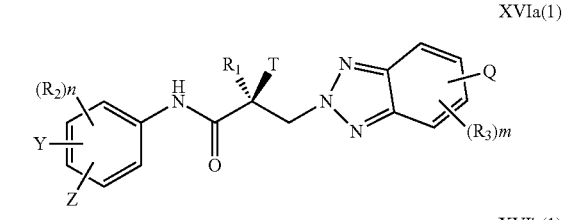

XVIa(1)

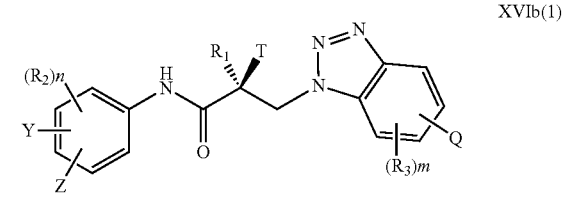

XVIb(1)

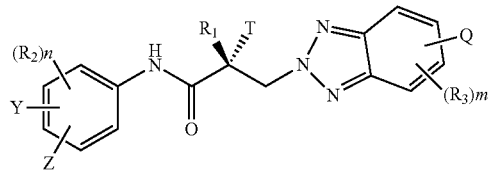

XVIa(2)

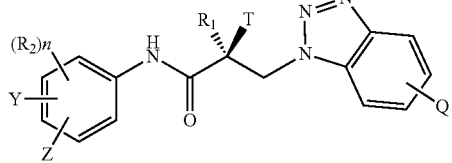

XVIb(2)

wherein
T is OH, OR, —NHCOCH$_3$, or NHCOR;
Z is NO$_2$, CN, COOH, COR, NHCOR or CONHR;
Y is CF$_3$, F, I, Br, Cl, CN or C(R)$_3$;
R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
R$_1$ is CH$_3$, CH$_2$F, CHF$_2$, CF$_3$, CH$_2$CH$_3$, or CF$_2$CF$_3$;
R$_2$ is hydrogen, halogen, CN, NO$_2$, COOH, COOR, COR, NHCOR, CONHR, OH, OR, SH, SR, NH$_2$, NHR, NR$_2$, C$_1$-C$_{12}$-alkyl, C$_1$-C$_{12}$-haloalkyl, O—C$_1$-C$_{12}$-alkyl, O—C$_1$-C$_{12}$-haloalkyl, —SO$_2$-aryl, —SO$_2$-phenyl, —CO-aryl, arylalkyl, benzyl, aryl, or C$_3$-C$_7$-cycloalkyl;
Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
R$_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
n is an integer between 1-3; and
m is an integer between 1-3;
or its isomer, pharmaceutically acceptable salt, pharmaceutical product, polymorph, hydrate or any combination thereof.

In one embodiment, Q of compound of any one of the formulas as described herein is hydrogen. In one embodiment, Q is halogen. In one embodiment, Q is F. In one embodiment, Q is Br. In one embodiment, Q is C$_1$. In one embodiment, Q is I. In one embodiment, Q is CN. In one embodiment, Q is NO$_2$. In one embodiment, Q is optionally substituted linear or branched alkyl. In one embodiment, Q is CH$_3$. In one embodiment, Q is alkoxy. In one embodiment, Q is OCH$_3$. In one embodiment, Q is CF$_3$. In one embodiment, Q is optionally substituted phenyl. In one embodiment, Q is unsubstituted phenyl.

In one embodiment, R$_3$ of compound of any one of the formulas as described herein is hydrogen. In one embodiment, R$_3$ is halogen. In one embodiment, R$_3$ is C$_1$. In one embodiment, R$_3$ is Br. In one embodiment, R$_3$ is I. In one embodiment, R$_3$ is CN. In one embodiment, R$_3$ is COOH. In one embodiment, R$_3$ is NO$_2$. In one embodiment, R$_3$ is CF$_3$.

In one embodiment, R$_4$ of compound of any one of the formulas as described herein is hydrogen. In one embodiment, R$_4$ of compound of any one of the formulas as described herein is halogen. In one embodiment, R$_4$ of compound of any one of the formulas as described herein is F. In one embodiment, R$_4$ of compound of any one of the formulas as described herein is C$_1$. In one embodiment, R$_4$ of compound of any one of the formulas as described herein is Br. In one embodiment, R$_4$ of compound of any one of the formulas as described herein is I. In one embodiment, R$_4$ of compound of any one of the formulas as described herein is CN. In one embodiment, R$_4$ of compound of any one of the formulas as described herein is COOH. In one embodiment, R$_4$ of compound of any one of the formulas as described herein is NO$_2$. In one embodiment, R$_4$ of compound of any one of the formulas as described herein is CF$_3$. In one embodiment, R$_4$ of compound of any one of the formulas as described herein is methyl. In one embodiment, R$_4$ of compound of any one of the formulas as described herein is COOR.

In one embodiment, Z of compound of any one of the formulas as described herein is CN. In another embodiment, Z is NO$_2$. In another embodiment, Z is COOH. In another embodiment, Z is COR. In another embodiment, Z is NHCOR. In another embodiment, Z is CONHR. In another embodiment, Z is in the para position.

In one embodiment, Y of compound of any one of the formulas as described herein is CF$_3$. In another embodiment, Y is F. In another embodiment, Y is I. In another embodiment, Y is Br. In another embodiment, Y is C$_1$. In another embodiment, Y is CN. In another embodiment, Y is C(R)$_3$. In another embodiment, Y is in the meta position.

In one embodiment, Z of compound of any one of the formulas as described herein is CN and Y is CF$_3$. In another embodiment, Z is NO$_2$ and Y is CF$_3$. In another embodiment, Z is NO$_2$ and Y is halogen. In another embodiment, Z is CN and Y is halogen. In another embodiment, Z of compound of any one of the formulas as described herein is in the para position and Y is in the meta position.

In one embodiment, R$_2$ of compound of any one of the formulas as described herein is hydrogen. In one embodiment, R$_2$ is halogen. In one embodiment, R$_2$ is CN. In one embodiment, R$_2$ is NO$_2$. In one embodiment, R$_2$ is C$_1$-C$_{12}$-alkyl. In one embodiment, R$_2$ is aryl. In one embodiment, R$_2$ is phenyl. In one embodiment, R$_2$ is COOH. In one embodiment, R$_2$ is COOR. In one embodiment, R$_2$ is COR. In one embodiment, R$_2$ is NHCOR. In one embodiment, R$_2$ is CONHR. In one embodiment, R$_2$ is OH. In one embodiment, R$_2$ is OR. In one embodiment, R$_2$ is SH. In one embodiment, R$_2$ is SR. In one embodiment, R$_2$ is NH$_2$. In one embodiment, R$_2$ is NHR. In one embodiment, R$_2$ is N(R)$_2$. In one embodiment, R$_2$ is C$_1$-C$_{12}$-haloalkyl. In one embodiment, R$_2$ is 0-C$_1$-C$_{12}$-alkyl. In one embodiment, R$_2$ is O—C$_1$-C$_{12}$-haloalkyl. In one embodiment, R$_2$ is —SO$_2$-aryl. In one embodiment, R$_2$ is —SO$_2$-phenyl. In one embodiment, R$_2$ is —CO-aryl. In one embodiment, $R_2$ is arylalkyl. In one embodiment, $R_2$ is benzyl. In one embodiment, $R_2$ is $C_3$-$C_7$-cycloalkyl.

In one embodiment, $R_1$ of compound of any one of the formulas as described herein is $CH_3$. In another embodiment, $R_1$ is $CF_3$.

In one embodiment, T of compound of any one of the formulas as described herein is OH. In another embodiment, T is $OCH_3$. In another embodiment, T is

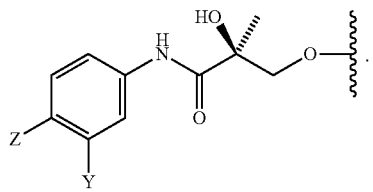

In one embodiment, R of compound of any one of the formulas as described herein is alkyl. In another embodiment, R is haloalkyl. In another embodiment, R is dihaloalkyl. In another embodiment, R is trihaloalkyl. In another embodiment, R is $CH_2F$. In another embodiment, R is $CHF_2$. In another embodiment, R is $CF_3$. In another embodiment, R is $CF_2CF_3$. In another embodiment, R is aryl. In another embodiment, R is phenyl. In another embodiment, R is F. In another embodiment, R is $C_1$. In another embodiment, R is Br. In another embodiment, R is I. In another embodiment, R is alkenyl. In another embodiment, R is hydroxyl (OH).

In one embodiment, m of compound of any one of the formulas as described herein is 1. In one embodiment, m is 2. In one embodiment, m is 3.

In one embodiment, n of compound of any one of the formulas as described herein is 1. In one embodiment, n is 2. In one embodiment, m is 3.

In one embodiment, $X_1$, $X_2$, $X_3$, $X_4$, and $X_5$ are CH. In one embodiment, $X_1$ or $X_5$ is N. In one embodiment, at least one of $X_1$, $X_2$, $X_3$, $X_4$, and $X_5$ is N. In one embodiment, $X_2$ or $X_4$ is N. In one embodiment, $X_3$ is N. In one embodiment, $X_1$ is N and $X_2$, $X_3$, $X_4$, and $X_5$ are CH. In one embodiment, $X_2$ is N and $X_1$, $X_3$, $X_4$, and $X_5$ are CH. In one embodiment, $X_3$ is N and $X_1$, $X_2$, $X_4$, and $X_5$ are CH. In one embodiment, two of $X_1$, $X_2$, $X_3$, $X_4$, and $X_5$ are N. In one embodiment, $X_1$ and $X_3$ are both N. In one embodiment, $X_1$ and $X_5$ are both N. In one embodiment, $X_2$ and $X_4$ are both N. In one embodiment, $X_4$ is N and $X_1$, $X_2$, $X_3$, and $X_5$ are CH.

In one embodiment, this invention is directed to a selective androgen receptor degrader (SARD) compound selected from the following structures:

Indoles:

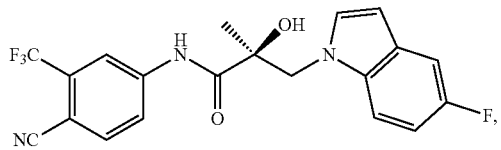

11

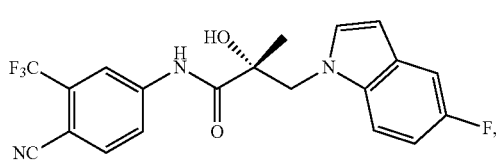

11R

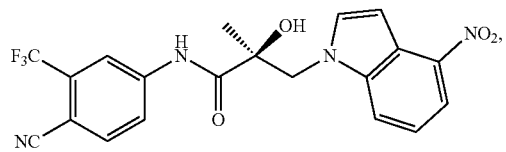

12

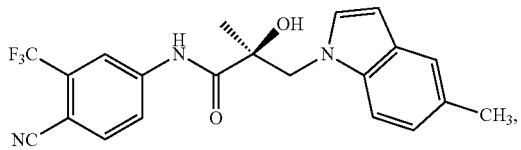

13

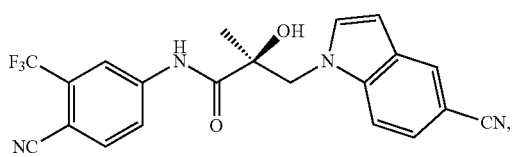

14

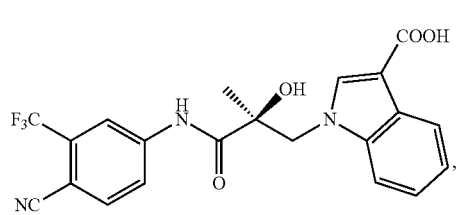

15

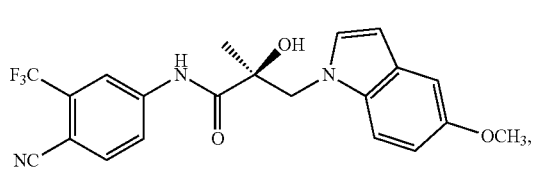

16

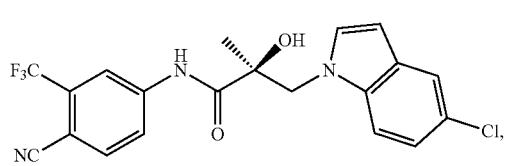

17

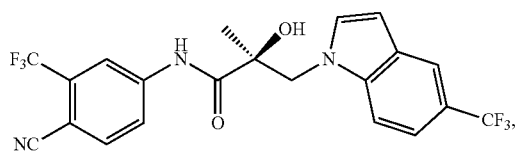

18

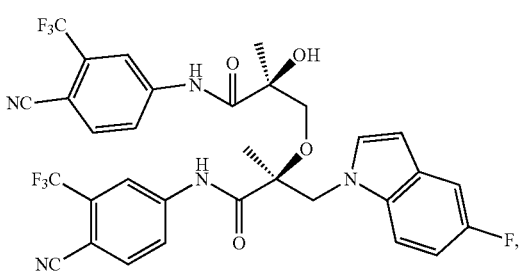

19

38
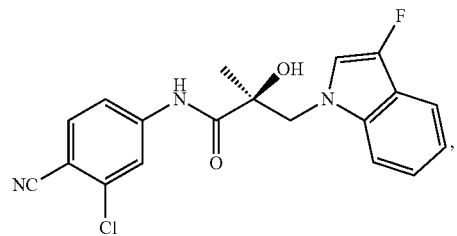
39
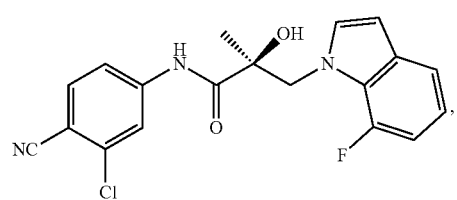
40
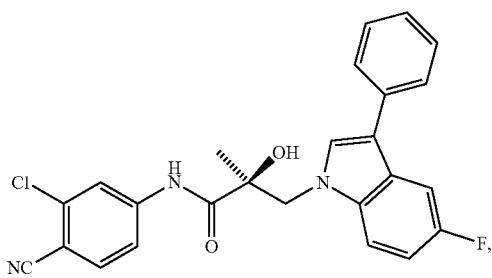
41
42
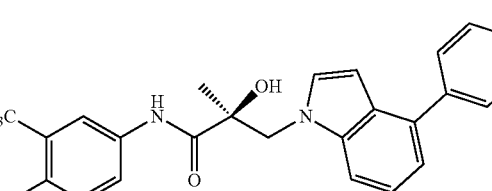
43
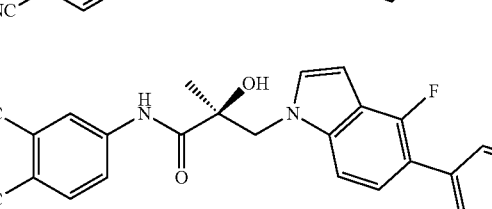
44
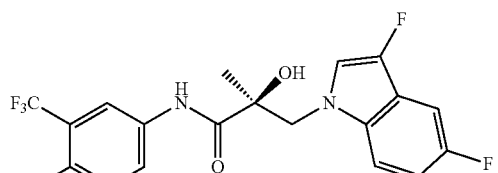
45
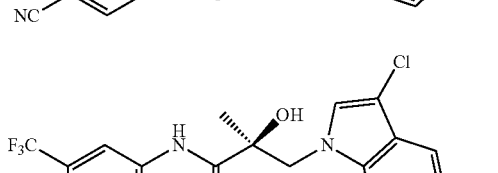
46
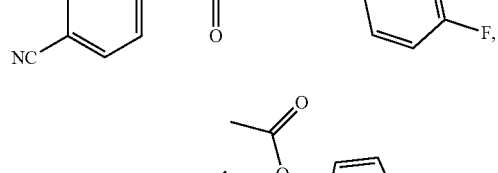
47
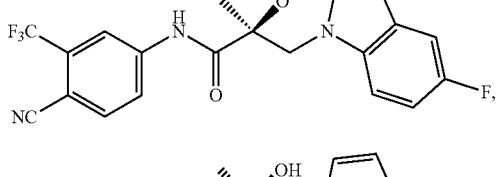
benzimidazoles:
70
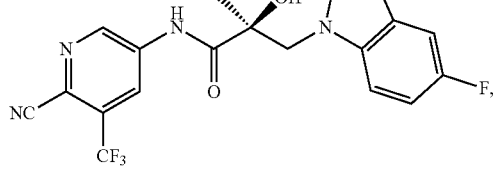
71
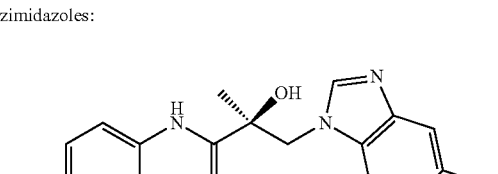
72
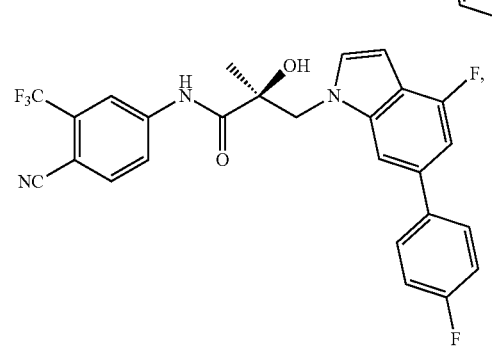

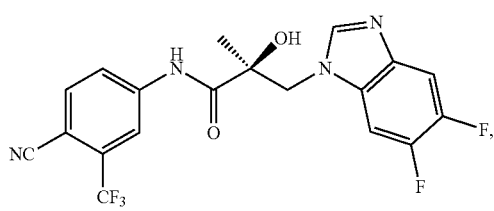
73
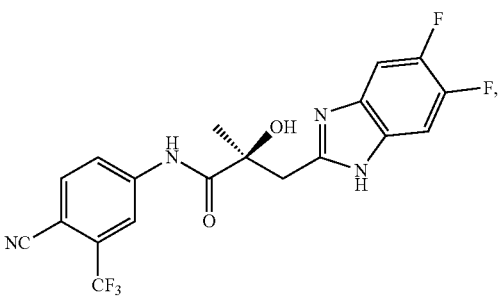
74
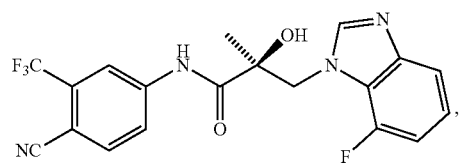
75
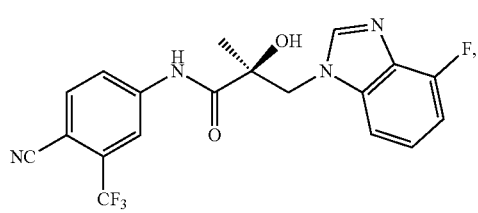
76
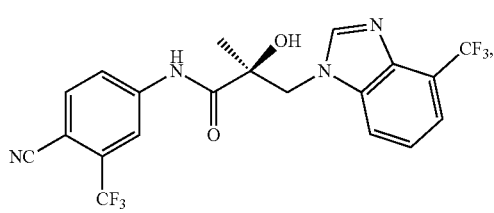
77
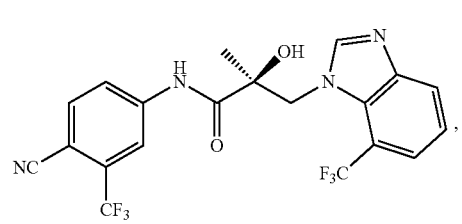
78
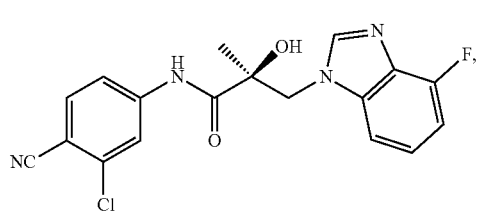
79
pyrrolo-pyridine:
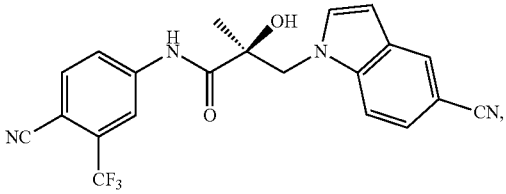
80
indazoles:
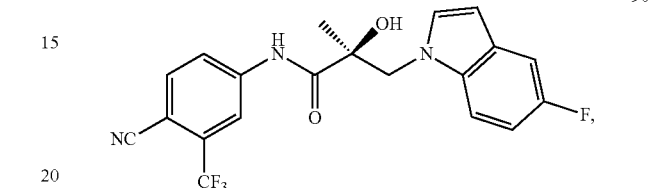
90
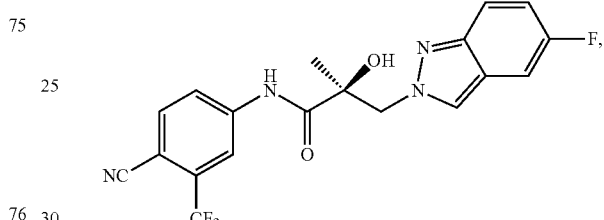
91
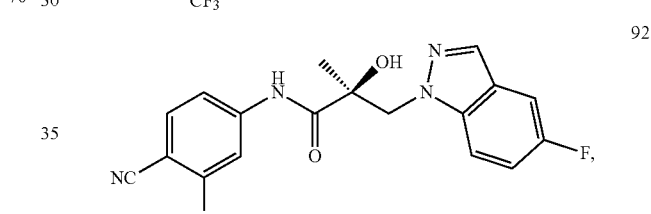
92
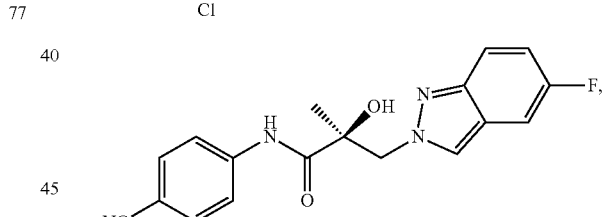
93
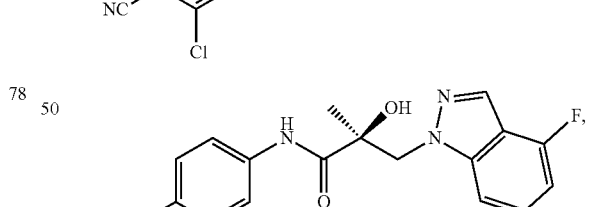
94
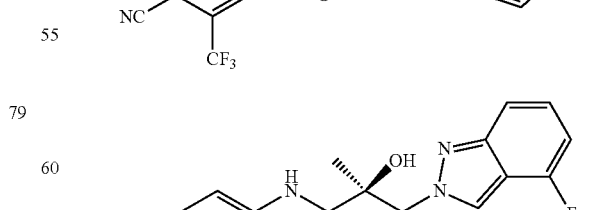
95

96
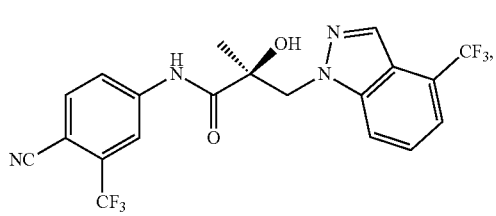
97
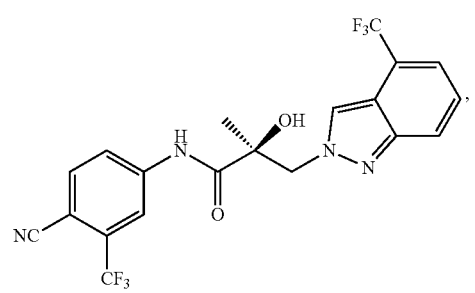
98
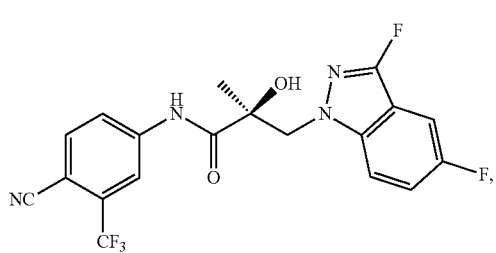
99
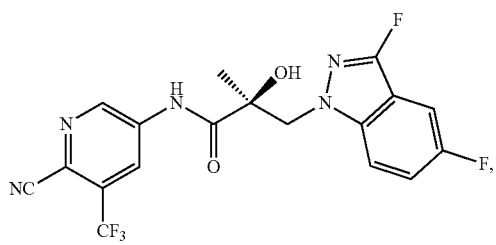
benzotriazoles:
300
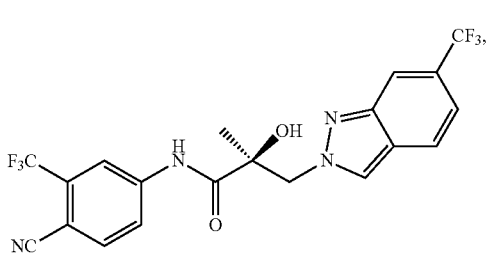
301
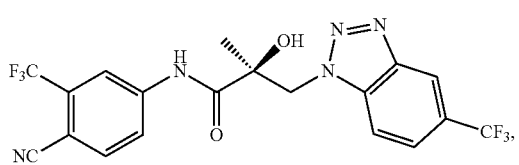
302
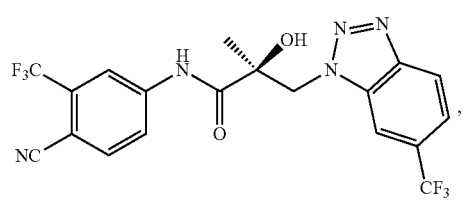
303
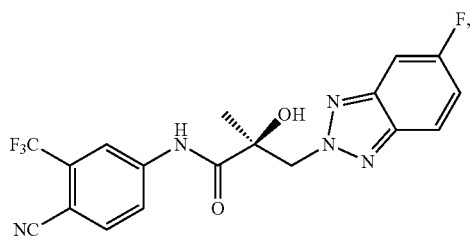
304
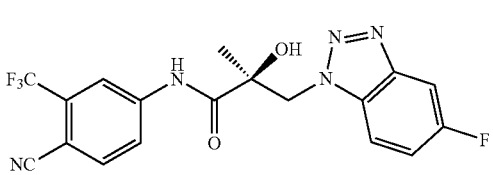
305
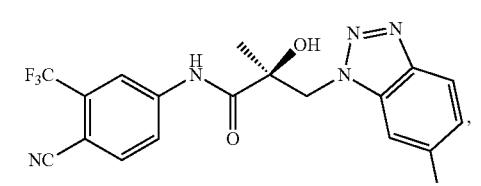
306
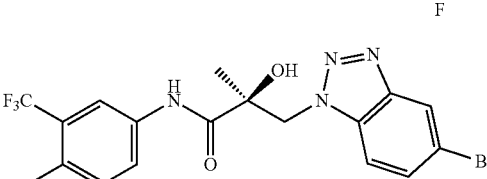
307
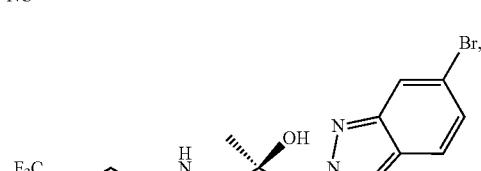
308
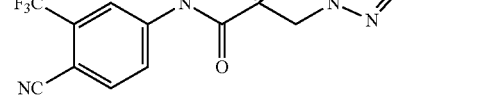
indolines:
100
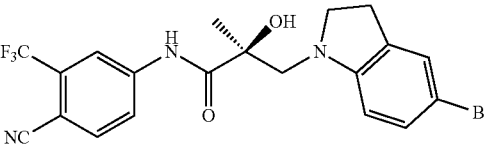
101
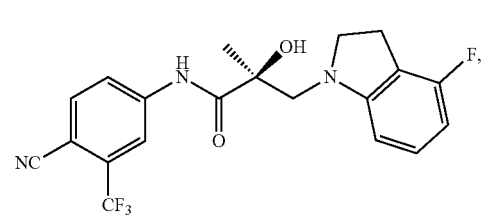

-continued
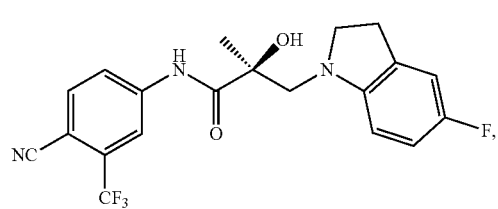
102
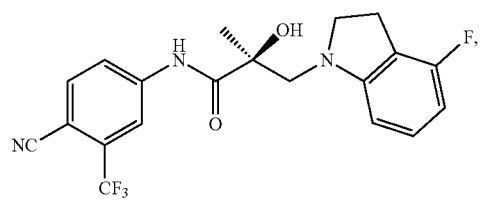
103
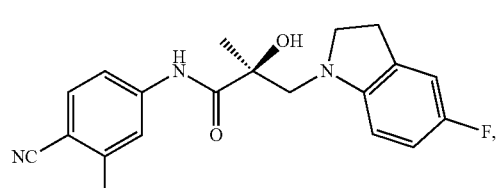
104
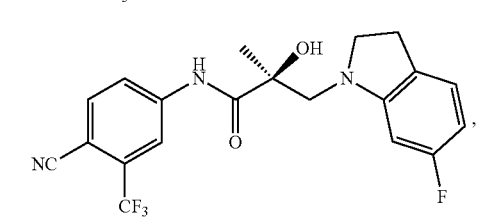
105
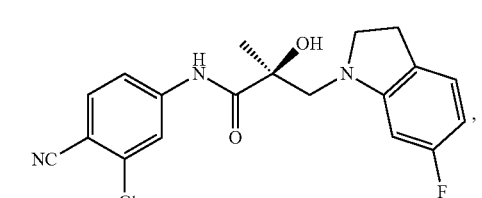
106
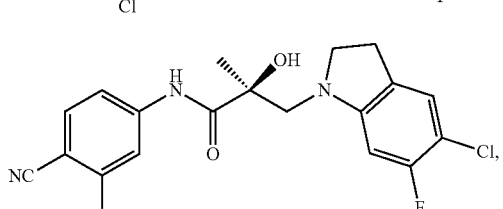
107
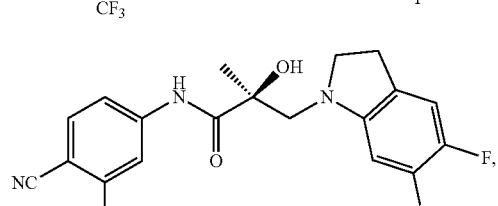
108
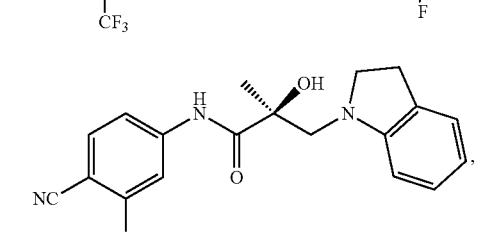
109
-continued
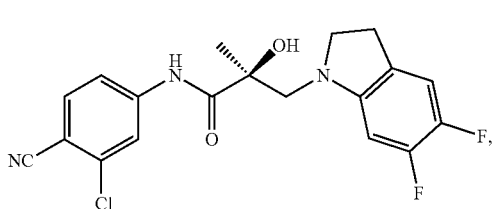
110
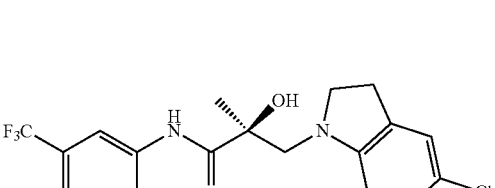
111
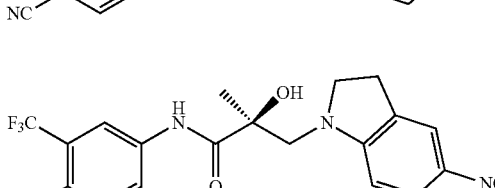
112
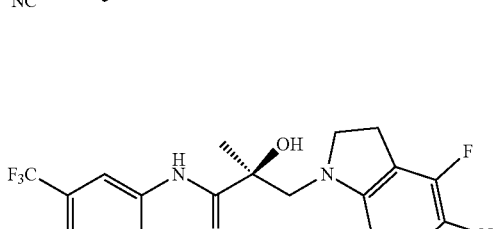
113
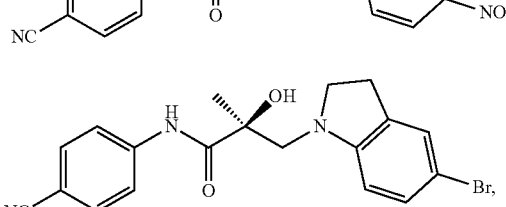
114
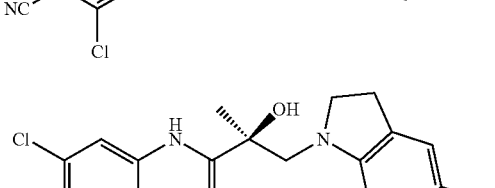
115
isoquinolines and quinolines:
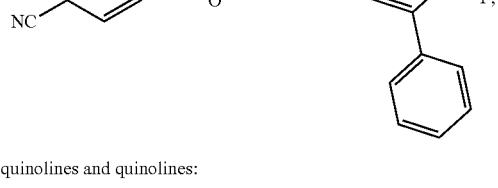
130

131 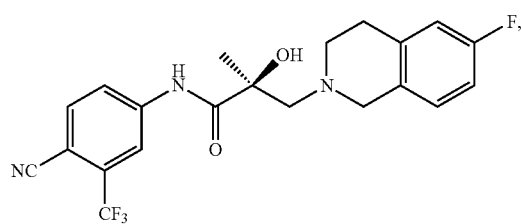
132 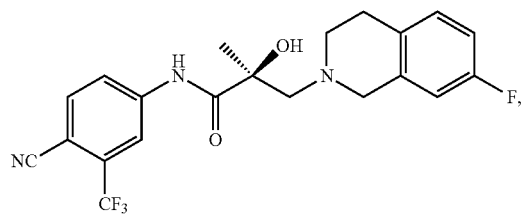
133 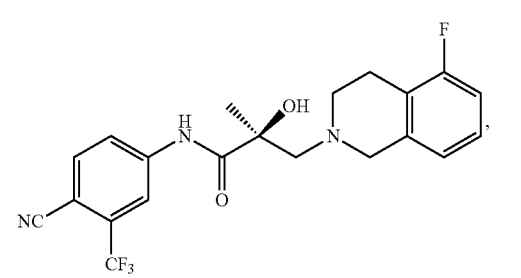
134 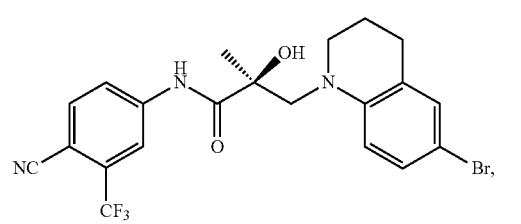
135 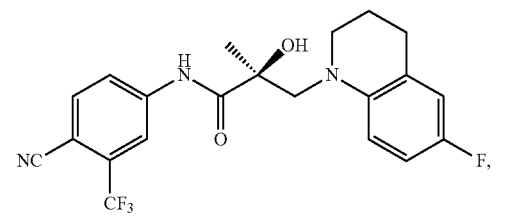
136 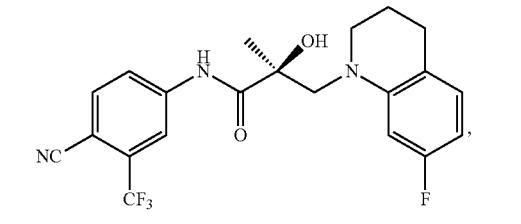
137 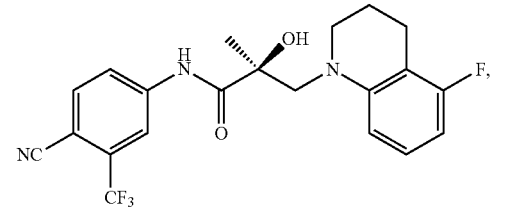
carbazoles:
200 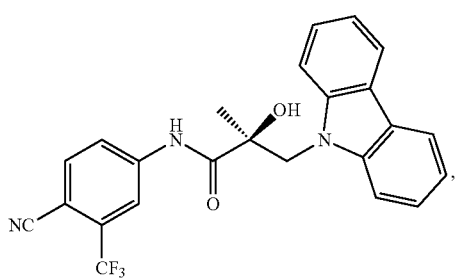
201 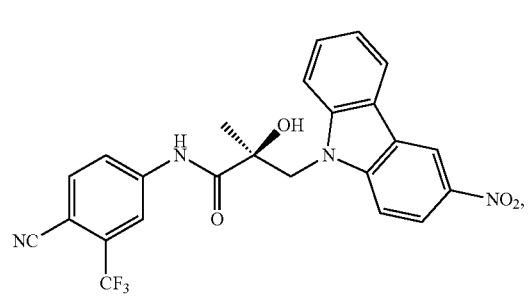
202 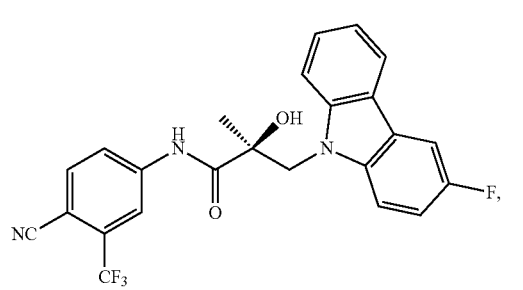
203 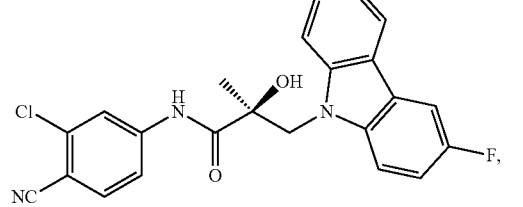
204 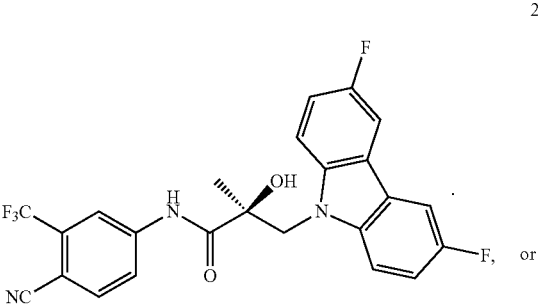
or

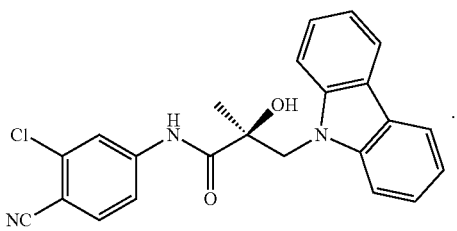

205

The term "heterocycloalkyl" group refers, in one embodiment, to a cycloalkyl structure comprising in addition to carbon atoms, sulfur, oxygen, nitrogen or any combination thereof, as part of the ring. In another embodiment, the heterocycloalkyl is a 3-12 membered ring. In another embodiment, the heterocycloalkyl is a 6 membered ring. In another embodiment, the heterocycloalkyl is a 5-7 membered ring. In another embodiment, the heterocycloalkyl is a 4-8 membered ring. In another embodiment, the heterocycloalkyl group may be unsubstituted or substituted by a halogen, haloalkyl, hydroxyl, alkoxy, carbonyl, amido, alkylamido, dialkylamido, cyano, nitro, $CO_2H$, amino, alkylamino, dialkylamino, carboxyl, thio and/or thioalkyl. In another embodiment, the heterocycloalkyl ring may be fused to another saturated or unsaturated cycloalkyl or heterocyclic 3-8 membered ring. In another embodiment, the heterocyclic ring is a saturated ring. In another embodiment, the heterocyclic ring is an unsaturated ring. In another embodiment, the heterocycloalkyl is piperidine, tetrahydrofuran, morpholine, pyrrolidine, or piperazine.

The term "cycloalkyl" refers to a non-aromatic, monocyclic or polycyclic ring comprising carbon and hydrogen atoms. A cycloalkyl group can have one or more carbon-carbon double bonds in the ring so long as the ring is not rendered aromatic by their presence. Examples of cycloalkyl groups include, but are not limited to, ($C_3$-$C_7$) cycloalkyl groups, such as cyclopropyl, cyclobutyl, cyclopentyl, cyclohexyl, and cycloheptyl, and saturated cyclic and bicyclic terpenes and ($C_3$-$C_7$) cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two substituents. Preferably, the cycloalkyl group is a monocyclic ring or bicyclic ring.

The term "alkyl" refers, in one embodiment, to a saturated aliphatic hydrocarbon, including straight-chain, branched-chain and cyclic alkyl groups. In one embodiment, the alkyl group has 1-12 carbons. In another embodiment, the alkyl group has 1-7 carbons. In another embodiment, the alkyl group has 1-6 carbons. In another embodiment, the alkyl group has 1-4 carbons. In another embodiment, the cyclic alkyl group has 3-8 carbons. In another embodiment, the cyclic alkyl group has 3-12 carbons. In another embodiment, the branched alkyl is an alkyl substituted by alkyl side chains of 1 to 5 carbons. In another embodiment, the branched alkyl is an alkyl substituted by haloalkyl side chains of 1 to 5 carbons. The alkyl group may be unsubstituted or substituted by a halogen, haloalkyl, hydroxyl, alkoxy carbonyl, amido, alkylamido, dialkylamido, nitro, amino, alkylamino, dialkylamino, carboxyl, thio and/or thioalkyl.

The term "heteroalkyl" refers to any alkyl as defined above wherein one or more of the carbons are being replaced by oxygen, nitrogen, sulfur, phosphorous or combination thereof.

An "arylalkyl" group refers to an alkyl bound to an aryl, wherein alkyl and aryl are as defined above. An example of an arylalkyl group is a benzyl group.

An "alkenyl" group refers, in another embodiment, to an unsaturated hydrocarbon, including straight chain, branched chain and cyclic groups having one or more double bonds. The alkenyl group may have one double bond, two double bonds, three double bonds, etc. In another embodiment, the alkenyl group has 2-12 carbons. In another embodiment, the alkenyl group has 2-6 carbons. In another embodiment, the alkenyl group has 2-4 carbons. Examples of alkenyl groups are ethenyl, propenyl, butenyl, cyclohexenyl, etc. The alkenyl group may be unsubstituted or substituted by a halogen, hydroxy, alkoxy carbonyl, amido, alkylamido, dialkylamido, nitro, amino, alkylamino, dialkylamino, carboxyl, thio and/or thioalkyl.

An "aryl" group refers to an aromatic group having at least one carbocyclic aromatic group or heterocyclic aromatic group, which may be unsubstituted or substituted by one or more groups selected from halogen, haloalkyl, hydroxy, alkoxy carbonyl, amido, alkylamido, dialkylamido, nitro, amino, alkylamino, dialkylamino, carboxy or thio or thioalkyl. Nonlimiting examples of aryl rings are phenyl, naphthyl, pyranyl, pyrrolyl, pyrazinyl, pyrimidinyl, pyrazolyl, pyridinyl, furanyl, thiophenyl, thiazolyl, imidazolyl, isoxazolyl, and the like. In one embodiment, the aryl group is a 4-8 membered ring. In another embodiment, the aryl group is a 4-12 membered ring(s). In another embodiment, the aryl group is a 6 membered ring. In another embodiment, the aryl group is a 5 membered ring. In another embodiment, the aryl group is 2-4 fused ring system. In another embodiment, the aryl is phenyl.

A "haloalkyl" group refers, in another embodiment, to an alkyl group as defined above, which is substituted by one or more halogen atoms, e.g. by F, Cl, Br or I.

A "hydroxyl" group refers, in another embodiment, to an OH group. It is understood by a person skilled in the art that when T, Q, $R_2$ $R_3$ or $R_4$ in the compounds of the present invention is OR, then the corresponding R is not OH.

In one embodiment, the term "halogen" or "halo" refers to a halogen, such as F, Cl, Br or I.

In one embodiment, this invention provides for the use of a compound as herein described and/or, its derivative, isomer, metabolite, pharmaceutically acceptable salt, pharmaceutical product, hydrate, N-oxide, prodrug, polymorph, crystal or combinations thereof.

In one embodiment, the methods of this invention make use of "pharmaceutically acceptable salts" of the compounds, which may be produced, by reaction of a compound of this invention with an acid or base.

Suitable pharmaceutically acceptable salts of amines of the compounds of the methods of this invention may be prepared from an inorganic acid or from an organic acid. In one embodiment, examples of inorganic salts of amines are bisulfates, borates, bromides, chlorides, hemisulfates, hydrobromates, hydrochlorates, 2-hydroxyethylsulfonates (hydroxyethanesulfonates), iodates, iodides, isothionates, nitrates, persulfates, phosphate, sulfates, sulfamates, sulfanilates, sulfonic acids (alkylsulfonates, arylsulfonates, halogen substituted alkylsulfonates, halogen substituted arylsulfonates), sulfonates and thiocyanates.

In one embodiment, examples of organic salts of amines may be selected from aliphatic, cycloaliphatic, aromatic, araliphatic, heterocyclic, carboxylic and sulfonic classes of organic acids, examples of which are acetates, arginines, aspartates, ascorbates, adipates, anthranilates, algenates, alkane carboxylates, substituted alkane carboxylates, alginates, benzenesulfonates, benzoates, bisulfates, butyrates, bicarbonates, bitartrates, carboxylates, citrates, camphorates, camphorsulfonates, cyclohexylsulfamates, cyclopentanepropionates, calcium edetates, camsylates, carbonates, clavulanates, cinnamates, dicarboxylates, digluconates, dodecylsulfonates, dihydrochlorides, decanoates, enanthuates, ethanesulfonates, edetates, edisylates, estolates, esylates, fumarates, formates, fluorides, galacturonates, gluconates, glutamates, glycolates, glucorates, glucoheptanoates, glycerophosphates, gluceptates, glycollylarsanilates, glutarates, glutamates, heptanoates, hexanoates, hydroxymaleates, hydroxycarboxlic acids, hexylresorcinates, hydroxybenzoates, hydroxynaphthoates, hydrofluorates, lactates, lactobionates, laurates, malates, maleates, methylenebis(beta-oxynaphthoate), malonates, mandelates, mesylates, methane sulfonates, methylbromides, methylnitrates, methylsulfonates, monopotassium maleates, mucates, monocarboxylates, nitrates, naphthalenesulfonates, 2-naphthalenesulfonates, nicotinates, napsylates, N-methylglucamines, oxalates, octanoates, oleates, pamoates, phenylacetates, picrates, phenylbenzoates, pivalates, propionates, phthalates, pectinates, phenylpropionates, palmitates, pantothenates, polygalacturates, pyruvates, quinates, salicylates, succinates, stearates, sulfanilates, subacetates, tartarates, theophyllineacetates, p-toluenesulfonates (tosylates), trifluoroacetates, terephthalates, tannates, teoclates, trihaloacetates, triethiodide, tricarboxylates, undecanoates and valerates.

In one embodiment, examples of inorganic salts of carboxylic acids or phenols may be selected from ammonium, alkali metals to include lithium, sodium, potassium, cesium; alkaline earth metals to include calcium, magnesium, aluminium; zinc, barium, cholines, quaternary ammoniums.

In another embodiment, examples of organic salts of carboxylic acids or phenols may be selected from arginine, organic amines to include aliphatic organic amines, alicyclic organic amines, aromatic organic amines, benzathines, t-butylamines, benethamines (N-benzylphenethylamine), dicyclohexylamines, dimethylamines, diethanolamines, ethanolamines, ethylenediamines, hydrabamines, imidazoles, lysines, methylamines, meglamines, N-methyl-D-glucamines, N,N'-dibenzylethylenediamines, nicotinamides, organic amines, ornithines, pyridines, picolies, piperazines, procaine, tris(hydroxymethyl)methylamines, triethylamines, triethanolamines, trimethylamines, tromethamines and ureas.

In one embodiment, the salts may be formed by conventional means, such as by reacting the free base or free acid form of the product with one or more equivalents of the appropriate acid or base in a solvent or medium in which the salt is insoluble or in a solvent such as water, which is removed in vacuo or by freeze drying or by exchanging the ions of a existing salt for another ion or suitable ion-exchange resin.

In one embodiment, the methods of this invention make use of a pharmaceutically acceptable salt of the compounds of this invention. In one embodiment, the methods of this invention make use of a pharmaceutically acceptable salt of compounds of this invention. In one embodiment, the methods of this invention make use of a salt of an amine of the compounds of this invention. In one embodiment, the methods of this invention make use of a salt of a phenol of the compounds of this invention.

In one embodiment, the methods of this invention make use of a free base, free acid, non charged or non-complexed compounds of this invention and/or its isomer, pharmaceutical product, hydrate, polymorph, or combinations thereof.

In one embodiment, the methods of this invention make use of an isomer of a compound of this invention. In one embodiment, the methods of this invention make use of a pharmaceutical product of a compound of this invention. In one embodiment, the methods of this invention make use of a hydrate of a compound of this invention. In one embodiment, the methods of this invention make use of a polymorph of a compound of this invention. In one embodiment, the methods of this invention make use of a metabolite of a compound of this invention. In another embodiment, the methods of this invention make use of a composition comprising a compound of this invention, as described herein, or, in another embodiment, a combination of isomer, metabolite, pharmaceutical product, hydrate, polymorph of a compound of this invention.

In one embodiment, the term "isomer" includes, but is not limited to, optical isomers and analogs, structural isomers and analogs, conformational isomers and analogs, and the like.

In one embodiment, the term "isomer" is meant to encompass optical isomers of the SARD compound. It will be appreciated by those skilled in the art that the SARDs of the present invention contain at least one chiral center. Accordingly, the SARDs used in the methods of the present invention may exist in, and be isolated in, optically-active or racemic forms. Some compounds may also exhibit polymorphism. It is to be understood that the present invention encompasses any racemic, optically-active, polymorphic, or stereroisomeric form, or mixtures thereof, which form possesses properties useful in the treatment of androgen-related conditions described herein. In one embodiment, the SARDs are the pure (R)-isomers. In another embodiment, the SARDs are the pure (S)-isomers. In another embodiment, the SARDs are a mixture of the (R) and the (S) isomers. In another embodiment, the SARDs are a racemic mixture comprising an equal amount of the (R) and the (S) isomers. It is well known in the art how to prepare optically-active forms (for example, by resolution of the racemic form by recrystallization techniques, by synthesis from optically-active starting materials, by chiral synthesis, or by chromatographic separation using a chiral stationary phase).

In another embodiment, this invention further includes hydrates of the compounds. The invention also includes use of N-oxides of the amino substituents of the compounds described herein.

In one embodiment, the term "hydrate" refers to hemihydrate, monohydrate, dihydrate, trihydrate or others, as known in the art.

This invention provides, in other embodiments, use of metabolites of the compounds as herein described. In one embodiment, "metabolite" means any substance produced from another substance by metabolism or a metabolic process.

In one embodiment, the compounds of this invention are prepared according to Examples 1-4.

Biological Activity of Selective Androgen Receptor Degraders

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, represented by the structure of formula I, I(1)-I(2), la-le, Ia(1)-Ie(1), Ia(2)-Ie(2), II-VIII, II(1), V(1)-

V(2), IXa-IXj, X, XIa-XIj, XII, XIIIa-XIIIj, XIV, XIV(1)-XIV(2), XV, XVIa, XVIb, XVIa(1), XVIb(1), XVIa(2), and XVIb(2) as described above. In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, flutamide, bicalutamide, abiraterone, ARN-509, ODM-201, EPI-001, AZD-3514, galeterone, ASC-J9, flutamide, hydroxyflutamide, nilutamide, cyproterone acetate, ketoconazole, spironolactone, or any combination thereof.

In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject. In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a compound or its isomer, pharmaceutically acceptable salt, pharmaceutical product, polymorph, hydrate or any combination thereof, said compound selected from the following structures:

Indoles:

11

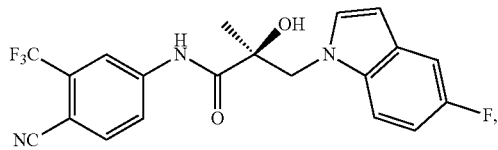

11R

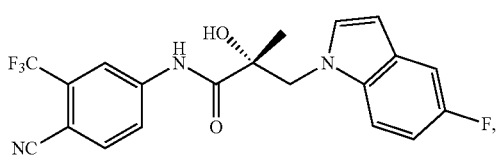

12

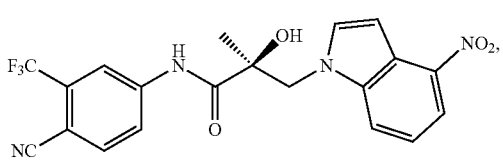

13

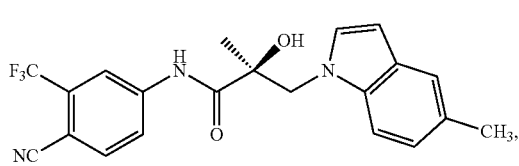

-continued

14

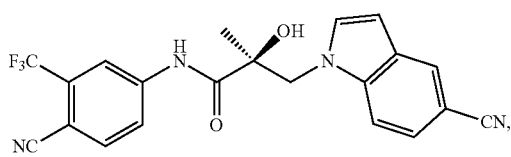

15

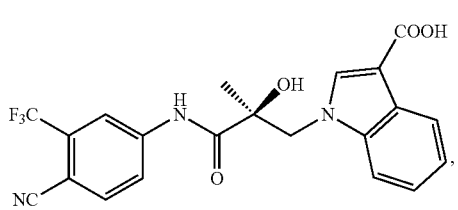

16

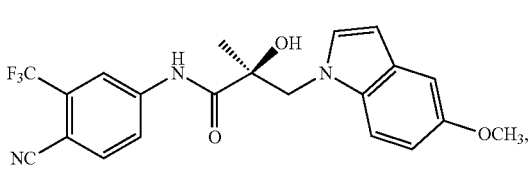

17

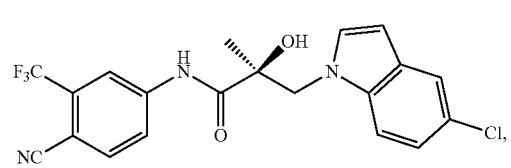

18

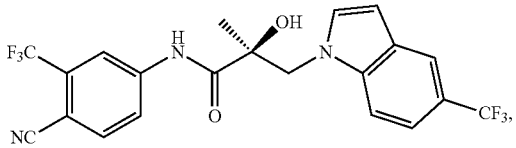

19

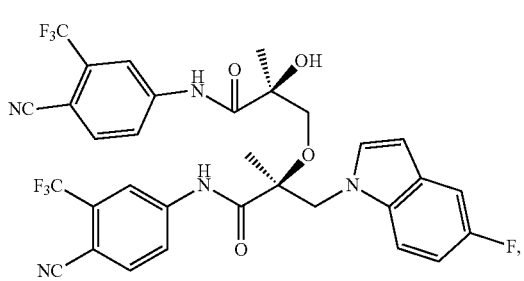

20

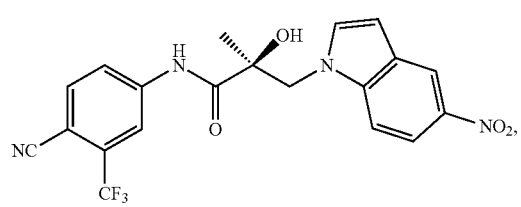

21

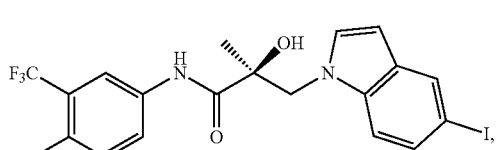

22 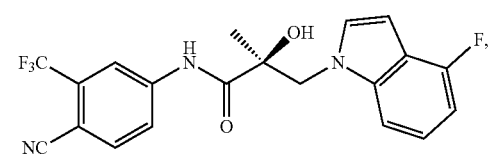
23 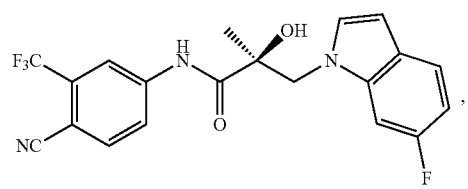
24 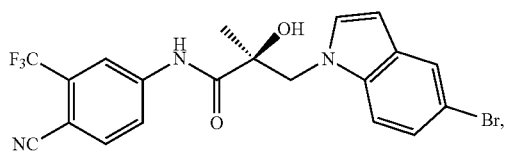
25 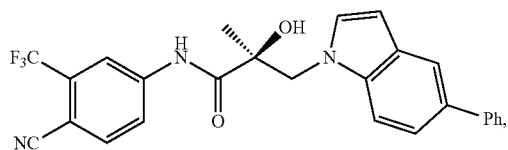
26 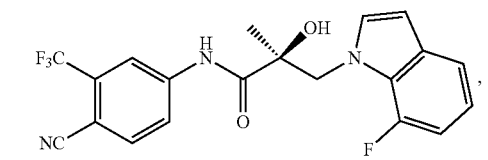
27 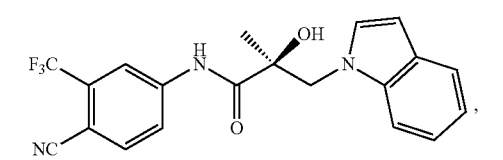
30 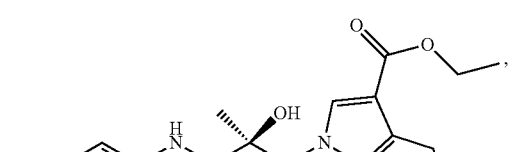
31 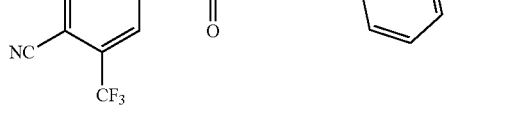
32 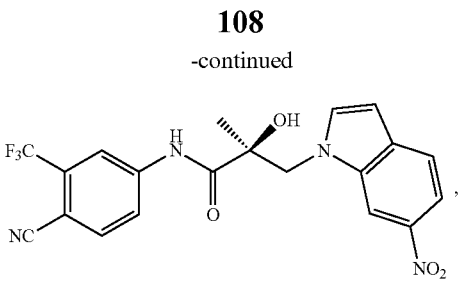
33 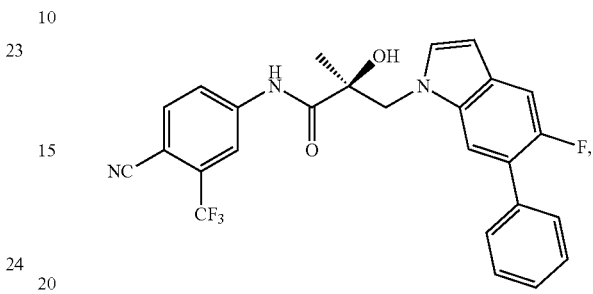
34 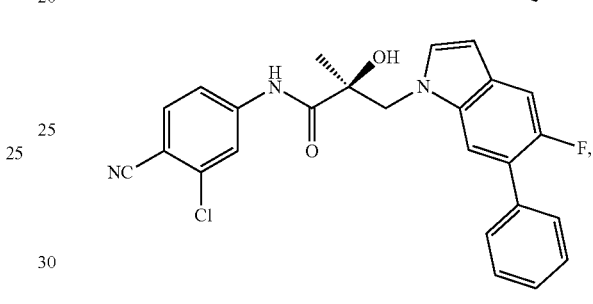
35 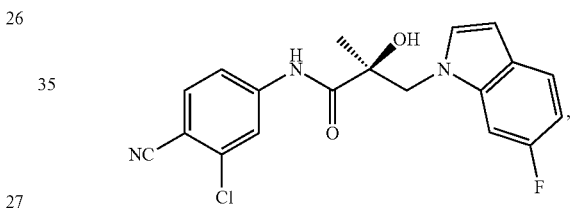
36 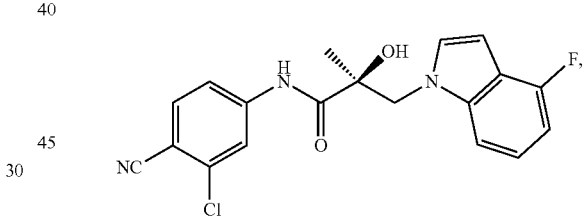
37 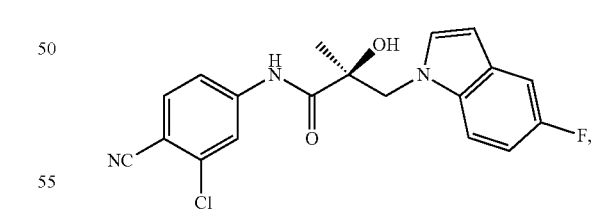
38 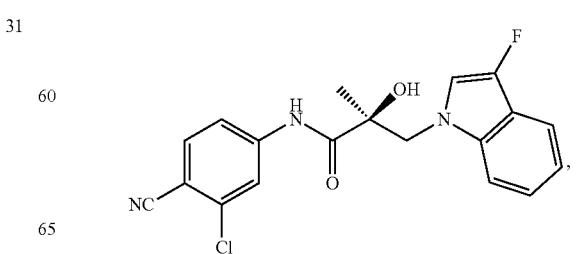

39
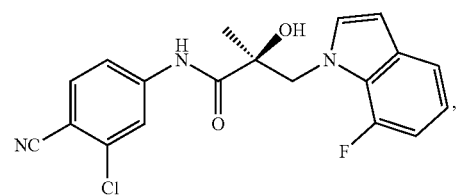
40
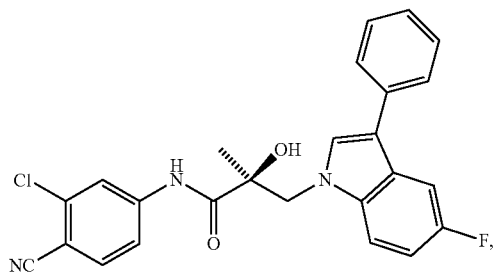
41
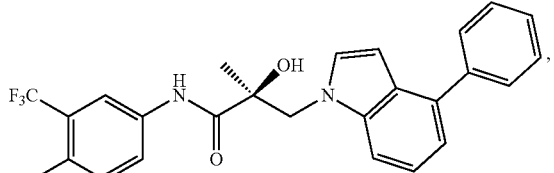
42

43
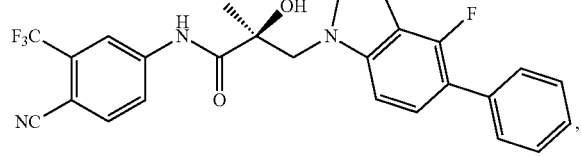
44
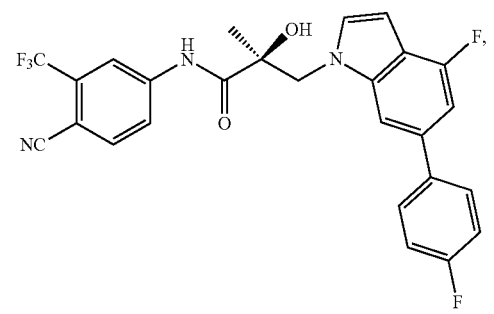
45
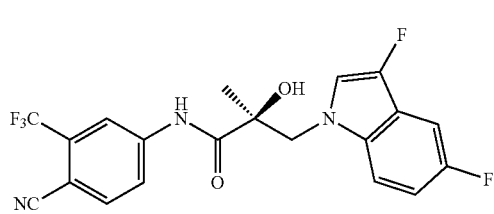
45
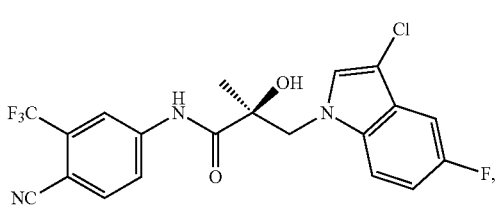
46
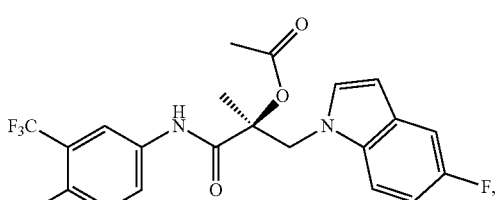
47
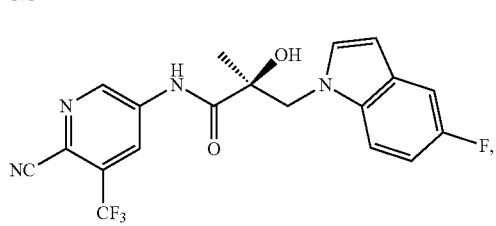
benzimidazoles:
70
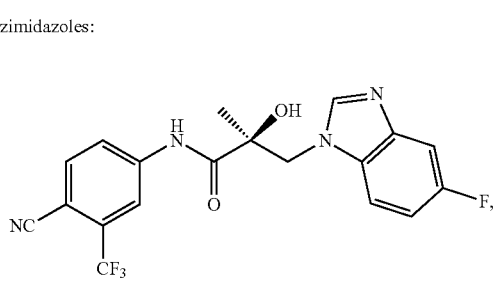
71
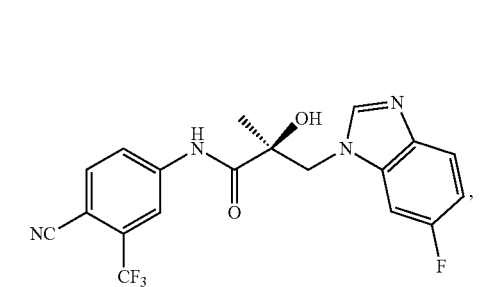
72
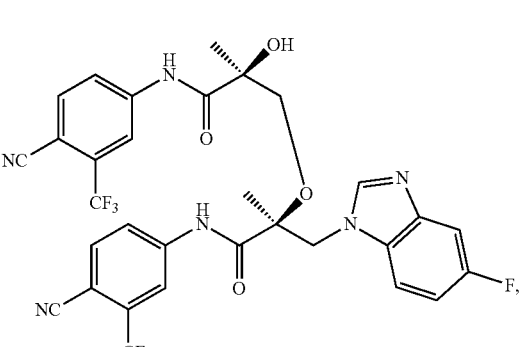
73
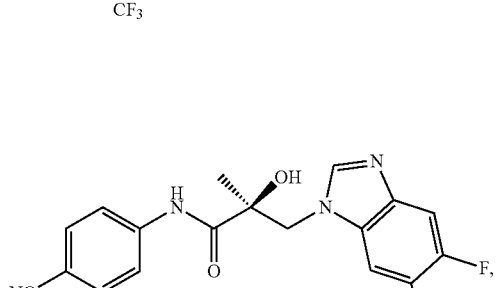

74 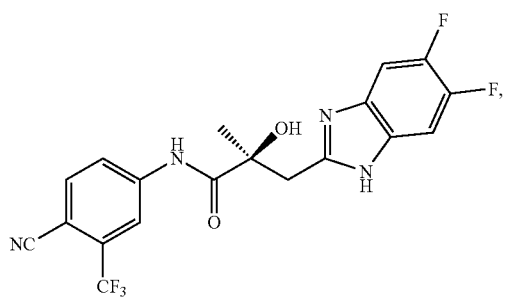
75 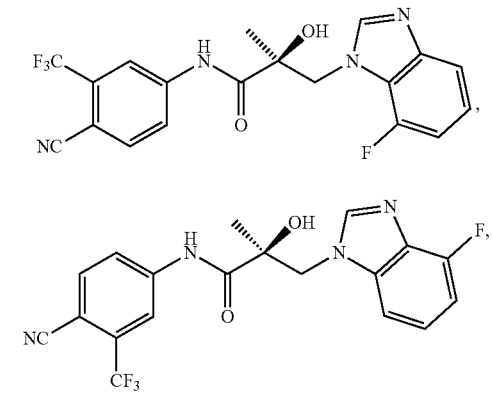
76 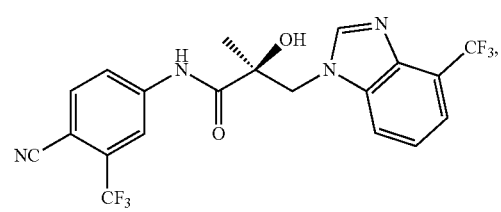
77 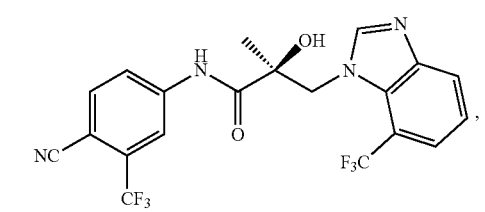
78 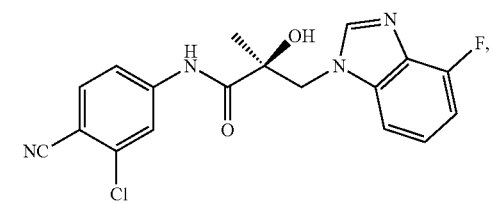
79 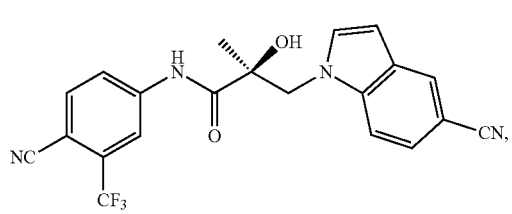
pyrrolo-pyridine:
indazoles:
5 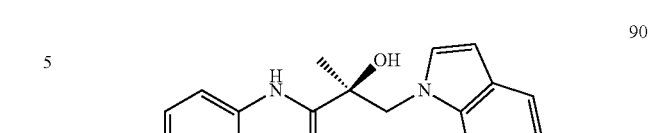
91 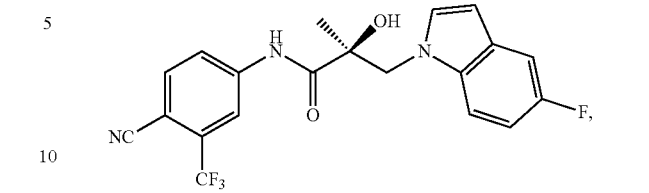
92 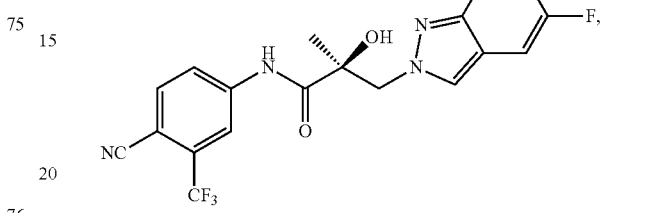
93 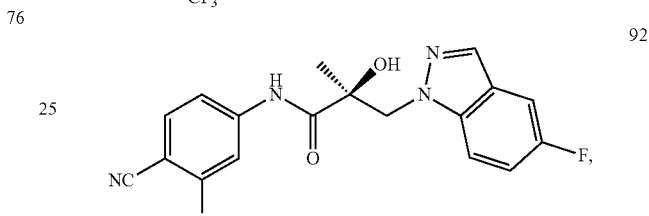
94 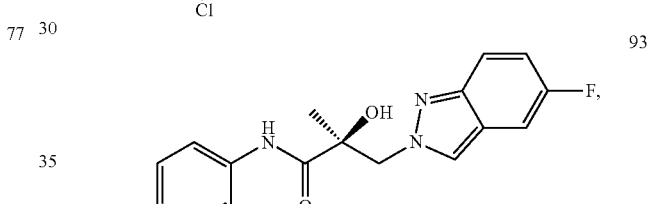
95 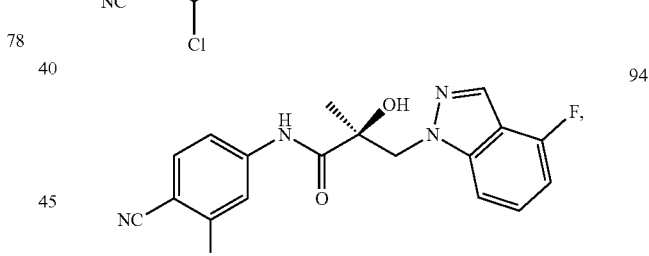
96 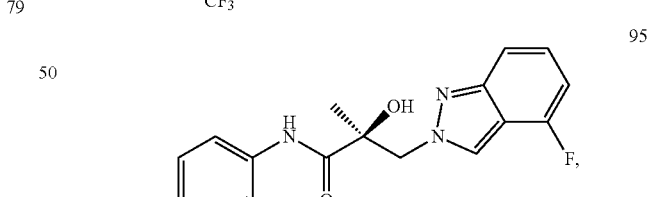

97
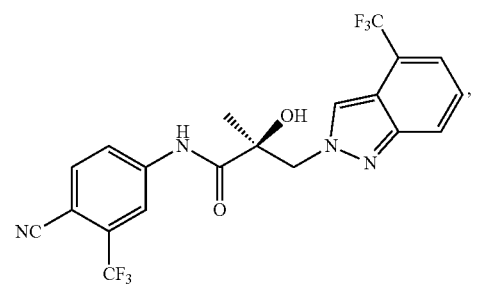
98
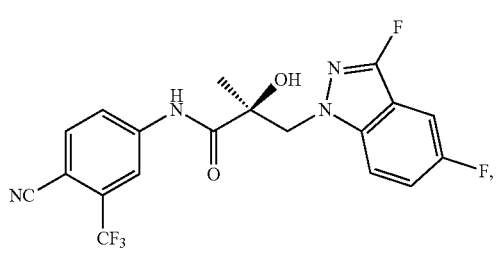
99
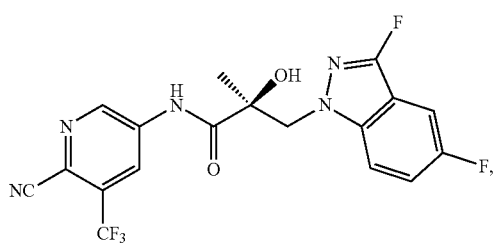
benzotriazoles:
300
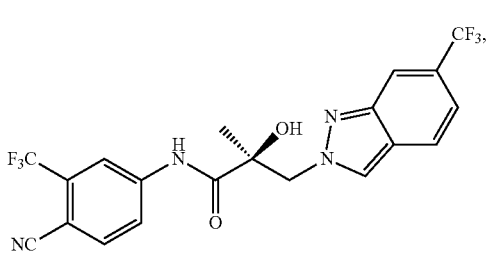
301
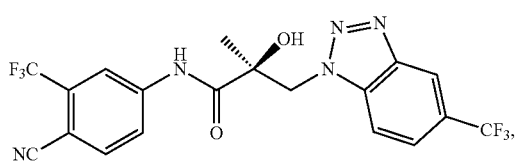
302
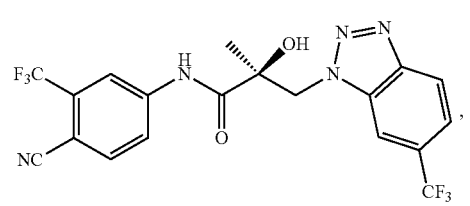
303
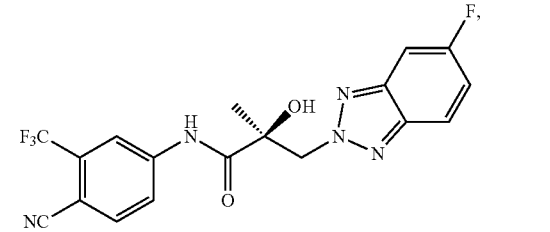
304
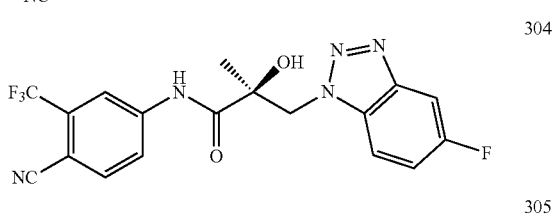
305
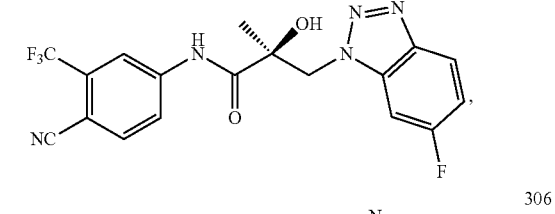
306
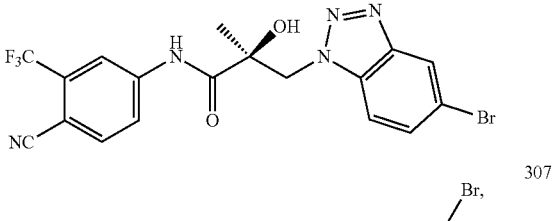
307
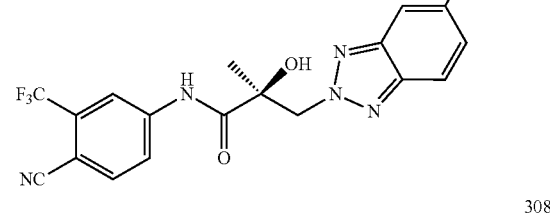
308
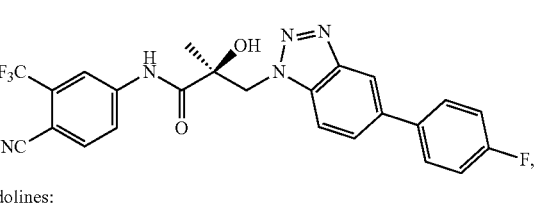
Indolines:
100
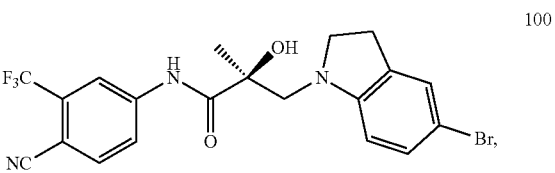
101
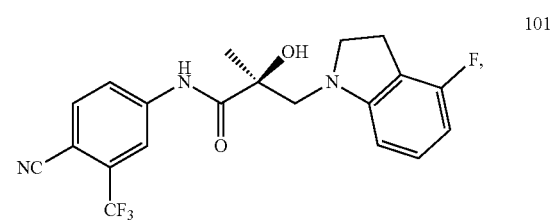

102 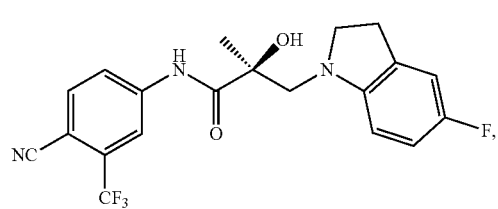
103 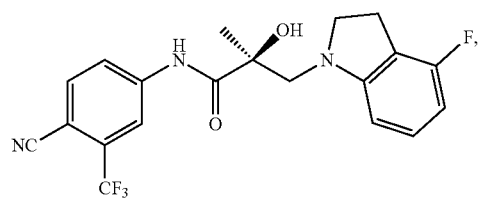
104 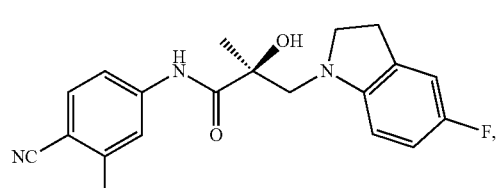
105 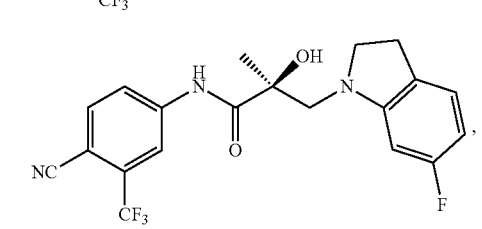
106 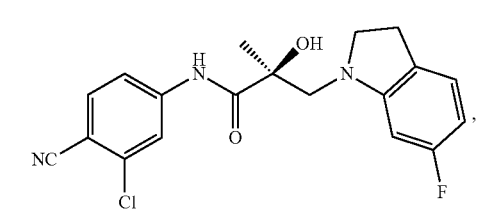
107 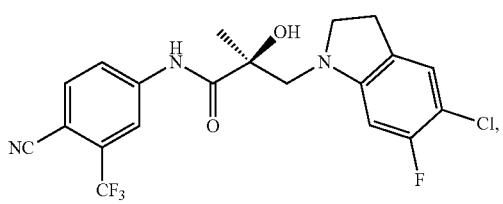
108 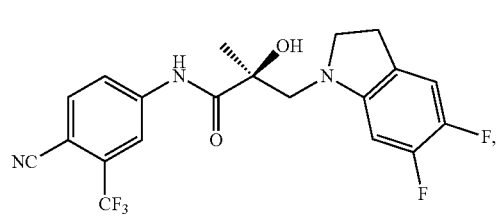
109 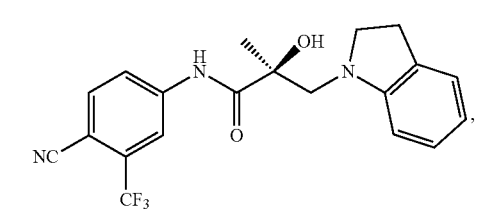
110 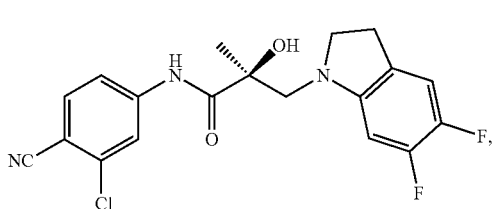
111 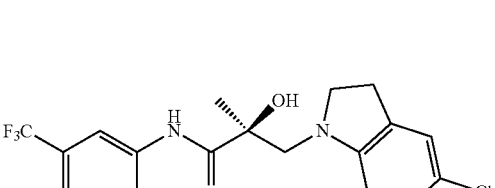
112 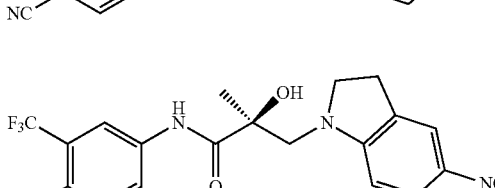
113 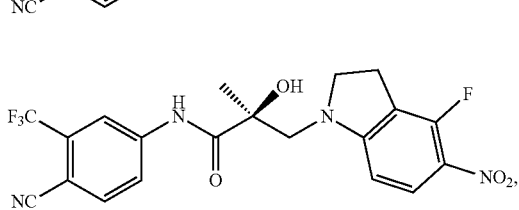
114 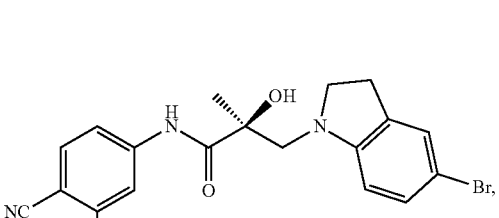
115 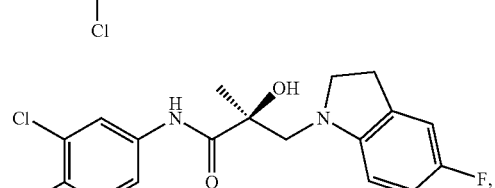
Isoquinolines and Quinolines:
130 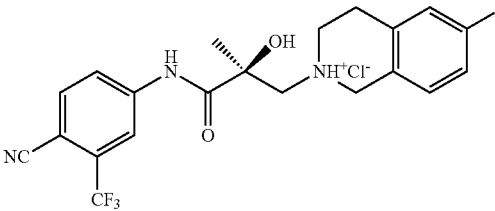

131 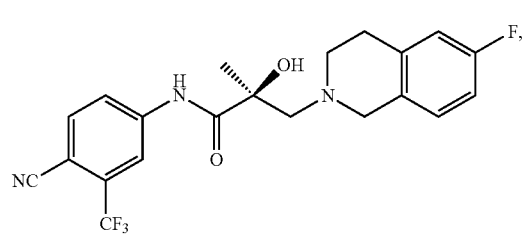
132 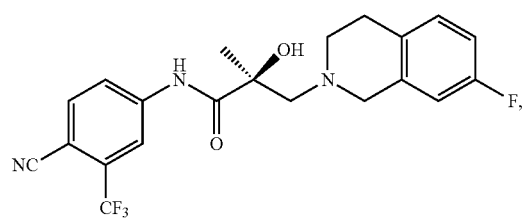
133 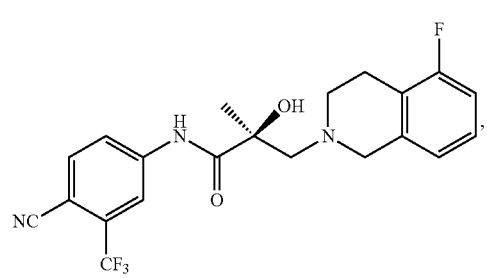
134 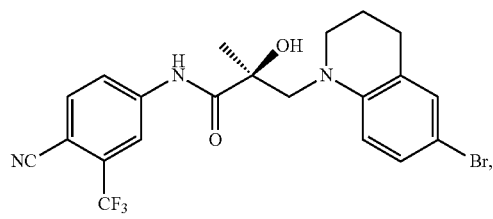
135 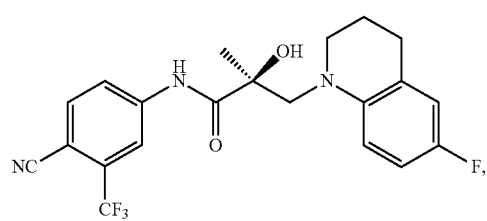
136 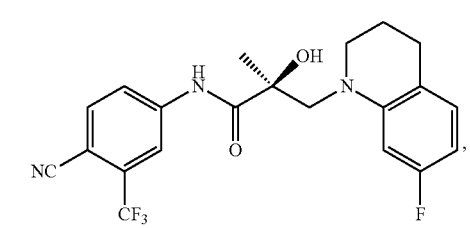
137 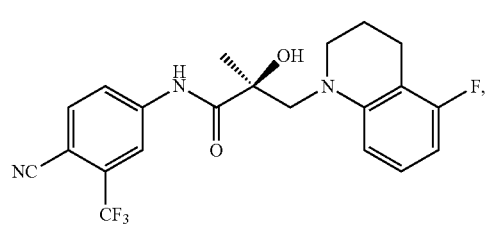
Carbazoles:
200 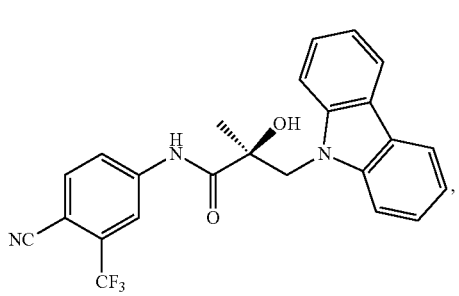
201 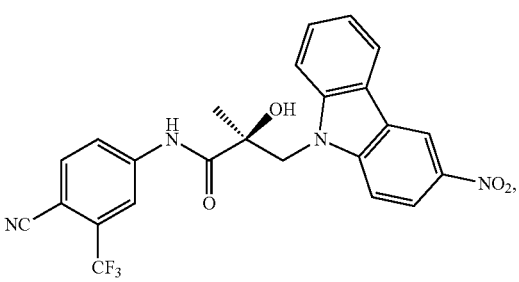
202 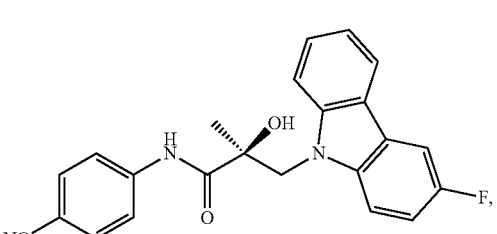
203 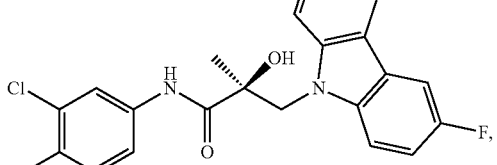
204 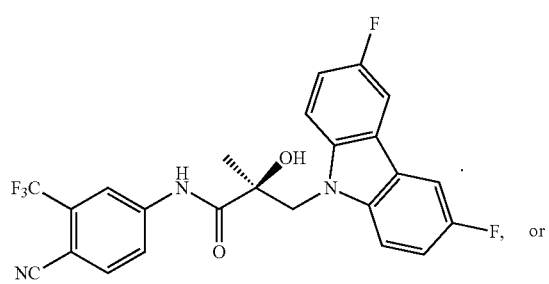, or

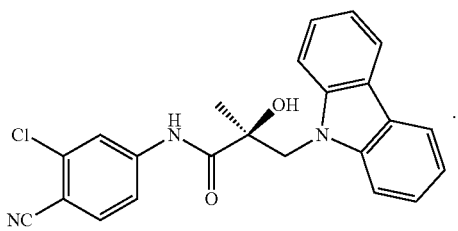

205

In another embodiment, the prostate cancer is advanced prostate cancer, castration resistant prostate cancer (CRPC), metastatic CRPC (mCRPC), non-metastatic CRPC (nmCRPC), high-risk nmCRPC or any combination thereof. In another embodiment, the prostate cancer depends on AR-FL and/or AR-SV for proliferation. In another embodiment, the subject further receives androgen deprivation therapy (ADT). In another embodiment, the subject has failed androgen deprivation therapy (ADT). In another embodiment, the cancer is resistant to treatment with an androgen receptor antagonist. In another embodiment, the cancer is resistant to treatment with enzalutamide, flutamide, bicalutamide, abiraterone, ARN-509, ODM-201, EPI-001, AZD-3514, galeterone, ASC-J9, flutamide, hydroxyflutamide, nilutamide, cyproterone acetate, ketoconazole, spironolactone, or any combination thereof. In another embodiment, administering the compound to a subject reduces the levels of AR, AR-full length (AR-FL), AR-FL with antiandrogen resistance-conferring AR-LBD mutations, AR-splice variant (AR-SV), gene-amplified AR, or any combination thereof, in said subject.

In one embodiment, the methods of this invention are directed to treating, suppressing, reducing the incidence, reducing the severity, inhibiting, providing palliative care, or increasing the survival of a subject suffering from prostate cancer. In one embodiment, the methods of this invention are directed to methods of treating, suppressing, reducing the incidence, reducing the severity, inhibiting, providing palliative care, or increasing the survival of advanced prostate cancer in a subject.

In one embodiment, the methods of this invention are directed to treating, suppressing, reducing the incidence, reducing the severity, inhibiting, providing palliative care, or increasing the survival of a subject suffering from castration resistant prostate cancer (CRPC). In one embodiment, the methods of this invention are directed to treating, suppressing, reducing the incidence, reducing the severity, inhibiting, providing palliative care, or increasing the survival of a subject suffering from metastatic castration resistant prostate cancer (mCRPC). In one embodiment, the methods of this invention are directed to treating, suppressing, reducing the incidence, reducing the severity, inhibiting, providing palliative care, or increasing the survival of a subject suffering from non-metastatic castration resistant prostate cancer (nmCRPC). In one embodiment, the nmCRPC is high-risk nmCRPC. In another embodiment, the subject has high or increasing prostate specific antigen (PSA) levels.

In one embodiment, this invention provides a method of treating, suppressing, reducing the incidence, reducing the severity, or inhibiting the progression of prostate cancer (PCa) and its symptoms, or increasing the survival of a male subject suffering from prostate cancer comprising administering to said subject a therapeutically effective amount of a SARD compound or its isomer, pharmaceutically acceptable salt, pharmaceutical product, polymorph, hydrate or any combination thereof, said compound is represented by a compound of any one of the formulas as describe herein or any one of compounds 11-27, 30-47, 11R, 70-79, 80, 90-99, 100-115, 130-137, 200-205 and 300-308 described herein.

In one embodiment, this invention provides a method of treating, suppressing, reducing the incidence, reducing the severity, or inhibiting the progression of advanced prostate cancer and its symptoms, or increasing the survival of a male subject suffering from advanced prostate cancer comprising administering to said subject a therapeutically effective amount of a SARD compound or its isomer, pharmaceutically acceptable salt, pharmaceutical product, polymorph, hydrate or any combination thereof, said compound is represented by a compound of any one of the formulas as described herein or any one of compounds 11-27, 30-47, 11R, 70-79, 80, 90-99, 100-115, 130-137, 200-205 and 300-308 described herein.

In one embodiment, this invention provides a method of treating, suppressing, reducing the incidence, reducing the severity, or inhibiting the progression of metastatic prostate cancer and its symptoms, or increasing the survival of a male subject suffering from metastatic prostate cancer comprising administering to said subject a therapeutically effective amount of a SARD compound or its isomer, pharmaceutically acceptable salt, pharmaceutical product, polymorph, hydrate or any combination thereof, said compound is represented by a compound of any one of the formulas as described herein or any one of compounds 11-27, 30-47, 11R, 70-79, 80, 90-99, 100-115, 130-137, 200-205 and 300-308 described herein.

In one embodiment, this invention provides a method of treating, suppressing, reducing the incidence, reducing the severity, or inhibiting the progression of castration resistant prostate cancer (CRPC) and its symptoms, or increasing the survival of a male subject suffering from castration resistant prostate cancer (CRPC) comprising administering to said subject a therapeutically effective amount of a SARD compound or its isomer, pharmaceutically acceptable salt, pharmaceutical product, polymorph, hydrate or any combination thereof, said compound is represented by a compound of any one of the formulas as described herein or any one of compounds 11-27, 30-47, 11R, 70-79, 80, 90-99, 100-115, 130-137, 200-205 and 300-308 described herein.

In one embodiment, the SARD compounds as described herein and/or compositions comprising the same may be used for treating, suppressing, reducing the incidence, reducing the severity, or inhibiting the progression of castration resistant prostate cancer (CRPC) and its symptoms, or increasing the survival of men with castration resistant prostate cancer. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

As used herein, the terms "increase" and "prolong" may be used interchangeably having all the same meanings and qualities, wherein these terms may in one embodiment refer to a lengthening of time. In another embodiment, as used herein, the terms "increase", "increasing" "increased" may be used interchangeably and refer to an entity becoming progressively greater (as in size, amount, number, or intensity), wherein for example the entity is sex hormone-binding globulin (SHBG) or prostate-specific antigen (PSA).

In one embodiment, the compounds as described herein and/or compositions comprising the same may be used for increasing metastasis-free survival (MFS) in a subject suffering from non-metastatic prostate cancer. In one embodiment, the non-metastatic prostate cancer is non-metastatic advanced prostate cancer. In another embodiment, the non-metastatic prostate cancer is non-metastatic CRPC (nmCRPC). In one embodiment, the nmCRPC is high-risk nmCRPC.

In one embodiment, the SARD compounds as described herein and/or compositions comprising the same may be used to provide a dual action, for example treating prostate cancer and preventing metastases. In one embodiment, the prostate cancer being treated is advanced prostate cancer. In one embodiment, the prostate cancer being treated is castration resistant prostate cancer (CRPC). In one embodiment, the prostate cancer being treated is metastatic CRPC (mCRPC). In one embodiment, the prostate cancer being treated is non-metastatic CRPC (nmCRPC). In one embodiment, the nmCRPC is high-risk nmCRPC.

Men with advanced prostate cancer who are at high risk for progression to castration resistant prostate cancer (CRPC), in one embodiment, are men on ADT with serum total testosterone concentrations greater than 20 ng/dL or in another embodiment, men with advanced prostate cancer who at the time of starting ADT had either (1) confirmed Gleason pattern 4 or 5 prostate cancer, (2) metastatic prostate cancer, (3) a PSA doubling time <3 months, (4) a PSA>20 ng/mL, or (5) a PSA relapse in <3 years after definitive local therapy (radical prostatectomy or radiation therapy).

Men with high risk non-metastatic castration resistant prostate cancer (high-risk nmCRPC) may include those with rapid PSA doubling times, having an expected progression-free survival of approximately 18 months or less (Miller K, Moul J W, Gleave M, et al. 2013. Phase III, randomized, placebo-controlled study of once-daily oral zibotentan (ZD4054) in patients with non-metastatic castration-resistant prostate cancer. *Prostate Canc Prost Dis. February;* 16:187-192). This relatively rapid progression of their disease underscores the importance of novel therapies for these individuals. In one embodiment, the PSA levels are greater than 8 ng/mL in a subject suffering from high-risk nmCRPC. In one embodiment, the PSA doubling time is less than 8 months in a subject suffering from high-risk nmCRPC. In another embodiment, the PSA doubling time is less than 10 months in a subject suffering from high-risk nmCRPC. In one embodiment, the total serum testosterone levels are greater than 20 ng/mL in a subject suffering from high-risk nmCRPC. In one embodiment, the serum free testosterone levels are greater than those observed in an orchidectomized male in a subject suffering from high-risk nmCRPC.

In one embodiment, the compounds as described herein and/or compositions comprising the same may be used in combination with LHRH agonist or antagonist for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-programmed death receptor 1 (anti-PD-1) drugs (e.g., AMP-224, nivolumab, pembrolizumab, pidilizumab, AMP-554, and the like) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In one embodiment, the compounds as described herein and/or compositions comprising the same may be used in combination with anti-PD-L1 drugs or anti-CTLA-4 drugs (anti-PD-L1 drugs include, but are not limited to, BMS-936559, atezolizumab, durvalumab, avelumab, and MPDL3280A. Anti-CTLA-4 drugs include, but are not limited to, ipilimumab and tremelimumab.) for increasing the progression free survival or overall survival of a subject suffering from prostate cancer. In another embodiment, the prostate cancer is advanced prostate cancer. In another embodiment, the prostate cancer is castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject is surgically castrated. In another embodiment, the subject is chemically castrated.

In certain embodiments, treatment of prostate cancer, advanced prostate cancer, CRPC, mCRPC and/or nmCRPC may result in clinically meaningful improvement in prostate cancer related symptoms, function and/or survival. Clinically meaningful improvements include but are not limited to increasing radiographic progression free survival (rPFS) if cancer is metastatic, and increasing metastasis-free survival (MFS) if cancer is non-metastatic.

In one embodiment, the compounds as described herein and/or compositions comprising the same may be used for increasing the survival of men with castration resistant prostate cancer (CRPC). In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the subject further receives androgen deprivation therapy.

In one embodiment, levels of prostate specific antigen (PSA) considered normal are age dependent. In one embodiment, levels of prostate specific antigen (PSA) considered normal are dependent on the size of a male subject's prostate. In one embodiment, PSA levels in the range between 2.5-10 ng/mL are considered "borderline high". In another embodiment, PSA levels above ng/mL are considered "high".

In one embodiment, the rate of change or "PSA velocity" is high. In one embodiment, a rate of change or "PSA velocity" greater than 0.75/year is considered high.

In one embodiment, this invention provides a method of lowering serum prostate specific antigen (PSA) levels in a male subject suffering from prostate cancer, advanced prostate cancer, metastatic prostate cancer or castration resistant prostate cancer (CRPC), comprising administering a therapeutically effective amount of a SARD compound or its isomer, pharmaceutically acceptable salt, pharmaceutical product, polymorph, hydrate or any combination thereof, said compound is represented by the structure of any one of the formulas as described herein or any one of compounds 11-27, 30-47, 11R, 70-79, 80, 90-99, 100-115, 130-137, 200-205, or 300-308 described herein. In one embodiment, this invention is directed to treatment of a subject with high or increasing PSA levels comprising administering a SARD compound of this invention. In one embodiment, this invention is directed to treatment of a subject with high or increasing PSA levels despite ongoing ADT or a history of ADT, surgical castration or despite treatment with antiandrogens and/or LHRH agonist. In another embodiment, the treatment makes use of compounds of the invention or any one of compounds 11-27, 30-47, 11R, 70-79, 80, 90-99, 100-115, 130-137, 200-205, and 300-308 described herein.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of the invention or its isomer, pharmaceutically acceptable salt, pharmaceutical product, polymorph, hydrate or any combination thereof. In another embodiment, the compound is compound 11. In another embodiment, the compound is compound 11R. In another embodiment, the compound is compound 12. In another embodiment, the compound is compound 13. In another embodiment, the compound is compound 14. In another embodiment, the compound is compound 15. In another embodiment, the compound is compound 16. In another embodiment, the compound is compound 17. In another embodiment, the compound is compound 18. In another embodiment, the compound is compound 19. In another embodiment, the compound is compound 20. In another embodiment, the compound is compound 21. In another embodiment, the compound is compound 22. In another embodiment, the compound is compound 23. In another embodiment, the compound is compound 24. In another embodiment, the compound is compound 25. In another embodiment, the compound is compound 26. In another embodiment, the compound is compound 27. In another embodiment, the compound is compound 30. In another embodiment, the compound is compound 31. In another embodiment, the compound is compound 32. In another embodiment, the compound is compound 33. In another embodiment, the compound is compound 34. In another embodiment, the compound is compound 35. In another embodiment, the compound is compound 36. In another embodiment, the compound is compound 37. In another embodiment, the compound is compound 38. In another embodiment, the compound is compound 39. In another embodiment, the compound is compound 40. In another embodiment, the compound is compound 41. In another embodiment, the compound is compound 42. In another embodiment, the compound is compound 43. In another embodiment, the compound is compound 44. In another embodiment, the compound is compound 45. In another embodiment, the compound is compound 46. In another embodiment, the compound is compound 45. In another embodiment, the compound is compound 47. In another embodiment, the compound is compound 70. In another embodiment, the compound is compound 71. In another embodiment, the compound is compound 72. In another embodiment, the compound is compound 73. In another embodiment, the compound is compound 74. In another embodiment, the compound is compound 75. In another embodiment, the compound is compound 76. In another embodiment, the compound is compound 77. In another embodiment, the compound is compound 78. In another embodiment, the compound is compound 79. In another embodiment, the compound is compound 80. In another embodiment, the compound is compound 90. In another embodiment, the compound is compound 91. In another embodiment, the compound is compound 92. In another embodiment, the compound is compound 93. In another embodiment, the compound is compound 94. In another embodiment, the compound is compound 95. In another embodiment, the compound is compound 96. In another embodiment, the compound is compound 97. In another embodiment, the compound is compound 98. In another embodiment, the compound is compound 99. In another embodiment, the compound is compound 300. In another embodiment, the compound is compound 301. In another embodiment, the compound is compound 302. In another embodiment, the compound is compound 303. In another embodiment, the compound is compound 304. In another embodiment, the compound is compound 211. In another embodiment, the compound is compound 305. In another embodiment, the compound is compound 306. In another embodiment, the compound is compound 307. In another embodiment, the compound is compound 308.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of the invention or its isomer, pharmaceutically acceptable salt, pharmaceutical product, polymorph, hydrate or any combination thereof. In another embodiment, the compound is compound 100. In another embodiment, the compound is compound 101. In another embodiment, the compound is compound 102. In another embodiment, the compound is compound 103. In another embodiment, the compound is compound 104. In another embodiment, the compound is compound 105. In another embodiment, the compound is compound 106. In another embodiment, the compound is compound 107. In another embodiment, the compound is compound 108. In another embodiment, the compound is compound 109. In another embodiment, the compound is compound 110. In another embodiment, the compound is compound 111. In another embodiment, the compound is compound 112. In another embodiment, the compound is compound 113. In another embodiment, the compound is compound 114. In another embodiment, the compound is compound 115. In another embodiment, the compound is compound 130. In another embodiment, the compound is compound 131. In another embodiment, the compound is compound 132. In another embodiment, the compound is compound 133. In another embodiment, the compound is compound 134. In another embodiment, the compound is compound 135. In another embodiment, the compound is compound 136. In another embodiment, the compound is compound 137.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a compound of this invention or its isomer, pharmaceutically acceptable salt, pharmaceutical product, polymorph, hydrate or any combination thereof. In another embodiment, the compound is compound 200. In another embodiment, the compound is compound 201. In another embodiment, the compound is compound 202. In another embodiment, the compound is compound 203. In another embodiment, the compound is compound 204. In another embodiment, the compound is compound 205.

In one embodiment, this invention provides a method of secondary hormonal therapy that reduces serum PSA in a male subject suffering from castration resistant prostate cancer (CRPC) comprising administering a therapeutically effective amount of a compound of this invention or its isomer, pharmaceutically acceptable salt, pharmaceutical product, polymorph, hydrate or any combination thereof. In another embodiment, the castration is surgical castration.

In another embodiment, with regards to the methods described above, the prostate cancer depends on AR-FL and/or AR-SV for proliferation. In another embodiment, the cancer is resistant to treatment with an androgen receptor antagonist. In another embodiment, the prostate cancer or other cancer is resistant to treatment with enzalutamide, flutamide, bicalutamide, abiraterone, ARN-509, apalutamide, darolutamide, ODM-201, EPI-001, AZD-3514, galeterone, ASC-J9, flutamide, hydroxyflutamide, nilutamide, cyproterone acetate, ketoconazole, spironolactone, or any combination thereof. In another embodiment, administration of the compounds of this invention reduces the levels of AR, AR-full length (AR-FL), AR-FL with antiandrogen resistance-conferring AR-LBD mutations, AR-splice variant (AR-SV), gene-amplified AR, poly-Q AR, or any combination thereof, in the subject. In another embodiment, the castration is surgical castration. In another embodiment, the castration is chemical castration. In another embodiment, the CRPC is metastatic CRPC (mCRPC). In another embodiment, the CRPC is non-metastatic CRPC (nmCRPC). In one embodiment, the nmCRPC is high-risk nmCRPC. In another embodiment, the method further increases radiographic progression free survival (rPFS) in a subject suffering from a metastatic cancer. In another embodiment, the method further increases metastasis-free survival (MFS) in a subject suffering from non-metastatic cancer. In one embodiment, the method may be used to provide a dual action, for example treating prostate cancer and preventing metastases. In another embodiment, the subject has failed androgen deprivation therapy (ADT). In another embodiment, the subject further receives androgen deprivation therapy (ADT). In another embodiment, the subject further receives LHRH agonist or antagonist. In another embodiment, the LHRH agonist is leuprolide acetate. In another embodiment, the subject had undergone orchidectomy. In another embodiment, the subject has high or increasing prostate specific antigen (PSA) levels. In another embodiment, the subject is a prostate cancer patient. In another embodiment, the subject is a prostate cancer patient on ADT. In another embodiment, the subject is a prostate cancer patient on ADT with castrate levels of total T. In another embodiment, the subject is an advanced prostate cancer patient. In another embodiment, the subject is an advanced prostate cancer patient on ADT. In another embodiment, the subject is an advanced prostate cancer patient on ADT with castrate levels of total T. In another embodiment, the subject is a CRPC patient. In another embodiment, the subject is a CRPC patient on ADT. In another embodiment, the subject is a CRPC patient on ADT with castrate levels of total T. In another embodiment, the subject is a metastatic castration resistant prostate cancer (mCRPC) patient. In another embodiment, the subject is a mCRPC patient maintained on ADT. In another embodiment, the subject is a mCRPC patient maintained on ADT with castrate levels of total T. In another embodiment, the subject is a non-metastatic castration resistant prostate cancer (nmCRPC) patient. In another embodiment, the subject is an nmCRPC patient maintained on ADT. In another embodiment, the subject is an nmCRPC patient maintained on ADT with castrate levels of total T. In one embodiment, the nmCRPC is high-risk nmCRPC. In another embodiment, the method further treats, suppresses, reduces the incidence, reduces the severity, or inhibits advanced prostate cancer. In another embodiment, the method further provides palliative treatment of advanced prostate cancer.

In one embodiment, this invention is directed to a method of reducing the levels of AR, AR-full length, AR-FL with antiandrogen resistance-conferring AR-LBD mutations, polyQ AR, and/or AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the reduction is achieved by degradation of said AR, AR-full length (AR-FL), polyQ AR, and/or AR-splice variants (AR-SV). In another embodiment, the reduction is achieved by inhibition of said AR, AR-full length (AR-FL) and/or AR-splice variants (AR-SV). In another embodiment, the reduction is achieved by dual AR-SV/AR-FL degradation and AR-SV/AR-FL inhibitory functions.

In one embodiment, this invention is directed to a method of reducing the levels of AR-splice variants in a subject, comprising administering to said subject a therapeutically effective amount of a SARD compound according to this invention, or its isomer, pharmaceutically acceptable salt, pharmaceutical product, polymorph, hydrate or any combination thereof. In another embodiment, the method further reduces the levels of AR-full length (AR-FL) in the subject. In another embodiment, the reduction is achieved by degradation of said AR-splice variants (AR-SV). In another embodiment, the reduction is further achieved by degradation of said AR-FL. In another embodiment, the reduction is achieved by inhibition of said AR-splice variants (AR-SV). In another embodiment, the reduction is further achieved by inhibition of said AR-FL. In another embodiment, the reduction is achieved by dual AR-SV degradation and AR-SV inhibitory functions. In another embodiment, the reduction is achieved by dual AR-FL degradation and AR-FL inhibitory functions.

In one embodiment, "a subject suffering from castration resistant prostate cancer" refers to a subject which has been previously treated with androgen deprivation therapy (ADT), has responded to the ADT and currently has a serum PSA>2 ng/mL or >2 ng/mL and representing a 25% increase above the nadir achieved on the ADT. In another embodiment, the term refers to a subject which despite being maintained on androgen deprivation therapy is diagnosed to have serum PSA progression. In another embodiment, the subject has a castrate level of serum total testosterone (<50 ng/dL). In another embodiment, the subject has a castrate level of serum total testosterone (<20 ng/dL). In another embodiment, the subject has rising serum PSA on two successive assessments at least 2 weeks apart. In another embodiment, the subject had been effectively treated with ADT. In another embodiment, the subject has a history of serum PSA response after initiation of ADT. In another embodiment, the subject has been treated with ADT and had an initial serum PSA response, but now has a serum PSA>2 ng/mL and a 25% increase above the nadir observed on ADT. In one embodiment, the CRPC is metastatic CRPC (mCRPC). In another embodiment, the CRPC is non-metastatic CRPC (nmCRPC). In one embodiment, the nmCRPC is high-risk nmCRPC.

The term "serum PSA response" refers to, in one embodiment, at least 90% reduction in serum PSA value prior to the initiation of ADT, to <10 ng/mL or undetectable level of serum PSA (<0.2 ng/mL) at any time, or in another embodiment to at least 50% decline from baseline in serum PSA, or in another embodiment to at least 90% decline from baseline in serum PSA, or in another embodiment to at least 30% decline from baseline in serum PSA, or in another embodiment to at least 10% decline from baseline in serum PSA.

The term "serum PSA progression" refers to in one embodiment, a 25% or greater increase in serum PSA and an absolute increase of 2 ng/ml or more from the nadir; or in another embodiment, to serum PSA>2 ng/mL, or >2 ng/mL and a 25% increase above the nadir after the initiation of androgen deprivation therapy (ADT).

In another embodiment, the term "nadir" refers to the lowest PSA level while a patient is undergoing ADT.

Testosterone can be measured as "free" (that is, bioavailable and unbound) or as "total" (including the percentage which is protein bound and unavailable) serum levels. In one embodiment, total serum testosterone comprises free testosterone and bound testosterone.

The methods of this invention comprise administering a combination of forms of ADT and a compound of this invention. In one embodiment, forms of ADT include a LHRH agonist. In another embodiment, the LHRH agonist includes leuprolide acetate (Lupron®)(U.S. Pat. Nos. 5,480,656; 5,575,987; 5,631,020; 5,643,607; 5,716,640; 5,814,342; 6,036,976 which are all incorporated by reference herein) or goserelin acetate (Zoladex®) (U.S. Pat. Nos. 7,118,552; 7,220,247; 7,500,964 which are all incorporated by reference herein). In one embodiment, forms of ADT include an LHRH antagonist. In another embodiment, the LHRH antagonist includes degarelix. In another embodiment, the LHRH antagonist includes abarelix. In one embodiment, forms of ADT include reversible antiandrogens. In another embodiment, the antiandrogens include bicalutamide, flutamide, finasteride, dutasteride, enzalutamide, nilutamide, chlormadinone, abiraterone or any combination thereof. In one embodiment, forms of ADT include bilateral orchidectomy.

In one embodiment, this invention provides a method of treating, suppressing, reducing the incidence, reducing the severity, or inhibiting the progression of castration resistant prostate cancer (CRPC) and its symptoms, or increasing the survival of men with castration resistant prostate cancer comprising administering a therapeutically effective amount of a combination of one or more forms of ADT and a compound of this invention or its isomer, pharmaceutically acceptable salt, pharmaceutical product, polymorph, hydrate or any combination thereof. In another embodiment, the subject has failed androgen deprivation therapy (ADT).

In one embodiment, this invention provides a method of lowering serum PSA levels in a male subject suffering from castration resistant prostate cancer (CRPC) comprising administering a therapeutically effective amount of a combination of one or more forms of ADT and a compound of this invention or its isomer, pharmaceutically acceptable salt, pharmaceutical product, polymorph, hydrate or any combination thereof. In another embodiment, the subject has failed androgen deprivation therapy (ADT).

In one embodiment, the methods of this invention comprise administering a therapeutically effective amount of an antiandrogen and a compound of this invention. In one embodiment, the methods of this invention comprise administering a therapeutically effective amount of an LHRH agonist and a compound of this invention. In one embodiment, the methods of this invention comprise administering a therapeutically effective amount of an antiandrogen, LHRH agonist and a compound of this invention. In another embodiment, the compound is a compound of this invention or any one of compounds 11-27, 30-47, 11R, 70-79, 80, 90-99, 100-115, 130-137, 200-205, or 300-308 described herein.

In one embodiment, the methods of this invention comprise administering a therapeutically effective amount of a lyase inhibitor (e.g., abiraterone) and a compound of this invention. In another embodiment, the compound is a compound of this invention or any one of compounds 11-27, 30-47, 11R, 70-79, 80, 90-99, 100-115, 130-137, 200-205, or 300-308 described herein.

In another embodiment, this invention provides a method for androgen deprivation therapy (ADT) in a subject, comprising administering a therapeutically effective amount of a compound of this invention or its isomer, pharmaceutically acceptable salt, pharmaceutical product, polymorph, hydrate or any combination thereof. In another embodiment, said subject has prostate cancer. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC. In another embodiment, the compound is any one of compounds 11-27, 30-47, 11R, 70-79, 80, 90-99, 100-115, 130-137, 200-205, or 300-308 described herein. In another embodiment, the subject has failed androgen deprivation therapy (ADT). In another embodiment, the subject further receives androgen deprivation therapy (ADT).

In one embodiment, this invention provides a method of treating prostate cancer or delaying the progression of prostate cancer comprising administering a SARD compound of this invention. In one embodiment, this invention provides a method of preventing and/or treating the recurrence of prostate cancer comprising administering a SARD compound of this invention. In another embodiment, the prostate cancer is castration resistant prostate cancer (CRPC). In another embodiment, the CRPC is metastatic CRPC (mCRPC). In one embodiment, the CRPC is non-metastatic castration resistant prostate cancer (nmCRPC). In one embodiment, the nmCRPC is high-risk nmCRPC.

In one embodiment, this invention provides a method of increasing the survival of a subject having prostate cancer, advanced prostate cancer, castration resistant prostate cancer or metastatic castration resistant prostate cancer or non-metastatic castration resistant prostate cancer or high-risk non metastatic castration resistant prostate cancer, comprising administering a compound of this invention. In another embodiment, administering a compound of this invention in combination with LHRH analogs, reversible antiandrogens (such as bicalutamide, flutamide, or enzalutamide), anti-estrogens, estrogens (such as estradiol, ethinyl estradiol, or capesaris), anticancer drugs, 5-alpha reductase inhibitors, aromatase inhibitors, progestins, selective androgen receptor modulators (SARMs) or agents acting through other nuclear hormone receptors. In another embodiment, the subject has failed androgen deprivation therapy (ADT). In one embodiment, the compound is a compound of this invention or any one of compounds 11-27, 30-47, 11R, 70-79, 80, 90-99, 100-115, 130-137, 200-205, or 300-308 described herein.

The term "advanced prostate cancer" refers to metastatic cancer having originated in the prostate, and having widely metastasized to beyond the prostate such as the surrounding tissues to include the seminal vesicles the pelvic lymph nodes or bone, or to other parts of the body. Prostate cancer pathologies are graded with a Gleason grading from 1 to 5 in order of increasing malignancy. In another embodiment, patients with significant risk of progressive disease and/or death from prostate cancer should be included in the definition and that any patient with cancer outside the prostate capsule with disease stages as low as IIB clearly has "advanced" disease. In another embodiment, "advanced prostate cancer" can refer to locally advanced prostate cancer.

Men with advanced prostate cancer often receive treatment to block the production of androgens, which are male sex hormones that may help prostate tumors grow. However, prostate cancers that initially respond to antiandrogen therapy eventually develop the ability to grow without androgens. Such cancers are often referred to as hormone refractory, androgen independent, or castration resistant.

In one embodiment, the advanced prostate cancer is castration resistant prostate cancer.

The term "castration resistant prostate cancer" (CRPC) refers to advanced prostate cancer that is worsening or progressing while the patient remains on ADT or other therapies to reduce testosterone, or prostate cancer which is considered hormone refractory, hormone naïve, androgen independent or chemical or surgical castration resistant. In another embodiment, CRPC is a result of AR activation by intracrine androgen synthesis. In another embodiment, CRPC is a result of expression of AR splice variants (AR-SV) that lack ligand binding domain (LBD). In another embodiment, CRPC is a result of expression of AR-LBD mutations with potential to resist antagonists. In another embodiment, castration resistant prostate cancer (CRPC) is an advanced prostate cancer which developed despite ongoing ADT and/or surgical castration. In one embodiment, castration resistant prostate cancer is defined as prostate cancer that continues to progress or worsen or adversely affect the health of the patient despite prior surgical castration, continued treatment with gonadotropin releasing hormone agonists (e.g., leuprolide) or antagonists (e.g., degarelix), antiandrogens (e.g., bicalutamide, flutamide, enzalutamide, ketoconazole, aminoglutethamide), chemotherapeutic agents (e.g., docetaxel, paclitaxel, cabazitaxel, adriamycin, mitoxantrone, estramustine, cyclophosphamide), kinase inhibitors (imatinib (Gleevec®) or gefitinib (Iressa), cabozantinib (Cometriq™, also known as XL184)) or other prostate cancer therapies (e.g., vaccines (sipuleucel-T (Provenge), GVAX, etc.), herbal (PC-SPES) and lyase inhibitor (abiraterone) as evidenced by increasing or higher serum levels of prostate specific antigen (PSA), metastasis, bone metastasis, pain, lymph node involvement, increasing size or serum markers for tumor growth, worsening diagnostic markers of prognosis, or patient condition.

In one embodiment, castration resistant prostate cancer is defined as hormone naïve prostate cancer.

Many early prostate cancers require androgens for growth, but advanced prostate cancers are in some embodiments, androgen-independent, or hormone naïve. In one embodiment, in men with castration resistant prostate cancer, the tumor cells may have the ability to grow in the absence of androgens (hormones that promote the development and maintenance of male sex characteristics).

In one embodiment, the term "androgen deprivation therapy" (ADT) or "traditional androgen deprivation therapy" is directed to orchidectomy (surgical castration) wherein the surgeon removes the testicles. In another embodiment, the term "androgen deprivation therapy" or "traditional androgen deprivation therapy" is directed to administering luteinizing hormone-releasing hormone (LHRH) analogs: these drugs lower the amount of testosterone made by the testicles. Examples of LHRH analogs available in the United States include leuprolide (Lupron®, Viadur, Eligard®), goserelin (Zoladex®), triptorelin (Trelstar®), and histrelin (Vantas®). In another embodiment, the term "androgen deprivation therapy" or "traditional androgen deprivation therapy" is directed to administering anti-androgens: anti-androgens block the body's ability to use any androgens. Even after orchidectomy or during treatment with LHRH analogs, a small amount of androgens is still made by the adrenal glands. Examples of antiandrogens drugs include enzalutamide (Xtandi®), apalutamide (Erleada), flutamide (Eulexin®), bicalutamide (Casodex®), and nilutamide (Nilandron®). In another embodiment, the term "androgen deprivation therapy" or "traditional androgen deprivation therapy" is directed to administering luteinizing hormone-releasing hormone (LHRH) antagonists such as abarelix (Plenaxis®) or degarelix (Firmagon®) (approved for use by the FDA in 2008 to treat advanced prostate cancer). In another embodiment, the term "androgen deprivation therapy" or "traditional androgen deprivation therapy" is directed to administering 5α-reductase inhibitors such as finasteride (Proscar®) and dutasteride (Avodart®): 5α-reductase inhibitors block the body's ability to convert testosterone to the more active androgen, 5α-dihydrotestosterone (DHT). In another embodiment, the term "androgen deprivation therapy" or "traditional androgen deprivation therapy" is directed to administering inhibitors of testosterone biosynthesis such as ketoconazole (Nizoral®). In another embodiment, the term "androgen deprivation therapy" or "traditional androgen deprivation therapy" is directed to administering estrogens such as diethylstilbestrol, ethinyl estradiol, capesaris, or 17β-estradiol. In another embodiment, the term "androgen deprivation therapy" or "traditional androgen deprivation therapy" is directed to administering 17α-hydroxylase/C17,20 lyase (CYP17A1) inhibitors such as abiraterone (Zytiga®).

In one embodiment, this invention provides a method of treating, suppressing, reducing the incidence, reducing the severity, increasing the survival, or inhibiting an antiandrogen-resistant prostate cancer. In another embodiment, the antiandrogen is bicalutamide, hydroxyflutamide, flutamide, apalutamide, or enzalutamide.

In one embodiment, this invention provides a method of treating, suppressing, reducing the incidence, reducing the severity, increasing the survival, or inhibiting an abiraterone-resistant prostate cancer.

In one embodiment, this invention provides a method of treating prostate cancer in a subject in need thereof, wherein said subject has AR overexpressing prostate cancer, castration-resistant prostate cancer, castration-sensitive prostate cancer, AR-V7 expressing prostate cancer, or d567ES expressing prostate cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 described herein.

In one embodiment, the castration-resistant prostate cancer is AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, and/or castration-resistant prostate cancer characterized by intratumoral androgen synthesis.

In one embodiment, the castration-sensitive cancer is F876L mutation expressing castration-sensitive prostate cancer, F876L_T877A double mutation castration-sensitive prostate cancer, and/or castration-sensitive prostate cancer characterized by intratumoral androgen synthesis.

In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

In one embodiment, this invention provides a method of treating AR overexpressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, or 300-308 described herein.

In one embodiment, this invention provides a method of treating castration-resistant prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, or 300-308 described herein. In one embodiment, the castration-resistant prostate cancer is AR overexpressing castration-resistant prostate cancer, F876L mutation expressing castration-resistant prostate cancer, F876L_T877A double mutation expressing castration-resistant prostate cancer, AR-V7 expressing castration-resistant prostate cancer, d567ES expressing castration-resistant prostate cancer, and/or castration-resistant prostate cancer characterized by intratumoral androgen synthesis.

In one embodiment, this invention provides a method of treating castration-sensitive prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 described herein. In one embodiment, the castration-sensitive prostate cancer is F876L mutation expressing castration-sensitive prostate cancer, F876L_T877A double mutation castration-sensitive prostate cancer, and/or castration-sensitive prostate cancer characterized by intratumoral androgen synthesis. In one embodiment, the treating of castration-sensitive prostate cancer is conducted in a non-castrate setting, or as monotherapy, or when castration-sensitive prostate cancer tumor is resistant to enzalutamide, apalutamide, and/or abiraterone.

In one embodiment, this invention provides a method of treating AR-V7 expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating d567ES expressing prostate cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating breast cancer in a subject in need thereof, wherein said subject has AR expressing breast cancer, AR-SV expressing breast cancer, and/or AR-V7 expressing breast cancer, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating AR expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating AR-SV expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating AR-V7 expressing breast cancer in a subject in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, this invention provides a method of treating, suppressing, reducing the incidence, reducing the severity, or inhibiting the progression of a hormonal condition in a male in need thereof, comprising administering to the subject a therapeutically effective amount of a selective androgen receptor degrader (SARD) compound, or its isomer, pharmaceutically acceptable salt, pharmaceutical product, polymorph, hydrate or any combination thereof, wherein said SARD compound is represented by the structure of any one of the formulas as described herein or any one of compounds 11-27, 30-47, 11R, 70-79, 80, 90-99, 100-115, 130-137, 200-205, and 300-308 as described herein.

In one embodiment, the condition is hypergonadism, hypersexuality, sexual dysfunction, gynecomastia, precocious puberty in a male, alterations in cognition and mood, depression, hair loss, hyperandrogenic dermatological disorders, pre-cancerous lesions of the prostate, benign prostate hyperplasia, prostate cancer and/or other androgen-dependent cancers.

In one embodiment, the terms "treating" or "treatment" includes preventative as well as disorder remitative treatment. In another embodiment, "treating" or "treatment" does not include preventative. The terms "reducing", "suppressing" and "inhibiting" have their commonly understood meaning of lessening or decreasing, in another embodiment, or delaying, in another embodiment, or reducing, in another embodiment, the incidence, severity or pathogenesis of a disease, disorder or condition. In embodiment, the term treatment refers to delayed progression of, prolonged remission of, reduced incidence of, or amelioration of symptoms associated with the disease, disorder or condition. In one embodiment, the terms "treating" "reducing", "suppressing" or "inhibiting" refer to a reduction in morbidity, mortality, or a combination thereof, in association with the indicated disease, disorder or condition. In one embodiment, the term "progression" refers to an increasing in scope or severity, advancing, growing or becoming worse. The term "recurrence" means, in another embodiment, the return of a disease after a remission. In one embodiment, the methods of treatment of the invention reduce the severity of the disease, or in another embodiment, symptoms associated with the disease, or in another embodiment, reduces the levels of biomarkers expressed during disease.

Muscle atrophy (MA) is characterized by wasting away or diminution of muscle and a decrease in muscle mass. For example, post-polio MA is a muscle wasting that occurs as part of the post-polio syndrome (PPS). The atrophy includes weakness, muscle fatigue, and pain.

Another type of MA is X-linked spinal-bulbar muscular atrophy (SBMA—also known as Kennedy's Disease). This disease arises from a defect in the androgen receptor gene on the X chromosome, affects only males, and its onset is in late adolescence to adulthood. Proximal limb and bulbar muscle weakness results in physical limitations including dependence on a wheelchair in some cases. The mutation results in an extended polyglutamine tract at the N-terminal domain of the androgen receptor (polyQ AR). Binding and activation of the polyQ AR by endogeneous androgens (testosterone and DHT) results in unfolding and nuclear translocation of the mutant androgen receptor. These steps are required for pathogenesis and results in partial loss of transactivation function (i.e., an androgen insensitivity) and a poorly understood neuromuscular degeneration. Currently there are no disease-modifying treatments but rather only symptom directed treatments. Efforts to target the polyQ AR as the proximal mediator of toxicity by harnessing cellular machinery to promote its degradation hold promise for therapeutic invention. Selective androgen receptor degraders such as those reported herein bind to and degrade a variety of androgen receptors (full length, splice variant, antiandrogen resistance mutants, etc.), indicating that they are promising leads for treatment of SBMA. This view is supported by the observation that peripheral polyQ AR anti-sense therapy rescues disease in mouse models of SBMA (*Cell Reports* 7, 774-784, May 8, 2014).

In one embodiment, this invention is directed to a method of treating, suppressing, reducing the incidence, reducing the severity, or inhibiting the progression of the Kennedy's disease comprising administering therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

As used herein, "androgen receptor associated conditions" or "androgen sensitive diseases or disorders" are conditions, diseases, or disorders that are modulated by or whose pathogenesis is dependent upon the activity of the androgen receptor. The androgen receptor is expressed in most tissues of the body however it is overexpressed in, inter alia, the prostate and skin. ADT has been the mainstay of prostate cancer treatment for many years, and a SARD may also be useful also in treating various prostate cancers, benign prostatic hypertrophy, prostamegaly, and other maladies of the prostate.

In one embodiment, this invention is directed to a method of treating, suppressing, reducing the incidence, reducing the severity, or inhibiting the progression of benign prostatic hypertrophy comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of prostamegaly comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of hyperproliferative prostatic disorders and diseases comprising administering a therapeutically effective amount of a compound of the invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308.

The effect of the AR on the skin is apparent in the gender dimorphism and puberty related dermatological problems common to teens and early adults. The hyperandrogenism of puberty stimulates terminal hair growth, sebum production, and predisposes male teens to acne, acne vulgaris, seborrhea, excess sebum, hidradenitis suppurativa, hirsutism, hypertrichosis, hyperpilosity, androgenic alopecia, male pattern baldness, and other dermatological maladies. Although antiandrogens theoretically should prevent the hyperandrogenic dermatological diseases discussed, they are limited by toxicities, sexual side effects, and lack of efficacy when topically applied. The SARDs of this invention potently inhibit ligand-dependent and ligand-independent AR activation, and have short biological half-lives in the serum (in some cases), suggesting that topically formulated SARDs of this invention could be applied to the areas affected by acne, seborrheic dermatitis, and/or hirsutism without risk of systemic side effects.

In one embodiment, this invention is directed to a method of treating, suppressing, reducing the incidence, reducing the severity, or inhibiting the progression of acne comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of acne vulgaris comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of seborrhea comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of seborrheic dermatitis comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of hidradenitis supporativa comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of hirsutism comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of hypertrichosis comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of hyperpilosity comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of alopecia comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In some embodiments, the compounds as described herein and/or compositions may be used for applications in or treating hair loss, alopecia, androgenic alopecia, alopecia areata, alopecia secondary to chemotherapy, alopecia secondary to radiation therapy, alopecia induced by scarring or alopecia induced by stress. In one embodiment, "hair loss" or "alopecia" refers to baldness as in the very common type of male-pattern baldness. Baldness typically begins with patch hair loss on the scalp and sometimes progresses to complete baldness and even loss of body hair. Hair loss affects both males and females.

In one embodiment, this invention is directed to a method of treating, suppressing, reducing the incidence, reducing the severity, or inhibiting the progression of androgenic alopecia comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

SARDs of this invention may also be useful in the treatment of hormonal conditions in females such as precocious puberty, early puberty, dysmenorrhea, amenorrhea, multilocular uterus syndrome, endometriosis, hysteromyoma, abnormal uterine bleeding, early menarche, fibrocystic breast disease, fibroids of the uterus, ovarian cysts, polycystic ovary syndrome, pre-eclampsia, eclampsia of pregnancy, preterm labor, premenstrual syndrome, and vaginal dryness.

In one embodiment, this invention is directed to a method of treating, suppressing, reducing the incidence, reducing the severity, or inhibiting the progression of any hyperandrogenic diseases (for example polycystic ovary syndrome (PCOS)) comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of precocious puberty or early puberty comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, or 300-308 as described herein.

In one embodiment, this invention is directed to a method of treating, suppressing, reducing the incidence, reducing the severity, or inhibiting the progression of dysmenorrhea or amenorrhea comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of multilocular uterus syndrome, endometriosis, hysteromyoma, or abnormal uterine bleeding comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of fibrocystic breast disease, fibroids of the uterus, ovarian cysts, or polycystic ovary syndrome comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of pre-eclampsia, eclampsia of pregnancy, preterm labor, premenstrual syndrome, or vaginal dryness comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

SARDS of this invention may also find utility in treatment of sexual perversion, hypersexuality, paraphilias, androgen psychosis, virilization, androgen insensitivity syndromes (AIS) such as complete AIS (CAIS) and partial AIS (PAIS), and improving ovulation in an animal.

In one embodiment, this invention is directed to a method of treating, suppressing, reducing the incidence, reducing the severity, or inhibiting the progression of sexual perversion, hypersexuality, or paraphilias comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of androgen psychosis comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of virilization comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of androgen insensitivity syndromes comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, the androgen insensitivity syndrome is a complete androgen insensitivity syndrome. In another embodiment, the androgen insensitivity syndrome is a partial androgen insensitivity syndrome.

In one embodiment, this invention is directed to a method of increasing, modulating, or improving ovulation in an animal comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. SARDs of this invention may also be useful for the treating of hormone-dependent cancers such as prostate cancer, breast cancer, testicular cancer, ovarian cancer, and urogenital cancer, etc. Further, local or systemic SARD administration may be useful for treatment of precursors of hormone dependent cancers such as prostatic intraepithelial neoplasia (PIN) and atypical small acinar proliferation (ASAP).

In one embodiment, this invention is directed to a method of treating, suppressing, reducing the incidence, reducing the severity, or inhibiting the progression of AR related solid tumors. In another embodiment, the tumor is hepatocellular carcinoma (HCC). In another embodiment, the tumor is bladder cancer. Serum testosterone may be positively linked to the development of HCC. Based on epidemiologic, experimental observations, and notably the fact that men have a substantially higher risk of bladder cancer than women, androgens and/or the AR also play a role in bladder cancer initiation.

In one embodiment, this invention is directed to a method of treating, suppressing, reducing the incidence, reducing the severity, or inhibiting the progression of breast cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, this invention is directed to a method of treating, suppressing, reducing the incidence, reducing the severity, or inhibiting the progression of testicular cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, this invention is directed to a method of treating, suppressing, reducing the incidence, reducing the severity, or inhibiting the progression of uterine cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, this invention is directed to a method of treating, suppressing, reducing the incidence, reducing the severity, or inhibiting the progression of ovarian cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of urogenital cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of precursors of prostate cancer comprising local or systemic administration of a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, the precursor of prostate cancers is prostatic intraepithelial neoplasia (PIN). In another embodiment, the precursor of prostate cancer is atypical small acinar proliferation (ASAP).

Although traditional antiandrogens such as enzalutamide, apalutamide (ARN-509), bicalutamide and flutamide and androgen deprivation therapies (ADT) such as leuprolide were approved for use in prostate cancer, there is significant evidence that antiandrogens could also be used in a variety of other hormone dependent and hormone independent cancers. For example, antiandrogens have been successfully tested in breast cancer (enzalutamide; Breast Cancer Res. (2014) 16(1): R7), non-small cell lung cancer (shRNAi AR), renal cell carcinoma (ASC-J9), partial androgen insensitivity syndrome (PAIS) associated malignancies such as gonadal tumors and seminoma, advanced pancreatic cancer (World J. Gastroenterology 20(29):9229), cancer of the ovary, fallopian tubes, or peritoneum, cancer of the salivary gland (Head and Neck (2016) 38: 724-731; ADT was tested in AR-expressing recurrent/metastatic salivary gland cancers and was confirmed to have benefit on progression free survival and overall survival endpoints), bladder cancer (Oncotarget 6 (30): 29860-29876); Int J. Endocrinol (2015), Article ID 384860), pancreatic cancer, lymphoma (including mantle cell), and hepatocellular carcinoma. Use of a more potent antiandrogen such as a SARD in these cancers may treat the progression of these and other cancers. Many hormonal and non-hormonal cancers may benefit from SARD treatment such as testicular cancer, uterine cancer, ovarian cancer, urogenital cancer, brain cancer, skin cancer, lymphoma, liver cancer, renal cancer, osteosarcoma, pancreatic cancer, endometrial cancer, lung cancer, non-small cell lung cancer (NSCLC), gastric cancer, colon cancer, perianal adenoma, or central nervous system cancer.

SARDs of this invention may also be useful for the treating other cancers containing AR such as breast, brain, skin, ovarian, bladder, lymphoma, liver, kidney, pancreas, endometrium, lung (e.g., NSCLC) colon, perianal adenoma, osteosarcoma, CNS, melanoma, etc.

In one embodiment, this invention is directed to a method of treating, suppressing, reducing the incidence, reducing the severity, or inhibiting the progression of brain cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of skin cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of ovarian cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of bladder cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of lymphoma comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of liver cancer comprising administering a therapeutically effective amount of a compound of this invention or its isomer, pharmaceutically acceptable salt, pharmaceutical product, polymorph, hydrate or any combination thereof. In another embodiment, the compound is any one of 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of renal cancer comprising administering a therapeutically effective amount of a compound of the inventio or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of osteosarcoma comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of pancreatic cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. In one embodiment, this invention is directed to a method of treating, suppressing, reducing the incidence, reducing the severity, or inhibiting the progression of endometrial cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of lung cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, the lung cancer is non-small cell lung cancer (NSCLC).

In one embodiment, this invention is directed to a method of treating, suppressing, reducing the incidence, reducing the severity, or inhibiting the progression of a central nervous system cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of colon cancer comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of melanoma comprising administering a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

SARDs of this invention may also be useful for the treating of non-hormone-dependent cancers. Non-hormone dependent cancers include liver, salivary duct, etc.

In another embodiment, the SARDs of this invention are used for treating gastric cancer. In another embodiment, the SARDs of this invention are used for treating salivary duct carcinoma. In another embodiment, the SARDs of this invention are used for treating bladder cancer. In another embodiment, the SARDs of this invention are used for treating esophageal cancer. In another embodiment, the SARDs of this invention are used for treating pancreatic cancer. In another embodiment, the SARDs of this invention are used for treating colon cancer. In another embodiment, the SARDs of this invention are used for treating non small cell lung cancer. In another embodiment, the SARDs of this invention are used for treating renal cell carcinoma.

AR plays a role in cancer initiation in hepatocellular carcinoma (HCC). Therefore, targeting AR may be appropriate treatment for patients with early stage HCC. In late-stage HCC disease, there is evidence that metastasis is suppressed by androgens. In another embodiment, the SARDs of this invention are used for treating hepatocellular carcinoma (HCC).

Locati et al Head & Neck, 2016, 724-731 demonstrated the use of androgen deprivation therapy (ADT) in AR-expressing recurrent/metastatic salivary gland cancers was confirmed to improve progression free survival and overall survival endpoints. In another embodiment, the SARDs of this invention are used for treating salivary gland cancer.

Kawahara et al. Oncotarget, 2015, Vol 6 (30), 29860-29876 demonstrated that ELK1 inhibition, together with AR inactivation, has the potential of being a therapeutic approach for bladder cancer. McBeth et al. Int. J Endocrinology, 2015, Vol 2015 1-10 suggested that the combination of anti-androgen therapy plus glucocorticoids since bladder cancer is believed to have an inflammatory etiology. In another embodiment, the SARDs of this invention are used for treating bladder cancer.

Abdominal Aortic Aneurysm (AAA)

An abdominal aortic aneurysm (AAA) is an enlarged area in the lower part of the aorta, the major blood vessel that supplies blood to the body. The aorta, about the thickness of a garden hose, runs from your heart through the center of your chest and abdomen. Because the aorta is the body's main supplier of blood, a ruptured abdominal aortic aneurysm can cause life-threatening bleeding. Depending on the size and the rate at which your abdominal aortic aneurysm is growing, treatment may vary from watchful waiting to emergency surgery. Once an abdominal aortic aneurysm is found, doctors will closely monitor it so that surgery can be planned if it's necessary. Emergency surgery for a ruptured abdominal aortic aneurysm can be risky. AR blockade (pharmacologic or genetic) reduces AAA. Davis et al. (J Vase Surg Vol. 63, Issue 6, p 1602-1612.e2) showed that flutamide (50 mg/kg) or ketoconazole (150 mg/kg) attenuated porcine pancreatic elastase (0.35 U/mL) induced AAA by 84.2% and 91.5% compared to vehicle (121%). Further AR −/−mice showed attenuated AAA growth (64.4%) compared to wildtype (both treated with elastase). Correspondingly, administration of a SARD to a patient suffering from an AAA may help reverse, treat or delay progression of AAA to the point where surgery is needed.

In one embodiment, this invention is directed to a method of treating, suppressing, reducing the incidence, reducing the severity, or inhibiting the progression of amyotrophic lateral sclerosis (ALS) in a subject, comprising administering a therapeutically effective amount of the compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention is directed to a method of treating, suppressing, reducing the incidence, reducing the severity, or inhibiting the progression of uterine fibroids in a subject, comprising administering a therapeutically effective amount of the compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein.

In one embodiment, this invention provides a method of treating a subject suffering from a wound, or reducing the incidence of, or mitigating the severity of, or enhancing or hastening healing of a wound in a subject, the method comprises administering to said subject a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308.

In one embodiment, this invention provides a method of treating a subject suffering from a burn, or reducing the incidence of, or mitigating the severity of, or enhancing or hastening healing of a burn in a subject, the method comprises administering to said subject a therapeutically effective amount of a compound of this invention or its isomer, pharmaceutically acceptable salt, pharmaceutical product, polymorph, hydrate or any combination thereof. In another embodiment, the compound is any one of compounds 11-27, 30-47, 11R, 70-79, 80, 90-99, 100-115, 130-137, 200-205, and 300-308 as described herein. Wounds and/or ulcers are normally found protruding from the skin or on a mucosal surface or as a result of an infarction in an organ. A wound may be a result of a soft tissue defect or a lesion or of an underlying condition. In one embodiment, the term "wound" denotes a bodily injury with disruption of the normal integrity of tissue structures. The term is also intended to encompass the terms "sore", "lesion", "necrosis" and "ulcer". In one embodiment, the term "sore" refers to any lesion of the skin or mucous membranes and the term "ulcer" refers to a local defect, or excavation, of the surface of an organ or tissue, which is produced by the sloughing of necrotic tissue. Lesion generally relates to any tissue defect. Necrosis is related to dead tissue resulting from infection, injury, inflammation or infarctions. All of these are encompassed by the term "wound", which denotes any wound at any particular stage in the healing process including the stage before any healing has initiated or even before a specific wound like a surgical incision is made (prophylactic treatment).

Examples of wounds which can be prevented and/or treated in accordance with the present invention are, e.g., aseptic wounds, contused wounds, incised wounds, lacerated wounds, non-penetrating wounds (i.e. wounds in which there is no disruption of the skin but there is injury to underlying structures), open wounds, penetrating wounds, perforating wounds, puncture wounds, septic wounds, subcutaneous wounds, etc. Examples of sores are bed sores, canker sores, chrome sores, cold sores, pressure sores etc. Examples of ulcers are, e.g., peptic ulcer, duodenal ulcer, gastric ulcer, gouty ulcer, diabetic ulcer, hypertensive ischemic ulcer, stasis ulcer, ulcus cruris (venous ulcer), sublingual ulcer, submucous ulcer, symptomatic ulcer, trophic ulcer, tropical ulcer, veneral ulcer, e.g. caused by gonorrhoea (including urethritis, endocervicitis and proctitis). Conditions related to wounds or sores which may be successfully treated according to the invention are burns, anthrax, tetanus, gas gangrene, scalatina, erysipelas, sycosis barbae, folliculitis, impetigo contagiosa, or impetigo bullosa, etc. There is often a certain overlap between the use of the terms "wound" and "ulcer" and "wound" and "sore" and, furthermore, the terms are often used at random. Therefore as mentioned above, in the present context the term "wounds" encompasses the term "ulcer", "lesion", "sore" and "infarction", and the terms are indiscriminately used unless otherwise indicated.

The kinds of wounds to be treated according to the invention include also: i) general wounds such as, e.g., surgical, traumatic, infectious, ischemic, thermal, chemical and bullous wounds; ii) wounds specific for the oral cavity such as, e.g., post-extraction wounds, endodontic wounds especially in connection with treatment of cysts and abscesses, ulcers and lesions of bacterial, viral or autoimmunological origin, mechanical, chemical, thermal, infectious and lichenoid wounds; herpes ulcers, stomatitis aphthosa, acute necrotising ulcerative gingivitis and burning mouth syndrome are specific examples; and iii) wounds on the skin such as, e.g., neoplasm, burns (e.g. chemical, thermal), lesions (bacterial, viral, autoimmunological), bites and surgical incisions. Another way of classifying wounds is as: i) small tissue loss due to surgical incisions, minor abrasions and minor bites, or as ii) significant tissue loss. The latter group includes ischemic ulcers, pressure sores, fistulae, lacerations, severe bites, thermal burns and donor site wounds (in soft and hard tissues) and infarctions.

In other aspects of the invention, the wound to be prevented and/or treated is selected from the group consisting of aseptic wounds, infarctions, contused wounds, incised wounds, lacerated wounds, non-penetrating wounds, open wounds, penetrating wounds, perforating wounds, puncture wounds, septic wounds and subcutaneous wounds.

Other wounds which are of importance in connection with the present invention are wounds like ischemic ulcers, pressure sores, fistulae, severe bites, thermal burns and donor site wounds.

Ischemic ulcers and pressure sores are wounds, which normally only heal very slowly and especially in such cases an improved and more rapid healing is of course of great importance for the patient. Furthermore, the costs involved in the treatment of patients suffering from such wounds are markedly reduced when the healing is improved and takes place more rapidly.

Donor site wounds are wounds which e.g. occur in connection with removal of hard tissue from one part of the body to another part of the body e.g. in connection with transplantation. The wounds resulting from such operations are very painful and an improved healing is therefore most valuable.

The term "skin" is used in a very broad sense embracing the epidermal layer of the skin and in those cases where the skin surface is more or less injured also the dermal layer of the skin. Apart from the stratum corneum, the epidermal layer of the skin is the outer (epithelial) layer and the deeper connective tissue layer of the skin is called the dermis.

Since the skin is the most exposed part of the body, it is particularly susceptible to various kinds of injuries such as, e.g., ruptures, cuts, abrasions, burns and frostbites or injuries arising from various diseases. Furthermore, much skin is often destroyed in accidents. However, due to the important barrier and physiologic function of the skin, the integrity of the skin is important to the well-being of the individual, and any breach or rupture represents a threat that must be met by the body in order to protect its continued existence.

Apart from injuries on the skin, injuries may also be present in all kinds of tissues (i.e. soft and hard tissues). Injuries on soft tissues including mucosal membranes and/or skin are especially relevant in connection with the present invention.

Healing of a wound on the skin or on a mucosal membrane undergoes a series of stages that results either in repair or regeneration of the skin or mucosal membrane. In recent years, regeneration and repair have been distinguished as the two types of healing that may occur. Regeneration may be defined as a biological process whereby the architecture and function of lost tissue are completely renewed. Repair, on the other hand, is a biological process whereby continuity of disrupted tissue is restored by new tissues which do not replicate the structure and function of the lost ones.

The majority of wounds heal through repair, meaning that the new tissue formed is structurally and chemically unlike the original tissue (scar tissue). In the early stage of the tissue repair, one process which is almost always involved is the formation of a transient connective tissue in the area of tissue injury. This process starts by formation of a new extracellular collagen matrix by fibroblasts. This new extracellular collagen matrix is then the support for a connective tissue during the final healing process. The final healing is, in most tissues, a scar formation containing connective tissue. In tissues which have regenerative properties, such as, e.g., skin and bone, the final healing includes regeneration of the original tissue. This regenerated tissue has frequently also some scar characteristics, e.g. a thickening of a healed bone fracture.

Under normal circumstances, the body provides mechanisms for healing injured skin or mucosa in order to restore the integrity of the skin barrier or the mucosa. The repair process for even minor ruptures or wounds may take a period of time extending from hours and days to weeks. However, in ulceration, the healing can be very slow and the wound may persist for an extended period of time, i.e. months or even years.

Burns are associated with reduced testosterone levels, and hypogonadism is associated with delayed wound healing. In one embodiment, the methods of this invention, provide for treating a subject suffering from a wound or a burn via the administration of a SARD according to this invention. In one embodiment, the SARD promotes resolving of the burn or wound, or in another embodiment, participates in the healing process of a burn or a wound, or in another embodiment, treats a secondary complication of a burn or wound.

In one embodiment, the treatment of burns or wounds further incorporates the use of additional growth factors like epidermal growth factor (EGF), transforming growth factor-α (TGF-α), platelet derived growth factor (PDGF), fibroblast growth factors (FGFs) including acidic fibroblast growth factor (α-FGF) and basic fibroblast growth factor (β-FGF), transforming growth factor-β (TGF-β) and insulin like growth factors (IGF-1 and IGF-2), or any combination thereof, which are promoters of wound healing.

Wound healing may be measured by many procedures known in the art, including wound tensile strength, hydroxyproline or collagen content, procollagen expression, and re-epithelialization. As an example, a SARD as described herein is administered orally or topically, at a dosage of about 0.1-1 mg per day. Therapeutic effectiveness is measured as effectiveness in enhancing wound healing. Enhanced wound healing may be measured by known techniques such as decrease in healing time, increase in collagen density, increase in hydroxyproline, reduction in complications, increase in tensile strength, and increased cellularity of scar tissue.

In one embodiment, the term "treating" and its included aspects, refers to the administration to a subject with the indicated disease, disorder or condition, or in some embodiments, to a subject predisposed to the indicated disease, disorder or condition. The term "predisposed to" is to be considered to refer to, inter alia, a genetic profile or familial relationship which is associated with a trend or statistical increase in incidence, severity, etc. of the indicated disease. In some embodiments, the term "predisposed to" is to be considered to refer to inter alia, a lifestyle which is associated with increased risk of the indicated disease. In some embodiments, the term "predisposed to" is to be considered to refer to inter alia, the presence of biomarkers which are associated with the indicated disease, for example, in cancer, the term "predisposed to" the cancer may comprise the presence of precancerous precursors for the indicated cancer.

In some embodiments, the term "reducing the pathogenesis" is to be understood to encompass reducing tissue damage, or organ damage associated with a particular disease, disorder or condition. In another embodiment, the term "reducing the pathogenesis" is to be understood to encompass reducing the incidence or severity of an associated disease, disorder or condition, with that in question. In another embodiment, the term "reducing the pathogenesis" is to be understood to encompass reducing the number of associated diseases, disorders or conditions with the indicated, or symptoms associated thereto.

Pharmaceutical Compositions

In some embodiments, this invention provides methods of use which comprise administering a composition comprising the described compounds. As used herein, "pharmaceutical composition" means a "therapeutically effective amount" of the active ingredient, i.e. the compound of this invention, together with a pharmaceutically acceptable carrier or diluent. A "therapeutically effective amount" as used herein refers to that amount which provides a therapeutic effect for a given condition and administration regimen.

As used herein, the term "administering" refers to bringing a subject in contact with a compound of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a male subject. In one embodiment, the present invention encompasses administering the compounds of the present invention to a female subject.

This invention provides, in other embodiments, pharmaceutical products of the compounds described herein. The term "pharmaceutical product" refers, in other embodiments, to a composition suitable for pharmaceutical use (pharmaceutical composition), for example, as described herein.

The compounds of the invention can be administered alone or as an active ingredient of a formulation. Thus, the present invention also includes pharmaceutical compositions of compounds of the invention or its isomer, pharmaceutically acceptable salt, pharmaceutical product, polymorph, hydrate or any combination thereof containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

The mode of administration and dosage form are closely related to the therapeutic amounts of the compounds or compositions which are desirable and efficacious for the given treatment application.

The pharmaceutical compositions containing a compound of this invention can be administered to a subject by any method known to a person skilled in the art, such as orally, parenterally, paracancerally, transmucosally, transdermally, intramuscularly, intranasally, intravenously, intradermally, subcutaneously, sublingually, intraperitoneally, intraventricularly, intracranially, intravaginally, by inhalation, rectally, intratumorally, or by any means in which the composition can be delivered to tissue (e.g., needle or catheter). Alternatively, topical administration may be desired for application to the dermal, ocular or mucosal surfaces. Another method of administration is via aspiration or aerosol formulation. Further, in another embodiment, the pharmaceutical compositions may be administered topically to body surfaces, and are thus formulated in a form suitable for topical administration. Suitable topical formulations include gels, ointments, creams, lotions, drops and the like. For topical administration, the compounds of this invention or their physiologically tolerated derivatives such as salts, esters, N-oxides, and the like are prepared and applied as solutions, suspensions, or emulsions in a physiologically acceptable diluent with or without a pharmaceutical carrier.

Suitable dosage forms include but are not limited to oral, rectal, sub-lingual, mucosal, nasal, ophthalmic, subcutaneous, intramuscular, intravenous, transdermal, spinal, intrathecal, intra-articular, intra-arterial, sub-arachinoid, bronchial, lymphatic, and intra-uterile administration, and other dosage forms for systemic delivery of active ingredients. In some applications, formulations suitable for oral administration are preferred. In some applications, formulations suitable for topical administration are preferred.

Topical Administration: In a typical embodiment, the compounds of the invention are administered topically. Topical administration is especially appropriate for hirsutism, alopecia, acne and excess sebum. The dose will vary, but as a general guideline, the compound will be present in a dermatologically acceptable carrier in an amount of from about 0.01 to 50 w/w %, and more typically from about 0.1 to 10 w/w %. Typically, the dermatological preparation will be applied to the affected area from 1 to 4 times daily. "Dermatologically acceptable" refers to a carrier which may be applied to the skin or hair, and which will allow the drug to diffuse to the site of action. More specifically, it refers to a site where inhibition of androgen receptor or degradation of androgen receptor is desired.

In a further embodiment, the compounds of the invention are used topically to relieve alopecia, especially androgenic alopecia. Androgens have a profound effect on both hair growth and hair loss. In most body sites, such as the beard and pubic skin, androgens stimulate hair growth by prolonging the growth phase of the hair cycle (anagen) and increasing follicle size. Hair growth on the scalp does not require androgens but, paradoxically, androgens are necessary for the balding on the scalp in genetically predisposed individuals (androgenic alopecia) where there is a progressive decline in the duration of anagen and in hair follicle size. Androgenic alopecia is also common in women where it usually presents as a diffuse hair loss rather than showing the patterning seen in men.

While the compounds of the invention will most typically be used to alleviate androgenic alopecia, the invention is not limited to this specific condition. The compounds of the invention may be used to alleviate any type of alopecia. Examples of non-androgenic alopecia include alopecia areata, alopecia due to radiotherapy or chemotherapy, scarring alopecia, stress related alopecia, etc. As used in this application "alopecia" refers to partial or complete hair loss on the scalp.

Thus, the compounds of the invention can be applied topically to the scalp and hair to prevent or alleviate balding. Further, the compound of the invention can be applied topically in order to induce or promote the growth or regrowth of hair on the scalp.

In a further embodiment of the invention, a compound of the invention is applied topically in order to prevent the growth of hair in areas where such hair growth in not desired. One such use will be to alleviate hirsutism. Hirsutism is excessive hair growth in areas that typically do not have hair (i.e., a female face). Such inappropriate hair growth occurs most commonly in women and is frequently seen at menopause. The topical administration of the compounds of the invention will alleviate this condition leading to a reduction, or elimination of this inappropriate, or undesired, hair growth.

The compounds of the invention may also be used topically to decrease sebum production. Sebum is composed of triglycerides, wax esters, fatty acids, sterol esters and squalene. Sebum is produced in the acinar cells of the sebaceous glands and accumulates as these cells age. At maturation, the acinar cells lyse, releasing sebum into the luminal duct so that it may be deposited on the surface of the skin.

In some individuals, an excessive quantity of sebum is secreted onto the skin. This can have a number of adverse consequences. It can exacerbate acne, since sebum is the primary food source for *Propionbacterium acnes*, the causative agent of acne. It can cause the skin to have a greasy appearance, typically considered cosmetically unappealing.

Formation of sebum is regulated by growth factors and a variety of hormones including androgens. The cellular and molecular mechanism by which androgens exert their influence on the sebaceous gland has not been fully elucidated. However, clinical experience documents the impact androgens have on sebum production. Sebum production is significantly increased during puberty, when androgen levels are their highest. Thus the compounds of the invention inhibit the secretion of sebum and thus reduce the amount of sebum on the surface of the skin. The compounds of the invention can be used to treat a variety of dermal diseases such as acne or seborrheic dermatitis.

In addition to treating diseases associated with excess sebum production, the compounds of the invention can also be used to achieve a cosmetic effect. Some consumers believe that they are afflicted with overactive sebaceous glands. They feel that their skin is oily and thus unattractive. These individuals can utilize the compounds of the invention to decrease the amount of sebum on their skin. Decreasing the secretion of sebum will alleviate oily skin in individuals afflicted with such conditions.

The compounds of the invention of this invention will typically be administered topically. As used herein, topical refers to application of the compounds of the invention (and optional carrier) directly to the skin and/or hair. The topical composition according to the present invention can be in the form of solutions, lotions, salves, creams, ointments, liposomes, sprays, gels, foams, roller sticks, and any other formulation routinely used in dermatology.

Thus, a further embodiment relates to cosmetic or pharmaceutical compositions, in particular dermatological compositions, which comprise at least one of the compounds of the invention. Such dermatological compositions will contain from 0.001% to 10% w/w % of the compounds in admixture with a dermatologically acceptable carrier, and more typically, from 0.1 to w/w % of the compounds. Such compositions will typically be applied from 1 to 4 times daily. The reader's attention is directed to *Remington's Pharmaceutical Science*, Edition 17, Mark Publishing Co., Easton, Pa. for a discussion of how to prepare such formulations.

The compositions according to the invention can also consist of solid preparations constituting cleansing soaps or bars. These compositions are prepared according to the usual methods.

The compounds of the invention can also be used for the hair in the form of aqueous, alcoholic or aqueous-alcoholic solutions, or in the form of creams, gels, emulsions or mousses, or alternatively in the form of aerosol compositions also comprising a propellant under pressure. The composition according to the invention can also be a hair care composition, and in particular a shampoo, a hair-setting lotion, a treating lotion, a styling cream or gel, a dye composition, a lotion or gel for preventing hair loss, etc. The amounts of the various constituents in the dermatological compositions according to the invention are those conventionally used in the fields considered.

The medicinal and cosmetics containing the compounds of the invention will typically be packaged for retail distribution (i.e., an article of manufacture). Such articles will be labeled and packaged in a manner to instruct the patient how to use the product. Such instructions will include the condition to be treated, duration of treatment, dosing schedule, etc.

Antiandrogens, such as finasteride or flutamide, have been shown to decrease androgen activity or block androgen action in the skin to some extent but suffer from undesirable systemic effects. An alternative approach is to topically apply a selective androgen receptor degrader (SARD) compound to the affected areas. In one embodiment, such a SARD compound would exhibit potent but local inhibition of AR activity. In another embodiment, the SARD compound would exhibit potent but local degradation of AR activity. In another embodiment, the SARD compound would not penetrate to the systemic circulation of the subject. In another embodiment, the SARD compound would be rapidly metabolized upon entry into the blood, limiting systemic exposure.

To prepare such pharmaceutical dosage forms, the active ingredient may be mixed with a pharmaceutical carrier according to conventional pharmaceutical compounding techniques. The carrier may take a wide variety of forms depending on the form of preparation desired for administration.

As used herein "pharmaceutically acceptable carriers or diluents" are well known to those skilled in the art. The carrier or diluent may be a solid carrier or diluent for solid formuations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

Oral or Parenteral Administration: In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. Due to their ease in administration, tablets and capsules represent the most advantageous oral dosage unit form. If desired, tablets may be sugar coated or enteric coated by standard techniques.

For parenteral formulations, the carrier will usually comprise sterile water, though other ingredients, for example, ingredients that aid solubility or for preservation, may be included. Injectable solutions may also be prepared in which case appropriate stabilizing agents may be employed.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

Treatment methods of the present invention using formulations suitable for oral administration may be presented as discrete units such as capsules, cachets, tablets, or lozenges, each containing a predetermined amount of the active ingredient as, for example, a powder or granules. Optionally, a suspension in an aqueous liquor or a non-aqueous liquid may be employed, such as a syrup, an elixir, an emulsion, or a draught.

A tablet may be made by compression or molding, or wet granulation, optionally with one or more accessory ingredients. Compressed tablets may be prepared by compressing in a suitable machine, with the active compound being in a free-flowing form such as a powder or granules which optionally is mixed with, for example, a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration may comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

Nasal and other mucosal spray formulations (e.g. inhalable forms) can comprise purified aqueous solutions of the active compounds with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

Formulations for rectal administration may be presented as a suppository with a suitable carrier such as cocoa butter, hydrogenated fats, or hydrogenated fatty carboxylic acids.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from, for example, diluents, buffers, flavoring agents, binders, disintegrants, surface active agents, thickeners, lubricants, preservatives (including antioxidants), and the like.

The formulations of the present invention can have immediate release, sustained release, delayed-onset release or any other release profile known to one skilled in the art.

It is to be understood that this invention encompasses any embodiment of a compound as described herein, which in some embodiments is referred to as "a compound of this invention".

For administration to mammals, and particularly humans, it is expected that the physician will determine the actual dosage and duration of treatment, which will be most suitable for an individual and can vary with the age, weight and response of the particular individual. In one embodiment, the methods of this invention may comprise administration of a compound of this invention at various dosages. In one embodiment, a compound of this invention is administered at a dosage of 1-3000 mg per day. In additional embodiments, a compound of this invention is administered at a dose of 1-10 mg per day, 3-26 mg per day, 3-60 mg per day, 3-16 mg per day, 3-30 mg per day, 10-26 mg per day, 15-60 mg, 50-100 mg per day, 50-200 mg per day, 100-250 mg per day, 125-300 mg per day, 20-50 mg per day, 5-50 mg per day, 200-500 mg per day, 125-500 mg per day, 500-1000 mg per day, 200-1000 mg per day, 1000-2000 mg per day, 1000-3000 mg per day, 125-3000 mg per day, 2000-3000 mg per day, 300-1500 mg per day or 100-1000 mg per day. In one embodiment, a compound of this invention is administered at a dosage of 25 mg per day. In one embodiment, a compound of this invention is administered at a dosage of 40 mg per day. In one embodiment, a compound of this invention is administered at a dosage of 50 mg per day. In one embodiment, a compound of this invention is administered at a dosage of 67.5 mg per day. In one embodiment, a compound of this invention is administered at a dosage of 75 mg per day. In one embodiment, a compound of this invention is administered at a dosage of 80 mg per day. In one embodiment, a compound of this invention is administered at a dosage of 100 mg per day. In one embodiment, a compound of this invention is administered at a dosage of 125 mg per day. In one embodiment, a compound of this invention is administered at a dosage of 250 mg per day. In one embodiment, a compound of this invention is administered at a dosage of 300 mg per day. In one embodiment, a compound of this invention is administered at a dosage of 500 mg per day. In one embodiment, a compound of this invention is administered at a dosage of 600 mg per day. In one embodiment, a compound of this invention is administered at a dosage of 1000 mg per day. In one embodiment, a compound of this invention is administered at a dosage of 1500 mg per day. In one embodiment, a compound of this invention is administered at a dosage of 2000 mg per day. In one embodiment, a compound of this invention is administered at a dosage of 2500 mg per day. In one embodiment, a compound of this invention is administered at a dosage of 3000 mg per day. In another embodiment, the compound is any one of compounds 11-27, 30-47, 11R, 70-79, 80, 90-99, 100-115, 130-137, 200-205, and 300-308 as described herein. In one embodiment, the methods of this invention may comprise administration of a compound of this invention at various dosages. In one embodiment, a compound of this invention is administered at a dosage of 3 mg. In additional embodiments, a compound of this invention is administered at a dosage of 10 mg, 30 mg, 40 mg, 50 mg, 80 mg, 100 mg, 120 mg, 125 mg, 200 mg, 250 mg, 300 mg, 450 mg, 500 mg, 600 mg, 900 mg, 1000 mg, 1500 mg, 2000 mg, 2500 mg or 3000 mg. In another embodiment, the compound is any one of compounds 11-27, 30-47, 11R, 70-79, 80, 90-99, 100-115, 130-137, 200-205, and 300-308 as described herein.

In one embodiment, the methods of this invention may comprise administration of a compound of this invention at various dosages. In one embodiment, a compound of this invention is administered at a dosage of 0.1 mg/kg/day. In additional embodiments, a compound of this invention is administered at a dosage between 0.2 to 30 mg/kg/day, or 0.2 mg/kg/day, 0.3 mg/kg/day, 1 mg/kg/day, 3 mg/kg/day, 5 mg/kg/day, 10 mg/kg/day, 20 mg/kg/day, 30 mg/kg/day, 50 mg/kg/day or 100 mg/kg/day.

In one embodiment, the methods of this invention provide for the use of a pharmaceutical composition comprising a compound of the invention or any one of compounds 11-27, 30-47, 11R, 70-79, 80, 90-99, 100-115, 130-137, 200-205, and 300-308 as described herein. In a certain embodiment, the pharmaceutical composition is a solid dosage form. In another embodiment, the pharmaceutical composition is a tablet. In another embodiment, the pharmaceutical composition is a capsule. In another embodiment, the pharmaceutical composition is a solution. In another embodiment, the pharmaceutical composition is a transdermal patch.

In one embodiment, use of a compound of this invention or a composition comprising the same, will have utility in inhibiting, suppressing, enhancing or stimulating a desired response in a subject, as will be understood by one skilled in the art. In another embodiment, the compositions may further comprise additional active ingredients, whose activity is useful for the particular application for which the compound of this invention is being administered.

For administration to mammals, and particularly humans, it is expected that the physician will determine the actual dosage and duration of treatment, which will be most suitable for an individual and can vary with the age, weight, genetics and/or response of the particular individual.

In some embodiments, any of the compositions of this invention will comprise a compound of this invention, in any form or embodiment as described herein. In some embodiments, any of the compositions of this invention will consist of a compound of this invention, in any form or embodiment as described herein. In some embodiments, of the compositions of this invention will consist essentially of a compound of this invention, in any form or embodiment as described herein. In some embodiments, the term "comprise" refers to the inclusion of the indicated active agent, such as the compound of this invention, as well as inclusion of other active agents, and pharmaceutically acceptable carriers, excipients, emollients, stabilizers, etc., as are known in the pharmaceutical industry. In some embodiments, the term "consisting essentially of" refers to a composition, whose only active ingredient is the indicated active ingredient, however, other compounds may be included which are for stabilizing, preserving, etc. the formulation, but are not involved directly in the therapeutic effect of the indicated active ingredient. In some embodiments, the term "consisting essentially of" may refer to components which facilitate the release of the active ingredient. In some embodiments, the term "consisting" refers to a composition, which contains the active ingredient and a pharmaceutically acceptable carrier or excipient.

It is to be understood that any use of any of the compounds as herein described may be used in the treatment of any disease, disorder or condition as described herein, and represents an embodiment of this invention. In one embodiment, the compounds are a free base, free acid, non charged or non-complexed compound.

The following examples are presented in order to more fully illustrate the preferred embodiments of the invention. They should in no way, however, be construed as limiting the broad scope of the invention.

EXAMPLES

Example 1

Synthesis of Indole/Pyrrolo-Pyridine SARD Compounds of this Invention

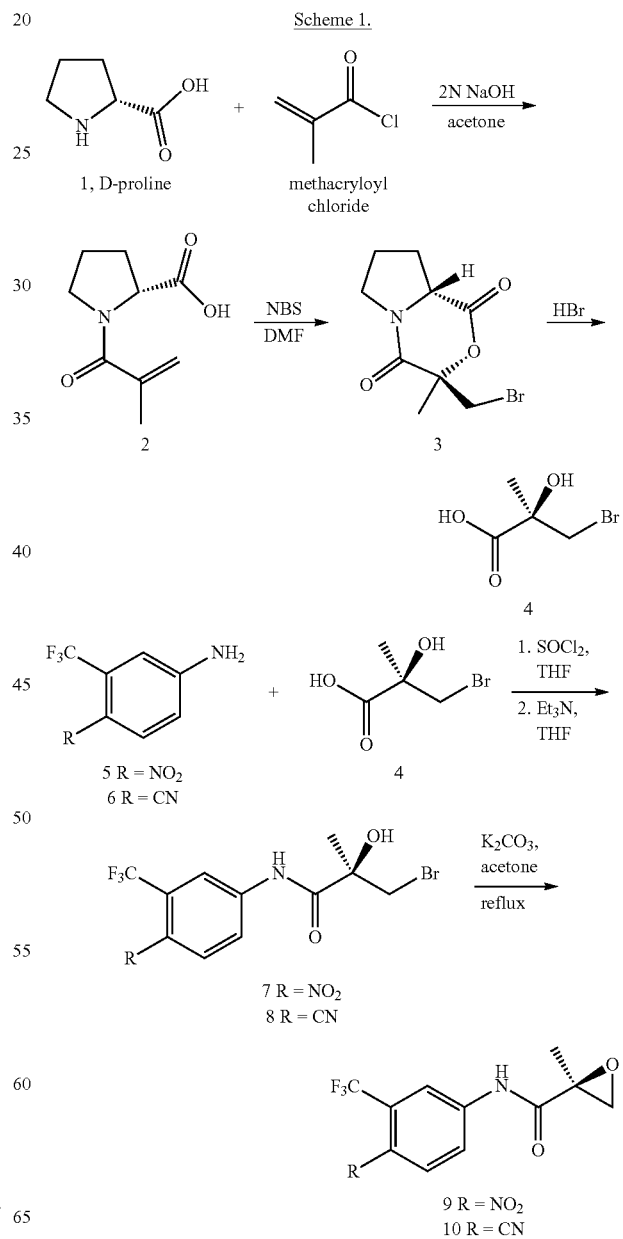

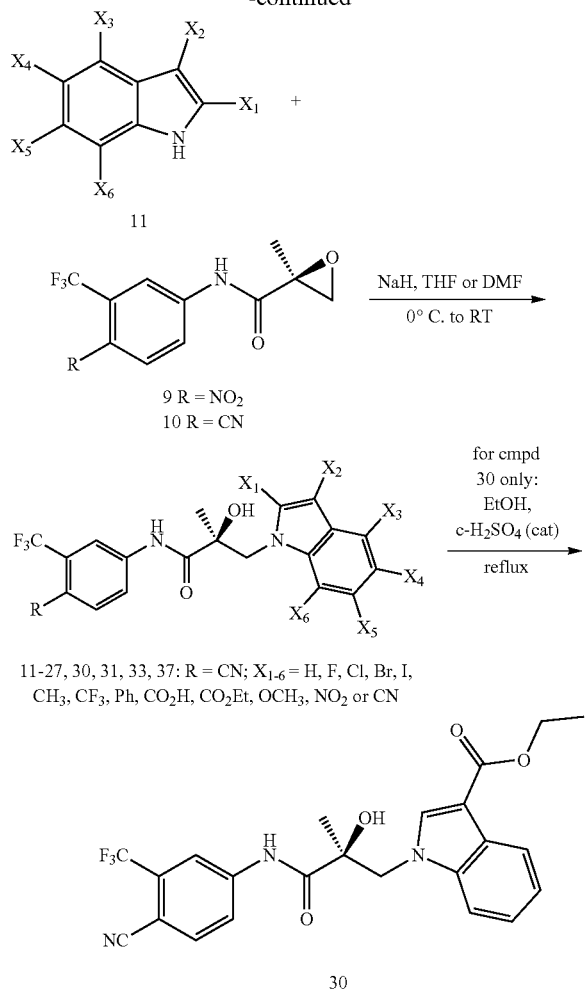

102.5-103.5° C.); the NMR spectrum of this compound demonstrated the existence of two rotamers of the title compound. $^1$H NMR (300 MHz, DMSO-d$_6$) δ 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (in) for the second rotamer (totally 1H for both rotamers, CH at the chiral center), 3.57-3.38 (m, 2H, CH$_2$), 2.27-2.12 (1H, CH), 1.97-1.72 (m, 6H, CH$_2$, CH, Me); $^{13}$C NMR (75 MHz, DMSO-d$_6$) δ for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C=O), 1647 (CO, COOH), 1584, 1508, 1459, 1369, 1348, 1178 cm$^{-1}$; $[α]_D^{26}$+80.8 (c=1, MeOH); Anal. Calcd. for C$_9$H$_{13}$NO$_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3)

A solution of NBS (23.5 g, 0.132 mol) in 100 mL of DMF was added dropwise to a stirred solution of the (2R)-1-methacryloylpyrrolidin-2-carboxylic acid (2) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried 34%) of the titled bromolactone (3) as a yellow solid: mp 158.1-160.3° C.; $^1$H NMR (300 MHz, DMSO-d$_6$) δ 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (in, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C=O), 1687 (C=O), 1448, 1377, 1360, 1308, 1227, 1159, 1062 cm$^{-1}$; $[α]_D^{26}$+124.5° (c=1.3, chloroform); Anal. Calcd. for C$_9$H$_{12}$BrNO$_3$: C, 41.24, H, 4.61, N, 5.34.
Found: C, 41.46, H, 4.64, N, 5.32.

(2R)-3-Bromo-2-hydroxy-2-methylpropanoic acid (4)

A mixture of bromolactone (3) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.; $^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me); IR (KBr) 3434 (OH), 3300-2500 (COOH), 1730 (C=O), 1449, 1421, 1380, 1292, 1193, 1085 cm$^1$; $[α]_D^{26}$+10.5° (c=2.6, MeOH); Anal. Calcd. for C$_4$H$_7$BrO$_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8)

Thionyl chloride (46.02 g, 0.39 mol) was added dropwise to a cooled solution (less than 4° C.) of (R)-3-bromo-2-

(2R)-1-Methacryloylpyrrolidin-2-carboxylic acid (2)

D-Proline (14.93 g, 0.13 mol) was dissolved in 71 mL of 2 N NaOH and cooled in an ice bath. The resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10$^{-11}$° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B. M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40: mp hydroxy-2-methylpropanoic acid (4) (51.13 g, 0.28 mol) in 300 mL of THF under an argon atmosphere. The resulting mixture was stirred for 3 h under the same condition. To this was added Et₃N (39.14 g, 0.39 mol) and stirred for 20 min under the same condition. After 20 min, 5-amino-2-cyano-benzotrifluoride (40.0 g, 0.21 mol), 400 mL of THF were added and then the mixture was allowed to stir overnight at RT. The solvent was removed under reduced pressure to give a solid which was treated with 300 mL of H₂O, extracted with EtOAc (2×400 mL). The combined organic extracts were washed with saturated NaHCO₃ solution (2×300 mL) and brine (300 mL). The organic layer was dried over MgSO₄ and concentrated under reduced pressure to give a solid which was purified from column chromatography using CH₂Cl₂/EtOAc (80:20) to give a solid. This solid was recrystallized from CH₂Cl₂/hexane to give 55.8 g (73.9%) of (2R)-3-bromo-N-[4-cyano-3-(trifluoromethyl)phenyl]-2-hydroxy-2-methylpropanamide (8) as a light-yellow solid. M.p. 134.0-136.5° C.; $^1$H NMR (CDCl₃/TMS) δ 1.66 (s, 3H, CH), 3.11 (s, 1H, OH), 3.63 (d, J=10.8 Hz, 1H, CH₂), 4.05 (d, J=10.8 Hz, 1H, CH₂), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]⁻ 349.0.

Structures of Compounds Synthesized with Different Substituents: (R)- or (S)—N-(4-cyano-3-(trifluoromethyl)-phenyl)-3-(Substituted-1H-indol-1-yl)-2-hydroxy-2-methylpropanamides (11-27, 11R, 30-32, and 80)

Compounds 11-27, 11R, 30-32, and 80 were prepared by the general procedures as shown in Scheme 1 or Scheme 2, or Example 2. 11R was synthesized by same procedures as the other compounds but using L-proline instead of D-proline as a starting material. And also, 19 was isolated from the synthetic product of 11 as a by-product.

11
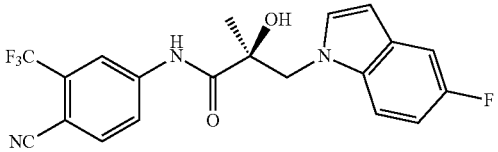

11R
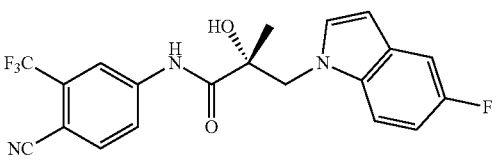

12
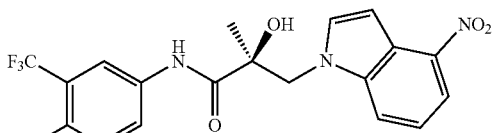

13
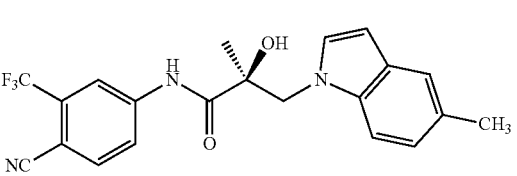

14
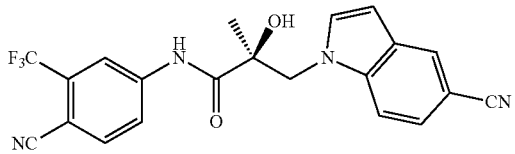

15
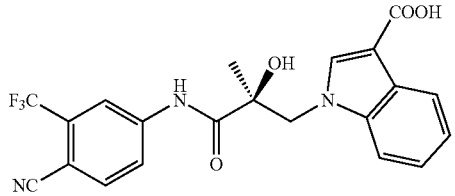

16
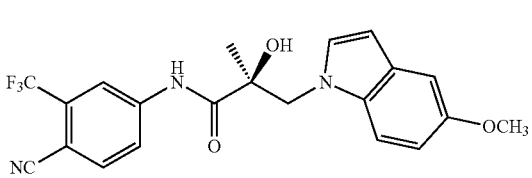

17
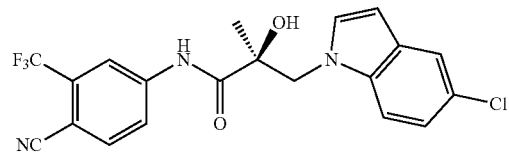

18
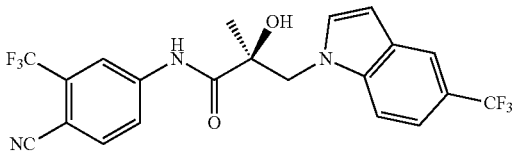

19
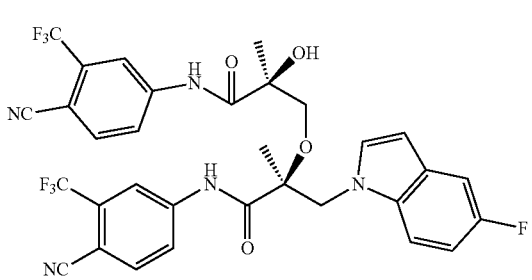

20
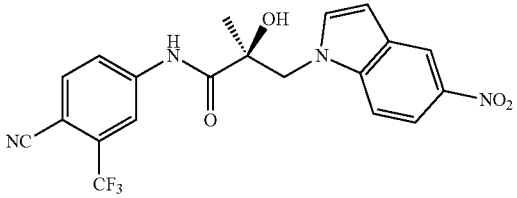

21
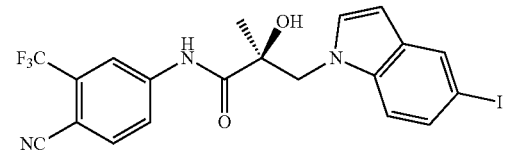

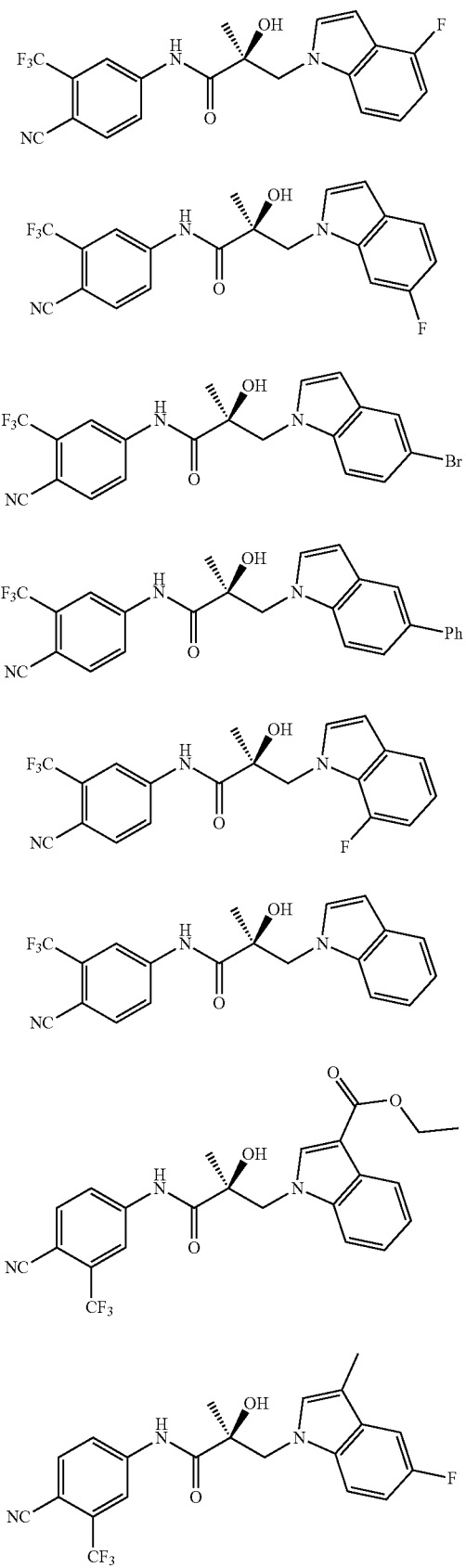

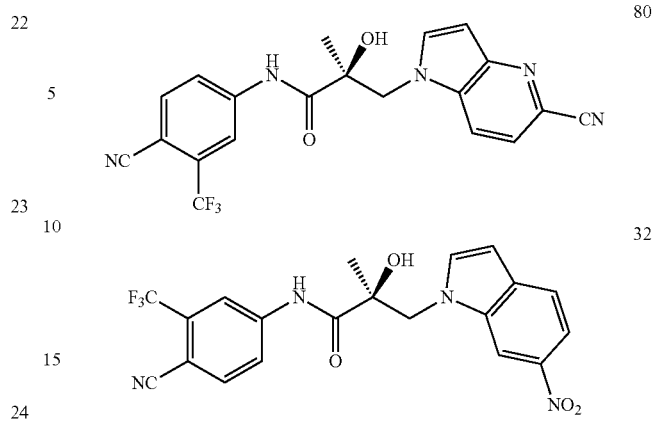

General Synthetic Procedure of Compounds 11-27, 11R, 30-32, and 80.

Step 1. Preparation of (S)—N-(4-cyano-3-(trifluoromethyl)phenyl)-2-methyloxirane-2-carboxamide (10) in THF: A mixture of hydroxylbromide 8 (1.0 g, 2.84 mmol) and potassium carbonate (790 mg, 5.70 mmol) in 60 mL acetone was heated to reflux for 30 min. After complete conversion of starting bromide 8 to desired epoxide 10 as monitored by TLC, the solvent was evaporated under reduced pressure to give yellowish residue, which was poured into 20 mL of anhydrous EtOAc. The solution was filtered through Celite® pad to remove $K_2CO_3$ residue and condensed under reduced pressure to give a yellowish solid of epoxide 10, which was dissolved in 5 mL of anhydrous THF to prepare a solution of epoxide 10 in THF. The resulting solution was directly used as next reactant without analysis.

Step 2. NaH of 60% dispersion in mineral oil (228 mg, 5.7 mmol) was added in 30 mL of anhydrous THF solvent into a 100 mL dried two necked round bottom flask equipped with a dropping funnel and substituted indole/pyrrolo-pyridine (2.84 mmol) was added to the solution under argon atmosphere in ice-water bath, and the resulting solution was stirred for 30 min in an ice-water bath. Into the flask, the prepared solution of epoxide 10 (2.84 mmol in THF) was added through dropping funnel under argon atmosphere at the ice-water bath and stirred overnight at RT. After adding 1 mL of $H_2O$ (1N HCl in case for compound 15), the reaction mixture was condensed under reduced pressure, and then dispersed into 50 mL of EtOAc, washed with 50 mL (×2) water, brine, dried over anhydrous $MgSO_4$, and evaporated to dryness. The mixture was purified with flash column chromatography as an eluent EtOAc/hexane, and then the condensed compounds were then recrystallized in EtOAc/hexane to give any one of the target products 11-27, 11R, 30-32, and 80.

(S)—N-(4-Cyano-3-(trifluoromethyl)phenyl)-3-(5-fluoro-1H-indol-1-yl)-2-hydroxy-2-methylpropanamide (11): Yield 68%; White solid. MS (ESI): 404.0 [M−H]$^-$; 428.2 [M+Na]$^+$; mp 147.5-148.9° C.; $^1$H NMR (CDCl$_3$, 400 MHz) δ 8.77 (bs, 1H, NH), 7.90 (d, J=1.7 Hz, 1H), 7.78-7.76 (m, 2H), 7.38 (dd, J=9.0, 4.2 Hz, 1H), 7.23 (dd, J=9.3, 2.5 Hz, 1H), 7.19 (d, J=3.2 Hz, 1H), 6.98 (dt, J=9.0, 2.5 Hz, 1H), 6.50 (d, J=3.2 Hz, 1H), 4.62 (d, J=14.8 Hz, 1H), 4.38 (d, J=14.8 Hz, 1H), 2.49 (bs, 1H, OH), 1.61 (s, 3H).

(S)—N-(4-Cyano-3-(trifluoromethyl)phenyl)-2-hydroxy-2-methyl-3-(4-nitro-1H-indol-1-yl)propanamide (12): Yield 41%; Yellowish solid; mp 152.9-154.8° C.; MS (ESI): 430.9 [M−H]$^-$; $^1$H NMR (CDCl$_3$, 400 MHz) δ 8.88 (bs, 1H), 8.04

(d, J=1.6 Hz, 1H), 7.89 (s, 1H), 7.79-7.75 (m, 3H), 7.31 (m, 1H), 7.26 (m, 2H), 4.69 (d, J=14.8 Hz, 1H), 4.42 (d, J=14.8 Hz, 1H), 2.43 (bs, 1H, OH), 1.63 (s, 3H).

(S)—N-(4-Cyano-3-(trifluoromethyl)phenyl)-2-hydroxy-2-methyl-3-(5-methyl-1H-indol-1-yl)propanamide (13): Yield 59%; Yellowish solid: mp 148.6-150.2° C.; MS (ESI): 400.0 [M–H]⁻; 424.2 [M+Na]⁺; ¹H NMR (CDCl₃, 400 MHz) δ 8.72 (bs, 1H), 7.86 (d, J=2.0 Hz, 1H), 7.78 (m, 2H), 7.31 (d, J=8.8 Hz, 1H), 6.84 (dd, J=21.2, 3.2 Hz, 1H), 6.84 (dd, J=8.8, 2.4 Hz, 1H), 6.43 (d, J=2.4 Hz, 1H), 6.63 (d, J=14.8 Hz, 1H), 4.31 (d, J=14.8 Hz, 1H), 3.82 (s, 3H), 2.51 (s, 1H, OH), 1.60 (s, 3H).

(S)-3-(5-Cyano-1H-indol-1-yl)-N-(4-cyano-3-(trifluoromethyl)phenyl)-2-hydroxy-2-methylpropanamide (14): Yield 54%; White solid: MS (ESI): 411.0 [M–H]⁻; ¹H NMR (CDCl₃, 400 MHz) δ 8.85 (bs, 1H), 7.91 (d, J=1.6 Hz, 1H), 7.85 (s, 1H), 7.80-7.73 (m, 2H), 7.53 (d, J=8.6 Hz, 1H), 7.34 (d, J=8.6 Hz, 1H), 7.26 (m, 1H), 6.59 (d, J=3.2 Hz, 1H), 4.68 (d, J=14.8 Hz, 1H), 4.40 (d, J=14.8 Hz, 1H), 2.94 (bs, 1H, OH), 1.64 (s, 3H).

(S)-1-(3-((4-Cyano-3-(trifluoromethyl)phenyl)amino)-2-hydroxy-2-methyl-3-oxopropyl)-1H-indole-3-carboxylic acid (15): Yield 31%; Light yellowish solid: MS (ESI): 429.9 [M–H]⁻; ¹H NMR (CDCl₃, 400 MHz) δ 9.10 (bs, 1H), 8.11 (m, 1H), 8.01 (s, 1H), 7.91 (m, 2H), 7.84 (d, J=1.6 Hz, 1H), 7.74-7.67 (m, 2H), 7.51-7.49 (m, 1H), 7.22-7.20 (m, 1H), 4.62 (d, J=14.8 Hz, 1H), 4.43 (d, J=14.8 Hz, 1H), 2.94 (s, 1H, OH), 1.61 (s, 3H).

(S)—N-(4-Cyano-3-(trifluoromethyl)phenyl)-2-hydroxy-3-(5-methoxy-1H-indol-1-yl)-2-methylpropanamide (16): Yield 53%; Brown solid: MS (ESI): 416.0 [M–H]⁻; 418.2 [M+H]⁺; 440.2 [M+Na]⁺; ¹H NMR (CDCl₃, 400 MHz) δ 8.74 (bs, 1H), 7.87 (d, J=2.2 Hz, 1H), 7.81-7.75 (m, 2H), 7.30 (d, J=3.2 Hz, 1H), 7.09 (d, J=3.2 Hz, 1H), 7.03 (d, J=2.2 Hz, 1H), 6.43 (d, J=2.8 Hz, 1H), 4.63 (d, J=14.8 Hz, 1H), 4.30 (d, J=14.8 Hz, 1H), 3.82 (s, 3H), 2.60 (bs, 1H, OH), 1.62 (s, 3H).

(S)-3-(5-Chloro-1H-indol-1-yl)-N-(4-cyano-3-(trifluoromethyl)phenyl)-2-hydroxy-2-methylpropanamide (17): Yield 62%; White solid: MS (ESI): 420.0 [M–H]⁻; ¹H NMR (CDCl₃, 400 MHz) δ 8.85 (bs, 1H), 7.88 (d, J=1.6 Hz, 1H), 7.78 (m, 2H), 7.62 (s, 1H), 7.32 (d, J=3.2 Hz, 1H), 7.12 (m, 2H), 6.65 (d, J=3.2 Hz, 1H), 4.65 (d, J=14.8 Hz, 1H), 4.31 (d, J=14.8 Hz, 1H), 2.52 (bs, 1H, OH), 1.61 (s, 3H).

(S)—N-(4-Cyano-3-(trifluoromethyl)phenyl)-2-hydroxy-2-methyl-3-(5-(trifluoromethyl)-1H-indol-1-yl)propanamide (18): Yield 57%; White solid: MS (ESI): 453.9 [M–H]⁻; ¹H NMR (CDCl₃, 400 MHz) δ 8.80 (bs, 1H), 7.83 (d, J=1.6 Hz, 1H), 7.75 (m, 2H), 7.51 (d, J=3.2 Hz, 1H), 7.41 (m, 1H), 7.21 (m, 1H), 6.62 (d, J=3.2 Hz, 1H), 4.68 (d, J=14.8 Hz, 1H), 4.38 (d, J=14.8 Hz, 1H), 2.49 (s, 1H, OH), 1.61 (s, 3H).

(S)—N-(4-Cyano-3-(trifluoromethyl)phenyl)-2-((S)-3-((4-cyano-3-(trifluoromethyl)phenyl)amino)-2-hydroxy-2-methyl-3-oxopropoxy)-3-(5-fluoro-1H-indol-1-yl)-2-methylpropanamide (19): White solid: MS (ESI): 673.9 [M–H]⁻; 698.2 [M+Na]⁺; ¹H NMR (CDCl₃, 400 MHz) δ 9.14 (bs, 1H), 8.62 (bs, 1H), 8.16 (d, J=1.8 Hz, 1H), 8.06 (dd, J=8.8, 1.8 Hz, 1H), 7.94 (d, J=1.8 Hz, 1H), 7.84 (d, J=8.8 Hz, 1H), 7.75 (d, J=8.8 Hz, 1H), 7.55 (dd, J=8.4, 2.0 Hz, 1H), 7.45 (s, 1H), 7.35 (m, 1H), 7.24 (m, 1H), 6.98 (d, J=3.2 Hz, 1H), 6.24 (d, J=3.2 Hz, 1H), 4.54 (d, J=14.8 Hz, 1H), 4.36 (d, J=14.8 Hz, 1H), 3.96 (d, J=8.8 Hz, 1H), 3.55 (d, J=8.8 Hz, 1H), 2.76 (s, 1H, OH), 1.69 (s, 3H), 1.38 (s, 3H).

(S)—N-(4-Cyano-3-(trifluoromethyl)phenyl)-2-hydroxy-2-methyl-3-(5-nitro-1H-indol-1-yl)propanamide (20): Yield 47%; Yellowish solid: MS (ESI): 431.0 [M–H]⁻; ¹H NMR (Acetone-d₆, 400 MHz) δ 9.68 (bs, 1H, NH), 8.35 (d, J=2.0 Hz, 1H), 8.16 (s, 1H), 8.01 (m, 1H), 7.88-7.81 (m, 2H), 7.58 (d, J=8.8 Hz, 1H), 7.38 (d, J=3.4 Hz, 1H), 6.58 (d, J=3.4 Hz, 1H), 5.49 (s, 1H, OH), 4.66 (d, J=14.8 Hz, 1H), 4.38 (d, J=14.8 Hz, 1H), 1.50 (s, 3H).

(S)—N-(4-Cyano-3-(trifluoromethyl)phenyl)-2-hydroxy-3-(5-iodo-1H-indol-1-yl)-2-methylpropanamide (21): Yield 48%; MS (ESI) 511.9 [M–H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(4-fluoro-1H-indol-1-yl)-2-hydroxy-2-methylpropanamide (22): Yield 48%; MS (ESI) 511.9 [M–H]⁻; ¹H NMR (CDCl₃, 400 MHz) δ 8.71 (bs, 1H, NH), 7.91 (d, J=1.6 Hz, 1H), 7.74 (m, 2H), 7.43 (dd, J=8.8, 1.6 Hz, 1H), 7.21 (d, J=8.8 Hz, 1H), 7.08 (d, J=3.2 Hz, 1H), 6.44 (d, J=3.2 Hz, 1H), 4.62 (d, J=15.0 Hz, 1H), 4.32 (d, J=15.0 Hz, 1H), 2.44 (bs, 1H, OH), 1.61 (s, 3H).

(S)—N-(4-Cyano-3-(trifluoromethyl)phenyl)-3-(6-fluoro-1H-indol-1-yl)-2-hydroxy-2-methylpropanamide (23): Yield 48%; White solid; MS (ESI) 404.0 [M–H]⁻; ¹H NMR (CDCl₃, 400 MHz) δ 8.79 (bs, 1H, NH), 7.89 (d, J=1.6 Hz, 1H), 7.83 (d, J=8.4 Hz, 1H), 7.77 (d, J=8.0 Hz, 1H), 7.51 (dd, J=8.4, 5.2 Hz, 1H), 7.14 (dd, J=10.0, 2.0 Hz, 1H), 7.11 (d, J=3.2 Hz, 1H), 6.87 (dt, J=8.8, 2.0 Hz, 1H), 6.51 (d, J=3.2 Hz, 1H), 4.62 (d, J=14.8 Hz, 1H), 4.32 (d, J=14.8 Hz, 1H), 2.56 (bs, 1H, OH), 1.65 (s, 3H).

(S)-3-(5-Bromo-1H-indol-1-yl)-N-(4-cyano-3-(trifluoromethyl)phenyl)-2-hydroxy-2-methylpropanamide (24): Yield; 71%; MS (ESI) 465.1 [M–H]⁻; ¹H NMR (CDCl₃, 400 MHz) δ 8.73 (bs, 1H, NH), 7.88 (s, 1H), 7.74 (d, J=1.8 Hz, 1H), 7.69 (d, J=1.8 Hz, 1H), 7.30 (d, J=8.8 Hz, 1H), 7.24 (m, 1H), 7.24 (dd, J=8.8, 2.0 Hz, 1H), 7.13 (d, J=3.2 Hz, 1H), 6.45 (d, J=3.2 Hz, 1H), 4.39 (d, J=14.8 Hz, 1H), 2.60 (bs, 1H, OH), 1.65 (s, 3H).

(S)—N-(4-Cyano-3-(trifluoromethyl)phenyl)-2-hydroxy-3-(1H-indol-1-yl)-2-methylpropanamide (27)

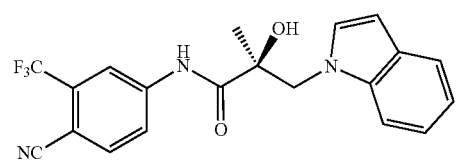

Yield 55%; Light brown solid; MS (ESI) 358.9 [M–H]; ¹H NMR (CDCl₃, 400 MHz) δ 8.67 (bs, 1H, NH), 7.96 (dd, J=8.4, 2.0 Hz, 1H), 7.80 (s, 1H), 7.71-7.65 (m, 2H), 7.51 (d, J=8.0 Hz, 1H), 7.35 (d, J=8.0 Hz, 1H), 7.12 (t, J=8.0 Hz, 1H), 7.02 (m, 1H), 6.45 (d, J=3.2 Hz, 1H), 4.58 (d, J=14.8 Hz, 1H), 4.30 (d, J=14.8 Hz, 1H), 2.50 (bs, 1H, OH), 1.54 (s, 3H).

Preparation of 30 from 15

(S)-Ethyl 1-(3-((4-cyano-3-(trifluoromethyl)phenyl)amino)-2-hydroxy-2-methyl-3-oxopropyl)-1H-indole-3-carboxylate (30)

To a solution of carboxylic acid 15 (200 mg, 0.46 mmol) in absolute ethanol of 10 mL was added dropwise a catalytic amount of c-H₂SO₄ under argon atmosphere. The solution was heated to reflux for 30 min and cooled down to RT. The solution was concentrated under reduced pressure and dispersed in EtOAc and then washed with water. The resulting solution was dried over anhydrous Na₂SO₄ and purified with flash column chromatography as an eluent EtOAc/hexane (½, v/v) to give the title compound.

Yield; 92%; MS (ESI) m/z 458.1 [M−H]⁻; 482.4 [M+Na]⁺; ¹H NMR (400 MHz, CDCl₃) δ 8.86 (bs, 1H, NH), 8.00 (m, 2H), 7.81 (s, 1H), 7.65 (s, 2H), 7.46 (d, J=8.0 Hz, 1H), 7.24-7.18 (m, 2H), 4.65 (d, J=14.4 Hz, 1H), 4.39 (d, J=14.4 Hz, 1H), 4.36 (bs, 1H, OH), 4.23-4.11 (m, 2H), 1.66 (s, 3H), 1.35 (t, J=7.2 Hz, 3H).

(S)—N-(4-Cyano-3-(trifluoromethyl)phenyl)-3-(5-fluoro-3-methyl-1H-indol-1-yl)-2-hydroxy-2-methylpropanamide (31)

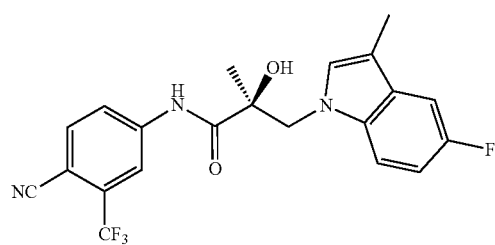 [SMILES: Cc1cn(C[C@](C)(O)C(=O)Nc2ccc(C#N)c(C(F)(F)F)c2)c2ccc(F)cc12]

Yield; 64%; MS (ESI) m/z 418.1 [M−H]⁻; ¹H NMR (400 MHz, CDCl₃) δ 8.85 (bs, 1H, NH), 7.86 (m, 1H), 7.81-7.74 (m, 2H), 7.29 (dd, J=9.0, 4.0 Hz, 1H), 7.14 (dd, J=9.0, 2.4 Hz, 1H), 6.92 (m, 2H), 4.60 (d, J=15.2 Hz, 1H), 4.27 (d, J=15.2 Hz, 1H), 2.22 (s, 3H), 1.57 (s, 3H).

(S)-3-(5-Cyano-1H-pyrrolo[3,2-b]pyridin-1-yl)-N-(4-cyano-3-(trifluoromethyl)phenyl)-2-hydroxy-2-methylpropanamide (80)

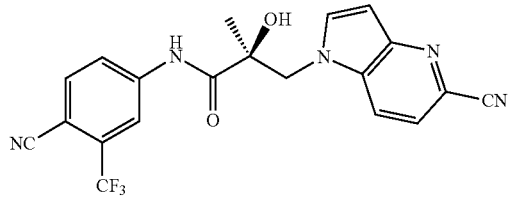

Yield; 67%; MS (ESI) m/z 412.1 [M−H]; 436.1 [M+Na]⁺; ¹H NMR (400 MHz, acetone-d₆) δ 9.84 (bs, 1H, NH), 8.31 (s, 1H), 8.14 (m, 2H), 8.01 (m, 1H), 7.81 (d, J=2.8 Hz, 1H), 7.60 (d, J=8.4 Hz, 1H), 6.67 (d, J=2.8 Hz, 1H), 5.64 (bs, 1H), 4.84 (d, J=14.8 Hz, 1H), 4.52 (d, J=14.8 Hz, 1H), 1.66 (s, 3H).

(S)—N-(4-Cyano-3-(trifluoromethyl)phenyl)-2-hydroxy-2-methyl-3-(6-nitro-1H-indol-1-yl)propanamide (32)

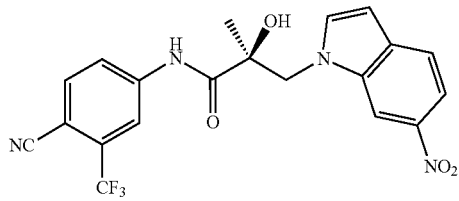 [SMILES: C[C@](O)(Cn1ccc2ccc([N+](=O)[O-])cc21)C(=O)Nc1ccc(C#N)c(C(F)(F)F)c1]

Yield; 31%; MS (ESI) m/z 431.1 [M−H]; ¹H NMR (400 MHz, CDCl₃) δ 8.87 (bs, 1H, NH), 8.53 (m, 1H), 8.01 (dd, J=8.8, 2.0 Hz, 1H), 7.92 (d, J=2.0 Hz, 1H), 7.86 (dd, J=8.4, 2.0 Hz, 1H), 7.78 (d, J=8.4 Hz, 1H), 7.64 (d, J=8.8 Hz, 1H), 7.43 (d, J=3.0 Hz, 1H), 6.61 (d, J=3.0 Hz, 1H), 4.76 (d, J=14.8 Hz, 1H), 4.48 (d, J=14.8 Hz, 1H), 3.14 (s, 1H, OH), 1.74 (s, 3H).

(R)—N-(4-Cyano-3-(trifluoromethyl)phenyl)-3-(5-fluoro-1H-indol-1-yl)-2-hydroxy-2-methylpropanamide (11R): 11R was synthesized by the same procedures as the other compounds but using L-proline instead of D-proline as a starting material.

Scheme 2

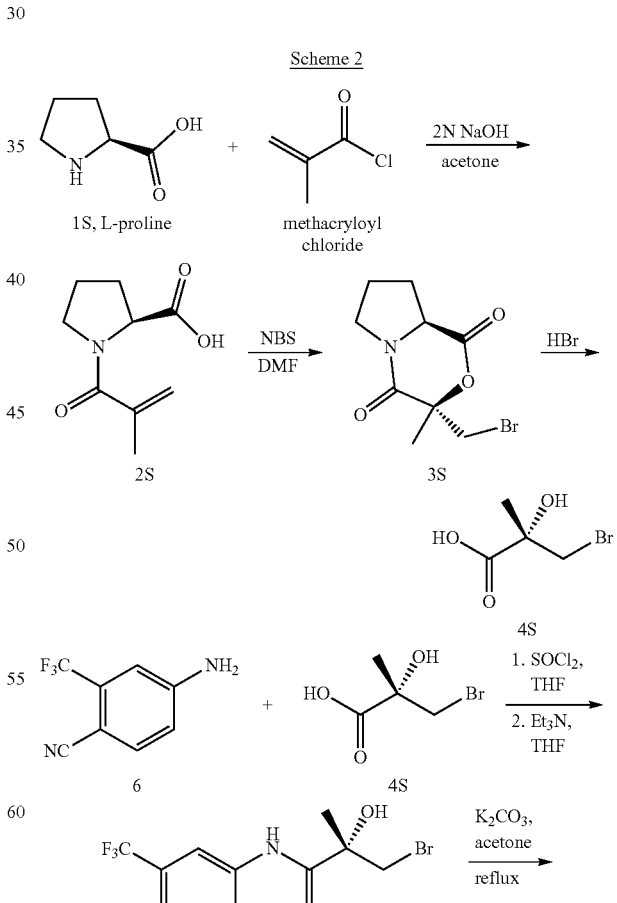

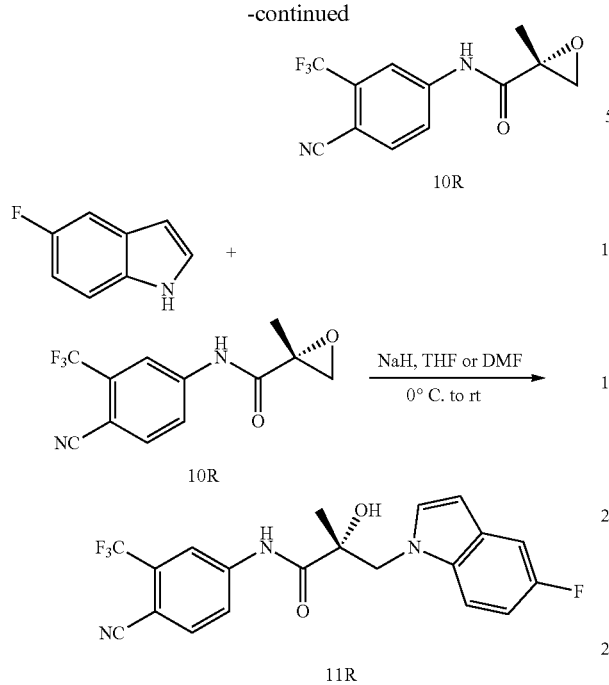

11R

NaH of 60% dispersion in mineral oil (228 mg, 5.7 mmol) was added in 20 mL of anhydrous THF solvent into a 100 mL dried two necked round bottom flask equipped with a dropping funnel. 5-Fluoroindole (390 mg, 2.84 mmol) was added to the solution under argon atmosphere in ice-water bath, and the resulting solution was stirred for 30 min in an ice-water bath. Into the flask, epoxide 10R (2.84 mmol in THF) was added through a dropping funnel under argon atmosphere in an ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product 11R.

Yield 69%; White solid. MS (ESI): 404.1 [M−H]$^-$; 428.1 [M+Na]$^-$; $^1$H NMR (CDCl$_3$, 400 MHz) δ 8.69 (bs, 1H, NH), 7.80 (d, J=1.2 Hz, 1H), 7.71-7.66 (m, 2H), 7.29-7.26 (m, 2H), 7.14 (dd, J=9.2, 2.4 Hz, 1H), 7.09 (d, J=3.2 Hz, 1H), 6.86 (dt, J=9.0, 2.5 Hz, 1H), 6.39 (d, J=3.2 Hz, 1H), 4.56 (d, J=14.8 Hz, 1H), 4.26 (d, J=14.8 Hz, 1H), 2.51 (bs, 1H, OH), 1.54 (s, 3H).

Example 2

Synthesis of Benzimidazole and Indazole SARD Compounds of this Invention

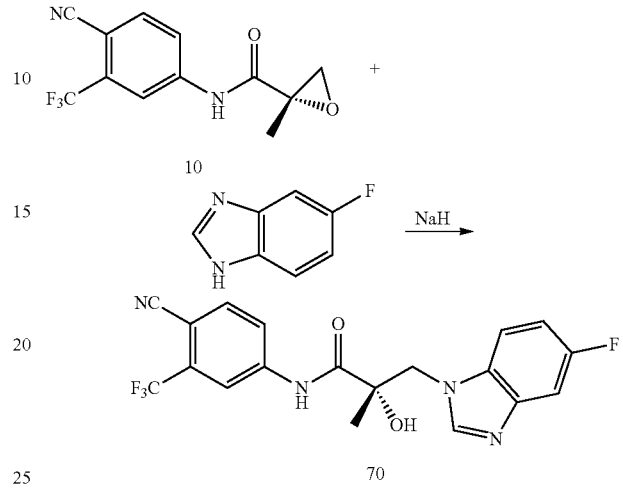

70

(S)—N-(4-Cyano-3-trifluoromethyl-phenyl)-3-(5-fluoro-benzoimidazol-1-yl)-2-hydroxy-2-methyl-propionamide (C$_{19}$H$_{14}$F$_4$N$_4$O$_2$) (70)

To a solution of 5-fluoro-1H-benzoimidazole (0.50 g, 0.00367 mol) in anhydrous THF (10 mL), which was cooled in an ice water bath under an argon atmosphere, was added sodium hydride (60% dispersion in oil, 0.44 g, 0.011 mol). After addition, the resulting mixture was stirred for 2 h. (S)—N-(4-Cyano-3-(trifluoromethyl)phenyl)-2-methyloxirane-2-carboxamide (1.29 g, 0.00367 mol) was added to above solution, and the resulting reaction mixture was allowed to stir overnight at RT under argon. The reaction was quenched by water, extracted with ethyl acetate. The organic layer was dried with MgSO$_4$, filtered, and concentrated under vacuum. The product was purified by a silicon gel column using methylene chloride and methanol (19:1) as eluent to afford 0.17 g of the desired compound as white solid.

$^1$H NMR (400 MHz, DMSO-d$_6$) δ 10.37 (s, 1H, NH), 8.31 (d, J=17.2 Hz, 1H, ArH), 8.16-8.05 (m, 3H, ArH), 7.62-7.56 (m, 1H, ArH), 7.44 (dd, J=9.60 Hz, J=2.4 Hz, 1H, ArH), 7.04 (dd, J=9.60 Hz, J=2.4 Hz, 1H, ArH), 6.49 (s, 1H, OH), 4.65 (d, J=5.6 Hz, 1H, CH), 4.62 (d, J=5.6 Hz, 1H, CH), 1.47 (s, 3H, CH$_3$). Mass (ESI, Negative): 404.8[M−H]$^-$; (ESI, Positive): 429.0[M+Na]$^+$.

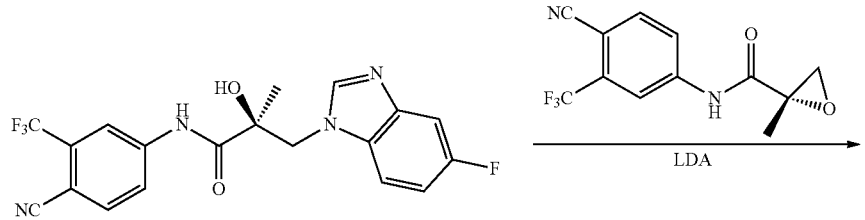

70

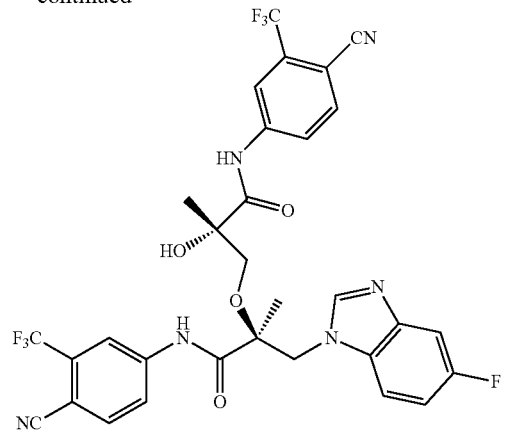

72

(S)—N-(4-Cyano-3-(trifluoromethyl)phenyl)-24S)-3-((4-cyano-3-(trifluoromethyl)phenyl)amino)-2-hydroxy-2-methyl-3-oxopropoxy)-3-(5-fluoro-1H-benzo[d]imidazol-1-yl)-2-methylpropanamide ($C_{31}H_{23}F_7N_6O_4$) (72)

This byproduct was purified by a silicon gel column using methylene chloride and methanol (19:1) as eluent to afford 50 mg of the titled compound as yellowish solid.

$^1$H NMR (400 MHz, DMSO-d6) δ 10.75 (s, 1H, NH), 9.64 (s, 1H, NH), 8.31 (d, J=17.2 Hz, 1H, ArH), 8.33-8.30 (m, 1H, ArH), 8.11-7.86 (m, 6H, ArH), 7.54-7.52 (m, 1H, ArH), 7.35-7.33 (m, 1H, ArH), 6.77-6.73 (m, 1H, ArH), 6.31 (s, 1H, OH), 4.66-4.63 (m, 1H, CH), 4.50-4.44 (m, 1H, CH), 3.83-3.82 (m, 1H, CH), 3.66-3.64 (m, 1H, CH), 1.54 (s, 3H, $CH_3$), 1.34 (s, 3H, $CH_3$). Mass (ESI, Negative): 675.0[M−H]$^-$; (ESI, Positive): 699.3[M+Na]+.

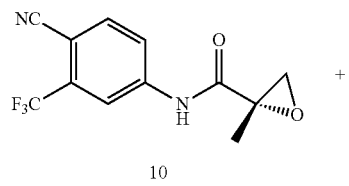

10

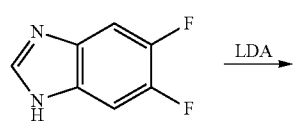

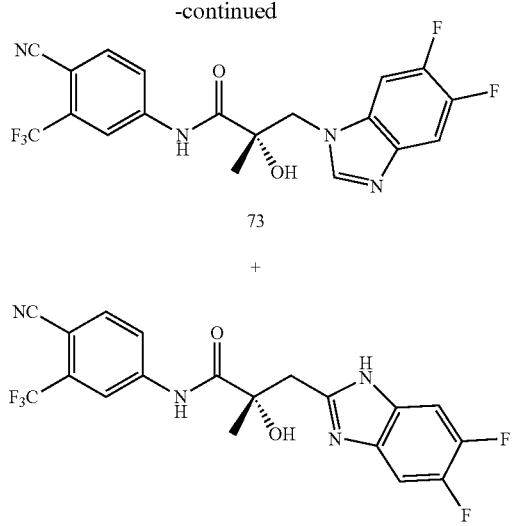

73

+

74

To a solution of 5,6-difluoro-1H-benzoimidazole (0.23 g, 0.00148 mol) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at RT under argon. The reaction was quenched by water, extracted with ethyl acetate. The organic layer was dried with $MgSO_4$, filtered, and concentrated under vacuum. The product was purified by a silicon gel column using methylene chloride and methanol (19:1) as eluent to afford the desired compound as white solid.

(S)—N-(4-Cyano-3-trifluoromethyl-phenyl)-3-(5,6-difluoro-benzoimidazol-1-yl)-2-hydroxy-2-methyl-propionamide ($C_{19}H_{13}F_5N_4O_2$) (73)

$^1$H NMR (400 MHz, DMSO-d$_6$) δ 10.36 (s, 1H, NH), 8.25 (d, J=2.0 Hz, 1H, ArH), 8.21 (s, 1H, ArH), 8.14 (dd, J=8.8 Hz, J=2.0 Hz, 1H, ArH), 8.06 (d, J=8.8 Hz, 1H, ArH), 7.43-7.40 (m, 1H, ArH), 7.26-7.19 (m, 1H, ArH), 6.51 (s,

1H, OH), 4.65 (d, J=14.8 Hz, 1H, CH), 4.41 (d, J=14.8 Hz, 1H, CH), 1.42 (s, 3H, CH₃). Mass (ESI, Negative): 422.7 [M−H]⁻; (ESI, Positive): 447.0 [M+Na]⁺.

(S)—N-(4-Cyano-3-(trifluoromethyl)phenyl)-3-(5,6-difluoro-1H-benzo[d]imidazol-2-yl)-2-hydroxy-2-methylpropanamide (C₁₉H₁₃F₅N₄O₂) (74)

¹H NMR (400 MHz, DMSO-d₆) δ 10.44 (s, 1H, NH), 8.36 (d, J=2.0 Hz, 1H, ArH), 8.17 (dd, J=8.4 Hz, J=2.0 Hz, 1H, ArH), 8.11 (s, 1H, ArH), 8.07 (d, J=8.4 Hz, 1H, ArH), 7.44-7.41 (m, 1H, ArH), 7.21-7.14 (m, 1H, ArH), 6.54 (s, 1H, OH), 4.62 (d, J=14.4 Hz, 1H, CH), 4.52 (d, J=14.4 Hz, 1H, CH), 1.41 (s, 3H, CH₃). Mass (ESI, Negative): 422.7 [M−H]⁻; (ESI, Positive): 447.0[M+Na]⁺.

(S)—N-(4-Cyano-3-(trifluoromethyl)phenyl)-3-(7-fluoro-1H-benzo[d]imidazol-1-yl)-2-hydroxy-2-methylpropanamide (C₁₉H₁₄F₄N₄O₂) (75)

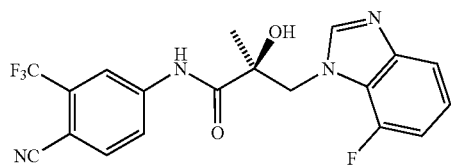

75

To a solution of 7-fluoro-benzimidazole (0.30 g, 0.0022 mol) in anhydrous THF (10 mL), which was cooled in an ice water bath under an argon atmosphere, was added sodium hydride (60% dispersion in oil, 0.132 g, 0.00331 mol). After addition, the resulting mixture was stirred for two hours. (R)-3-Bromo-N-(4-cyano-3-trifluoromethyl-phenyl)-2-hydroxy-2-methylpropanamide (0.77 g, 0.0022 mol) was added to above solution, and the resulting reaction mixture was allowed to stir overnight at RT under argon. The reaction was quenched by water, and extracted with ethyl acetate. The organic layer was dried with MgSO₄, filtered, and concentrated under vacuum. The product was purified by a silica gel column using methylene chloride and methanol (19:1) as eluent to afford 0.18 g of the titled compound as yellowish solid.

¹H NMR (400 MHz, DMSO-d₆) δ 10.49 (s, 1H, NH), 8.39 (d, J=2.0 Hz, 1H, ArH), 8.21 (dd, J=8.8 Hz, J=2.0 Hz, 1H, ArH), 8.11 (s, 1H, ArH), 8.08 (d, J=8.8 Hz, 1H, ArH), 7.46 (d, J=8.0 Hz, 1H, ArH), 7.16-7.10 (m, 1H, ArH), 7.05-7.00 (m, 1H, ArH), 6.52 (s, 1H, OH), 4.64-4.56 (m, 2H, CH), 1.35 (s, 3H, CH₃). Mass (ESI, Negative): 404.8[M−H]⁻.

Synthesis of(S)—N-(4-cyano-3-(trifluoromethyl)phenyl)-3-(4-fluoro-1H-benzo[d]imidazol-1-yl)-2-hydroxy-2-methylpropanamide (76) & (S)—N-(4-cyano-3-(trifluoromethyl)phenyl)-3-(7-fluoro-1H-benzo[d]imidazol-1-yl)-2-hydroxy-2-methylpropanamide(75)

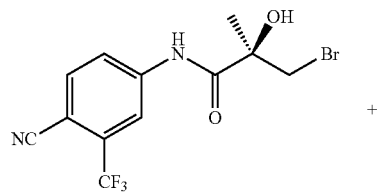

+

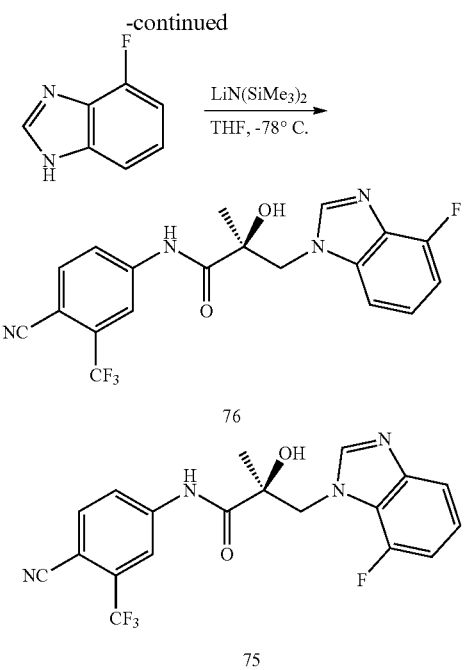

Under an argon atmosphere, 1.5 mL of lithium bis(trimethylsilyl)amide in THF (1.5 mmol, Aldrich, 1 M solution in THF) was slowly added to a solution of 4-fluoro-1H-benzo [d]imidazole (136 mg, 1 mmol) in THF (10 mL) at −78° C. and stirred for 30 min at the same temperature. A solution of 8R (318 mg, 1 mmol) in 5 mL of THF was added dropwise to the solution. The reaction mixture was stirred at the same temperature for 30 min and stirred overnight at RT, quenched by an addition of sat. NH₄Cl solution. The mixture was concentrated under reduced pressure and dispersed into excess EtOAc and dried over Na₂SO₄, concentrated and purified by flash column chromatography (EtOAc/hexane) to give the target compound give total 70% yield of 76 (30%, 120.3 mg) and 75 (40%, 163.1 mg) as white solid.

(S)—N-(4-Cyano-3-(trifluoromethyl)phenyl)-3-(4-fluoro-1H-benzo[d]imidazol-1-yl)-2-hydroxy-2-methylpropanamide (76)

HRMS (ESI) m/z calcd for C₁₉H₁₅F₄N₄O₂: 407.1131 [M+H]⁺. Found: 407.1137 [M+H]⁺.

¹H NMR (CDCl₃, 400 MHz) δ 9.10 (bs, 1H, NH), 8.11 (s, 1H), 7.79 (s, 1H), 7.75-7.71 (m, 2H), 7.38 (m, 1H), 7.31-7.26 (m, 1H), 6.81 (t, J=8.0 Hz, 1H), 6.01 (bs, 1H, OH), 4.93 (d, J=14.0 Hz, 1H), 4.44 (d, J=14.0 Hz, 1H), 1.53 (s, 3H).

¹⁹F NMR (CDCl₃, 400 MHz) δ −62.22, −117.60.

(S)—N-(4-Cyano-3-(trifluoromethyl)phenyl)-3-(7-fluoro-1H-benzo[d]imidazol-1-yl)-2-hydroxy-2-methylpropanamide (75)

HRMS (ESI) m/z calcd for C₁₉H₁₅F₄N₄O₂: 407.1131. Found: 407.1126 [M+H]⁺.

¹H NMR (CDCl₃, 400 MHz) δ 9.14 (bs, 1H, NH), 8.08 (s, 1H), 7.96 (s, 1H), 7.82 (d, J=8.2 Hz, 1H), 7.73 (d, J=8.4 Hz, 1H), 7.72 (d, J=8.4 Hz, 1H), 7.42 (d, J=8.8 Hz, 1H), 7.23 (m, 1H), 7.67 (dd, J=10.0, 7.6 Hz, 1H), 6.67 (bs, 1H, OH), 4.96 (d, J=13.6 Hz, 1H), 4.54 (d, J=13.6 Hz, 1H), 1.54 (s, 3H).

¹⁹F NMR (CDCl₃, 400 MHz) δ −62.22, −116.56.

2-Dimensional nuclear Overhauser effect (NOE) spectroscopy (NOESY): NOESY was used to assign the correct chemical structures to these two isomers. 76 demonstrated an NOEs between the aromatic proton located at the 7-position of the benzo[d]imidazole ring (annotated as H) and the methylene protons (annotated as $H_1$ and $H_2$),

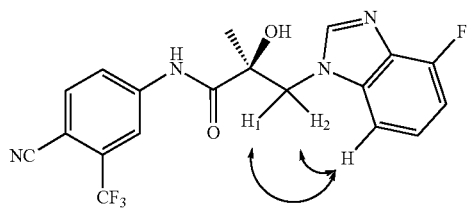

76

NOEs indicating that the point of attachment to the benzo[d]imidazole ring must be the 1-position. Whereas for 75, an NOE was observed between 2-position aromatic proton of the benzo[d]imidazole ring (annotated as H) and the methylene protons (annotated as $H_1$ and $H_2$),

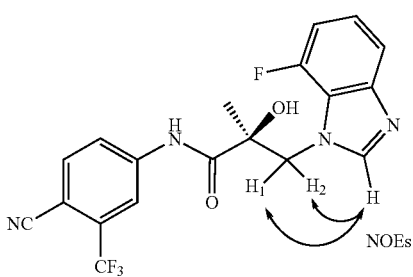

75

NOEs indicating that the point of attachment to the benzo[d]imidazole ring must be the 1-position (opposite nitrogren as for 76) hence fluorine is substituted at the 7-position of the benzo[d]imidazole ring and this product is identical to the other 75 reported above. The variable NMR values are due to the different NMR solvents used.

Synthesis of (S)—N-(4-cyano-3-(trifluoromethyl)phenyl)-2-hydroxy-2-methyl-3-(4-(trifluoromethyl)-1H-benzo[d]imidazol-1-yl)propanamide (77) and (S)—N-(4-cyano-3-(trifluoromethyl)phenyl)-2-hydroxy-2-methyl-3-(7-(trifluoromethyl)-1H-benzo[d]imidazol-1-yl)propanamide (78)

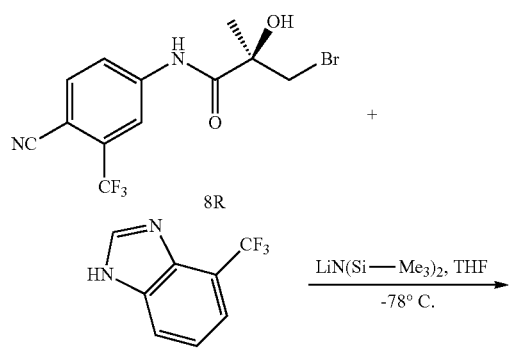

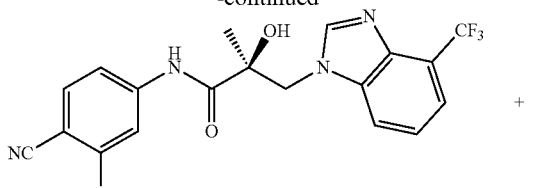

77

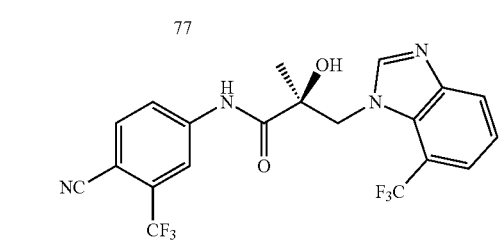

78

Under an argon atmosphere, 2.0 mL of lithium bis(trimethylsilyl)amide in THF (2 mmol, Aldrich, 1 M solution in THF) was slowly added to a solution of 4-(trifluoromethyl)-1H-benzo[d]imidazole (186 mg, 1 mmol) in THF (10 mL) at −78° C. and stirred for 30 min at that temperature. A solution of R-bromo amide 8R (351 mg, 1 mmol) in 5 mL of THF was added dropwise to the solution. The reaction mixture was stirred at the same temperature for 30 min and stirred overnight at RT, quenched by an addition of sat. $NH_4Cl$ solution. The mixture was concentrated under reduced pressure and dispersed into excess EtOAc and dried over $Na_2SO_4$, concentrated and purified by flash column chromatography (EtOAc/hexane; 1/1 and then EtOAc only) to give 77 and 78 as a white solid.

(S)—N-(4-Cyano-3-(trifluoromethyl)phenyl)-2-hydroxy-2-methyl-3-(4-(trifluoromethyl)-1H-benzo[d]imidazol-1-yl)propanamide (77)

HRMS (ESI) m/z calcd for $C_{20}H_{15}F_6N_4O_2$: 457.1099 [M+H]$^+$. Found: 457.1094 [M+H]$^+$.

$^1$H NMR (CDCl$_3$, 400 MHz) δ 9.16 (bs, 1H, NH), 8.07 (s, 1H), 9.95 (s, 1H), 7.76 (m, 2H), 7.73 (d, J=8.0 Hz, 1H), 7.54 (d, J=7.6 Hz, 1H), 7.34 (t, J=7.8 Hz, 1H), 6.37 (bs, 1H, OH), 4.70 (d, J=14.4 Hz, 1H), 4.47 (d, J=14.4 Hz, 1H), 1.58 (s, 3H).

$^{19}$F NMR (CDCl$_3$, 400 MHz) δ −60.52, −62.29.

(S)—N-(4-Cyano-3-(trifluoromethyl)phenyl)-2-hydroxy-2-methyl-3-(7-(trifluoromethyl)-1H-benzo[d]imidazol-1-yl)propanamide (78)

HRMS (ESI) m/z calcd for $C_{20}H_{15}F_6N_4O_2$: 457.1099 [M+H]$^+$. Found: 457.1090 [M+H]$^+$.

$^1$H NMR (CDCl$_3$, 400 MHz) 9.32 (bs, 1H, NH), 8.26 (s, 1H), 8.12 (d, J=2.0 Hz, 1H), 7.99 (dd, J=8.6, 2.0 Hz, 1H), 7.83 (d, J=8.6 Hz, 1H), 7.77 (d, J=8.0 Hz, 1H), 7.65 (d, J=7.6 Hz, 1H), 7.29 (t, J=7.6 Hz, 1H), 5.91 (bs, 1H, OH), 4.94 (d, J=15.2 Hz, 1H), 4.67 (d, J=15.2 Hz, 1H), 1.48 (s, 3H).

$^{19}$F NMR (CDCl$_3$, 400 MHz) δ −55.42, 62.14.

Synthesis of (S)—N-(3-chloro-4-cyanophenyl)-3-(4-fluoro-1H-benzo[d]imidazol-1-yl)-2-hydroxy-2-methylpropanamide (79)

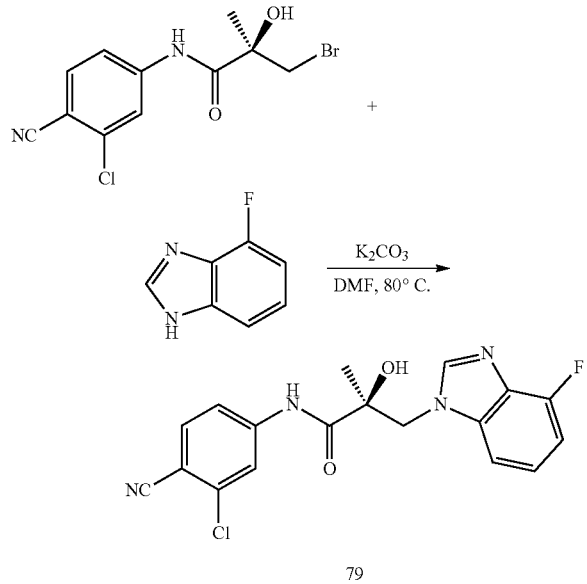

79

To a dry, nitrogen-purged 50 mL round-bottom flask, (R)-3-bromo-N-(3-chloro-4-cyanophenyl)-2-hydroxy-2-methylpropanamide (318 mg, 1 mmol), 4-fluoro-1H-benzo[d]imidazole (136 mg, 1 mmol) and $K_2CO_3$ (415 mg, 3 mmol) were dissolved into 10 mL of DMF. The mixture was heated up to 80° C. for 3 h. The resulting mixture was cooled down to RT. The volume of the mixture was reduced under reduced pressure and poured into water, and extracted with ethyl acetate (3 times). The organic layer was dried over anhydrous $MgSO_4$, concentrated and purified by flash column chromatography (ethyl acetate only, rf=0.31) on silica gel to produce 79 (38%).

(S)—N-(3-Chloro-4-cyanophenyl)-3-(4-fluoro-1H-benzo[d]imidazol-1-yl)-2-hydroxy-2-methylpropanamide (79)

HRMS (ESI) m/z calcd for $C_{18}H_{15}ClF_4N_4O_2$: 373.0868 [M+H]$^+$. Found: 373.0878 [M+H]$^+$.
$^1$H NMR (Acetone-$d_6$, 400 MHz) δ 9.77 (bs, 1H, NH), 8.16 (d, J=1.6 Hz, 1H), 8.04 (s, 1H), 7.83 (dd, J=8.4, 1.6 Hz, 1H), 7.75 (d, J=1.6 Hz, 1H), 7.44 (d, J=4.8 Hz, 1H), 7.18 (m, 1H), 6.99 (dd, J=11.6, 8.0 Hz, 1H), 5.83 (bs, 1H, OH), 4.78 (d, J=14.4 Hz, 1H), 4.69 (d, J=14.4 Hz, 1H), 1.56 (s, 3H).

Synthesis of Indazole SARDs

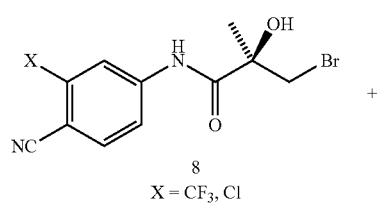

8
X = CF$_3$, Cl

-continued

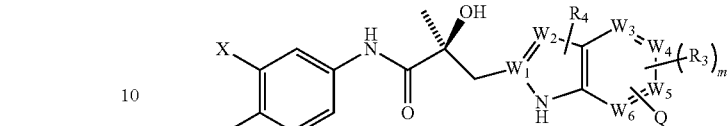

To a solution of substituted-1H-indazole (0.00148 mol; e.g., 5-fluoro-1H-indazole for 90) in anhydrous THF (10 mL), which was cooled in an dry-ice acetone bath under an argon atmosphere, was added LDA (2.0 M in THF, 1.11 mL, 0.0022 mol). After addition, the resulting mixture was stirred for 2 h. (S)—N-(4-Cyano-3-(trifluoromethyl)phenyl)-2-methyloxirane-2-carboxamide (0.40 g, 0.00148 mol) was added to above solution, and the resulting reaction mixture was allowed to stir overnight at RT under argon. The reaction was quenched by water, extracted with ethyl acetate. The organic layer was dried with $MgSO_4$, filtered, and concentrated under vacuum. The product was purified by a silicon gel column using methylene chloride and methanol (19:1) as eluent to afford the desired compound as white solid.

Example 3

Synthesis of Quinoline, Isoquinoline, and Indoline SARD Compounds of this Invention Quinoline compounds

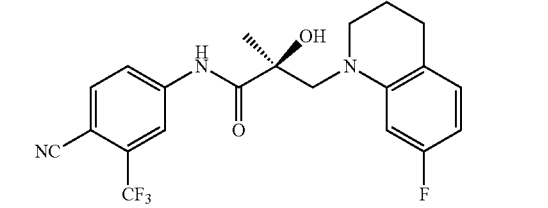

-continued
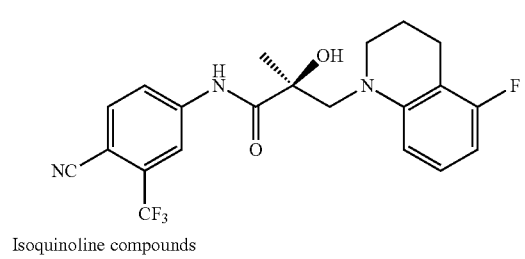
137
Isoquinoline compounds
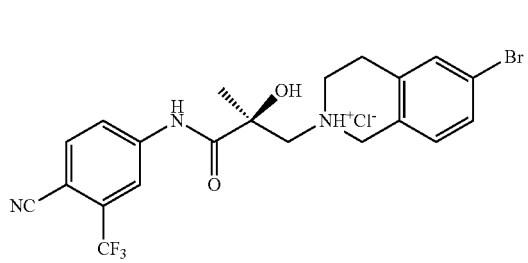
130
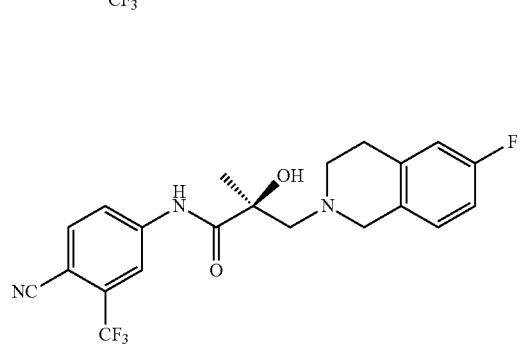
131
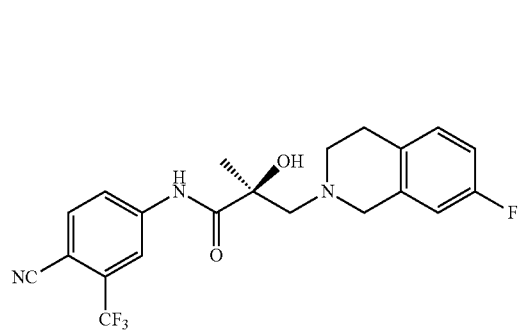
132
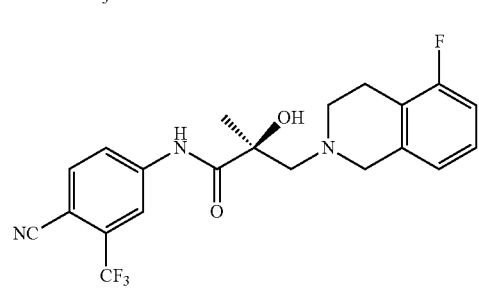
133
Indoline Compounds
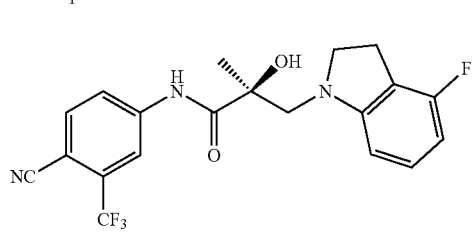
101
-continued
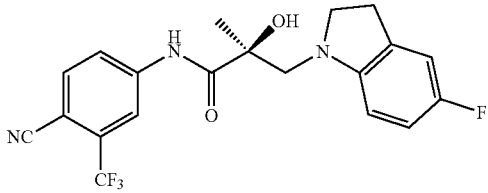
102
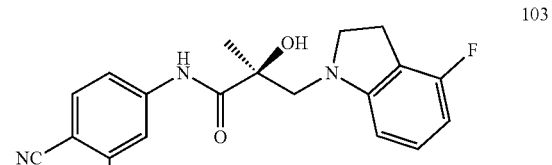
103
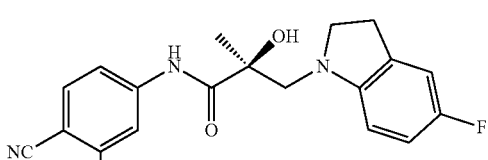
104
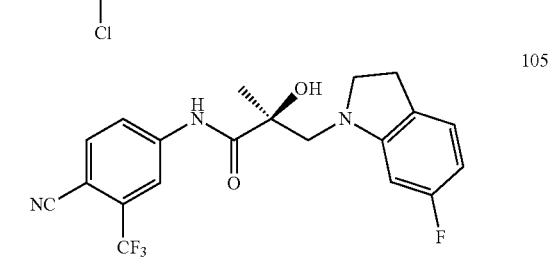
105
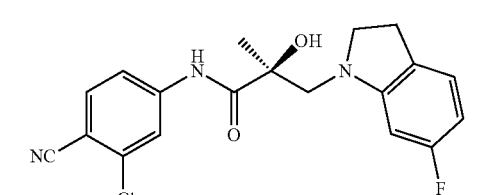
106
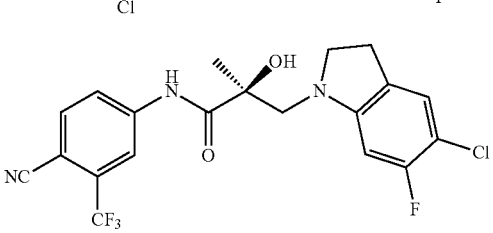
107
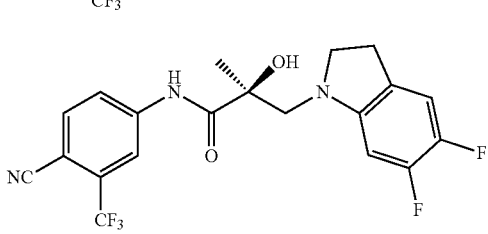
108
109

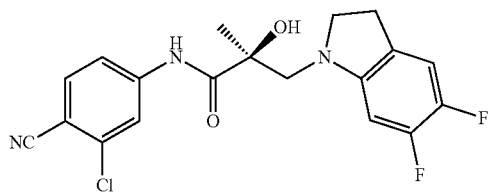

General Procedure: Method A: General scheme for the synthesis of indoline, quinoline and isoquinoline derivatives

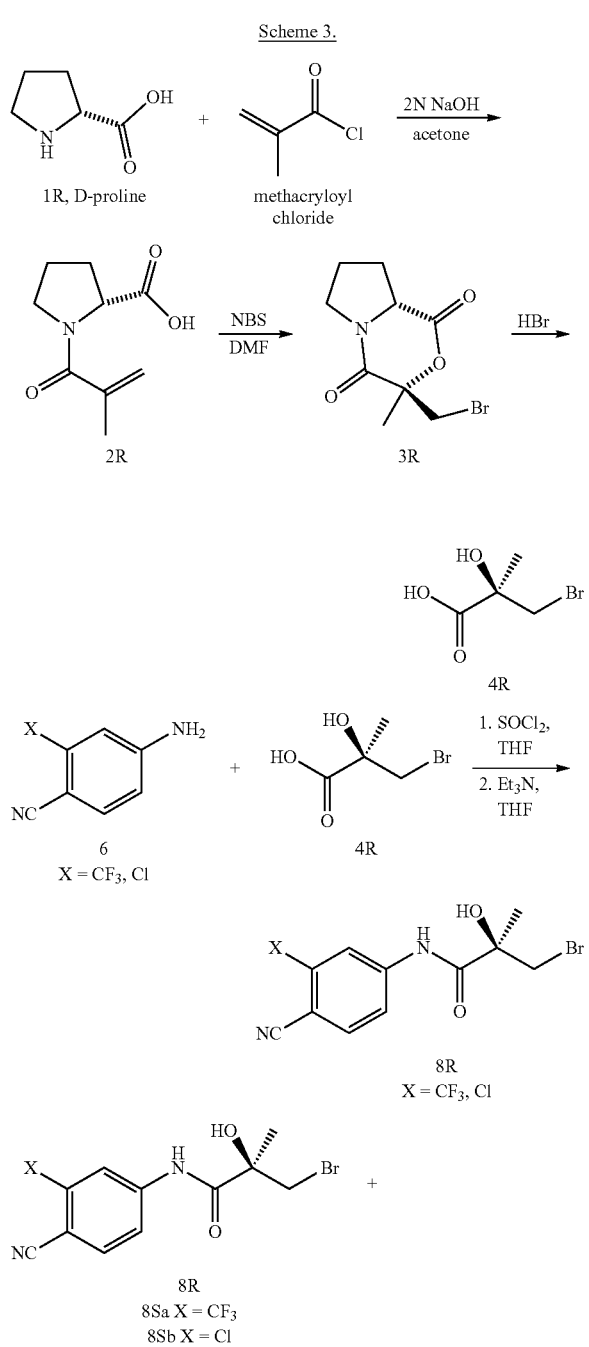

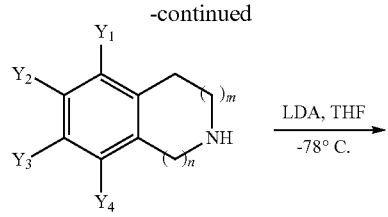

$Y_{1-4}$ = H, F, Cl, Br, etc.
m = 1, 2
n = 0, 1

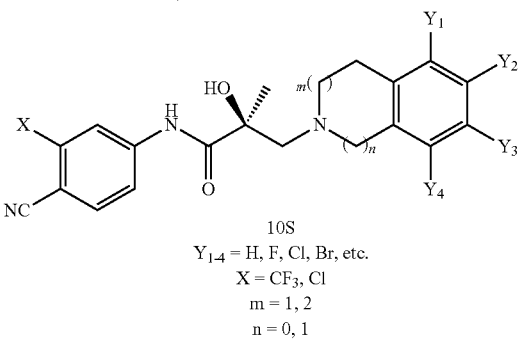

$Y_{1-4}$ = H, F, Cl, Br, etc.
X = CF$_3$, Cl
m = 1, 2
n = 0, 1

(2R)-1-Methacryloylpyrrolidin-2-carboxylic acid
(2R)

D-Proline (1R) (14.93 g, 0.13 mol) was dissolved in 71 mL of 2 N NaOH and cooled in an ice bath; the resulting alkaline solution was diluted with acetone (71 mL). An acetone solution (71 mL) of methacryloyl chloride (13.56 g, 0.13 mol) and 2 N NaOH solution (71 mL) were simultaneously added over 40 min to the aqueous solution of D-proline in an ice bath. The temperature of the mixture was kept at 10$^{-11}$° C. during the addition of the methacryloyl chloride. After stirring (3 h, room temperature (RT)), the mixture was evaporated in vacuo at a temperature at 35-45° C. to remove acetone. The resulting solution was washed with ethyl ether and was acidified to pH 2 with concentrated HCl. The acidic mixture was saturated with NaCl and was extracted with EtOAc (100 mL×3). The combined extracts were dried over Na$_2$SO$_4$, filtered through Celite®, and evaporated in vacuo to give the crude product as a colorless oil. Recrystallization of the oil from ethyl ether and hexanes afforded 16.2 g (68%) of the desired compound as colorless crystals: mp 102.1-103.4° C. (Marhefka, C. A.; Moore, B. M., 2nd; Bishop, T. C.; Kirkovsky, L.; Mukherjee, A.; Dalton, J. T.; Miller, D. D. Homology modeling using multiple molecular dynamics simulations and docking studies of the human androgen receptor ligand binding domain bound to testosterone and nonsteroidal ligands. *J Med Chem* 2001, 44, 1729-40) mp 102.5-103.5° C.; the NMR spectrum of this compound demonstrated the existence of two rotamers of the title compound.

$^1$H NMR (300 MHz, DMSO-d$_6$) 5.28 (s) and 5.15 (s) for the first rotamer, 5.15 (s) and 5.03 (s) for the second rotamer (totally 2H for both rotamers, vinyl CH$_2$), 4.48-4.44 for the first rotamer, 4.24-4.20 (m) for the second rotamer (totally 1H for both rotamers, CH at the chiral center), 3.57-3.38 (m, 2H, CH$_2$), 2.27-2.12 (1H, CH), 1.97-1.72 (m, 6H, CH$_2$, CH, Me); $^{13}$C NMR (75 MHz, DMSO-d$_6$) for major rotamer 173.3, 169.1, 140.9, 116.4, 58.3, 48.7, 28.9, 24.7, 19.5: for minor rotamer 174.0, 170.0, 141.6, 115.2, 60.3, 45.9, 31.0, 22.3, 19.7; IR (KBr) 3437 (OH), 1737 (C═O), 1647 (CO, COOH), 1584, 1508, 1459, 1369, 1348, 1178 cm$^{-1}$; $[\alpha]_D^{26}$+80.8 (c=1, MeOH); Anal. Calcd. for $C_9H_1NO_3$: C, 59.00, H, 7.15, N, 7.65. Found: C, 59.13, H, 7.19, N, 7.61.

(3R,8aR)-3-Bromomethyl-3-methyl-tetrahydro-pyrrolo[2,1-c][1,4]oxazine-1,4-dione (3R)

A solution of NBS (23.5 g, 0.132 mol) in 100 mL of DMF was added dropwise to a stirred solution of the (2R)-1-methacryloylpyrrolidin-2-carboxylic acid (2R) (16.1 g, 88 mmol) in 70 mL of DMF under argon at RT, and the resulting mixture was stirred 3 days. The solvent was removed in vacuo, and a yellow solid was precipitated. The solid was suspended in water, stirred overnight at RT, filtered, and dried to give 18.6 g (81%) (smaller weight when dried 34%) of the titled bromolactone (3R) as a yellow solid: mp 158.1-160.3° C.

$^1$H NMR (300 MHz, DMSO-d$_6$) 4.69 (dd, J=9.6 Hz, J=6.7 Hz, 1H, CH at the chiral center), 4.02 (d, J=11.4 Hz, 1H, CHH$_a$), 3.86 (d, J=11.4 Hz, 1H, CHH$_b$), 3.53-3.24 (m, 4H, CH$_2$), 2.30-2.20 (m, 1H, CH), 2.04-1.72 (m, 3H, CH$_2$ and CH), 1.56 (s, 2H, Me); $^{13}$C NMR (75 MHz, DMSO-d$_6$) δ 167.3, 163.1, 83.9, 57.2, 45.4, 37.8, 29.0, 22.9, 21.6; IR (KBr) 3474, 1745 (C═O), 1687 (C═O), 1448, 1377, 1360, 1308, 1227, 1159, 1062 cm$^{-1}$; $[\alpha]_D^{26}$+124.5° (c=1.3, chloroform); Anal. Calcd. for $C_9H_{12}BrNO_3$: C, 41.24, H, 4.61, N, 5.34. Found: C, 41.46, H, 4.64, N, 5.32.

(2R)-3-Bromo-2-hydroxy-2-methylpropanoic acid (4R)

A mixture of bromolactone (3R) (18.5 g, 71 mmol) in 300 mL of 24% HBr was heated at reflux for 1 h. The resulting solution was diluted with brine (200 mL), and was extracted with ethyl acetate (100 mL×4). The combined extracts were washed with saturated NaHCO$_3$ (100 mL×4). The aqueous solution was acidified with concentrated HCl to pH=1, which, in turn, was extracted with ethyl acetate (100 mL×4). The combined organic solution was dried over Na$_2$SO$_4$, filtered through Celite®, and evaporated in vacuo to dryness. Recrystallization from toluene afforded 10.2 g (86%) of the desired compound as colorless crystals: mp 110.3-113.8° C.

$^1$H NMR (300 MHz, DMSO-d$_6$) δ 3.63 (d, J=10.1 Hz, 1H, CHH$_a$), 3.52 (d, J=10.1 Hz, 1H, CHH$_b$), 1.35 (s, 3H, Me).
IR (KBr) 3434 (OH), 3300-2500 (COOH), 1730 (C═O), 1449, 1421, 1380, 1292, 1193, 1085 cm$^{-1}$.
$[\alpha]_D^{26}$+10.5° (c=2.6, MeOH).
Anal. Calcd. for $C_4H_7BrO_3$: C, 26.25, H, 3.86. Found: C, 26.28, H, 3.75.

(2R)-3-Bromo-N-[4-cyano-3-(trifluoromethyl)phenyl]-2-hydroxy-2-methylpropanamide (8R, X═CF$_3$)

Thionyl chloride (46.02 g, 0.39 mol) was added dropwise to a cooled solution (less than 4° C.) of (R)-3-bromo-2-hydroxy-2-methylpropanoic acid (4R) (51.13 g, 0.28 mol) in 300 mL of THF under an argon atmosphere. The resulting mixture was stirred for 3 h under the same condition. To this was added Et$_3$N (39.14 g, 0.39 mol) and stirred for 20 min under the same condition. After 20 min, 5-amino-2-cyanobenzotrifluoride (40.0 g, 0.21 mol), 400 mL of THF were added and then the mixture was allowed to stir overnight at RT. The solvent was removed under reduced pressure to give a solid which was treated with 300 mL of H$_2$O, extracted with EtOAc (2×400 mL). The combined organic extracts were washed with saturated NaHCO$_3$ solution (2×300 mL) and brine (300 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 55.8 g (73.9%) of (2R)-3-bromo-N-[4-cyano-3-(trifluoromethyl)phenyl]-2-hydroxy-2-methylpropanamide (8R, X═CF$_3$) as a light-yellow solid. M.p. 134.0-136.5° C.

$^1$H NMR (CDCl$_3$/TMS) δ 1.66 (s, 3H, CH$_3$), 3.11 (s, 1H, OH), 3.63 (d, J=10.8 Hz, 1H, CH$_2$), 4.05 (d, J=10.8 Hz, 1H, CH$_2$), 7.85 (d, J=8.4 Hz, 1H, ArH), 7.99 (dd, J=2.1, 8.4 Hz, 1H, ArH), 8.12 (d, J=2.1 Hz, 1H, ArH), 9.04 (bs, 1H, NH). Calculated Mass: 349.99, [M−H]$^-$ 349.0.

General Procedure for Preparation of Indoline, Quinoline and Isoquinoline Derivatives (Last Step):

Preparation of LDA solution in THF. To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or 2.0 M LDA was slowly warmed to 0° C. and stirred for 10 min and cooled again to −78° C.

To the LDA solution was added dropwise a solution of 9 (1.0 mmol) in 5 mL of THF for 20 min. The reaction mixture was stirred at the same temperature for 30 min and quenched by addition of sat. NH$_4$C$_1$. The solution was concentrated under reduced pressure and dispersed into excess EtOAc and dried over Na$_2$SO$_4$. The solution was concentrated and the resulting solid was recrystallized from EtOAc/hexane or DCM/hexane to give desired compound 10S. The mother liquor was concentrated and purified by flash column chromatography (EtOAc/hexane) to give additional 10S.

Alternative Procedure for Preparation of Indoline Compounds (Last Step):

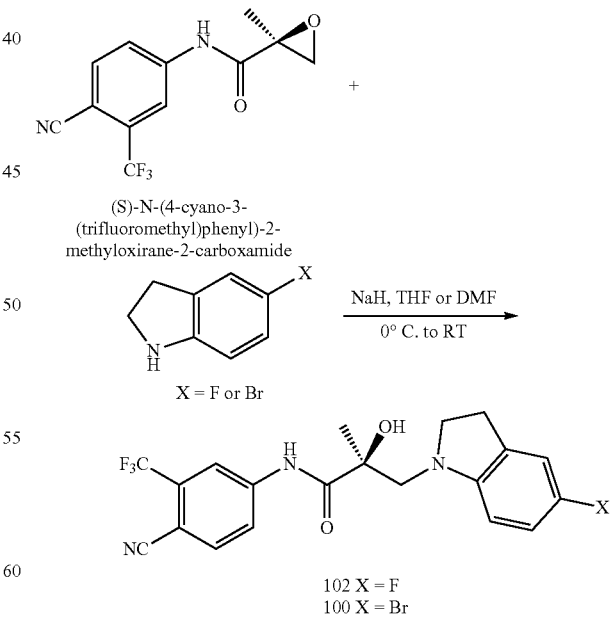

NaH of 60% dispersion in mineral oil (61 mg, 1.5 mmol) was added in 5 mL of anhydrous THF solvent into a 50 mL dried two necked round bottom flask equipped with a dropping funnel. 5-Fluoroindoline or 5-bromoindoline (1.48 mmol) was added to the solution under argon atmosphere in an ice-water bath, and the resulting solution was stirred for 30 min in an ice-water bath. Into the flask, the prepared solution of the oxirane: (S)—N-(4-cyano-3-(trifluoromethyl)phenyl)-2-methyloxirane-2-carboxamide, (1.48 mmol in THF) was added through dropping funnel under argon atmosphere in an ice-water bath and stirred overnight at RT. After adding 1 mL of H$_2$O, the reaction mixture was condensed under reduced pressure, and then dispersed into 20 mL of EtOAc, washed with 20 mL (×2) water, brine, dried over anhydrous Na$_2$SO$_4$, and evaporated to dryness. The mixture was purified with flash chromatography (EtOAc/hexane 40% solvent, SiO$_2$) and afforded the desired products 100 or 102.

(S)-3-(5-Bromoindolin-1-yl)-N-(4-cyano-3-(trifluoromethyl)phenyl)-2-hydroxy-2-methylpropanamide (100)

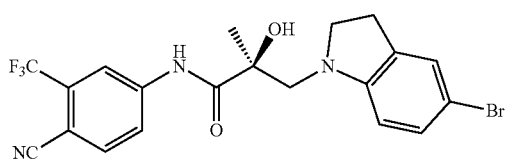 [SMILES: C[C@](O)(CN1CCc2cc(Br)ccc21)C(=O)Nc1ccc(C#N)c(C(F)(F)F)c1]

Yield 45%; Light brown solid; MS (ESI) 466.3 [M−H]; $^1$H NMR (CDCl$_3$, 400 MHz) δ 9.17 (bs, 1H, NH), 8.09 (d, J=2.0 Hz, 1H), 7.96 (dd, J=8.4, 2.0 Hz, 1H), 7.80 (d, J=8.4 Hz, 1H), 7.19-7.16 (m, 2H), 6.49 (d, J=8.4 Hz, 1H), 3.66 (d, J=14.4 Hz, 1H), 3.48 (bs, 1H, OH), 3.47-3.41 (m, 1H), 3.34 (q, J=9.2 Hz, 1H), 3.25 (d, J=14.4 Hz, 1H), 3.00-2.91 (m, 2H), 1.56 (s, 3H).

(S)-3-(6-Bromo-3,4-dihydroquinolin-1(2H)-yl)-N-(4-cyano-3-(trifluoromethyl) phenyl)-2-hydroxy-2-methylpropanamide (134). Yield; 62%; MS (ESI) m/z 481.6 [M−H]; $^1$H NMR (400 MHz, CDCl$_3$) δ 9.19 (bs, 1H, NH), 8.00 (s, 1H), 7.97-7.92 (m, 1H), 7.78 (d, J=8.4 Hz, 1H), 7.12 (dd, J=8.8, 2.4 Hz, 1H), 7.08 (d, J=2.4 Hz, 1H), 6.67 (d, J=8.8 Hz, 1H), 3.86 (d, J=15.2 Hz, 1H), 3.45 (d, J=15.2 Hz, 1H), 3.21 (t, J=5.4 Hz, 2H), 2.74 (m, 2H), 1.87 (m, 2H), 1.60 (s, 3H).

(S)—N-(4-Cyano-3-(trifluoromethyl)phenyl)-3-(4-fluoroindolin-1-yl)-2-hydroxy-2-methylpropanamide (101). Yield; 68%; MS (ESI) m/z 406.0 [M−H]; $^1$H NMR (400 MHz, CDCl$_3$) δ 9.21 (bs, 1H, NH), 8.10 (d, J=2.4 Hz, 1H), 7.96 (dd, J=8.8, 2.4 Hz, 1H), 7.89 (d, J=8.8 Hz, 1H), 7.07-7.02 (m, 1H), 6.47 (t, J=8.4 Hz, 1H), 6.39 (d, J=8.0 Hz, 1H), 3.69 (d, J=14.4 Hz, 1H), 3.53 (bs, 1H, OH), 3.50 (m, 1H), 3.40 (q, J=8.0 Hz, 1H), 3.29 (d, J=14.4 Hz, 1H), 3.09 (m, 1H), 2.99 (m, 1H), 1.57 (s, 3H).

(S)—N-(4-Cyano-3-(trifluoromethyl)phenyl)-3-(5-fluoroindolin-1-yl)-2-hydroxy-2-methylpropanamide (102). Yield; 75%; MS (ESI) m/z 406.0 [M−H]; $^1$H NMR (400 MHz, CDCl$_3$) δ 9.24 (bs, 1H, NH), 8.10 (d, J=2.2 Hz, 1H), 7.95 (dd, J=8.8, 2.2 Hz, 1H), 7.79 (d, J=8.8 Hz, 1H), 6.83 (dd, J=8.4, 2.4 Hz, 1H), 6.77 (m. 1H), 6.52 (dd, J=8.4, 4.0 Hz, 1H), 3.75 (bs, 1H, OH), 3.64 (d, J=14.0 Hz, 1H), 3.44 (m, 1H), 3.30 (q, J=9.2 Hz, 1H), 3.22 (d, J=14.0 Hz, 1H), 2.94 (m, 2H), 1.56 (s, 3H).

(S)—N-(4-Cyano-3-(trifluoromethyl)phenyl)-3-(6-fluoro-3,4-dihydroquinolin-1(2H)-yl)-2-hydroxy-2-methylpropanamide (135). Yield; 42%; MS (ESI) m/z 420.0 [M−H]; $^1$H NMR (400 MHz, CDCl$_3$) δ 9.25 (bs, 1H, NH), 8.09 (d, J=2.0 Hz, 1H), 7.95 (dd, J=8.4, 2.0 Hz, 1H), 7.80 (d, J=8.4 Hz, 1H), 6.78-6.69 (m, 1H), 6.77 (m, 3H), 3.88 (d, J=15.2 Hz, 1H), 3.82 (bs, 1H, OH), 3.36 (d, J=15.2 Hz, 1H), 3.16 (m, 2H), 3.16-2.70 (m, 2H), 1.94-1.83 (m, 2H), 1.56 (s, 3H).

(S)—N-(4-Cyano-3-(trifluoromethyl)phenyl)-3-(6-fluoro-3,4-dihydroisoquinolin-2(1H)-yl)-2-hydroxy-2-methylpropanamide (131). Yield; 43%; MS (ESI) m/z 419.9 [M−H]; $^1$H NMR (400 MHz, CDCl$_3$) δ 9.51 (bs, 1H, NH), 8.10 (d, J=1.8 Hz, 1H), 7.95 (dd, J=8.6, 1.8 Hz, 1H), 7.79 (d, J=8.6 Hz, 1H), 6.88 (m, 1H), 6.81 (m. 2H), 3.69 (s, 2H), 3.42 (d, J=13.2 Hz, 1H), 2.91 (m, 4H), 2.60 (d, J=13.2 Hz, 1H), 2.17 (s, 1H, OH), 1.46 (s, 3H).

(S)—N-(4-Cyano-3-(trifluoromethyl)phenyl)-3-(6-fluoroindolin-1-yl)-2-hydroxy-2-methylpropanamide (105). Yield; 70%; MS (ESI) m/z 405.9 [M−H]; $^1$H NMR (400 MHz, CDCl$_3$) δ 9.21 (bs, 1H, NH), 8.10 (s, 1H), 7.97 (d, J=8.4 Hz, 1H), 7.79 (d, J=8.4 Hz, 1H), 6.98 (t, J=6.8 Hz, 1H), 6.41 (t, J=7.6 Hz, 1H), 3.35 (m, 1H), 3.66 (d, J=14.0 Hz, 1H), 3.52 (bs, 1H, OH), 3.47 (m, 1H), 3.41 (q, J=9.2 Hz, 1H), 3.24 (d, J=14.0 Hz, 1H), 3.00-2.87 (m, 2H), 1.57 (s, 3H).

(S)—N-(4-Cyano-3-(trifluoromethyl)phenyl)-3-(7-fluoro-3,4-dihydroisoquinolin-2(1H)-yl)-2-hydroxy-2-methylpropanamide (132). Yield; 69%; MS (ESI) 420.0 [M−H]; $^1$H NMR (400 MHz, CDCl$_3$) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Example 4

Synthesis of SARD Compounds of this Invention

Method A. General Scheme for Preparation of Indoline, Quinolone and Isoquinoline Derivatives

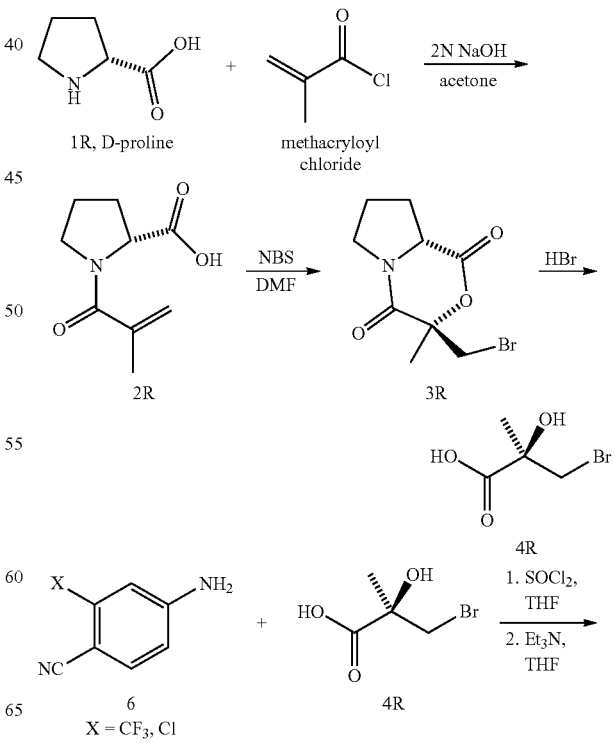

183
-continued

184
Method B. Preparation of Indoles and Carbazoles

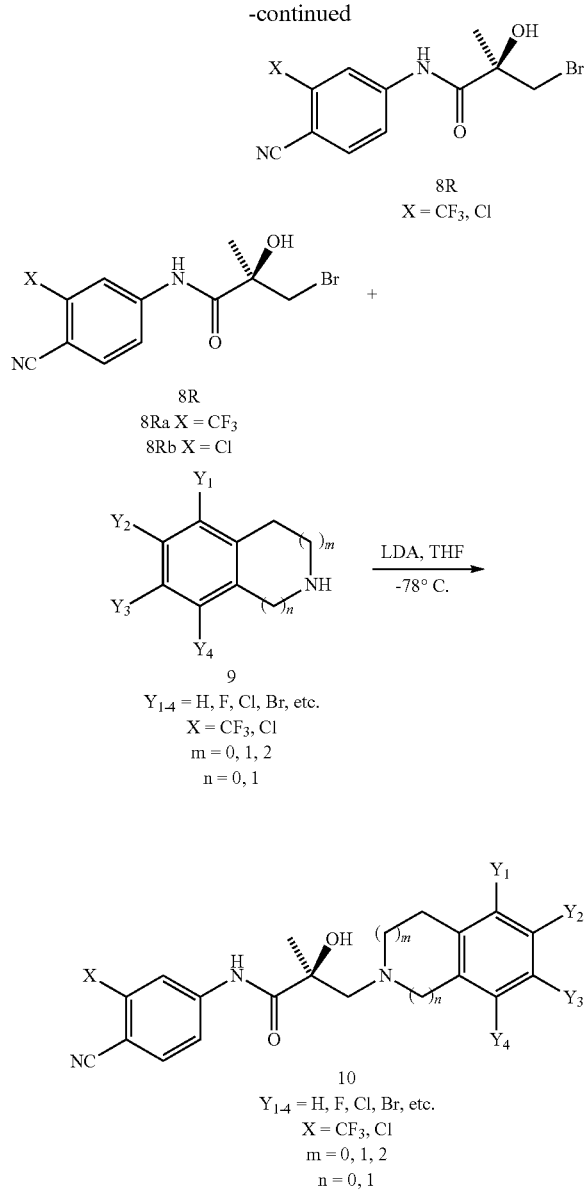

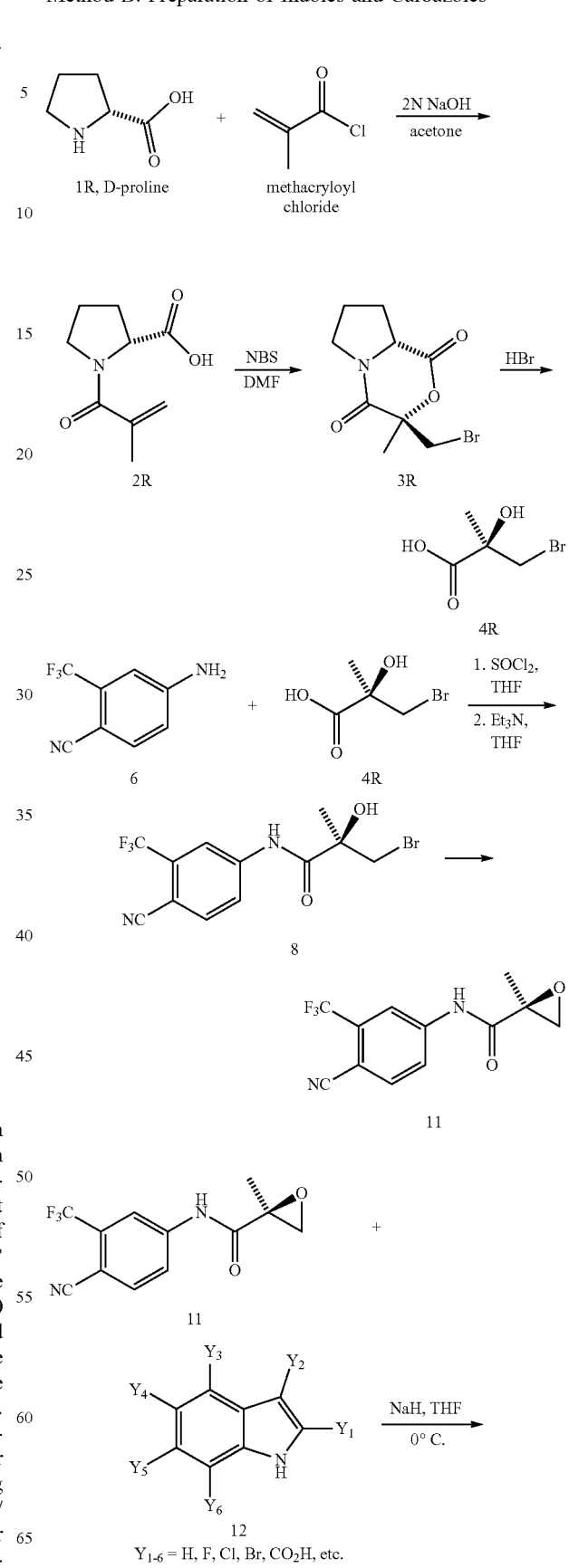

Preparation of LDA solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. The prepared solution of LDA or commercial 2.0 M LDA was slowly warmed to 0° C. and stirred for 10 min and cooled again to −78° C. To the LDA solution was added dropwise a solution of 9 (1.0 mmol) in 5 mL of THF for 20 min. 8R in THF was added dropwise through dropping funnel under argon atmosphere at −78° C. The reaction mixture was stirred at the same temperature for 30 min and quenched by addition of sat. $NH_4Cl$. The solution was concentrated under reduced pressure and dispersed into excess EtOAc and dried over $Na_2SO_4$. The solution was concentrated and the resulting solid was recrystallized from EtOAc/hexane or DCM/hexane to give designed compound 10. The mother liquor was concentrated and purified by flash column chromatography (EtOAc/hexane) to give the 10 additionally.

-continued

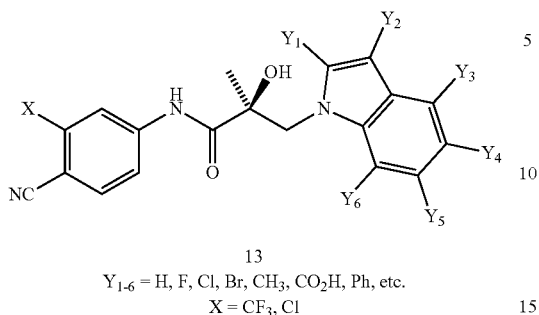

13
$Y_{1-6}$ = H, F, Cl, Br, $CH_3$, $CO_2H$, Ph, etc.
X = $CF_3$, Cl

NaH of 60% dispersion in mineral oil (228 mg, 5.7 mmol) was added in 20 mL of anhydrous THF solvent into a 100 mL dried two necked round bottom flask equipped with a dropping funnel. Indole (general structure 12, 2.84 mmol) was added to the solution under argon atmosphere in ice-water bath, and the resulting solution was stirred for 30 min at the ice-water bath. Into the flask, epoxide 11 (2.84 mmol in THF) was added through dropping funnel under argon atmosphere at the ice-water bath and stirred overnight at RT. After adding 1 mL of $H_2O$, the reaction mixture was condensed under reduced pressure, and then dispersed into 50 mL of EtOAc, washed with 50 mL (×2) water, brine, dried over anhydrous $MgSO_4$, and evaporated to dryness. The mixture was purified with flash column chromatography with an eluent of EtOAc/hexane, and then the condensed compounds were then recrystallized in EtOAc/hexane to give a target product of general structure 13.

(S)—N-(3-Chloro-4-cyanophenyl)-2-methyloxirane-2-carboxamide (epoxide intermediate)

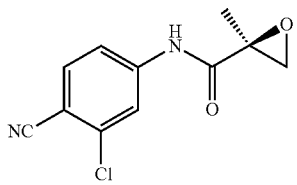 [SMILES: C[C@@]1(C(=O)Nc2ccc(C#N)c(Cl)c2)CO1]

Yield 98%;
Light brown solid.
MS (ESI) m/z 235.4 [M−H]⁻.
¹H NMR (CDCl₃, 400 MHz) δ 7.90 (d, J=2.0 Hz, 1H), 7.61 (d, J=8.4 Hz, 1H), 7.50 (dd, J=8.4, 2.0 Hz, 1H), 2.99 (s, 2H), 1.67 (s, 3H).

Indole Derivatives (S)—N-(4-Cyano-3-(trifluoromethyl)phenyl)-3-(5-fluoro-6-phenyl-1H-indol-1-yl)-2-hydroxy-2-methylpropanamide (33)

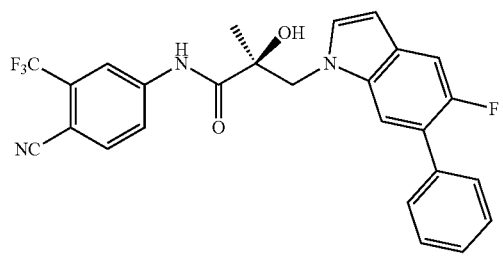 [SMILES: C[C@](O)(Cn1ccc2cc(F)c(-c3ccccc3)cc21)C(=O)Nc1ccc(C#N)c(C(F)(F)F)c1]

To a solution of 5-fluoro-6-phenyl-1H-indole (0.37 g, 0.00175 mol) in anhydrous THF (10 mL), which was cooled in an ice water bath under an argon atmosphere, was added sodium hydride (60% dispersion in oil, 0.11 g, 0.00263 mol). After addition, the resulting mixture was stirred for three hours. (S)—N-(4-Cyano-3-(trifluoromethyl)phenyl)-2-methyloxirane-2-carboxamide (0.47 g, 0.002175 mol) was added to above solution, and the resulting reaction mixture was allowed to stir overnight at RT under argon. The reaction was quenched by water, extracted with ethyl acetate. The organic layer was washed with brine, dried with $MgSO_4$, filtered, and concentrated under vacuum. The product was purified by a silica gel column using ethyl acetate and hexane (1:2) as eluent to afford 0.83 g (98%) of the titled compound as off-white foam.

¹H NMR (400 MHz, DMSO-d₆) δ 10.29 (s, 1H, NH), 8.28 (s, 1H, ArH), 8.08 (d, J=8.8 Hz, 1H, ArH), 7.96 (d, J=8.8 Hz, 1H, ArH), 7.58 (d, J=6.8 Hz, 1H, ArH), 7.49-7.31 (m, 7H, ArH), 6.42 (d, J=3.2 Hz, 1H, ArH), 6.35 (s, 1H, OH), 4.61 (d, J=14.4 Hz, 1H, CH), 4.35 (d, J=14.4 Hz, 1H, CH), 1.46 (s, 3H, CH₃).

Mass (ESI, Negative): 479.9[M−H]⁻; (ESI, Positive): 504.1[M+Na]⁺.

(S)—N-(3-Chloro-4-cyanophenyl)-3-(5-fluoro-6-phenyl-1H-indol-1-yl)-2-hydroxy-2-methylpropanamide (34)

5-Fluoro-6-phenyl-1H-indole ($C_{14}H_{10}FN$)

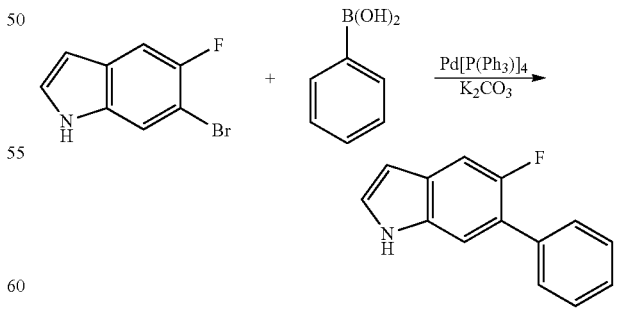

To a suspension of tetrakis(triphenylphosphine)palladium (0) [Pd(PPh₃)₄, 0.54 g, 0.467 mmol] in 20 mL of ethylene glycol dimethyl ether (DME) was added 6-bromo-5-fluoroindole (1.00 g, 4.67 mmol), and the mixture was stirred for 15 minutes under argon at RT. A solution of phenylboronic acid (0.57 g, 4.67 mmol) in 2-3 mL of ethanol was added and the mixture was stirred for 10 minutes under the same conditions. A solution of potassium carbonate (0.97 g, 7.01 mmol) in 2 mL of water was added to above mixture and the resulting reaction mixture was heated at reflux for 3-4 hours under the argon atmosphere. After the end of the reaction was established by TLC, the reaction was diluted by brine, and extracted with ethyl acetate. The organic layer was washed with brine, dried with MgSO$_4$, filtered, and concentrated under vacuum. The product was purified by a silica gel column using ethyl acetate and hexane (1:3) as eluent to afford 0.90 g (92% yield) of the titled compound as light brown solid.

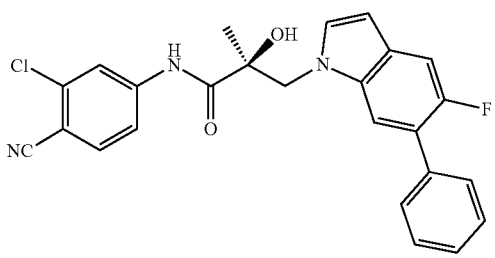 [SMILES: C[C@](O)(Cn1ccc2cc(F)c(-c3ccccc3)cc21)C(=O)Nc1ccc(C#N)c(Cl)c1]

To a solution of 5-fluoro-6-phenyl-1H-indole (0.20 g, 0.000947 mol) in anhydrous THF (10 mL), which was cooled in an ice water bath under an argon atmosphere, was added sodium hydride (60% dispersion in oil, 0.076 g, 0.00189 mol). After addition, the resulting mixture was stirred for three hours. (R)-3-Bromo-N-(4-cyano-3-chlorophenyl)-2-hydroxy-2-methylpropanamide (0.30 g, 0.000947 mol) was added to the above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexane (1:2) as eluent to afford 0.26 g of the titled compound as yellowish solid.

$^1$H NMR (400 MHz, DMSO-d$_6$) δ 10.11 (s, 1H, NH), 8.04 (d, J=1.6 Hz, 1H, ArH), 7.80 (d, J=8.8 Hz, 1H, ArH), 7.74 (dd, J=8.2 Hz, J=2.0 Hz, 1H, ArH), 7.62 (d, J=6.4 Hz, 1H, ArH), 7.51-7.44 (m, 4H, ArH), 7.39-7.32 (m, 3H, ArH), 6.42 (d, J=3.2 Hz, 1H, ArH), 6.33 (s, 1H, OH), 4.60 (d, J=15.2 Hz, 1H, CH), 4.35 (d, J=15.2 Hz, 1H, CH), 1.45 (s, 3H, CH$_3$).

Mass (ESI, Negative): 445.8[M−H]$^−$; (ESI, Positive): 470.0[M+Na]$^+$.

(S)—N-(3-Chloro-4-cyanophenyl)-3-(6-fluoro-1H-indol-1-yl)-2-hydroxy-2-methylpropanamide (35)

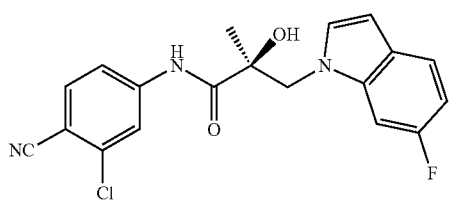 [SMILES: C[C@](O)(Cn1ccc2ccc(F)cc21)C(=O)Nc1ccc(C#N)c(Cl)c1]

Method B

Yield 67%;

White solid;

MS (ESI) n/z 376.9 [M−H].

$^1$H NMR (CDCl$_3$, 400 MHz) δ 8.67 (bs, 1H, NH), 7.79 (d, J=2.0 Hz, 1H), 7.56 (d, J=8.4 Hz, 1H), 7.49 (dd, J=8.4, 5.4 Hz, 1H), 7.38 (dd, J=8.4, 2.0 Hz, 1H), 7.13 (dd, J=10.0, 2.0 Hz, 1H), 7.09 (d, J=3.2 Hz, 1H), 6.86 (m, 2H), 6.48 (d, J=3.2 Hz, 1H), 4.58 (d, J=14.8 Hz, 1H), 4.28 (d, J=14.8 Hz, 1H), 2.61 (bs, 1H, OH), 1.60 (s, 3H);

$^{19}$F NMR (CDCl$_3$) δ −120.03.

(S)—N-(3-Chloro-4-cyanophenyl)-3-(4-fluoro-1H-indol-1-yl)-2-hydroxy-2-methylpropanamide (36)

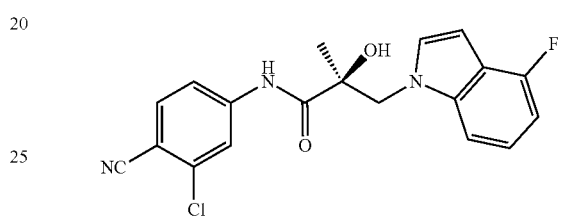

Method B

Under argon atmosphere into a 100 mL, dried, two-necked round bottom flask equipped with a dropping funnel in ice-water bath, NaH of 60% dispersion in mineral oil (228 mg, 5.70 mmol) was added in 20 mL of anhydrous THF solvent into the flask and 4-fluoroindole (390 mg, 2.84 mmol) solution in 10 mL of anhydrous THF was added to the solution under the argon atmosphere in the ice-water bath, and then the resulting solution was stirred at the ice-water bath. After 30 min, into the flask, a solution of (S)—N-(3-chloro-4-cyanophenyl)-2-methyloxirane-2-carboxamide (2.84 mmol in THF) was added through dropping funnel under argon atmosphere at the ice-water bath and stirred overnight at RT. After adding 1 mL of H$_2$O, the reaction mixture was condensed under reduced pressure, and then dispersed into 50 mL of EtOAc, washed with 50 mL (×2) water, brine, dried over anhydrous MgSO$_4$, and evaporated to dryness. The mixture was purified with flash column chromatography as an eluent EtOAc/hexane, and then the condensed compounds were then recrystallized in EtOAc/hexane to give a target product, 36.

Yield 73%.

White solid.

MS (ESI) m/z 369.9 [M−H]$^−$; HRMS (ESI) m/z calcd for C$_{19}$H$_{16}$ClFN$_3$O$_2$: 372.0915. Found: 372.0915 [M+H]$^+$.

$^1$H NMR (CDCl$_3$, 400 MHz) δ 8.64 (bs, 1H, NH), 7.81 (s, 1H), 7.57 (d, J=8.4 Hz, 1H), 7.35 (d, J=7.2 Hz, 1H), 7.21 (d, J=8.4 Hz, 1H), 7.14-7.10 (m, 2H), 6.77 (t, J=8.4 Hz, 1H), 6.63 (d, J=2.8 Hz, 1H), 6.60 (s, 1H), 4.64 (d, J=14.8 Hz, 1H), 4.35 (d, J=14.8 Hz, 1H), 2.48 (bs, 1H, OH), 1.60 (s, 3H).

$^{13}$C NMR (acetone-d$_6$, 100 MHz) δ 174.8, 158.1, 155.7, 144.3, 141.5 (d, J=11.0 Hz), 137.2, 135.5, 130.7, 122.4 (d, J=7.0 Hz), 121.0, 119.3, 118.0 (d, J=22.0 Hz), 116.6, 107.9 (t, J=5.0 Hz), 104.4 (d, J=19.0 Hz), 97.7, 77.6, 55.0, 24.2.

$^{19}$F NMR (CDCl$_3$, decoupled) δ −121.78.

(S)—N-(3-Chloro-4-cyanophenyl)-3-(5-fluoro-1H-indol-1-yl)-2-hydroxy-2-methylpropanamide (37)

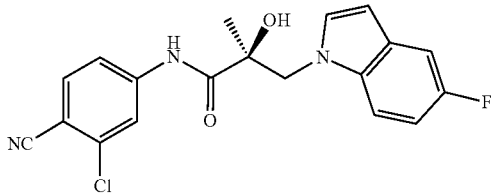 [SMILES: C[C@](O)(Cn1ccc2cc(F)ccc21)C(=O)Nc1ccc(C#N)c(Cl)c1]

Method B
 Yield 79%.
 White solid.
 MS (ESI) m/z 371.0 [M−H]; HRMS (ESI) m/z calcd for $C_{19}H_{16}ClFN_3O_2$: 372.0915.
 Found: 372.0922 [M+H]$^+$.
 $^1$H NMR (CDCl$_3$, 400 MHz) δ 8.62 (bs, 1H, NH), 7.80 (d, J=2.0 Hz, 1H), 7.56 (d, J=8.4 Hz, 1H), 7.38-7.34 (m, 2H), 7.23 (dd, J=9.2, 2.4 Hz, 1H), 7.15 (d, J=3.2 Hz, 1H), 7.22 (dt, J=9.2, 2.8 Hz, 1H), 6.47 (d, J=3.2 Hz, 1H), 4.63 (d, J=14.8 Hz, 1H), 4.32 (d, J=14.8 Hz, 1H), 2.49 (bs, 1H, OH), 1.60 (s, 3H). $^{19}$F NMR (CDCl$_3$) δ-124.52.

(S)—N-(3-Chloro-4-cyanophenyl)-3-(3-fluoro-1H-indol-1-yl)-2-hydroxy-2-methylpropanamide (38)

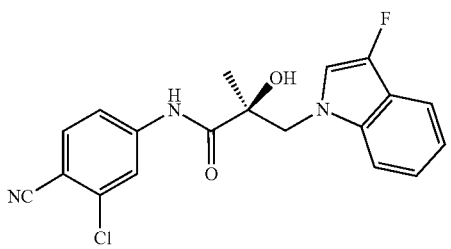 [SMILES: C[C@](O)(Cn1cc(F)c2ccccc21)C(=O)Nc1ccc(C#N)c(Cl)c1]

Method B
 Yield 68%;
 Mp 168.9-170.1° C.
 Light Brown solid.
 MS (ESI) m/z 369.8 [M−H]; LCMS (ESI) m/z calcd for $C_{19}H_{16}ClFN_3O_2$: 372.0915. Found: 372.0910 [M+H]$^+$.
 $^1$H NMR (CDCl$_3$, 400 MHz) 8.66 (bs, 1H, NH), 7.81 (d, J=2.0 Hz, 1H), 7.60-7.56 (m, 2H), 7.37 (dd, J=8.4, 2.0 Hz, 2H), 7.23 (m, 1H), 7.12 (t, J=7.4 Hz, 1H), 6.93 (d, J=2.8 Hz, 1H), 4.56 (d, J=15.2 Hz, 1H), 4.27 (d, J=15.2 Hz, 1H), 2.44 (s, 1H, OH), 1.59 (s, 3H). $^{19}$F NMR (CDCl$_3$) δ-173.91.

(S)—N-(3-Chloro-4-cyanophenyl)-3-(7-fluoro-1H-indol-1-yl)-2-hydroxy-2-methylpropanamide (39)

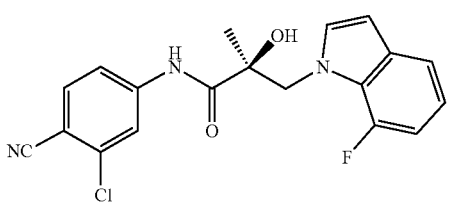 [SMILES: C[C@](O)(Cn1ccc2cccc(F)c21)C(=O)Nc1ccc(C#N)c(Cl)c1]

Method B
 Yield 73%.
 White solid.
 MS (ESI) m/z 370.0 [M−H]$^-$.
 $^1$H NMR (CDCl$_3$, 400 MHz) δ 8.60 (bs, 1H, NH), 8.82 (d, J=2.0 Hz, 1H), 7.55 (d, J=8.4 Hz, 1H), 7.37-7.34 (m, 2H), 7.02 (d, J=3.2 Hz, 1H), 7.00 (m, 1H), 7.01-6.98 (m, 1H), 6.91 (m, 1H), 6.46 (t, J=2.8 Hz, 1H), 4.68 (d, J=15.0 Hz, 1H), 4.62 (d, J=15.0 Hz, 1H), 2.73 (d, J=4.4 Hz, 1H, OH), 1.61 (s, 3H).
 $^{19}$F NMR (CDCl$_3$) δ −133.54.

(S)—N-(3-Chloro-4-cyanophenyl)-3-(5-fluoro-3-phenyl-1H-indol-1-yl)-2-hydroxy-2-methylpropanamide (40)

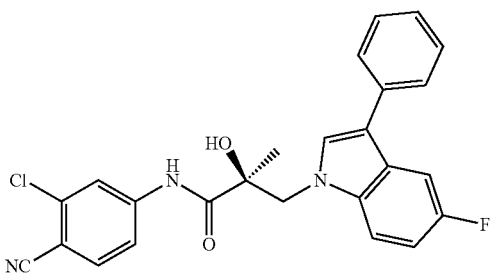 [SMILES: C[C@](O)(Cn1cc(-c2ccccc2)c2cc(F)ccc21)C(=O)Nc1ccc(C#N)c(Cl)c1]

To a solution of 5-fluoro-3-phenyl-1H-indole (0.50 g, 0.002267 mol) in anhydrous THF (10 mL), which was cooled in an ice water bath under an argon atmosphere, was added sodium hydride (60% dispersion in oil, 0.24 g, 0.005918 mol). After addition, the resulting mixture was stirred for three hours. (R)-3-Bromo-N-(4-cyano-3-chlorophenyl)-2-hydroxy-2-methylpropanamide (0.75 g, 0.002267 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexanes (1:2 to 1:1) as eluent to afford 0.43 g of the titled compound as yellowish solid.
 $^1$H NMR (400 MHz, DMSO-d$_6$) δ 10.17 (s, 1H, NH), 8.06 (d, J=2.0 Hz, 1H, ArH), 7.86-7.79 (m, 2H, ArH), 7.64 (s, 1H, ArH), 7.62-7.58 (m, 1H, ArH), 7.55-7.52 (m, 2H, ArH), 7.50 (dd, J=10.4 Hz, J=2.4 Hz, 1H, ArH), 7.43-7.40 (m, 2H, ArH), 7.26-7.22 (m, 1H, ArH), 7.03-6.98 (m, 1H, ArH), 6.37 (s, 1H, OH), 4.60 (d, J=14.8 Hz, 1H, CH), 4.38 (d, J=14.8 Hz, 1H, CH), 1.46 (s, 3H, CH$_3$).
 Mass (ESI, Negative): 446.8[M−H]$^-$; (ESI, Positive): 448.1248[M+H]$^+$.

(S)—N-(4-Cyano-3-(trifluoromethyl)phenyl)-2-hydroxy-2-methyl-3-(4-phenyl-1H-indol-1-yl)propanamide (41)

Phenyl-1H-indole ($C_{14}H_{11}N$)

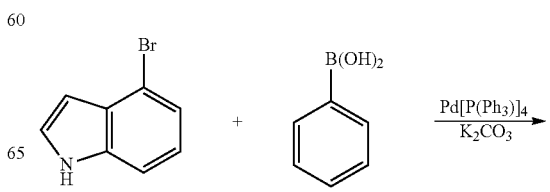

-continued

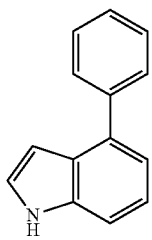

5

To a suspension of tetrakis(triphenylphosphine)palladium (0) [Pd(PPh₃)₄, 1.179 g, 1.0212 mmol] in 40 mL of ethylene glycol dimethyl ether (DME) was added 4-bromo-indole (2.00 g, 10.202 mmol), and the mixture was stirred for 15 minutes under argon at RT. A solution of phenylboronic acid (1.24 g, 10.202 mmol) in 4.5 mL of ethanol was added and the mixture was stirred for 10 minutes under the same conditions. A solution of potassium carbonate (2.16 g, 15.306 mmol) in 3.5 mL of water was added to above mixture and the resulting reaction mixture was heated at reflux for 3-4 hours under the argon atmosphere. After the end of the reaction was established by TLC, the reaction was diluted by brine, and extracted with ethyl acetate. The organic layer was washed with brine, dried with MgSO₄, filtered, and concentrated under vacuum. The product was purified by a silica gel column using ethyl acetate and hexane (1:3 to 2:1) as eluent to afford 1.67 g (84.8% yield) of the titled compound as yellowish oil.

41

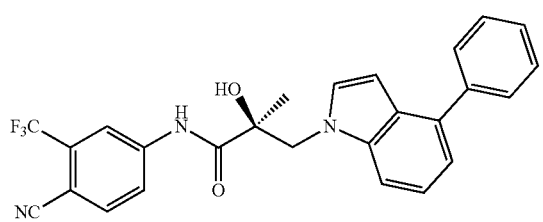

To a solution of 4-phenyl-1H-indole (0.42 g, 0.002173 mol) in anhydrous THF (10 mL), which was cooled in an ice water bath under an argon atmosphere, was added sodium hydride (60% dispersion in oil, 0.22 g, 0.005434 mol). After addition, the resulting mixture was stirred for three hours. (S)—N-(4-Cyano-3-(trifluoromethyl)phenyl)-2-methyloxirane-2-carboxamide (0.76 g, 0.002173 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.69 g (69%) of the titled compound as off-white solid.

¹H NMR (400 MHz, DMSO-d₆) 10.37 (s, 1H, NH), 8.37 (d, J=2.0 Hz, 1H, ArH), 8.18 (dd, J=8.4 Hz, J=2.0 Hz, 1H, ArH), 8.05 (d, J=8.4 Hz, 1H, ArH), 7.60-7.54 (m, 3H, ArH), 7.49-7.45 (m, 2H, ArH), 7.38-7.34 (m, 2H, ArH), 7.18-7.14 (m, 1H, ArH), 7.04 (d, J=7.2 Hz, 1H, ArH), 6.51 (d, J=3.2 Hz, 1H, ArH), 6.35 (s, 1H, OH), 4.58 (d, J=14.4 Hz, 1H, CH), 4.38 (d, J=14.4 Hz, 1H, CH), 1.45 (s, 3H, CH₃).

Mass (ESI, Positive): 464.1536[M+H]⁺; 486.1351[M+Na]⁺.

(S)—N-(4-Cyano-3-(trifluoromethyl)phenyl)-3-(4-fluoro-5-phenyl-1H-indol-1-yl)-2-hydroxy-2-methyl-propanamide(42)

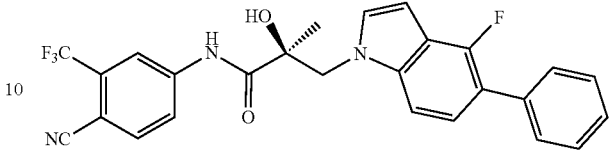

To a solution of 4-fluoro-5-phenyl-1H-indole (0.33 g, 0.00156 mol) in anhydrous THF (10 mL), which was cooled in an ice water bath under an argon atmosphere, was added sodium hydride (60% dispersion in oil, 0.16 g, 0.00391 mol). After addition, the resulting mixture was stirred for three hours. (S)—N-(4-Cyano-3-(trifluoromethyl)phenyl)-2-methyloxirane-2-carboxamide (0.55 g, 0.00156 mol) was added to above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.47 g (63%) of the titled compound as off-white solid.

¹H NMR (400 MHz, DMSO-d₆) 10.33 (s, 1H, NH), 8.35 (d, J=2.0 Hz, 1H, ArH), 8.17 (dd, J=8.4 Hz, J=2.0 Hz, 1H, ArH), 8.05 (d, J=8.4 Hz, 1H, ArH), 7.51-7.40 (m, 5H, ArH), 7.36-7.32 (m, 2H, ArH and indole-H), 7.17-7.13 (m, 1H, ArH), 6.53 (d, J=3.2 Hz, 1H, ArH), 6.38 (s, 1H, OH), 4.60 (d, J=14.8 Hz, 1H, CH), 4.38 (d, J=14.8 Hz, 1H, CH), 1.45 (s, 3H, CH₃).

Mass (ESI, Negative): [M−H]⁻; (ESI, Positive): 482.1490 [M+H]⁺; 504.1310[M+Na]⁺.

(S)—N-(4-Cyano-3-(trifluoromethyl)phenyl)-3-(4-fluoro-6-(4-fluorophenyl)-1H-indol-1-yl)-2-hydroxy-2-methylpropanamide (43)

4-Fluoro-6-(4-fluorophenyl)-1H-indole

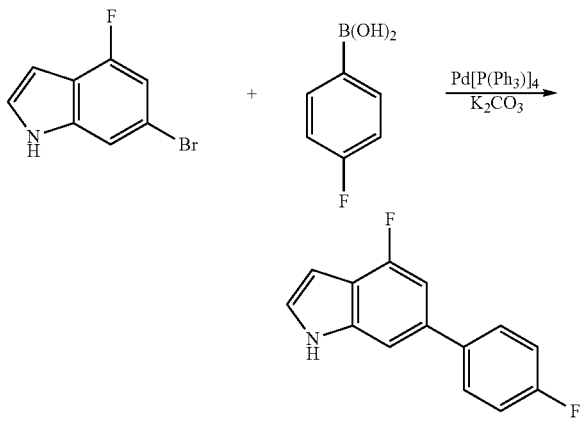

To a suspension of tetrakis(triphenylphosphine)palladium (0) [Pd(PPh₃)₄, 0.27 g, 0.2336 mmol] in 10 mL of ethylene glycol dimethyl ether (DME) was added 6-bromo-4-fluoroindole (0.50 g, 2.336 mmol), and the mixture was stirred for 15 minutes under argon at RT. A solution of 4-fluorophenylboronic acid (0.33 g, 2.336 mmol) in 1.2 mL of ethanol was added and the mixture was stirred for 10 minutes under the same conditions. A solution of potassium carbonate (0.48 g, 3.504 mmol) in 1.0 mL of water was added to above mixture and the resulting reaction mixture was heated at reflux for 3-4 h under the argon atmosphere. After the end of the reaction was established by TLC, the reaction was diluted by brine, and extracted with ethyl acetate. The organic layer was washed with brine, dried with MgSO₄, filtered, and concentrated under vacuum. The product was purified by a silica gel column using ethyl acetate and hexane (1:3) as eluent to afford 0.33 g (61.6% yield) of the titled compound as brown solid.

(S)—N-(4-Cyano-3-(trifluoromethyl)phenyl)-3-(4-fluoro-6-(4-fluorophenyl)-1H-indol-1-yl)-2-hydroxy-2-methylpropanamide_(43)

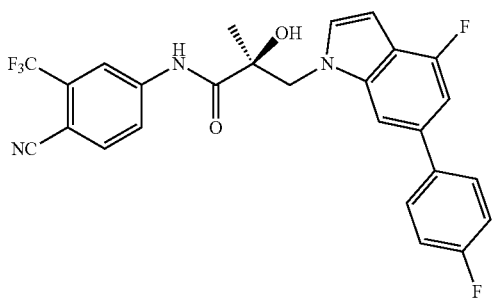 [SMILES: C[C@](O)(Cn1ccc2c(F)cc(-c3ccc(F)cc3)cc21)C(=O)Nc1ccc(C#N)c(C(F)(F)F)c1]

To a solution of 4-fluoro-6-(4-fluorophenyl)-1H-indole (0.32 g, 0.0014 mol) in anhydrous THF (10 mL), which was cooled in an ice water bath under an argon atmosphere, was added sodium hydride (60% dispersion in oil, 0.17 g, 0.00419 mol). After addition, the resulting mixture was stirred for three hours. (S)—N-(4-Cyano-3-(trifluoromethyl)phenyl)-2-methyloxirane-2-carboxamide (0.49 g, 0.00140 mol) was added to the above solution, and the resulting reaction mixture was allowed to stir overnight at RT under argon. The reaction was quenched by water, and extracted with ethyl acetate. The organic layer was washed with brine, dried with MgSO₄, filtered, and concentrated under vacuum. The product was purified by a silica gel column using ethyl acetate and hexane (1:2) as eluent to afford 0.35 g (50.5%) of the titled compound as off-white solid.

¹H NMR (400 MHz, DMSO-d₆) δ 10.30 (s, 1H, NH), 8.26 (d, J=2.0 Hz, 1H, ArH), 8.07 (dd, J=8.8 Hz, J=2.0 Hz, 1H, ArH), 7.97 (d, J=8.8 Hz, 1H, ArH), 7.68-7.64 (m, 2H, ArH), 7.60 (s, 1H, ArH), 7.35 (d, J=3.0 Hz, 1H, ArH), 7.28-7.24 (m, 2H, ArH)), 7.04 (dd, J=12.0 Hz, J=1.2 Hz, 1H, ArH), 6.48 (d, J=1.0 Hz, 1H, ArH), 6.39 (s, 1H, OH), 4.67 (d, J=14.8 Hz, 1H, CH), 4.42 (d, J=14.8 Hz, 1H, CH), 1.49 (s, 3H, CH₃).

Mass (ESI, Negative): [M–H]⁻; (ESI, Positive): 499.2056 [M+H]⁺.

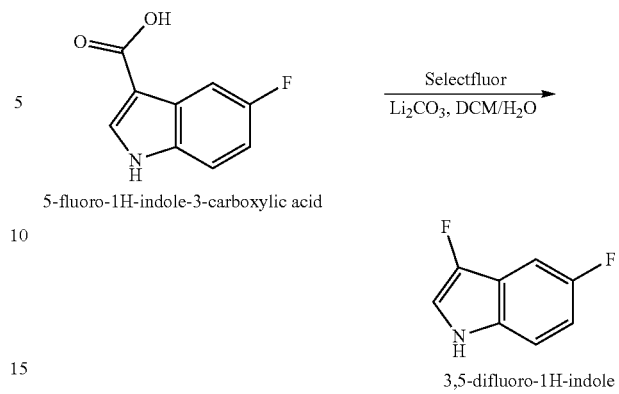

Synthesis of 3,5-difluoro-1H-indole

To a 50 mL round-bottle flask with a magnetic stirring bar were added Selectfluor® (872 mg, 2.0 mmol, 2.0 equiv), Li₂CO₃ (296 mg, 4.0 mmol, 4.0 equiv), dichloromethane (3.3 mL) and water (1.7 mL). Then 5-fluoro-1H-indole-3-carboxylic acid (1.0 mmol, 1.0 equiv) was added. The reaction mixture was stirred for 2 hours in ice bath. The reaction mixture was diluted with water (40 mL), followed by extracting with DCM (20 mL×2). The combined organic extracts were washed with brine, dried over anhydrous sodium sulfate and concentrated in vacuo. The crude product was purified by flash column chromatography (n-hexane:DCM=2:1) to afford 3,5-difluoro-1H-indole as deep brown oil. Yield=68%;

MS (ESI) m/z 154.83[M+H]⁺; 152.03 [M–H].

¹H NMR (CDCl₃, 400 MHz) δ 7.86 (bs, 1H, NH), 7.25 (dd, J=9.2, 2.4 Hz, 1H), 7.20-7.16 (m, 1H), 6.97 (t, J=2.6 Hz, 1H), 6.93 (dd, J=9.2, 2.4 Hz, 1H);

¹⁹F NMR (CDCl₃) δ –123.99 (d, $J_{F-F}$=2.8 Hz), –174.74 (d, $J_{F-F}$=4.0 Hz).

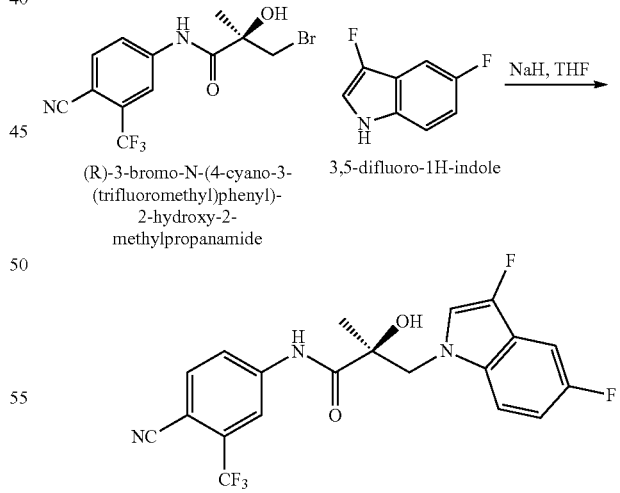

(S)—N-(4-Cyano-3-(trifluoromethyl)phenyl)-3-(3,5-difluoro-1H-indol-1-yl)-2-hydroxy-2-methylpropanamide (44)

To a dry, nitrogen-purged 50 mL round-bottom flask equipped with a dropping funnel under argon atmosphere, NaH of 60% dispersion in mineral oil (63 mg, 1.56 mmol) was added in 10 mL of anhydrous THF solvent in the flask at ice-water bath, and 3,5-difluoro-1H-indole (120 mg, 0.78 mmol) was stirred 30 min at the ice-water bath. Into the flask, (R)-3-bromo-N-(4-cyano-3-(trifluoromethyl)phenyl)-2-hydroxy-2-methylpropanamide (275 mg, 0.78 mmol) in 10 mL of anhydrous THF was added through dropping funnel under argon atmosphere at the ice-water bath and stirred overnight at room temperature. After adding 1 mL of H2O, the reaction mixture was condensed under reduced pressure, and then dispersed into 50 mL of EtOAc, washed with 50 mL (×2) water, evaporated, dried over anhydrous MgSO4, and evaporated to dryness. The mixture was purified with flash column chromatography as an eluent EtOAc/hexane=½ to produce 44 as white solid as white powder.

Yield 53%;

MS (ESI) m/z 424.11[M+H]+; 423.11 [M−H];

HRMS (ESI) m/z calcd for $C_{20}H_{15}F_5N_3O_2$ [M+H]+; Exact Mass: 424.1084 [M+H]+.

Found: 424.1065 [M+H]+.

HPLC: $t_R$ 2.77 min, purity 99.06%, UV ($\lambda_{abs}$) 196.45, 270.45 nm

1H NMR (CDCl3, 400 MHz) δ 8.80 (bs, 1H, NH), 7.89 (d, J=1.6 Hz, 1H), 7.77 (dd, J=8.4, 1.6 Hz, 1H), 7.74 (d, J=8.4 Hz, 1H), 7.33-7.29 (m, 1H), 7.20 (dd, J=9.0, 2.4 Hz, 1H), 6.99 (t, J=2.8 Hz, 1H), 6.97 (td, J=9.0, 2.4 Hz, 1H), 4.56 (d, J=14.8 Hz, 1H), 4.24 (d, J=14.8 Hz, 1H), 2.57 (s, OH), 1.61 (s, 3H);

13C NMR (CDCl3, 100 MHz) δ 172.3, 157.5 (d, $J_{F-F}$=235 Hz), 140.9, 135.8, 134.1 (d, $J_{F-F}$=32.8 Hz), 130.4 (d, $J_{F-F}$=4.5 Hz), 123.4, 121.9, 120.6, 117.4 (q, $J_{F-F}$=4.9 Hz), 115.3, 113.1 (d, $J_{F-F}$=2.59 Hz), 111.1 (d, $J_{F-F}$=9.3 Hz), 105.0, 102.3, 102.2, 102.0 (d, $J_{F-F}$=25 Hz), 77.6, 53.9, 24.2;

19F NMR (CDCl3) δ −62.25, −123.48 (d, $J_{F-F}$=3.2 Hz), −173.54 (d, $J_{F-F}$=2.8 Hz); assigned by 2D NMR as NOE and COSY.

(S)-3-(3-Chloro-5-fluoro-1H-indol-1-yl)-N-(4-cyano-3-(trifluoromethyl)phenyl)-2-hydroxy-2-methylpropanamide(45)

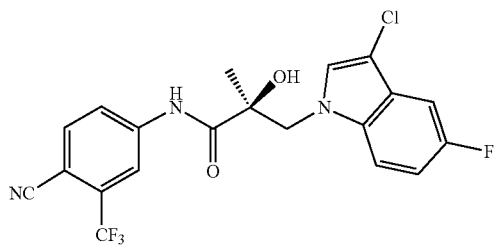

To a dry, nitrogen-purged 50 mL round-bottom flask equipped with a dropping funnel under argon atmosphere, NaH of 60% dispersion in mineral oil (167 mg, 2.5 mmol) was added in 10 mL of anhydrous THF solvent in the flask at ice-water bath, and 3-chloro-5-fluoro-1H-indole (170 mg, 1 mmol) was stirred 30 min at the ice-water bath. Into the flask, (R)-3-Bromo-N-(4-cyano-3-(trifluoromethyl)phenyl)-2-hydroxy-2-methylpropanamide (351 mg, 1 mmol) in 10 mL of anhydrous THF was added through dropping funnel under argon atmosphere at the ice-water bath and stirred overnight at room temperature. After adding 1 mL of H2O, the reaction mixture was condensed under reduced pressure, and then dispersed into 50 mL of EtOAc, washed with 50 mL (×2) water, evaporated, dried over anhydrous MgSO4, and evaporated to dryness. The mixture was purified with flash column chromatography as an eluent EtOAc/hexane=½ to produce 45 as white solid as white powder.

Yield 58%;

MS (ESI) m/z 440.08 [M+H]+; 439.01 [M−H];

HRMS (ESI) m/z calcd for $C_2H_{15}ClF_4N_3O_2$ Exact Mass: m/z $C_2H_{15}ClF_4N_3O_2$: 440.0789 [M+H]+; 440.0797 [M+H]+;

HPLC: $t_R$ 2.89 min, purity 99.06%;

UV ($\lambda_{abs}$) 196.45, 270.45 nm.

1H NMR (CDCl3, 400 MHz) δ 8.76 (bs, 1H, NH), 7.86 (s, 1H), 7.78-7.73 (m, 2H), 7.34 (dd, J=9.2, 4.0 Hz, 1H), 7.29 (dd, J=8.8, 2.4 Hz, 1H), 7.17 (s, 1H), 6.97 (td, J=9.2, 2.4 Hz, 1H), 4.58 (d, J=14.8 Hz, 1H), 4.28 (d, J=14.8 Hz, 1H), 2.64 (s, OH), 1.61 (s, 3H);

13C NMR (CDCl3, 100 MHz) δ 172.3, 157.5 (d, $J_{F-F}$=235 Hz), 140.8, 135.8, 134.0 (d, $J_{F-F}$=32 Hz), 132.6, 126.9, 126.2 (d, $J_{F-F}$=10 Hz), 123.4, 117.4 (q, $J_{F-F}$=4.9 Hz), 115.3, 112.0 (d, $J_{F-F}$=26.4 Hz), 111.1 (d, $J_{F-F}$=9.5 Hz), 106.1, 106.0, 105.0, 103.5 (d, $J_{F-F}$=25 Hz), 77.5, 53.8, 24.2.

19F NMR (CDCl3) δ −62.25, −12.76; assigned by 2D NMR as NOE and COSY.

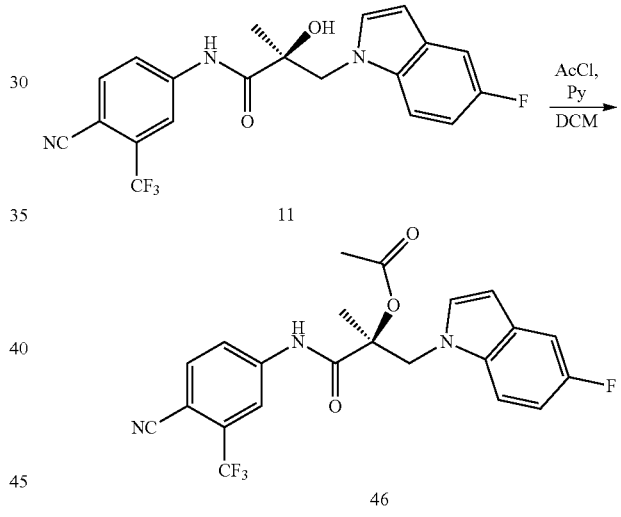

(S)-1-((4-Cyano-3-(trifluoromethyl)phenyl)amino)-3-(5-fluoro-1H-indol-1-yl)-2-methyl-1-oxopropan-2-yl acetate (46)

Under argon atmosphere, to a solution of 11 (100 mg, 0.247 mmol) and triethyl amine (0.07 mL, 0.5 mmol) in 10 mL of anhydrous DCM was added acetyl chloride (0.02 mL, 0.3 mmol) at ice-water bath. After stirring for 30 min, the temperature was raised to room temperature and the mixture stirred for 2 hours. The reaction mixture was washed with water, evaporated, dried over anhydrous MgSO4, and evaporated to dryness. The mixture was purified with flash column chromatography as an eluent EtOAc/hexane (1/1, v/v) to produce target product as white solid.

Yield=86%;

MS (ESI) m/z 446.0 [M−H].

1H NMR (CDCl3, 400 MHz) δ 8.75 (bs, 1H, C(O)NH), 7.88 (s, 1H, ArH), 7.79-7.73 (m, 2H, ArH), 7.35 (dd, J=8.8, 4.2 Hz, 1H, ArH), 7.22 (dd, J=9.6, 2.6 Hz, 1H, ArH), 7.16

(d, J=2.6 Hz, 1H, ArH), 6.94 (m, 1H, ArH), 6.46 (d, J=3.2 Hz, 1H, ArH), 4.65 (d, J=14.8 Hz, 1H, CH$_2$), 4.33 (d, J=14.8 Hz, 1H, CH$_2$), 2.59 (s, 3H, OC(O)CH$_3$), 1.57 (s, 3H, CH$_3$);

$^{19}$F NMR (CDCl$_3$, 400 MHz) δ −62.24, −124.54; assigned by 2D NMR as NOE and COSY.

Carbazole

Methods A and B: Preparation of Carbazoles

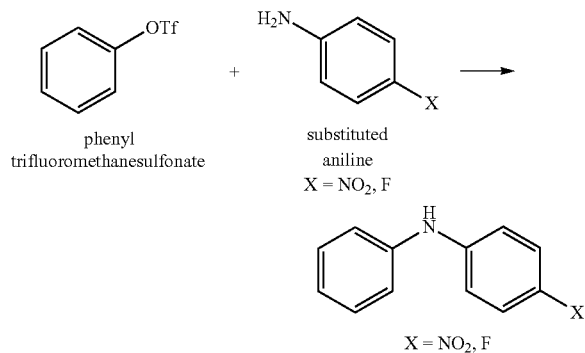

phenyl trifluoromethanesulfonate substituted aniline
X = NO$_2$, F

X = NO$_2$, F

Method A (non microwave): A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, substituted aniline (2.43 mmol) was added and the mixture was heated at 110° C. overnight. The reaction mixture was allowed to cool to RT and filtered through a pad of Celite®. The filtrate was diluted with CH$_2$Cl$_2$ and water. The phases were separated and the aqueous phase was re-extracted 2 times with CH$_2$Cl$_2$. The combined organic phases were dried over Na$_2$SO$_4$ and the solvent was evaporated.

Method B (microwave): A mixture of phenyl trifluoromethanesulfonate (200 mg, 0.88 mmol), palladium acetate (II) (20 mg, 0.09 mmol), (±) 2,2'-bis(diphenylphosphino)-1,1'-binaphthyl (64 mg, 0.13 mmol) and cesium carbonate (430 mg, 1.32 mmol), and substituted aniline (0.97 mmol) in 5 mL of toluene were loaded into a vessel with a cap. Reaction vessels were placed in a reactor block in the microwave. A programmable microwave irradiation cycle of 30 min at 300 W at 110° C. and 25 min of fan-cooling was executed (irradiation time, 30 min). The mixture was transferred to a round bottom flask to be concentrated under reduced pressure and poured into EtOAc, which was washed with water and dried over anhydrous MgSO$_4$, concentrated. The crude product obtained was purified by chromatography on silica gel using EtOAc/hexane (6/1, v/v) as an eluent to produce the target product (~89%) as deep brown oil.

4-Fluoro-N-phenyl aniline: $^1$H NMR (400 MHz, CDCl$_3$) δ 7.27-7.24 (m, 2H), 7.07-7.02 (m, 2H), 7.01-6.95 (m, 4H), 6.89 (t, J=7.2 Hz, 1H), 5.57 (bs, 1H, NH).

3-Nitro-9H-Carbazole

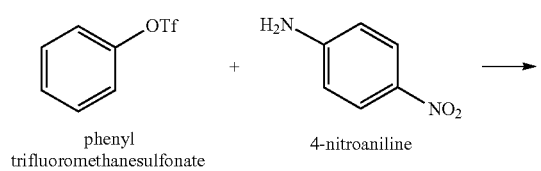

phenyl trifluoromethanesulfonate 4-nitroaniline

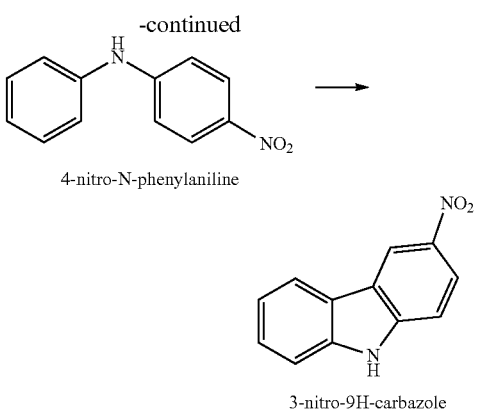

4-nitro-N-phenylaniline 3-nitro-9H-carbazole

A mixture of phenyl trifluoromethanesulfonate (500 mg, 2.21 mmol), palladium acetate (II) (50 mg, 0.22 mmol), (±) 2,2'-bis(diphenylphosphino)-1,1'-binaphthyl (317 mg, 0.66 mmol) and cesium carbonate (1.09 g, 3.31 mmol) in 50 mL of toluene were inertized with argon. Then, 4-nitroaniline (331 mg, 2.43 mmol) was added and the mixture was heated at 110° C. overnight. The reaction mixture was allowed to cool to RT and filtered through a pad of Celite®. The filtrate was diluted with CH$_2$Cl$_2$ and water. The phases were separated and the aqueous phase was re-extracted 2 times with CH$_2$Cl$_2$. The combined organic phases were dried over Na$_2$SO$_4$ and the resulting solution was dried over anhydrous Na$_2$SO$_4$ and purified with flash column chromatography as an eluent EtOAc/hexane (⅙, v/v) to give 4-nitro-N-phenylaniline. The aniline (450 mg, 2 mmol), Pd(OAc)$_2$ (23 mg, 0.1 mmol), K$_2$CO$_3$ (30 mg, 0.2 mmol), and pivalic acid (408 mg, 4 mmol) was placed into a glass test tube. The uncapped test tube was placed in an oil bath and the mixture was stirred under air at the indicated temperature. The solution was then cooled to RT, diluted with EtOAc, washed with a saturated Na$_2$CO$_3$, dried over Na$_2$SO$_4$, concentrated, and purified by flash column chromatography as an eluent of EtOAc/hexane to give 3-nitro-9H-carbazole.

(S)-3-(9H-Carbazol-9-yl)-N-(4-cyano-3-(trifluoromethyl)phenyl)-2-hydroxy-2-methylpropanamide (200)

Method B: Yield 88%; MS (ESI) m/z 436.1 [M−H].

$^1$H NMR (CDCl$_3$, 400 MHz) δ 8.82 (bs, 1H, NH), 8.09-8.06 (m, 3H), 7.84 (d, J=1.6 Hz, 1H), 7.77-7.71 (m, 2H), 7.54 (d, J=8.4 Hz, 2H), 7.45-7.39 (m, 3H), 7.24-7.23 (m, 2H), 4.80 (d, J=15.2 Hz, 1H), 4.63 (d, J=15.2 Hz, 1H) 2.57 (s, 1H, OH), 1.69 (s, 3H).

(S)—N-(4-Cyano-3-(trifluoromethyl)phenyl)-2-hydroxy-2-methyl-3-(3-nitro-9H-carbazol-9-yl)propanamide (201)

Method B: MS (ESI) m/z 481.1 [M−H]$^-$ $^1$H NMR (CDCl$_3$, 400 MHz) δ 9.01 (s, 1H), 8.92 (bs, 1H, NH), 8.39 (m, 1H), 8.08 (m, 1H), 7.92 (d, J=1.6 Hz, 1H), 7.78 (d, J=8.4 Hz, 1H), 7.62 (dd, J=8.4, 1.6 Hz, 1H), 7.45 (m, 1H), 7.48-7.22 (m, 3H), 4.91 (d, J=15.0 Hz, 1H), 4.85 (d, J=15.0 Hz, 1H) 2.62 (s, 1H, OH), 1.70 (s, 3H).

(S)—N-(4-Cyano-3-(trifluoromethyl)phenyl)-3-(3-fluoro-9H-carbazol-9-yl)-2-hydroxy-2-methylpropanamide (202)

To a solution of 4-fluoro-carbazole (0.20 g, 0.00108 mol) in anhydrous THF (10 mL), which was cooled in an ice water bath under an argon atmosphere, was added sodium hydride (60% dispersion in oil, 0.09 g, 0.00216 mol). After addition, the resulting mixture was stirred for two hours. (R)-3-Bromo-N-(4-cyano-3-trifluoromethyl-phenyl)-2-hydroxy-2-methylpropanamide (0.38 g, 0.00108 mol) was added to the above solution, and the resulting reaction mixture was allowed to stir overnight at RT under argon. The reaction was quenched by water, and extracted with ethyl acetate. The organic layer was dried with MgSO$_4$, filtered, and concentrated under vacuum. The product was purified by a silica gel column using methylene chloride as eluent to afford 0.36 g (73.5%) of the titled compound as white solid.

$^1$H NMR (400 MHz, DMSO-d$_6$) δ 10.36 (s, 1H, NH), 8.25 (d, J=1.6 Hz, 1H, ArH), 8.12-8.09 (m, 2H, ArH), 8.04 (d, J=8.8 Hz, 1H, ArH), 7.95 (dd, J=9.2 Hz, J=2.1 Hz, 1H, ArH), 7.66 (t, J=4.8 Hz, 1H, ArH), 7.64 (s, 1H, ArH), 7.37 (dt, J=9.2 Hz, J=1.2 Hz, 1H, ArH), 7.20 (td, J=9.2 Hz, J=2.0 Hz, 1H, ArH), 7.13 (t, J=8.0 Hz, 1H, ArH), 6.34 (s, 1H, OH), 4.70 (d, J=14.8 Hz, 1H, CH), 4.55 (d, J=14.8 Hz, 1H, CH), 1.52 (s, 3H, CH$_3$).

Mass (ESI, Negative): 453.9 [M−H]$^-$; (ESI, Positive): 478.1 [M+Na]$^+$.

(S)—N-(3-Chloro-4-cyanophenyl)-3-(3-fluoro-9H-carbazol-9-yl)-2-hydroxy-2-methylpropanamide (203)

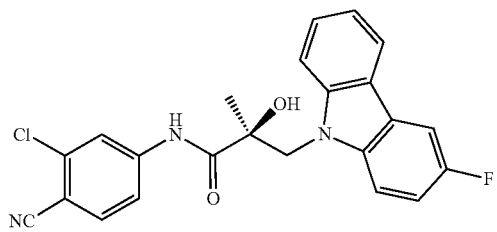 [SMILES: C[C@](O)(Cn1c2ccccc2c2cc(F)ccc21)C(=O)Nc1ccc(C#N)c(Cl)c1]

To a solution of 3-fluoro-carbazole (0.10 g, 0.00054 mol) in anhydrous THF (5 mL), which was cooled in an ice water bath under an argon atmosphere, was added sodium hydride (60% dispersion in oil, 0.033 g, 0.00081 mol). After addition, the resulting mixture was stirred for two hours. (R)-3-Bromo-N-(4-cyano-3-chloro-phenyl)-2-hydroxy-2-methylpropanamide (0.17 g, 0.00054 mol) was added to above solution, and the resulting reaction mixture was allowed to stir overnight at RT under argon. The reaction was quenched by water, and extracted with ethyl acetate. The organic layer was dried with MgSO$_4$, filtered, and concentrated under vacuum. The product was purified by a silica gel column using hexane and ethyl acetate (2:1) as eluent to afford 0.22 g (98%) of the titled compound as white solid/needles.

$^1$H NMR (400 MHz, DMSO-d$_6$) 10.20 (s, 1H, NH), 8.12 (d, J=7.6 Hz, 1H, ArH), 8.05 (d, J=2.0 Hz, 1H, ArH), 7.96 (dd, J=9.2 Hz, J=2.0 Hz, 1H, ArH), 7.86 (d, J=8.8 Hz, 1H, ArH), 7.80 (dd, J=8.4 Hz, J=2.0 Hz, 1H, ArH), 7.69-7.66 (m, 2H, ArH), 7.41 (t, J=8.0 Hz, 1H, ArH), 7.24 (dt, J=9.6 Hz, J=2.4 Hz, 1H, ArH), 7.16 (t, J=7.2 Hz, 1H, ArH), 6.34 (s, 1H, OH), 4.70 (d, J=15.2 Hz, 1H, CH), 4.54 (d, J=15.2 Hz, 1H, CH), 1.52 (s, 3H, CH$_3$).

Mass (ESI, Negative): 420.1[M−H]$^-$; (ESI, Positive): 444.1[M+Na]$^+$.

(S)—N-(4-Cyano-3-(trifluoromethyl)phenyl)-3-(3,6-difluoro-9H-carbazol-9-yl)-2-hydroxy-2-methylpropanamide (204)

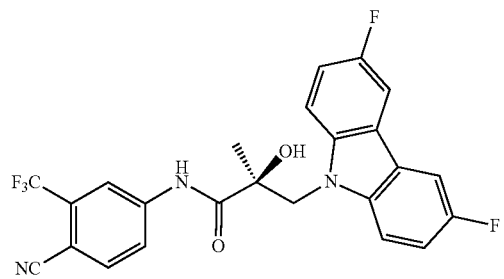 [SMILES: C[C@](O)(Cn1c2ccc(F)cc2c2cc(F)ccc21)C(=O)Nc1ccc(C#N)c(C(F)(F)F)c1]

To a solution of 3,6-difluorocarbazole (0.20 g, 0.00098 mol) in anhydrous THF (10 mL), which was cooled in an ice water bath under an argon atmosphere, was added sodium hydride (60% dispersion in oil, 0.06 g, 0.001476 mol). After addition, the resulting mixture was stirred for three hours. (S)—N-(4-Cyano-3-(trifluoromethyl)phenyl)-2-methyloxirane-2-carboxamide (0.266 g, 0.00098 mol) was added to above solution, and the resulting reaction mixture was allowed to stir overnight at RT under argon. The reaction was quenched by water, and extracted with ethyl acetate. The organic layer was washed with brine, dried with MgSO$_4$, filtered, and concentrated under vacuum. The product was purified by a silica gel column using ethyl acetate and hexane (1:2) as eluent to afford 0.40 g of the titled compound as white solid.

$^1$H NMR (400 MHz, DMSO-d$_6$) 10.33 (s, 1H, NH), 8.22 (d, J=1.6 Hz, 1H, ArH), 8.11 (dd, J=8.8 Hz, J=2.0 Hz, 1H, ArH), 8.05 (d, J=8.8 Hz, 1H, ArH), 7.98 (d, J=2.4 Hz, 1H, ArH), 7.96 (d, J=2.4 Hz, 1H, ArH), 7.68-7.65 (m, 2H, ArH), 7.27-7.22 (m, 2H, ArH), 6.36 (s, 1H, OH), 4.72 (d, J=15.2 Hz, 1H, CH), 4.54 (d, J=15.2 Hz, 1H, CH), 1.53 (s, 3H, CH$_3$).

Mass (ESI, Negative): 471.9[M−H]$^-$; (ESI, Positive): 496.1[M+Na]$^+$.

(S)-3-(9H-Carbazol-9-yl)-N-(3-chloro-4-cyanophenyl)-2-hydroxy-2-methylpropanamide (205)

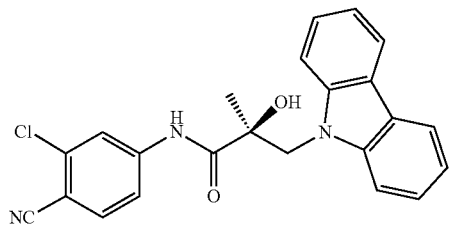

Method B
Yield 77%;
MS (ESI) m/z 402.3 [M−H]$^-$.
$^1$H NMR (400 MHz, CDCl$_3$) δ 8.75 (bs, 1H, NH), 8.08 (d, J=7.6 Hz, 2H), 7.78 (d, J=1.6 Hz, 1H), 7.56-7.54 (m, 3H), 7.44 (t, J=7.6 Hz, 2H), 7.37 (dd, J=8.8, 1.8 Hz, 1H), 7.27-7.25 (m, 2H), 4.78 (d, J=15.6 Hz, 1H), 4.63 (d, J=15.6 Hz, 1H), 2.65 (bs, 1H, OH), 1.66 (s, 3H).

Isoquinoline Derivative (S)—N-(4-Cyano-3-(trifluoromethyl)phenyl)-3-(7-fluoro-3,4-dihydroisoquinolin-2(1H)-yl)-2-hydroxy-2-methylpropanamide (132)

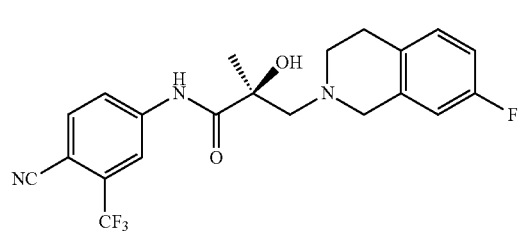

Method A
Yield 69%;
MS (ESI) m/z 420.0 [M−H].
$^1$H NMR (400 MHz, CDCl$_3$) δ 9.09 (bs, 1H, NH), 7.93 (d, J=8.4 Hz, 1H), 7.80 (d, J=8.4 Hz, 1H), 7.05 (t, J=8.0 Hz, 1H), 6.86 (m, 1H), 6.63 (d, J=8.0 Hz, 1H), 3.71 (s, 2H), 3.42 (d, J=13.2 Hz, 1H), 2.91-2.82 (m, 5H), 2.60 (d, J=13.2 Hz, 1H), 1.46 (s, 3H).

Indoline Derivatives (S)—N-(3-Chloro-4-cyanophenyl)-3-(4-fluoroindolin-1-yl)-2-hydroxy-2-methylpropanamide (103)

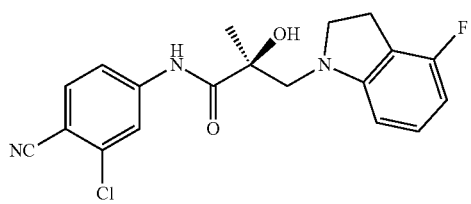 [SMILES: C[C@](O)(CN1CCc2c(F)cccc21)C(=O)Nc1ccc(C#N)c(Cl)c1]

Preparation of LDA solution in THF: To a stirred solution of freshly distilled diisopropylamine (0.14 mL, 1.2 mmol) in anhydrous 5 mL of THF was added a solution of n-butyllithium (0.53 mL, 1.32 mmol, 2.5 M solution in hexane) at −78° C. under argon atmosphere. Under the argon atmosphere into a 100 mL dried two necked round bottom flask equipped with a dropping funnel, the prepared solution of LDA or commercial 2.0 M LDA solution (1.2 mmol, Aldrich) in THF was placed in the flask, and then 4-fluoroindoline (1.0 mmol) in 10 mL of anhydrous THF was dropwise added to the LDA solution at the −78° C. under argon atmosphere. The solution was stirred for 10 min and warmed to 0° C. and cooled down again to −78° C. To the solution, a solution of (R)-3-bromo-N-(3-chloro-4-cyanophenyl)-2-hydroxy-2-methylpropanamide (1.0 mmol in THF) was added through dropping funnel under argon atmosphere at −78° C. and allowed to warm gradually to RT and stirred overnight. And then quenched by an addition of 0.5 mL of sat. NH$_4$C$_1$. The solution was reduced in volume under reduced pressure and dispersed into excess EtOAc, and then dried over anhydrous MgSO$_4$. The solution was concentrated on and purified by flash column chromatography (EtOAc/hexane) or recrystallized from EtOAc/hexane (or DCM/hexane) to give the designed compound, 103.

Yield 71%.
White solid.
MS (ESI) m/z 372.0 [M−H]$^-$.
HRMS (ESI) m/z calcd for C$_{19}$H$_{18}$ClFN$_3$O$_2$: 374.1072. Found: 374.1072 [M+H]$^+$. [α]$_D^{20}$-173° (c 1.0, CH$_3$OH).
$^1$H NMR (acetone-d$_6$, 400 MHz) δ 9.84 (bs, 1H, NH), 8.26 (d, J=2.0 Hz, 1H), 7.90 (dd, J=8.4, 2.0 Hz, 1H), 7.80 (d, J=8.4 Hz, 1H), 6.99 (m, 1H), 6.43 (d, J=8.0 Hz, 1H), 6.31 (t, J=8.4 Hz, 1H), 5.21 (bs, 1H, OH), 3.66 (m, 1H), 3.63 (d, J=14.4 Hz, 1H), 3.53 (q, J=8.0 Hz, 1H), 3.26 (d, J=14.4 Hz, 1H), 2.89 (m, 2H), 1.53 (s, 3H).
$^{13}$C NMR (acetone-d$_6$, 100 MHz) δ 175.9, 160.6 (d, J=239.7 Hz), 160.6 (d, J=9.3 Hz), 144.6, 137.3, 135.6, 129.9 (d, J=8.7 Hz), 120.8, 119.2, 116.7, 114.8 (d, J=21.7 Hz), 107.8, 105.1 (d, J=21.0 Hz), 104.1 (d, J=8.0 Hz), 77.8, 60.4, 56.7, 25.4, 24.3.
$^{19}$F NMR (CDCl$_3$, decoupled) δ 118.95.

(S)—N-(3-Chloro-4-cyanophenyl)-3-(5-fluoroindolin-1-yl)-2-hydroxy-2-methylpropanamide (104)

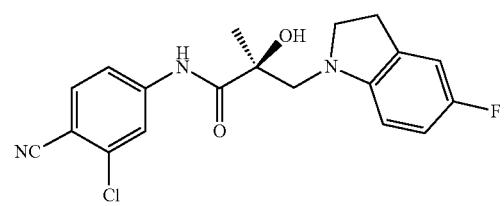 [SMILES: C[C@](O)(CN1CCc2cc(F)ccc21)C(=O)Nc1ccc(C#N)c(Cl)c1]

Method A
Yield; 68%.
$^1$H NMR (400 MHz, CDCl$_3$) δ 9.09 (bs, 1H, NH), 7.98 (d, J=2.0 Hz, 1H), 7.61 (d, J=8.4 Hz, 1H), 7.52 (dd, J=8.4, 2.0 Hz, 1H), 6.83 (m, 1H), 6.77 (m, 1H), 6.51 (m, 1H), 3.62 (d, J=14.4 Hz, 1H), 3.56 (bs, 1H, OH), 3.42 (m, 1H), 3.30 (q, J=9.2 Hz, 1H), 3.21 (d, J=14.4 Hz, 1H), 3.01 (t, J=8.4 Hz, 2H), 1.54 (s, 3H).
MS (ESI) m/z 372.0 [M−H];
[α]$_D^{20}$-202° (c 1.0, CH$_3$OH)
$^{19}$F NMR (CDCl$_3$, decoupled) S 125.35.

(S)—N-(3-Chloro-4-cyanophenyl)-3-(6-fluoroindolin-1-yl)-2-hydroxy-2-methylpropanamide (106)

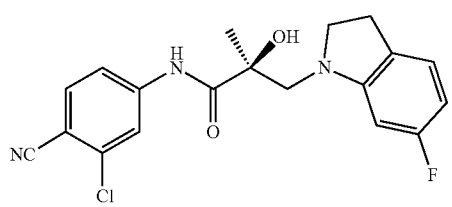

Method A
Yield 76%.
MS (ESI) m/z 372.1 [M−H]$^-$.
$^1$H NMR (400 MHz, CDCl$_3$) δ 9.08 (bs, 1H, NH), 7.97 (d, J=1.6 Hz, 1H), 7.60 (d, J=8.4 Hz, 1H), 7.53 (dd, J=8.4, 1.6 Hz, 1H), 6.77 (m, 1H), 6.39 (m, 1H), 6.33 (d, J=10.0 Hz, 1H), 3.64 (d, J=14.2 Hz, 1H), 3.49 (bs, 1H, OH), 3.47 (m, 1H), 3.38 (q, J=9.2 Hz, 1H), 3.23 (d, J=14.2 Hz, 1H), 2.95 (m, 2H), 1.56 (s, 3H).

(S)-3-(5-Chloro-6-fluoroindolin-1-yl)-N-(4-cyano-3-(trifluoromethyl)phenyl)-2-hydroxy-2-methylpropanamide (107)

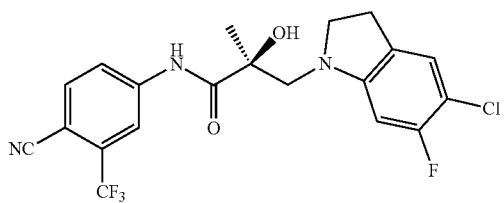 [SMILES: C[C@](O)(CN1CCc2cc(Cl)c(F)cc21)C(=O)Nc1ccc(C#N)c(C(F)(F)F)c1]

Method A
Yield; 47%.
MS (ESI) m/z 440.3 [M−H]⁻
$^1$H NMR (400 MHz, CDCl$_3$) δ 9.15 (bs, 1H, NH), 8.08 (s, 1H), 7.97 (d, J=8.4 Hz, 1H), 7.80 (d, J=8.4 Hz, 1H), 7.03 (d, J=7.2 Hz, 1H), 6.42 (d, J=10.0 Hz, 1H), 3.66 (d, J=14.4 Hz, 1H), 3.52-3.42 (m, 2H), 3.38 (s, 1H, OH), 3.21 (d, J=14.4 Hz, 1H), 2.96-2.80 (m, 2H), 1.52 (s, 3H).

(S)—N-(4-Cyano-3-(trifluoromethyl)phenyl)-3-(5,6-difluoroindolin-1-yl)-2-hydroxy-2-methylpropanamide (108)

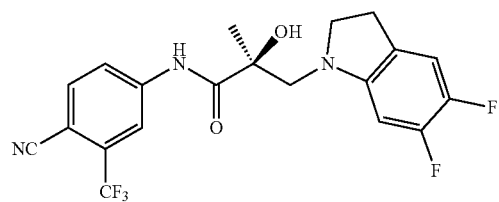

Method A
Yield; 59%.
MS (ESI) m/z 423.9 [M−H]⁻.
$^1$H NMR (400 MHz, CDCl$_3$) δ 9.18 (bs, 1H, NH), 8.09 (d, J=2.0 Hz, 1H), 7.97 (dd, J=8.4, 2.0 Hz, 1H), 7.80 (d, J=8.4 Hz, 1H), 6.89 (t, J=8.8 Hz, 1H), 6.43 (m, 1H), 3.64 (d, J=14.4 Hz, 1H), 3.46 (s, 1H, OH), 3.40-3.35 (m, 2H), 3.17 (d, J=14.4 Hz, 1H), 2.99-2.91 (m, 2H), 1.57 (s, 3H).

(S)—N-(4-Cyano-3-(trifluoromethyl)phenyl)-2-hydroxy-3-(indolin-1-yl)-2-methylpropanamide (109)

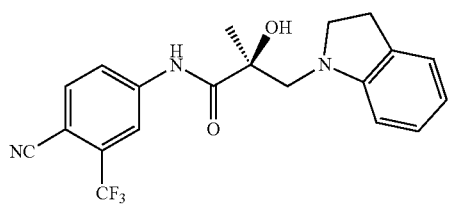 [SMILES: C[C@](O)(CN1CCc2ccccc21)C(=O)Nc1ccc(C#N)c(C(F)(F)F)c1]

Method A
Yield; 69%.
MS (ESI) m/z 387.8 [M−H]⁻.
$^1$H NMR (400 MHz, CDCl$_3$) δ 9.24 (bs, 1H, NH), 8.09 (d, J=2.0 Hz, 1H), 7.94 (dd, J=8.8, 2.0 Hz, 1H), 7.79 (d, J=2.0 Hz, 1H), 7.13-7.10 (m, 2H), 6.78 (dt, J=8.0, 0.8 Hz, 1H), 6.62 (d, J=8.0, 1H), 3.77 (bs, 1H, OH), 3.66 (d, J=14.4 Hz, 1H), 3.54 (t, J=8.4 Hz, 1H), 3.46-3.40 (m, 1H), 3.30 (d, J=14.4 Hz, 1H), 3.04-2.92 (m, 2H), 1.57 (s, 3H).

(S)—N-(3-Chloro-4-cyanophenyl)-3-(5,6-difluoroindolin-1-yl)-2-hydroxy-2-methylpropanamide(110)

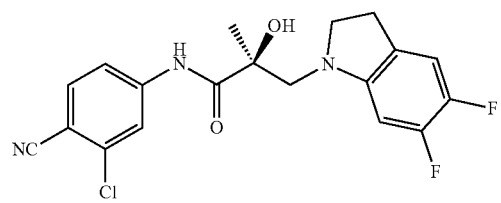 [SMILES: C[C@](O)(CN1CCc2cc(F)c(F)cc21)C(=O)Nc1ccc(C#N)c(Cl)c1]

Method A
Yield 64%.
MS (ESI) m/z 390.0 [M−H]⁻.
$^1$H NMR (400 MHz, CDCl$_3$) δ 9.05 (bs, 1H, NH), 7.98 (s, 1H), 7.62 (d, J=8.2 Hz, 1H), 7.53 (d, J=8.2 Hz, 1H), 6.88 (t, J=8.8 Hz, 1H), 6.43 (m, 1H), 3.64 (d, J=14.4 Hz, 1H), 3.46 (s, 1H, OH), 3.44 (m, 1H), 3.42-3.34 (m, 1H), 3.16 (d, J=14.4 Hz, 1H), 3.95-3.88 (m, 2H), 1.55 (s, 3H).

(S)-3-(5-Bromoindolin-1-yl)-N-(3-chloro-4-cyanophenyl)-2-hydroxy-2-methylpropanamide(114)

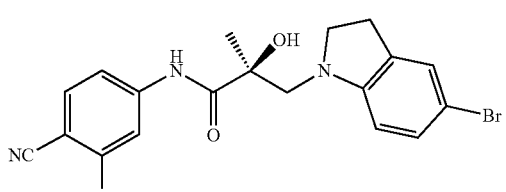

Method A
Yield 54%.
MS (ESI) m/z 433.6 [M−H]⁻.
$^1$H NMR (400 MHz, CDCl$_3$) δ 9.04 (bs, 1H, NH), 7.98 (d, J=2.0 Hz, 1H), 7.60 (d, J=6.0 Hz, 1H), 7.52 (dd, J=6.0, 2.0 Hz, 1H), 7.19-7.17 (m, 2H), 6.49 (d, J=8.4 Hz, 1H), 3.65 (d, J=14.4, 1H), 3.47 (bs, 1H, OH), 3.36-3.41 (m, 1H), 3.32 (q, J=9.2 Hz, 1H), 3.23 (d, J=14.4, 1H), 2.99-2.91 (m, 2H), 1.56 (s, 3H).

(S)—N-(3-Chloro-4-cyanophenyl)-3-(5-fluoro-6-phenylindolin-1-yl)-2-hydroxy-2-methylpropanamide (115)

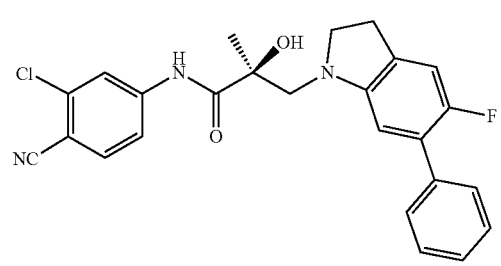 [SMILES: C[C@](O)(CN1CCc2cc(F)c(-c3ccccc3)cc21)C(=O)Nc1ccc(C#N)c(Cl)c1]

To a solution of (S)—N-(3-chloro-4-cyanophenyl)-3-(5-fluoro-6-phenyl-1H-indol-1-yl)-2-hydroxy-2-methylpropanamide (34, 0.185 g, 0.000413 mol) in 5 mL of glacial acetic acid, which was cooled in an ice-water bath, was added drop-wise sodium cyanoborohydride (1.0 M in THF, 0.62 mL, 0.00124 mol) under as argon atmosphere. After addition, the resulting reaction mixture was allowed to stir for overnight at RT under argon. The reaction was quenched by aqueous NH$_4$Cl solution, and extracted with ethyl acetate. The organic layer was washed with brine twice, dried with MgSO$_4$, filtered, and concentrated under vacuum. The product was purified by a silica gel column using ethyl acetate and hexane (1:2) as eluent to afford 0.17 g of the titled compound as yellowish foam.

$^1$H NMR (400 MHz, DMSO-d$_6$) δ 10.29 (s, 1H, NH), 8.21 (d, J=2.0 Hz, 1H, ArH), 7.92-7.84 (m, 2H, ArH), 7.45-7.34 (m, 5H, ArH), 6.95 (d, J=10.4 Hz, 1H, ArH), 6.55 (d, J=6.4 Hz, 1H, ArH), 6.02 (s, 1H, OH), 3.61 (q, J=8.8 Hz, 1H, CH), 4.50 (d, J=14.4 Hz, 1H, CH), 3.40 (d, J=14.4 Hz, 1H, CH), 4.19 (d, J=14.4 Hz, 1H, CH), 2.91 (t, J=8.4 Hz, 2H, CH$_2$), 1.42 (s, 3H, CH$_3$).

Mass (ESI, Negative): [M−H]$^-$; (ESI, Positive): 450.1394 [M+H]$^+$.

Indazole Derivatives (S)—N-(4-Cyano-3-(trifluoromethyl)phenyl)-3-(5-fluoro-1H-indazol-1-yl)-2-hydroxy-2-methylpropanamide (90) and (S)—N-(4-cyano-3-(trifluoromethyl)phenyl)-3-(5-fluoro-1H-indazol-2-yl)-2-hydroxy-2-methylpropanamide(91)

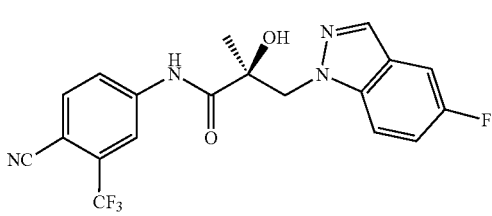

90

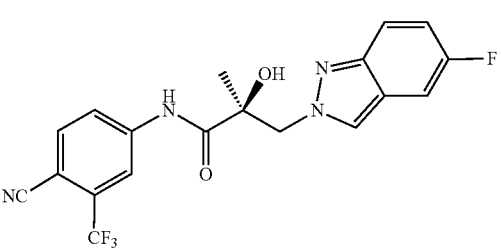

91

Method B

Yield; 67%.

MS (ESI) 405.1 [M−H]$^-$.

$^1$H NMR (400 MHz, CDCl$_3$) δ 9.16 (bs, 1H, NH), 8.05-7.88 (m, 2H), 7.81-7.72 (m, 2H), 7.62-7.13 (m, 4H), 6.72 (bs, OH, 0.56H), 6.15 (s, OH, 0.44H), 4.94 (d, J=13.6 Hz, 0.56H), 4.95 (d, J=14.2 Hz, 0.46H), 4.52 (d, J=13.6 Hz, 0.56H), 4.43 (d, J=14.2 Hz, 0.46H), 1.53 (s, 3H).

(S)—N-(3-Chloro-4-cyanophenyl)-3-(5-fluoro-1H-indazol-1-yl)-2-hydroxy-2-methylpropanamide (92) and (S)—N-(3-chloro-4-cyanophenyl)-3-(5-fluoro-1H-indazol-2-yl)-2-hydroxy-2-methylpropanamide (93)

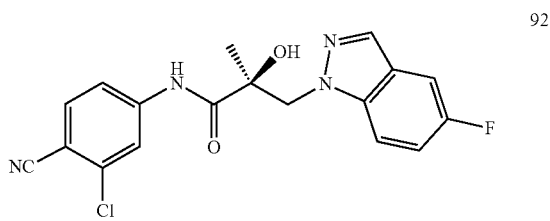

92

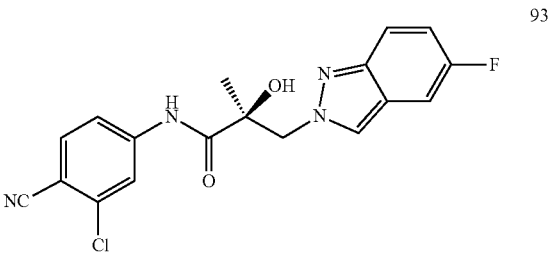

93

Method B

Yield; 74%.

MS (ESI) 370.8 [M−H]$^-$.

$^1$H NMR (400 MHz, CDCl$_3$) δ 8.97 (bs, 1H, NH), 7.99 (s, 0.56H), 7.95 (s, 0.46H), 7.83 (d, J=2.4 Hz, 0.46H), 7.83 (d, J=2.0 Hz, 0.54H), 7.64-7.45 (m, 2H), 7.39-7.31 (m, 1H), 7.24-7.22 (m, 1H), 7.16-7.11 (m, 1H), 6.63 (s, OH, 0.46H), 6.04 (s, OH, 0.54H), 4.92 (d, J=13.6 Hz, 0.46H), 4.92 (d, J=14.0 Hz, 0.54H), 4.50 (d, J=13.6 Hz, 0.46H), 4.40 (d, J=14.0 Hz, 0.54H), 1.58 (s, 3H).

Synthesis of (S)—N-(4-cyano-3-(trifluoromethyl)phenyl)-3-(4-fluoro-1H-indazol-1-yl)-2-hydroxy-2-methylpropanamide (94) and (S)—N-(4-cyano-3-(trifluoromethyl)phenyl)-3-(4-fluoro-2H-indazol-2-yl)-2-hydroxy-2-methylpropanamide(95)

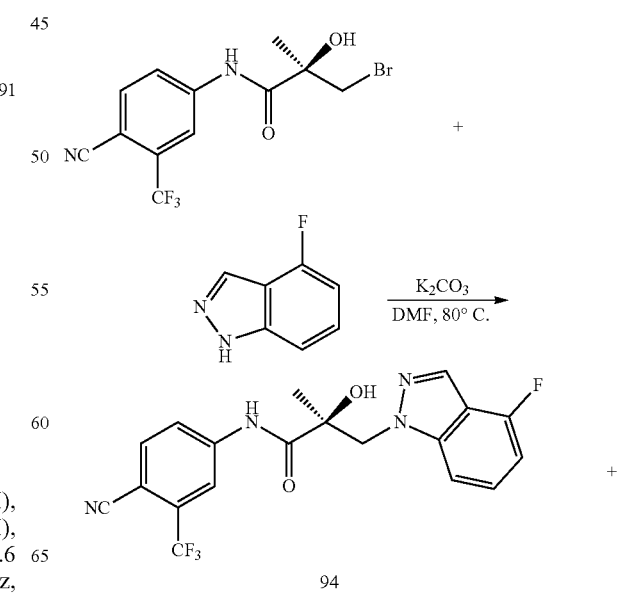

94

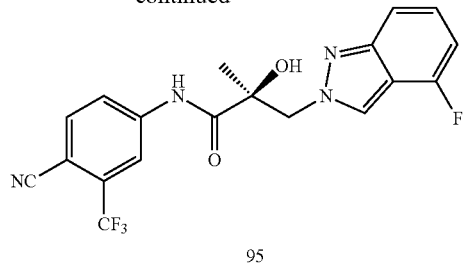

95

To a dry, nitrogen-purged 50 mL round-bottom flask, R-bromo amide of 8R (351 mg, 1 mmol), 4-fluoro-1H-indazole (136 mg, 1 mmol) and $K_2CO_3$ (415 mg, 3 mmol) were dissolved into 10 mL of DMF. The mixture was heated up to 80° C. and stirred overnight at that temperature. The resulting mixture was cooled down to RT. The volume of mixture was reduced under reduced pressure and poured into water, and extracted with ethyl acetate (3 times). The organic layer was dried over $MgSO_4$, concentrated and purified by flash column chromatography (ethyl acetate/hexane 1:2 v/v) on silica gel to produce two products (total 65% yield; 94 (36% yield at $R_f$=0.14) and 95 (29% yield at $R_f$=0.12).

(S)—N-(4-Cyano-3-(trifluoromethyl)phenyl)-3-(4-fluoro-1H-indazol-1-yl)-2-hydroxy-2-methylpropanamide (94)

HRMS (ESI) m/z calcd for $C_{19}H_{15}F_4N_4O_2$: 407.1131 [M+H]$^+$. Found: 407.1150 [M+H]$^+$.
$^1$H NMR (CDCl$_3$, 400 MHz) 9.10 (bs, 1H, NH), 8.11 (d, J=0.8 Hz, 1H), 7.91 (d, J=2.0 Hz, 1H), 7.76 (dd, J=8.4, 2.0 Hz, 1H), 7.71 (d, J=8.4 Hz, 1H), 7.41-7.36 (m, 1H), 7.30 (d, J=8.4 Hz, 1H), 6.80 (dd, J=9.6, 7.2 Hz, 1H), 6.02 (s, 1H, OH), 4.93 (d, J=14.0 Hz, 1H), 4.43 (d, J=14.0 Hz, 1H), 1.53 (s, 3H).
$^{19}$F NMR (CDCl$_3$, 400 MHz) δ −62.25, −117.48.

(S)—N-(4-Cyano-3-(trifluoromethyl)phenyl)-3-(4-fluoro-2H-indazol-2-yl)-2-hydroxy-2-methylpropanamide (95)

HRMS (ESI) m/z calcd for $C_{19}H_{15}F_4N_4O_2$: 407.1131 [M+H]$^+$. Found: 407.1168 [M+H]$^+$.
$^1$H NMR (CDCl$_3$, 400 MHz) 9.15 (bs, 1H, NH), 8.08 (s, 1H), 7.96 (d, J=1.6 Hz, 1H), 7.84 (dd, J=8.8, 1.6 Hz, 1H), 7.74 (d, J=8.8 Hz, 1H), 7.42 (d, J=8.8 Hz, 1H), 7.26 (m, 1H), 6.72 (dd, J=10.0, 7.2 Hz, 1H), 6.67 (bs, 1H, OH), 4.96 (d, J=13.6 Hz, 1H), 4.54 (d, J=13.6 Hz, 1H), 1.54 (s, 3H).
$^{19}$F NMR (CDCl$_3$, 400 MHz) δ −62.41, −116.55.

2-Dimensional nuclear Overhauser effect (NOE) spectroscopy (NOESY): NOESY was used to assign the correct chemical structures to these two isomers. 94 demonstrated NOEs between the aromatic proton located at the 7-position of the indazole ring (annotated as H) and the methylene protons (annotated as $H_1$ and $H_2$),

94

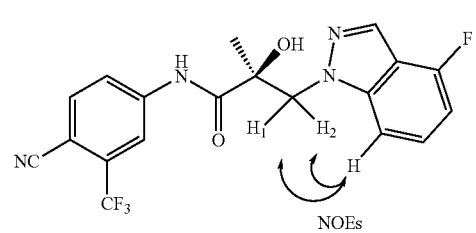

indicating that the point of attachment to the indazole ring must be the 1-position. Whereas for 95, an NOE was observed between 3-position aromatic proton of the indazole ring (annotated as H) and the methylene protons (annotated as $H_1$ and $H_2$),

95

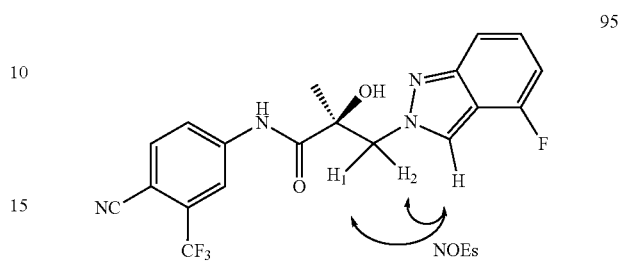

indicating that the point of attachment to the indazole ring must be the 2-position.

Synthesis of (S)—N-(4-cyano-3-(trifluoromethyl)phenyl)-2-hydroxy-2-methyl-3-(4-(trifluoromethyl)-1H-indazol-1-yl)propanamide (96) and (S)—N-(4-cyano-3-(trifluoromethyl)phenyl)-2-hydroxy-2-methyl-3-(4-(trifluoromethyl)-2H-indazol-2-yl)propanamide (97)

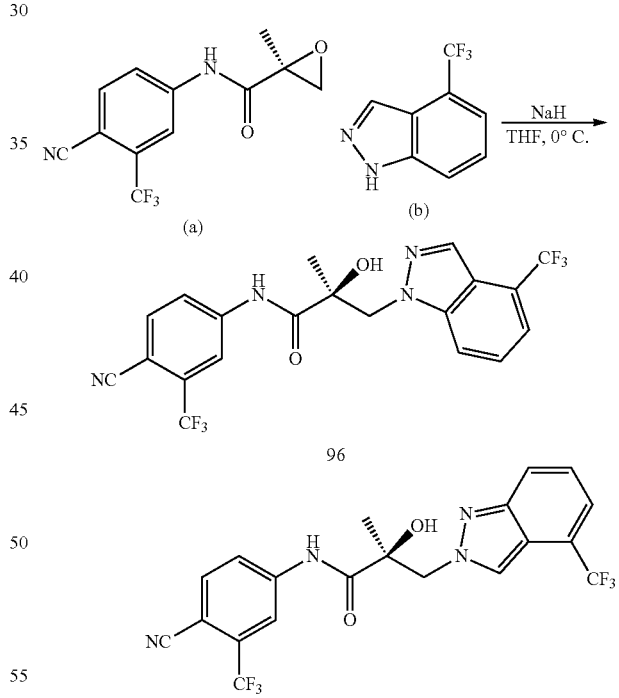

To a dry, nitrogen-purged 100 mL round-bottom flask equipped a dropping funnel under argon atmosphere, NaH of 60% dispersion in mineral oil (160 mg, 4.0 mmol) was added in 30 mL of anhydrous THF solvent to the flask at ice-water bath, and then 4-trifluoromethyl-indazole (b) (372 mg, 2.0 mmol) was stirred in over 30 min at the ice-water bath. Into the flask, a prepared solution of epoxide (a), (541 mg, 2.0 mmol) in 10 mL of anhydrous THF was added through dropping funnel under argon atmosphere at the ice-water bath and stirred overnight at RT. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography as an eluent EtOAc/hexane at a 1:2 ratio to produce compounds 97 (22.9%, @ rf=0.29) and 96 (30.1%, @ rf=0.37) as white solids (total 53% yield).

(S)—N-(4-Cyano-3-(trifluoromethyl)phenyl)-2-hydroxy-2-methyl-3-(4-(trifluoromethyl)-1H-indazol-1-yl)propanamide (96)

HRMS (ESI) m/z calcd for $C_2H_{14}F_6N_4O_2$ Exact Mass: 457.1099 [M+H]⁺. Found: 457.1117 [M+H]⁺.

¹H NMR (CDCl₃, 400 MHz) δ 9.08 (bs, 1H, NH), 8.19 (t, J=1.2 Hz, 1H), 7.90 (d, J=1.6 Hz, 1H), 7.61-7.70 (m, 3H), 7.55-7.47 (m, 2H), 5.93 (bs, 1H, OH), 5.01 (d, J=14.0 Hz, 1H), 4.47 (d, J=14.0 Hz, 1H), 1.55 (s, 3H).

¹⁹F NMR (CDCl₃, 400 MHz) δ −61.54, 62.27.

(S)—N-(4-Cyano-3-(trifluoromethyl)phenyl)-2-hydroxy-2-methyl-3-(4-(trifluoromethyl)-2H-indazol-2-yl)propanamide (97)

HRMS (ESI) m/z calcd for $C_2H_{14}F_6N_4O_2$ Exact Mass: 457.1099 [M+H]⁺. Found: 457.1110 [M+H]⁺.

¹H NMR (CDCl₃, 400 MHz) δ 9.09 (bs, 1H, NH), 8.14 (s, 1H), 7.92 (d, J=2.0 Hz, 1H), 7.85-7.82 (m, 1H), 7.73 (d, J=8.4 Hz, 1H), 7.44 (dt, J=6.8, 0.8 Hz, 1H), 7.41 (q, J=8.4 Hz, 1H), 6.56 (bs, 1H, OH), 4.98 (d, J=14.0 Hz, 1H), 4.57 (d, J=14.0 Hz, 1H), 1.54 (s, 3H).

¹⁹F NMR (CDCl₃, 400 MHz) δ −61.28, 62.55.

2-Dimensional nuclear Overhauser effect (NOE) spectroscopy (NOESY): NOESY was used to assign the correct chemical structures to these two isomers. 96 demonstrated an NOE between the aromatic proton located at the 7-position of the indazole ring (annotated as H₂) and the methylene protons (each annotated as H),

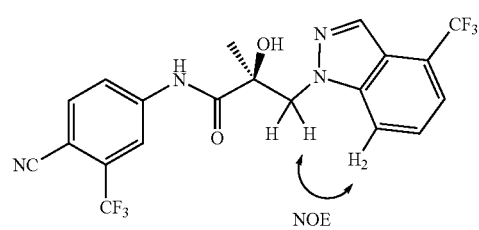

96 indicating that the point of attachment to the indazole ring must be the 1-position. Whereas for 97, an NOE was observed between 3-position aromatic proton of the indazole ring (annotated as H₁) and the methylene protons (each annotated as H),

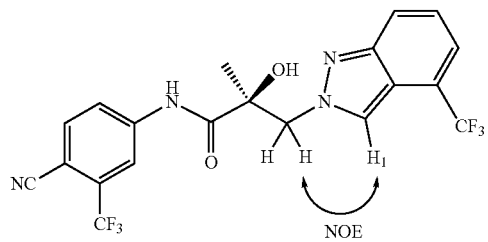

97 indicating that the point of attachment to the indazole ring must be the 2-position.

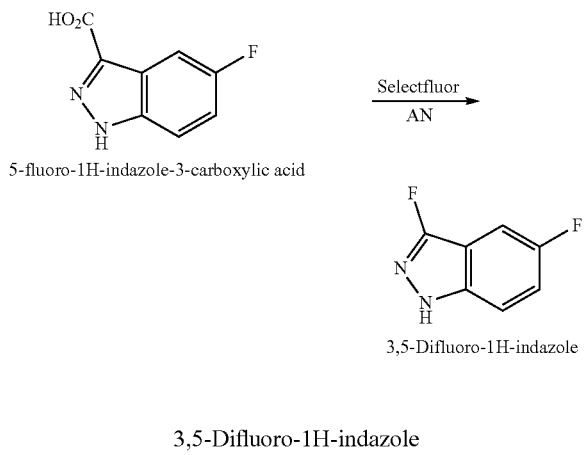

5-fluoro-1H-indazole-3-carboxylic acid 3,5-Difluoro-1H-indazole 3,5-Difluoro-1H-indazole To a 50 mL round-bottle flask with a magnetic stirring bar were added Selectfluor® (872 mg, 2.0 mmol, 2.0 equiv), Li₂CO₃ (296 mg, 4.0 mmol, 4.0 equiv), dichloromethane (3.3 mL) and water (1.7 mL). Then 5-fluoro-1H-indazole-3-carboxylic acid (1.0 mmol, 1.0 equiv) was added. The reaction mixture was stirred for 2 hours in ice bath. The reaction mixture was diluted with water (40 mL), followed by extracting with DCM (20 mL×2). The combined organic extracts were washed with brine, dried over anhydrous sodium sulfate and concentrated in vacuo. The crude product was purified by flash column chromatography (n-hexane:DCM=2:1) to afford the desired product.

Yield 48%;

MS (ESI) m/z 152.0 [M−H];

¹H NMR (CDCl₃, 400 MHz) δ 9.80 (bs, 1H, NH), 7.37 (dt, J=8.8, 2.4 Hz, 1H), 7.31 (dd, J=8.0, 1.6 Hz, 1H), 7.23 (td, J=8.8, 2.0 Hz, 1H);

¹⁹F NMR (CDCl₃) δ-121.46 (d, $J_{F-F}$=4.4 Hz), −133.92 (d, $J_{F-F}$=4.4 Hz).

(R)-3-bromo-N-(4-cyano-3-(trifluoromethyl)phenyl)-2-hydroxy-2-methylpropanamide

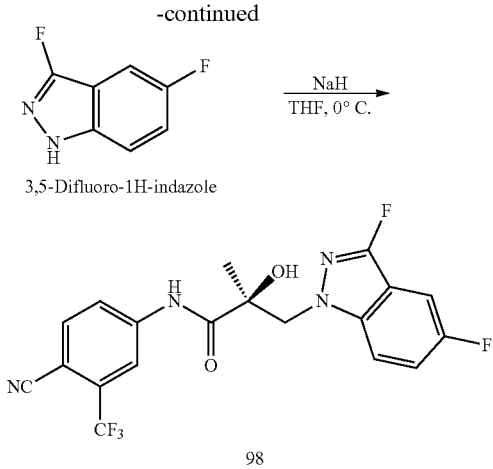

3,5-Difluoro-1H-indazole (S)—N-(4-Cyano-3-(trifluoromethyl)phenyl)-3-(3,5-difluoro-1H-indazol-1-yl)-2-hydroxy-2-methylpropanamide(98)

To a dry, nitrogen-purged 50 mL round-bottom flask equipped with a dropping funnel under argon atmosphere, NaH of 60% dispersion in mineral oil (32 mg, 0.8 mmol) was added in 5 mL of anhydrous THF solvent in the flask at ice-water bath, and 3,5-difluoro-1H-indazole (60 mg, 0.41 mmol) was stirred 30 min at the ice-water bath. Into the flask, (R)-3-bromo-N-(4-cyano-3-(trifluoromethyl)phenyl)-2-hydroxy-2-methylpropanamide (148 mg, 0.41 mmol) in 5 mL of anhydrous THF was added through dropping funnel under argon atmosphere at the ice-water bath and stirred overnight at room temperature. After adding 1 mL of H2O, the reaction mixture was condensed under reduced pressure, and then dispersed into 50 mL of EtOAc, washed with 50 mL (×2) water, evaporated, dried over anhydrous $MgSO_4$, and evaporated to dryness. The mixture was purified with flash column chromatography as an eluent EtOAc/hexane=2/3 to produce 98 as white solid.

Yield=57%;

MS (ESI) m/z 423.17 [M−H]$^-$; 447.21 [M+Na]$^+$.

$^1$H NMR (CDCl$_3$, 400 MHz) δ 9.07 (bs, 1H, NH), 7.92 (s, 1H), 7.78 (d, J=8.6 Hz, 1H), 7.73 (d, J=8.6 Hz, 1H), 7.42 (d, J=8.4 Hz, 1H), 7.28 (m, 1H), 7.25 (m, 1H), 5.28 (bs, 1H, OH), 4.82 (d, J=14.0 Hz, 1H), 4.27 (d, J=14.0 Hz, 1H), 1.52 (s, 3H);

$^{19}$F NMR (CDCl$_3$, 400 MHz) δ −61.27, −120.39, −131.15; assigned by 2D NMR as NOE and COSY.

Example 5

Androgen Receptor Binding, Transactivation, and Metabolism of Indole, Benzimidazole, and Indazole SARDs Ligand Binding Assay Objective: To determine SARD binding affinity to the AR-LBD.

Method: hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-2}$ M) were incubated with [$^3$H]mibolerone and AR LBD using the conditions described above. Following incubation, the ligand bound AR-LBD complex was isolated using BioGel® HT hydroxyapatite, washed and counted in a scintillation counter after adding scintillation cocktail. Values are expressed as $K_i$.

Transactivation Assay for Wt and Mutant AR

Objective: To determine the effect of SARDs on androgen-induced transactivation of AR wildtype (wt) or AR carrying known AR-LBD mutants (i.e., W741L or T877A).

Figure 1A:
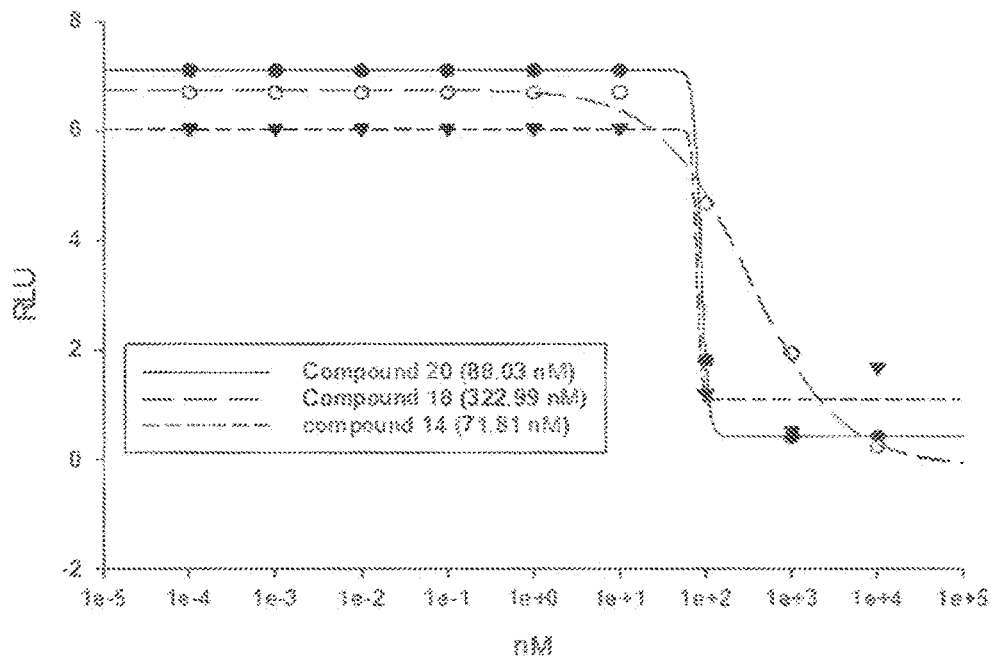
FIGS. 1A-1C present inhibition of AR transactivation for the SARD compounds.
Figure 1A:
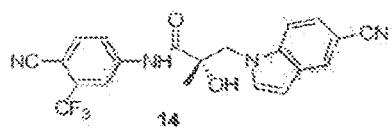
Figure 1A:
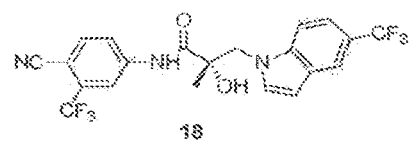
Figure 1A:
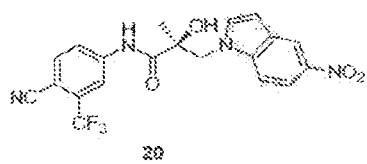
Figure 1B:
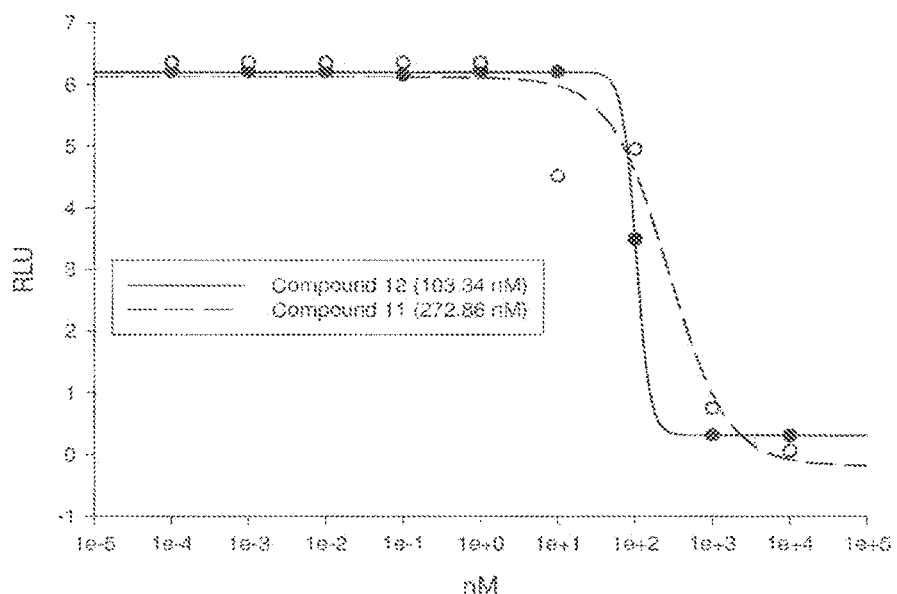
Figure 1B:
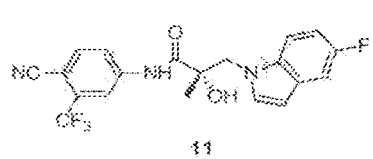
Figure 1B:
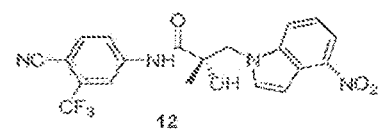
Figure 1C:
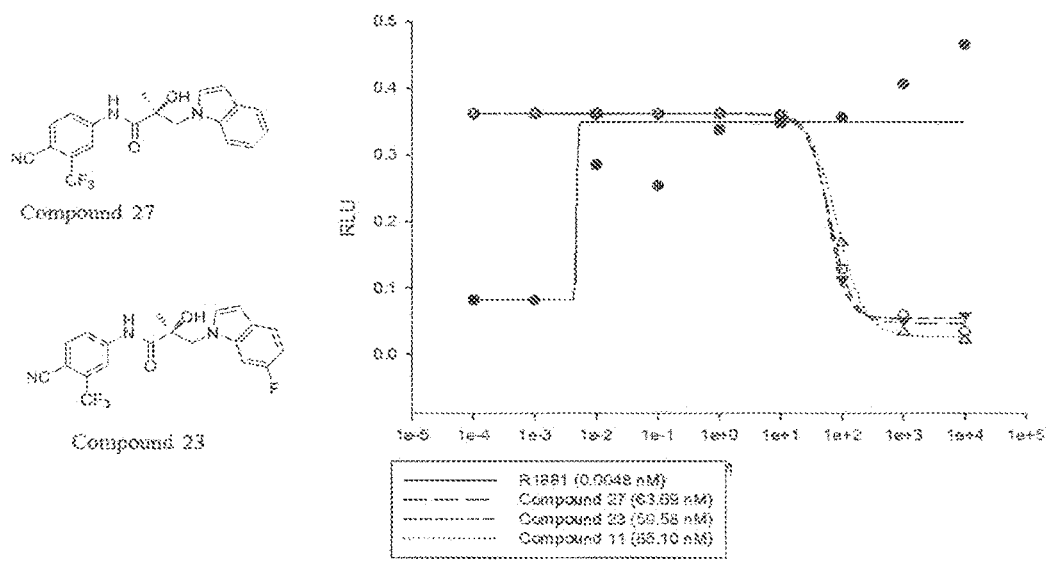

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR ($W_{741}$L) or CMV-hAR(T877A) using lipofectamine transfection reagent in optiMEM medium. Medium was changed 24 h after transfection to DME+5% csFBS without phenol red and treated with a dose response of various drugs (Table 1: 11-18, 20-27, 30, 31, 33, 70-74) (1 pM to 10 µM). SARDs and antagonists were treated in combination with known agonist 0.1 nM R1881 in order to produce an antagonism curve. Luciferase assay was performed 24 h after treatment on a Biotek synergy 4 plate reader. Firefly luciferase values were normalized to renilla luciferase values. For FIG. 1A-1C, the following variation of the method was used:

HEK cells were plated in 24 well plates at 60,000 cells per well in DMEM+5% csFBS without phenol red. After overnight incubation, changed medium to OptiMEM (0.25 ml). All the wells were transfected with 0.25 ug GRE-LUC, 5 ng CMV-renilla LUC, and 25 ng CMV-hAR. Twenty four hours after transfection, medium was replaced with 1 ml of DME+5% csFBS without phenol red. Twenty-four hrs after transfection, the cells were treated with 20, 18, and 14 (FIG. 1A), 12 and 11 (FIG. 1B), 11, 27, and 23 (FIG. 1C), or 34-42 (FIGS. 29A, 29B, 29D-29I, 29K, & 29O) and were harvested 48 hrs after transfection and firefly and renilla luciferase assay performed.

Transactivation. HEK-293 cells were plated at 120,000 cells per well of a 24 well plate in DME+5% csFBS. The cells were transfected using Lipofectamine (Invitrogen, Carlsbad, Calif.) with 0.25 g GRE-LUC, 0.01 g CMV-LUC (renilla luciferase) and 25 ng of the AR, PR, GR, or MR. The cells were treated 24 hrs after transfection as indicated in the figures and the luciferase assay performed 48 hrs after transfection. Data are represented as $IC_{50}$ values obtained from four parameter logistics curve.

AR Degradation Using Compounds of this Invention

Objective: To determine the efficacy and potency of AR degradation by SARD compounds in AD1 cells (full-length), LNCaP (T877A AR), D567es (splice variant lacking exons 5,6,&7) or 22RV-1 (full length AR and truncated splice variant AR (AR-V7)) cell lines.

Method: See Example 6 below.

Determination of Metabolic Stability (In Vitro $CL_{int}$) of Test Compounds:

Phase I Metabolism

The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (μl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

LC-MS/MS analysis: The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guardcartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage (IS) of −4200 V (negative mode). Declustering potential, entrance potential, collision energy, product ion mass, and cell exit potential were optimized for each compound.

Log P: Octanol-Water Partition Coefficient (Log P)

Log P is the log of the octanol-water partition coefficient, commonly used early in drug discovery efforts as a rough estimate of whether a particular molecule is likely to cross biological membranes. Log P was calculated using ChemDraw Ultra version is 12.0.2.1016 (Perkin-Elmer, Waltham, Mass. 02451). Calculated Log P values are reported in Tables 3 & 6 in the column labeled Log P (~0.4 to +5.6). Lipinski's rule of five is a set of criteria intended to predict oral bioavailability. One of these criteria for oral bioavailability is that the Log P is between the values shown in the column heading (−0.4 (relatively hydrophilic) to +5.6 (relatively lipophilic) range), or more generally stated <5. One of the goals of SARD design was to improve water solubility.

TABLE 1

AR Binding, Inhibition of AR (wt and Mutant) Transactivation, AR Degradation and in vitro Metabolic Stability of Indole and Benzimidazole SARDs.

| Compound | Binding $K_i$ (nM) | Transcriptional Activation (+0.1 nM R1881; R1881 $EC_{50}$ = 0.11 nM) | | | SARD activity (FIG. numbers herein) | $T_{1/2}$ (min) $CL_{int}$ (μl/min/mg) |
| --- | --- | --- | --- | --- | --- | --- |
| | | Wt $IC_{50}$ (nM) | W741L $IC_{50}$ (nM) | T877A $IC_{50}$ (nM) | | |
| DHT | 1 | — | — | — | | |
| R-Bicalutamide | 545.5 | 248.2 | — | 557 | | |
| Enzalutamide | 205.2 | 216.3 | 939 | 331.94 | 3, 9C | |
| ARN-509 (apalutamide) | — | 297.0 | 1939.41 | 390.50 | 3, 5, 6B, 14 | |
| ASC-J9 | — | 1008.0 | 3487.68 | 2288.16 | 5, 6A | |
| 11 | 57.8 | 33.4-272 | 13.68 | 48.47 | 2A, 3, 5, 6C, 9C | 12.35 min 56.14 μl/min/mg |
| 11R | — | 351.21 | — | — | | |
| 12 | 314.22 | 103.34 | | | 3, 11, 14 | 37.27 18.6 |
| 13 | 625.01 | — | | | 3 | |
| 14 | 223.74 | 71.81 (partial) | | | | 15.97 43.4 |
| 15 | >10,000 | — | | | | 29.79 23.28 |
| 16 | 489.88 | 2285.14 | | | | |
| 17 | 80.43 | | | | | |
| 18 | 416.03 | 322.99 | | | | 21.07 32.9 |
| 20 | 432.69 | 88.03 | | | 2A, 3, 4, 11, 12 | 19.27 35.97 |
| 21 | 293.84 | 984.52 | | | | 20.37 34.02 |
| 22 | 419.35 | 126.73 | | | | 36.32 19.08 |
| 23 | 212.49 | 85.10 | | | 11 | 22.39 30.96 |
| 24 | 315.84 | 917.68 | | | 12 | 17.02 40.73 |
| 27 | 2079.94 | 63.69 | | | 11 | 13.66 50.75 |

TABLE 1-continued

AR Binding, Inhibition of AR (wt and Mutant) Transactivation, AR Degradation
and in vitro Metabolic Stability of Indole and Benzimidazole SARDs.

| Compound | Binding $K_i$ (nM) | Transcriptional Activation (+0.1 nM R1881; R1881 $EC_{50}$ = 0.11 nM) Wt $IC_{50}$ (nM) | W741L $IC_{50}$ (nM) | T877A $IC_{50}$ (nM) | SARD activity (FIG. numbers herein) | $T_{1/2}$ (min) $CL_{int}$ (μl/min/mg) |
|---|---|---|---|---|---|---|
| 30 | 995.23 | 971.78 (11 38 nM in the same exp) | | | 12 | 25.78 26.89 |
| 31 | 547.27 | 157.41 | | | 13, 15 | 21.77 31.84 |
| 33 | >10,000 | 684.64 | | | | |
| 70 | 530.72 | 299.78 | | | 16 | |
| 72 | — | 1016 | | | | |
| 32 | 46.58 | 57.76 | | | 11 | 13.48 51.43 |
| 73 | 724.07 | 998.56 | | | 16 | |
| 74 | 1399.69 | 720.61 | | | | |

The short half-lives ($t_{1/2}$) and high metabolic clearance ($CL_{int}$) values in vitro of many of the compounds of this invention suggest rapid plasma clearance which could be favorable for topical treatment of androgenic dermatologic disorders as it would limit the risk of systemic side effects, even if the skin is penetrated.

AR transactivation assay was performed with wildtype, W741L, and T877A AR constructs. W741 mutation to leucine or cysteine (L/C) confers resistance to bicalutamide (Hara, T., Miyazaki, J., Araki, H., Yamaoka, M., Kanzaki, N., Kusaka, M., and Miyamoto, M. (2003). Novel mutations of androgen receptor: a possible mechanism of bicalutamide withdrawal syndrome. Cancer Research 63, 149-153), while T877 mutation results in resistance to hydroxyflutamide (Tan, J., Sharief, Y., Hamil, K. G., Gregory, C. W., Zang, D. Y., Sar, M., Gumerlock, P. H., deVere White, R. W., Pretlow, T. G., Harris, S. E., et al. (1997). Dehydroepiandrosterone activates mutant androgen receptors expressed in the androgen-dependent human prostate cancer xenograft CWR22 and LNCaP cells. Mol Endocrinol 11, 450-459). 11 potently inhibited the R1881-induced wildtype AR transactivation with much higher potency than enzalutamide (FIG. 37A). While 11 effectively antagonized both wildtype and mutant ARs comparably, similar to enzalutamide, was weaker in W741L mutant AR (FIG. 37B). Although 11 inhibited glucocorticoid receptor (GR) and mineralocorticoid receptor (MR) transactivation only at ~10 μM, it cross-reacted with the progesterone receptor (PR) robustly (FIG. 37C).

Kennedy's disease is a neuromuscular disease caused by AR with an extended polyglutamine tract (La Spada, A. R., Wilson, E. M., Lubahn, D. B., Harding, A. E., and Fischbeck, K. H. (1991). Androgen receptor gene mutations in X-linked spinal and bulbar muscular atrophy. Nature 352, 77-79). While in normal healthy humans, the AR contains 15-24 polyglutamines, in patients suffering from Kennedy's disease, the polyglutamine tracts are extended to over 40 or even 100 repeats (La Spada et al., 1991). This extended polyglutamine tract results in AR mis-folding causing neuromuscular toxicity (La Spada et al., 1991).

11 was tested in a transactivation assay with the AR containing an extended polyglutamine tract. 11 inhibited the R1881-stimulated transactivation of the AR that contains 65 polyglutamine repeats (FIG. 37D) with an $IC_{50}$ value comparable to that observed with the wildtype AR.

AR N—C interaction is a measure of the AR activity (He et al., 2002) and inhibiting the AR N—C interaction is another measure of antagonistic activity. A mammalian two hybrid assay was performed with a Gal-4-DBD-fused AR-LBD, VP16 activation domain fused AR-NTD, and a dose response of 11. 11 inhibited the R1881-induced AR N—C interaction at concentrations comparable to that observed in AR transactivation (FIG. 37E).

TABLE 2

Binding Affinity of Indole SARDs of this Invention.

| Compound | $K_i$ (nM) | Relative binding affinity (RBA) |
|---|---|---|
| DHT | 8.88 6.62 | 1.00 |
| 12 | 817.3 | 0.011 |
| 11 | 57.8 | 0.152 |
| 11R | 333.07 | 0.027 |
| 14 | 179.77 | 0.049 |
| 15 | 663.05 | 0.010 |

FIGS. 1A-1C and FIGS. 29A-29O and Tables 1-3 show that many of the SARDs of this invention had higher AR binding affinity (see tables) and more potent AR antagonism in vitro (see Tables 1-4 and figures referenced above and in the tables) than all the other AR antagonists tested (bicalutamide, enzalutamide, ARN-509, and ASC-J9). Further compounds 11-(Table 1 above) and 96 (Table 10 of Example 10) retained highly potent antagonist activity in the two resistance mutants tested unlike the known antiandrogens tested.

TABLE 3

AR Binding ($K_i$), Inhibition of AR Transactivation ($IC_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | $K_i$ (nM) (DHT = 1 nM) | $IC_{50}$ (nM) | Full Length % inhibition at 1, 10 μM | S.V. (22RV1) % inhibition at 10 μM | $T_{1/2}$ (min) | $CL_{int}$ (μL/min/mg) |
| Enobosarm | 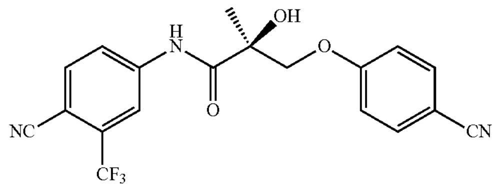 [SMILES: C[C@](O)(COc1ccc(C#N)cc1)C(=O)Nc1ccc(C#N)c(C(F)(F)F)c1] | 3.44 | 20.21 | ~20 | | | | |
| R-Bicalutamide | 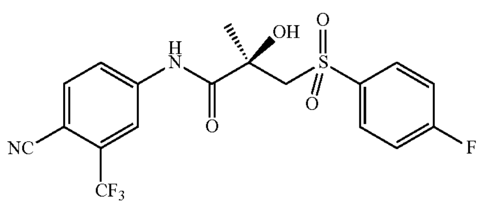 [SMILES: C[C@](O)(CS(=O)(=O)c1ccc(F)cc1)C(=O)Nc1ccc(C#N)c(C(F)(F)F)c1] | 2.57 | 508.84 | 248.2 | | | | |
| Enzalutamide | 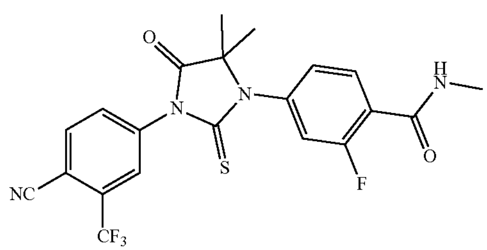 [SMILES: CNC(=O)c1ccc(N2C(=S)N(c3ccc(C#N)c(C(F)(F)F)c3)C(=O)C2(C)C)cc1F] | 4.56 | 3641.29 | 216.3 | | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| ARN-509 (apalutamide) | | 3.47 | 1452.29 | | 0 | 0 | | |
| | | 2.57 | 87.67 | | | | | |
| | | 1.86 | 407.08 | | | | | |
| 27 | | 3.31 | 2079.94 | 63.69 | 13, 89 | | 13.66 | 50.75 |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) |
|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) CL$_{int}$ (μL/min/mg) |
| 22 | 4-F indole structure | 3.47 | 419.35 | 126.73 | 54, 81 | | 36.32 / 19.08 |
| 11 | 5-F indole structure | 3.47 | 267.39 | 85.10 | 65-83 | 60-100 | 12.35 / 56.14 |
| 11R | 5-F indole structure | 3.47 | >10000 | 589.84 | 83 | | |
| 23 | 6-F indole structure | 3.47 | 212.49 | 85.10 | 0, 100 | | 22.39 / 30.96 |

TABLE 3-continued

AR Binding ($K_i$), Inhibition of AR Transactivation ($IC_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | $K_i$ (nM) (DHT = 1 nM) | $IC_{50}$ (nM) | Full Length % inhibition at 1, 10 μM | S.V. (22RV1) % inhibition at 10 μM | $T_{1/2}$ (min) | $CL_{int}$ (μL/min/mg) |
| 12 | 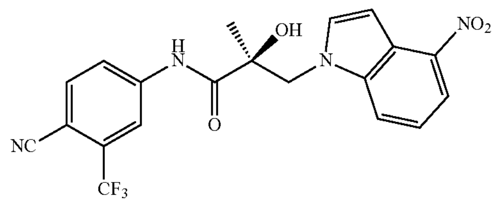 [SMILES: C[C@](O)(Cn1ccc2c([N+](=O)[O-])cccc21)C(=O)Nc1ccc(C#N)c(C(F)(F)F)c1] | 3.34 | 314.22 | 103.34 | 43, 100 | | 37.27 | 18.6 |
| 20 | 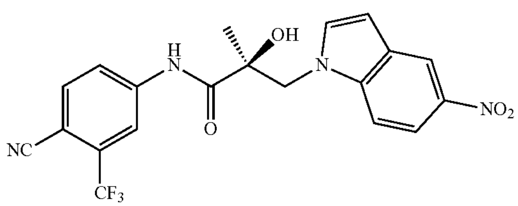 | 3.34 | 432.69 | 88.03 | 45, 100 | 78 | 19.27 | 35.97 |
| 32 | 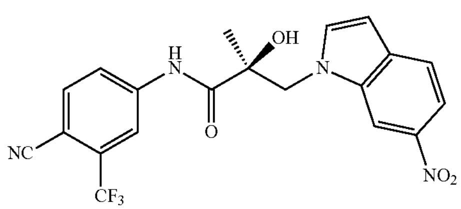 [SMILES: C[C@](O)(Cn1ccc2ccc([N+](=O)[O-])cc21)C(=O)Nc1ccc(C#N)c(C(F)(F)F)c1] | 3.34 | 46.58 | 57.76 | 0, 100 | | 13.48 | 51.43 |
| 24 | 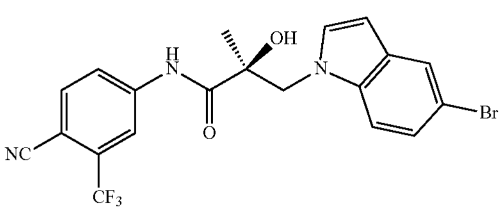 [SMILES: C[C@](O)(Cn1ccc2cc(Br)ccc21)C(=O)Nc1ccc(C#N)c(C(F)(F)F)c1] | 4.14 | 315.84 | 917.68 | | 0 | 17.02 | 40.73 |

TABLE 3-continued

AR Binding ($K_i$), Inhibition of AR Transactivation ($IC_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | $K_i$ (nM) (DHT = 1 nM) | $IC_{50}$ (nM) | Full Length % inhibition at 1, 10 µM | S.V. (22RV1) % inhibition at 10 µM | $T_{1/2}$ (min) | $CL_{int}$ (µL/min/mg) |
| 21 | 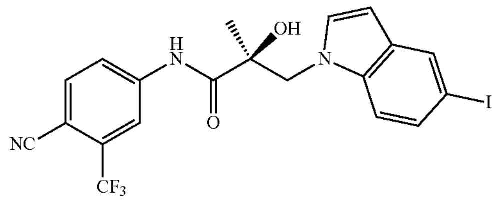 | 4.67 | 293.84 | 984.52 | | 13 | 20.37 | 34.02 |
| 18 | 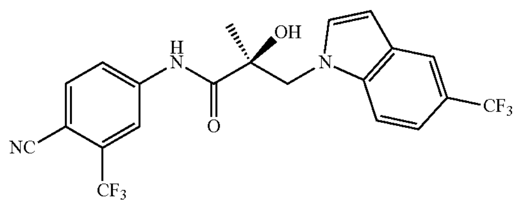 [SMILES: C[C@](O)(Cn1ccc2cc(C(F)(F)F)ccc21)C(=O)Nc1ccc(C#N)c(C(F)(F)F)c1] | 4.23 | 416.03 | 335.98 | 74, 79 | 47 | 21.07 | 32.9 |
| 16 | 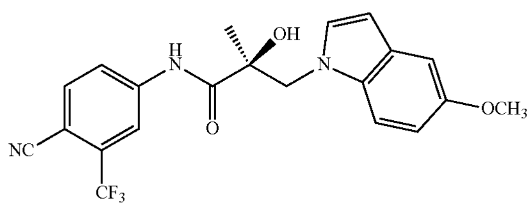 [SMILES: COc1ccc2c(ccn2C[C@](C)(O)C(=O)Nc2ccc(C#N)c(C(F)(F)F)c2)c1] | 3.18 | 489.88 | 2285.14 | | | | |
| 13 | 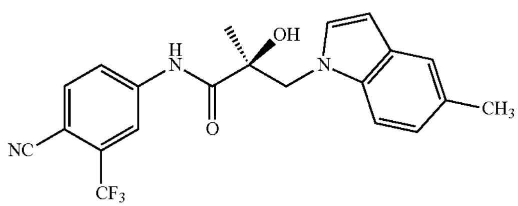 | 3.80 | 625.01 | | 52, 86 | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| 17 | (5-Cl indole, OH, Me, amide, 4-CN-3-CF$_3$-phenyl) | 3.87 | 80.43 | 545.48 | 0, 0 | | | |
| 14 | (5-CN indole, OH, Me, amide, 4-CN-3-CF$_3$-phenyl) | 3.34 | 223.74 | 71.81 (partial antagonism) 1018.73 (agonist EC$_{50}$)) | | | 15.97 | 43.4 |
| 15 | (3-CO$_2$H indole, OH, Me, amide, 4-CN-3-CF$_3$-phenyl) | 2.87 | >10,000 | | | | 29.79 | 23.28 |

TABLE 3-continued
AR Binding (K$_i$), Inhibition of AR Transactivation (IC$_{50}$), AR Degradation and Metabolic Stability of Indole Based SARDs.
| | | Binding/Transactivation (wt AR) | | SARD Activity | | DMPK (MLM) | |
|---|---|---|---|---|---|---|---|
| | | | | Full Length | S.V. (22RV1) | | |
| Compd ID | Structure | K$_i$ (nM) (DHT = 1 nM) | IC$_{50}$ (nM) | % inhibition at 1, 10 µM | % inhibition at 10 µM | T$_{1/2}$ (min) | CL$_{int}$ (µl/min/mg) |
| | Log P (−0.4 to +5.6) | | | | | | |
| 19 |  5.33 | | | | | | |
| |  6.09 | | | | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| 30 | 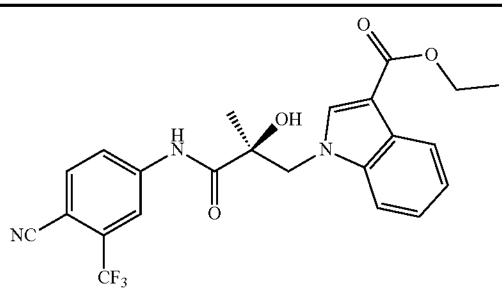 | 3.47 | 995.23 | 971.78 (11 was 38 nM in the same exp) | | | 25.78 | 26.89 |
| 31 | 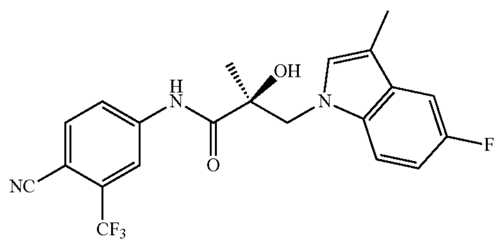 [SMILES: Cc1cn(C[C@](C)(O)C(=O)Nc2ccc(C#N)c(C(F)(F)F)c2)c2ccc(F)cc12] | 3.95 | 547.27 | 157.41 | | | 21.77 | 31.84 |
| 70, 71 (mixture) | 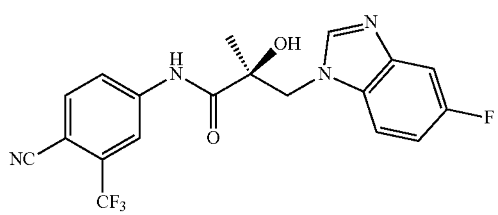 | 2.70 | 530.72 | 299.78 | 50 | | 48.58 | 14.27 |

TABLE 3-continued

AR Binding (K_i), Inhibition of AR Transactivation (IC_50), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K_i (nM) (DHT = 1 nM) | IC_50 (nM) | Full Length % inhibition at 1, 10 μM | S.V. (22RV1) % inhibition at 10 μM | T_{1/2} (min) | CL_{int} (μL/min/mg) |
| 72 | | 4.56 | | 1016 | | | | |
| 73 | | 2.86 | 724.07 | 998.56 | 7, 68 | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| 74 | | 3.50 | 1399.69 | 720.61 | 51 | 0 | | |
| 75 | | 2.70 | >1000 | 973.15 | 14 (FIG. 33B) | | | |
| 76 | | 2.70 | 1588.62 | 1023.94 | (FIG. 33A) | | | |
| 77 | | 3.47 | 492.56 | >10,000 | 50 | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 µM | S.V. (22RV1) % inhibition at 10 µM | T$_{1/2}$ (min) | CL$_{int}$ (µL/min/mg) |
| 78 | 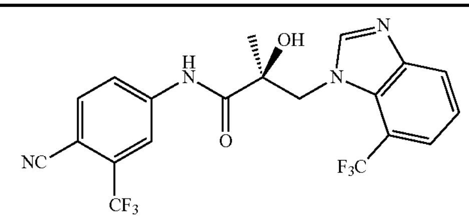 | 3.47 | 474.38 | 3616 | 76 | | | |
| 79 | 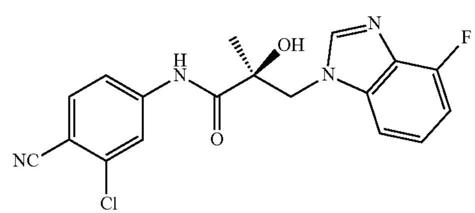 [SMILES: C[C@](O)(Cn1cnc2c(F)cccc21)C(=O)Nc1ccc(C#N)c(Cl)c1] | 2.34 | 882.75 | 1661.97 | | | | |
| 80 | 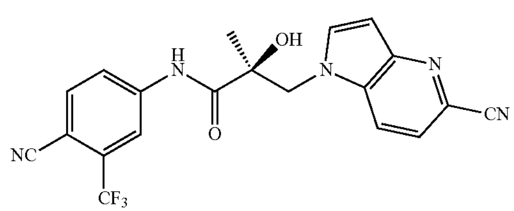 [SMILES: C[C@](O)(Cn1ccc2nc(C#N)ccc21)C(=O)Nc1ccc(C#N)c(C(F)(F)F)c1] | 2.85 | >10,000 | 684.64 | | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| 33 | (structure: 5-fluoro-6-phenyl indole with N-CH$_2$-C(OH)(CH$_3$)-C(O)NH-(3-CF$_3$-4-CN-phenyl)) | 5.14 | 124.66 | 214.66 | 54 | 22 | 15.43 | 44.94 |
| 34 | (structure: 5-fluoro-6-phenyl indole with N-CH$_2$-C(OH)(CH$_3$)-C(O)NH-(3-Cl-4-CN-phenyl)) | 4.78 | 132.94 See FIG. 29O | 202.67 See FIG. 29O | 55 (FIG. 29O) | 41 (FIG. 29O) | | |
| 35 | (structure: 6-fluoro indole with N-CH$_2$-C(OH)(CH$_3$)-C(O)NH-(3-Cl-4-CN-phenyl)) | 3.10 | 155.74 See FIG. 29K | 98.47 | 65, 80 (FIG. 29K) | 0 | 9.131 | 75.91 |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 µM | S.V. (22RV1) % inhibition at 10 µM | T$_{1/2}$ (min) | CL$_{int}$ (µl/min/mg) |
| 36 | 4-F indole structure | 3.10 | 315.32 See FIG. 29I | 141.99 See FIG. 29I | 71 (FIG. 29I) | 41 | 11.77 | 58.8 |
| 37 | 5-F indole structure | 3.10 | 252.58 See FIG. 29H | 94.33 See FIG. 29H | 81 (FIG. 29H) | 30 (FIG. 29H) | | |
| 38 | 3-F indole structure | 3.10 | 331.79 (FIG. 29G) | 44.50 (FIG. 29G) | 68 (100 nM) (FIG. 29G) | 62 (FIG. 29G) | 9.291 | 74.6 |
| 39 | 7-F indole structure | 3.10 | 719.81 (FIG. 29F) | 233.8 (FIG. 29F) | 40 (FIG. 29F) | 45 | | |

TABLE 3-continued

AR Binding ($K_i$), Inhibition of AR Transactivation ($IC_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | $K_i$ (nM) (DHT = 1 nM) | $IC_{50}$ (nM) | Full Length % inhibition at 1, 10 µM | S.V. (22RV1) % inhibition at 10 µM | $T_{1/2}$ (min) | $CL_{int}$ (µL/min/mg) |
| 90, 91 (mixture) | | 3.08, 3.45 | 806.67 | 851.94 | 0 | 8 | | |
| 92, 93 (mixture) | 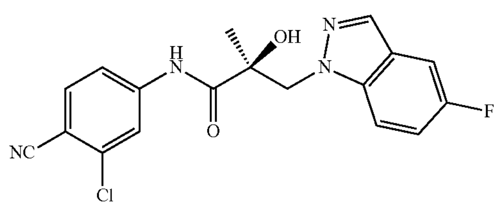 [SMILES: C[C@](O)(Cn1ccc2cc(F)ccc21)C(=O)Nc1ccc(C#N)c(Cl)c1] | 2.72, 3.08 | No binding (FIG. 29E) | 946.84 (FIG. 29E) | 40 (FIG. 29E) | 80 (FIG. 29E) | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) |
|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) CL$_{int}$ (μL/min/mg) |
| 94 | 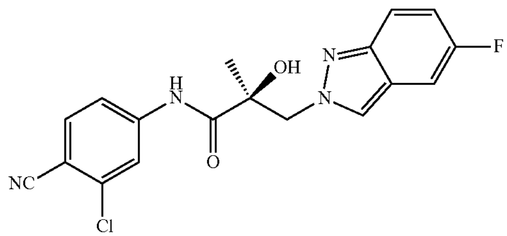 [SMILES: C[C@](O)(Cn1cc2cc(F)ccc2n1)C(=O)Nc1ccc(C#N)c(Cl)c1] | 3.08 | 137.47 | 172.86 | 92 | 34 | 13.29 52.16 |
| 95 | 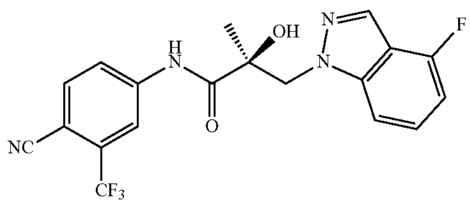 [SMILES: C[C@](O)(Cn1ncc2c(F)cccc21)C(=O)Nc1ccc(C#N)c(C(F)(F)F)c1] | 3.45 | 171.84 | No effect | 0 | 0 | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 µM | S.V. (22RV1) % inhibition at 10 µM | T$_{1/2}$ (min) | CL$_{int}$ (µL/min/mg) |
| 96 | 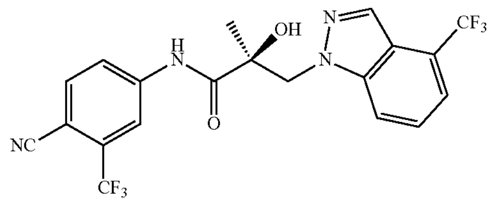 [SMILES: C[C@](O)(Cn1ncc2c(C(F)(F)F)cccc21)C(=O)Nc1ccc(C#N)c(C(F)(F)F)c1] | 3.84 | 1006.38 | 372.87 | 70 (FIG. 33C) | | 53.71 | 12.91 |
| 97 | 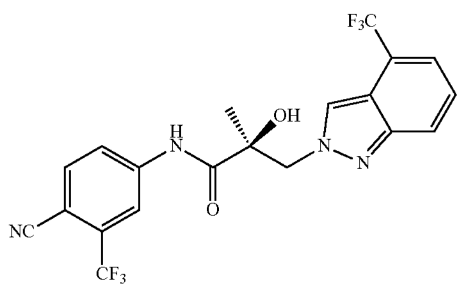 [SMILES: C[C@](O)(Cn1cc2c(C(F)(F)F)cccc2n1)C(=O)Nc1ccc(C#N)c(C(F)(F)F)c1] | 4.21 | 1232.45 | 208.78 | (FIG. 33D) | | 35.46 | 19.55 |
| 40 | 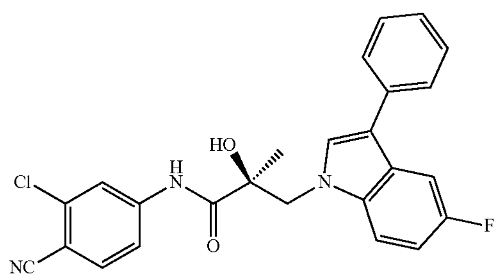 [SMILES: C[C@](O)(Cn1cc(-c2ccccc2)c2cc(F)ccc21)C(=O)Nc1ccc(C#N)c(Cl)c1] | 4.78 | 134.88 See FIG. 29D | 1032.14 See FIG. 29D | 0 | 0 | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) | |
|---|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) | CL$_{int}$ (μL/min/mg) |
| 41 | (structure) | 4.98 | 84.32 See FIG. 29B | >10000 See FIG. 269 | 0 | 0 | | |
| 42 | (structure) | 5.14 | 86.18 See FIG. 29A | 1015.12 See FIG. 29A | 0 | 0 | | |
| 43 | (structure) | 5.3 | 62.34 | 897.5 | 100 | | | |

TABLE 3-continued

AR Binding (K$_i$), Inhibition of AR Transactivation (IC$_{50}$), AR Degradation and Metabolic Stability of Indole Based SARDs.

| Compd ID | Structure | Log P (−0.4 to +5.6) | Binding/Transactivation (wt AR) | | SARD Activity | | DMPK (MLM) |
|---|---|---|---|---|---|---|---|
| | | | K$_i$ (nM) (DHT = 1 nM) | IC$_{50}$ (nM) | Full Length % inhibition at 1, 10 μM | S.V. (22RV1) % inhibition at 10 μM | T$_{1/2}$ (min) CL$_{int}$ (μL/min/mg) |
| 44 | 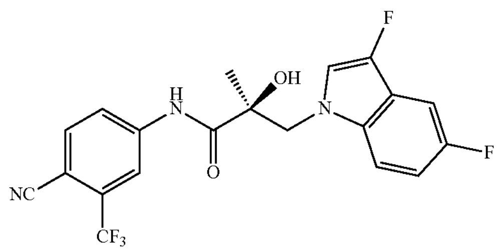 [SMILES: C[C@](O)(Cn1cc(Cl)c2cc(F)ccc21)C(=O)Nc1ccc(C#N)c(C(F)(F)F)c1] | 3.63 | 317.64 | 274.3 | 72 | 84 | |
| 45 | 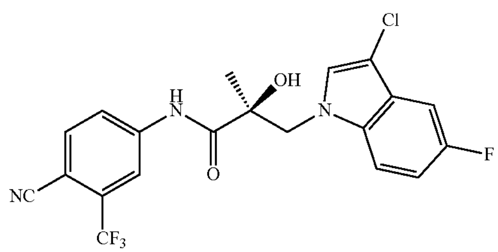 | 4.03 | 754.7 | 366.9 | 60 | 80 | |
| 46 | 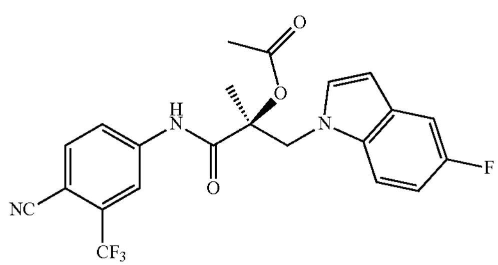 [SMILES: CC(=O)O[C@@](C)(Cn1ccc2cc(F)ccc21)C(=O)Nc1ccc(C#N)c(C(F)(F)F)c1] | 3.7 | 134.19 | 133.1 | 90 | 100 | |

TABLE 3A

AR Binding (K$_i$), Inhibition of AR Transactivation (IC$_{50}$), AR Degradation and in vitro Metabolic Stability of SARDs.

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) T$_{1/2}$ (min) CL$_{int}$ (μl/min/mg) |
|---|---|---|---|---|---|---|---|
| Eno-bosarm | | 3.44 | 20.21 | ~20 | | | |
| R-Bicalut-amide | | 2.57 | 508.84 | 248.2 | | | |
| Enzalut-amide | | 4.56 | 3641.29 | 216.3 | | | |
| ARN-509 | | 3.47 | 1452.29 | | 0 | 0 | |
| | | 2.57 | 87.67 | — | | | |
| | | 1.86 | 407.08 | | | | |

TABLE 3A-continued

AR Binding (K$_i$), Inhibition of AR Transactivation (IC$_{50}$), AR Degradation and in vitro Metabolic Stability of SARDs.

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) T$_{1/2}$ (min) CL$_{int}$ (μl/ min/mg) |
|---|---|---|---|---|---|---|---|
| 300 | 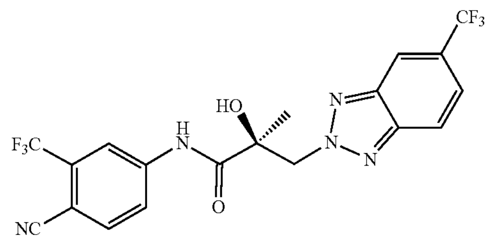 [SMILES: C[C@](O)(Cn1nc2ccc(C(F)(F)F)cc2n1)C(=O)Nc1ccc(C#N)c(C(F)(F)F)c1] | 4.25 | | No effect | | | |
| 301 | 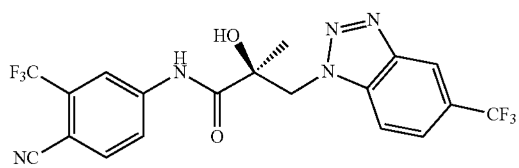 [SMILES: C[C@](O)(Cn1nnc2cc(C(F)(F)F)ccc21)C(=O)Nc1ccc(C#N)c(C(F)(F)F)c1] | 3.87 | | — | | | |
| 302 | 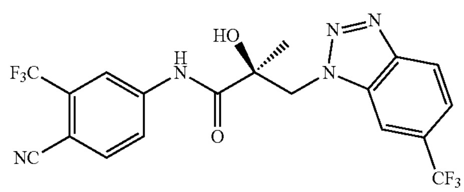 [SMILES: C[C@](O)(Cn1nnc2ccc(C(F)(F)F)cc21)C(=O)Nc1ccc(C#N)c(C(F)(F)F)c1] | 3.87 | | — | | | |
| 301/ 302 | 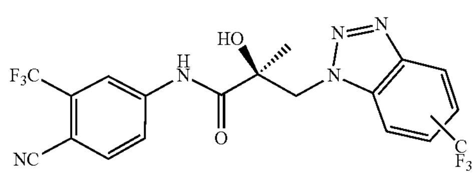 | 3.87 | | No effect | | | |
| 303 | 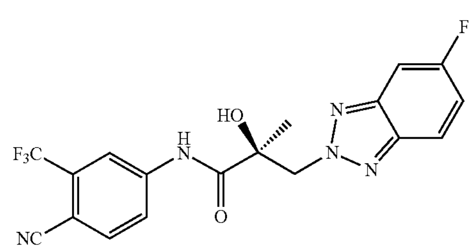 [SMILES: C[C@](O)(Cn1nc2ccc(F)cc2n1)C(=O)Nc1ccc(C#N)c(C(F)(F)F)c1] | 3.48 | 3615 | 277 | 70 | 0 | |
| 304 | 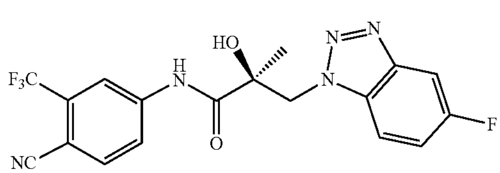 [SMILES: C[C@](O)(Cn1nnc2cc(F)ccc21)C(=O)Nc1ccc(C#N)c(C(F)(F)F)c1] | 3.11 | | 687 | 60 | 0 | |
| 305 | 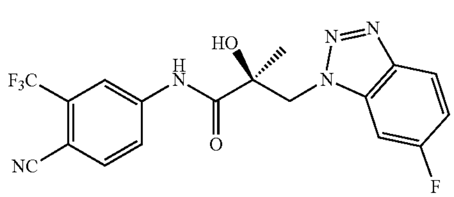 [SMILES: C[C@](O)(Cn1nnc2ccc(F)cc21)C(=O)Nc1ccc(C#N)c(C(F)(F)F)c1] | 3.11 | 1476 | 560 | 40 | 0 | |

TABLE 3A-continued

AR Binding (K$_i$), Inhibition of AR Transactivation (IC$_{50}$), AR Degradation and in vitro Metabolic Stability of SARDs.

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) T$_{1/2}$ (min) CL$_{int}$ (μl/ min/mg) |
|---|---|---|---|---|---|---|---|
| 306 | 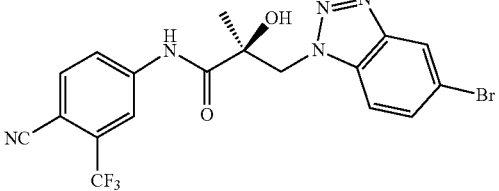 | 3.78 | | 2594 nM | | | |
| 308 | 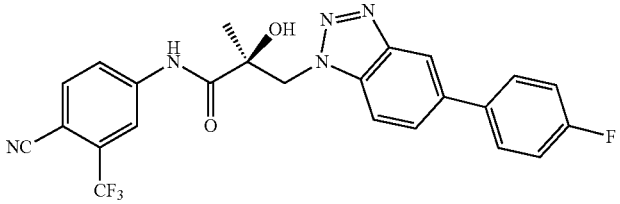 [SMILES: C[C@](O)(Cn1nnc2cc(-c3ccc(F)cc3)ccc21)C(=O)Nc1ccc(C#N)c(C(F)(F)F)c1] | 4.79 | | No effect | | | |

TABLE 3B

AR Binding (K$_i$), Inhibition of AR Transactivation (IC$_{50}$), AR Degradation and in vitro Metabolic Stability of SARDs.

| Compd ID (Scaffold) | Structure | Log P (−0.4 to +5.6) | M.W. | Binding/Wt. K$_i$ (nM) (DHT = 1 nM) | IC$_{50}$ (nM) | SARD Activity Full Length % degradation at 1, 10 μM | S.V. (22RV1) % degradation at 10 μM | DMPK (MLM) T$_{1/2}$ Clint |
|---|---|---|---|---|---|---|---|---|
| 98 | 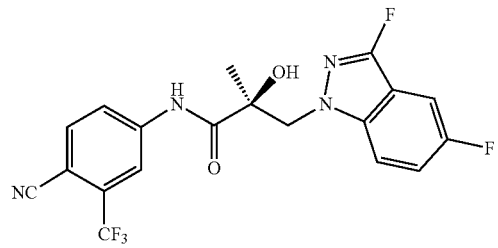 [SMILES: C[C@](O)(Cn1nc(F)c2cc(F)ccc21)C(=O)Nc1ccc(C#N)c(C(F)(F)F)c1] | 3.71 | 424.31 | 605.4 | 101.5 | 37, 81 | 53 | |
| 47 | 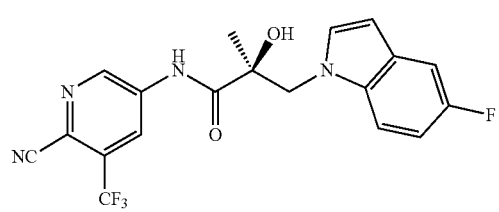 [SMILES: C[C@](O)(Cn1ccc2cc(F)ccc21)C(=O)Nc1cnc(C#N)c(C(F)(F)F)c1] | 2.55 | 406.33 | 757.29032 | 20.68 nM | | | |

TABLE 3B-continued

AR Binding (K$_i$), Inhibition of AR Transactivation (IC$_{50}$), AR Degradation and in vitro Metabolic Stability of SARDs.

| Compd ID (Scaffold) | Structure | Log P (−0.4 to +5.6) | M.W. | Binding/Wt. Ki (nM) (DHT = 1 nM) | IC$_{50}$ (nM) | SARD Activity Full Length % degradation at 1, 10 µM | S.V. (22RV1) % degradation at 10 µM | DMPK (MLM) T$_{1/2}$ Clint |
|---|---|---|---|---|---|---|---|---|
| 99 | 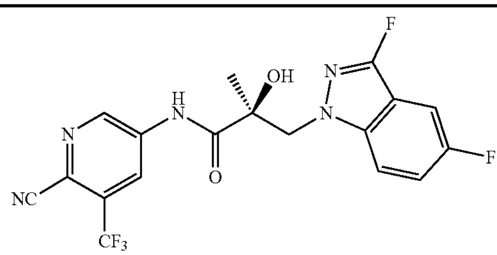 | 2.79 | 425.31 | 0.00 | 26.74 | 66, 78 | | |

TABLE 4

Liver Microsome (LM) Data of Indole and Benzimidazole SARDs in Mouse LM (MLM), Human LM (HLM), Rat LM (RLM) and Dog LM (DLM).

| | MLM | | HLM | | RLM | | DLM | |
|---|---|---|---|---|---|---|---|---|
| Compd ID | T$_{1/2}$ (min) | CL$_{int}$ (µl/min/mg) | T$_{1/2}$ (min) | CL$_{int}$ (µl/min/mg) | T$_{1/2}$ (min) | CL$_{int}$ (µl/min/mg) | T$_{1/2}$ (min) | CL$_{int}$ (µl/min/mg) |
| 27 | 13.66 | 50.75 | | | | | | |
| 22 (4-F) | 36.32 | 19.08 | | | | | | |
| 11 (5-F) | 14.35 | 48.30 | 14.62 | 47.40 | | | | |
| 23 (6-F) | 22.39 | 30.96 | | | | | | |
| 12 (4-NO$_2$) | 37.27 | 18.60 | | | | | | |
| 20 (5-NO$_2$) | 19.27 | 35.97 | 17.97 | 38.57 | | | | |
| 32 (6-NO$_2$) | 13.48 | 51.43 | | | | | | |
| 24 (5-Br) | 17.02 | 40.73 | | | | | | |
| 21 (5-I) | 29.39 | 20.37 | | | | | | |
| 18 (5-CF$_3$) | 37.71 | 18.38 | | | | | | |
| 14 (5-CN) | 15.97 | 43.40 | | | | | | |
| 15 (3-CO$_2$H) | 29.78 | 23.28 | | | | | | |
| 30 | 25.78 | 26.89 | 13.77 | 0.05034 | | | | |
| 70, 71 | 48.58 | 14.27 | 16.36 | 42.37 | | | | |
| 31 | 21.77 | 31.84[ | | | | | | |
| 33 | 15.43 | 44.94 | 7.31 | 94.82 | | | | |
| 34 | | | 9.131 | 75.91 | 15.50 | 58.87 | | |
| 38 | 9.291 | 74.6 | 6.611 | 104.9 | | | | |
| 36 | 11.77 | 58.8 | 12.66 | 54.7 | | | | |

Example 6

Androgen Receptor Binding and Transactivation, AR Degradation, and In Vitro Metabolism of Indoline, Quinolone and Isoquinoline Based SARDs (Tables 5-7)

Ligand Binding Assay

Objective: To determine SARDs binding affinity to the AR-LBD.

Method: hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (K$_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the K$_d$ of mibolerone.

Increasing concentrations of SARDs or DHT (range: 10$^{-12}$ to 10$^{-2}$ M) were incubated with [$^3$H]mibolerone and AR LBD using the conditions described above. Following incubation, the ligand bound AR-LBD complex was isolated using Bio Gel HT® hydroxyapatite, washed and counted in a scintillation counter after adding scintillation cocktail. Values are expressed as K$_i$.

Transactivation Assay with wt AR

Objective: To determine the effect of SARDs on androgen-induced transactivation of AR wildtype (wt).

Method: HEK-293 cells were plated at 125,000 cells/well of a 24 well plate in DME+5% csFBS without phenol red.

Cells were transfected with 0.25 ug GRE-LUC, 10 ng CMV-renilla LUC, and 50 ng CMV-hAR(wt) using Lipofectamine transfection reagent in optiMEM medium. Medium was changed 24 h after transfection to DME+5% csFBS without phenol red and treated with a dose response of various drugs (1 pM to 10 μM). SARDs and antagonists were treated in combination with 0.1 nM R1881. Luciferase assay was performed 24 h after treatment on a Biotek synergy 4 plate reader. Firefly luciferase values were normalized to renilla luciferase values. (Tables 5 and 6)

Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 g GRE-LUC, 0.01 g CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 μM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods: Cell growth was evaluated as described before by SRB assay. Cells were plated in a 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Determination of Metabolic Stability (In Vitro $CL_{int}$) of Test Compounds (Table 7)

Phase I Metabolism

The assay was done in a final volume of 0.5 ml in duplicates (n=2). Test compound (1 M) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (μl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

Lc-Ms/Ms Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

TABLE 5

AR Binding ($K_i$), Inhibition of AR Transactivation ($IC_{50}$), AR Degradation and in vitro Metabolic Stability of Indoline, Quinoline and Isoquinoline SARDs.

| Compd ID | Structure | Binding/Tranactivation (wtAR) | | SARD activity (estimated median effect (nM)) | DMPK (MLM) $T_{1/2}$ (min) CLint (µl/min/mg) |
|---|---|---|---|---|---|
| | | $K_i$ (nM) | $IC_{50}$ (nM) | | |
| Eno-bosarm | 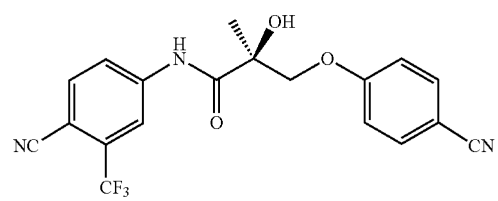 [SMILES: C[C@](O)(COc1ccc(C#N)cc1)C(=O)Nc1ccc(C#N)c(C(F)(F)F)c1] | 8.385 | ~20 | | |
| R-Bicalut-amide | 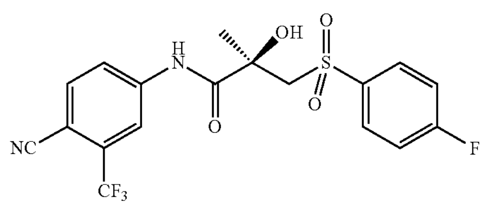 [SMILES: C[C@](O)(CS(=O)(=O)c1ccc(F)cc1)C(=O)Nc1ccc(C#N)c(C(F)(F)F)c1] | 211.12 | 248.2 | — | |
| Enzalut-amide | 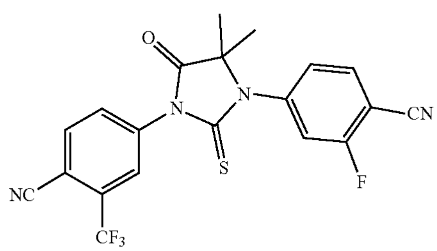 [SMILES: CC1(C)C(=O)N(c2ccc(C#N)c(C(F)(F)F)c2)C(=S)N1c1ccc(C#N)c(F)c1] | 678.9 | 216.3 | — | |
| ARN-509 (apalut-amide) | 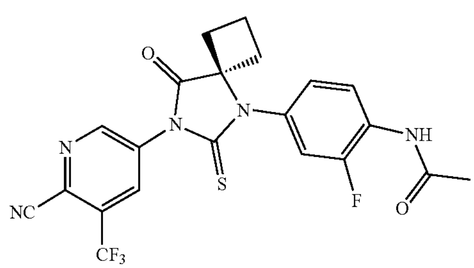 | >1000 | | + (FIG. 18) | |
| 100 | 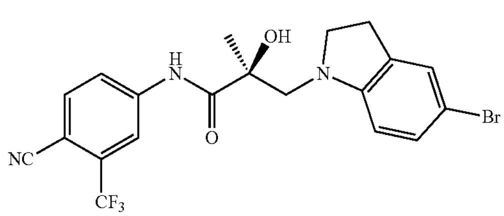 [SMILES: C[C@](O)(CN1CCc2cc(Br)ccc21)C(=O)Nc1ccc(C#N)c(C(F)(F)F)c1] | 23.17 34.16 | 530.95 | 10-100 (FIGS. 18 & 19) | 66.87 min 10.38 µl/min/mg |
| 101 | 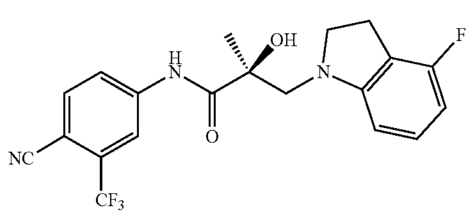 [SMILES: C[C@](O)(CN1CCc2c(F)cccc21)C(=O)Nc1ccc(C#N)c(C(F)(F)F)c1] | 83.1 | 58.96 | 100-500 (FIG. 25) | 25.06 min 27.67 µl/min/mg |

TABLE 5-continued

AR Binding ($K_i$), Inhibition of AR Transactivation ($IC_{50}$), AR Degradation and in vitro Metabolic Stability of Indoline, Quinoline and Isoquinoline SARDs.

| Compd ID | Structure | Binding/ Tranactivation (wtAR) $K_i$ (nM) | Binding/ Tranactivation (wtAR) $IC_{50}$ (nM) | SARD activity (estimated median effect (nM)) | DMPK (MLM) $T_{1/2}$ (min) CLint (µl/min/mg) |
|---|---|---|---|---|---|
| 102 | 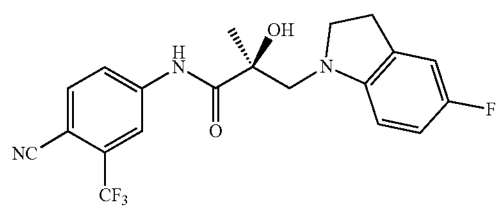 [SMILES: C[C@](O)(CN1CCc2cc(F)ccc21)C(=O)Nc1ccc(C#N)c(C(F)(F)F)c1] | 126.8 | 26.28 | 100-500 (FIGS. 19 & 21) | 55.14 min 12.57 µl/min/mg |
| 103 | 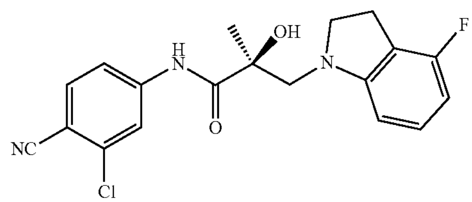 [SMILES: C[C@](O)(CN1CCc2c(F)cccc21)C(=O)Nc1ccc(C#N)c(Cl)c1] | 382.44 | 126.13 | 10000 (FIG. 22) | |
| 104 | 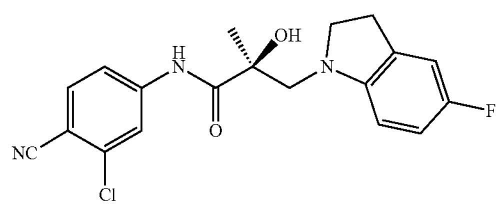 [SMILES: C[C@](O)(CN1CCc2cc(F)ccc21)C(=O)Nc1ccc(C#N)c(Cl)c1] | 326.14 | 130.37 | 10-100 (FIG. 22) | 29.16 min 23.77 µl/min/mg |
| 105 | 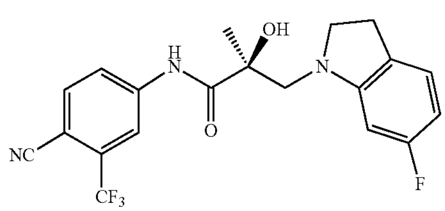 [SMILES: C[C@](O)(CN1CCc2ccc(F)cc21)C(=O)Nc1ccc(C#N)c(C(F)(F)F)c1] | 273.04 | 38.74 | (FIG. 25) | |
| 106 | 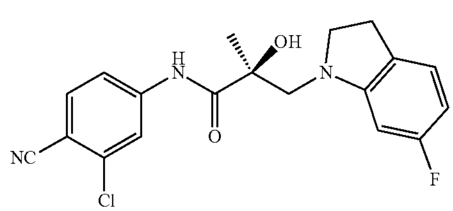 [SMILES: C[C@](O)(CN1CCc2ccc(F)cc21)C(=O)Nc1ccc(C#N)c(Cl)c1] | 489.95 | 36.45 | (FIG. 25) | |
| 130 | 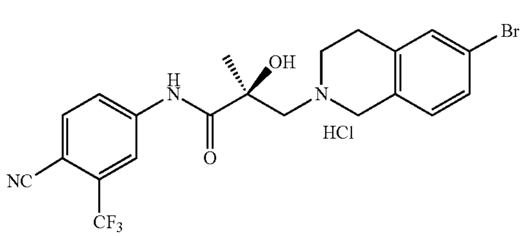 [SMILES: C[C@](O)(CN1CCc2cc(Br)ccc2C1)C(=O)Nc1ccc(C#N)c(C(F)(F)F)c1 ; Cl] | 1530.58 | 420.07 | 1000-5000 (FIGS. 19, 20, 23 & 24) | 161.7 min 4.286 µl/min/mg |

TABLE 5-continued

AR Binding (K$_i$), Inhibition of AR Transactivation (IC$_{50}$), AR Degradation and in vitro Metabolic Stability of Indoline, Quinoline and Isoquinoline SARDs.

| Compd ID | Structure | Binding/ Tranactivation (wtAR) | | SARD activity (estimated median effect (nM)) | DMPK (MLM) T$_{1/2}$ (min) CLint (μl/min/mg) |
|---|---|---|---|---|---|
| | | K$_i$ (nM) | IC$_{50}$ (nM) | | |
| 134 | (structure with NC, CF$_3$, amide, OH, tetrahydroquinoline-Br) | 201.98 | 573.98 | 5000-10000 (FIG. 24) | 38.25 min 18.12 μl/min/mg |
| 135 | (structure with NC, CF$_3$, amide, gem-dimethyl, tetrahydroquinoline-F) | 3112.73 | 867.48 | 10-100 nM (FIG. 21) | 15.25 min 45.45 μl/min/mg |
| 131 | (structure with NC, CF$_3$, amide, OH, tetrahydroisoquinoline-F) | 398.63 | 1002.73 | — | 25.42 min 27.27 μl/min/mg |
| 107 | (structure with NC, CF$_3$, amide, OH, indoline-Cl,F) | 67.65 | 74.65 | (FIG. 25) | |
| 108 | (structure with NC, CF$_3$, amide, OH, indoline-F,F) | 114.84 | 100.55 | (FIG. 25) | |

The short half-lives ($t_{1/2}$) and high metabolic clearance ($CL_{int}$) values in vitro of some of the compounds of this invention suggest rapid plasma clearance for those compounds which could be favorable for topical treatment of androgenic dermatologic disorders as it would limit the risk of systemic side effects, even if the skin is penetrated. Other compounds demonstrate relatively long half-lives and low metabolic clearances values in vitro suggesting that these compounds may be able to achieve systemic exposures necessary to have systemic antiandrogen effects such as would be necessary to treat prostate cancer.

TABLE 6

AR Binding ($K_i$), Inhibition of AR Transactivation ($IC_{50}$), AR Degradation and Metabolic Stability of Indoline, Quinoline and Isoquinoline SARDs.

| Compd ID | Structure | Log P (−0.4 to +5.6) | Binding/Transactivation (wt AR) $K_i$ (nM) (DHT = 1 nM) | Binding/Transactivation (wt AR) $IC_{50}$ (nM) | SARD Activity Full Length % inhibition at 1, 10 μM | SARD Activity S.V. (22RV1) % inhibition at 10 μM | DMPK (MLM) $T_{1/2}$ (min) $CL_{int}$ (μl/min/mg) |
|---|---|---|---|---|---|---|---|
| Eno-bosarm | | 3.44 | 20.21 | ~20 | | | |
| R-Bicalut-amide | | 2.57 | 508.84 | 248.2 | | | |
| Enzalut-amide | | 4.56 | 3641.29 | 216.3 | | | |
| ARN-509 (apalut-amide) | | 3.47 | 1452.29 | | 0 | 0 | |
| DJ-I-223 | | 2.57 | 87.67 | — | | | |

TABLE 6-continued

AR Binding (K$_i$), Inhibition of AR Transactivation (IC$_{50}$), AR Degradation and Metabolic Stability of Indoline, Quinoline and Isoquinoline SARDs.

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) T$_{1/2}$ (min) CL$_{int}$ (μl/min/mg) |
|---|---|---|---|---|---|---|---|
| DJ-VI-5E | 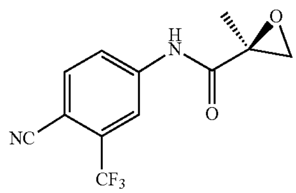 [SMILES: C[C@@]1(C(=O)Nc2ccc(C#N)c(C(F)(F)F)c2)CO1] | 1.86 | 407.08 | | | | |
| 100 | 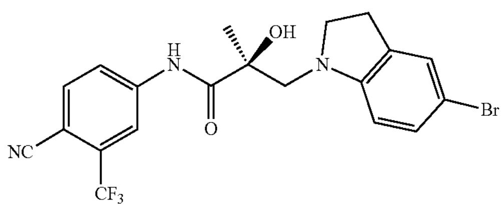 [SMILES: C[C@](O)(CN1CCc2cc(Br)ccc21)C(=O)Nc1ccc(C#N)c(C(F)(F)F)c1] | 4.62 | 197.67 | 530.95 | 60 | 41 | 66.87 10.38 |
| 101 | 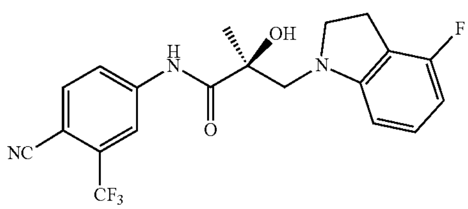 [SMILES: C[C@](O)(CN1CCc2c(F)cccc21)C(=O)Nc1ccc(C#N)c(C(F)(F)F)c1] | 3.95 | 169.86 | 58.96 | 61 | 5 | 25.06 27.67 |
| 102 | 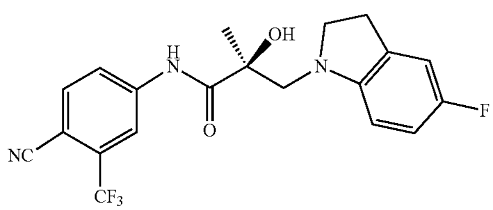 [SMILES: C[C@](O)(CN1CCc2cc(F)ccc21)C(=O)Nc1ccc(C#N)c(C(F)(F)F)c1] | 3.95 | 807.22 | 137.04 | 95 | 63 | 55.14 12.57 |
| 103 | 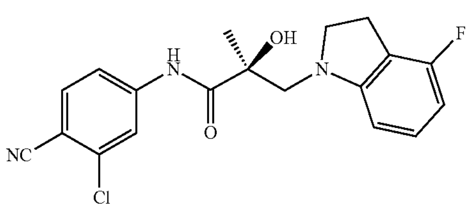 [SMILES: C[C@](O)(CN1CCc2c(F)cccc21)C(=O)Nc1ccc(C#N)c(Cl)c1] | 3.59 | 382.44 | 126.13 | 58 | 71 | 15 46.22 |
| 104 | 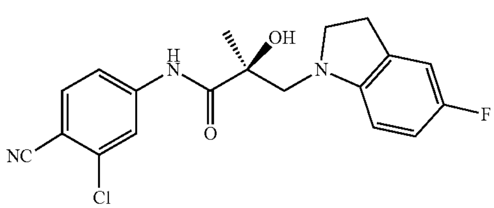 [SMILES: C[C@](O)(CN1CCc2cc(F)ccc21)C(=O)Nc1ccc(C#N)c(Cl)c1] | 3.59 | 326.14 | 130.37 | 47, 69 | 15 | 29.16 23.77 |

TABLE 6-continued

AR Binding (K$_i$), Inhibition of AR Transactivation (IC$_{50}$), AR Degradation and Metabolic
Stability of Indoline, Quinoline and Isoquinoline SARDs.

| | | | Binding/ Transactivation (wt AR) | | SARD Activity | | DMPK (MLM) |
|---|---|---|---|---|---|---|---|
| | | Log P | | | Full Length % | S.V. (22RV1) | |
| Compd ID | Structure | (−0.4 to +5.6) | K$_i$ (nM) (DHT = 1 nM) | IC$_{50}$ (nM) | inhibition at 1, 10 μM | % inhibition at 10 μM | T$_{1/2}$ (min) CL$_{int}$ (μl/min/mg) |
| 105 | | 3.95 | 273.04 | 38.74 | 60 | 30 | |
| 106 | | 3.59 | 489.95 | 36.45 | 99 | 12 | |
| 107 | | 4.51 | 67.65 | Agonist | 30-48 | 0 | |
| 108 | | 4.11 | 114.84 | 100.55 | 54 | 36 | |
| 109 | | 3.80 | >1000 | 142.13 | 84 | 45 | |
| 110 | | 3.75 | 251.94 | 31.71 | 79 | 40 | |

TABLE 6-continued

AR Binding (K$_i$), Inhibition of AR Transactivation (IC$_{50}$), AR Degradation and Metabolic Stability of Indoline, Quinoline and Isoquinoline SARDs.

Figure 29A:
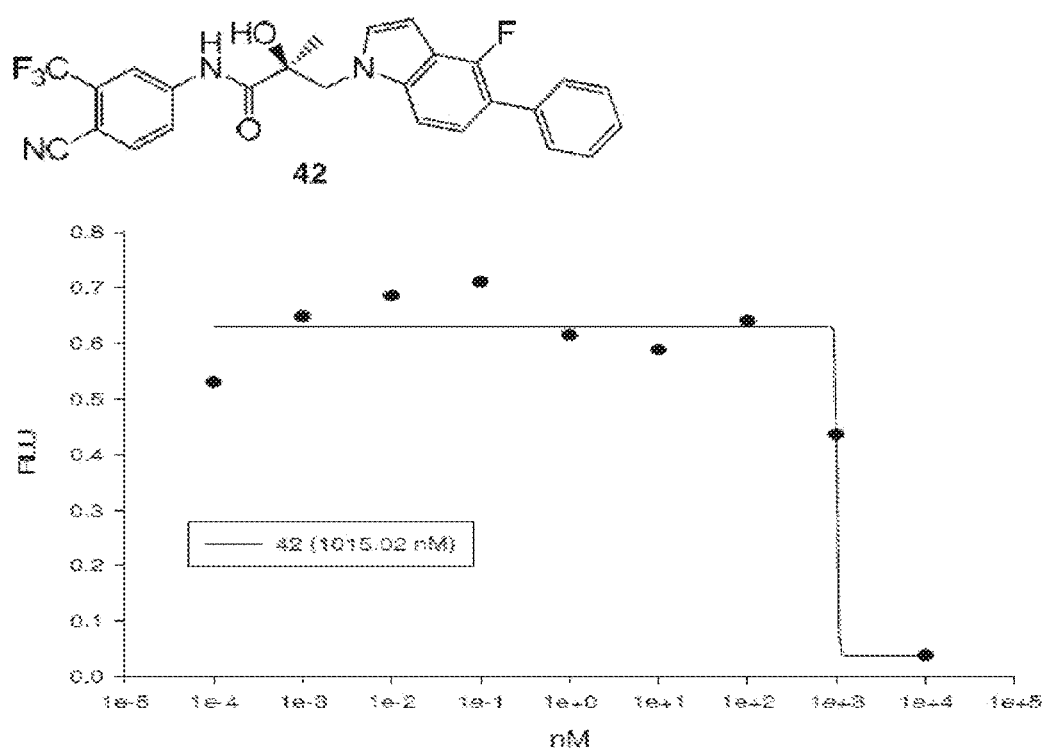
FIGS. 29A-29O depict transactivation data, binding, and AR-FL and AR-SV degradation for SARDs compounds of this invention.
Figure 29B:
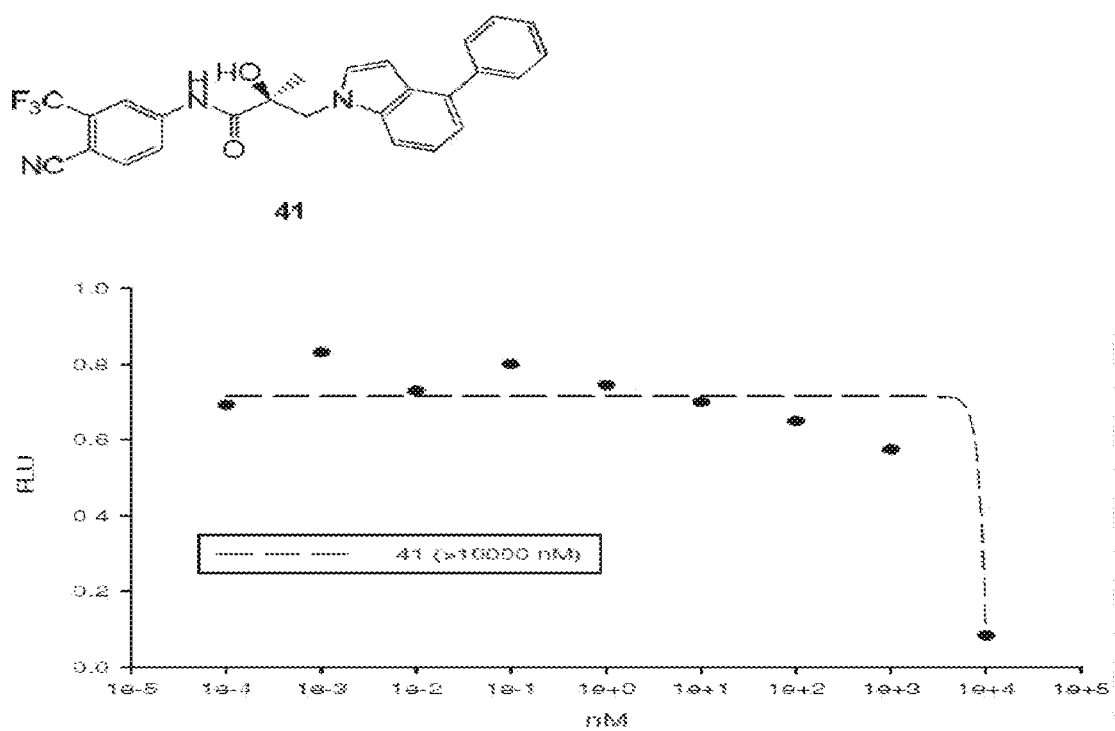
Figure 29C:
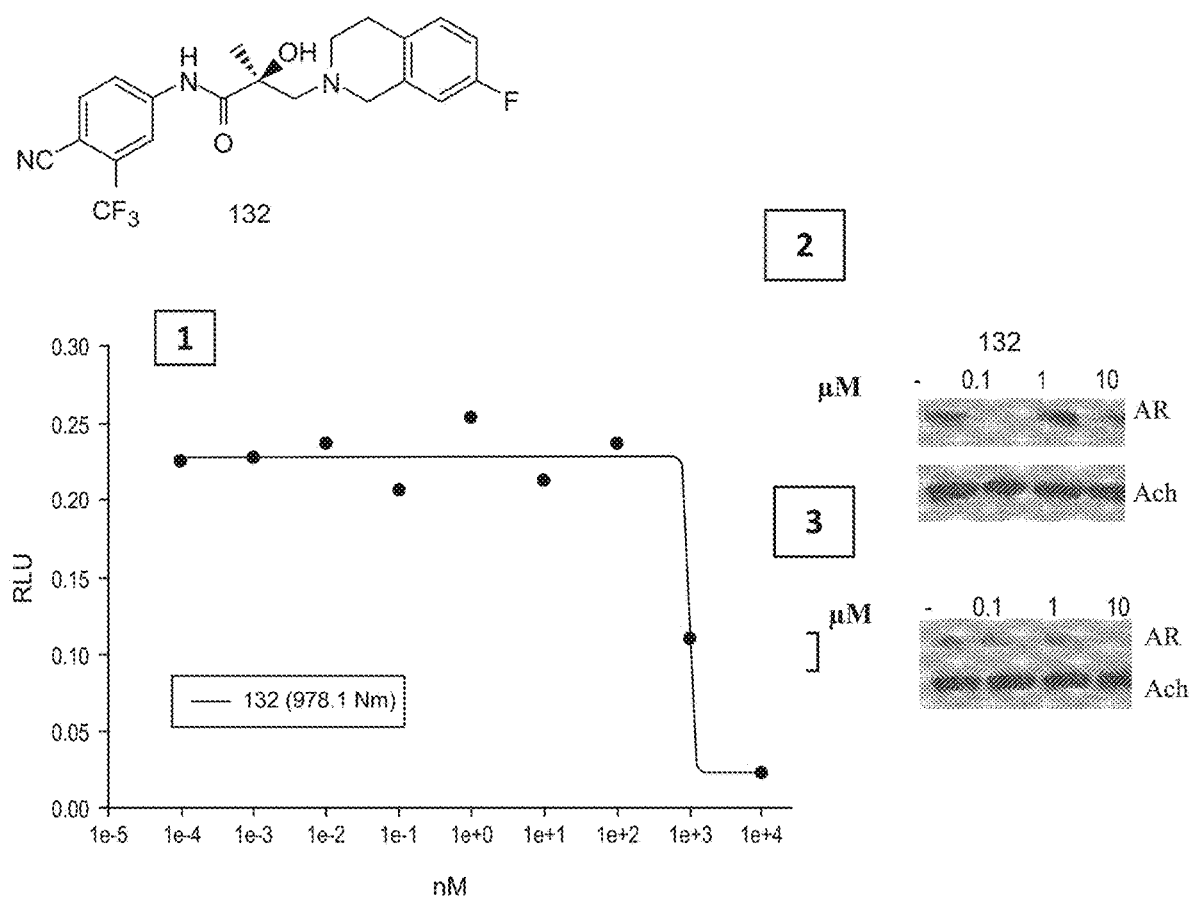
Figure 29D:
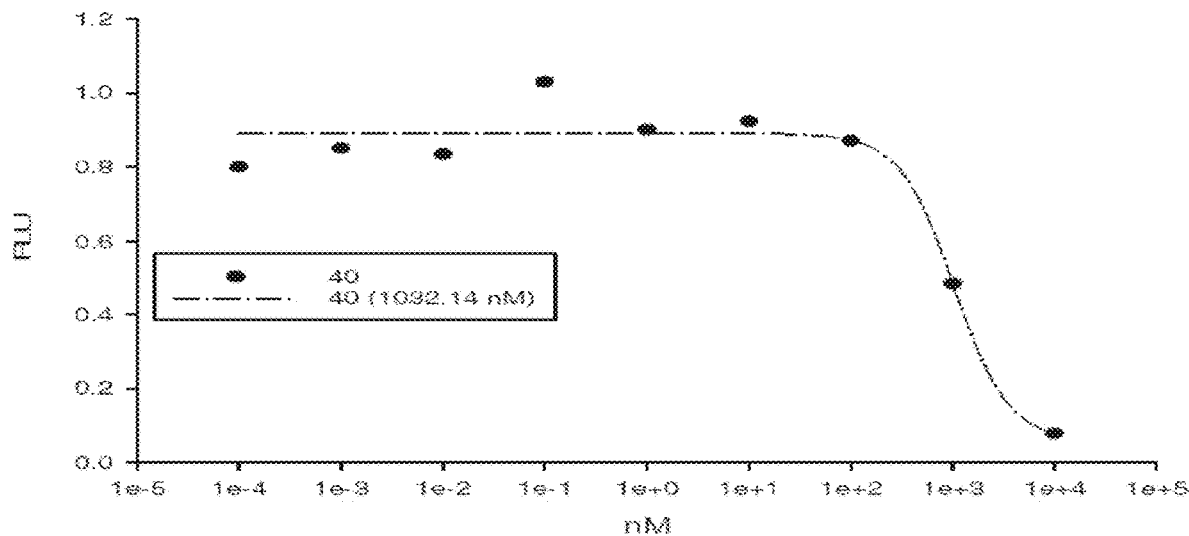
Figure 29D:
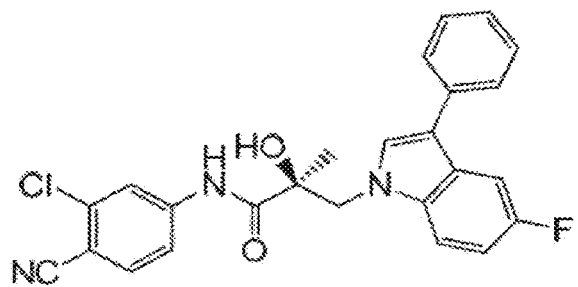
Figure 29E:
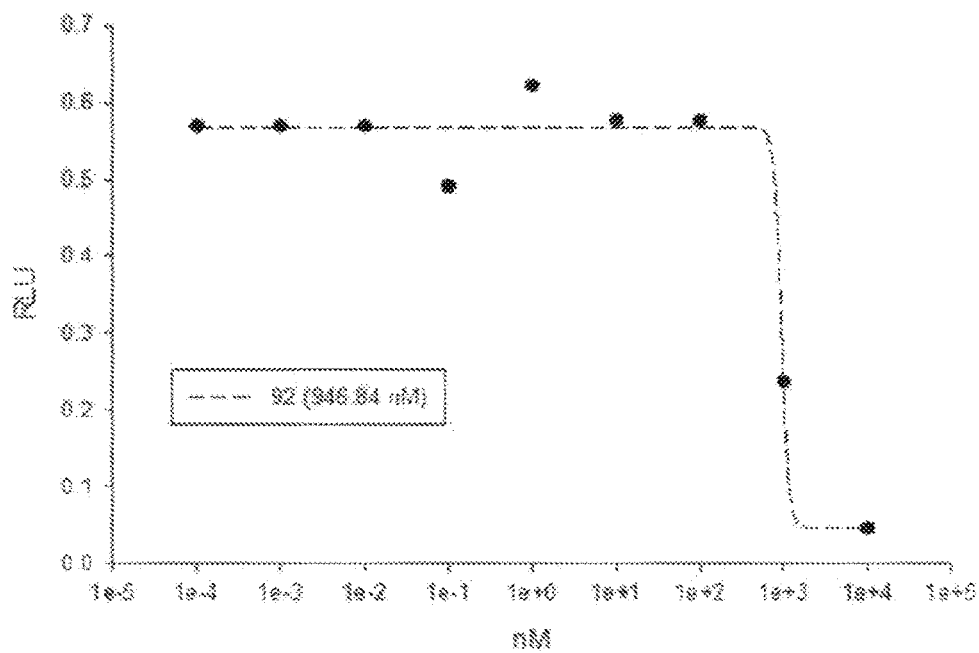
Figure 29E:
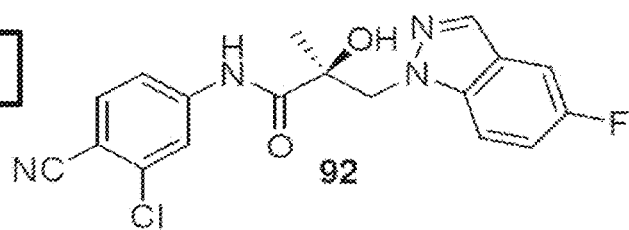
Figure 29E:
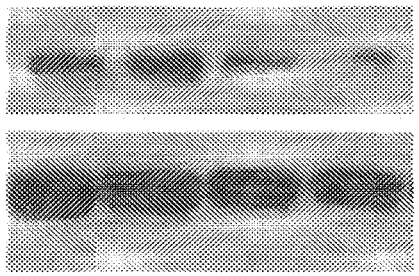
Figure 29E:
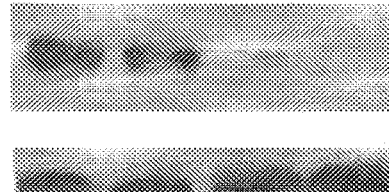
Figure 29F:
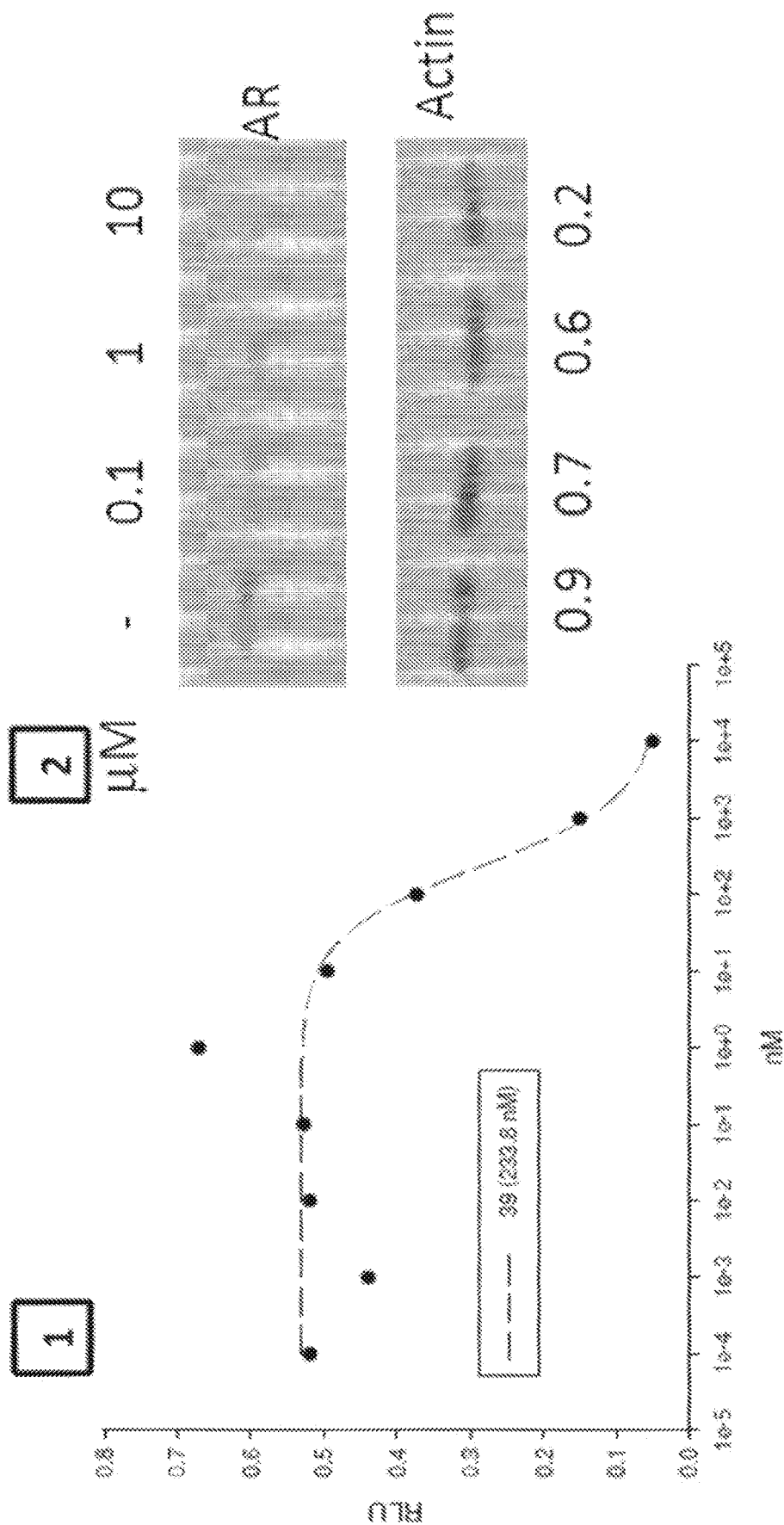
Figure 29G:
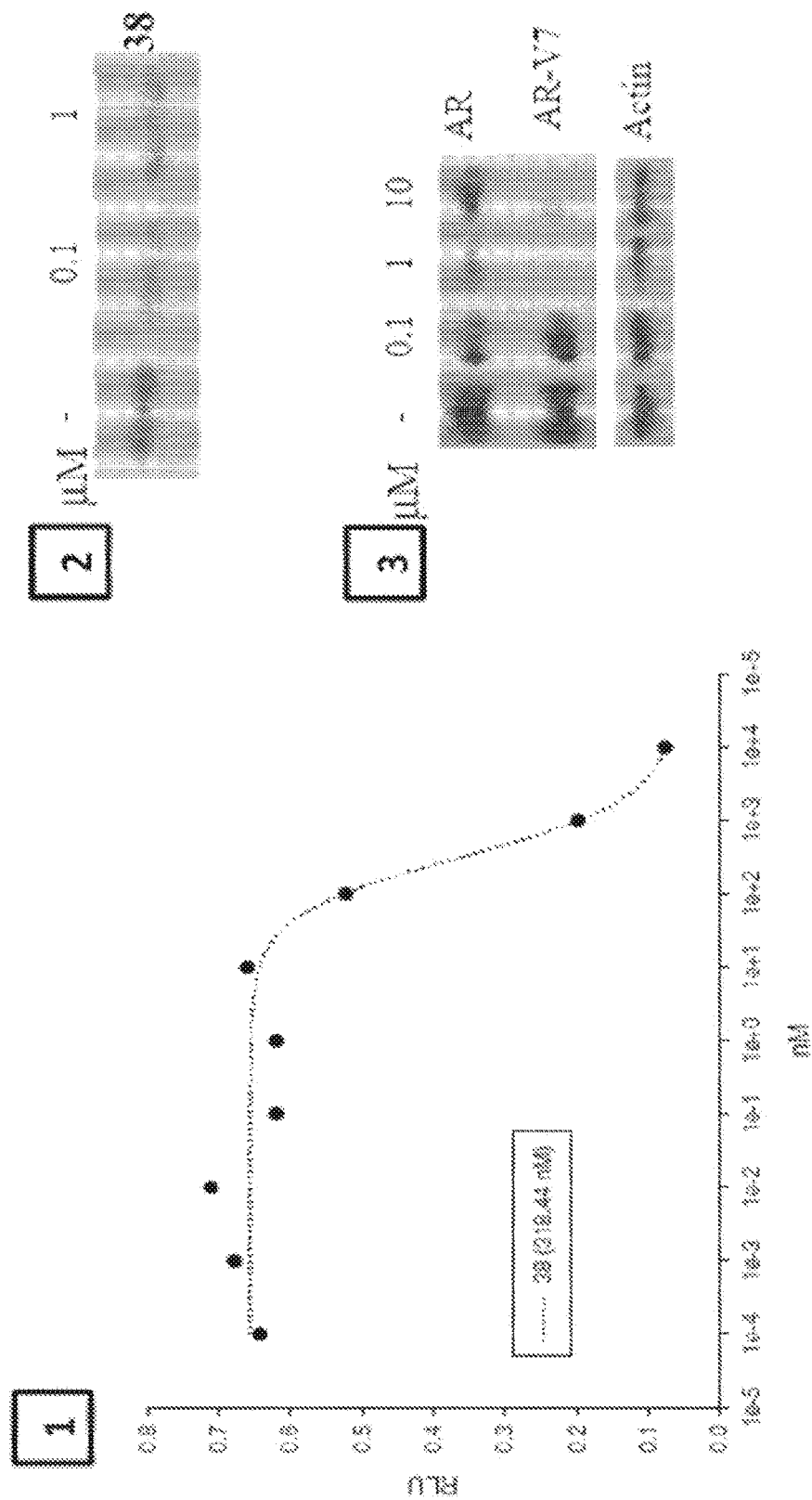
Figure 29H:
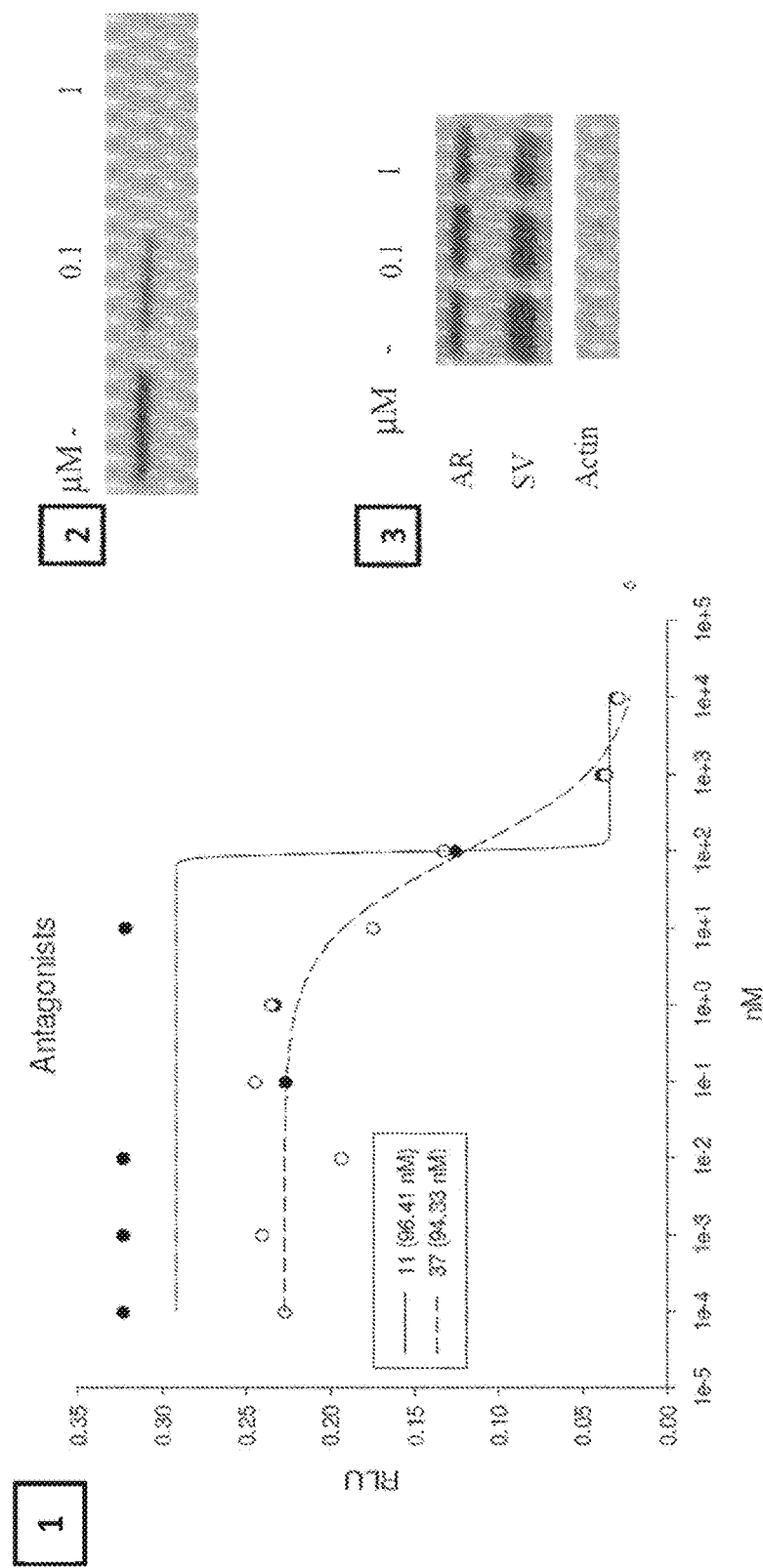
Figure 29H:
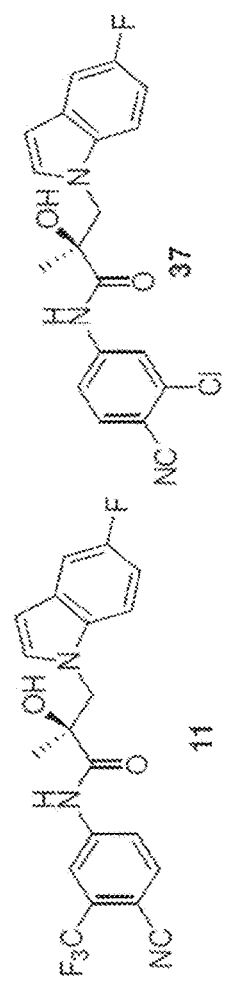
Figure 29I:
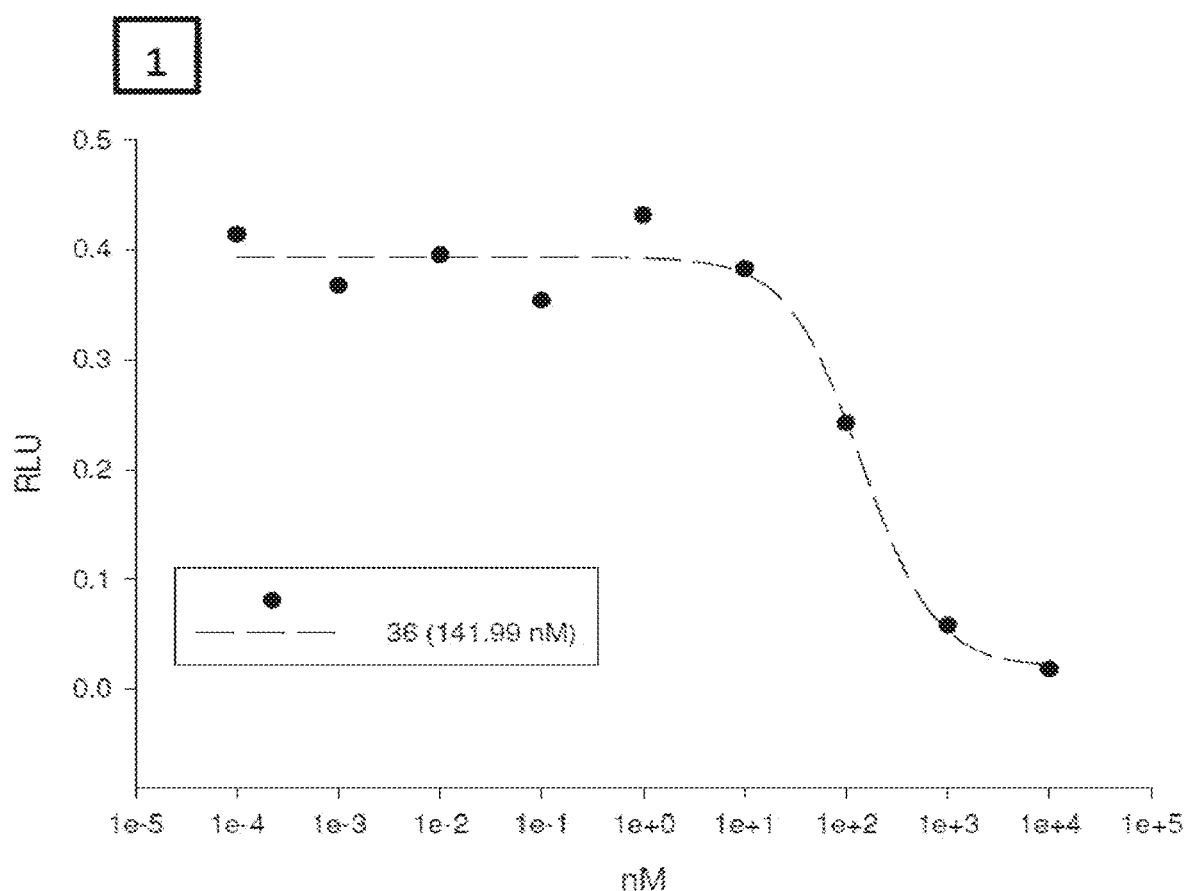
Figure 29I:
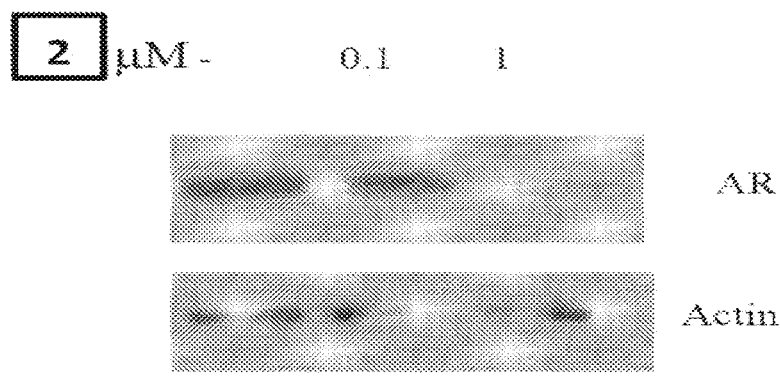
Figure 29I:
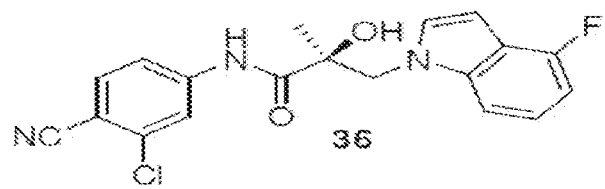
Figure 29J:
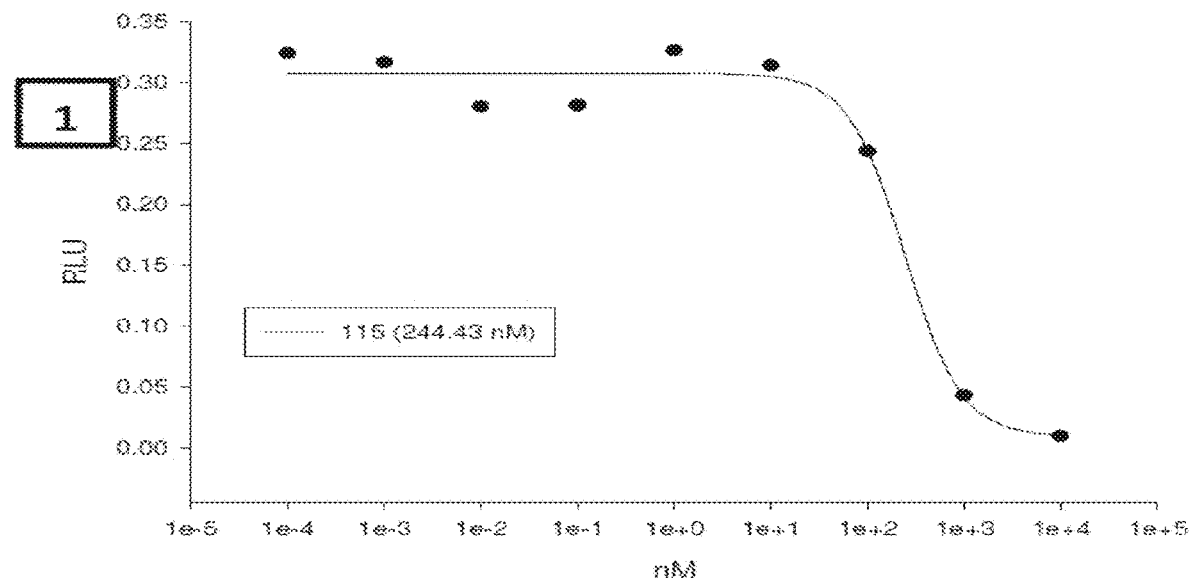
Figure 29J:
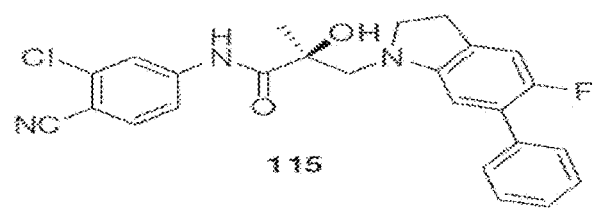
Figure 29J:
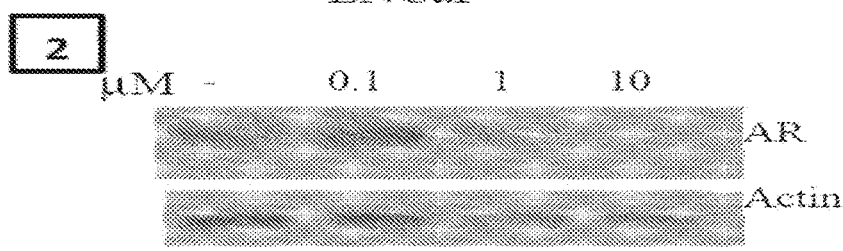
Figure 29J:
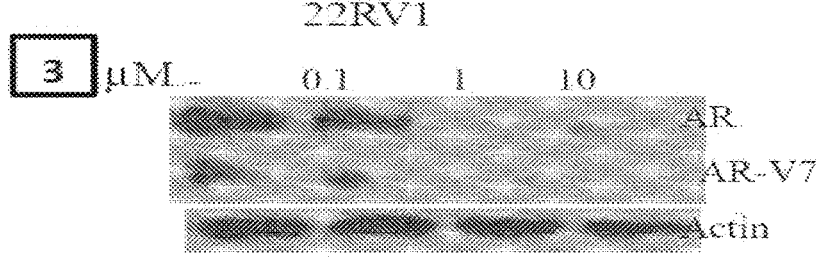
Figure 29K:
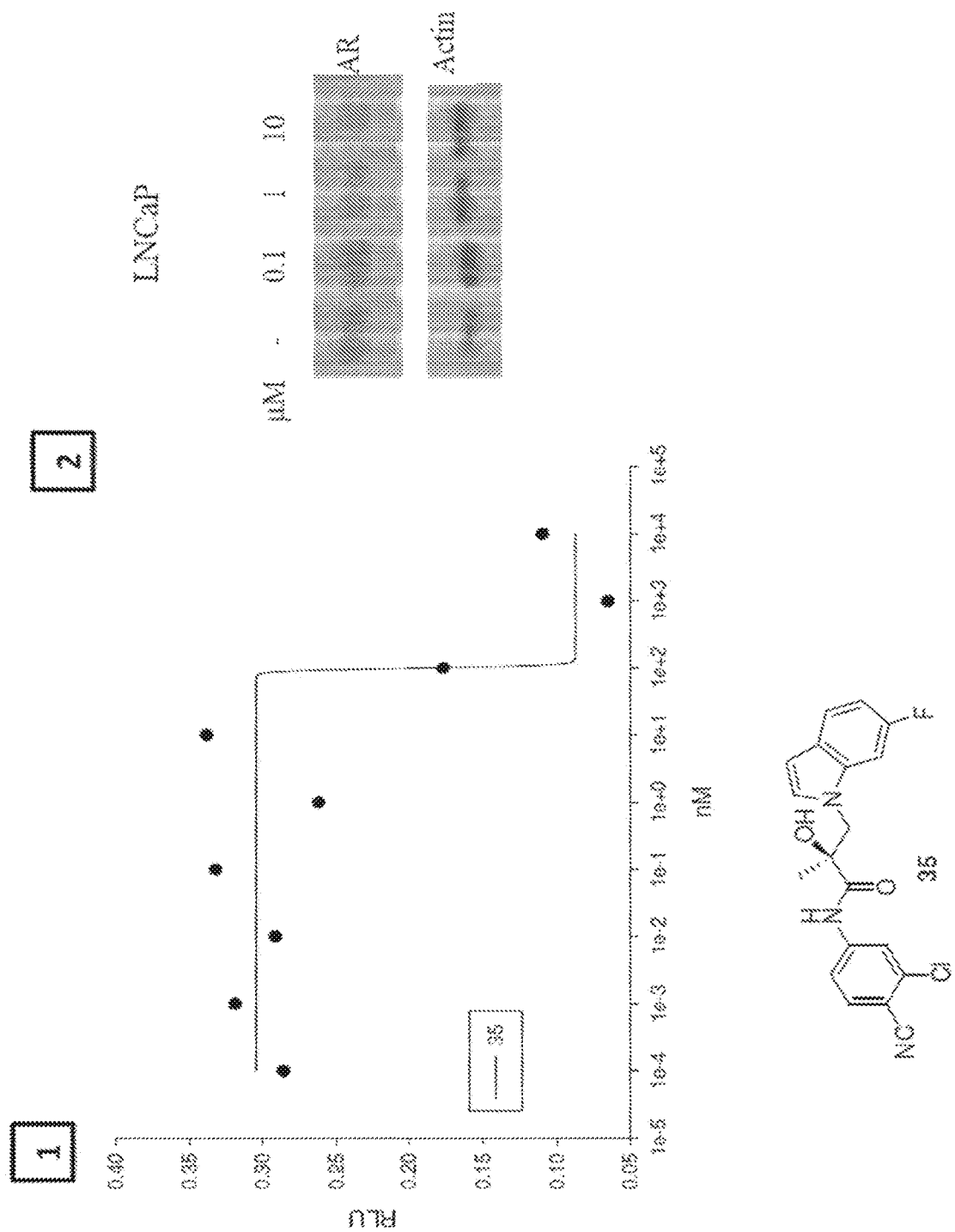
Figure 29L:
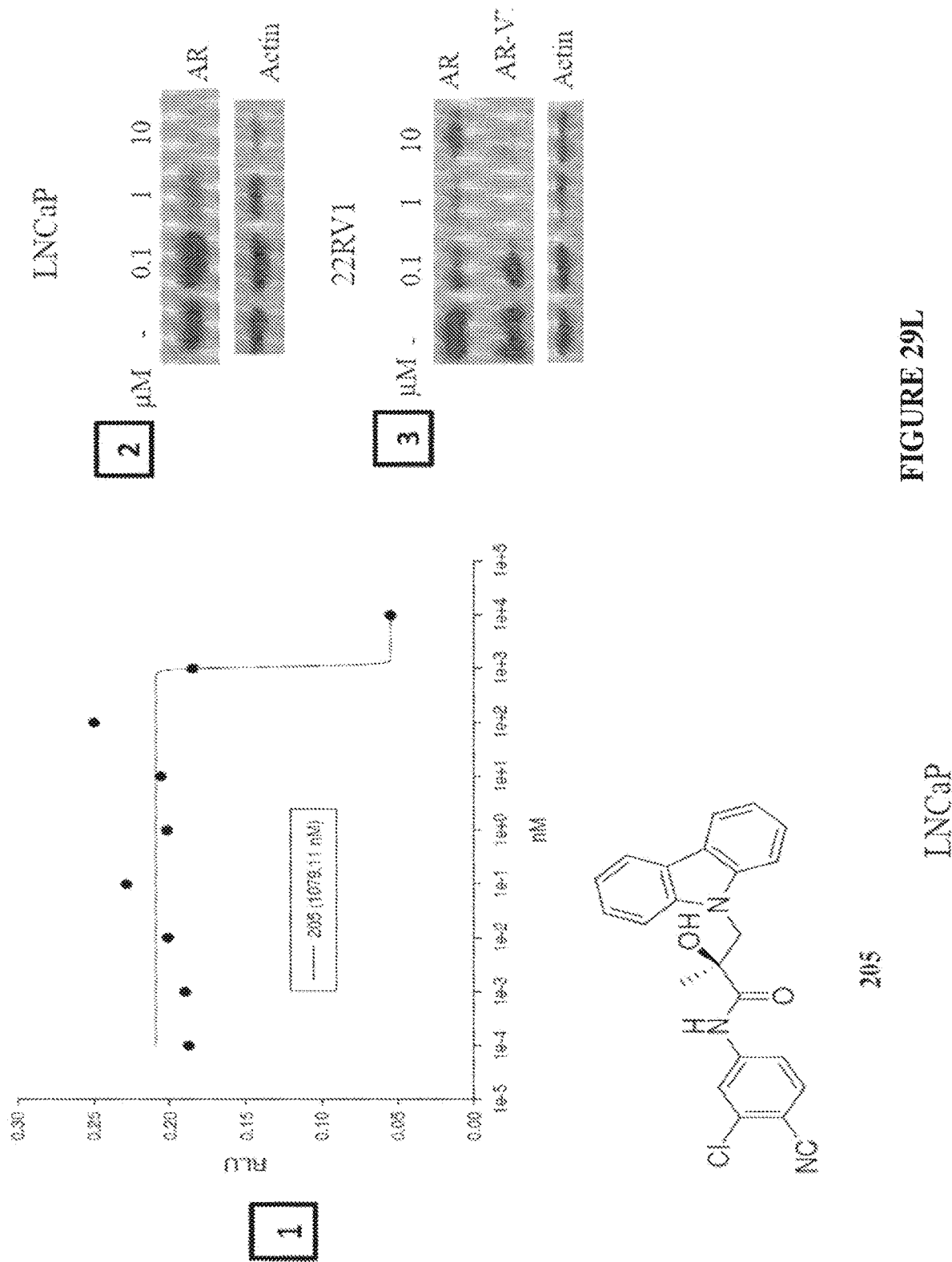
Figure 29M:
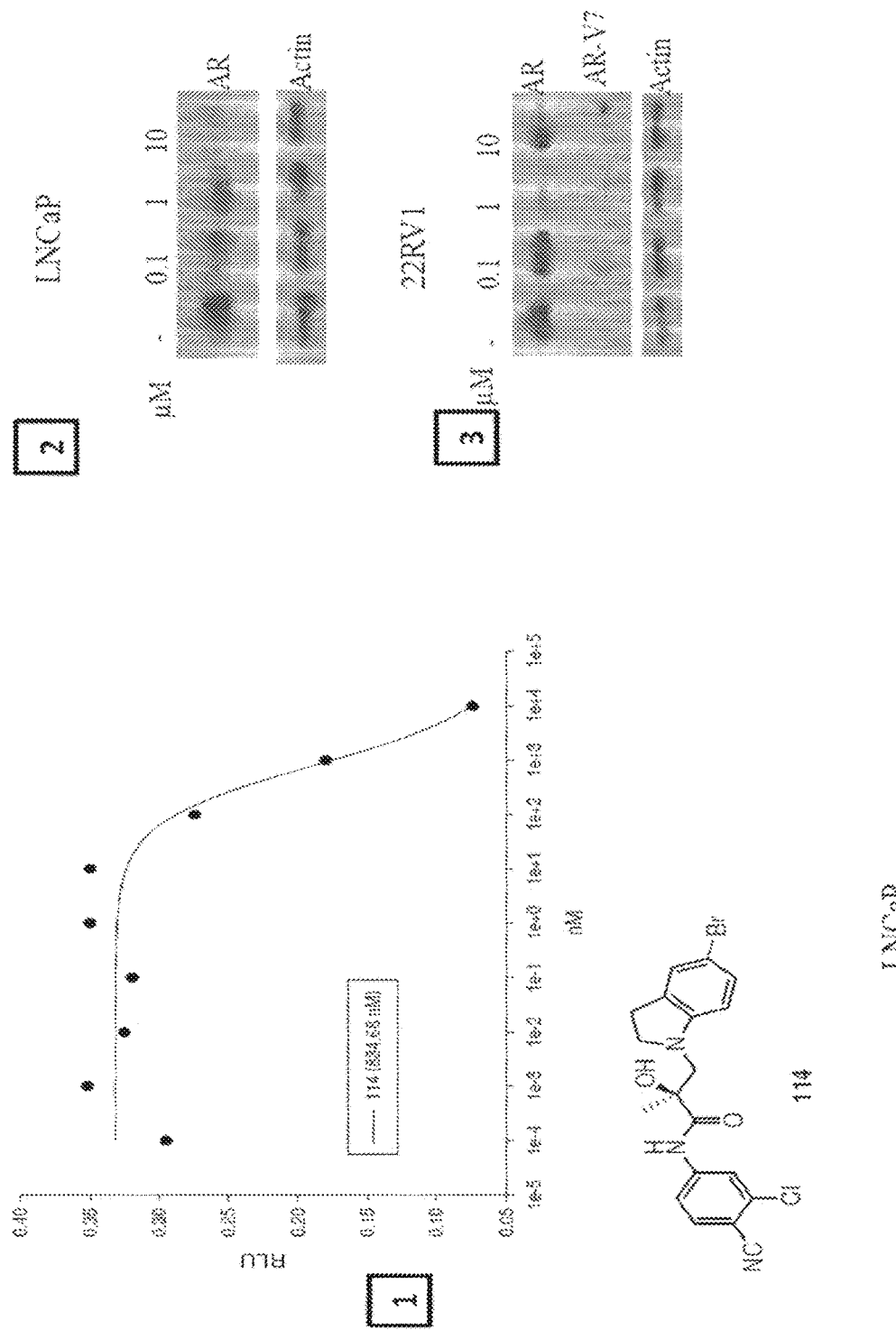

| Compd ID | Structure | Log P (−0.4 to +5.6) | Binding/ Transactivation (wt AR) K$_i$ (nM) (DHT = 1 nM) | IC$_{50}$ (nM) | SARD Activity Full Length % inhibition at 1, 10 µM | S.V. (22RV1) % inhibition at 10 µM | DMPK (MLM) T$_{1/2}$ (min) CL$_{int}$ (µl/min/mg) |
|---|---|---|---|---|---|---|---|
| 114 | | 4.25 | 204.36 See FIG. 26M | 834.68 See FIG. 26M | 37, 84 (FIG. 29M) | 0 (FIG. 29M) | 17.35 39.36 |
| 115 | | 5.27 | 71.48 See FIG. 26J | 244.43 See FIG. 26J | 93 (100 nM) (FIG. 29J) | 90 (FIG. 29J) | 21.37 32.44 |
| 130 | | 4.28 | 1530.58 | 420.07 | 70, 78 | 65 | 161.7 4.286 |
| 131 | | 3.61 | 398.63 | 1002.73 | | 24 | 25.42 27.27 |
| 132 | | 3.61 | 353.19 (FIG. 29C legend) | 978.91 (FIG. 29C) | 0 | 60 | |
| 134 | | 5.04 | 201.98 | 573.98 | | | 38.25 18.12 |

TABLE 6-continued

AR Binding (K$_i$), Inhibition of AR Transactivation (IC$_{50}$), AR Degradation and Metabolic Stability of Indoline, Quinoline and Isoquinoline SARDs.

| | | | Binding/ | | SARD Activity | | |
|---|---|---|---|---|---|---|---|
| | | Log P | Transactivation (wt AR) | | Full Length % | S.V. (22RV1) | DMPK (MLM) |
| Compd ID | Structure | (−0.4 to +5.6) | K$_i$ (nM) (DHT = 1 nM) | IC$_{50}$ (nM) | inhibition at 1, 10 µM | % inhibition at 10 µM | T$_{1/2}$ (min) CL$_{int}$ (µl/min/mg) |
| 135 | | 4.37 | 3112.73 | 867.48 | | 21 | 15.25 45.45 |

TABLE 7

Liver Microsome (LM) Data for Indoline, Quinoline and Isoquinoline SARDs in Mouse LM (MLM), Human LM (HLM), Rat LM (RLM), and Dog LM (DLM).

| | MLM | | HLM | | RLM | | DLM | |
|---|---|---|---|---|---|---|---|---|
| Compd ID | T$_{1/2}$ (min) | CL$_{int}$ (µl/min/mg) | T$_{1/2}$ (min) | CL$_{int}$ (µl/min/mg) | T$_{1/2}$ (min) | CL$_{int}$ (µl/min/mg) | T$_{1/2}$ (min) | CL$_{int}$ (µl/min/mg) |
| 102 (5F-indoline) | 55.14 | 0.01257 | | | | | | |
| 100 (5Br-indoline) | 66.87 | 10.38 | 64.84 | 0.01069 | | | | |
| 102 | 28.13 | 24.64 | 17.71 | 39.13 | | | | |
| 101 | 25.06 | 27.67 | | | | | | |
| 135 | 15.21 | 45.57 | 7.54 | 91.94 | | | | |
| 131 | 25.42 | 27.27 | 6.553 | 105.8 | | | | |
| 104 | 29.16 | 23.77 | 24.7 | 28.06 | 3.33 | 208 | 49.44 | 14 |
| 103 | 15 | 46.22 | 20.07 | 34.54 | 2.09 | 330 | 42.8 | 16.19 |
| 114 | | | 17.35 | 39.96 | 6.084 | 113.9 | | |
| 115 | 21.37 | 32.44 | 11.77 | 58.87 | | | | |

Example 7

AR Degradation Using Compounds of this Invention (Indoles, Benzimidazoles, Indazoles)

LNCaP Gene Expression Assay

Objective: To determine the effect of SARDs on AR-target gene expression in LNCaP cells.

Method: LNCaP cells were plated at 15,000 cells/well of a 96 well plate in RPMI+1% csFBS without phenol red. Forty-eight hours after plating, cells were treated with a dose response of SARDs. Sixteen-twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay

Objective: To determine the effect of SARDs on LNCaP cell growth.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP Degradation Assay

Objective: To determine the effect of SARDs on AR expression in LNCaP cells.

Method: LNCaP cells were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV-1 Degradation Assay

Objective: To determine the effect of SARDs on AR full length and splice variant expression in 22RV-1 cells.

Method: 22RV-1 cells were plated at 750,000-1,000,000 cells/well of a 6 well plate in growth medium (RPMI+10% FBS). Twenty four hours after plating, medium was changed and treated. After 16-20 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

AD1 Androgen Receptor Degradation (Full Length AR)

Objective: To determine the effect of compounds of this invention (SARDs) on full length AR protein expression in AD1 cells.

Method: AD1 cells expressing full length AR were plated at 750,000-1,000,000 cells/well of a 6 well plate in growth medium (RPMI+10% FBS). Twenty four hours after plating, the medium was changed to RPMI+1% csFBS without phenol red and maintained in this medium for 2 days. The medium again was changed to RPMI+1% csFBS without phenol red and cells were treated with SARDs (1 nM to 10 mM) in combination with 0.1 nM R1881. After 24 h of treatment, cells were washed with cold PBS and harvested. Protein was extracted using salt-containing lysis buffer with three freeze-thaw cycles. The protein concentration was estimated and five microgram of total protein was loaded on a SDS-PAGE, fractionated, and transferred to a PVDF membrane. The membrane was probed with AR N-20 antibody (SantaCruz Biotechnology, Inc., Dallas, Tex. 75220) and actin antibody (Sigma-Aldrich, St. Louis, Mo.). The results of this assay in AD1 cells were reported in FIGS. 33A (76), 33B (75), 33C (96) and 33D (97) as images of Western blot films (chemiluminescence exposed films). Also reported in FIGS. 33A-33D are results from wt AR binding ($K_i$), inhibition of transactivation ($IC_{50}$), and in vitro metabolic stability in mouse liver microsomes (MLM). One advantage of the indazole template is metabolic stability in vitro compared to indole and benzimidazole analogs. For example, 96 (4-$CF_3$ indazole) demonstrated a half-life of 53.7 minutes and intrinsic clearance of 12.91 µg/min/mg which is a two-fold improvement compared to 18 (5-$CF_3$ indole; 21 min and 32.9 µg/min/mg).

Figure 2A:
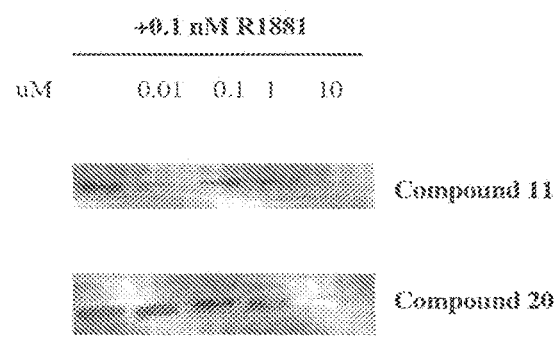
FIG. 2A demonstrates degradation in LNCaP cells using SARD compounds of this invention (11 and 20): LNCaP cells were plated in 6 well plates at 1 million cells/well. The cells were maintained in serum free conditions for 3 days. The cells were treated as indicated in the figure, harvested, protein extracted, and Western blotted for AR.

FIG. 2A presents degradation in LNCaP cells using 11 and 20. LNCaP cells were plated in 6 well plates at 1 million cells/well. The cells were maintained in serum free condition for 3 days. The cells were treated as indicated in the figure, harvested, protein extracted, and Western blotted for AR. 11 demonstrated selective degradation of AR (i.e., SARD activity) in the nM range, i.e., at concentrations comparable to its antagonist $IC_{50}$ value. LNCaP cells are known to express the AR mutant T877A, demonstrating the ability to degrade resistance conferring mutant androgen receptors.

Figure 2B:
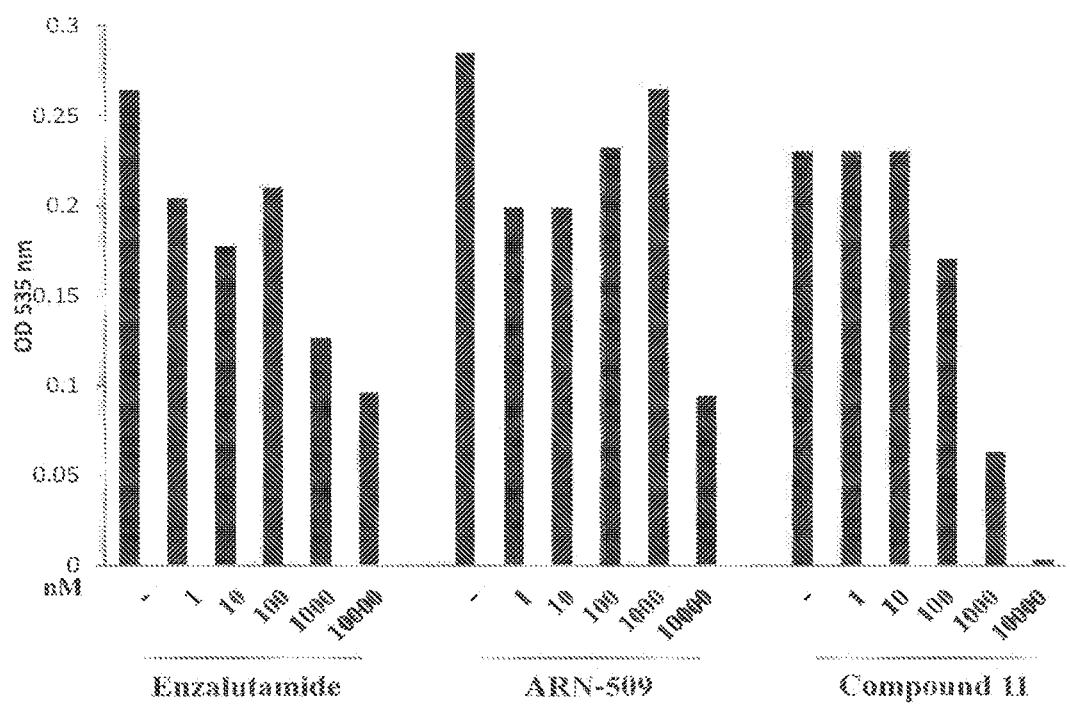
FIG. 2B presents the effect of AR antagonists and SARD 11 on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. (Example 7)

FIG. 2B presents the effect of AR antagonists and SARDs on LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. 11 demonstrated more potent anti-proliferative activity in LNCaP cells at 1 and 10 M when compared to enzalutamide and ARN-509.

Figure 3:
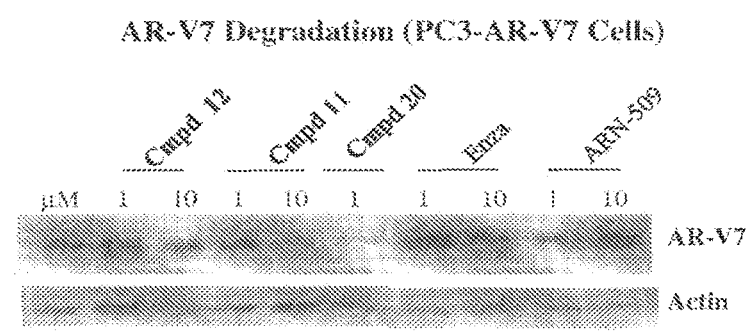
FIG. 3 presents AR-V7 degradation (PC3-AR-V7 cells) using SARD compounds of this invention (11, 12 and 20). PC-3 prostate cancer cells were serum stably transfected with a lentivirus construct for AR-V7. Once the stable cells were selected, the cells were plated in 6 well plates at 1 million cells/well. The cells were treated as indicated in the figure (µM) and Western blot performed for AR and actin. The results show that the SARDs have the potential to degrade truncated versions of AR such AR-V7, while enzalutamide or ARN-509 have no effect of the AR-V7 expression, suggesting that SARDs of this invention, unlike enzalutamide and ARN-509, can treat AR-V7 dependent CRPC. (Example 7)
Figure 4:
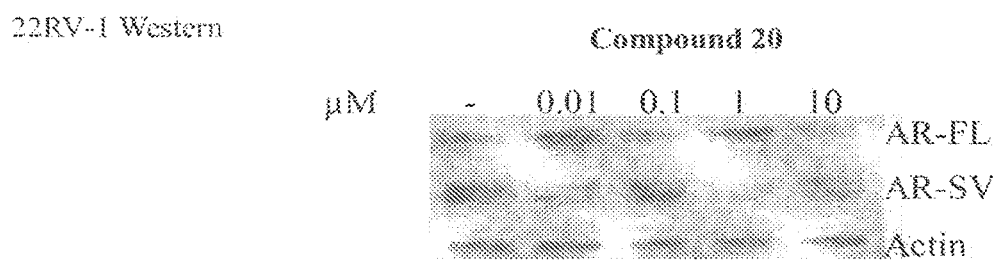
FIG. 4 demonstrates via Western blot that 20 degraded AR-FL and AR-SV in 22RV-1 cells, further supporting their use in the treatment of AR-SV-driven CRPC. (Example 7)

FIG. 3 presents AR-V7 degradation (PC3-AR-V7 cells) using 11, 12 and 20 at 1 M and 10 M. PC-3 prostate cancer cells were serum stably transfected with a lentivirus construct for AR-V7. Once the stable cells were selected, the cells were plated in 6 well plates at 1 million cells/well. The cells were treated as indicated in the figure and Western blot performed for AR and actin. The results show that the SARDs have the potential to degrade the truncated version of AR, while enzalutamide or ARN-509 had no effect of the AR-V7 expression.

SARD Compounds of this Invention Degrade AR-SV in 22RV-1 Cells

Figure 5:
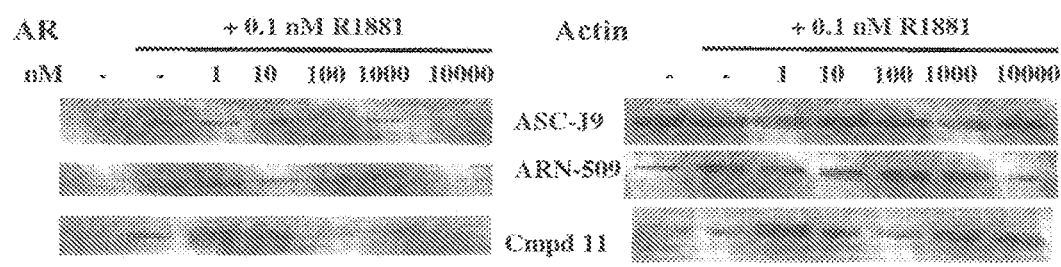
FIG. 5 presents SARD degradation of AR in LNCaP cells using 11. (Example 7)
Figure 6A:
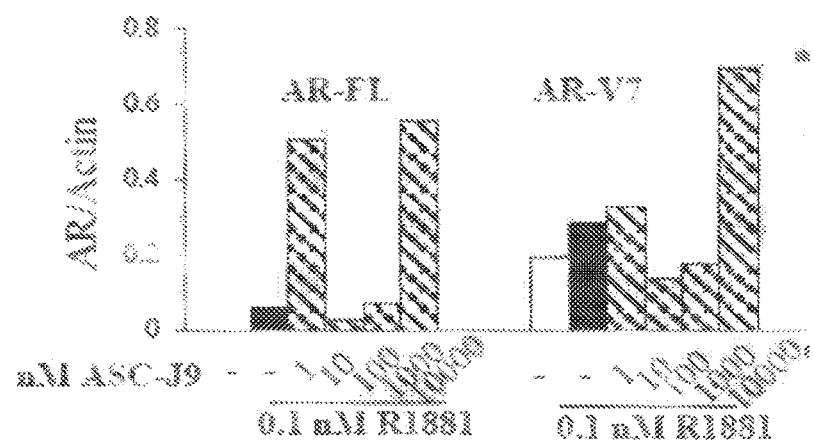
FIGS. 6A-6C present SARD degradation of AR-FL and AR-V7 in 22RV-1 cells using (FIG. 6A) ASC-J9, (FIG. 6B) ARN-509 and (FIG. 6C) 11. (Example 7)
Figure 6B:
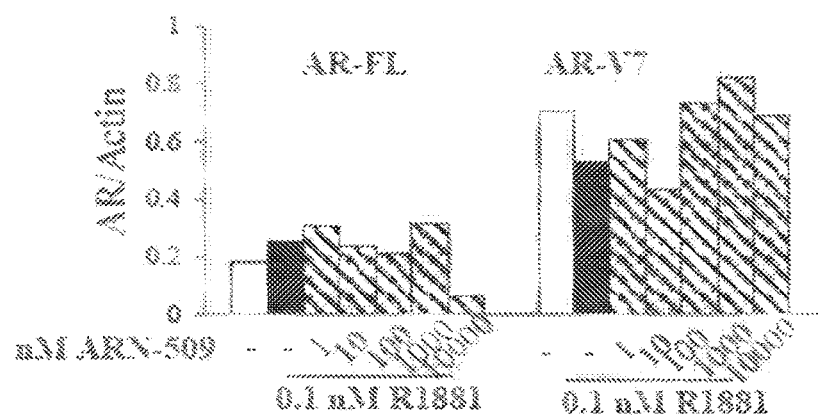
Figure 6C:
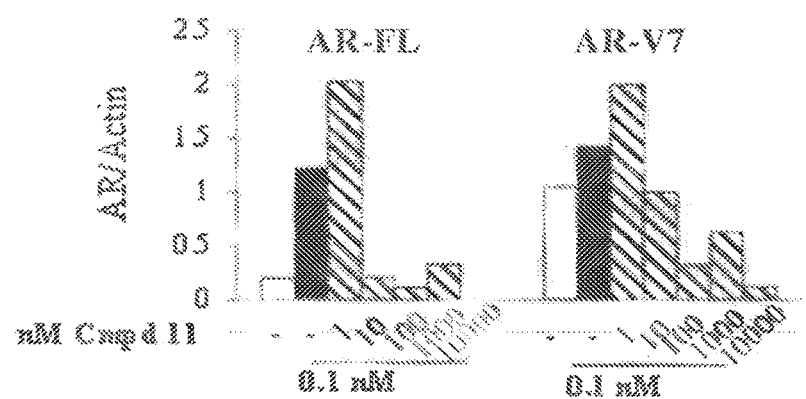
Figure 7A:
FIGS. 7A-7D present that 11 inhibits transactivation of AR-NTD-DBD-hinge (A/BCD) AR construct which lacks the LBD.
Figure 7B:
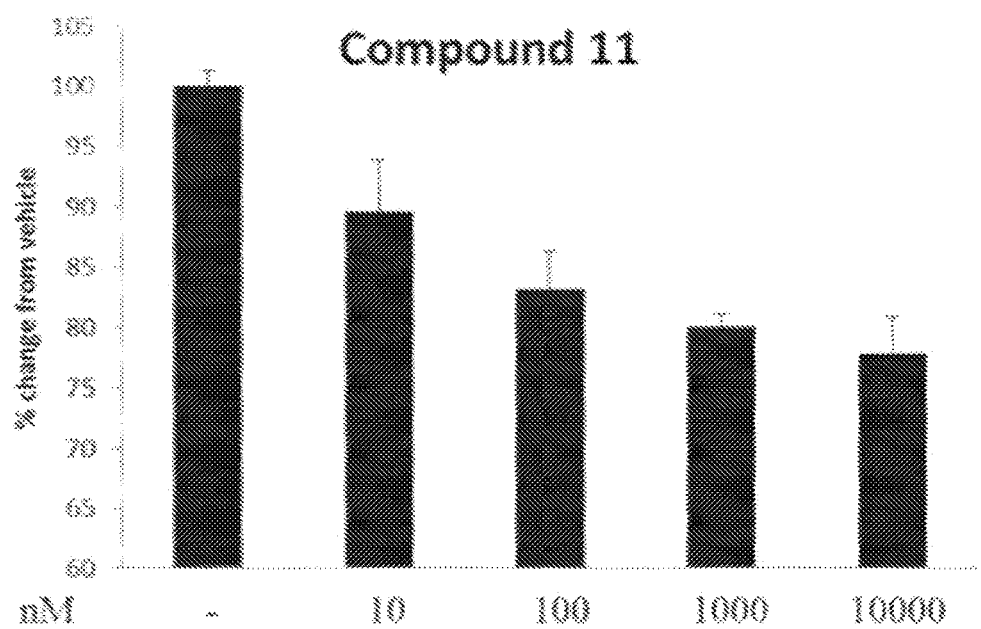
Figure 7C:
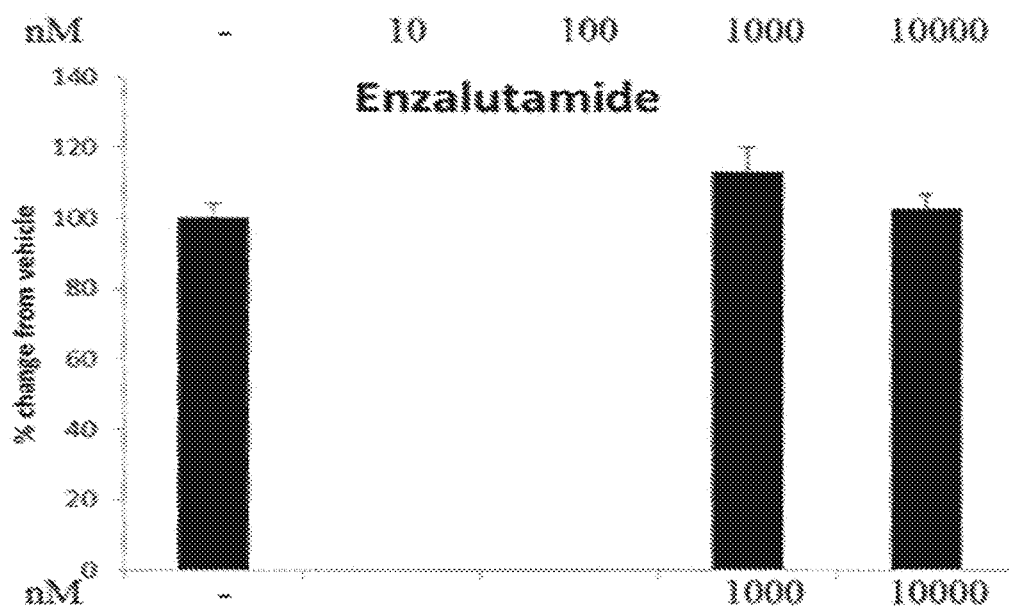
Figure 7D:
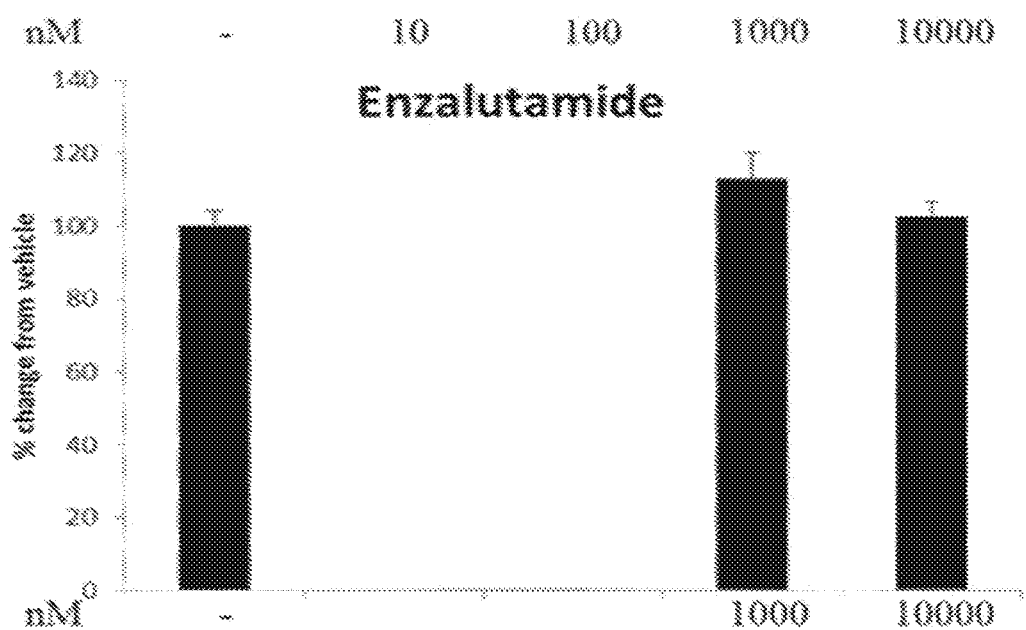

FIG. 4—22RV-1 Western blot: 22RV-1 cells were plated in 6 well plate at 1-1.5 million cells/well in growth medium (RPMI+10% FBS). Next day, medium was changed and treated with vehicle or a dose response of 20. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody (N20 from SCBT) and actin antibody. 20 was capable of degrading full length androgen receptor (AR-FL) and truncated AR (AR-SV) in 22RV-1 cells, suggesting that SARDs may be able to overcome AR-V7 dependent prostate cancers (e.g., CRPC). 11 degraded AR-FL but not actin in LNCaP cells (FIG. 5) and AR-FL and AR-SV in 22RV-1 cells (FIGS. 6A-6C). FIGS. 6A-6C show that 11 degraded AR-FL and AR-V7 at nM concentrations (FIG. 6C) whereas ARN-509 did not degrade either (FIG. 6B). Although ASC-J9 did exhibit some degradation in the nM range, M concentrations failed to degrade AR (FIG. 6A). 11 also inhibited AR-dependent gene expression (PSA and TMPRSS2) in LNCaP cells, transactivation of AR in 22RV-1 cells and cellular growth in both the cell types (Table 8 and Table 9). Cumulatively, these observations suggest that SARDs of this invention may be useful in prostate cancers that are dependent on mutant ARs, AR-FL and/or AR-SV.

Figure 11:
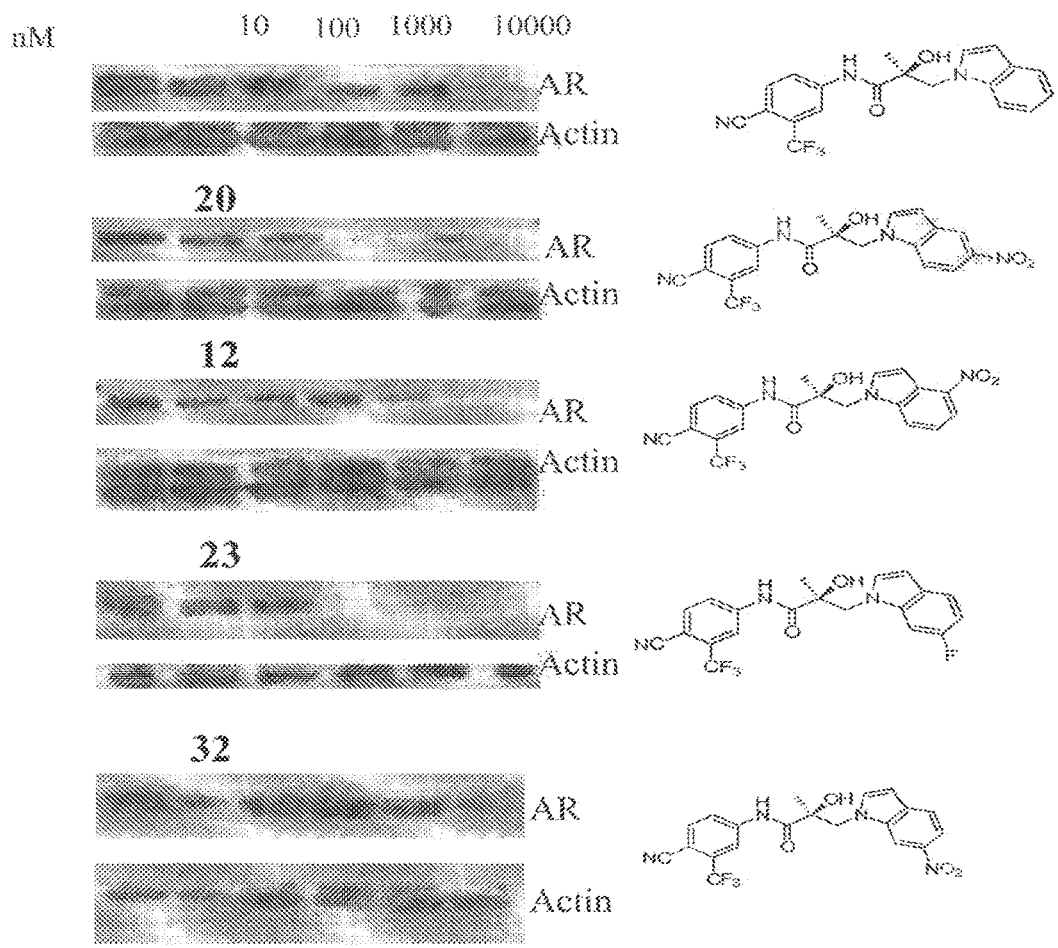
FIG. 11 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. SARDs demonstrated selective degradation of AR (i.e., SARD activity) in the nM range, i.e., at concentrations comparable to their antagonist $IC_{50}$ values. LNCaP cells are known to express the AR mutant T877A, demonstrating the ability to degrade resistance conferring mutant androgen receptors. (Example 7)

FIG. 11 presents degradation in LNCaP cells using 27, 20, 12, 23 and 32. LNCaP cells were plated in 6 well plates at 1 million cells/well. The cells were maintained in serum free conditions for 3 days. The cells were treated as indicated in the figure, harvested, protein extracted, and Western blotted for AR. All SARDs demonstrated selective degradation of AR (i.e., SARD activity) at concentrations comparable to their antagonist $IC_{50}$ values. LNCaP cells are known to express the AR mutant T877A, demonstrating the ability to degrade antiandrogen resistance conferring mutant androgen receptors (i.e., advanced prostate cancers and CRPC).

Figure 12:
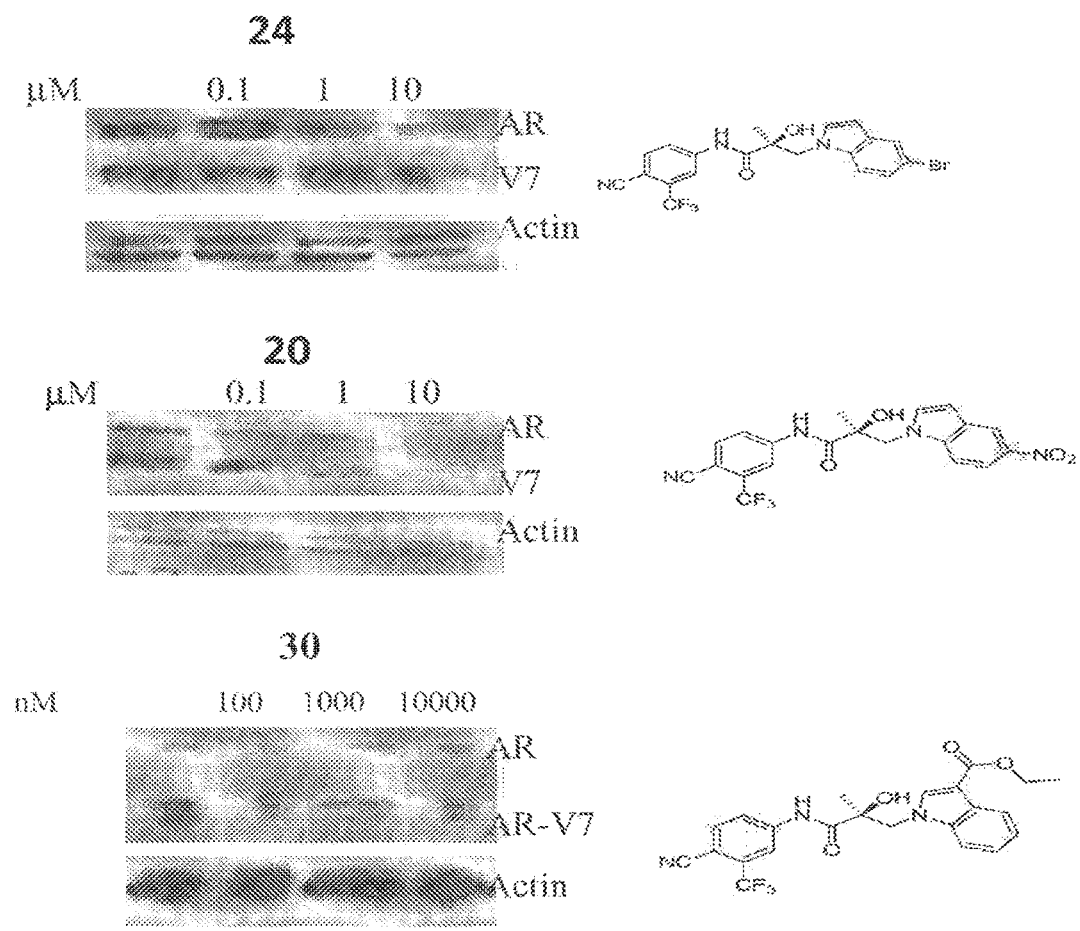
FIG. 12 presents 22RV-1 Western blots: 22RV-1 cells were plated in 6 well plates at 1-1.5 million cells/well in growth medium (RPMI+10% FBS). Next day, medium was changed and treated with vehicle or a dose response of compounds 20, 24 and 30. After overnight treatment (12-16 hrs), cells were washed in ice cold PBS and harvested by scrapping in 1 mL PBS. Cells were pelleted, protein extracted, quantified using BCA assay, and equal quantity of protein was fractionated on an SDS-PAGE. The proteins were transferred to nylon membrane and Western blotted with AR antibody (N20 from SCBT) and actin antibody. Compounds 20, 24 and 30 were capable of degrading full length androgen receptor (AR-FL) and truncated AR (AR-SV) in 22RV-1 cells, suggesting that SARDs may be able to overcome wildtype or AR-V7 dependent prostate cancers. (Example 7)

FIG. 12: 22RV-1 Western blot: 22RV-1 cells were plated in 6 well plate at 1-1.5 million cells/well in growth medium (RPMI+10% FBS). Next day, medium was changed and treated with vehicle or a dose response of 20, 24 and 30. After overnight treatment (12-16 hrs), cells were washed in ice cold PBS and harvested by scrapping in 1 mL PBS. Cells were pelleted, protein extracted, quantified using BCA assay, and equal quantity was fractionated on a SDS-PAGE. The proteins were transferred to nylon membrane and Western blotted with AR antibody ($N_{20}$ from SCBT) and actin antibody. 20, 24 and 30 were capable of degrading full length androgen receptor (AR-FL) and truncated AR (AR-V7) in 22RV-1 cells, suggesting that SARDs may be able to overcome AR-V7 dependent prostate cancers (i.e., CRPC).

Figure 13:
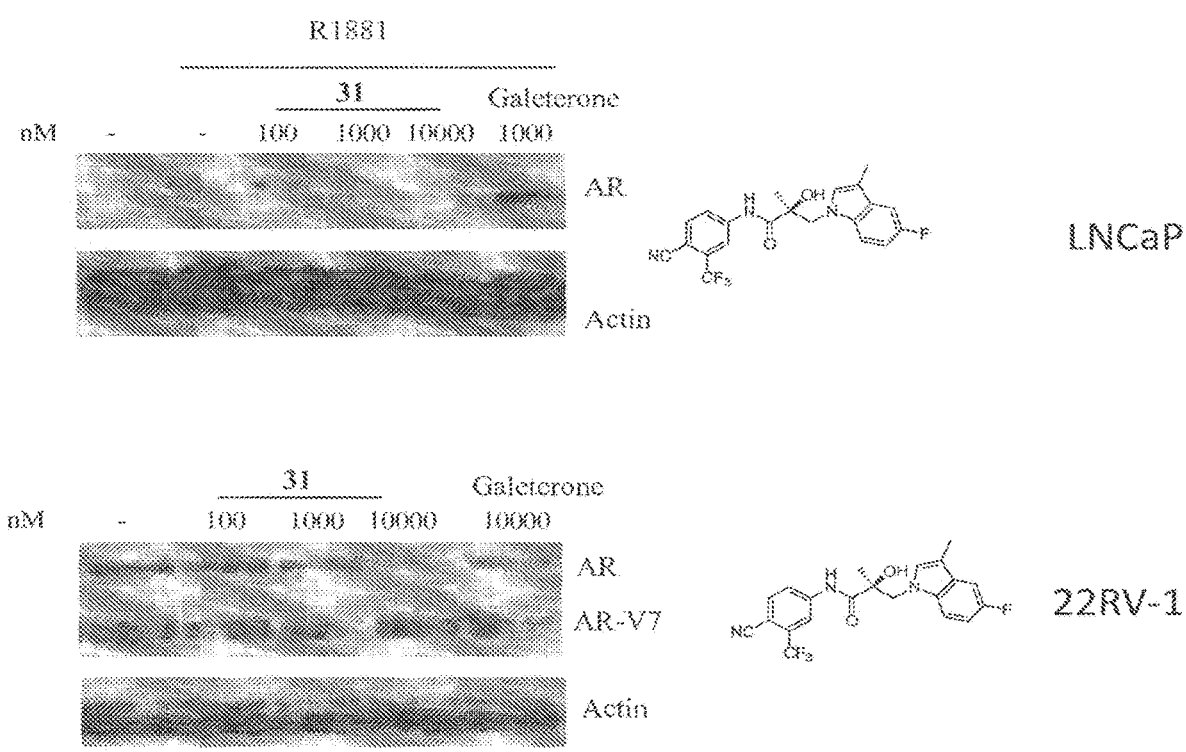
FIG. 13 presents degradation in LNCaP cells (top) and 22RV-1 cells (bottom) using 31 vs. galeterone. Using the methods described in the legends for FIG. 11 (LNCaP) and FIG. 12 (22RV-1), 31 was compared to galeterone (a clinical lead SARD). While 31 demonstrated SARD activity in both LNCaP (mutant AR harboring T877A mutation) and 22RV-1 (growth dependent on AR-SV lacking a LBD) cells, galeterone demonstrated little to no AR degradation in these models. (Example 7)

FIG. 13 presents degradation in LNCaP cells and 22RV-1 cells using 31 vs. galeterone. The experiments were performed by the methods cited above. A dose response of SARD 31 demonstrated the ability to degrade full length AR in LNCaP and 22RV-1 cell lines, whereas galeterone was not able to substantially degrade AR in either cell line.

Figure 14:
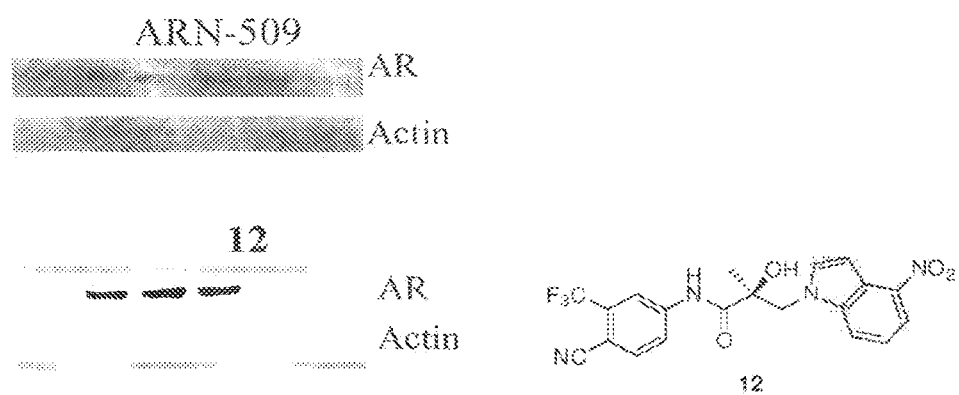
FIG. 14 presents degradation in LNCaP cells using a dose-response of 12 or ARN-509. Using the methods described in the legend for FIG. 11 (LNCaP), SARD activity for 12 was compared to known SARD ARN-509. 12 demonstrated activity in the nM range (100-1000 nM) whereas ARN-509 only had activity at 10,000 nM. (Example 7)

FIG. 14 presents degradation in LNCaP cells using 12 vs. ARN-509. 12 and ARN-509 both demonstrated the ability to degrade AR in LNCaP cells, however 12 demonstrated activity at 1 μM whereas ARN-509 only demonstrated activity at 10 M.

Figure 15:
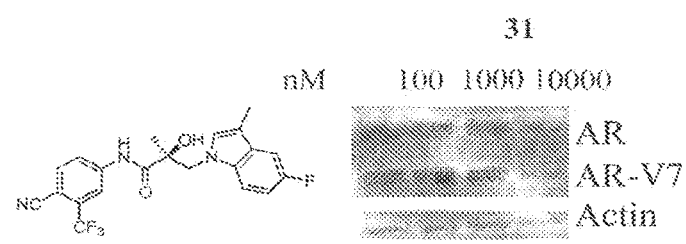
FIG. 15 presents degradation in 22RV-1 cells using 31. Using the methods described in the legend for FIG. 12 (22RV-1), SARD activity for 31 was demonstrated as degradation of full length (AR) and truncated splice variant (AR-V7) androgen receptor. (Example 7)

FIG. 15 presents degradation in 22RV-1 cells using 31. Using the methods described in the legend for FIG. 12 (22RV-1), SARD activity for 31 was demonstrated as degradation of full length (AR) and truncated splice variant (AR-V7) androgen receptor.

Figure 16:
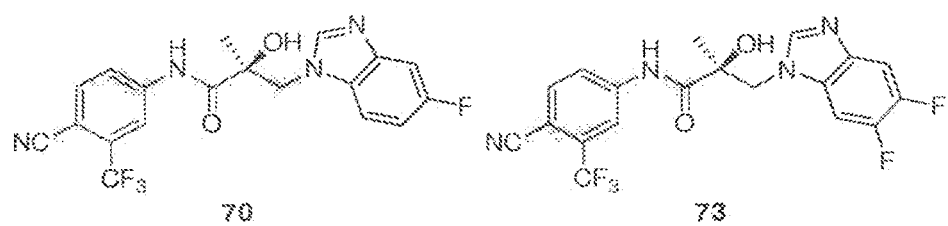
FIG. 16 presents degradation in LNCaP cells using 70 and 73. Using the methods described in the legend for FIG. 11 (LNCaP), SARD activity for 70 and 73 was demonstrated at concentrations as low as 100 nM. This demonstrates that benzimidazoles of this invention also demonstrate potent SARD activity. (Example 7)
Figure 16:
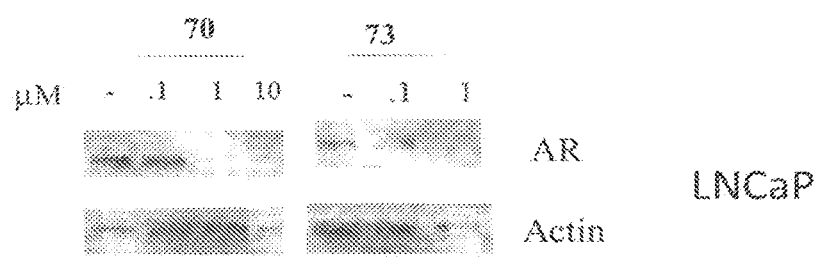

FIG. 16 presents degradation in LNCaP cells using benzimidazoles 70 and 73. Using the methods described in the legend for FIG. 11 (LNCaP), SARD activity for 70 and 73 was demonstrated at concentrations as low as 100 nM. This demonstrates that benzimidazoles of this invention also demonstrate potent SARD activity.

These selected SARD activity demonstrations as well of those reported in the tables suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction, kinase activation, and/or high levels of coactivators, etc.; and suggests that the SARDs should also degrade the polyQ polymorphisms in hyperandrogenic dermatologic disorders (shortened polyQ) or Kennedy's disease (extended polyQ), providing a rationale for treating either type of disease by destroying the AR in the affected tissues (skin and neuromuscular system, respectively).

TABLE 8

Inhibition of Growth and Gene Expression of LNCaP PCa Cells.

| Compound | Gene Expression $IC_{50}$ (nM) | | Growth $IC_{50}$ (nM) |
| --- | --- | --- | --- |
| | PSA | TMPRSS2 | |
| Bicalutamide | 783.7 | 831.4 | |
| Enzalutamide | 384.4 | 72.3 | 872 |
| Compound 11 | 5.0 | 13.1 | 271 |
| ARN-509 | 169.7 | 517.1 | 994 |
| ASC-J9 | >10,000 | >10,000 | 1064 |

TABLE 9

Effects of SARDs on AR Transactivation and Growth of 22RV-1 Cells.

| Compound | Transactivation $IC_{50}$ (nM) | Growth $IC_{50}$ (nM) |
| --- | --- | --- |
| Bicalutamide | 3133.52 | >10,000 |
| Enzalutamide | 101.87 | >10,000 |
| Compound 11 | 420.62 | 1041 |
| ARN-509 | 64.54 | >10,000 |
| ASC-J9 | 1026.91 | >10,000 |

To validate the results obtained in 22RV1 cells, AR degradation effect of 11 was tested in various PCa cell lines. AD-1 cells that express only AR-FL, D567es cells that express only AR-v567es, and LNCaP-95 cells that co-express AR-FL and AR-SV (FIG. 38A) were treated under various conditions with a dose response of 11. Cells were harvested 24 hrs after treatment and Western blot for the AR and its isoforms was performed. As indicated in the figures, 11 consistently degraded the AR and its SVs at concentrations ranging between 100 and 1000 nM, indicating that these SARDs degrade the AR and its SVs under various conditions and irrespective of the specific combination of the AR-FL and SV expressed. The D567es result was unexpected based on our hypothesis of SARD binding solely to the LBD, and earlier findings [Watson, P. A., Chen, Y. F., Balbas, M. D., Wongvipat, J., Socci, N. D., Viale, A., Kim, K., and Sawyers, C. L. (2010) Constitutively active androgen receptor splice variants expressed in castration-resistant prostate cancer require full-length androgen receptor. Proceedings of the National Academy of Sciences of the United States of America 107, 16759-16765) that the AR-SV function depends on the AR. The D567es result argues for the direct interaction of the SARDS of this invention with AR-SV such as D567es which lacks themLBD.

To determine if the degradation is a direct effect due to destabilization of already synthesized AR protein, LNCaP and 22RV1 cells were treated with 11, protein synthesis inhibitor cycloheximide, or a combination of cycloheximide and 11. While 11 degraded the AR and AR-V7 starting from 4-6 hrs, addition of cycloheximide accelerated the degradation, indicating that the 11-dependent AR and AR-SV degradation was not dependent on the expression of other proteins and that 11 destabilized the already synthesized AR and AR-SV (FIG. 38B) at the protein level. The graph below FIG. 38B shows the reduction in half-life of both the AR and AR-SV by 11.

Degradation of the AR and AR-V7 by 11 was rapid and sustained. To evaluate the time-course of degradation, LNCaP cells were treated with 11 in combination with 0.1 nM R1881. Cells were harvested at different time-points and Western blot for AR and actin was performed. 11 degraded the AR starting at 4 hrs with complete degradation observed by 12 hrs (FIG. 39A). Almost comparable time-course was followed for the inhibition of AR function as measured by the expression of the AR-target genes PSA and FKBP5 (FIG. 39B). To determine the endurance of this degradation upon removal of 11, D567es cells were treated with vehicle or 11 for 24 hrs. Cells were washed and one set of plates was harvested immediately (time point 0 hrs), while the rest of the plates were harvested 24 or 72 hrs after the drug removal. Western blot for AR-V7 and actin was performed. AR was degraded by 11 by 24 hrs (time-point 0 hrs) and remained degraded up to 72 hrs after the 11 removal (FIG. 39C).

11 degraded the AR through ubiquitin-proteasome degradation machinery. To evaluate the role of ubiquitin-proteasome machinery in the SARD-dependent AR degradation, LNCaP cells were treated with 11 for 4 hrs, AR was immunoprecipitated, and a Western blot for ubiquitin was performed (FIG. 38C). AR co-immunoprecipitated with ubiquitin in the presence of 11, indicating that ubiquitination of the AR in response to these SARDs is a potential mechanism for AR degradation.

11 inhibited AR-dependent gene expression and PCa cell proliferation. To evaluate whether the highly potent AR antagonism translates to inhibition of AR function and PCa cell proliferation, 11 was tested in LNCaP cells and compared to enzalutamide. Treatment of LNCaP cells with 11 inhibited 0.1 nM R1881-induced PSA and FKBP5 gene expression at low nanomolar concentrations with at least 10-fold better potency than enzalutamide (FIG. 40A).

To determine the effect of 11 on AR-V7-dependent gene expression, PC-3 cells stably transfected with AR-V7 were treated with vehicle or 10 μM 11 for 24 hrs and RNA-sequencing was performed. Expression of several genes was altered by AR-V7, which were reversed back to PC-3-GFP cell levels by 11 (FIG. 40B left panel; selected genes from the list shown in FIG. 40B right panel). These results show that the genes induced by AR-V7 were inhibited by 11. The effect on AR-V7-dependent gene expression was confirmed in 22RV1 cells, where androgen-independent expression of FKBP5 was inhibited by 11, but not by enzalutamide (FIG. 40C).

The effect of the SARD compounds of this invention on the proliferation of AR-FL- and AR-SV-expressing cell lines was evaluated. R1881-induced LNCaP proliferation was completely inhibited by 11 with nanomolar $IC_{50}$, while enzalutamide inhibited the proliferation at concentrations greater than 1 μM (FIG. 40D). 11 also inhibited the proliferation of 22RV1 cells at concentrations between 1 and 10 M, while enzalutamide failed to inhibit the proliferation (FIG. 40D). These results were reproduced in various cell lines, including LNCaP-abl and LNCaP-EnzR, both containing enzalutamide-resistant AR, and in AR-SV-expressing LNCaP-95 cells. 11 modestly inhibited the proliferation of HeLa cells at 30 M, demonstrating its specificity. In addition to these cells, 11 also inhibited the proliferation of AD-1 (FIG. 41A) and transactivation of v567es AR and proliferation of D567es cells that carry AR-v567es (FIG. 41B). 11, but not enzalutamide, inhibited the expression of PSA in LNCaP-EnzR, indicating that the F876L mutant that is resistant to enzalutamide is sensitive to 11 (FIG. 40E).

The SARDs compounds of this invention inhibited the AR nuclear translocation and recruitment to PSA regulatory regions. To determine if the SARD compounds inhibit the recruitment of the AR to cis regulatory elements, LNCaP cells were treated with 11 in the presence of 0.1 nM R1881. Two hours after the treatment, cells were fixed to cross-link the protein to DNA, AR was immunoprecipitated, and recruitment to the PSA enhancer was quantified by realtime PCR. 11 inhibited the recruitment of the AR to PSA enhancer (FIG. 42A). These studies were performed at a time-point when no AR degradation could be detected.

Inhibition of AR DNA binding could be a result of nuclear translocation inhibition. Microscopic evaluation of nuclear translocation shows that 11 inhibited the R1881-induced translocation of F876L enzalutamide-resistant AR (FIG. 42B).

The SARD compounds of this invention did not require binding to the LBD to degrade the AR. As these SARDs bind to two domains and degrade the AR, they serve as a tool to probe into the role of each domain for degradation and proliferation. Molecular modeling was performed to determine the amino acids in the AR-LBD with which 11 interacted. 11 formed hydrogen bonds with Q711, R752, N705, and L704 (FIG. 42C). These sites were mutated and performed a transactivation assay. Mutating these amino acids individually compromised the ability of R1881 to activate the AR. While the $EC_{50}$ of R1881 for the wildtype AR was 0.11 nM, the $EC_{50}$ for the mutant ARs was 7.48 nM for Q711A, 8.72 nM for L704A, 15.41 nM for R752L, and 2037 nM for N705A (FIG. 42C; left panel).

The effect of 11 was determined on the transactivation of wildtype and mutants AR's. In these studies R1881 was used at the respective $EC_{50}$ for each mutant. While 11 effectively inhibited the wildtype AR transactivation at 63 nM, it inhibited the transactivation of the LBD mutants at concentrations greater than 1 M. 11 failed to inhibit the function of N705A mutant AR (FIG. 42C; right panel). These studies show that mutating the interacting amino acids in the LBD weaken 11's ability to inhibit ligand-dependent AR transactivation and that 11's binding to LBD is important to antagonize androgen-dependent function of the AR.

To determine if mutating the LBD will also impact 11's degradation role, HeLa cells transfected with wildtype or mutant ARs were treated with 11 and AR expression was evaluated by Western blot. These studies were performed under the same conditions as indicated for the transactivation. 11 degraded the wildtype and mutant ARs comparably (FIG. 42D), indicating that binding to LBD can be spared to retain the degradation activity.

To confirm this observation the R-isomer of 11 was synthesized (11R). 11 has a chiral center and the active form is the S-isomer. Hence, an R-isomer is expected to be a weaker LBD binder than the S-isomer. We tested the effect of 11R on R1881-induced AR transactivation and AR expression. While the 11R was 10-fold weaker to inhibit the AR transactivation, no difference was observed between the S- and R-isomers of 11 in their ability to degrade the AR (FIG. 43).

To determine if 11's anti-proliferative effect is dependent on its competitive binding to the LBD, we performed proliferation assay in LNCaP cells in the presence of increasing concentrations of R1881. We expected that increasing concentration of R1881 will displace 11 from the ligand binding pocket, resulting in reduced or lack of anti-proliferative effects. Interestingly, increasing concentrations of R1881 weakened enzalutamide's effects, but failed to affect 11's effect on proliferation (FIG. 44) suggesting that anti-proliferative effects are not dependent of competitive binding to the LBD.

Collectively these studies provide compelling evidence to show that 11 elicits AR degradation and possibly anti-proliferative activity through its AF-1, while the antagonistic effect of ligand-dependent transactivation is through the LBD.

11 inhibited PCa xenografts growth. In vitro studies proved that 11 were extremely potent to inhibit and degrade both AR and AR-SVs. 11 was tested in vivo in various xenograft models. In addition to LNCaP and 22RV1 xenografts, we developed a PDX, Pr-3001, from a CRPC patient specimen. Pr-3001 is a CRPC that expresses AR-FL and AR-SV and grows in castrated mice.

Pr-3001 is an aggressively growing patient-derived specimen. Typically, it is very hard to grow patient-derived PCa in mice due to their slow growing property. Pr-3001 developed tumors robustly and attained approximately 1000 $mm^3$ in less than 2 months. Pr-3001 expresses AR-FL and AR-SV and grows in castrated mice. Pr-3001 at 1 $mm^3$ piece were implanted on the flanks of mice and its growth was monitored. When Pr-3001 attained 100-200 $mm^3$, the animals were randomized and treated with vehicle or 11. Consistent with the observations made in 22RV1 xenograft, 11 inhibited the growth Pr-3001 by over 50% (FIG. 45).

Example 8

AR Degradation Using Indoline, Quinoline, or Isoquinoline SARD Compounds of this Invention Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 g GRE-LUC, 0.01 g CMV-LUC (renilla luciferase) and 25 ng of the AR. The cells were treated 24 hrs after transfection as indicated in the figures and the luciferase assay performed 48 hrs after transfection. Data are represented as $IC_{50}$ obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using biogelHT hydroxyapatite, washed and counted in a scintillation counter after adding scintillation cocktail. Values are expressed as $K_i$.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using tagman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 Growth and Gene Expression.

Methods: Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 18:
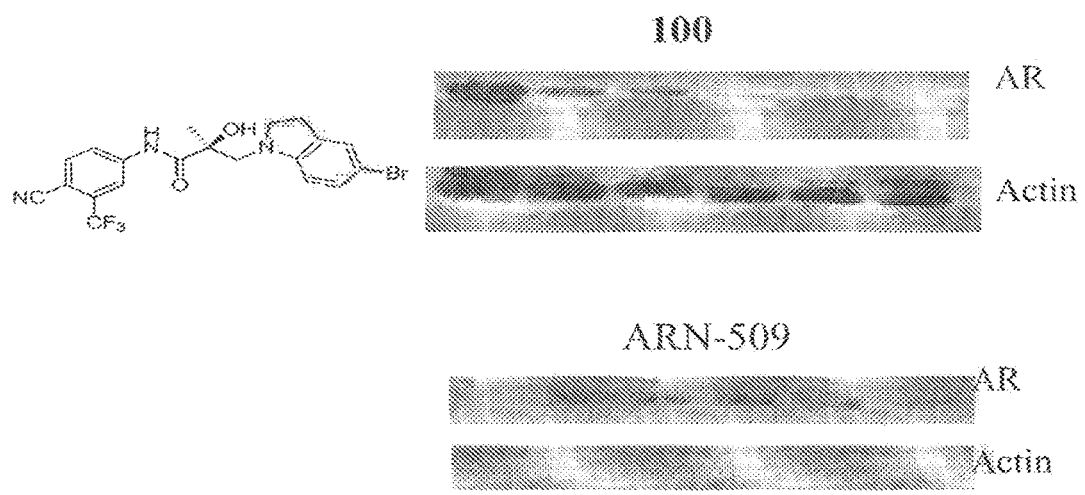
FIG. 18 demonstrates degradation in LNCaP cells using a SARD compound of this invention (100). LNCaP cells were plated in 6 well plates at 1 million cells/well. The cells were maintained in serum free conditions for 3 days. The cells were treated as indicated in the figure, harvested, protein extracted, and Western blotted for AR. (Example 8)

Results:

FIG. 18 presents degradation in LNCaP cells using 100 compared to ARN-509. LNCaP cells were plated in 6 well plates at 1 million cells/well. The cells were maintained in serum free conditions for 3 days. The cells were treated as indicated in the figure, harvested protein extracted, and Western blotted for AR. 100 demonstrated selective degradation of AR (i.e., SARD activity) in the nM range, i.e., at concentrations comparable to its antagonist $IC_{50}$ value whereas ARN-509 only demonstrated SARD activity at the highest concentration tested. LNCaP cells are known to express the AR mutant T877A, demonstrating the ability of compounds of this invention to degrade antiandrogen resistance conferring mutant androgen receptors.

Figure 19:
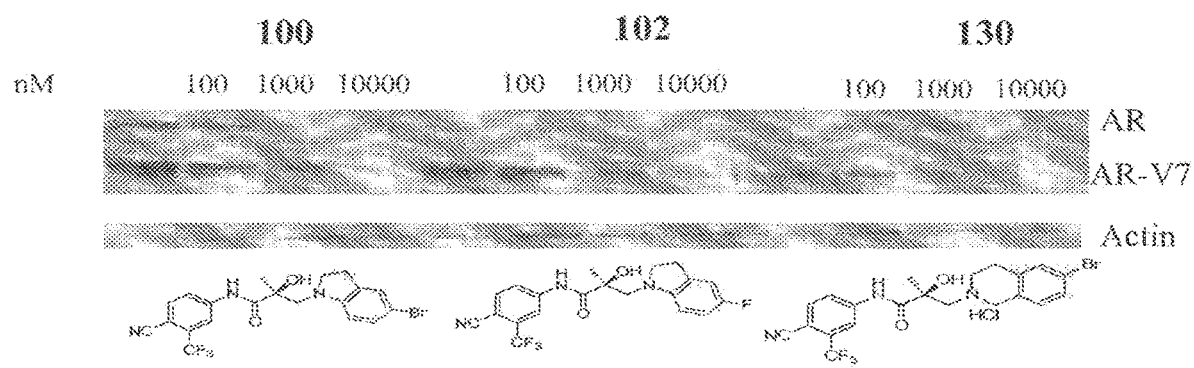
FIG. 19 demonstrates via Western blot as described above for FIG. 12, that 100, 102, and 130 degraded AR-FL and AR-SV in 22RV-1 cells. 100, 102, and 130 were capable of degrading full length androgen receptor (AR-FL) and truncated AR (AR-SV) in 22RV-1 cells, suggesting that SARDs of this invention may be able to overcome AR-V7 dependent prostate cancers. (Example 8)

FIG. 19 demonstrates via Western blot that 100, 102, and 130 degraded AR-FL and AR-SV in 22RV-1 cells. 22RV-1 cells were plated in 6 well plates at 1-1.5 million cells/well in growth medium (RPMI+10% FBS). Next day, medium was changed and treated with vehicle or a dose response of 100, 102, and 130. After overnight treatment (12-16 hrs), cells were washed in ice cold PBS and harvested by scrapping in 1 mL PBS. Cells were pelleted, protein extracted, quantified using BCA assay, and equal quantity of protein was fractionated on a SDS-PAGE. The proteins were transferred to nylon membrane and Western blotted with AR antibody ($N_{20}$ from SCBT) and actin antibody. 100, 102, and 130 were capable of degrading full length androgen receptor (AR-FL) and truncated AR (AR-SV) in 22RV-1 cells, suggesting that SARDs may be able to overcome AR-V7 dependent prostate cancers.

Figure 20:
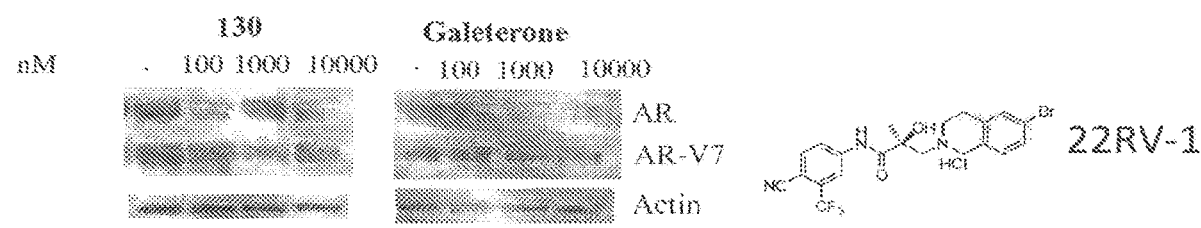
FIG. 20 presents degradation in 22RV-1 cells as described above for FIG. 12, using 130 vs. galeterone. 130 was compared to galeterone (a clinical lead SARD). 130 demonstrated SARD activity in 22RV-1 (growth dependent on AR-SV, an AR variant lacking a LBD) cells which was comparable to galeterone. (Example 8)

FIG. 20 presents degradation in 22RV-1 cells using 130 vs. galeterone. Using the methods described in the legend for FIG. 19 (22RV-1), 130 was compared to galeterone (a clinical lead SARD). 130 demonstrated SARD activity in 22RV-1 (growth dependent on AR-SV, an AR variant lacking a LBD) cells which was comparable to galeterone.

Figure 21:
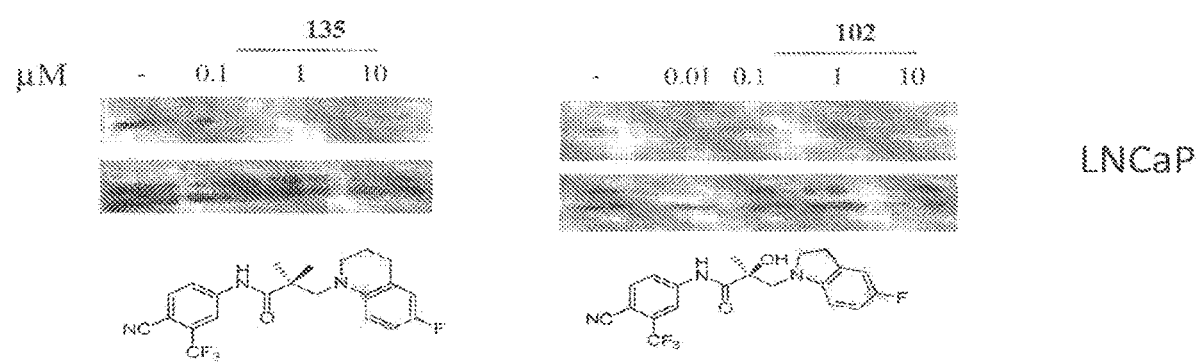
FIG. 21 presents degradation in LNCaP cells using 135 and 102. Using the methods described in the legend for FIG. 11, SARD activities for 135 and 102 were demonstrated. These compounds partially to fully degraded mutant AR (T877A), suggesting that SARDs of this invention such as these may be useful in advanced prostate cancer and/or CRPC. (Example 8)

FIG. 21 presents degradation in LNCaP cells using 135 and 102. Using the methods described in the legend for FIG. 18, SARD activities for 135 and 102 was demonstrated. These compounds partially and fully degraded mutant AR (T877A), suggesting that SARDs such as these may be useful in advanced prostate cancer and/or CRPC.

Figure 22:
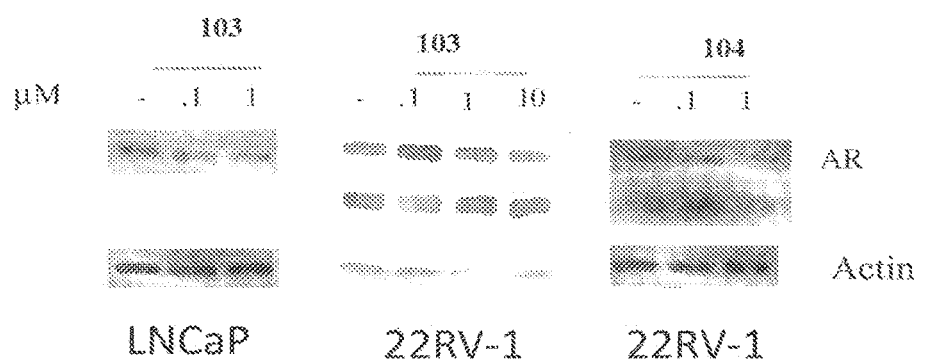
FIG. 22 presents degradation in LNCaP cells and 22RV-1 cells using 103 and 104. Using the methods described in the legends for FIG. 11 (LNCaP) and FIG. 12 (22RV-1), 103 and 104 demonstrated SARD activity in both LNCaP (mutant AR harboring T877A mutation) and 22RV-1 (growth dependent on AR-SV lacking a LBD) cells. (Example 8)
Figure 22:
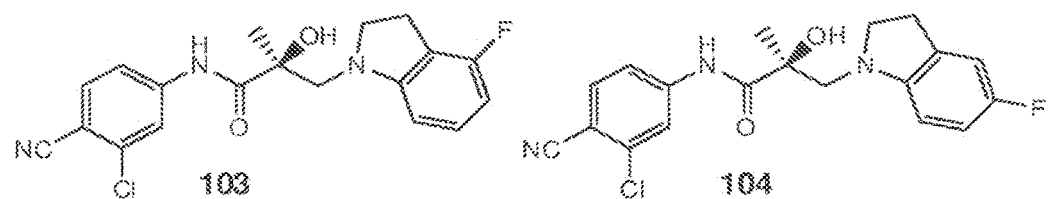

FIG. 22 presents degradation in LNCaP cells and 22RV-1 cells using 103 and 104. Using the methods described in the legends for FIG. 18 (LNCaP) and FIG. 19 (22RV-1), 103 and 104 demonstrated SARD activity in both LNCaP (mutant AR harboring T877A mutation) and 22RV-1 (growth dependent on AR-SV lacking a LBD) cells.

Figure 23:
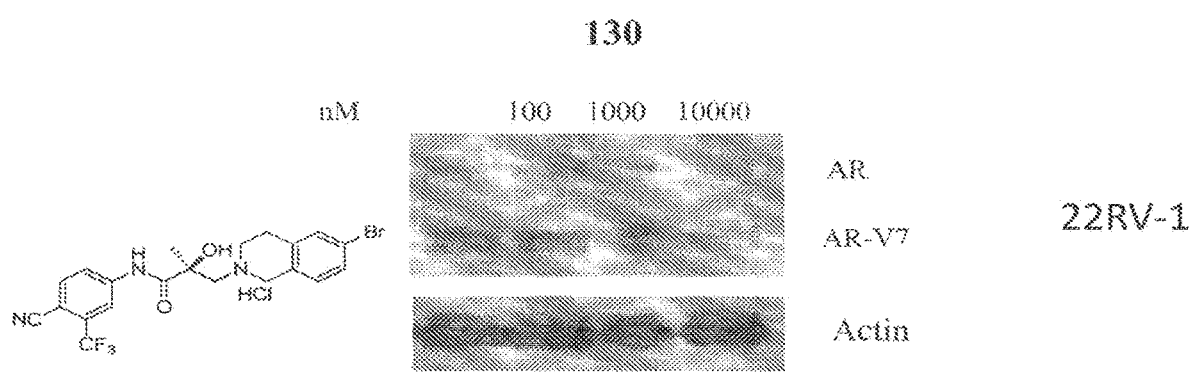
FIG. 23 presents degradation in 22RV-1 cells using 130. Using the methods described in the legend for FIG. 12, compound 130 demonstrated SARD activity at least at the 10 M concentration. (Example 8)

FIG. 23 presents degradation in 22RV-1 cells using 130. Using the methods described in the legend for FIG. 19, compound 130 demonstrated SARD activity at least at the 10 M concentration.

Figure 24:
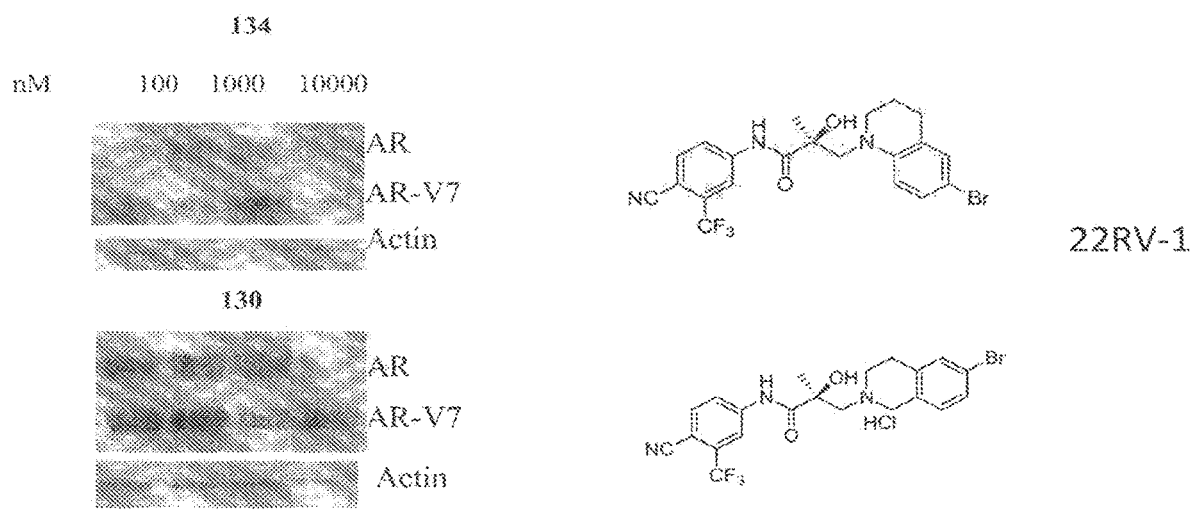
FIG. 24 presents degradation in 22RV-1 cells using 134 and 130. Using the methods described in the legend for FIG. 12, compounds 134 and 130 each demonstrated SARD activity at least at the 10 M concentration. (Example 8)

FIG. 24 presents degradation in 22RV-1 cells using 134 and 130. Using the methods described in the legend for FIG.

19, compounds 134 and 130 each demonstrated SARD activity at least at the 10 μM concentration.

Figure 25:
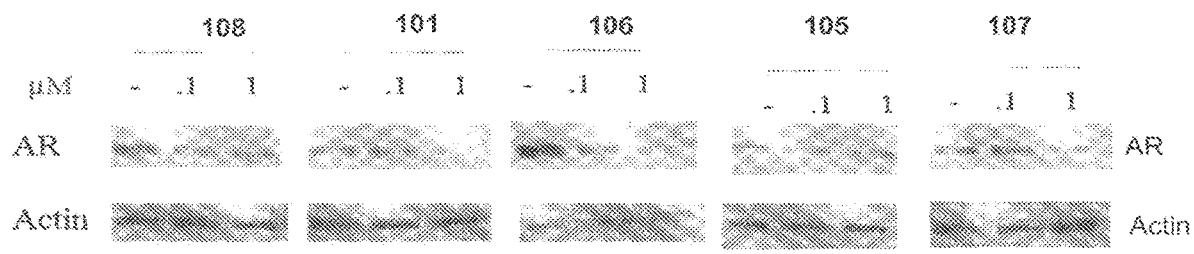
FIG. 25 presents degradation in LNCaP cells using 101, 105, 106, 107 and 108. Using the methods for FIG. 11 above, 101, 105, 106, 107 and 108 each demonstrated the ability to degrade the AR in the nM range. (Example 8)
Figure 25:
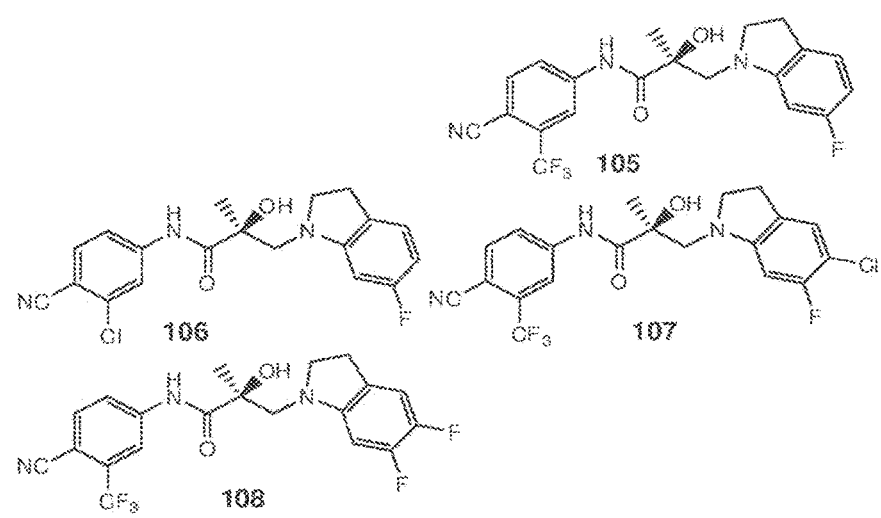

FIG. 25 presents degradation in LNCaP cells using -101, 105, 106, 107 and 108. LNCaP cells were plated in 6 well plates at 500,000 cells/well and maintained in RPMI+1% csFBS without phenol red for 2 days. Cells were treated as indicated above in combination with 0.1 nM R1881 for 24 hrs. Cells were harvested 24 hrs after treatment, protein extracted, Western blotted with AR antibody (SantaCruz antibody AR N-20) and actin antibody (Sigma). 101, 105, 106, 107 and 108 each demonstrated the ability to degrade the AR in the nM range.

FIGS. 49A and 49B present degradation of FL AR and AR SV by selected SARDs. LNCaP (FIG. 49A) or 22RV1 (FIG. 49B) cells were plated in full-serum containing medium. Medium was changed to 1% charcoal-stripped serum containing medium and maintained in this medium for 2 days. Medium was changed again and the cells were treated with 0.1 nM R1881 (agonist) and either vehicle or a titration of SARD as indicated in the figure. Twenty-four hours after treatment, cells were harvested, protein extracted, and the proteins were blotted with AR-$N_{20}$ antibody. Blots were stripped and re-probed with an actin antibody. AR—full length androgen receptor; AR-SV—androgen receptor splice variant. In FIGS. 49A and 49B, SARD activity was measured by treating cells with 0.1, 1.0 or 10 μM concentrations of SARDs in the presence of agonist (0.1 nM R1881). The Western blots were quantified densitometrically and the AR/Actin values are represented as fold change or percent change from vehicle-treated cells.

FIG. 49A showed the degradation of FL AR in LNCaP cells and FIG. 49B showed degradation of SV in 22RV1 cells, while actin in each lane serves as an internal standard to correct for variations in protein loading which complicate the visual interpretation of the immunoblots. The % degradation values reported in Tables 3 and 6 are normalized for variations in protein loading and are relied upon for relative efficacy determinations. Concentration-dependent degradation was seen in LNCaP cells for 115 (3'-Cl, 5-F, 6-Ph indoline), 34 (3'-Cl, 5-F, 6-Ph indole), 101 (3'-$CF_3$, 4-F indoline), 104 (3'-Cl, 5-F indoline) and 106 (3'-Cl, 6-F indoline). From FIG. 49A, it is apparent that >50% of FL AR is already degraded at 1 μM of these SARDs, i.e. nM range SARD activity. SV AR degradation (the lower molecular weight band in FIG. 49B; upper band is disregarded in % degradation values) of 34 (3'-Cl, 5-F, 6-Ph indole), 102, 115 (3'-Cl, 5-F, 6-Ph indoline), 103 (3'-Cl, 4-F indoline), and 11 (3'-$CF_3$, 5-F indole) was observed to be dose-dependent and generally about 10-fold less potent (FIG. 49B) for selected SARDs, which is consistent with other SARDs. Some compounds degrade FL AR better than SV AR (e.g., 106) or vice versa (e.g., 32) (Tables 3 and 6), whereas the optimal SARD potently and completely (i.e., ++++) degrades both and has a high potency antagonism. 115 comes closest to displaying the perfect profile with complete/strong degradation of FL/SV and antagonism comparable to enzalutamide, 0.244 μM (115) vs. 0.216 μM (5).

These selected SARD activity demonstrations and well as other reported in the tables suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction, kinase activation, high levels of coactivators, etc.; and suggests that the SARDs should also degrade the polyQ polymorphisms in hyperandrogenic dermatologic disorders (shortened polyQ) or Kennedy's disease (extended polyQ), providing a rationale for treating either type of diseases by destroying the AR in the affected tissues (skin and neuromuscular system, respectively). Further, a spectrum of in vitro metabolic stabilities were observed suggesting the possibility of either topical administration (short half-life such that systemic exposure are limited) or systemic (e.g., oral; requires relatively long half-lives) administration.

Example 9

SARDs Inhibit Ligand Independent AR Transcription

Compound 11 inhibited transactivation in the AR-NTD-DBD-hinge (A/BCD) AR construct which lacks the ligand binding domain (FIGS. 7A-7D). (A.) AR A/BCD increased GRE-LUC reporter activity. AR A/BCD construct that lacks the ligand binding domain (labeled as A/BCD) or empty vector (labeled as pCR3.1) was transfected into HEK-293 cells along with GRE-LUC and CMV-renilla LUC. Forty eight hours after transfection cells were harvested and luciferase assay performed. As expected, the empty vector did not produce a strong signal compared to the A/BCD construct. (B.-D.) AR A/BCD activity was inhibited by 11. AR ABCD construct that lacks the ligand binding domain (LBD) was transfected along with GRE-LUC and CMV-LUC. Cells were treated 24 hrs after transfection as indicated in the figure and luciferase assay performed 48 hrs after transfection. 11 (a SARD) inhibited the activity of construct lacking LBD confirming the binding to an alternate site in addition to the LBD. Non-SARD antagonists ARN-509 and enzalutamide did not inhibit the activity of this AR construct lacking the LBD, suggesting that SARDs can inhibit ligand independent AR activity via an alternative binding and degradation domain (BDD) located outside of the LBD. Subsequently, experiments have indicated the NTD as the location of this binding site (see Example 12).

Example 10

Comparison of SARDs and Clinical Candidates in Binding and Transactivation

Plasmid Constructs and Transient Transfection. Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 mg GRE-LUC, 0.02 mg CMV-LUC (renilla luciferase) and 25 ng of the AR. The cells were treated 24 h after transfection as indicated in the figures and the luciferase assay performed 48 h after transfection. Data are represented as $IC_{50}$ obtained from a four parameter logistics curve.

Figure 8A:
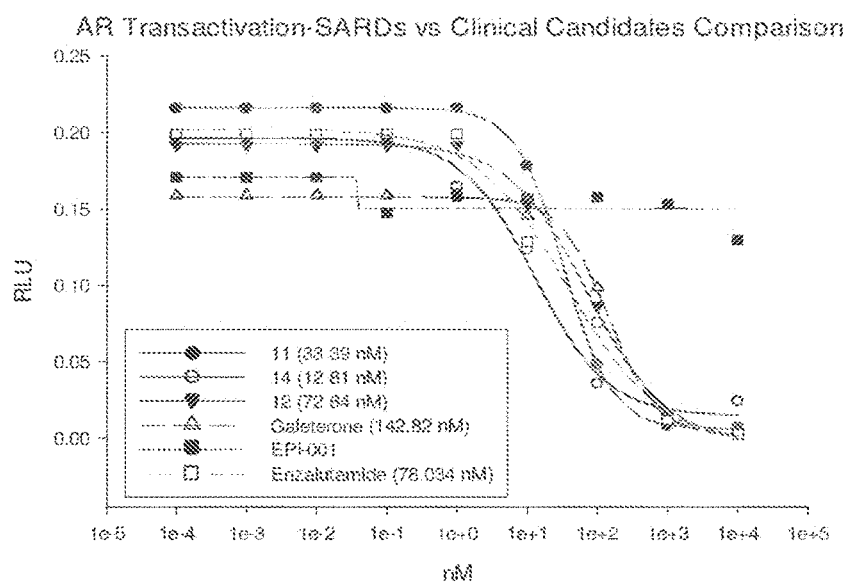
FIGS. 8A-8B present data comparing compounds 11, 12, and 14 with galeterone, EPI-001, and enzalutamide in AR transactivation studies.
Figure 8B:
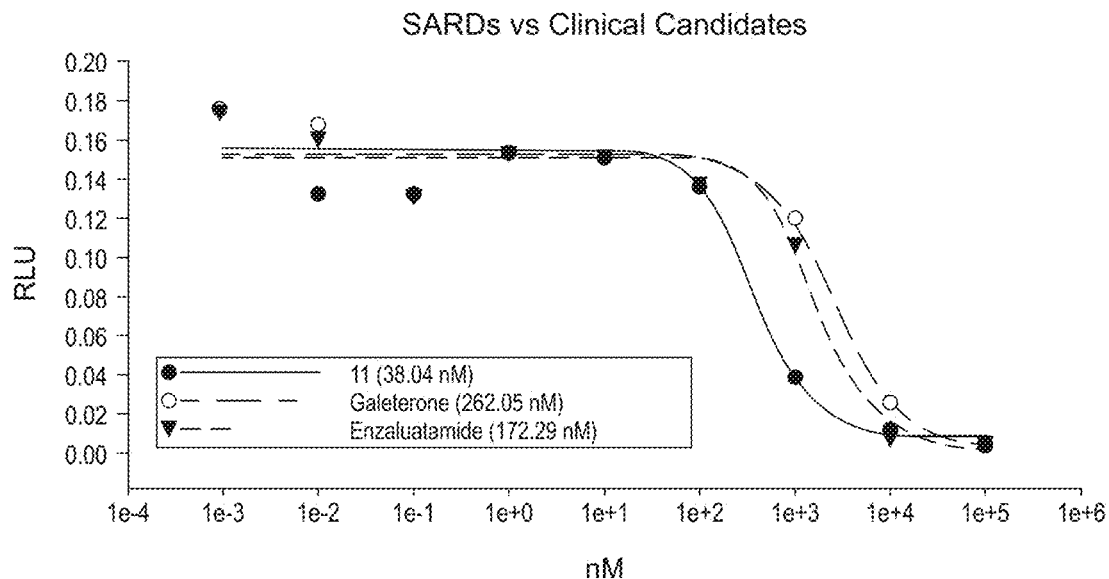

FIG. 8A presents the data comparing 11, 12, and 14 with galeterone, EPI-001, and enzalutamide, in the transactivation study. In general the SARDs of this invention were equipotent to more potent than enzalutamde which was the most potent known AR antagonist tested. EPI-001 did not demonstrate any inhibition in this assay. FIG. 8B shows the data comparing 11 with galeterone and enzalutamide in the transactivation study. The results show that the SARD compounds of the present invention were several-fold more potent than galeterone and enzalutamide in inhibition of DHT activated AR transactivation in vitro.

FIGS. 34-36 present data comparing compound 96 with enzalutamide, galeterone and ARN-509. FIG. 34 presents the effect of known AR antagonists and SARD 96 on FKBP5. FIG. 35 presents the effect of known AR antagonists and SARD 96 on PSA. FIG. 36 presents the effect of AR antagonists and SARD 96 on SRB-LNCaP cell growth: LNCaP cells were plated in 96 well plates at 10,000 cells/well in RPMI+1% csFBS without phenol red. Cells were treated as indicated in the figure in combination with 0.1 nM R1881 for 6 days with medium change on day 3. At the end of 6 days, the cells were fixed and stained with sulphorhodamine blue stain. Table 10 summarizes the above and presents it as a panel of in vitro characterizations of 96 with regard to AR binding ($K_i$), nuclear hormone receptor transactivation including AR wt and mutant ($IC_{50}$), and inhibition of LNCaP cell growth and AR-dependent gene expression in LNCaP cells. 96 binds to the LBD of AR with relatively low affinity (1 μM) but inhibits AR transactivation in wildtype (301 nM) and T877A (343 nM) and W741L (14 nM) mutants with greater potency suggesting that AR inhibition may not be mediated by the LBD. 96 demonstrates good nuclear receptor specificity with no inhibition of transactivation in the glucocorticoid receptor (GR) and mineralocorticoid receptor (MR), and inhibition in the progesterone receptor (PR) that is 3-fold less potent than inhibition of the AR (wt). The anti-androgenic activity of 96 is also evidenced in LNCaP cells, a prostate cancer cell line whose growth is dependent on mutant T877A AR. 96 was anti-proliferative (FIG. 36) and inhibited AR-dependent gene expression of FKBP5 (FIG. 34) and PSA (FIG. 35) in LNCaP cells demonstrating the potential for the treatment of prostate cancer with 96 and other SARDs of this invention based on their activity in well known models of prostate cancer such as LNCaP cells. This panel suggests that 96 is more potent in AR escape mutants than wt AR unlike the known AR antagonists tested, and more nuclear hormone receptor selective than the AR antagonists in use (enzalutamide) or advanced clinical testing (ARN-509 and galeterone).

sion for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR-LBD using the conditions described above. Following incubation, the ligand bound AR-LBD complex was isolated using BioGel HT hydroxyapatite, washed and counted in a scintillation counter after adding scintillation cocktail. Values are expressed as $K_i$. Table 11 shows that the SARD compounds of the present invention are at least approximately 8-10 folds more tightly bound than galeterone and enzalutamide in AR binding assay studies.

TABLE 11

Binding Assay Results.

| Compound | Binding ($K_i$) nM |
|---|---|
| 11 | 62.7 |
| 14 | 47.9 |
| 12 | 72.9 |
| Galeterone | 922.8 |
| Enzalutamide | 678.9 |
| EPI-001 | Does Not Bind |

Example 11

Compound 11 Inhibits Tumor Growth of an Aggressive Prostate Cancer Expressing AR Splice Variant Xenograft experiment. NOD SCID gamma (NSG) mice (n=8-10) were housed as five animals per cage and were allowed free access to tap water and commercial rat chow (Harlan Teklad 22/5 rodent diet—8640). Cell line xenografts were performed as previously published (Narayanan et al., 2010; Yepuru et al., 2013). LNCaP tumors were grown in

TABLE 10

AR Binding ($K_i$), Inhibition of AR (wt and mutants), PR, GR, and MR Transactivation ($IC_{50}$), LNCaP Cell Growth Inhibition and Gene Expresssion of Compound 96 and Known AR Antagonists.

| | Ki | Transactivation (IC50 nM) | | | | | | LNCaP | | |
|---|---|---|---|---|---|---|---|---|---|---|
| | | | | | | | | Growth | Gene Expression | |
| | (nM) | AR | T877A | W741L | PR | GR | MR | nM | PSA | FKBP5 |
| 96 | 1006.38 | 301.26 | 342.67 | 14.24 | 1057 | >=10 | >10 | 1015.23 | 980.74 | 105.28 |
| Galeterone | >1000 | 243.84 | 1530.74 | | 636.02 | N.I. | >10 | | | |
| Enzalutamide | >1000 | 183.41 | 54.91 | 619.73 | 196.97 | N.I. | >10 | 304.9 | 220.69 | 38.08 |
| ARN 509 | >1000 | 216.58 | 292.52 | 998.83 | 1195.9 | N.I. | >10 | 1907 | >=10 | >=10 |

Ligand binding assay. hAR-LBD (633-919) was cloned into pGex4t.1. Large scale GST-tagged AR-LBD was prepared and purified using a GST column. Recombinant AR-LBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regresintact mice, while 22RV-1 tumors were grown in castrated mice. Once tumor size reached 100 mm$^3$, the animals were randomized and treated with vehicle control (polyethylene glycol: DMSO 9:1 ratio) or 11 (50 mg/kg/day s.c.). Tumor volume was calculated using the formula length*width*width*0.5236. At the end of the experiment, animals were sacrificed, tumors were collected, weighed, and stored for further analysis. Blood was collected, serum separated, and serum PSA was measured using ELISA.

All experiments were performed thrice and each in vitro experiment was performed in triplicate. Statistical analysis was performed using JMP-Pro software (SAS; Cary, N.C.). Experiments containing only two groups were analyzed by simple t-test, while experiments containing more than two groups were analyzed by One Way ANOVA, followed by appropriate post-hoc test.

Figure 9A:
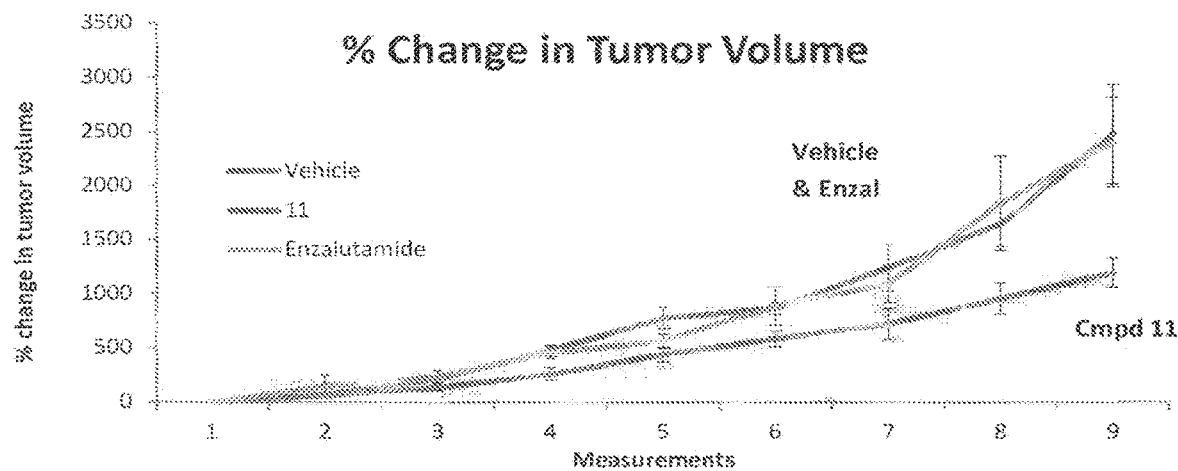
FIGS. 9A-9D demonstrate that 11 inhibited tumor growth of an aggressive prostate cancer (22RV-1) that expresses an AR splice variant (growth driven by AR-V7).
Figure 9B:
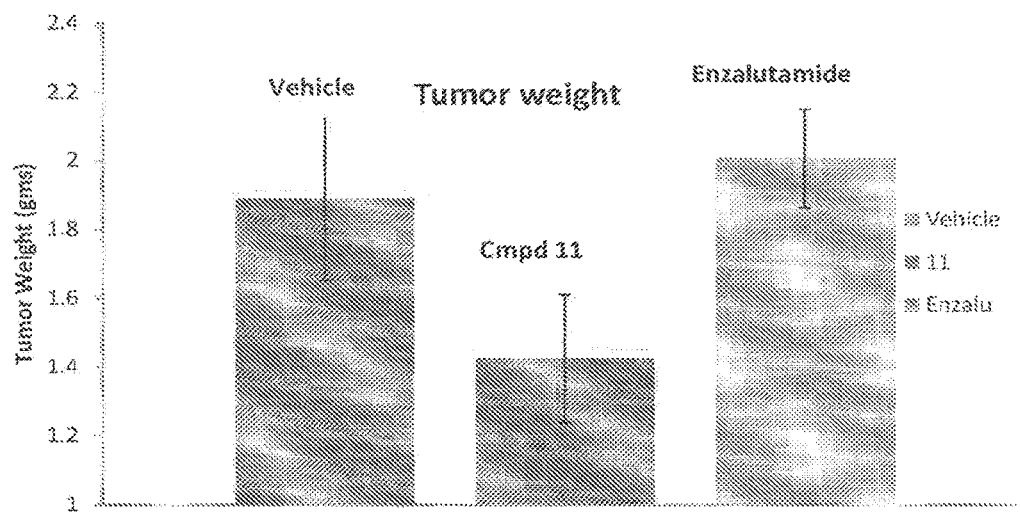
Figure 9C:
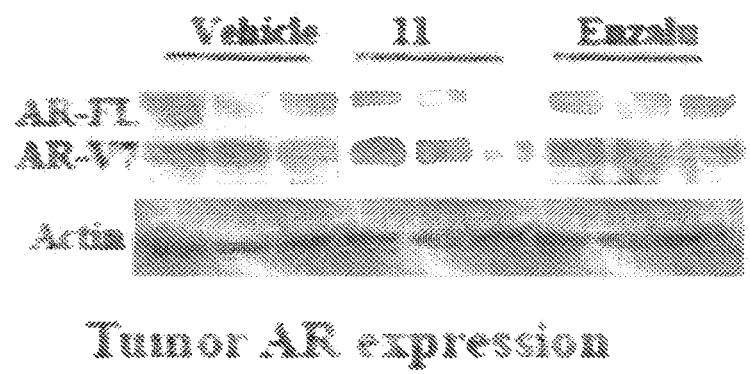
Figure 9D:
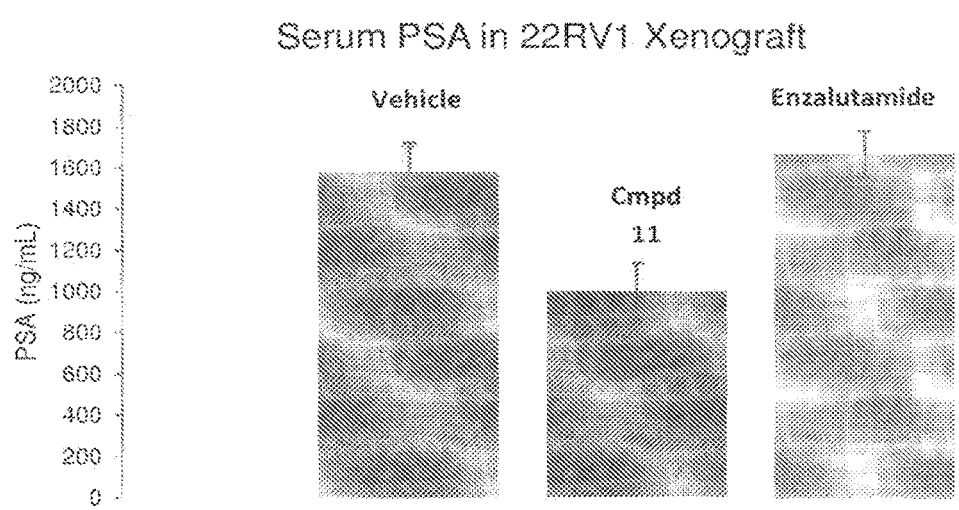

22RV-1 xenograft studies with Compound 11: Since 11 degraded both AR-FL and AR-SV in 22RV-1 and LNCaP cells, the molecule was evaluated in 22RV-1 (FIGS. 9A-9D) and LNCaP (FIGS. 10A-10C) xenograft studies described below. FIGS. 9A-9B show that 11 (100 mg/kg bid) inhibited tumor growth of a prostate cancer that expresses an AR splice variant (AR-V7) and full-length AR (AR-FL). 22RV-1 is a highly aggressive tumor model that is unresponsive to any currently available treatments. A SARD compound of the present invention, 11, restricted its growth by approximately 50%, whereas enzalutamide (Enzal) was ineffective. No side-effects were observed in the 3-4 weeks study. FIG. 9C demonstrated that 11 degraded both AR-FL and AR-V7 in the 22RV-1 xenografts whereas enzalutamide (Enzalu) demonstrated no degradation of either AR in these xenografts. FIG. 9D demonstrated that 11 but not enzalutamide suppressed serum PSA in xenograft bearing animals, demonstrating that 11 suppressed AR gene expression in these tumors. This demonstrated that 11 but not enzalutamide can overcome the antiandrogen resistance present in 22RV-1 cells (e.g., AR-V7 dependent growth) by degrading the AR-V7 and AR-FL, resulting in significantly suppressing androgenic tone in these tumors. This provided a proof-of-concept that SARDs such as 11 would be of clinical benefit to CRPC patients, particularly if systemic exposures could be improved.

Figure 10A:
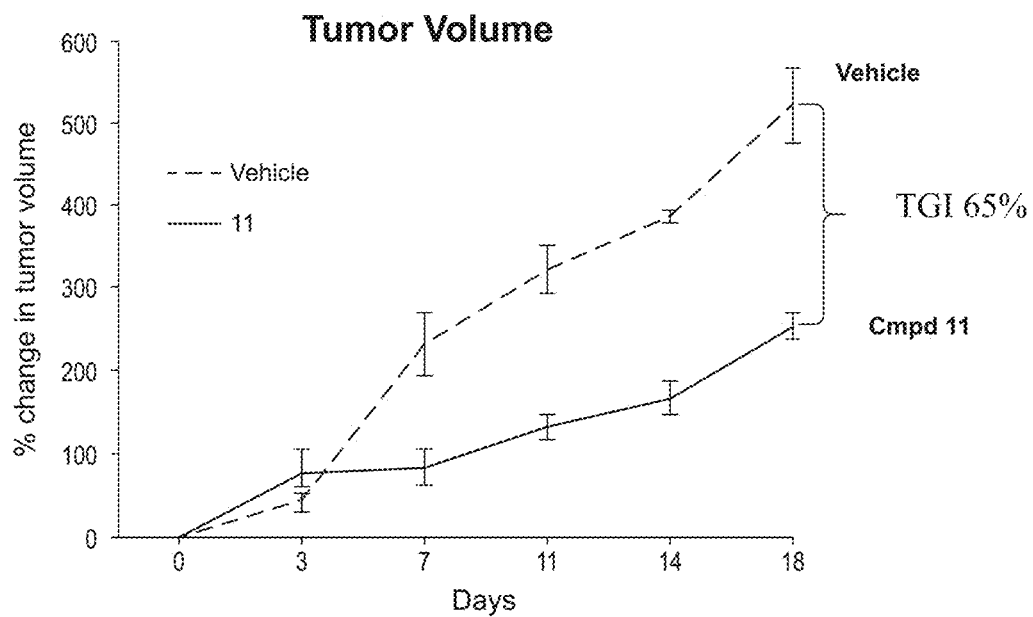
FIGS. 10A-10C demonstrate that 11 inhibited LNCaP tumor xenograft growth via (FIG. 10A) decreased tumor volume and (FIG. 10B) weights, and (FIG. 10C) serum PSA levels in animals treated with 11 when compared to vehicle. (Example 11)
Figure 10B:
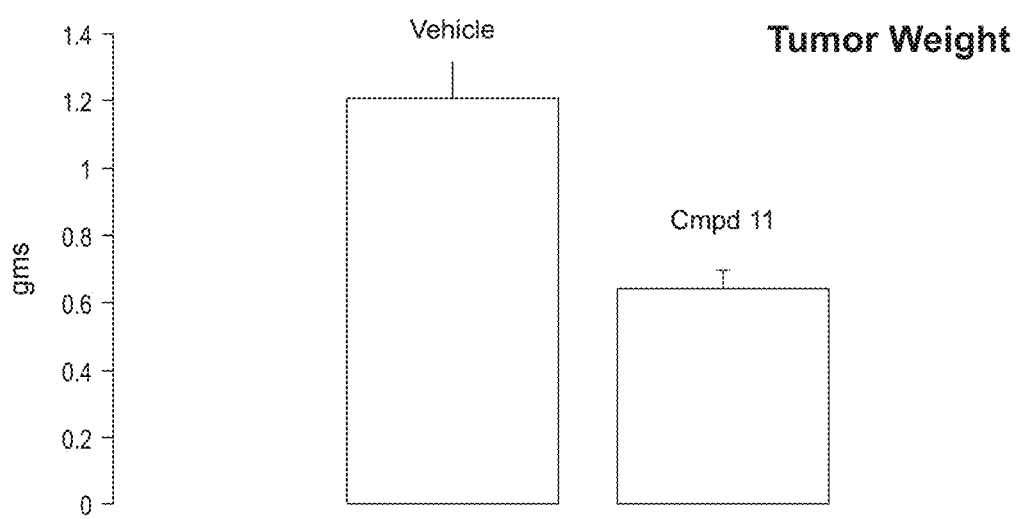
Figure 10C:
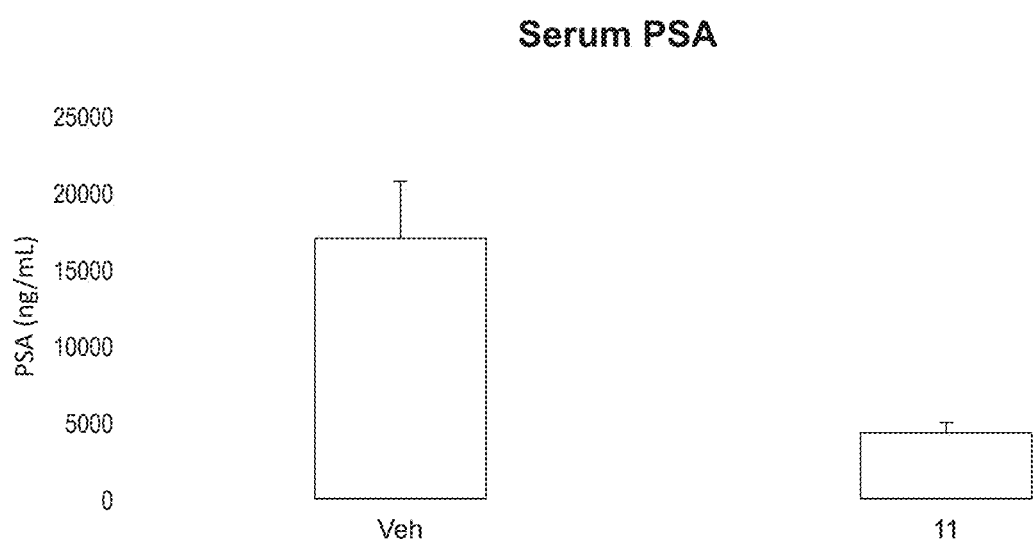

FIGS. 10A-10C show that 11 (100 mg/kg bid) inhibited LNCaP tumor xenograft growth with a % tumor growth inhibition (% TGI) of 65% (FIG. 10A) and inhibited tumor weight by about 50% (FIG. 10B). As shown in FIG. 10C, the serum PSA level was inhibited by >75%, indicating the AR-axis was suppressed in the xenograft as expected for a SARD. Cumulatively, these results indicated that SARDs should be effective in AR-driven prostate cancers regardless of whether the prostate cancers are driven by wt or mutant AR-FL and/or AR-SV such as AR-V7 which lack the LBD. As such SARDs, would be able to treat enzalutamide or abiraterone resistant prostate cancers.

Example 12

SARDs Bind to the AF1 of NTD of AR

Figure 17A:
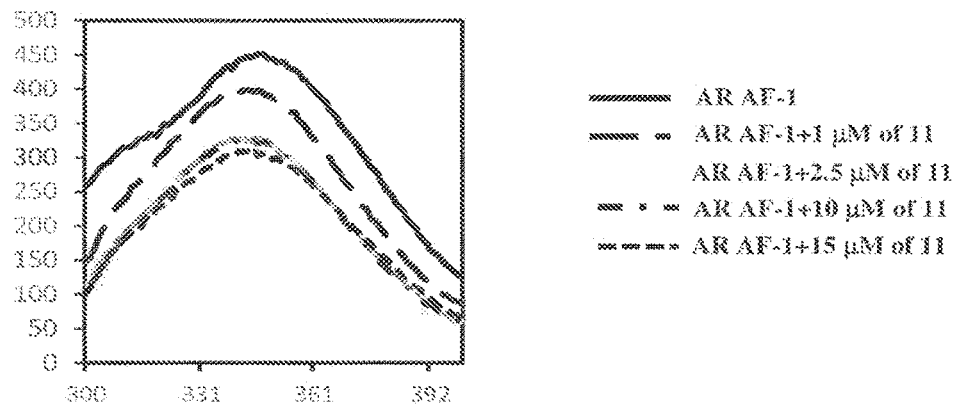
FIGS. 17A-17C present biophysical data that suggests that SARDs bind to the N-terminal domain of the AR (in addition to the LBD in the C-terminus).
Figure 17B:
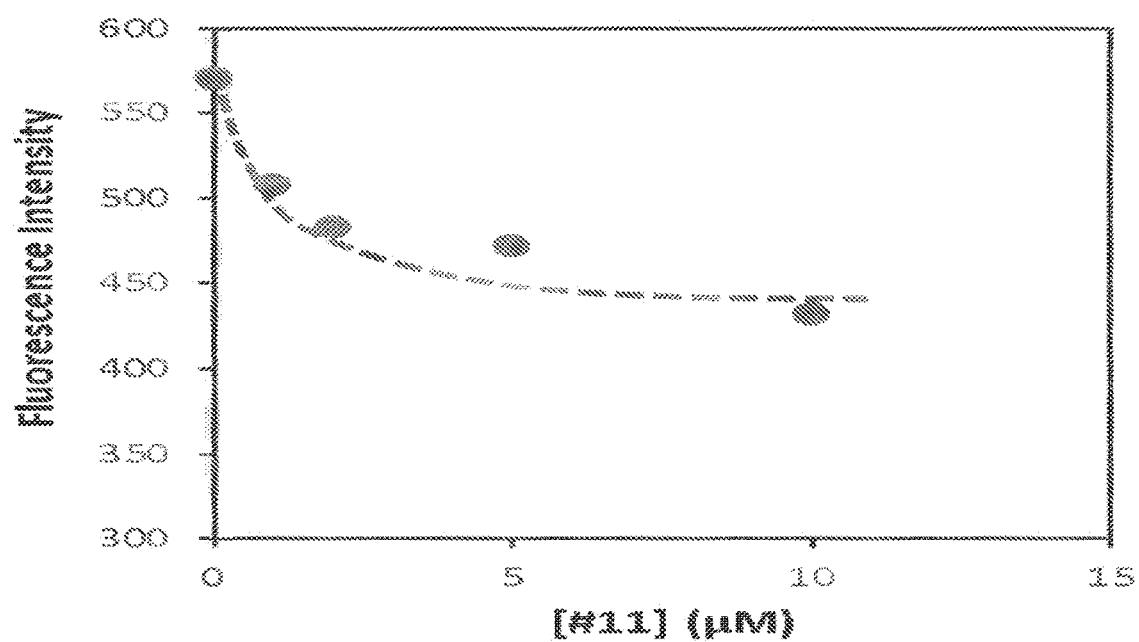
Figure 17C:
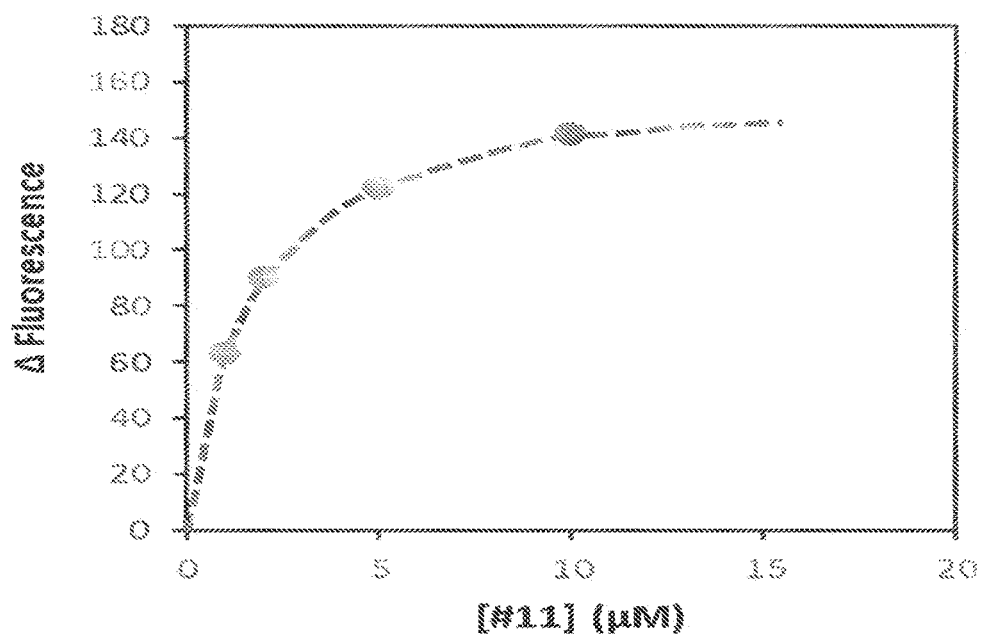

Fluorescent Polarization (FP): There are two tryptophan residues and up to 12 tyrosine residues in the AF of the AR which is located in the N-terminal domain (NTD) of AR. This has allowed the study of the folding properties of this domain using intrinsic steady state fluorescence emission spectra. Excitation at 287 nm excites both tyrosine and tryptophan residues. The emission maximum ($\lambda$max) for the tryptophan is sensitive to the exposure to solvent. In the presence of the natural osmolyte TMAO there is a characteristic 'blue shift' consistent with the tryptophan residues being less solvent exposed and a loss of the shoulder (~307 nm) for tyrosine as there is increased energy transfer to tryptophan as the polypeptide folds. To test if the compounds (a nonsteroidal agonist enobosarm (negative control), and the SARD 11) interact with AF-1 and/or alter the folding of this domain the steady state fluorescence was measured for each compound with AR-AF alone or in the presence of TMAO (3 M) or the denaturant urea (4 or 6 M). 1 µM of AR-AF1 and 5 µM of the individual compounds were used, and preincubated for at least 30 minutes prior to measuring the emission spectra. The emission spectra were all corrected for buffer alone or buffer with TMAO/urea/compounds as necessary. FIG. 17A-C presents biophysical data that suggests that SARDs bind to the N-terminal domain of the AR (in addition to the LBD in the C-terminus reported as $K_i$ values herein). FIG. 17A: Dose-dependent shift in the fluorescence intensity by 11 when incubated with AR AF-1. The fluorescence shoulder observed at 307 nm, which corresponds to tyrosine residues in the AF-1, is shifted by 11. FIG. 17B: The overall fluorescence is also markedly altered by increasing concentrations of 11. FIG. 17C: Data shown in FIG. 17A was plotted as a difference in fluorescence between control and 11 treated samples (fluorescence in the absence of compound—fluorescence in the presence of compound), a dose dependent increase was observed in the presence of 11, consistent with binding to and stabilization of the intrinsically disordered AR-AF1 peptide derived from the NTD of AR. This data demonstrated binding of SARDs to the NTD domain. Only EPI-001 is reported to bind NTD but is not orally bioavailable. Enzalutamide and ARN-509 bind to the LBD only. This demonstrates the uniqueness of the compounds of this invention that are highly potent and selective androgen receptor degraders of a variety of full-length and splice-variant androgen receptors (Examples 5-8 and 13), potent inhibitors of LBD-dependent transactivation (Examples 5-8, 10, and 13), and inhibit NTD-dependent activity (Example 9) via binding to the NTD (Example 12). Based on their unique profile of AR antagonistic mechanisms, there is great expectation to expand the scope of diseases treatable with the androgen receptor antagonist compounds of this invention reported herein.

Based on half-maximum saturation for the change in fluorescence signal (at $\lambda$max 242 nm), the binding constant to AR-AF1 was calculated to be of KD=1.34±0.32 µM (n=3, mean±SEM).

1 µM AR-AF1 was pre-incubated without or with increasing concentrations of compound 11 (up to 15 µM) and steady-state fluorescence emission, after excitation at 287 nm, measured from 300 to 400 nm. Data was analysed as described by Epps et al (1999) J. Pharm 51, 41-48, Rawel et al (2006) Mol. Nutr. Food Res. 50, 705-713 and Wang et al (2011) Mol. Endcor. 25, 2041-2053 which are hereby incorporated by reference.

Surface Plasmon Resonance (SPR): To confirm the results obtained by FP assay, a biotin labeled method using AF-1 was employed. Biacore assay uses surface plasmon resonance (SPR) to measure protein-protein interaction and protein-small molecule interaction. In this assay, AR AF-1 and 50 nM of 11 were added to a Biacore chip and SPR was measured. 11 demonstrated a change in the refraction index in the SPR, indicating an interaction with the AR AF-1 protein (FIG. 47).

NMR studies confirm the binding of 11 to AF-1 between amino acids 244-360. $^1$H NMR is consistently used in high-throughput screens to detect the binding of small molecules less than 500 Da to large proteins greater than 5 KDa [Dias, D. M., and Ciulli, A. (2014). NMR approaches in structure-based lead discovery: recent developments and new frontiers for targeting multi-protein complexes. Prog Biophys Mol Biol 116, 101-112; Shortridge, M. D., Hage, D. S., Harbison, G. S., and Powers, R. (2008). Estimating protein-ligand binding affinity using high-throughput screening by NMR. J Comb Chem 10, 948-958.]. It is easier to use one-dimensional (1D) NMR to observe changes in line-width or line broadening as a high-throughput method to identify the binding of the molecules to proteins and then use two-dimensional (2D) NOE-based NMR techniques such as Water ligand-observed spectroscopy (Water-LOGSY) as confirmatory methodology [Dalvit, C., Pevarello, P., Tato, M., Veronesi, M., Vulpetti, A., and Sundstrom, M. (2000). Identification of compounds with binding affinity to proteins via magnetization transfer from bulk water. J Biomol NMR 18, 65-68; Shortridge et al., 2008].

All these experiments are based on the fact that NMR observables such as linewidths and NOE's vary dramatically between small molecules and heavy molecules. The decreased rotational correlation times upon binding of a small molecule ligand to a heavy target molecule produce an atypical heavy molecule NMR result characterized by broadened and weaker of ligand peaks in 1D NMR and negative NOE peaks in the waterLOGSY as compared to the free state. In the absence of any affinity, the small molecule NMR result is obtained (sharp peaks in 1D NMR and positive NOE's). This distinction provides the basis for NMR screening experiments.

Using these principles $^1$H NMR was used to confirm the binding of 11 to AF-1 protein. In the first experiment, 11 or enzalutamide (500 µM) was dissolved in deuterated DMSO (DMSO-d$_6$) and was incubated alone or mixed with 5 µM GST-AF-1 or GST and the binding of the molecules to the protein was determined by NMR. While 11 alone or in combination with GST exhibited sharp peaks revealing that the ligand was present in the free state, 11 in combination with GST-AF-1 provided a broadened and weaker peaks (FIG. 46A; peaks in box) revealing that 11 has affinity for the AF-1 protein. Enzalutamide is a traditional AR antagonist known to competitively bind to the LBD. No line broadening was observed upon addition of enzalutamide to AF-1 revealing no affinity for AF-1. This result confirms that the 11, but not enzalutamide, binds to the AF-1 domain. To further confirm the 1D NMR results, we performed WaterLOGSY with 11 alone or in combination with AF-1. While the 11 alone gave a flat signal, i.e., no negative NOE's as expected for a free state small molecule, 11 in combination with AF-1 provided a negative signal characteristic of binding to the protein (FIG. 46B).

To determine precisely the region where 11 binds to the AF-1 region (since the AF-1 region is between 141 and 486 amino acids), we created smaller fragments of the AF-1 gene and purified the proteins coded for by fragments (FIG. 46C). 11 was incubated alone or in combination with GST, GST-AF-1 or with various fragments of the AF-1 region and 1D $^1$H NMR profile was obtained. Similar to the results shown in FIG. 46A, 11 provided a sharp signal by itself and when co-incubated with GST, but line broadening when incubated with the AF-1 (FIG. 46D). Similar to the unbound ligand, 11 in combination with fragments 1A and 5T produced spectra suggestive of free state. However, when 11 was incubated with fragment 1T, the signal was almost indistinguishable from line, indicating a strong binding affinity to this region. The profile of 11 in combination with 1B looked similar to that of the AF-1, confirming the binding to this region. Binding of 11 to 1T and 1B, but not to 1A, indicates that amino acids 51-211 could be excluded and that potentially the binding occurs between amino acids 244 and 360.

Three separate biophysical phenomena, FP, SPR, and NMR indicate that 11 and other SARDs of this invention have significant affinity for AF-1, suggestive of binding strong enough to mediate some of the unique characteristics of the AR antagonists reported herein.

Example 13

Androgen Receptor Binding and Transactivation of Carbazole Based SARDs

Ligand Binding Assay

Objective: To determine SARDs binding affinity to the AR-LBD.

Method: hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant (K$_d$) of [$^3$H]mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the K$_d$ of mibolerone.

Increasing concentrations of SARDs or DHT (range: $10^{-12}$ to $10^{-2}$ M) were incubated with [$^3$H]mibolerone and AR LBD using the conditions described above. Following incubation, the ligand bound AR-LBD complex was isolated using BioGel HT® hydroxyapatite, washed and counted in a scintillation counter after adding scintillation cocktail. Values are expressed as K$_i$ (Table 12).

Transactivation Assay for Wt and Mutant AR

Objective: To determine the effect of SARDs on androgen-induced transactivation of AR wildtype (wt) or AR carrying known AR-LB mutants (i.e., W741L or T877A).

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR(wt) or CMV-hAR (W741L) or CMV-hAR(T877A) using Lipofectamine transfection reagent in optiMEM medium. Medium was changed 24 h after transfection to DME+5% csFBS without phenol red and treated with a dose response of various drugs (Table 12: compounds 200-205) (1 µM to 10 DM). SARDs and antagonists were treated in combination with 0.1 nM R1881. Luciferase assay was performed 24 h after treatment on a Biotek synergy 4 plate reader. Firefly luciferase values were normalized to renilla luciferase values.

Transactivation Assay: Wt and Mutant AR Objective

To determine the effect of SARDs on androgen-induced transactivation of AR carrying known AR-LBD mutants.

Method: HEK-293 cells were plated at 125,000 cells/well of a 24 well plate in DME+5% csFBS without phenol red. Cells were transfected with 0.25 ug GRE-LUC, 10 ng CMV-renilla LUC, and 50 ng CMV-hAR/W741L-AR/T877A-AR using Lipofectamine transfection reagent in optiMEM medium. Medium was changed 24 h after transfection to DME+5% csFBS without phenol red and treated with a dose response of various drugs (1 μM to 10 QM). SARDs and antagonists were treated in combination with 0.1 nM R1881. Luciferase assay was performed 24 h after treatment on a Biotek synergy 4 plate reader. Firefly luciferase values were normalized to renilla luciferase values. (Table 12)

AR Degradation was Performed Using LNCaP, 22RV1, and AD1 Cells as Described Herein Above and in Example 13

Determination of Metabolic Stability (In Vitro $CL_{int}$) of Test Compounds:

Phase I metabolism

The assay was done in a final volume of 0.5 ml in duplicates (n=2). Test compound (1 μM) was pre-incubated for 10 minutes at 37° C. in 100 mM Tris-HCl, pH 7.5 containing 0.5 mg/ml liver microsomal protein. After pre-incubation, reaction was started by addition of 1 mM NADPH (pre-incubated at 37° C.). Incubations were carried out in triplicate and at various time-points (0, 5, 10, 15, 30 and 60 minutes) 100 aliquots were removed and quenched with 100 μl of acetonitrile containing internal standard. Samples were vortex mixed and centrifuged at 4000 rpm for 10 minutes. The supernatants were transferred to 96 well plates and submitted for LC-MS/MS analysis. As control, sample incubations done in absence of NADPH were included. From % PCR (% Parent Compound Remaining), rate of compound disappearance is determined (slope) and in vitro $CL_{int}$ (μl/min/mg protein) was calculated.

Metabolic Stability in Phase I & Phase II Pathways

In this assay, test compound was incubated with liver microsomes and disappearance of drug was determined using discovery grade LC-MS/MS. To stimulate Phase II metabolic pathway (glucuronidation), UDPGA and alamethicin was included in the assay.

Lc-Ms/Ms Analysis:

The analysis of the compounds under investigation was performed using LC-MS/MS system consisting of Agilent 1100 HPLC with an MDS/Sciex 4000 Q-Trap™ mass spectrometer. The separation was achieved using a $C_{18}$ analytical column (Alltima™, 2.1×100 mm, 3 μm) protected by a $C_{18}$ guard cartridge system (SecurityGuard™ ULTRA Cartridges UHPLC for 4.6 mm ID columns, Phenomenex). Mobile phase was consisting of channel A (95% acetonitrile+5% water+0.1% formic acid) and channel C (95% water+5% acetonitrile+0.1% formic acid) and was delivered at a flow rate of 0.4 mL/min. The volume ratio of acetonitrile and water was optimized for each of the analytes. Multiple reaction monitoring (MRM) scans were made with curtain gas, collision gas, nebulizer gas, and auxiliary gas optimized for each compound, and source temperature at 550° C. Molecular ions were formed using an ion spray voltage of −4200 V (negative mode). Declustering potential, entrance potential, collision energy, product ion mass, and cell exit potential were optimized for each compound.

TABLE 12

AR Binding, Inhibition of wt and mutant AR Transactivation, AR degradation and in vitro metabolic stability of SARDs.

| | | Transcriptional Activation (+0.1 nM R1881; R1881 $EC_{50}$ = 0.11 nM) | | | |
|---|---|---|---|---|---|
| Compound | Binding $K_i$ (nM) | Wt. $IC_{50}$ (nM) | W741L $IC_{50}$ (nM) | T877A $IC_{50}$ (nM) | $T_{1/2}$ (min) $CL_{int}$ (μl/min/mg) |
| DHT | 1 | — | — | — | |
| R-Bicalutamide | 545.5 | 248.2 | — | 557 | |
| Enzalutamide | 205.2 | 216.3 | 939 | 331.94 | |
| ARN-509 (apalutamide) | — | 297.0 | 1939.41 | 390.50 | |
| ASC-J9 | — | 1008.0 | 3487.68 | 2288.16 | |
| 200 | 728.59 | 871.21 | | | 41.77 min 16.6 μl/min/mg |
| 201 | 506.94 | 237.91 | | | 89.68 min 7.729 μl/min/mg |
| 202 | | | | | |

The relatively long half-lives ($T_{1/2}$) and low metabolic clearance ($CL_{int}$) values in vitro for compounds 200-202 of this invention suggest the possibility of oral bioavailability and stability in serum which would be favorable for systemic treatment of diseases of this invention such as prostate cancer, breast cancer, Kennedy's disease, and various androgen-dependent diseases. Similarly, indazoles such as 96 also demonstrated enhanced stability, as discussed herein above.

TABLE 13

AR Binding (Ki), Inhibition of AR Transactivation (IC50), AR Degradation and in vitro Metabolic Stability of SARDs.

| Compd ID | Structure | Log P (−0.4 to +5.6) | Binding/ Transactivation (wt AR) | | SARD Activity | | DMPK (MLM) |
|---|---|---|---|---|---|---|---|
| | | | $K_i$ (nM) (DHT = 1 nM) | $IC_{50}$ (nM) | Full Length % inhibition at 1, 10 μM | S.V. (22RV1) % inhibition at 10 μM | $T_{1/2}$ (min) $CL_{int}$ (μl/min/mg) |
| Enobosarm | | 3.44 | 20.21 | ~20 | | | |
| R-Bicalutamide | | 2.57 | 508.84 | 248.2 | | | |
| Enzalutamide | | 4.56 | 3641.29 | 216.3 | | | |
| ARN-509 (apalutamide) | | 3.47 | 1452.29 | | 0 (FIG. 26) | 0 | |
| | | 2.57 | 87.67 | — | | | |

TABLE 13-continued
AR Binding (Ki), Inhibition of AR Transactivation (IC50), AR Degradation and in vitro Metabolic Stability of SARDs.
| | | | Binding/ Transactivation (wt AR) | | SARD Activity | | DMPK |
|---|---|---|---|---|---|---|---|
| | | Log P (−0.4 to +5.6) | | | Full Length | S.V. (22RV1) | (MLM) $T_{1/2}$ (min) |
| Compd ID | Structure | | $K_i$ (nM) (DHT = 1 nM) | $IC_{50}$ (nM) | % inhibition at 1, 10 μM | % inhibition at 10 μM | $CL_{int}$ (μl/min/mg) |
| | 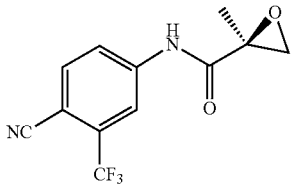 [SMILES: C[C@@]1(C(=O)Nc2ccc(C#N)c(C(F)(F)F)c2)CO1] | 1.86 | 407.08 | | | | |
| 200 | 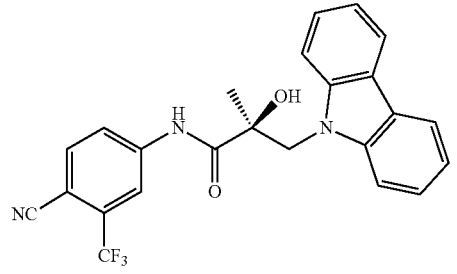 [SMILES: C[C@](O)(Cn1c2ccccc2c2ccccc21)C(=O)Nc1ccc(C#N)c(C(F)(F)F)c1] | 4.36 | 728.59 | 871.21 | 48 (FIGS. 26, 27) | 60 | 41.77 16.6 |
| 201 | 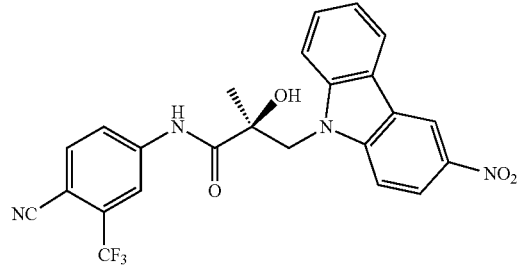 [SMILES: C[C@](O)(Cn1c2ccccc2c2cc([N+](=O)[O-])ccc21)C(=O)Nc1ccc(C#N)c(C(F)(F)F)c1] | 4.40 | 506.94 | 237.91 | 33 (FIGS. 27, 28) | | 89.68 7.729 |
| 202 | 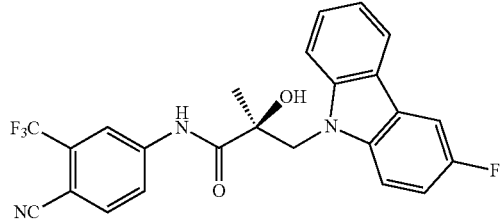 [SMILES: C[C@](O)(Cn1c2ccccc2c2cc(F)ccc21)C(=O)Nc1ccc(C#N)c(C(F)(F)F)c1] | 4.52 | 193.80 | 991.15 | 20 | 29 | 39.94 17.35 |
| 203 | 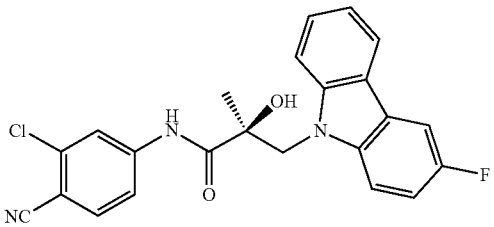 [SMILES: C[C@](O)(Cn1c2ccccc2c2cc(F)ccc21)C(=O)Nc1ccc(C#N)c(Cl)c1] | 4.16 | 248.54 | 1242.96 | 38 | 0 | |

TABLE 13-continued

AR Binding (Ki), Inhibition of AR Transactivation (IC50), AR Degradation and in vitro Metabolic Stability of SARDs.

Figure 29N:
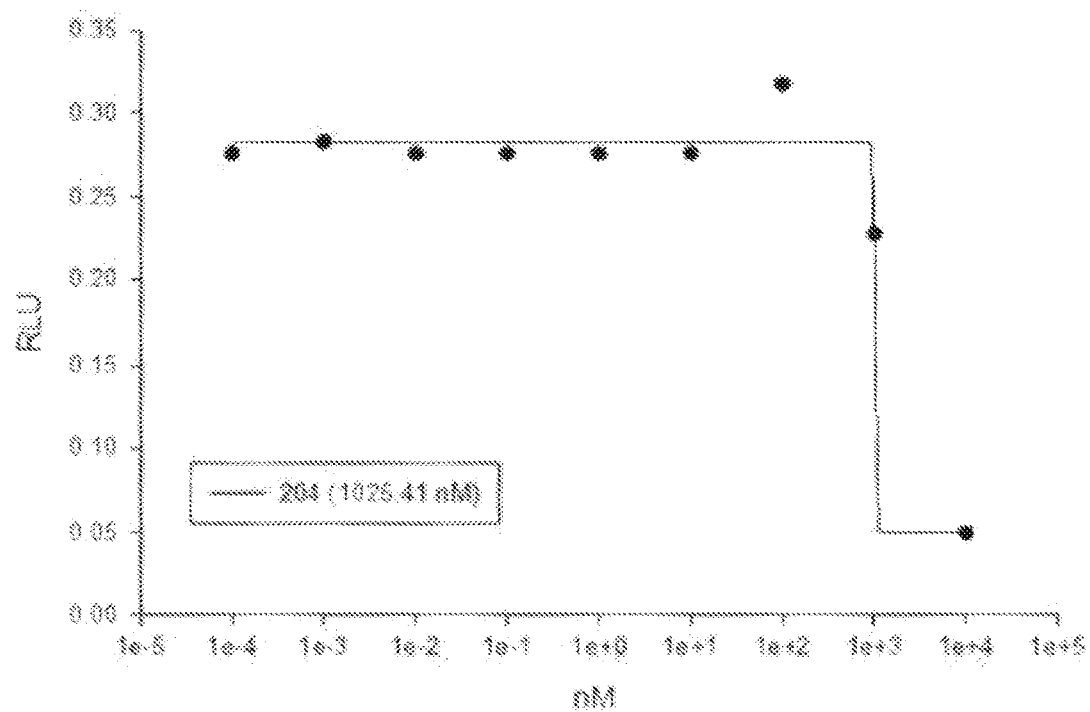
Figure 29O:
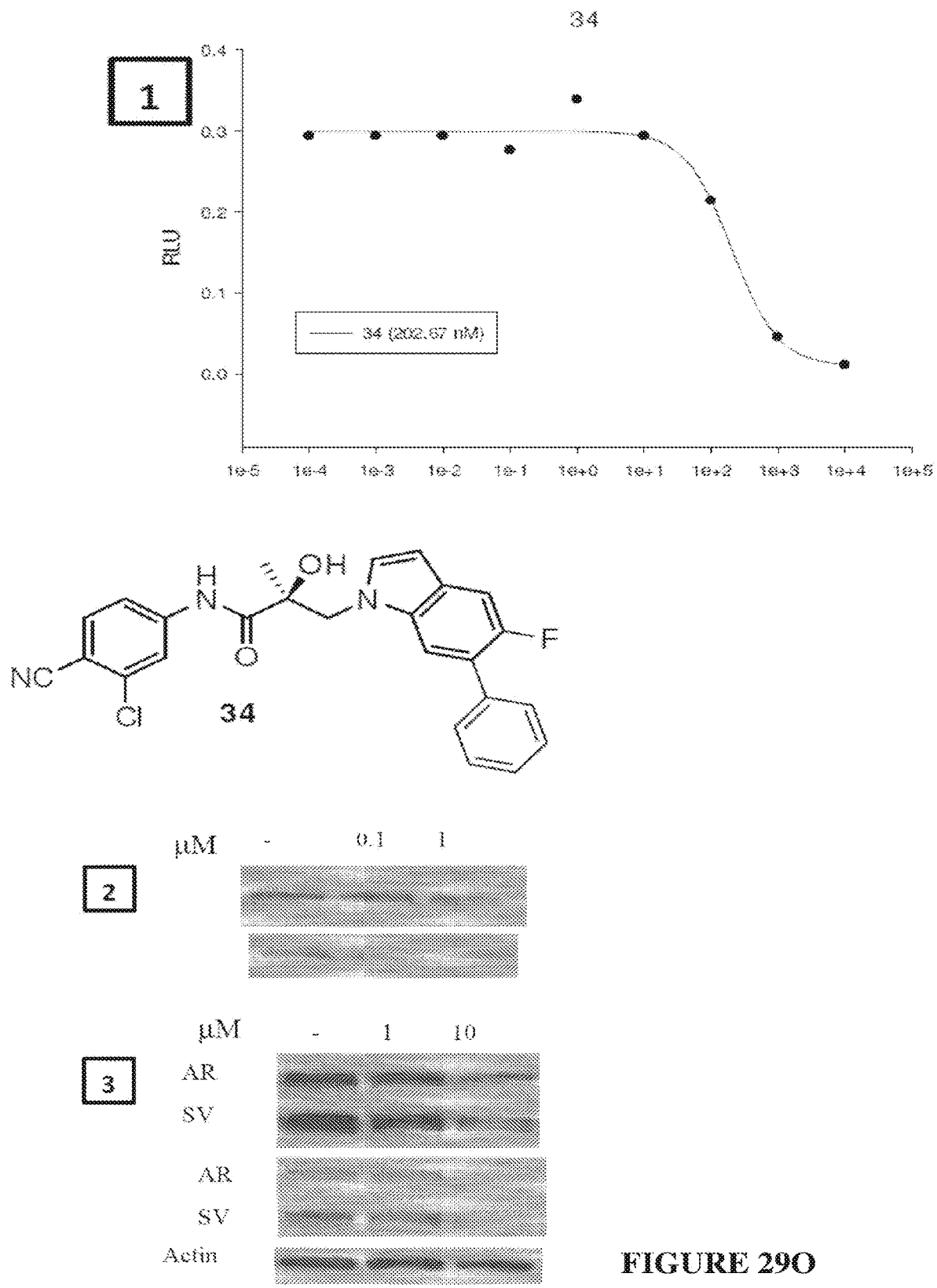

| Compd ID | Structure | Log P (−0.4 to +5.6) | Binding/ Transactivation (wt AR) $K_i$ (nM) (DHT = 1 nM) | IC$_{50}$ (nM) | SARD Activity Full Length % inhibition at 1, 10 μM | S.V. (22RV1) % inhibition at 10 μM | DMPK (MLM) $T_{1/2}$ (min) $CL_{int}$ (μl/min/mg) |
|---|---|---|---|---|---|---|---|
| 204 | 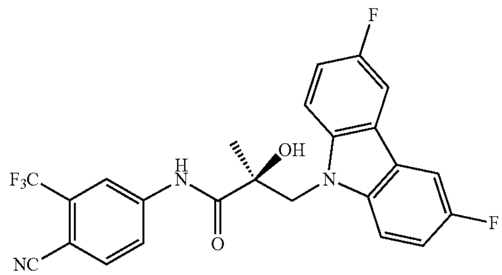 [SMILES: C[C@](O)(Cn1c2ccc(F)cc2c2cc(F)ccc21)C(=O)Nc1ccc(C#N)c(C(F)(F)F)c1] | 4.68 | 809.64 See FIG. 29N | 1025.41 See FIG. 29N | 51 | | |
| 205 | 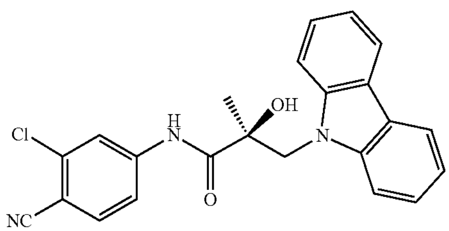 [SMILES: C[C@](O)(Cn1c2ccccc2c2ccccc21)C(=O)Nc1ccc(C#N)c(Cl)c1] | 4.00 | 90.68 See FIG. 29L | 1079.11 See FIG. 29L | 19, 87 See FIG. 29L | 87 See FIG. 29L | |

TABLE 14

Liver Microsome (LM) Data for Carbazoles of this Invention using Mouse LM (MLM), Human LM (HLM), Rat LM (RLM), and Dog LM (DLM).

| | MLM | | HLM | | RLM | | DLM | |
|---|---|---|---|---|---|---|---|---|
| Compd ID | $T_{1/2}$ (min) | $CL_{int}$ (μl/min/mg) | $T_{1/2}$ (min) | $CL_{int}$ (μl/min/mg) | $T_{1/2}$ (min) | $CL_{int}$ (μl/min/mg) | $T_{1/2}$ (min) | $CL_{int}$ (μl/min/mg) |
| 200 (5-carbazole) | 95.9 | 0.72 | | | | | | |
| 201 | 89.68 | 7.729 | 61.38 | 0.01129 | | | | |
| 202 | 39.94 | 17.35 | 14.28 | 48.54 | | | | |

Example 14

AR Degradation Using Compounds of this Invention

LNCaP Degradation Assay

Objective: To determine the effect of SARDs on AR expression in LNCaP cells.

Plasmid Constructs and Transient Transfection.

Human AR cloned into CMV vector backbone was used for the transactivation study. HEK-293 cells were plated at 120,000 cells per well of a 24 well plate in DME+5% csFBS. The cells were transfected using Lipofectamine (Invitrogen, Carlsbad, Calif.) with 0.25 g GRE-LUC, 0.01 g CMV-LUC (renilla luciferase) and 25 ng of the AR. The cells were treated 24 hrs after transfection as indicated in the figures and the luciferase assay performed 48 hrs after transfection. Data are represented as IC50 obtained from four parameter logistics curve.

Ligand Binding Assay.

hAR-LBD (633-919) was cloned into pGex4t.1. Large scale GST-tagged AR-LBD was prepared and purified using a GST column. Recombinant ARLBD was combined with [$^3$H]mibolerone (PerkinElmer, Waltham, Mass.) in buffer A (10 mM Tris, pH 7.4, 1.5 mM disodium EDTA, 0.25 M sucrose, 10 mM sodium molybdate, 1 mM PMSF) to determine the equilibrium dissociation constant ($K_d$) of [$^3$H] mibolerone. Protein was incubated with increasing concentrations of [$^3$H]mibolerone with and without a high concentration of unlabeled mibolerone at 4° C. for 18 h in order to determine total and non-specific binding. Non-specific binding was then subtracted from total binding to determine specific binding and non-linear regression for ligand binding curve with one site saturation to determine the $K_d$ of mibolerone.

Increasing concentrations of SARDs or DHT (range: $10^{-12}$ to $10^{-4}$ M) were incubated with [$^3$H]mibolerone and AR LBD using the conditions described above. Following incubation, the ligand bound AR-LBD complex was isolated using BioGel HT hydroxyapatite, washed and counted in a scintillation counter after adding scintillation cocktail. Values are expressed as $K_i$.

LNCaP Gene Expression Assay.

Method: LNCaP cells were plated at 15,000 cells/well of a 96 well plate in RPMI+1% csFBS without phenol red. Forty-eight hours after plating, cells were treated with a dose response of SARDs. Twenty four hours after treatment, RNA was isolated using cells-to-ct reagent, cDNA synthesized, and expression of various genes was measured by realtime rtPCR (ABI 7900) using taqman primers and probes. Gene expression results were normalized to GAPDH.

LNCaP Growth Assay.

Method: LNCaP cells were plated at 10,000 cells/well of a 96 well plate in RPMI+1% csFBS without phenol red. Cells were treated with a dose response of SARDs. Three days after treatment, cells were treated again. Six days after treatment, cells were fixed and cell viability was measured by SRB assay.

LNCaP or AD1 Degradation.

Method: LNCaP or AD1 cells expressing full length AR were plated at 750,000-1,000,000 cells/well of a 6 well plate in growth medium (RPMI+10% FBS). Twenty four hours after plating, medium was changed to RPMI+1% csFBS without phenol red and maintained in this medium for 2 days. Medium was again changed to RPMI+1% csFBS without phenol red and cells were treated with SARDs (1 nM to 10 µM) in combination with 0.1 nM R1881. After 24 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 and D567es Degradation.

Method: 22RV1 and D567es cells expressing AR splice variants were plated at 750,000-1,000,000 cells/well of a 6 well plate in growth medium (RPMI+10% FBS). Twenty four hours after plating, medium was changed and treated. After 24-30 h of treatment, cells were washed with cold PBS and harvested. Protein was extracted using salt-containing lysis buffer with three free-thaw cycles. Protein concentration was estimated and five microgram of total protein was loaded on a SDS-PAGE, fractionated, and transferred to a PVDF membrane. The membrane was probed with AR N-20 antibody from SantaCruz and actin antibody from Sigma.

22RV1 growth and gene expression.

Methods: Cell growth was evaluated as described before by SRB assay. Cells were plated in 96 well plate in full serum and treated for 6 days with medium change after day 3. Gene expression studies were performed in 22RV1 cells plated in 96 well plate at 10,000 cells/well in RPMI+10% FBS. Twenty four hours after plating, cells were treated for 3 days and gene expression studies were performed as described before.

Figure 26:
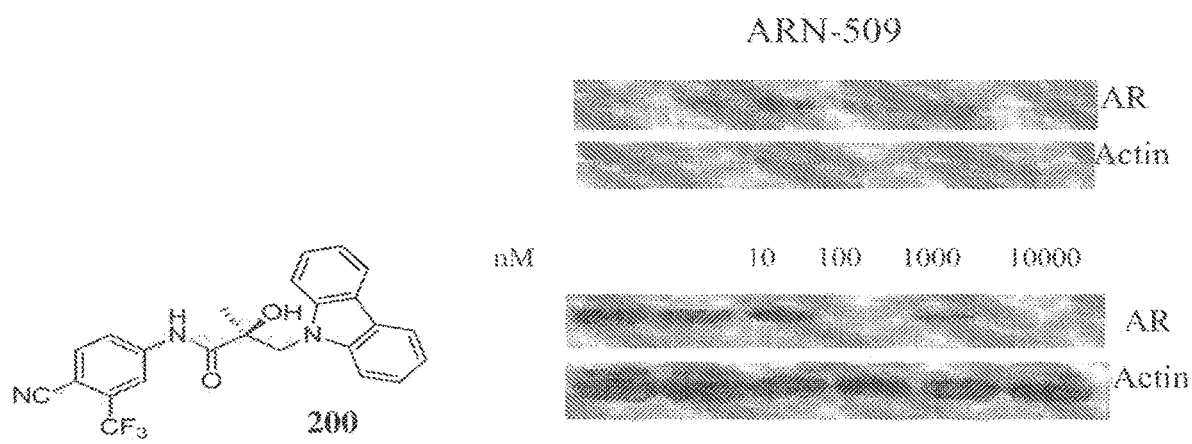
FIG. 26 depicts degradation in LNCaP cells using 200 and ARN-509. LNCaP cells treated with 200 were lysed and subjected to Western blot analysis, as described above. (Example 13 and 14)

Results:

FIG. 26 presents AR degradation by 200 vs. ARN-509 in LNCaP cells. Western blot analysis by the method described above demonstrated the ability of 200 to degrade a mutant AR (i.e., T877A) at 100 nM and 10 µM in LNCaP cells whereas ARN-509 only degraded at 10 M, suggesting that SARDs such as 200 will have clinical utility in prostate cancers including those whose growth is driven by antiandrogen resistance-conferring mutant AR's (i.e., advanced prostate cancers and CRPC).

Figure 27:
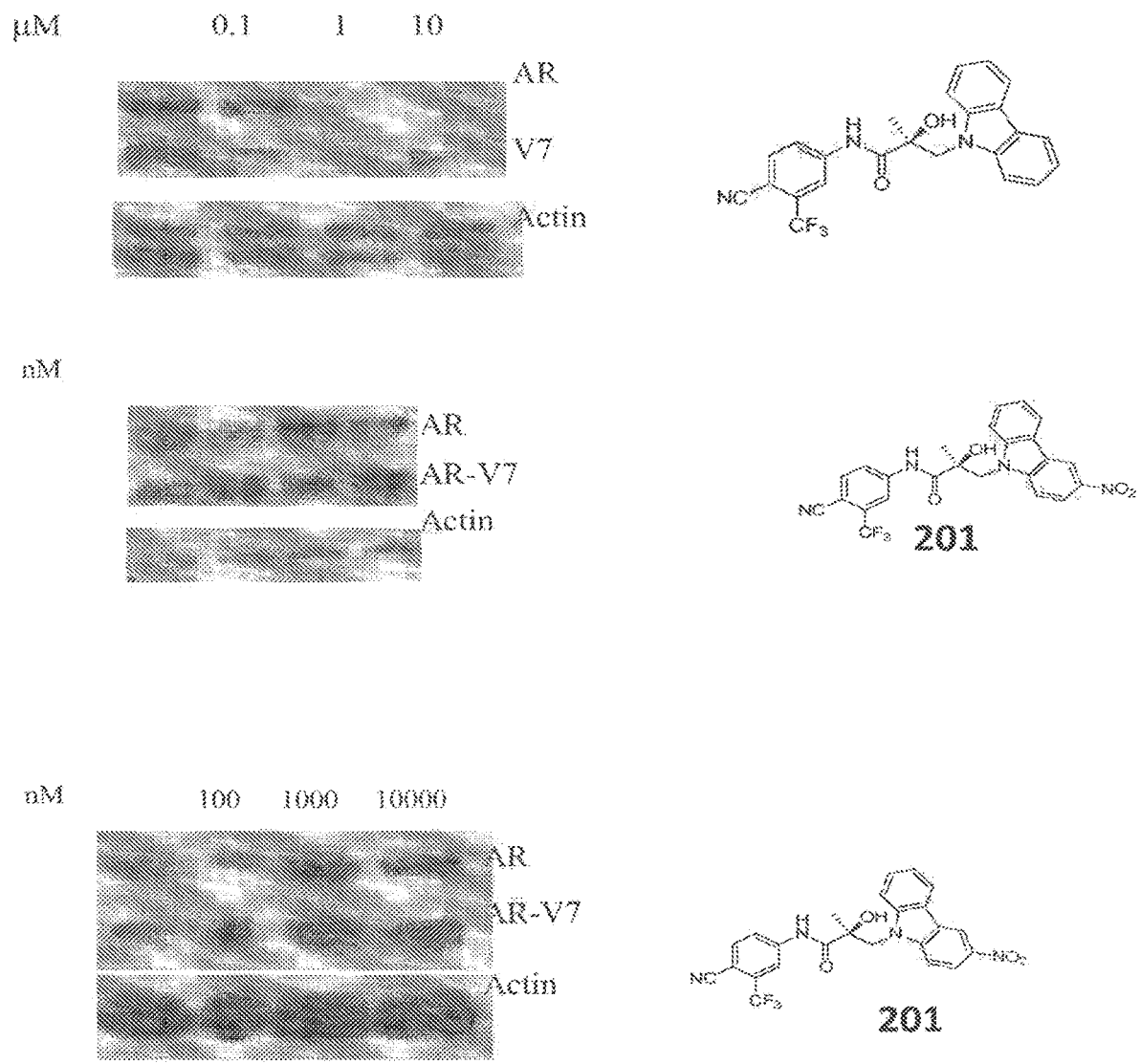
FIG. 27 depicts degradation in 22RV-1 cells using 200 and 201. 22RV-1 cells treated with 200 or 201 were lysed and subjected to Western blot analysis, as described above. (Example 13 and 14)
Figure 28:
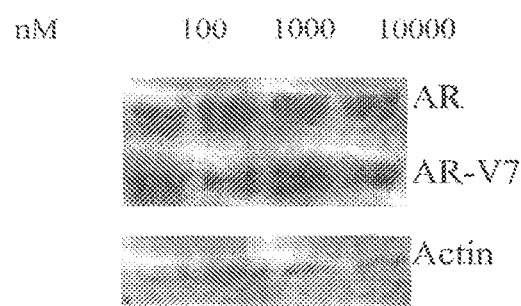
FIG. 28 depicts degradation in 22RV-1 cells using 201. 22RV-1 cells treated with 201 were lysed and subjected to Western blot analysis, as described above. (Example 13 and 14)
Figure 28:
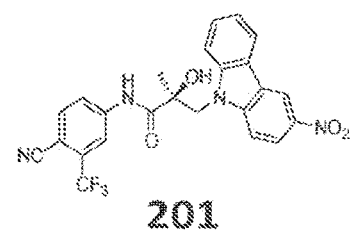

FIG. 27 and FIG. 28 present AR and AR-V7 degradation by 200 and 201 in 22RV-1 cells. 200 was capable of degrading full length androgen receptor (AR-FL) and truncated AR (AR-V7) in 22RV-1 cells, suggesting that SARDs may be able to overcome AR-V7 dependent prostate cancers (i.e., CRPC). By comparison, 201 demonstrated low levels of degradation in 22RV-1 cells.

These SARD activity demonstrations in FIGS. 26-28 as well as reported in the Tables suggest the compounds of this invention are able to degrade a variety of AR variants, and hence should provide the ability to inhibit the AR-axis activity whether it is androgen-dependent or androgen-independent. Degradation of the AR removes the possibility of promiscuous activation of mutant ARs, activation by intracellular processes such as signal transduction and kinase activation, etc.; and suggests that the SARDs should also degrade the polyQ polymorphism in hyperandrogenic dermatologic disorders (shortened polyQ) or Kennedy's disease (extended polyQ), providing a rationale for treating either type of diseases by destroying the AR in the affected tissues (skin and neuromuscular system, respectively).

Example 15

Further Studies with SARDs

PCa Gene Expression and Cell Growth:

PCa cells (LNCaP and 22RV1) will be plated at 10,000 cells per well of a 96 well plate in respective medium supplemented with 1% csFBS or in full serum. The cells will be maintained for 3 days and will be treated with SARDs or controls alone or in combination with 0.1 nM R1881 (1% csFBS). RNA will be isolated and cDNA prepared using cells-to-ct kits (Life Technologies). Expression of various androgen-regulated genes will be measured using TaqMan primer probe mix on an ABI 7900 realtime PCR machine. The expression of individual genes will be normalized to 18S rRNA levels.

PCa cells will be plated at 10,000 cells per well of a 96 well plate in respective medium supplemented with 1% csFBS or in full serum. The cells will be treated with SARDs alone or in combination with 0.1 nM R1881. The cell viability will be measured using Sulforhodamine blue reagent. As negative control, AR-negative PC3 cells will be treated similarly to ensure the absence of any non-specific growth inhibitory properties of SARDs.

Preclinical Rodent Pharmacokinetic (PK) Studies:

The PK parameters of SARDs in various formulations will be determined in rats and mice as appropriate. Approximately 250 gram Sprague-Dawley rats will be randomized into groups of 5 and a catheter surgically implanted into the jugular vein. After a recovery period the rats will be administered test compound and 250 µL of venous blood will be serially sampled from the catheter at 0, 10, 20, 30, 60, 120, 240, 480, 720, 1440 and 2880 minutes post administration for an intravenous dose or 0, 20, 40, 60, 90, 120, 150, 180, 210, 240, 480, 720, 1440, and 2880 minutes post administration for a non-intravenous dose. For mice, approximately 20 gram C57BL/6 mice will be grouped into three per time point per route of administration. Following administration of an intravenous dose mice will be sacrificed and blood collected by cardiac puncture at 0, 10, 20, 30, 60, 120, 240, 480, 720, 1440 and 2880 minutes after intravenous dosing or 0, 30, 60, 90, 120, 150, 180, 210, 240, 480, 720, 1440, 2880 minutes after dosing for a non-intravenous dose. Samples will be collected in appropriate anti-coagulant containing tubes and plasma prepared for LC-MS-MS analyses. Relevant PK parameters will be estimated via non-compartmental analyses using Phoenix WinNonlin.

PCa Xenograft Studies:

Nod Scid γ (NSG)/nude mice (6-8 weeks in age) will be used in the xenograft experiments. Briefly, a mixture of 1:1 LNCaP or 22RV-1 cells in medium (10% FBS supplemented medium):matrigel mixture will be implanted subcutaneously in male NSG mice. Cell number to be implanted will depend on the cell type. Tumors will be implanted in male nude mice that have high circulating androgens or in castrated animals supplemented with DHT to streamline the hormone circulation and to reduce variability between animals. For CRPC model, animals will be castrated when VCaP tumors reach 100 mm$^3$ and the tumors will be allowed to re-grow as CRPC. Animals will be randomized into groups once the tumors reach 200 mm$^3$ and will be treated daily with vehicle or respective SARD. Tumor volume will be measured thrice weekly and the animals will be sacrificed at the end of the study. At sacrifice, tumors will be weighed and stored for further histological and molecular biological analysis. Tumor volume will be calculated using the formula length×width×width×0.5236. Cai et al. (Cancer Research, 71(20), 2011) have characterized VCaP cells as expressing high levels of androgen biosynthesis enzymes CYP17A1, AKR1C3, and HSD6B resulting in high intratumoral androgen levels.

Example 16

In Vivo Studies of SARDs (Indoles and Indolines)

Hershberger assay: Mice (6-7 weeks old) were treated with vehicle or indicated SARDs (100 mg/kg/day twice daily) for 14 days orally. Animals were sacrificed and seminal vesicles (S.V.) weights were recorded and represented.

Figure 30B:
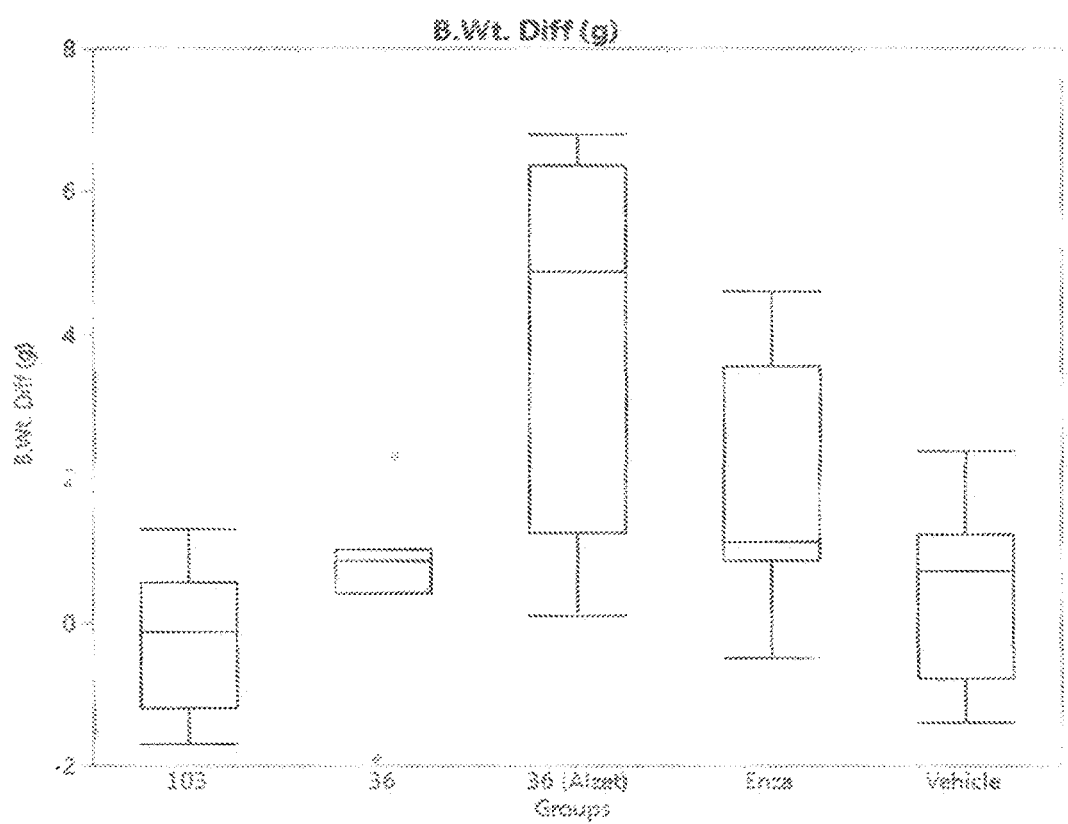
Figure 30C:
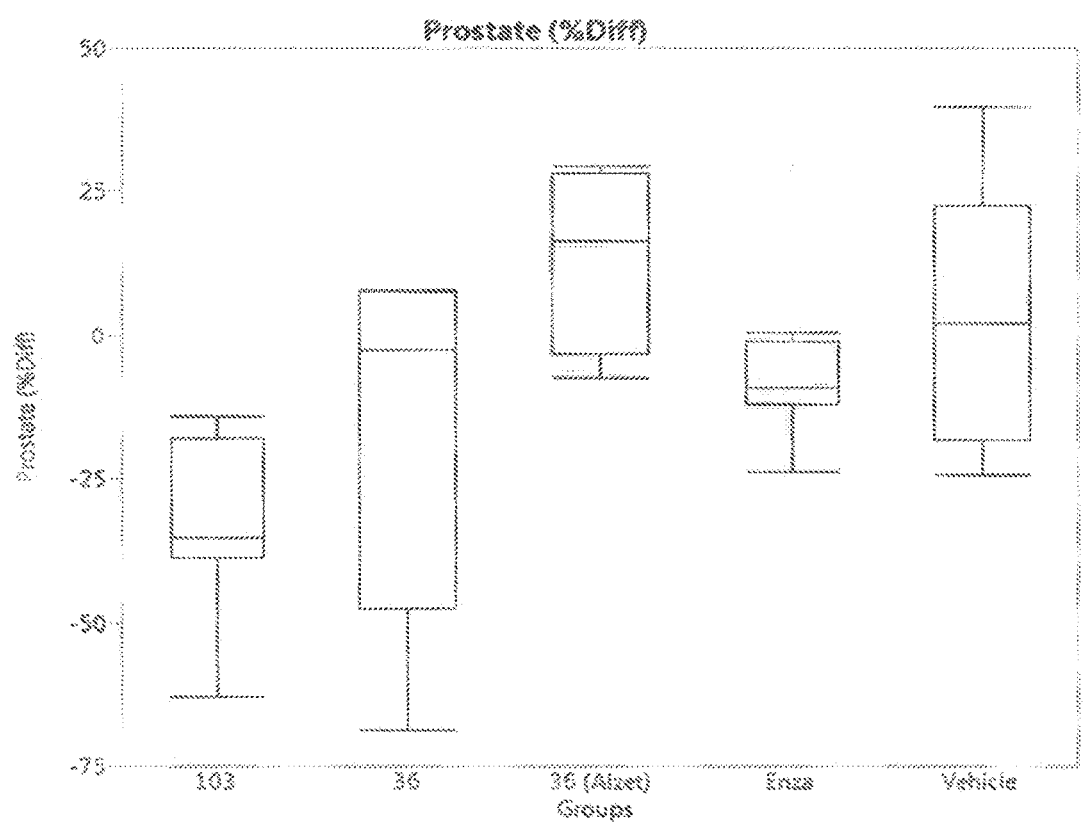
Figure 30D:
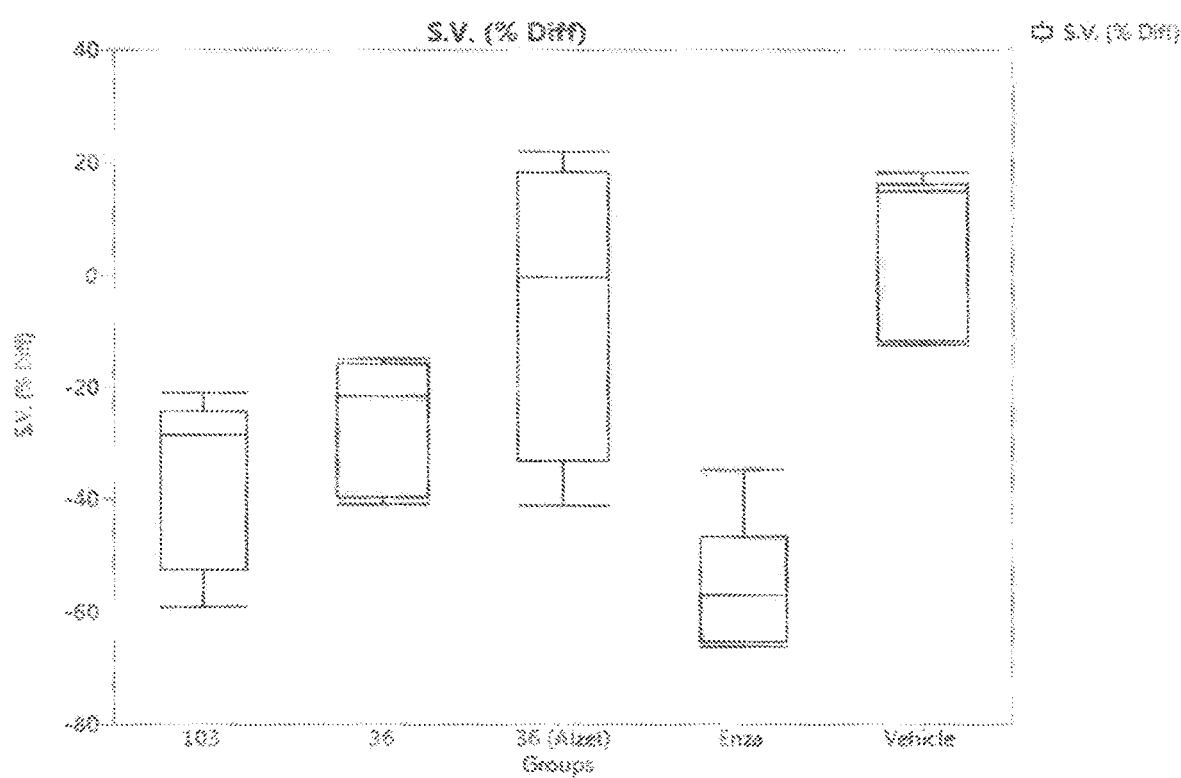

Results: SARDs 11, 34, 36, 37, 38, 103, and 115 demonstrated varying levels of inhibition of seminal vesicles (S.V.) growth. 103 and 36 had the greatest effect on suppressing S.V. growth (FIGS. 30A and 30D), prostate (FIG. 30C), and also had an effect of body weight (FIG. 30B). This suggests that these SARDs, despite low levels in the serum, were able to exert antiandrogenic effects on androgen dependent organs, supporting their potential use as treatments for prostate cancer and other diseases as described herein.

SARDs were also investigated in xenograft studies. 103 demonstrated low levels of efficacy in patient derived (FIG. 31) and mouse (FIG. 32) xenografts despite very low levels in the plasma.

TABLE 15

SARDs are detected in plasma and patient derived tumor.

| | Conc of 103 (nM) |
|---|---|
| Plasma Sample #768 | 3.81 |
| Plasma Sample #769 | 18.4 |
| Tumor Sample #768 | 142 |
| Tumor Sample #769 | 282 |

TABLE 15-continued

SARDs are detected in plasma and patient derived tumor.

| | Conc of 103 (nM) |
|---|---|
| Calibration Curve | |
| Range | 1.95-2000 Nm |
| $R^2$ | 0.9957 |
| Regression | Quadratic |
| Weighting | $1/x^2$ |

However, unexpectedly 103 was found to accumulate in the tumor (Table 15), possibly explaining its activity in the xenografts.

SARDs selectively accumulate in tumor: NSG mice were implanted with patient-derived prostate cancer xenograft. Animals were treated for 14 days and tumor volumes were measured twice weekly. Animals were sacrificed, 103 extracted from serum and tumor and measured using a LC-MS/MS method.

103 selectively accumulates in tumor with almost 10 times more tumor accumulation than in plasma. While 103 had weak activity in tumor xenografts, 36 demonstrated promising inhibition of tumor growth.

Example 17

SARDs Inhibit Transcriptional Activation of F876L

To validate that SARDs of the invention can antagonize the R1881-driven transcriptional activation of mutant AR F876L, COS cells were transfected with F876L AR with a GRE-driven luciferase reporter construct, and a Renilla reporter construct as a control for transfection efficiency. Cells were treated 24 h after transfection with 0.1 nM R1881 (AR agonist) and a dose response of SARDs. Luciferase (and Renilla) assays were performed 48 h after transfection and reported as relative light unit (RLU). COS is not a prostate cancer cell line, so transfection with F876L does not confer enzalutamide resistance (Enz-R). FIG. 50A (top middle panel) demonstrated potent (low nM) but not full efficacy antagonism by enzalutamide of R1881-driven F876L transactivation, whereas wt AR inhibition was less potent (low µM) and full efficacy. Importantly, at high concentrations (>1 µM), enzalutamide acts as an agonist of F876L transactivation (top right panel of FIG. 50A), which is not seen in wt AR. This is indicative that F876L acts like an agonist switch escape mutant of enzalutamide therapy. Given that SARDs of this invention were structurally novel high potency AR antagonists with a unique biological activity profile, representative compounds (i.e., 11 (5-F indole), 22 (4-F indole), 23 (6-F indole), 37 (5-F indole), 101 (4-F indoline), and 36 (4-F indole)) were tested for their ability to overcome the agonist switch behavior. Approximately equipotent nM range, full efficacy antagonism of R1881-driven transcriptional activation was observed in both F876L and wt. This suggested that SARDs of this invention would also exhibit activity in models of Enz-R (e.g., MR49F cells) and primary prostate cancer (PC) possessing wt AR.

Example 18

SARD Activity and Cellular Anti-Proliferation in the MR49F Model of Enzalutamide Resistant Prostate Cancer (Enz-R PC)

To ensure that SARD activity was also maintained in a Enz-R cell line, SARD assays were performed in MR49F LNCaP cells containing the F876L/T877A double mutant. As seen in FIG. 50B, 36 (4-F indole) and 115 (5-F, 6-Ph indoline) degraded this mutant FL AR in MR49F cells in the low μM and high nM range, respectively, consistent with the relative activities seen in Tables 3 and 6. Densitometric evaluation of the immunoblots suggests that 115 demonstrated similar to improved potency of SARD activities in the Enz-R LNCaP (FIG. 50A) when compared to the parental enzalutamide sensitive LNCaP shown supra (FIG. 49A). This suggests that the optimized activity profile for 115 reported in Table 6 was conserved in this model of Enz-R. Enzalutamide was inactive in SARD activity assays in LNCaP (FL) and 22RV1 (SV) cells and was not tested in MR49F cells as it was not expected to be a SARD in this or any cellular context. The preservation of SARD activity for these representative compounds even in the Enz-R context suggested that SARDs of the invention may exhibit broad spectrum anti-proliferative and/or anti-tumor activities across many prostate cancers including enzalutamide-resistant prostate cancers.

Anti-proliferative assays in MR49F cells showed that 103 (4-F indoline), 36 (4-F indole), and 34 (5-F, 6-Ph indole) completely and dose-dependently inhibited cell growth with estimated $IC_{50}$ values of less than 3 μM for 103 and 36, and less than 1 μM for 34 (FIG. 51). For 36 at least, this correlates well with in vitro proliferative antagonism and SARD activity in MR49F cells (FIGS. 50A and 50B), suggesting that SARDs of this invention retained their unique biological profile in Enz-R PC. By comparison, enzalutamide demonstrated weak and incomplete efficacy as revealed by poor dose-dependence and only partial inhibition of growth. E.g., growth inhibitions at 3 μM, 10 μM and 30 μM were approximately 30%, 15% and 45%. This result demonstrated the enzalutamide resistant of these MR49F cells, and further affirmed our ability to overcome the Enz-R phenotype with representative examples of SARDs of this invention, supporting testing in MR49F xenografts.

Example 19

In Vivo Antagonism

Hershberger assays. Hershberger assays were performed on several SARDs of this invention in intact mice and rats. Surprisingly, despite poor mouse liver microsome (MLM) stabilities, the tested SARDs (103, 104, 23, 34, 11, 36, 37, 38 and 115) caused atrophy of AR-dependent seminal vesicles tissue in intact mice (FIG. 52A, left panels) whereas vehicle did not have any effect (0% change). Similar efficacy atrophy was also observed for 103 and 104 in rats (FIG. 52A, right panel) and was demonstrated to be dose-dependent in prostate and seminal vesicles, with up to ~40% change in organ weights relative to castrated control (100%). This confirms that orally administered compounds are being absorbed and distributed to the site of action in these organs and suggests that the compound should also distribute to tumors in xenograft models to exert anti-tumor effects in sensitive models.

MR49F Xenografts in mice: MR49F xenografts were established by implanting the Enz-R LNCaP cells (from University of British Columbia) mixed with Matrigel (BD Biosciences, San Jose, Calif.) at 1:1 ratio and injecting subcutaneously in NOD SCID gamma (NSG) mice. Once tumor sizes reached 100-200 mm³, the mice were castrated and the tumors were allowed to regrow as CRPC. The animals were randomized once the tumors started to regrow and treated with vehicle (polyethylene glycol-300: DMSO 85:15 ratio) or 100 mg per kg of SARDs 34 or 36 for 14 d. In FIG. 52B, 34 and 36 significantly reduced the tumor volume with a 40-60% tumor growth inhibition (TGI).

Further, the significant levels of TGI activity indicated that the oral bioavailability demonstrated in Hershberger assays translated to adequate levels of 34 and 36 in tumor to reveal to some extent the pharmacodynamic behavior of the SARDs of this invention. The proof-of-concept that the SARDs of the invention can overcome Enz-R CRPC in vivo was established through the susceptibility of these Enz-R xenografts to 34 and 36. This promising result is surprising given the poor metabolic stability of these SARDs as a whole in the same species (mice) as seen in MLM (Tables 4 and 6; $T_{1/2}$ for 34 and 36 were 9.13 min and 11.77 min). These experiments indicate that the SARDs of this invention with their unique biological profile could be used to overcome enzalutamide, and by extension apalutamide and abiraterone, resistances, in CRPC patients.

SARD compounds of the invention as described herein are potent AR antagonists and with a broad activity profile in models of prostate cancer, and in vivo AR antagonism when orally administered. For example, SARDs exhibited strong AR antagonistic activity in vitro in transcriptional activation and cellular proliferative assays including in models of enzalutamide sensitive and resistant PCs, and/or castration resistant PCs (CRPCs).

Additionally, SARDs of the invention showed selective AR [protein] degradation of full-length (FL AR; e.g., from LNCaP cells (T877A)) and splice variant (SV AR; e.g., from 22RV1 cells (AR-V7)) isoforms of AR, all at sub to low micromolar treatment levels, and in a variety of prostate cancer cell contexts including enzalutamide resistant PCs (e.g., MR49F). The ability to degrade SV AR in the study suggested the potential of SARDs of this invention to treat various currently untreatable advanced and refractory PCs, for example, those lacking the ligand binding domain (LBD) of AR such as AR-V7 and D567es AR truncations, which are not susceptible to androgen-deprivation therapy, abiraterone, or LBD-directed antiandrogens (e.g., enzalutamide, apalutamide, and bicalutamide), and are associated with short survival.

Further, in vivo investigation found that the SARDs of the invention overcome a variety of escape mutants including F876L and F876L/T877A (MR49F) that are known to emerge due to enzalutamide treatment. These mutations convert enzalutamide and apalutamide to agonists, conferring resistance to prostate cancer cells and tumors via an agonist switch mechanism as seen with other LBD-binding antiandrogens, e.g. W741L for bicalutamide and T877A for flutamide (N-(4-nitro-3-(trifluoromethyl)phenyl)isobutyramide). The intractability of truncation mutants and the frequency of the agonist switch mutations suggest that novel ways, potentially LBD-independent ways, of targeting the AR are needed. Moreover, these orally bioavailable SARDs are dual acting agents, i.e., potent inhibitors and degraders of AR, providing a higher evolutionary barrier to the development of resistance to SARDs. N-terminally directed SARDs such as the SARDs of this invention may provide a next generation of AR antagonists to treat a variety of refractory and/or advanced prostate cancers, including enzalutamide-resistant, castration resistant, and/or AR-V7 dependent PCs which are not amendable with current hormone therapies. As such, SARDs may delay the need to rely solely on chemotherapy.

SARDs of the invention have a unique biological activity profile optimized to address Enz-R CPRC, including:

1) Generally bind to LBD of AR;

2) Inhibit transcriptional activation of wildtype AR, escape mutant ARs (T877A in Tables 3 and 6, F876L in FIG. 50A, and Q711A 3) Exert high efficacy and potency SARD activity against FL and SV AR whether wildtype or harboring point-mutations (LNCaP in Tables 3 and 6) or truncations (22RV1 in Tables 3 and 6), including an Enz-R cellular contexts (e.g., MR49F in FIG. 50B);

4) Exert AR antagonism in vivo when administered orally in intact animals (FIG. 52A);

5) Exert PC anti-proliferative activity in vitro (FIG. 51) and in vivo (see LNCaP, 22RV1) including in Enz-R CRPC (FIG. 52B); and 6) Bind to a secondary binding site in AF-1 believed to mediate SARD activity as demonstrated for 11 by steady fluorescence and NMR studies, as demonstrated herein.

Example 20

SBMA Method

Transgenic mice that express AR121Q (121 polyglutamine repeats instead of the usual 15-24 repeats) will be treated with vehicle or SARD orally. One group of mice will be castrated to serve as positive control as circulating androgens will worsen the SBMA (X-linked spinal-bulbar muscular atrophy) condition. Body weight, composition, and grip strength will be measured before the initiation of the experiment. Animals will be treated and weekly measurements will be performed. Animals will be treated and monitored until they die. AR121Q mice live only up to 60-80 days and hence evaluating the survival in the presence of SARD treatment is possible.

ALS Method

All experiments will be performed in male hSOD1-G93A mice (Jax labs; PMID: 26786249) as a model of anterior lateral sclerosis (ALS). Mice will be randomized and treated with either vehicle or SARD of this invention dissolved in DMSO+PEG-300 (15%+85%). Simultaneously, a group of mice will be castrated and used as positive control as castration has been shown to extend survival and disease duration in this model (PMID: 24630363). Mice will be treated orally every day until they reach morbidity. Weekly body weight and composition by magnetic resonance imaging (MRI) will be recorded. The mice performance will be measured each week by using a grip strength meter (Columbus instruments) or rotarod. Inability for the mice to move will be considered as a terminal disease state and the mice will be sacrificed.

Example 21

Synthesis of Benzotriazole SARD Compounds (S)—N-(4-Cyano-3-(trifluoromethyl)phenyl)-2-hydroxy-2-methyl-3-(5-(trifluoromethyl)-2H-benzo[d][1,2,3]triazol-2-yl)propanamide ($C_{19}H_{13}F_6N_5O_2$) (300)

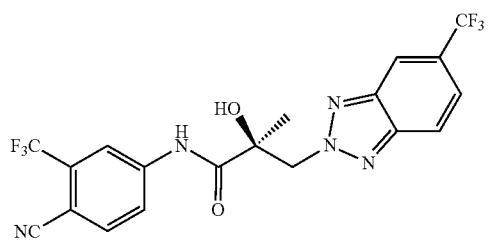 [SMILES: C[C@](O)(Cn1nc2ccc(C(F)(F)F)cc2n1)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with $MgSO_4$, filtered, and concentrated under vacuum. The product was purified by a silica gel column using DCM and ethyl acetate (9:1) as eluent to afford 0.044 g (9%) of the titled compound as yellowish solid.

$^1$H NMR (400 MHz, DMSO-$d_6$) δ 10.33 (s, 1H, NH), 8.40 (s, 1H, ArH), 8.38 (s, 1H, ArH), 8.23 (d, J=8.4 Hz, 1H, ArH), 8.11 (d, J=8.4 Hz, 2H, ArH), 7.67 (d, J=8.6 Hz, 1H, ArH), 6.67 (s, 1H, OH), 5.24 (d, J=14.0 Hz, 1H, CH), 4.99 (d, J=14.0 Hz, 1H, CH), 1.55 (s, 3H, $CH_3$).

Mass (ESI, Negative): 456.25 [M−H]$^-$; (ESI, Positive): 458.10[M+H]$^+$.

(S)—N-(4-Cyano-3-(trifluoromethyl)phenyl)-2-hydroxy-2-methyl-3-(5-(trifluoromethyl)-1H-benzo[d][1,2,3]triazol-1-yl)propanamide ($C_{19}H_{13}F_6N_5O_2$) (301)

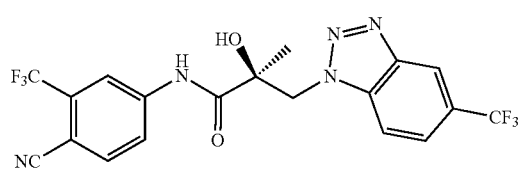 [SMILES: C[C@](O)(Cn1nnc2cc(C(F)(F)F)ccc21)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (3:1 to 2:1) as eluent to afford 0.025 g (5%) of the titled compound as yellowish solid.

$^1$H NMR (400 MHz, DMSO-$d_6$) δ 10.30 (s, 1H, NH), 8.39 (d, J=1.6 Hz, 1H, ArH), 8.33 (s, 1H, ArH), 8.25 (d, J=8.8 Hz, 1H, ArH), 8.12 (dd, J=8.8 Hz, J=2.0 Hz, 1H, ArH), 8.07 (d, J=8.4 Hz, 1H, ArH), 7.64 (dd, J=8.8 Hz, J=1.6 Hz, 1H, ArH), 6.64 (s, 1H, OH), 5.21 (d, J=14.4 Hz, 1H, CH), 5.01 (d, J=14.4 Hz, 1H, CH), 1.54 (s, 3H, CH₃).

Mass (ESI, Negative): 456.25 [M−H]⁻; (ESI, Positive): 458.10[M+H]⁺.

(S)—N-(4-Cyano-3-(trifluoromethyl)phenyl)-2-hydroxy-2-methyl-3-(6-(trifluoromethyl)-1H-benzo[d][1,2,3]triazol-1-yl)propanamide ($C_{19}H_{13}F_6N_5O_2$) 302

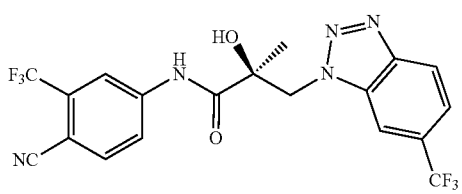 [SMILES: C[C@](O)(Cn1nnc2ccc(C(F)(F)F)cc21)C(=O)Nc1ccc(C#N)c(C(F)(F)F)c1]

To a solution of 5-(trifluoromethyl)-1H-benzo[d][1,2,3]triazole (0.20 g, 0.0010688 mol) in anhydrous THF (5 mL), which was cooled in an ice water bath under an argon atmosphere, was added sodium hydride (60% dispersion in oil, 0.13 g, 0.0033134 mol). After addition, the resulting mixture was stirred for three hours. (R)-3-Bromo-N-(4-cyano-3-(trifluoromethyl)phenyl)-2-hydroxy-2-methylpropanamide (0.375 g, 0.0010688 mol) was added to above solution, and the resulting reaction mixture was allowed to stir overnight at room temperature under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (3:1 to 2:1) as eluent to afford 0.023 g (5%) of the titled compound as yellowish solid.

$^1$H NMR (400 MHz, DMSO-$d_6$) δ 10.31 (s, 1H, NH), 8.50 (s, 1H, ArH), 8.34 (d, J=1.6 Hz, 1H, ArH), 8.18 (dd, J=8.8 Hz, J=2.0 Hz, 1H, ArH), 8.10 (d, J=8.8 Hz, 1H, ArH), 8.08 (d, J=8.4 Hz, 1H, ArH), 7.84 (dd, J=8.8 Hz, J=1.6 Hz, 1H, ArH), 6.49 (s, 1H, OH), 5.15 (d, J=14.4 Hz, 1H, CH), 4.97 (d, J=14.4 Hz, 1H, CH), 1.52 (s, 3H, CH₃).

Mass (ESI, Negative): 456.25 [M−H]⁻; (ESI, Positive): 458.10[M+H]⁺.

(S)—N-(4-Cyano-3-(trifluoromethyl)phenyl)-2-hydroxy-2-methyl-3-(5-fluoro-2H-benzo[d][1,2,3]triazol-2-yl)propanamide ($C_{18}H_{13}F_4N_5O_2$) (303)

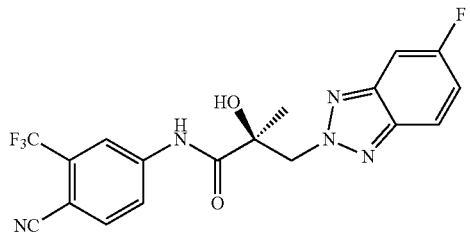 [SMILES: C[C@](O)(Cn1nc2ccc(F)cc2n1)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (3:1 to 2:1) as eluent to afford 0.115 g (19.4%) of the titled compound as yellowish solid.

$^1$H NMR (400 MHz, DMSO-$d_6$) δ 10.35 (s, 1H, NH), 8.43 (s, 1H, ArH), 8.32 (d, J=8.2 Hz, 1H, ArH), 8.11 (d, J=8.2 Hz, 1H, ArH), 7.95-7.91 (m, 1H, ArH), 7.67 (d, J=8.8 Hz, 1H, ArH), 7.33-6-7.31 (m, 1H, ArH), 6.53 (s, 1H, OH), 5.14 (d, J=13.6 Hz, 1H, CH), 4.90 (d, J=13.6 Hz, 1H, CH), 1.53 (s, 3H, CH₃).

Mass (ESI, Positive): 430.09 [M+Na]⁺.

(S)—N-(4-Cyano-3-(trifluoromethyl)phenyl)-2-hydroxy-2-methyl-3-(5-fluoro-1H-benzo[d][1,2,3]triazol-1-yl)propanamide ($C_{18}H_{13}F_4N_5O_2$) (304)

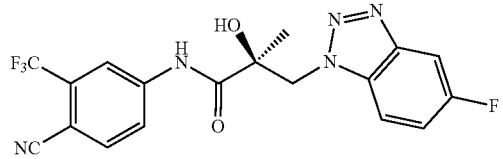 [SMILES: C[C@](O)(Cn1nnc2cc(F)ccc21)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (3:1 to 2:1) as eluent to afford 0.075 g (12.6%) of the titled compound as yellowish solid.

¹H NMR (400 MHz, DMSO-d₆) δ 10.35 (s, 1H, NH), 8.40 (s, 1H, ArH), 8.19 (d, J=8.4 Hz, 1H, ArH), 8.10 (d, J=8.0 Hz, 1H, ArH), 8.07-8.04 (m, 1H, ArH), 7.70 (d, J=8.2 Hz, 1H, ArH), 7.28-6-7.23 (m, 1H, ArH), 6.45 (s, 1H, OH), 5.05 (d, J=14.4 Hz, 1H, CH), 4.87 (d, J=14.4 Hz, 1H, CH), 1.50 (s, 3H, CH₃).

Mass (ESI, Positive): 430.09 [M+Na]⁺.

(S)—N-(4-Cyano-3-(trifluoromethyl)phenyl)-2-hydroxy-2-methyl-3-(6-fluoro-1H-benzo[d][1,2,3]triazol-1-yl)propanamide (C₁₈H₁₃F₄N₅O₂) (305)

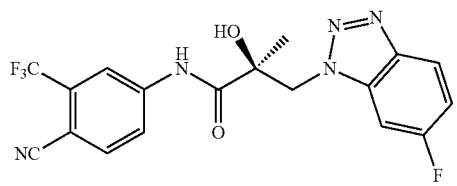 [SMILES: C[C@](O)(Cn1nnc2ccc(F)cc21)C(=O)Nc1ccc(C#N)c(C(F)(F)F)c1]

To a solution of 5-fluoro-1H-benzo[d][1,2,3]triazole (0.20 g, 0.001459 mol) in anhydrous THF (5 mL), which was cooled in an ice water bath under an argon atmosphere, was added sodium hydride (60% dispersion in oil, 0.18 g, 0.004522 mol). After addition, the resulting mixture was stirred for three hours. (R)-3-Bromo-N-(4-cyano-3-(trifluoromethyl)phenyl)-2-hydroxy-2-methylpropanamide (0.51 g, 0.001459 mol) was added to above solution, and the resulting reaction mixture was allowed to stir overnight at room temperature under argon. The reaction was quenched by water, and extracted with ethyl acetate. The organic layer was washed with brine, dried with MgSO₄, filtered, and concentrated under vacuum. The product was purified by a silica gel column using hexanes and ethyl acetate (3:1 to 2:1) as eluent to afford 0.052 g (8.8%) of the titled compound as yellowish solid.

¹H NMR (400 MHz, DMSO-d₆) δ 10.35 (s, 1H, NH), 8.38 (s, 1H, ArH), 8.20 (d, J=8.8 Hz, 1H, ArH), 8.10 (d, J=8.4 Hz, 1H, ArH), 7.92-7.89 (m, 1H, ArH), 7.84 (d, J=8.8 Hz, 1H, ArH), 7.46-7.42 (m, 1H, ArH), 6.46 (s, 1H, OH), 5.08 (d, J=14.4 Hz, 1H, CH), 4.90 (d, J=14.4 Hz, 1H, CH), 1.49 (s, 3H, CH₃).

Mass (ESI, Positive): 430.09 [M+Na]⁺.

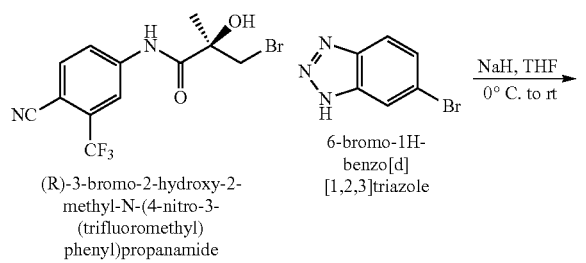

(R)-3-bromo-2-hydroxy-2-methyl-N-(4-nitro-3-(trifluoromethyl)phenyl)propanamide 6-bromo-1H-benzo[d][1,2,3]triazole NaH, THF
0° C. to rt

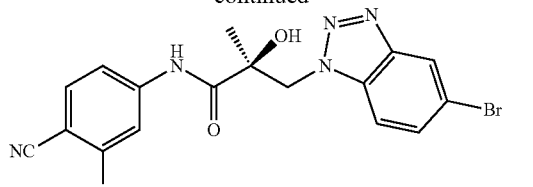

306

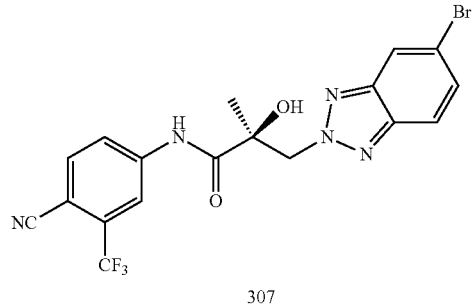

307

(S)-3-(5-Bromo-1H-benzo[d][1,2,3]triazol-1-yl)-N-(4-cyano-3-(trifluoromethyl)phenyl)-2-hydroxy-2-methylpropanamide (306)

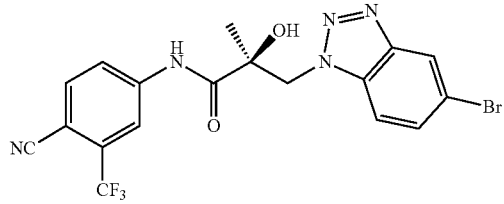 [SMILES: C[C@](O)(Cn1nnc2cc(Br)ccc21)C(=O)Nc1ccc(C#N)c(C(F)(F)F)c1]

To a dry, nitrogen-purged 100 mL round-bottom flask equipped with a dropping funnel under argon atmosphere, NaH of 60% dispersion in mineral oil (260 mg, 6.5 mmol) was added in 30 mL of anhydrous THF solvent in the flask at ice-water bath, and 6-bromo-1H-benzo[d][1,2,3]triazole (514 mg, 2.6 mmol) was stirred in over 30 min at the ice-water bath. Into the flask, the solution of (R)-3-bromo-2-hydroxy-2-methyl-N-(4-nitro-3-(trifluoromethyl)phenyl)propanamide (911 mg, 2.6 mmol) in 5 mL of anhydrous THF was added through dropping funnel under argon atmosphere at the ice-water bath and stirred overnight at room temperature. After adding 1 mL of H₂O, the reaction mixture was condensed under reduced pressure, and then dispersed into 50 mL of EtOAc, washed with 50 mL (×2) water, evaporated, dried over anhydrous MgSO₄, and evaporated to dryness. The mixture was purified with flash column chromatography as an eluent EtOAc/hexane=½ to produce designed compounds (Yield=65%: 42% for 306 and 23% of 307) as yellowish solid.

(S)-3-(5-Bromo-1H-benzo[d][1,2,3]triazol-1-yl)-N-(4-cyano-3-(trifluoromethyl)phenyl)-2-hydroxy-2-methylpropanamide (306)

MS (ESI) m/z 467.81 [M−H]⁻; 492.00 [M+Na]⁺.
¹H NMR (400 MHz, CDCl₃) δ 9.10 (bs, 1H, NH), 8.04 (s, 1H), 8.02 (s, 1H), 7.90 (d, J=8.0 Hz, 1H), 7.76 (d, J=8.0 Hz,

1H), 7.74 (d, J=8.8 Hz, 1H), 7.49 (d, J=8.8 Hz, 1H), 5.48 (s, 1H, OH), 5.26 (d, J=13.6 Hz, 1H), 4.94 (d, J=13.6 Hz, 1H), 1.54 (s, 3H);
$^{19}$F NMR (CDCl$_3$, decoupled) δ-62.19.

(S)-3-(5-Bromo-2H-benzo[d][1,2,3]triazol-2-yl)-N-(4-cyano-3-(trifluoromethyl)phenyl)-2-hydroxy-2-methylpropanamide(307))

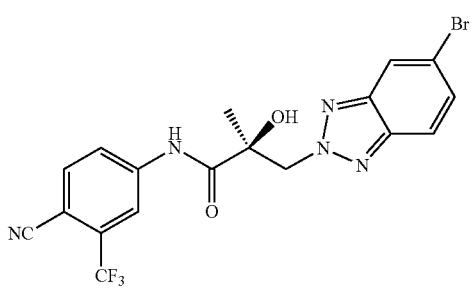 [SMILES: C[C@](O)(Cn1nc2ccc(Br)cc2n1)C(=O)Nc1ccc(C#N)c(C(F)(F)F)c1]

MS (ESI) m/z 467.84 [M−H].
$^1$H NMR (400 MHz, CDCl$_3$) δ 8.97 (bs, 1H, NH), 8.15 (s, 1H), 7.92 (s, 1H), 7.75 (m, 2H), 7.62 (d, J=9.0 Hz, 1H), 7.53 (d, J=9.0 Hz, 1H), 5.16 (d, J=14.2 Hz, 1H), 4.79 (s, 1H, OH), 4.78 (d, J=14.2 Hz, 1H), 1.65 (s, 3H);
$^{19}$F NMR (CDCl$_3$, decoupled) δ-62.26.

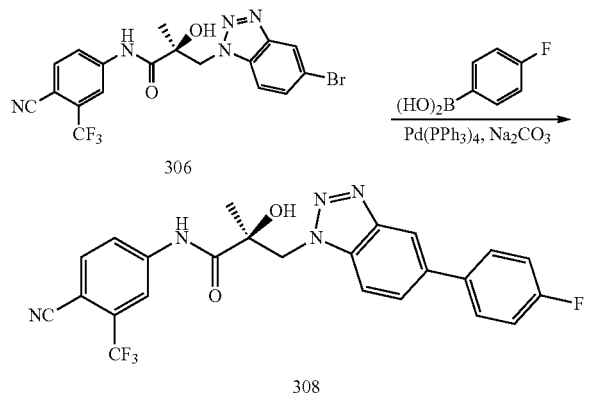

(S)—N-(4-Cyano-3-(trifluoromethyl)phenyl)-3-(5-(4-fluorophenyl)-1H-benzo[d][1,2,3]triazol-1-yl)-2-hydroxy-2-methylpropanamide (308)

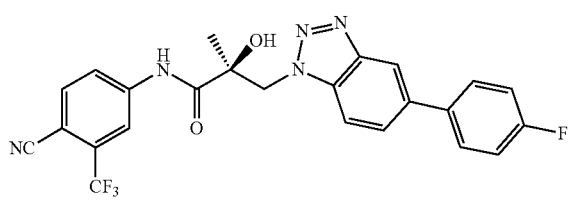 [SMILES: C[C@](O)(Cn1nnc2cc(-c3ccc(F)cc3)ccc21)C(=O)Nc1ccc(C#N)c(C(F)(F)F)c1]

A mixture of 306 (150 mg, 0.32 mmol), tetrakis(triphenylphosphine)palladium (0) (13 mg, 12 mmol) and trimethoxyboric acid (50 mg, 0.35 mmol) in THF/MeOH (1/1 mL) with sodium carbonate (82 mg, 7.69 mmol) in ethanol/water (5 mL/1 mL) were heated to reflux overnight. The mixture was cooled down to be concentrated under reduced pressure and poured into EtOAc, which was washed with water and dried over MgSO$_4$, concentrated, purified by silica gel chromatography (EtOAc/n-hexane=2:3) to afford 308 as a yellow solid.
Yield=90%;
MS (ESI) m/z 482.25 [M−H].
$^1$H NMR (400 MHz, CDCl$_3$) δ 9.12 (bs, 1H, NH), 8.02 (s, 1H), 7.96 (s, 1H), 7.92 (d, J=9.2 Hz, 1H), 7.76 (d, J=8.4 Hz, 1H), 7.64 (d, J=9.2 Hz, 1H), 7.59 (dd, J=7.6, 5.2 Hz, 2H), 7.17 (t, J=8.4 Hz, 2H), 5.72 (s, 1H, OH), 5.28 (d, J=14.0 Hz, 1H), 4.97 (d, J=14.0 Hz, 1H), 1.55 (s, 3H); $^{19}$F NMR (CDCl$_3$, decoupled) δ-62.20, −114.49.

Example 22

Synthesis of (R)-3-Bromo-N-(6-cyano-5-(trifluoromethyl)pyridin-3-yl)-2-hydroxy-2-methylpropanamide (8a)

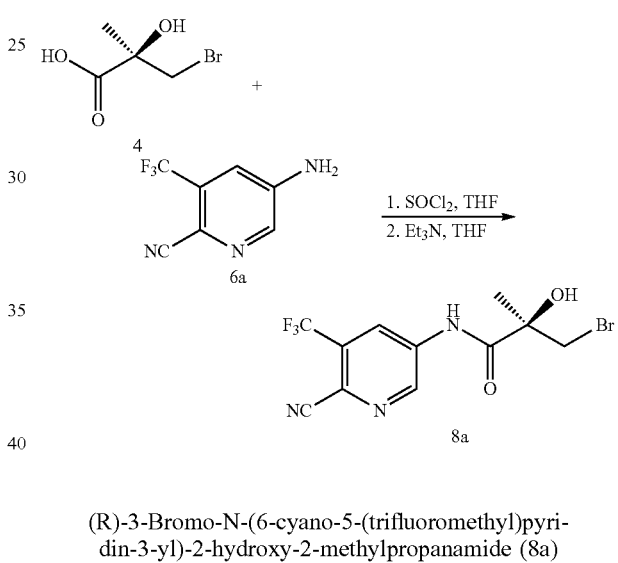

(R)-3-Bromo-N-(6-cyano-5-(trifluoromethyl)pyridin-3-yl)-2-hydroxy-2-methylpropanamide (8a)

Thionyl chloride (0.8 mL, 1.07 mol) was added dropwise to a cooled solution (less than 4° C.) of (R)-3-bromo-2-hydroxy-2-methylpropanoic acid (4, 1.27 g, 6.94 mmol) in 50 mL of THF under an argon atmosphere. The resulting mixture was stirred for 3 h under the same condition. To this was added Et$_3$N (1.8 mL, 1.28 mmol) and stirred for 20 min under the same condition. After 20 min, 5-amino-3-(trifluoromethyl)picolinonitrile (6a, 1 g, 5.34 mmol), 50 mL of THF were added and then the mixture was allowed to stir overnight at room temperature. The solvent was removed under reduced pressure to give a solid which was treated with 50 mL of H$_2$O, extracted with EtOAc (2×400 mL). The combined organic extracts were washed with saturated NaHCO$_3$ solution (2×50 mL) and brine (50 mL). The organic layer was dried over MgSO$_4$ and concentrated under reduced pressure to give a solid which was purified from column chromatography using CH$_2$Cl$_2$/EtOAc (80:20) to give a solid. This solid was recrystallized from CH$_2$Cl$_2$/hexane to give 1.32 g (70.2%) of (R)-3-bromo-N-(6-cyano-5-(trifluoromethyl)pyridin-3-yl)-2-hydroxy-2-methylpropanamide (8a) as a light-yellow solid. MS (ESI) m/z 351.08 [M−H]$^−$.
$^1$H NMR (CDCl$_3$, 400 MHz) δ 9.15 (bs, 1H, NH), 8.90 (s, 1H), 8.78 (s, 1H), 4.02 (d, J=10.8 Hz, 1H), 3.60 (d, J=10.8 Hz, 1H), 3.17 (bs, 1H, OH), 1.66 (s, 3H); $^{19}$F NMR (CDCl$_3$, 400 MHz) δ −62.09.

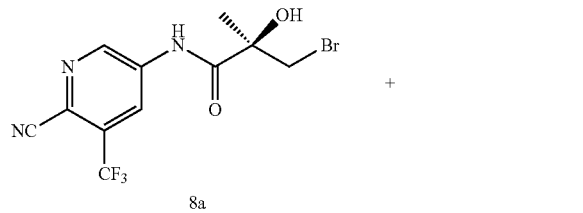

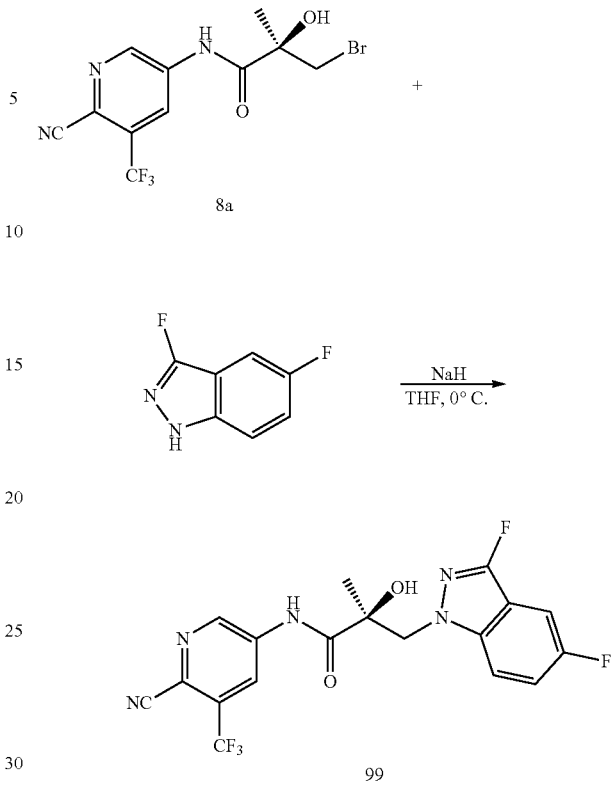

(S)—N-(6-Cyano-5-(trifluoromethyl)pyridin-3-yl)-3-(5-fluoro-1H-indol-1-yl)-2-hydroxy-2-methylpropanamide (47)

To a dry, nitrogen-purged 50 mL round-bottom flask equipped a dropping funnel under argon atmosphere, NaH of 60% dispersion in mineral oil (80 mg, 2.0 mmol) was added in 5 mL of anhydrous THF solvent in the flask at ice-water bath, and 5-fluoro-1H-indole (154 mg, 1.0 mmol) was stirred 30 min at the ice-water bath. Into the flask, (R)-3-bromo-N-(6-cyano-5-(trifluoromethyl)pyridin-3-yl)-2-hydroxy-2-methylpropanamide (8a, 352 mg, 1.0 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=⅔ to produce the designed compound (47) as white solid.

Yield 83%;

MS (ESI) m/z 407.20 [M+H]$^+$; 405.02 [M−H];

HRMS (ESI) m/z calcd for C$_{19}$H$_{14}$F$_4$N$_4$O$_2$ 407.1131 [M+H]$^+$ found 407.1128 [M+H]$^+$.

$^1$H NMR (CDCl$_3$, 400 MHz) δ 8.85 (bs, 1H, NH), 8.58 (d, J=2.0 Hz, 1H), 8.51 (s, 1H), 7.33 (dd, J=8.8, 4.0 Hz, 1H), 7.19 (d, J=2.4 Hz, 1H), 7.17 (d, J=2.8 Hz, 1H), 6.92 (m, 1H), 6.45 (d, J=2.8 Hz, 1H), 4.64 (d, J=15.2 Hz, 1H), 4.33 (d, J=15.2 Hz, 1H), 2.93 (bs, 1H, OH), 1.64 (s, 3H);

$^{19}$F NMR (CDCl$_3$, 400 MHz) δ −82.08, −156.13; Assigned by NOESY and COSY.

(S)—N-(6-Cyano-5-(trifluoromethyl)pyridin-3-yl)-3-(3,5-difluoro-1H-indazol-1-yl)-2-hydroxy-2-methylpropanamide(99)

To a dry, nitrogen-purged 50 mL round-bottom flask equipped with a dropping funnel under argon atmosphere, NaH of 60% dispersion in mineral oil (15 mg, 0.36 mmol) was added in 5 mL of anhydrous THF solvent in the flask at ice-water bath, and 3,5-difluoro-1H-indazole (27 mg, 0.18 mmol) was stirred 30 min at the ice-water bath. Into the flask, (R)-3-bromo-N-(6-cyano-5-(trifluoromethyl)pyridin-3-yl)-2-hydroxy-2-methylpropanamide (8a, 62 mg, 0.18 mmol) in 5 mL of anhydrous THF was added through dropping funnel under argon atmosphere at the ice-water bath and stirred overnight at room temperature. After adding 1 mL of H$_2$O, the reaction mixture was condensed under reduced pressure, and then dispersed into 50 mL of EtOAc, washed with 50 mL (×2) water, evaporated, dried over anhydrous MgSO$_4$, and evaporated to dryness. The mixture was purified with flash column chromatography as an eluent EtOAc/hexane=⅔ to produce the designed compound (99) as white solid.

Yield 56%;

MS (ESI) m/z 424.18 [M−H]$^−$; 426.22 [M+H]$^+$;

HRMS (ESI) m/z calcd for C$_{18}$H$_{12}$F$_5$N$_5$O$_2$ 426.0989 [M+H]$^+$ found 426.0997 [M+H]$^+$.

$^1$H NMR (CDCl$_3$, 400 MHz) δ 9.20 (bs, 1H, NH), 8.79 (s, 1H), 8.55 (s, 1H), 7.41 (s, 1H), 7.26 (m, 2H), 5.41 (bs, 1H, OH), 4.82 (d, J=12.4 Hz, 1H), 4.29 (d, J=12.4 Hz, 1H), 1.54 (s, 3H); $^{19}$F NMR (CDCl$_3$, decoupled) δ −85.46, −156.21, −175.96; Assigned by NOESY and COSY.

What is claimed is:

1. A selective androgen receptor degrader (SARD) compound represented by the structure of formula XVII(1):

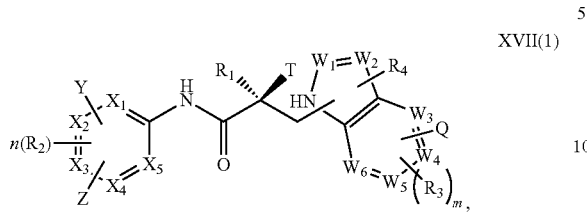

XVII(1)

wherein
- $X_1$, $X_2$, $X_3$, $X_4$, and $X_5$ are each independently N or CH, wherein if any one of $X_1$, $X_2$, $X_3$, $X_4$, and $X_5$ is CH, then the H is optionally replaced with $R_2$, Y, or Z in the respective position, and if any one of $X_1$, $X_2$, $X_3$, $X_4$, and $X_5$ is not CH, then the respective position is unsubstituted; wherein at least one of $X_1$, $X_2$, $X_3$, $X_4$, or $X_5$ is nitrogen;
- $W_1$ and $W_2$ are each independently selected from N or CH;
- $W_3$, $W_4$, $W_5$ and $W_6$ are CH;
- wherein if any one of $W_1$, $W_2$, $W_3$, $W_4$, $W_5$, and $W_6$ is CH, then the H is optionally replaced with $R_4$, Q or $R_3$ in the respective position, and if any one of $W_1$, $W_2$, $W_3$, $W_4$, $W_5$, and $W_6$ is not CH, then the respective position is unsubstituted;
- T is OH, OR, —NHCOCH$_3$, NHCOR or

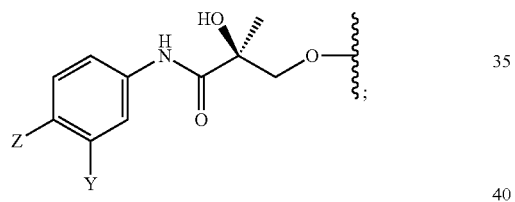

- Z is NO$_2$, CN, or COOH;
- Y is CF$_3$, F, I, Br, Cl, CN or C(R)$_3$;
- R is alkyl, haloalkyl, dihaloalkyl, trihaloalkyl, CH$_2$F, CHF$_2$, CF$_3$, CF$_2$CF$_3$, aryl, phenyl, F, Cl, Br, I, alkenyl or OH;
- $R_1$ is CH$_3$, CH$_2$F, CHF$_2$, CF$_3$, CH$_2$CH$_3$, or CF$_2$CF$_3$;
- $R_2$ is hydrogen, halogen, CN, NO$_2$, COOH, COOR, COR, NHCOR, CONHR, OH, OR, SH, SR, NH$_2$, NHR, NR$_2$, $C_1$-$C_{12}$-alkyl, $C_1$-$C_{12}$-haloalkyl, O—$C_1$-$C_{12}$-alkyl, O—$C_1$-$C_{12}$-haloalkyl, —SO$_2$-aryl, —SO$_2$-phenyl, —CO-aryl, arylalkyl, benzyl, aryl, or $C_3$-$C_7$-cycloalkyl;
- Q is hydrogen, F, Cl, Br, I, CF$_3$, CN, NO$_2$, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_3$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- $R_4$ is hydrogen, F, Cl, Br, I, CF$_3$, CN, NO$_2$, NH$_2$, SH, COOH, COOR, alkoxy, haloalkyl, optionally substituted linear or branched alkyl, optionally substituted linear or branched heteroalkyl, optionally substituted aryl, optionally substituted phenyl, optionally substituted cycloalkyl, optionally substituted heterocycloalkyl, optionally substituted arylalkyl, C(R)$_3$, N(R)$_2$, NHCOCH$_3$, NHCOCF$_3$, NHCOR, NHCONHR, NHCOOR, OCONHR, CONHR, NHCSCH$_3$, NHCSCF$_3$, NHCSR, NHSO$_2$CH$_3$, NHSO$_2$R, OR, COR, OCOR, OSO$_2$R, SO$_2$R, SR, NCS, SCN, NCO or OCN;
- n is 1, 2, or 3; and
- m is 1, 2, or 3;
- or its isomer, pharmaceutically acceptable salt, pharmaceutical product, polymorph, hydrate or any combination thereof.

2. The compound of claim 1, wherein the compound is a compound of formula XVIIa(1):

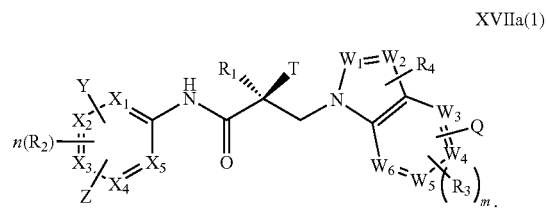

XVIIa(1)

3. The compound of claim 1, wherein the compound is a compound of formula XVII(2):

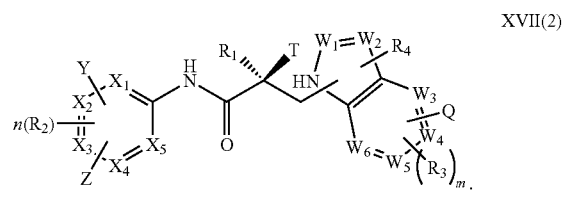

XVII(2)

4. The compound of claim 1, wherein $W_2$ is N and $W_1$, $W_3$, $W_4$, $W_5$, and $W_6$ are CH; or $W_1$ is N and $W_2$, $W_3$, $W_4$, $W_5$, $W_6$ are CH.

5. The compound of claim 1, wherein $X_1$ is N.

6. The compound of claim 1, wherein $X_2$ is N.

7. The compound of claim 1, wherein the compound is represented by the structure of formula XIX:

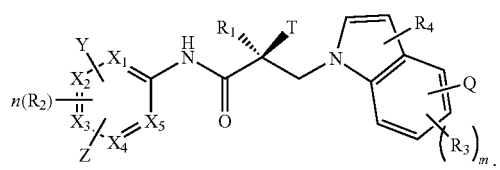

8. The compound of claim 1, wherein Q is H, $NO_2$, COR, alkyl, alkoxy, aryl, CN, $CF_3$, F, Cl, Br or I.

9. The compound of claim 1, wherein Z is CN.

10. The compound of claim 1, wherein Y is Cl or $CF_3$.

11. A pharmaceutical composition comprising a SARD compound according to claim 1, or its isomer, pharmaceutically acceptable salt, pharmaceutical product, hydrate or any combination thereof, and a pharmaceutically acceptable carrier.

12. A method of treating prostate cancer (PCa) or increasing the survival of a male subject suffering from prostate cancer comprising administering to the subject a therapeutically effective amount of a compound according to claim 1, or its isomer, pharmaceutically acceptable salt, pharmaceutical product, hydrate or any combination thereof.

13. The method according to claim 12, wherein the prostate cancer is at least one of advanced prostate cancer, refractory prostate cancer, castration resistant prostate cancer (CRPC), metastatic CRPC (mCRPC), non-metastatic CRPC (nmCRPC), or high-risk nmCRPC.

14. The method according to claim 12 further comprising administering androgen deprivation therapy (ADT).

15. The method according to claim 12, wherein the prostate cancer is resistant to treatment with an androgen receptor antagonist(s).

16. The method according to claim 15, wherein the androgen receptor antagonist is at least one of enzalutamide, apalutamide, bicalutamide, abiraterone, ODM-201, EPI-001, EPI-506, AZD-3514, galeterone, AS C-J9, flutamide, hydroxyflutamide, nilutamide, cyproterone acetate, ketoconazole, or spironolactone.

17. A method of treating enzalutamide resistant prostate cancer, apalutamide resistant prostate cancer, abiraterone resistant prostate cancer, or triple negative breast cancer in a subject comprising administering to the subject a therapeutically effective amount of a compound according to claim 1, or its isomer, pharmaceutically acceptable salt, pharmaceutical product, hydrate or any combination thereof.

18. The compound of claim 1, wherein the compound is represented by compound 47:

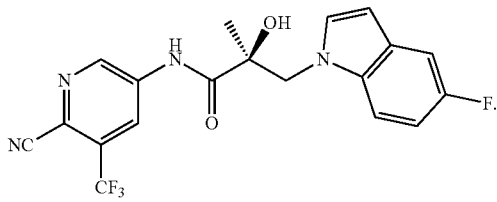

19. The compound of claim 1, wherein the compound is represented by compound 99:

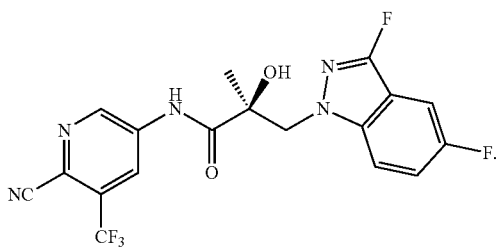

20. The compound of claim 1, wherein the compound is represented by compound 96:

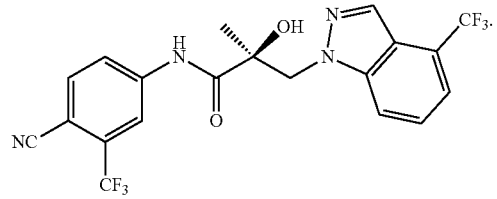

21. The compound of claim 1, wherein the compound is represented by compound 38:

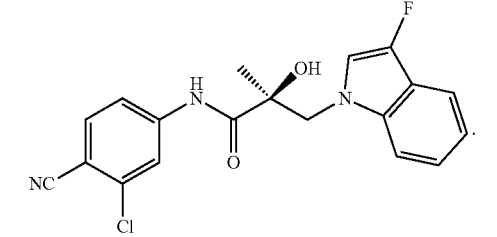

* * * * *

UNITED STATES PATENT AND TRADEMARK OFFICE
CERTIFICATE OF CORRECTION

PATENT NO. : 11,873,282 B2  
APPLICATION NO. : 17/027707  
DATED : January 16, 2024  
INVENTOR(S) : Ramesh Narayanan Page 1 of 14

It is certified that error appears in the above-identified patent and that said Letters Patent is hereby corrected as shown below:

On the Title Page

Column 2 (Other Publications), Line 4, delete "is" and insert -- to --.

Column 2 (Other Publications), Line 7, delete "at" and insert -- of --.

Column 2 (Other Publications), Line 8, delete "at" and insert -- of --.

Page 3, Column 1 (Other Publications), Line 22, delete "Serivce;" and insert -- Service; --.

Page 3, Column 1 (Other Publications), Line 36-37, delete "Soceity." and insert -- Society. --.

Page 3, Column 1 (Other Publications), Line 37, delete "Washsngton," and insert -- Washington, --.

Page 3, Column 2 (Other Publications), Line 21, delete "Nonsteroida" and insert -- Nonsteroidal --.

Page 4, Column 1 (Other Publications), Line 2, delete "advancad" and insert -- advanced --.

Page 4, Column 1 (Other Publications), Line 5-6, delete "hepatocelluar" and insert -- hepatocellular --.

Page 4, Column 2 (Other Publications), Line 8, delete "develpments" and insert -- developments --.

Page 4, Column 2 (Other Publications), Line 19, delete "interation" and insert -- interaction --.

Page 5, Column 1 (Other Publications), Line 34, delete "melonoma" and insert -- melanoma --.

Page 5, Column 2 (Other Publications), Line 43, delete "dimehylhydrazine" and insert -- dimethylhydrazine --.

Signed and Sealed this  
Third Day of December, 2024

Katherine Kelly Vidal  
*Director of the United States Patent and Trademark Office*

In the Specification

Column 1, Line 34, delete "heterocyles," and insert -- heterocycles, --.

Column 2, Line 14, delete "amplications" and insert -- amplifications --.

Column 3, Line 12 (approx.), delete "Napthetenone" and insert -- Naphthalene --.

Column 4, Line 12, delete "endogeneous" and insert -- endogenous --.

Column 4, Line 23, delete "preferrable." and insert -- preferable. --.

Column 4, Line 60, delete "Africian" and insert -- African --.

Column 5, Line 19, delete "Vase" and insert -- Vasc --.

Column 5, Line 37, delete "endogeneous" and insert -- endogenous --.

Column 8, Line 1, delete "embodiment" and insert -- embodiment, --.

Column 10, Line 4, delete "sehorrhea," and insert -- seborrhea, --.

Column 11, Line 50, delete "ABCD" and insert -- A/BCD --.

Column 11, Line 51, delete "ABCD" and insert -- A/BCD --.

Column 11, Line 55, delete "ABCD" and insert -- A/BCD --.

Column 11, Line 56, delete "ABCD" and insert -- A/BCD --.

Column 12, Line 5, delete "enzaluatamide." and insert -- enzalutamide. --.

Column 13, Line 63, delete "10 M" and insert -- 10 μM --.

Column 13, Line 67, delete "10 M" and insert -- 10 μM --.

Column 16, Line 24, delete "M." and insert -- 10 μM. --.

Column 18, Line 1, delete "10 M" and insert -- 10 μM --.

Column 19, Line 3, delete "(6 ppm)." and insert -- (δ ppm). --.

Column 19, Line 13, delete "5 M" and insert -- 5 μM --.

Column 20, Line 59, delete "amplication" and insert -- amplification --.

Column 41, Line 59 (approx.), delete "$C_1$," and insert -- Cl, --.

Column 43, Line 4 (approx.), delete "$C_1$," and insert -- Cl, --.

Column 45, Line 30, delete "$C_1$," and insert -- Cl, --.

Column 71, Line 4 (approx.), delete "$C_1$," and insert -- Cl, --.

Column 72, Line 17 (approx.), delete "$C_1$," and insert -- Cl, --.

Column 73, Line 20 (approx.), delete "$C_1$," and insert -- Cl, --.

Column 75, Line 14 (approx.), delete "$C_1$," and insert -- Cl, --.

Column 75, Line 63 (approx.), delete "$C_1$," and insert -- Cl, --.

Column 77, Line 48 (approx.), delete "$C_1$," and insert -- Cl, --.

Column 78, Line 29, delete "$C_1$," and insert -- Cl, --.

Column 79, Line 61, delete "$C_1$," and insert -- Cl, --.

Column 80, Line 33, delete "$C_1$," and insert -- Cl, --.

Column 85, Line 65, delete "$C_1$." and insert -- Cl. --.

Column 86, Line 8 (approx.), delete "$C_1$." and insert -- Cl. --.

Column 86, Line 19, delete "$C_1$." and insert -- Cl. --.

Column 86, Line 42, delete "$C_1$." and insert -- Cl. --.

Column 86, Line 65, delete "0" and insert -- O --.

Column 87, Line 28, delete "$C_1$." and insert -- Cl. --.

Column 94, Line 3-11 (approx.), delete " 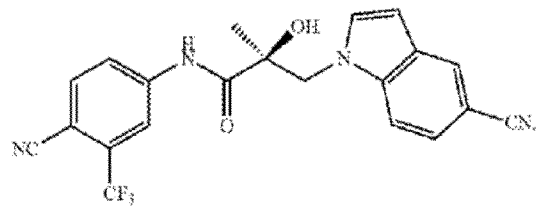 " and

Column 94, Line 13-21 (approx.), delete " 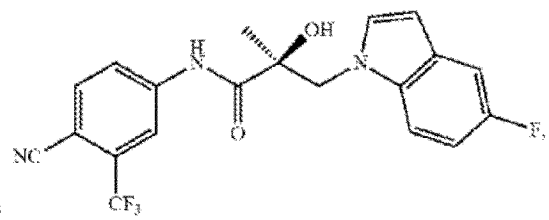 " and insert -- 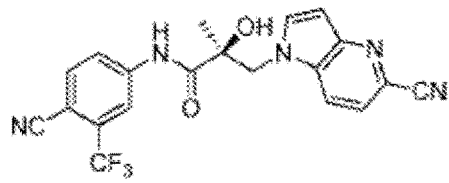 ' --.

insert -- 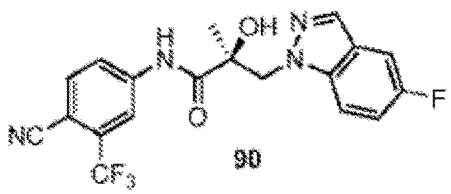 ' --.

Column 102, Line 66, delete "algenates," and insert -- alginates, --.

Column 103, Line 6-7, delete "enanthuates," and insert -- enanthates, --.

Column 103, Line 9, delete "glucoheptanoates," and insert -- glucoheptonates, --.

Column 103, Line 12, delete "hydroxycarboxlic" and insert -- hydroxycarboxylic --.

Column 103, Line 23, delete "polygalacturates," and insert -- polygalacturonates, --.

Column 103, Line 24-25, delete "tartarates," and insert -- tartrates, --.

Column 103, Line 41, delete "meglamines," and insert -- meglumines, --.

Column 103, Line 43, delete "picolies," and insert -- picolines, --.

Column 104, Line 29, delete "stereroisomeric" and insert -- stereoisomeric --.

Column 104, Line 67, delete "la-le," and insert -- Ia-Ie, --.

Column 111, Line 57-66 (approx.), delete " 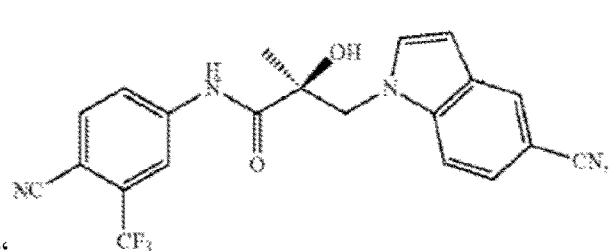 "
and insert -- 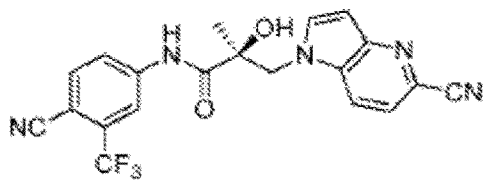 --.

Column 112, Line 3-12 (approx.), delete " 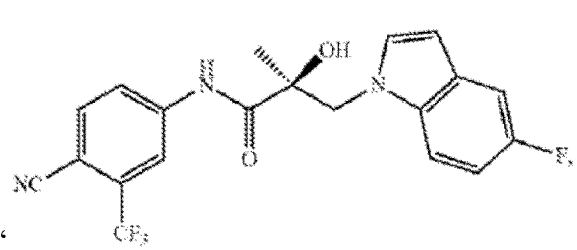 " and
insert -- 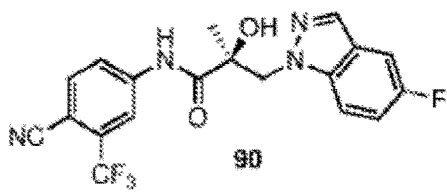 --.

Column 121, Line 25, delete "PSA>20" and insert -- PSA ≥20 --.

Column 121, Line 47, delete "orchidectomized" and insert -- orchiectomized --.

Column 122, Line 50, delete "ng/mL" and insert -- 10 ng/mL --.

Column 129, Line 42, delete "(Iressa)," and insert -- (Iressa®), --.

Column 129, Line 44, delete "(Provenge)," and insert -- (Provenge®), --.

Column 130, Line 2, delete "Viadur," and insert -- Viadur®, --.

Column 130, Line 10-11, delete "(Erleada)," and insert -- (Erleada®), --.

Column 133, Line 53, delete "endogeneous" and insert -- endogenous --.

CERTIFICATE OF CORRECTION (continued)
U.S. Pat. No. 11,873,282 B2

Column 134, Line 23, delete "prostamegaly," and insert -- prostatomegaly, --.

Column 134, Line 37, delete "prostamegaly" and insert -- prostatomegaly --.

Column 135, Line 49, delete "supporativa" and insert -- suppurativa --.

Column 141, Line 28, delete "inventio" and insert -- invention --.

Column 144, Line 41, delete "veneral" and insert -- venereal --.

Column 144, Line 45, delete "scalatina," and insert -- scarlatina, --.

Column 147, Line 57, delete "paracancerally," and insert -- paracentrally, --.

Column 148, Line 12, delete "sub-arachinoid," and insert -- sub-arachnoid, --.

Column 148, Line 13, delete "intra-uterile" and insert -- intra-uterine --.

Column 149, Line 15, delete "Propionbacterium" and insert -- Propionibacterium --.

Column 149, Line 53, delete "to" and insert -- to 5 --.

Column 150, Line 38, delete "formuations," and insert -- formulations, --.

Column 150, Line 41, delete "pregeletanized" and insert -- pregelatinized --.

Column 155, Line 51, delete "$10^{-11}$° C." and insert -- 10-11° C. --.

Column 156, Line 6, delete "(in)" and insert -- (m) --.

Column 156, Line 14, delete "80.8" and insert -- 80.8° --.

Column 156, Line 15, delete "C," and insert -- C --.

Column 156, Line 15, delete "H," and insert -- H --.

Column 156, Line 15, delete "N," and insert -- N --.

Column 156, Line 15, delete "C," and insert -- C --.

Column 156, Line 16, delete "H," and insert -- H --.

Column 156, Line 16, delete "N," and insert -- N --.

Column 156, Line 29, delete "34%)" and insert -- ~34%) --.

Column 156, Line 34, delete "(in," and insert -- (m, --.

Column 156, Line 38, delete "C," and insert -- C --.

Column 156, Line 39, delete "H," and insert -- H --.

Column 156, Line 39, delete "N," and insert -- N --.

Column 156, Line 40, delete "C," and insert -- C --.

Column 156, Line 40, delete "H," and insert -- H --.

Column 156, Line 40, delete "N," and insert -- N --.

Column 156, Line 60, delete "C," and insert -- C --.

Column 156, Line 61, delete "H," and insert -- H --.

Column 156, Line 61, delete "C," and insert -- C --.

Column 156, Line 61, delete "H," and insert -- H --.

Column 157, Line 21 (approx.), delete "CH)," and insert -- CH$_3$), --.

Column 162, Line 52, delete "[M–H];" and insert -- [M–H]–; --.

Column 163, Line 62, delete "[M–H];" and insert -- [M–H]–; --.

Column 164, Line 17, delete "[M–H];" and insert -- [M–H]–; --.

Column 165, Line 48 (approx.), delete "[M+Na]–;" and insert -- [M+Na]+; --.

Column 167, Line 22 (approx.), delete "24S)-" and insert -- 2-((S)- --.

Column 167, Line 32, delete "d6)" and insert -- d$_6$) --.

Column 167, Line 39 (approx.), delete "[M+Na]+." and insert -- [M+Na]$^+$. --.

Column 170, Line 48 (approx.), delete "[M+H]$^+$." and insert -- [M+H]$^+$; --.

Column 170, Line 61 (approx.), delete "[M+H]$^+$." and insert -- [M+H]$^+$; --.

Column 171, Line 40 (approx.), delete "nitrogren" and insert -- nitrogen --.

Column 172, Line 45 (approx.), delete "[M+H]$^+$." and insert -- [M+H]$^+$; --.

CERTIFICATE OF CORRECTION (continued)
U.S. Pat. No. 11,873,282 B2

Column 172, Line 60 (approx.), delete "[M+H]$^+$." and insert -- [M+H]$^+$; --.

Column 172, Line 61 (approx.), delete "9.32" and insert -- δ 9.32 --.

Column 173, Line 49, delete "[M+H]$^+$." and insert -- [M+H]$^+$; --.

Column 178, Line 39, delete "10$^{-11°}$ C." and insert -- 10-11° C. --.

Column 178, Line 59, delete "5.28" and insert -- δ 5.28 --.

Column 178, Line 65, delete "for" and insert -- δ for --.

Column 179, Line 3, delete "80.8" and insert -- 80.8° --.

Column 179, Line 3, delete "C$_9$H$_1$NO$_3$: C, 59.00, H," and insert -- C$_9$H$_{13}$NO$_3$: C 59.00, H --.

Column 179, Line 4, delete "N," and insert -- N --.

Column 179, Line 4, delete "C," and insert -- C --.

Column 179, Line 4, delete "H," and insert -- H --.

Column 179, Line 4, delete "N," and insert -- N --.

Column 179, Line 17, delete "34%)" and insert -- ~34%) --.

Column 179, Line 19, delete "4.69" and insert -- δ 4.69 --.

Column 179, Line 27, delete "C," and insert -- C --.

Column 179, Line 27, delete "H," and insert -- H --.

Column 179, Line 28, delete "N," and insert -- N --.

Column 179, Line 28, delete "C," and insert -- C --.

Column 179, Line 28, delete "H," and insert -- H --.

Column 179, Line 28, delete "N," and insert -- N --.

Column 179, Line 50, delete "C," and insert -- C --.

Column 179, Line 50, delete "H," and insert -- H --.

Column 179, Line 50, delete "C," and insert -- C --.

Column 179, Line 51, delete "H," and insert -- H --.

Column 180, Line 28, delete "NH$_4$C$_1$." and insert -- NH$_4$Cl. --.

Column 181, Line 30, delete "[M–H];" and insert -- [M–H]–; --.

Column 181, Line 39, delete "[M–H];" and insert -- [M–H]–; --.

Column 181, Line 60, delete "(m. 1H)," and insert -- (m, 1H), --.

Column 182, Line 10 (approx.), delete "(m. 2H)," and insert -- (m, 2H), --.

Column 183, Line 60 (approx.), delete "NH$_4$C$_1$." and insert -- NH$_4$Cl. --.

Column 188, Line 5, delete "n/z" and insert -- m/z --.

Column 188, Line 5, delete "[M–H]." and insert -- [M–H]$^-$; --.

Column 189, Line 17, delete "[M–H];" and insert -- [M–H]$^-$; --.

Column 189, Line 46 (approx.), delete "[M–H];" and insert -- [M–H]$^-$; --.

Column 189, Line 48, delete "8.66" and insert -- δ 8.66 --.

Column 191, Line 59, delete "10.37" and insert -- δ 10.37 --.

Column 192, Line 30, delete "10.33" and insert -- δ 10.33 --.

Column 194, Line 33 (approx.), delete "[M–H]." and insert -- [M–H]$^-$; --.

Column 195, Line 18 (approx.), delete "[M–H];" and insert -- [M–H]$^-$; --.

Column 195, Line 21 (approx.), delete "[M+H]$^+$." and insert -- [M+H]$^+$; --.

Column 196, Line 7, delete "[M–H];" and insert -- [M–H]$^-$; --.

Column 196, Line 8, delete "C$_2$H$_{15}$ClF$_4$N$_3$O$_2$" and insert -- C$_{20}$H$_{15}$ClF$_4$N$_3$O$_2$ --.

Column 196, Line 9, delete "C$_2$H$_{15}$ClF$_4$N$_3$O$_2$:" and insert -- C$_{20}$H$_{15}$ClF$_4$N$_3$O$_2$: --.

Column 196, Line 12 (approx.), delete "nm." and insert -- nm; --.

Column 196, Line 64, delete "[M–H]." and insert -- [M–H]$^-$; --.

Column 198, Line 44 (approx.), delete "[M–H]." and insert -- [M–H]$^-$; --.

Column 198, Line 55, delete "[M–H]" and insert -- [M–H]$^-$; --.

Column 199, Line 57, delete "10.20" and insert -- δ 10.20 --.

Column 200, Line 34, delete "10.33" and insert -- δ 10.33 --.

Column 200, Line 62, delete "[M–H] $^-$." and insert -- [M–H]$^-$; --.

Column 201, Line 21 (approx.), delete "[M–H]." and insert -- [M–H]$^-$; --.

Column 201, Line 62, delete "NH$_4$C$_1$." and insert -- NH$_4$Cl. --.

Column 202, Line 41 (approx.), delete "[M–H];" and insert -- [M–H]$^-$; --.

Column 202, Line 43 (approx.), delete "S" and insert -- δ --.

Column 203, Line 18, delete "[M–H] $^-$" and insert -- [M–H]$^-$. --.

Column 207, Line 31, delete "9.10" and insert -- δ 9.10 --.

Column 207, Line 44, delete "9.15" and insert -- δ 9.15 --.

Column 209, Line 16 (approx.), delete "C$_2$H$_{14}$F$_6$N$_4$O$_2$" and insert -- C$_{20}$H$_{14}$F$_6$N$_4$O$_2$ --.

Column 209, Line 17 (approx.), delete "[M+H]$^+$." and insert -- [M+H]$^+$; --.

Column 209, Line 29 (approx.), delete "C$_2$H$_{14}$F$_6$N$_4$O$_2$" and insert -- C$_{20}$H$_{14}$F$_6$N$_4$O$_2$ --.

Column 209, Line 30 (approx.), delete "[M+H]$^+$." and insert -- [M+H]$^+$; --.

Column 210, Line 48, delete "[M–H];" and insert -- [M–H]$^-$; --.

Column 211, Line 44, delete "[M+Na]$^+$." and insert -- [M+Na]$^+$; --.

Column 212, Line 27, delete "(W$_{741}$L)" and insert -- (W741L) --.

Column 212, Line 37, delete "FIG." and insert -- FIGS. --.

Column 212, Line 55 (approx.), delete "g" and insert -- μg --.

Column 212, Line 55 (approx.), delete "0.01 g" and insert -- 0.01 μg --.

Column 213, Line 11, delete "100" and insert -- 100 μl --.

Column 214, Line 1, delete "guardcartridge" and insert -- guard cartridge --.

CERTIFICATE OF CORRECTION (continued)
U.S. Pat. No. 11,873,282 B2

Column 241-242 (TABLE 3-continued), Line 12 (approx.), delete "FIG.e" and insert -- FIG. --.

Column 253-254 (TABLE 3A), Line 9-10 (approx.), delete "Eno- bosarm" and insert -- Enobosarm --.

Column 253-254 (TABLE 3A), Line 11-13 (approx.), delete "R- Bicalut- amide" and insert -- R-Bicalutamide --.

Column 253-254 (TABLE 3A), Line 14-15 (approx.), delete "Enzalut- amide" and insert -- Enzalutamide --.

Column 259-260 (TABLE 4), Line 45 (approx.), delete "31.84[" and insert -- 31.84 --.

Column 261, Line 17, delete "g" and insert -- μg --.

Column 261, Line 17, delete "0.01 g" and insert -- 0.01 μg --.

Column 262, Line 22, delete "(1 M)" and insert -- (1 μM) --.

Column 262, Line 28, delete "100" and insert -- 100 μl --.

Column 263-264 (TABLE 5), Line 5 (approx.), delete "Tranactivation" and insert -- Transactivation --.

Column 263-264 (TABLE 5), Line 9-10 (approx.), delete "Eno- bosarm" and insert -- Enobosarm --.

Column 263-264 (TABLE 5), Line 11-13 (approx.), delete "R- Bicalut- amide" and insert -- R-Bicalutamide --.

Column 263-264 (TABLE 5), Line 14-15 (approx.), delete "Enzalut- amide" and insert -- Enzalutamide --.

Column 263-264 (TABLE 5), Line 16-19 (approx.), delete "ARN- 509 (apalut- amide)" and insert -- ARN-509 (apalutamide) --.

Column 265-266 (TABLE 5-continued), Line 6 (approx.), delete "Tranactivation" and insert -- Transactivation --.

Column 267-268 (TABLE 5-continued), Line 5 (approx.), delete "Tranactivation" and insert -- Transactivation --.

Column 269-270 (TABLE 6), Line 21-22 (approx.), delete "Eno- bosarm" and insert -- Enobosarm --.

Column 269-270 (TABLE 6), Line 23-25 (approx.), delete "R- Bicalut- amide" and insert -- R-Bicalutamide --.

Column 269-270 (TABLE 6), Line 26-27 (approx.), delete "Enzalut- amide" and insert -- Enzalutamide --.

Column 269-270 (TABLE 6), Line 28-31 (approx.), delete "ARN- 509 (apalut- amide)" and insert -- ARN-509 (apalutamide) --.

Column 269-270 (TABLE 6), Line 32-33, delete "DJ-I- 223" and insert -- DJ-I-223 --.

Column 271-272 (TABLE 6), Line 10-11, delete "DJ-VI- 5E" and insert -- DJ-VI-5E --.

Column 279, Line 62, delete "M" and insert -- µM --.

Column 279, Line 65, delete "1 M and 10 M." and insert -- 1 µM and 10 µM. --.

Column 280, Line 29, delete "M" and insert -- µM --.

Column 280, Line 57, delete "($N_{20}$" and insert -- (N20 --.

Column 281, Line 5, delete "10 M." and insert -- 10 µM. --.

Column 282, Line 15, delete "themLBD." and insert -- them LBD. --.

Column 283, Line 15 (approx.), delete "M," and insert -- µM, --.

Column 283, Line 20, delete "M," and insert -- µM, --.

Column 283, Line 62, delete "1 M." and insert -- 1 µM. --.

Column 284, Line 65, delete "g" and insert -- µg --.

Column 284, Line 65, delete "0.01 g" and insert -- 0.01 µg --.

Column 285, Line 34, delete "tagman" and insert -- taqman --.

Column 286, Line 39, delete "($N_{20}$" and insert -- (N20 --.

Column 286, Line 65, delete "10 M" and insert -- 10 µM --.

Column 287, Line 22, delete "$N_{20}$" and insert -- N20 --.

Column 288, Line 27, delete "ABCD" and insert -- A/BCD --.

Column 289, Line 18, delete "(1 µM)" and insert -- (~1 µM) --.

Column 289-290 (TABLE 10), Line 41, delete "Expresssion" and insert -- Expression --.

Column 291, Line 48, delete "AF" and insert -- AF1 --.

CERTIFICATE OF CORRECTION (continued)
U.S. Pat. No. 11,873,282 B2

Column 291, Line 63, delete "AF" and insert -- AF1 --.

Column 292, Line 2, delete "FIG." and insert -- FIGS. --.

Column 294, Line 53, delete "(1 μM" and insert -- (1 pM --.

Column 295, Line 5, delete "(1 μM" and insert -- (1 pM --.

Column 295, Line 28, delete "100" and insert -- 100 μl --.

Column 297-298 (TABLE 13), Line 18-19 (approx.), delete "Eno- bosarm" and insert -- Enobosarm --.

Column 297-298 (TABLE 13), Line 20-22 (approx.), delete "R-mBicalut- amide" and insert -- R-Bicalutamide --.

Column 297-298 (TABLE 13), Line 23-24 (approx.), delete "Enzalut- amide" and insert -- Enzalutamide --.

Column 297-298 (TABLE 13), Line 25-28 (approx.), delete "ARN- 509 (apalut- amide)" and insert -- ARN-509 (apalutamide) --.

Column 301, Line 65, delete "g" and insert -- μg --.

Column 301, Line 65, delete "0.01 g" and insert -- 0.01 μg --.

Column 303, Line 10, delete "$K_1$." and insert -- $K_i$. --.

Column 304, Line 3, delete "10 M," and insert -- 10 μM, --.

Column 309, Line 7, delete "Q711A" and insert -- Q711A; --.

Column 314, Line 65, delete "$[M+Na]^+$." and insert -- $[M+Na]^+$; --.

Column 315, Line 4, delete "6" and insert -- δ --.

Column 315, Line 24, delete "[M–H]." and insert -- $[M–H]^-$; --.

Column 315, Line 29, delete "6" and insert -- δ --.

Column 316, Line 8, delete "[M–H]." and insert -- $[M–H]^-$; --.

Column 316, Line 15 (approx.), delete "6" and insert -- δ --.

Column 317, Line 57, delete "[M–H];" and insert -- $[M–H]^-$; --.

Column 317, Line 59 (approx.), delete "[M+H]$^+$." and insert -- [M+H]$^+$; --.

Column 318, Line 62, delete "[M+H]$^+$." and insert -- [M+H]$^+$; --.

Column 318, Line 66, delete "8" and insert -- δ --.

In the Claims

Column 321, Line 44 (approx.), Claim 16, delete "AS C-J9," and insert -- ASC-J9, --.